(12) United States Patent
Reynolds et al.

(10) Patent No.: US 10,786,489 B2
(45) Date of Patent: Sep. 29, 2020

(54) FORMULATIONS OF 6-(2-HYDROXY-2-METHYLPROPXY)-4-(6-(6-((6-METHOXYPYRIDIN-3-YL)METHYL)-3,6-DIAZABICYCLO[3.1.1]HEPTAN-3-YL)PYRIDIN-3-YL)PYRAZOLO[1,5-A]PYRIDINE-3-CARBONITRILE

(71) Applicant: Loxo Oncology, Inc., Stamford, CT (US)

(72) Inventors: Mark Reynolds, Stamford, CT (US); Charles Todd Eary, Longmont, CO (US)

(73) Assignee: Loxo Oncology Inc., Stamford, CT (US)

( * ) Notice: Subject to any disclaimer, the term of this patent is extended or adjusted under 35 U.S.C. 154(b) by 0 days.

(21) Appl. No.: 16/156,903

(22) Filed: Oct. 10, 2018

(65) Prior Publication Data
US 2019/0262322 A1    Aug. 29, 2019

Related U.S. Application Data

(60) Provisional application No. 62/570,601, filed on Oct. 10, 2017.

(51) Int. Cl.
| | | |
|---|---|---|
| *A61K 31/439* | (2006.01) | |
| *A61P 35/00* | (2006.01) | |
| *A61K 9/00* | (2006.01) | |
| *A61K 9/16* | (2006.01) | |
| *A61K 9/48* | (2006.01) | |
| *A61K 47/02* | (2006.01) | |
| *A61K 47/10* | (2017.01) | |
| *A61K 47/12* | (2006.01) | |
| *A61K 47/26* | (2006.01) | |
| *A61K 47/38* | (2006.01) | |
| *A61K 9/20* | (2006.01) | |
| *A61K 31/498* | (2006.01) | |
| *A61K 9/08* | (2006.01) | |

(52) U.S. Cl.
CPC .......... *A61K 31/439* (2013.01); *A61K 9/0053* (2013.01); *A61K 9/08* (2013.01); *A61K 9/1611* (2013.01); *A61K 9/1623* (2013.01); *A61K 9/1641* (2013.01); *A61K 9/1652* (2013.01); *A61K 9/1682* (2013.01); *A61K 9/2009* (2013.01); *A61K 9/2018* (2013.01); *A61K 9/2031* (2013.01); *A61K 9/2054* (2013.01); *A61K 9/4825* (2013.01); *A61K 31/498* (2013.01); *A61K 47/02* (2013.01); *A61K 47/10* (2013.01); *A61K 47/12* (2013.01); *A61K 47/26* (2013.01); *A61K 47/38* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 8,574,625 B2 * | 11/2013 | Jain ...................... | A61K 9/2072 424/465 |
| 10,112,942 B2 | 10/2018 | Andrews et al. | |
| 10,137,124 B2 | 11/2018 | Andrews et al. | |
| 10,172,851 B2 | 1/2019 | Andrews et al. | |
| 2016/0002215 A1 * | 1/2016 | Eidam .................. | C07D 401/12 514/340 |
| 2019/0183886 A1 | 6/2019 | Andrews et al. | |

FOREIGN PATENT DOCUMENTS

WO    2016/210034 A1    12/2016

OTHER PUBLICATIONS

Annals of Oncology Developmental Therapeutics, vol. 28, No. 5, 417TIP (Poster Abstract), (Sep. 1, 2017), pp. 138-138.
PCT International Search Report and the Written Opinion of the International Searching Authority pertaining to international Application No. PCT/2018/055285; dated Feb. 20, 2019; 21 pages.

* cited by examiner

*Primary Examiner* — James D. Anderson
*Assistant Examiner* — Stephanie K Springer
(74) *Attorney, Agent, or Firm* — Bradley W. Crawford

(57) ABSTRACT

6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile, or a pharmaceutically acceptable salt, amorphous form, polymorph form, or pharmaceutical composition (including solid formulations or liquid formulations) thereof and the use thereof for treating diseases and disorders which can be treated with a RET kinase inhibitor, such as RET-associated diseases and disorders, e.g., proliferative disorders such as cancers, including hematological cancers and solid tumors, and gastrointestinal disorders such as IBS are disclosed.

18 Claims, 56 Drawing Sheets
Specification includes a Sequence Listing.

FORMULATIONS OF 6-(2-HYDROXY-2-METHYLPROPXY)-4-(6-(6-((6-METHOXYPYRIDIN-3-YL)METHYL)-3,6-DIAZABICYCLO[3.1.1]HEPTAN-3-YL)PYRIDIN-3-YL)PYRAZOLO[1,5-A]PYRIDINE-3-CARBONITRILE

CROSS-REFERENCE TO RELATED APPLICATIONS

This application claims priority to U.S. Provisional Application Ser. No. 62/570,601, filed on Oct. 10, 2017, the contents of which are hereby incorporated by reference in their entirety.

PARTIES TO A JOINT RESEARCH AGREEMENT

The present invention was made under a Joint Research Agreement between Array BioPharma Inc. and Loxo Oncology, Inc. The Joint Research Agreement was in effect on or before the date the present invention was made, and the present invention was made as a result of the activities undertaken within the scope of the Joint Research Agreement.

FIELD OF THE INVENTION

Provided herein are solid formulations that contain the compound of Formula (I)

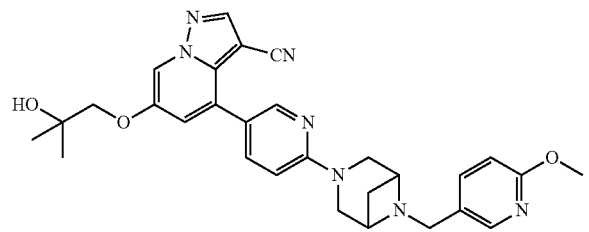

including pharmaceutically acceptable salts, amorphous forms, and polymorph forms thereof. Further provided are methods for using the same.

BACKGROUND

The compound of Formula (I)

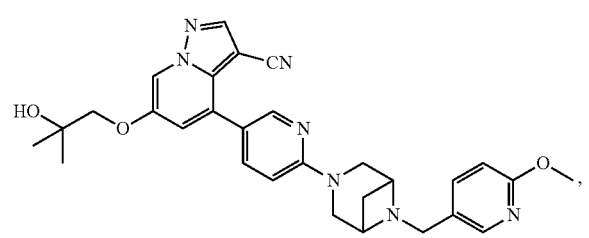

6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile, including polymorphs and pharmaceutically acceptable salts thereof, exhibits rearranged during transfection (RET) kinase inhibition. The compound of Formula (I) can be used in the treatment and prevention of diseases which can be treated with a RET kinase inhibitor, including RET-associated diseases and disorders. A need exists for formulations containing the compound of Formula (I), such as solid formulations. Such formulations are provided herein.

SUMMARY

Provided herein are solid formulations containing the compound of Formula (I)

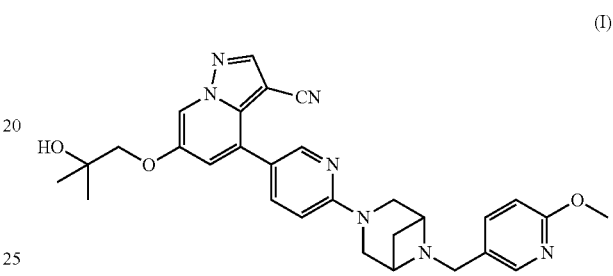

or a pharmaceutically acceptable salt, amorphous form, or polymorph form thereof.

In some embodiments, the solid formulation comprises 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I)

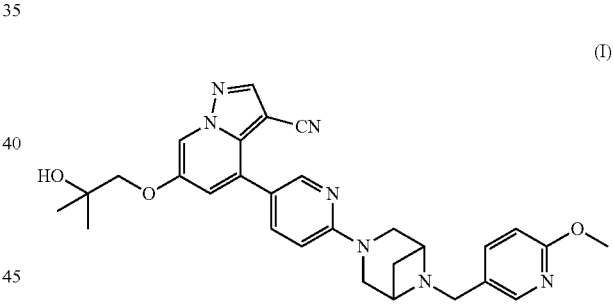

or a pharmaceutically acceptable salt, amorphous form, or polymorph form thereof and an excipient selected from the group consisting of diluents or fillers, binders, granulating agents, adhesives, polymers and copolymers, disintegrants, stabilizers, lubricants, anti-adherents, glidants, surfactants, dispersing or wetting agents, dissolution retardants or enhancers, adsorbents, buffers, chelating agents, preservatives, colors, flavors, and sweeteners, or combinations thereof.

In some embodiments of the solid formulation, the excipient comprises a diluent or filler. In some embodiments, the diluent or filler is selected from the group consisting of dibasic calcium phosphate, kaolin, lactose, dextrose, magnesium carbonate, sucrose, mannitol, glucose or other monosaccharaides, dextrin or other polysaccharides, microcrystalline cellulose, powdered cellulose, cellulose derivatives, precipitated calcium carbonate, calcium sulfate, sorbitol, inositol, and starch, or combinations thereof. In some embodiments, the diluent or filler is present in an amount of about 60 wt % to about 90 wt %.

In some embodiments of the solid formulation, the diluent or filler comprises microcrystalline cellulose. In some embodiments, the microcrystalline cellulose is present in an amount of about 65 wt % to about 85 wt %.

In some embodiments of the solid formulation, the diluent or filler comprises mannitol. In some embodiments, the excipient comprises a glidant. In some embodiments, the glidant is selected from the group consisting of colloidal silica, colloidal silicon dioxide, fumed silica, silicon dioxide, cornstarch, talc, calcium silicate, magnesium silicate, tribasic calcium phosphate, and silicon hydrogel. In some embodiments, the glidant is fumed silica or silicon dioxide. In some embodiments, the glidant is present in an amount of about 0.1 wt % to about 5 wt %.

In some embodiments of the solid formulation, the excipient comprises a dispersing agent. In some embodiments, the dispersing agent is selected from the group consisting of a hydrophilic polymer, an electrolyte, Tween® 60 or 80, polyvinylpyrrolidone, a hydroxypropyl cellulose, a hydroxypropyl methylcellulose, carboxymethylcellulose sodium, methylcellulose, hydroxyethylcellulose, hydroxypropylcellulose, hydroxypropylmethylcellulose phthalate, hydroxypropyl methylcellulose acetate succinate (HPMC-AS), noncrystalline cellulose, magnesium aluminum silicate, triethanolamine, polyvinyl alcohol (PVA), vinyl pyrrolidone/vinyl acetate copolymer (S630), tyloxapol, a poloxamine, a poloxamer (polyoxypropylene-polyoxyethylene block copolymers), a polyvinylpyrrolidone, a polyvinylpyrrolidone/vinyl acetate copolymer, polyethylene glycol (PEG), sodium carboxymethylcellulose, polysorbate-80, sodium alginate, gum tragacanth, gum acacia, guar gum, a xanthan, a sugar, polyethoxylated sorbitan monolaurate, povidone, a carbomer, a chitosan, cellulose, and triethyl cellulose, or combinations thereof. In some embodiments, the dispersing agent comprises a poloxamer. In some embodiments, the poloxamer is poloxamer 188.

In some embodiments of the solid formulation, the excipient comprises a disintegrant. In some embodiments, the disintegrant is selected from the group consisting of a starch, sodium carboxymethyl starch (sodium starch glycolate), pregelatinized starch (starch 1500), microcrystalline starch, water insoluble starch, sodium starch glycolate, calcium carbonate, sodium carbonate, sodium bicarbonate, cellulose and cellulose derivatives, calcium carboxymethyl cellulose, microcrystalline cellulose, carboxymethylcellulose calcium, croscarmellose sodium, croscarmellose calcium, carmellose calcium, cellulose polacrilin potassium, magnesium aluminum silicate (Veegum), sweeteners, clays, bentonite, alginic acid, sodium alginate, alginates, gums, agar, guar, locust bean, karaya, pectin, tragacanth, citrus pulp, and crospovidone, or combinations thereof. In some embodiments, the disintegrant is a cellulose derivative selected from the group consisting of calcium carboxymethyl cellulose, microcrystalline cellulose, carboxymethylcellulose calcium, croscarmellose sodium, croscarmellose calcium, carmellose calcium, and cellulose polacrilin potassium. In some embodiments, the cellulose derivative is croscarmellose sodium.

In some embodiments of the solid formulation, the excipient comprises a lubricant. In some embodiments, the lubricant is selected from the group consisting of a stearate, stearic acid, talc, mineral oil, a silica, malt, glyceryl behenate, hydrogenated vegetable oils, polyethylene glycol, sodium benzoate, sodium acetate, sodium chloride, leucine, magnesium lauryl sulfate, and sodium lauryl sulfate, or combinations thereof. In some embodiments, the lubricant is a stearate. In some embodiments, the stearate is magnesium stearate.

In some embodiments of the solid formulation, the compound of Formula (I) is present in an amount from about 0.5 wt % to about 50 wt %. In some embodiments, the compound of Formula (I) is present in an amount from about 5 wt % to about 35 wt %.

In some embodiments, the solid formulation is formulated as a tablet, capsule, sachet, powder, granules, coated particle, coated tablet, enterocoated tablet, enterocoated capsule, melting strip, or melting film. In some embodiments, the solid formulation is a powder. In some embodiments, the powder is spray dried. In some embodiments, the powder is encapsulated. In some embodiments, the powder is encapsulated in a hard gelatin capsule.

In some embodiments, the solid formulation is formulated as a 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg dosage form. In some embodiments, the solid formulation is formulated as a 10 mg, 20 mg, or 80 mg dosage form.

Provided herein is a solid formulation comprising 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I):

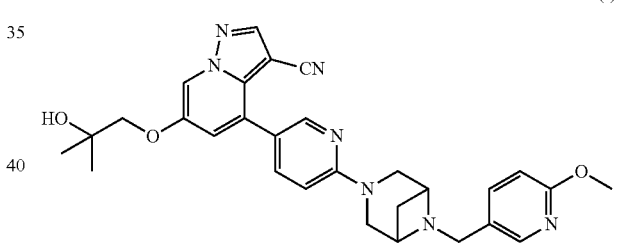

or a pharmaceutically acceptable salt, amorphous form, or polymorph form thereof; a diluent or filler; and a glidant.

In some embodiments of the solid formulation, the diluent or filler is microcrystalline cellulose.

In some embodiments of the solid formulation, the glidant is fumed silica or silicon dioxide.

In some embodiments, the solid formulation is a powder. In some embodiments, the powder is encapsulated in a hard gelatin capsule.

In some embodiments, the solid formulation is formulated as a 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg dosage form. In some embodiments, the solid formulation is formulated as a 10 mg, 20 mg, or 80 mg dosage form.

Provided herein is a solid formulation comprising 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I):

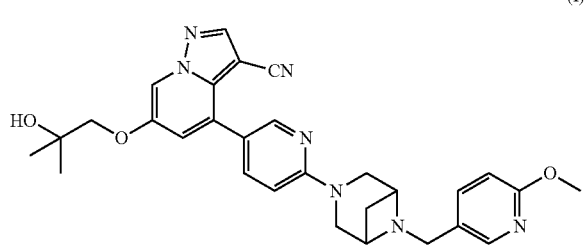

(I)

or a pharmaceutically acceptable salt, amorphous form, or polymorph form thereof in an amount from about 15 wt % to about 25 wt %; a diluent or filler in an amount from about 75 wt % to about 85 wt %; and a glidant in an amount from about 0.1 wt % to about 5 wt %.

In some embodiments of the solid formulation, the diluent or filler is microcrystalline cellulose.

In some embodiments of the solid formulation, the glidant is fumed silica or silicon dioxide.

In some embodiments, the solid formulation is a powder. In some embodiments, the powder is encapsulated in a hard gelatin capsule.

In some embodiments, the solid formulation is formulated as a 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg dosage form. In some embodiments, the solid formulation is formulated as a 10 mg, 20 mg, or 80 mg dosage form.

Provided herein is a solid formulation comprising 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I):

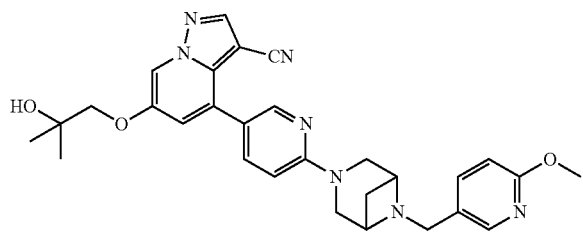

(I)

or a pharmaceutically acceptable salt, amorphous form, or polymorph form thereof; a diluent or filler; a dispersing agent; a disintegrant; and a lubricant.

In some embodiments of the solid formulation, the diluent or filler comprises microcrystalline cellulose and mannitol.

In some embodiments of the solid formulation, the dispersing agent comprises HPMC-AS and poloxamer 188.

In some embodiments of the solid formulation, the disintegrant is croscarmellose sodium.

In some embodiments of the solid formulation, the lubricant is magnesium stearate.

In some embodiments, the solid formulation is a spray dried dispersion.

Provided herein is a solid formulation comprising 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I):

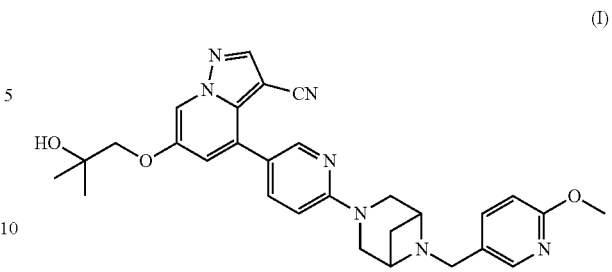

(I)

or a pharmaceutically acceptable salt, amorphous form, or polymorph form thereof; microcrystalline cellulose; mannitol; HPMC-AS; poloxamer 188; croscarmellose sodium; and magnesium stearate.

In some embodiments, the solid formulation is prepared from a crystalline form of the compound of Formula (I). In some embodiments, the crystalline form of the compound of Formula (I) has the formula

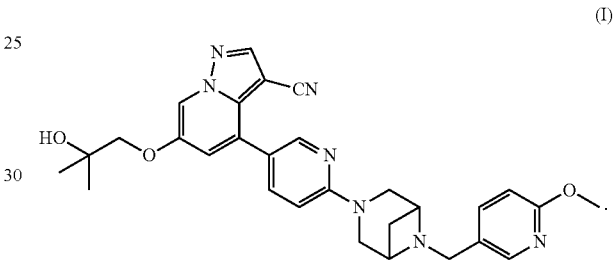

(I)

In some embodiments of the solid formulation, the crystalline form is Form 1, characterized by having an XRPD pattern comprising peaks at °2θ values of 16.5±0.2, 18.9±0.2, 23.8±0.2, 25.3±0.2, and 26.0±0.2.

In some embodiments of the solid formulation, the crystalline form is Form 1, characterized by having an XRPD pattern comprising peaks at °2θ values of 16.5±0.2, 17.8±0.2, 18.9±0.2, 23.8±0.2, 25.3±0.2, 25.6±0.2, 26.0±0.2, and 28.3±0.2.

In some embodiments of the solid formulation, the crystalline form is Form 1, characterized by having an XRPD pattern comprising peaks at °2θ values of 9.8±0.2, 16.5±0.2, 17.8±0.2, 18.9±0.2, 23.8±0.2, 25.0±0.2, 25.3±0.2, 25.6±0.2, 26.0±0.2, and 28.3±0.2.

Provided herein is a solid formulation comprising a crystalline form of the compound of Formula (I) having the formula

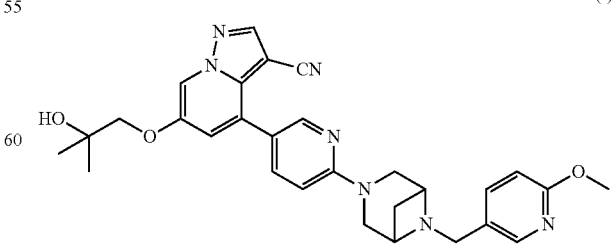

(I)

wherein the crystalline form is Form 1, characterized by having an X-ray powder diffraction (XRPD) pattern comprising peaks at °2θ values of 16.5±0.2, 18.9±0.2, and 26.0±0.2; and an excipient selected from the group consisting of diluents or fillers, binders, granulating agents, adhesives, polymers and copolymers, disintegrants, stabilizers, lubricants, anti-adherents, glidants, surfactants, dispersing or wetting agents, dissolution retardants or enhancers, adsorbents, buffers, chelating agents, preservatives, colors, flavors, and sweeteners, or combinations thereof.

In some embodiments of the solid formulation, the crystalline form is Form 1, characterized by having an XRPD pattern comprising peaks at °2θ values of 16.5±0.2, 18.9±0.2, 23.8±0.2, 25.3±0.2, and 26.0±0.2.

In some embodiments of the solid formulation, the crystalline form is Form 1, characterized by having an XRPD pattern comprising peaks at °2θ values of 16.5±0.2, 17.8±0.2, 18.9±0.2, 23.8±0.2, 25.3±0.2, 25.6±0.2, 26.0±0.2, and 28.3±0.2.

In some embodiments of the solid formulation, the crystalline form is Form 1, characterized by having an XRPD pattern comprising peaks at °2θ values of 9.8±0.2, 16.5±0.2, 17.8±0.2, 18.9±0.2, 23.8±0.2, 25.0±0.2, 25.3±0.2, 25.6±0.2, 26.0±0.2, and 28.3±0.2.

Provided herein is a solid formulation comprising a crystalline form of the compound of Formula (I) having the formula

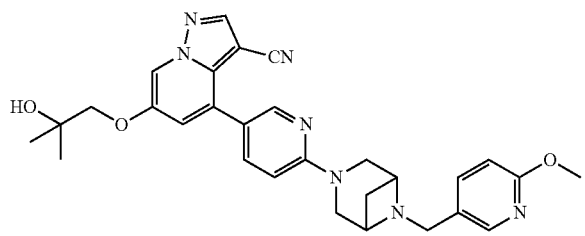

(I)

wherein the crystalline form is Form 1, characterized by having an X-ray powder diffraction (XRPD) pattern comprising peaks at °2θ values of 16.5±0.2, 18.9±0.2, and 26.0±0.2; a diluent or filler; and a glidant.

In some embodiments of the solid formulation, the diluent or filler is microcrystalline cellulose.

In some embodiments of the solid formulation, the glidant is fumed silica or silicon dioxide.

Provided herein is a solid formulation comprising a crystalline form of the compound of Formula (I) having the formula

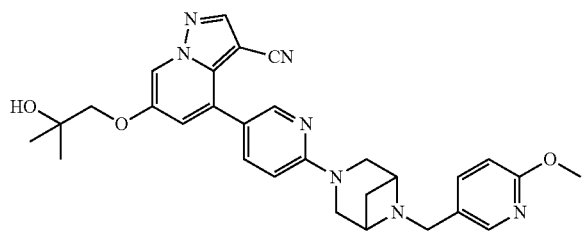

(I)

wherein the crystalline form is Form 1, characterized by having an X-ray powder diffraction (XRPD) pattern comprising peaks at °2θ values of 16.5±0.2, 18.9±0.2, and 26.0±0.2 in an amount from about 15 wt % to about 25 wt %; a diluent or filler in an amount from about 75 wt % to about 85 wt %; and a glidant in an amount from about 0.1 wt % to about 5 wt %.

In some embodiments of the solid formulation, the diluent or filler is microcrystalline cellulose.

In some embodiments of the solid formulation, the glidant is fumed silica or silicon dioxide.

Provided herein is a solid formulation comprising a crystalline form of the compound of Formula (I) having the formula

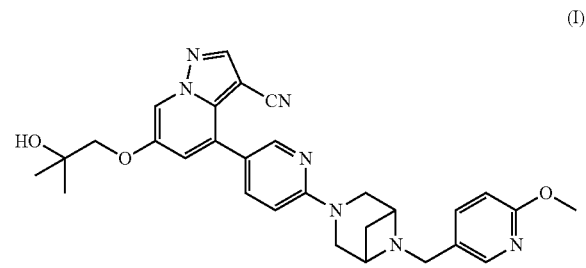 [SMILES: COc1ccc(CN2C3CC2CN(c2ccc(-c4cc(OCC(C)(C)O)cn5ncc(C#N)c45)cn2)C3)cn1]

(I)

wherein the crystalline form is Form 1, characterized by having an X-ray powder diffraction (XRPD) pattern comprising peaks at °2θ values of 16.5±0.2, 18.9±0.2, and 26.0±0.2; a diluent or filler; a dispersing agent; a disintegrant; and a lubricant.

In some embodiments of the solid formulation, the diluent or filler comprises microcrystalline cellulose and mannitol.

In some embodiments of the solid formulation, the dispersing agent comprises HPMC-AS and poloxamer 188.

In some embodiments of the solid formulation, the disintegrant is croscarmellose sodium.

In some embodiments of the solid formulation, the lubricant is magnesium stearate.

Provided herein is a solid formulation comprising a crystalline form of the compound of Formula (I) having the formula

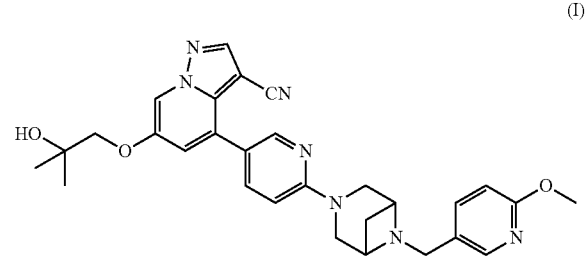 [SMILES: COc1ccc(CN2C3CC2CN(c2ccc(-c4cc(OCC(C)(C)O)cn5ncc(C#N)c45)cn2)C3)cn1]

(I)

wherein the crystalline form is Form 1, characterized by having an X-ray powder diffraction (XRPD) pattern comprising peaks at °2θ values of 16.5±0.2, 18.9±0.2, and 26.0±0.2; microcrystalline cellulose; mannitol; HPMC-AS; poloxamer 188; croscarmellose sodium; and magnesium stearate.

In some embodiments of the solid formulations provided herein, the compound of Formula (I) is present in an amount from about 5 wt % to about 35 wt %.

In some embodiments, the solid formulation is formulated as a tablet, capsule, sachet, powder, granules, coated particle, coated tablet, enterocoated tablet, enterocoated capsule, melting strip, or melting film. In some embodiments, the solid formulation is a powder. In some embodiments, the powder is spray dried. In some embodiments, the powder is encapsulated. In some embodiments, the powder is encapsulated in a hard gelatin capsule.

In some embodiments, the solid formulation is formulated as a 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg dosage form. In some embodiments, the solid formulation is formulated as a 10 mg, 20 mg, or 80 mg dosage form.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is an x-ray powder diffraction scan of fully dried Form 1. FIG. 1B is a differential scanning calorimetry scan of Form 1. FIG. 1C is a thermogravimetric/differential thermal analysis scan of Form 1. FIG. 1D is a gravimetric vapor sorption isotherm of Form 1. FIG. 1E is a kinetic gravimetric vapor sorption scan of Form 1. FIG. 1F is a $^1$H NMR spectrum of Form 1 in $d_6$-DMSO.

FIG. 2A shows x-ray powder diffraction scans of Form 2 (small scale slurry, large scale slurry, and fully dried). FIG. 2B is a differential scanning calorimetry scan of Form 2. FIG. 2C is a thermogravimetric/differential thermal analysis scan of Form 2. FIG. 2D is a gravimetric vapor sorption isotherm of Form 2. FIG. 2E is a kinetic gravimetric vapor sorption scan of Form 2.

FIG. 3A shows x-ray powder diffraction scans of Form 7 (small scale slurry, large scale slurry, and fully dried). FIG. 3B is a differential scanning calorimetry scan of Form 7. FIG. 3C is a thermogravimetric/differential thermal analysis scan of Form 7. FIG. 3D is a gravimetric vapor sorption isotherm of Form 7. FIG. 3E is a kinetic gravimetric vapor sorption scan of Form 7. FIG. 3F is a $^1$H NMR spectrum of Form 7 in $d_6$-DMSO.

FIG. 4A shows x-ray powder diffraction scans of Form 8 (small scale slurry, large scale slurry, and fully dried). FIG. 4B is a differential scanning calorimetry scan of Form 8. FIG. 4C is a thermogravimetric/differential thermal analysis scan of Form 8. FIG. 4D is a gravimetric vapor sorption isotherm of Form 8. FIG. 4E is a kinetic gravimetric vapor sorption scan of Form 8. FIG. 4F is a $^1$H NMR spectrum of Form 8 in $d_6$-DMSO.

FIG. 5A is an x-ray powder diffraction scan of the fully dried phosphate salt. FIG. 5B is a differential scanning calorimetry scan of the phosphate salt. FIG. 5C is a thermogravimetric/differential thermal analysis scan of the phosphate salt. FIG. 5D is a gravimetric vapor sorption isotherm of the phosphate salt. FIG. 5E is a kinetic gravimetric vapor sorption scan of the phosphate salt. FIG. 5F is a $^1$H NMR spectrum of Form 1 in $d_6$-DMSO.

FIG. 6A shows the scans of the compound of Formula (I) in each solvent tested after the samples were temperature cycled between room temperature and 40° C. in 4-hour cycles over 24 hours (post-cycling). FIG. 6B shows the scans of the compound of Formula (I) in each solvent tested after overnight storage of the samples in an oven at 40° C. and 75% relative humidity (post-stability).

FIG. 7A shows the scans of the compound of Formula (I) in each solvent tested after the samples were temperature cycled between room temperature and 40° C. in 4-hour cycles over 24 hours (post-cycling). FIG. 7B shows the scans of the compound of Formula (I) in each solvent tested after overnight storage of the samples in an oven at 40° C. and 75% relative humidity (post-stability).

FIG. 8A shows the scans of the compound of Formula (I) in each solvent tested after the samples were temperature cycled between room temperature and 40° C. in 4-hour cycles over 24 hours (post-cycling). FIG. 8B shows the scans of the compound of Formula (I) in each solvent tested after overnight storage of the samples in an oven at 40° C. and 75% relative humidity (post-stability).

FIG. 9A shows the scans of the compound of Formula (I) in each solvent tested after the samples were temperature cycled between room temperature and 40° C. in 4-hour cycles over 24 hours (post-cycling). FIG. 9B shows the scans of the compound of Formula (I) in each solvent tested after overnight storage of the samples in an oven at 40° C. and 75% relative humidity (post-stability).

FIG. 10A shows the scans of the compound of Formula (I) in each solvent tested after the samples were temperature cycled between room temperature and 40° C. in 4-hour cycles over 24 hours (post-cycling). FIG. 10B shows the scans of the compound of Formula (I) in each solvent tested after overnight storage of the samples in an oven at 40° C. and 75% relative humidity (post-stability).

FIG. 11A shows the scans of the compound of Formula (I) in each solvent tested after the samples were temperature cycled between room temperature and 40° C. in 4-hour cycles over 24 hours (post-cycling). FIG. 11B shows the scans of the compound of Formula (I) in each solvent tested after overnight storage of the samples in an oven at 40° C. and 75% relative humidity (post-stability).

FIG. 12A shows the scans of the compound of Formula (I) in each solvent tested after the samples were temperature cycled between room temperature and 40° C. in 4-hour cycles over 24 hours (post-cycling). FIG. 12B shows the scans of the compound of Formula (I) in each solvent tested after overnight storage of the samples in an oven at 40° C. and 75% relative humidity (post-stability).

FIG. 13A shows the scans of the compound of Formula (I) in each solvent tested after the samples were temperature cycled between room temperature and 40° C. in 4-hour cycles over 24 hours (post-cycling). FIG. 13B shows the scans of the compound of Formula (I) in each solvent tested after overnight storage of the samples in an oven at 40° C. and 75% relative humidity (post-stability).

FIG. 14A shows the scans of the compound of Formula (I) in each solvent tested after the samples were temperature cycled between room temperature and 40° C. in 4-hour cycles over 24 hours (post-cycling). FIG. 14B shows the scans of the compound of Formula (I) in each solvent tested after overnight storage of the samples in an oven at 40° C. and 75% relative humidity (post-stability).

FIG. 15A shows the scans of the compound of Formula (I) in each solvent tested after the samples were temperature cycled between room temperature and 40° C. in 4-hour cycles over 24 hours (post-cycling). FIG. 15B shows the scans of the compound of Formula (I) in each solvent tested after overnight storage of the samples in an oven at 40° C. and 75% relative humidity (post-stability).

FIG. 16A shows the scans of the compound of Formula (I) in each solvent tested after the samples were temperature cycled between room temperature and 40° C. in 4-hour cycles over 24 hours (post-cycling). FIG. 16B shows the scans of the compound of Formula (I) in each solvent tested after overnight storage of the samples in an oven at 40° C. and 75% relative humidity (post-stability).

FIG. 17A shows the scans of the compound of Formula (I) in each solvent tested after the samples were temperature cycled between room temperature and 40° C. in 4-hour cycles over 24 hours (post-cycling). FIG. 17B shows the scans of the compound of Formula (I) in each solvent tested after overnight storage of the samples in an oven at 40° C. and 75% relative humidity (post-stability).

FIG. 18A shows the scans of the compound of Formula (I) in each solvent tested after the samples were temperature cycled between room temperature and 40° C. in 4-hour cycles over 24 hours (post-cycling). FIG. 18B shows the scans of the compound of Formula (I) in each solvent tested after overnight storage of the samples in an oven at 40° C. and 75% relative humidity (post-stability).

FIG. 19A shows the scans of the compound of Formula (I) in each solvent tested after the samples were temperature cycled between room temperature and 40° C. in 4-hour cycles over 24 hours (post-cycling). FIG. 19B shows the scans of the compound of Formula (I) in each solvent tested after overnight storage of the samples in an oven at 40° C. and 75% relative humidity (post-stability).

FIG. 20A shows the scans of the compound of Formula (I) in each solvent tested after the samples were temperature cycled between room temperature and 40° C. in 4-hour cycles over 24 hours (post-cycling). FIG. 20B shows the scans of the compound of Formula (I) in each solvent tested after overnight storage of the samples in an oven at 40° C. and 75% relative humidity (post-stability).

FIG. 21A shows the scans of the compound of Formula (I) in each solvent tested after the samples were temperature cycled between room temperature and 40° C. in 4-hour cycles over 24 hours (post-cycling). FIG. 21B shows the scans of the compound of Formula (I) in each solvent tested after overnight storage of the samples in an oven at 40° C. and 75% relative humidity (post-stability).

FIG. 22A shows the scans of the compound of Formula (I) in each solvent tested after the samples were temperature cycled between room temperature and 40° C. in 4-hour cycles over 24 hours (post-cycling). FIG. 22B shows the scans of the compound of Formula (I) in each solvent tested after overnight storage of the samples in an oven at 40° C. and 75% relative humidity (post-stability).

FIG. 23A shows the scans of the compound of Formula (I) in each solvent tested after the samples were temperature cycled between room temperature and 40° C. in 4-hour cycles over 24 hours (post-cycling). FIG. 23B shows the scans of the compound of Formula (I) in each solvent tested after overnight storage of the samples in an oven at 40° C. and 75% relative humidity (post-stability).

FIG. 24A shows the scans of the compound of Formula (I) in each solvent tested after the samples were temperature cycled between room temperature and 40° C. in 4-hour cycles over 24 hours (post-cycling). FIG. 24B shows the scans of the compound of Formula (I) in each solvent tested after overnight storage of the samples in an oven at 40° C. and 75% relative humidity (post-stability).

FIG. 25A shows the scans of the compound of Formula (I) in each solvent tested after the samples were temperature cycled between room temperature and 40° C. in 4-hour cycles over 24 hours (post-cycling). FIG. 25B shows the scans of the compound of Formula (I) in each solvent tested after overnight storage of the samples in an oven at 40° C. and 75% relative humidity (post-stability).

FIG. 26A shows the scans of the compound of Formula (I) in each solvent tested after the samples were temperature cycled between room temperature and 40° C. in 4-hour cycles over 24 hours (post-cycling). FIG. 26B shows the scans of the compound of Formula (I) in each solvent tested after overnight storage of the samples in an oven at 40° C. and 75% relative humidity (post-stability).

FIG. 27A shows the scans of the compound of Formula (I) in each solvent tested after the samples were temperature cycled between room temperature and 40° C. in 4-hour cycles over 24 hours (post-cycling). FIG. 27B shows the scans of the compound of Formula (I) in each solvent tested after overnight storage of the samples in an oven at 40° C. and 75% relative humidity (post-stability).

FIG. 28A shows the scans of the compound of Formula (I) in each solvent tested after the samples were temperature cycled between room temperature and 40° C. in 4-hour cycles over 24 hours (post-cycling). FIG. 28B shows the scans of the compound of Formula (I) in each solvent tested after overnight storage of the samples in an oven at 40° C. and 75% relative humidity (post-stability).

FIG. 29A shows the scans of the compound of Formula (I) in each solvent tested after the samples were temperature cycled between room temperature and 40° C. in 4-hour cycles over 24 hours (post-cycling). FIG. 29B shows the scans of the compound of Formula (I) in each solvent tested after overnight storage of the samples in an oven at 40° C. and 75% relative humidity (post-stability).

FIG. 44A is an x-ray powder diffraction scan of the compound of Formula (I). FIG. 44B is a differential scanning calorimetry scan of the compound of Formula (I). FIG. 44C is a thermogravimetric/differential thermal analysis scan of the compound of Formula (I). FIG. 44D is a dynamic vapor sorption isotherm of the compound of Formula (I). FIG. 44E is a kinetic dynamic vapor sorption scan of the compound of Formula (I). FIG. 44F is a $^1$H NMR spectrum of the compound of Formula (I) in $d_6$-DMSO.

DETAILED DESCRIPTION

Definitions

Figure 1A:
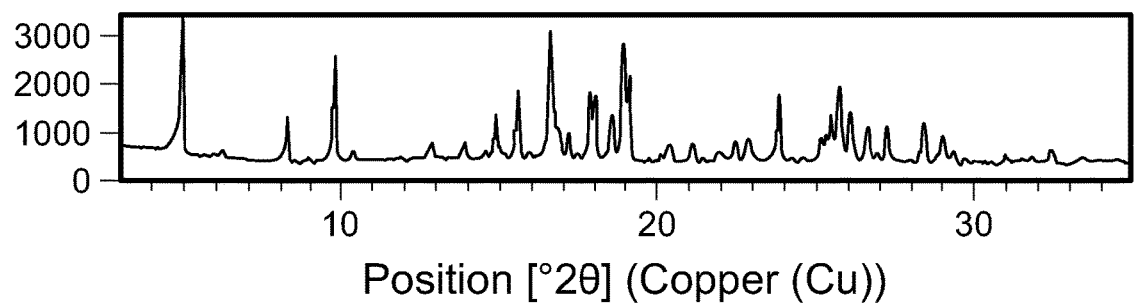
FIGS. 1A-1F are scans of polymorph Form 1 of the compound of Formula (I).
Figure 1B:
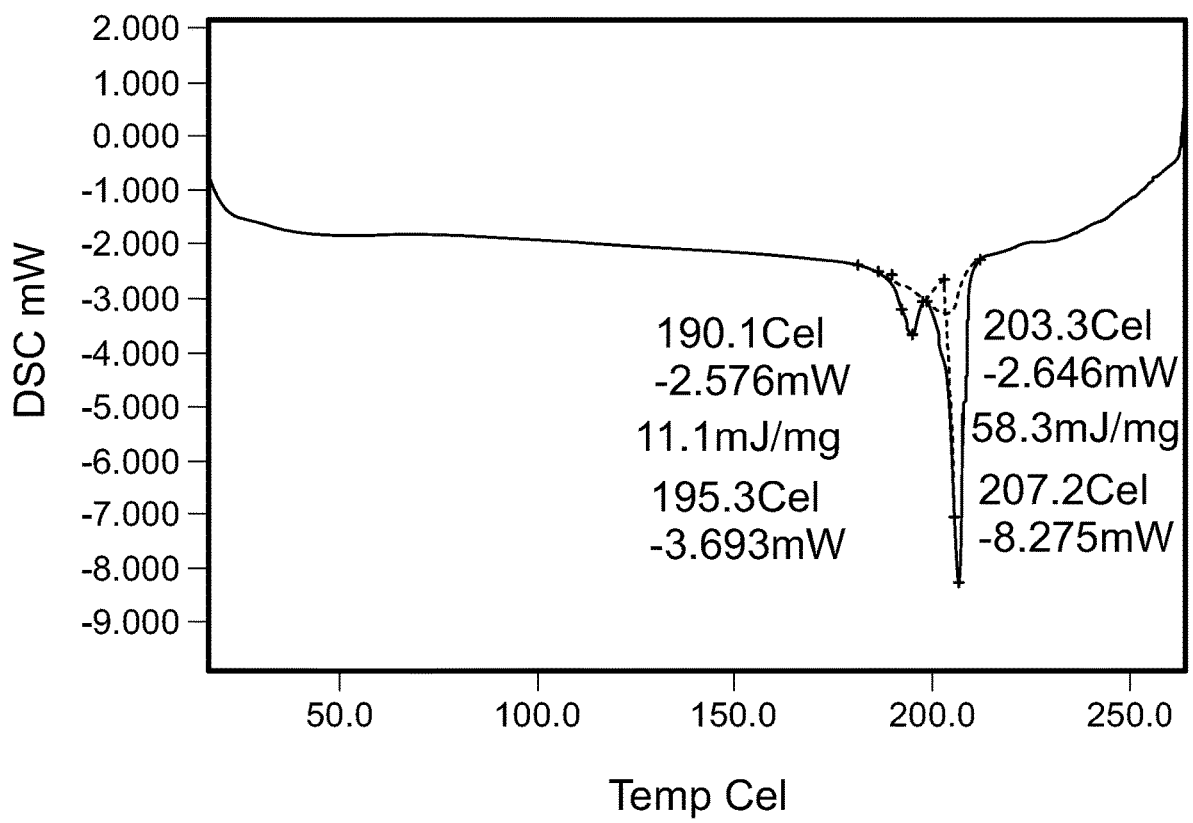
Figure 1C:
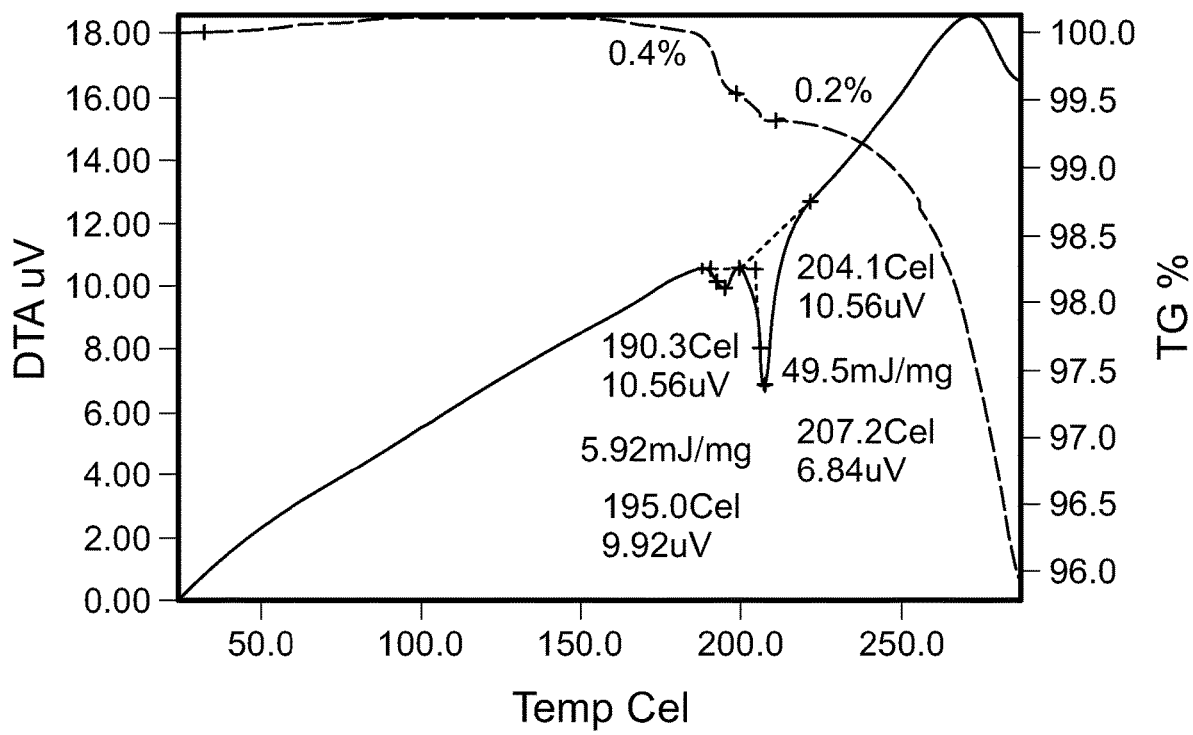
Figure 1D:
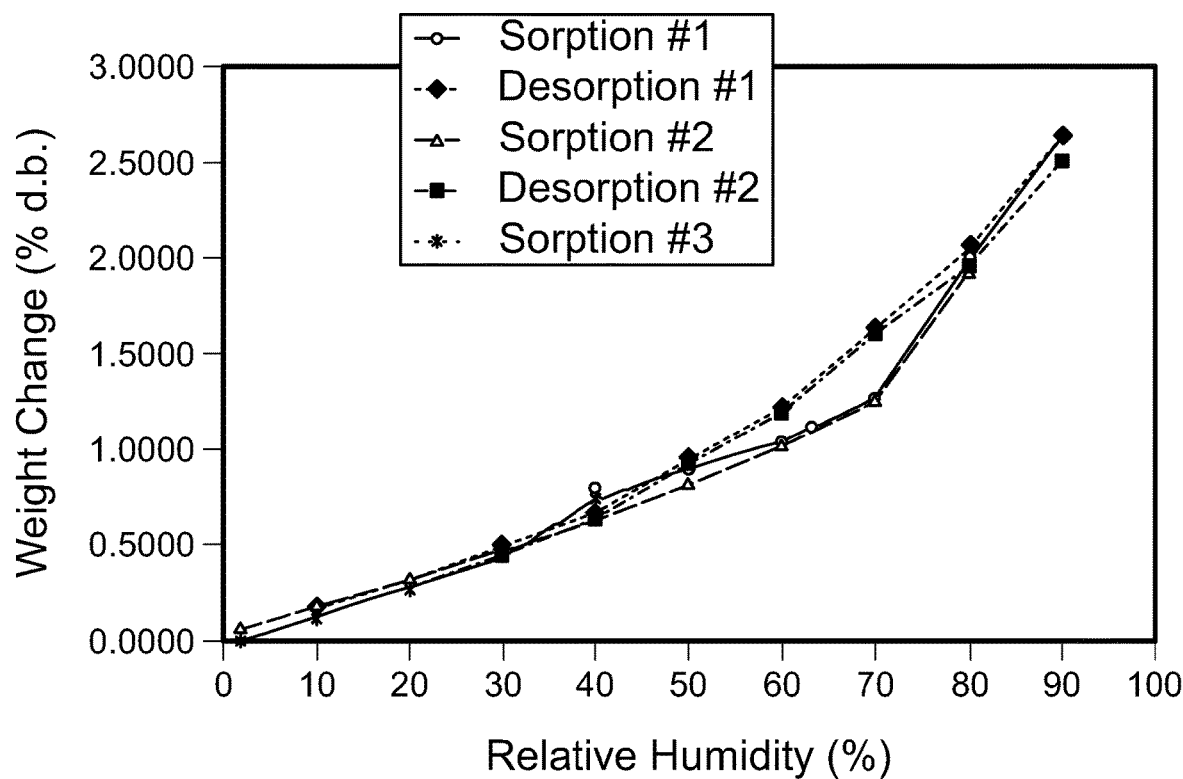
Figure 1E:
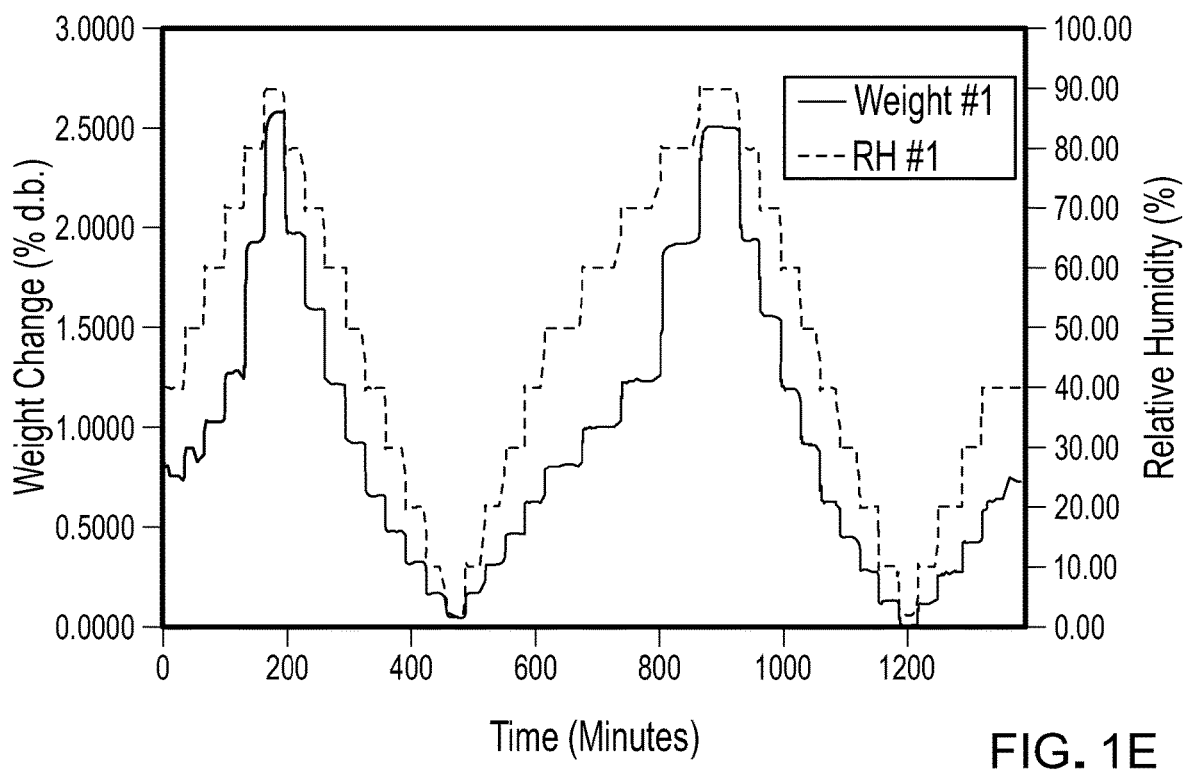

The term "polymorph," as used herein, refers to crystals of the same compound having different physical properties as a result of the order of the molecules in the crystal lattice. Different polymorphs of a single compound have one or more different chemical, physical, mechanical, electrical, thermodynamic, and/or biological properties from each other. Differences in physical properties exhibited by polymorphs can affect pharmaceutical parameters such as storage stability, compressibility, density (important in composition and product manufacturing), dissolution rates (an important factor in determining bio-availability), solubility, melting point, chemical stability, physical stability, powder flowability, water sorption, compaction, and particle morphology. Differences in stability can result from changes in chemical reactivity (e.g., differential oxidation, such that a dosage form discolors more rapidly when comprised of one polymorph than when comprised of another polymorph) or mechanical changes (e.g., crystal changes on storage as a kinetically favored polymorph converts to a thermodynamically more stable polymorph) or both (e.g., one polymorph is more hygroscopic than the other). As a result of solubility/dissolution differences, some transitions affect potency and/or toxicity. In addition, the physical properties of the crystal may be important in processing; for example, one polymorph might be more likely to form solvates or might be difficult to filter and wash free of impurities (i.e., particle shape and size distribution might be different between one polymorph relative to the other). "Polymorph", as used herein, does not include amorphous forms of the compound. As used herein, "amorphous" refers to a noncrystalline form of a compound which can be a solid state form of the compound or a solubilized form of the compound. For example, "amorphous" refers to a compound (e.g., a solid form of the compound) without a regularly repeating arrangement of molecules or external face planes.

The term "anhydrous," as used herein, refers to a crystal form of the compound of Formula (I) that has 1% or less by weight water. For example, 0.5% or less, 0.25% or less, or 0.1% or less by weight water.

The term "solvate" as used herein refers to a crystalline form of the compound of Formula (I), such as a polymorph form of the compound, where the crystal lattice comprises one or more solvents of crystallization.

The terms "hydrate" or "hydrated polymorph form" refer to a crystalline form of the compound of Formula (I), such as a polymorph form of the compound, where the crystal lattice comprises water. Unless specified otherwise, the term "hydrate" as used herein refers to a "stoichiometric hydrate." A stoichiometric hydrate contains the water molecules as an integral part of the crystal lattice, where removal of the water molecules will cause instability of the crystal network. In comparison, a non-stoichiometric hydrate comprises water, but changes in the water content does not cause significant changes to the crystal structure. During drying of non-stoichiometric hydrates, a considerable proportion of water can be removed without significantly disturbing the crystal network, and the crystals can subsequently rehydrate to give the initial non-stoichiometric hydrated crystalline form. Unlike stoichiometric hydrates, the dehydration and rehydration of non-stoichiometric hydrates is not accompanied by a phase transition, and thus all hydration states of a non-stoichiometric hydrate represent the same crystal form.

"Purity," when used in reference to a composition including a polymorph of the compound of Formula (I), refers to the percentage of one specific polymorph form relative to another polymorph form or an amorphous form of the compound of Formula (I) in the referenced composition. For example, a composition comprising polymorph Form 1 having a purity of 90% would comprise 90 weight parts Form 1 and 10 weight parts of other polymorph and/or amorphous forms of the compound of Formula (I).

As used herein, a compound or composition is "substantially free of" one or more other components if the compound or composition contains no significant amount of such other components. For example, the composition can contain less than 5%, 4%, 3%, 2%, or 1% by weight of other components. Such components can include starting materials, residual solvents, or any other impurities that can result from the preparation of and/or isolation of the compounds and compositions provided herein. In some embodiments, a polymorph form provided herein is substantially free of other polymorph forms. In some embodiments, a particular polymorph of the compound of Formula (I) is "substantially free" of other polymorphs if the particular polymorph constitutes at least about 95% by weight of the compound of Formula (I) present. In some embodiments, a particular polymorph of the compound of Formula (I) is "substantially free" of other polymorphs if the particular polymorph constitutes at least about 97%, about 98%, about 99%, or about 99.5% by weight of the compound of Formula (I) present. In certain embodiments, a particular polymorph of the compound of Formula (I) is "substantially free" of water if the amount of water constitutes no more than about 2%, about 1%, or about 0.5% by weight of the polymorph.

As used herein, "substantially pure," when used in reference to a polymorph form of the compound of Formula (I), means a sample of a polymorph form of the compound having a purity greater than 90%, including greater than 90%, 91%, 92%, 93%, 94%, 95%, 96%, 97%, 98%, and 99%, and also including equal to about 100% of the compound, based on the weight of the compound. The remaining material comprises other form(s) of the compound, and/or reaction impurities and/or processing impurities arising from its preparation. For example, a polymorph form of the compound of Formula (I) may be deemed substantially pure in that it has a purity greater than 90% of a polymorph form of the compound of Formula (I), as measured by means that are at this time known and generally accepted in the art, where the remaining less than 10% of material comprises other form(s) of the compound of Formula (I) and/or reaction impurities and/or processing impurities. The presence of reaction impurities and/or processing impurities may be determined by analytical techniques known in the art, such as, for example, chromatography, nuclear magnetic resonance spectroscopy, mass spectrometry, or infrared spectroscopy.

To provide a more concise description, some of the quantitative expressions herein are recited as a range from about amount X to about amount Y. It is understood that when a range is recited, the range is not limited to the recited upper and lower bounds, but rather includes the full range from about amount X through about amount Y, or any range therein.

"Room temperature" or "RT" refers to the ambient temperature of a typical laboratory, which is typically around 25° C.

As used herein, the term "excipient" refers to any substance needed to formulate the composition to a desired form. For example, suitable excipients include but are not limited to, diluents or fillers, binders or granulating agents or adhesives, disintegrants, lubricants, antiadherants, glidants, dispersing or wetting agents, dissolution retardants or enhancers, adsorbents, buffers, chelating agents, preservatives, colors, flavors and sweeteners.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents, and the like, which are not biologically or otherwise undesirable. The use of such media and agents for pharmaceutically active substances is well known in the art. Except insofar as any conventional media or agent is incompatible with the active ingredient, its use in the therapeutic formulations is contemplated. Supplementary active ingredients can also be incorporated into the formulations. In addition, various excipients, such as are commonly used in the art, can be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics*, 12th Ed., The McGraw-Hill Companies.

As used herein, the singular forms "a," "an," and "the" include plural referents unless the context clearly dictates otherwise.

As used herein, ranges and amounts can be expressed as "about" a particular value or range. About also includes the exact amount. Hence, "about 5 grams" means "about 5 grams" and also "5 grams." It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range including, but not limited to, 5.25, 6.5, 8.75 and 11.95 grams. The term "about" preceding a value for DSC, TGA, TG, or DTA, which are reported as degrees Celsius, have an allowable variability of ±5° C.

As used herein, "optional" or "optionally" means that the subsequently described event or circumstance does or does not occur and that the description includes instances where said event or circumstance occurs and instances where it does not. For example, a reaction mixture that "optionally includes a catalyst" means that the reaction mixture contains a catalyst or it does not contain a catalyst.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

All combinations of the embodiments pertaining to the aspects described herein are specifically embraced by the present invention just as if each and every combination was individually explicitly recited, to the extent that such combinations embrace possible aspects. In addition, all sub-combinations of the embodiments contained within the aspects described herein, as well as all sub-combinations of the embodiments contained within all other aspects described herein, are also specifically embraced by the present invention just as if each and every sub-combination of all embodiments are explicitly recited herein.

Solid Formulations

The present disclosure relates to solid formulations of 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile, or a pharmaceutically acceptable salt, amorphous form, or polymorph form thereof, and to the use of the formulations for treating diseases such as proliferative diseases, including cancers.

Provided herein are solid formulations comprising 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I):

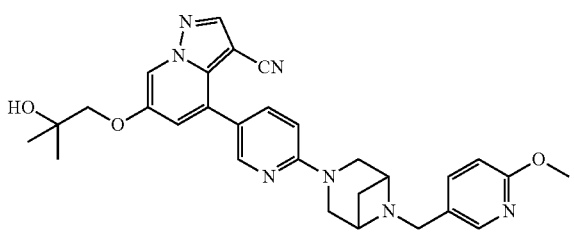

or a pharmaceutically acceptable salt, amorphous form, or polymorph form thereof, and one or more excipients. In some embodiments, the formulations are powder blends. In some embodiments, the powder blends are encapsulated. In some embodiments, the powder blends are encapsulated in a gelatin capsule. In some embodiments, the formulations are spray dried dispersions.

The compound of Formula (I) provided herein can be prepared using methods known and understood by those of ordinary skill in the art. For example, synthetic methods such as those provided and described herein.

In some embodiments, the compound of Formula (I), or a pharmaceutically acceptable salt, amorphous form, or polymorph form thereof, is present in the solid formulation in an amount from about 0.5 wt % to about 50 wt %, such as about 1 wt % to about 50 wt %, about 1 wt % to about 45 wt %, about 1 wt % to about 40 wt %, about 1 wt % to about 35 wt %, about 1 wt % to about 30 wt %, about 1 wt % to about 25 wt %, about 1 wt % to about 20 wt %, about 1 wt % to about 15 wt %, about 1 wt % to about 10 wt %, about 1 wt % to about 5 wt %, about 5 wt % to about 50 wt %, about 5 wt % to about 45 wt %, about 5 wt % to about 40 wt %, about 5 wt % to about 35 wt %, about 5 wt % to about 30 wt %, about 5 wt % to about 25 wt %, about 5 wt % to about 20 wt %, about 5 wt % to about 15 wt %, about 5 wt % to about 10 wt %, about 10 wt % to about 50 wt %, about 10 wt % to about 45 wt %, about 10 wt % to about 40 wt %, about 10 wt % to about 35 wt %, about 10 wt % to about 30 wt %, about 10 wt % to about 25 wt %, about 10 wt % to about 20 wt %, about 10 wt % to about 15 wt %, about 15 wt % to about 50 wt %, about 15 wt % to about 45 wt %, about 15 wt % to about 40 wt %, about 15 wt % to about 35 wt %, about 15 wt % to about 30 wt %, about 15 wt % to about 25 wt %, about 15 wt % to about 20 wt %, about 15 wt % to about 25 wt %, about 15 wt % to about 30 wt %, about 15 wt % to about 35 wt %, about 20 wt % to about 50 wt %, about 20 wt % to about 45 wt %, about 20 wt % to about 40 wt %, about 20 wt % to about 35 wt %, about 20 wt % to about 30 wt %, about 20 wt % to about 25 wt %, about 25 wt % to about 50 wt %, about 25 wt % to about 45 wt %, about 25 wt % to about 40 wt %, about 25 wt % to about 35 wt %, about 25 wt % to about 30 wt %, about 30 wt % to about 50 wt %, about 30 wt % to about 45 wt %, about 30 wt % to about 40 wt %, about 30 wt % to about 35 wt %, about 35 wt % to about 50 wt %, about 35 wt % to about 45 wt %, about 35 wt % to about 40 wt %, about 40 wt % to about 50 wt %, about 40 wt % to about 45 wt %, or about 45 wt % to about 50 wt %. In some embodiments, the compound of Formula (I), or a pharmaceutically acceptable salt, amorphous form, or polymorph form thereof, is present in the solid formulation in an amount of about 0.5 wt %, 1 wt %, 5 wt %, 6.7 wt %, 10 wt %, 15 wt %, 20 wt %, 25 wt %, 30 wt %, 35 wt %, 40 wt %, 45 wt %, or about 50 wt %. In some embodiments, the compound of Formula (I), or a pharmaceutically acceptable salt, amorphous form, or polymorph form thereof, is present in the solid formulation in an amount of about 6.7 wt %. In some embodiments, the compound of Formula (I), or a pharmaceutically acceptable salt, amorphous form, or polymorph form thereof, is present in the solid formulation in an amount of about 20 wt %. In some embodiments, the compound of Formula (I), or a pharmaceutically acceptable salt, amorphous form, or polymorph form thereof, is present in the solid formulation in an amount of about 30 wt %.

The solid formulations provided herein comprise one or more excipients. In some embodiments, the one or more excipients are selected from the group consisting of diluents or fillers, binders, granulating agents, adhesives, polymers and copolymers, disintegrants, stabilizers, lubricants, anti-adherents, glidants, surfactants, dispersing or wetting agents, dissolution retardants or enhancers, adsorbents, buffers, chelating agents, preservatives, colors, flavors, and sweeteners.

In some embodiments, the solid formulations provided herein comprise one or more diluents or fillers. As used herein, the terms "diluent" and "filler" are used interchangeably and are intended to mean an inert substance used as a filler to create the desired bulk, flow properties, and compression characteristics in the preparation of a solid dosage form. Such compounds include, but are not limited to, dibasic calcium phosphate, kaolin, lactose, dextrose, magnesium carbonate, sucrose, mannitol, glucose or other monosaccharaides, dextrin or other polysaccharides, microcrystalline cellulose, powdered cellulose, cellulose derivatives, precipitated calcium carbonate, calcium sulfate, sorbitol, inositol, and starch and other materials known to one of ordinary skill in the art. In some embodiments, the diluent or filler is microcrystalline cellulose. In some embodiments, the diluent or filler is mannitol. In some embodiments, the diluent or filler is a combination of microcrystalline cellulose and mannitol.

In some embodiments, the diluent or filler or combination thereof is present in the solid formulation in an amount from about 1 wt % to about 99 wt %, such as about 1 wt % to about 90 wt %, about 1 wt % to about 80 wt %, about 1 wt % to about 70 wt %, about 1 wt % to about 60 wt %, about 1 wt % to about 50 wt %, about 1 wt % to about 40 wt %, about 1 wt % to about 30 wt %, about 1 wt % to about 20 wt %, about 1 wt % to about 10 wt %, about 1 wt % to about 5 wt %, about 5 wt % to about 99 wt %, about 5 wt % to about 90 wt %, about 5 wt % to about 80 wt %, about 5 wt % to about 70 wt %, about 5 wt % to about 60 wt %, about 5 wt % to about 50 wt %, about 5 wt % to about 40 wt %, about 5 wt % to about 30 wt %, about 5 wt % to about 20 wt %, about 5 wt % to about 10 wt %, about 10 wt % to about 99 wt %, about 10 wt % to about 90 wt %, about 10 wt % to about 80 wt %, about 10 wt % to about 70 wt %, about 10 wt % to about 60 wt %, about 10 wt % to about 50 wt %, about 10 wt % to about 40 wt %, about 10 wt % to about 30 wt %, about 10 wt % to about 20 wt %, about 20 wt % to about 99 wt %, about 20 wt % to about 90 wt %, about 20 wt % to about 80 wt %, about 20 wt % to about 70 wt %, about 20 wt % to about 60 wt %, about 20 wt % to about 50 wt %, about 20 wt % to about 40 wt %, about 20 wt % to about 30 wt %, about 30 wt % to about 99 wt %, about 30 wt % to about 90 wt %, about 30 wt % to about 80 wt %, about 30 wt % to about 70 wt %, about 30 wt % to about 60 wt %, about 30 wt % to about 50 wt %, about 30 wt % to about 40 wt %, about 40 wt % to about 99 wt %, about 40 wt % to about 90 wt %, about 40 wt % to about 80 wt %, about 40 wt % to about 70 wt %, about 40 wt % to about 60 wt %, about 40 wt % to about 50 wt %, about 50 wt % to about 99 wt %, about 50 wt % to about 90 wt %, about 50 wt % to about 80 wt %, about 50 wt % to about 70 wt %, about 50 wt % to about 60 wt %, about 60 wt % to about 99 wt %, about 60 wt % to about 90 wt %, about 60 wt % to about 80 wt %, about 60 wt % to about 70 wt %, about 65 wt % to about 99 wt %, about 65 wt % to about 90 wt %, about 65 wt % to about 85 wt %, about 65 wt % to about 80 wt %, about 65 wt % to about 75 wt %, about 65 wt % to about 70 wt %, about 70 wt % to about 99 wt %, about 70 wt % to about 90 wt %, about 70 wt % to about 80 wt %, about 80 wt % to about 99 wt %, about 80 wt % to about 90 wt %, or about 90 wt % to about 99 wt %. In some embodiments, the diluent or filler or combination thereof is present in the solid formulation in an amount of about 1 wt %, 5 wt %, 10 wt %, 20 wt %, 30 wt %, 40 wt %, 50 wt %, 60 wt %, 69 wt %, 70 wt %, 79 wt %, 80 wt %, 90 wt %, or about 99 wt %. In some embodiments, the diluent or filler or combination thereof is present in the solid formulation in an amount of about 69 wt %. In some embodiments, the diluent or filler or combination thereof is present in the solid formulation in an amount of about 72 wt %. In some embodiments, the diluent or filler or combination thereof is present in the solid formulation in an amount of about 79 wt %.

In some embodiments, the solid formulations comprise one or more disintegrants. As used herein, the term "disintegrant" is intended to mean a compound used in solid dosage forms to promote the disruption of the solid mass into smaller particles which are more readily dispersed or dissolved. Exemplary disintegrants include, but are not limited to, starches such as corn starch, potato starch, tapioca starch, pre-gelatinized and modified starches thereof, sodium carboxymethyl starch (sodium starch glycolate), pregelatinized starch (starch 1500), microcrystalline starch, water insoluble starch, sodium starch glycolate, calcium carbonate, sodium carbonate, sodium bicarbonate, cellulose and cellulose derivatives, such as calcium carboxymethyl cellulose, microcrystalline cellulose, carboxymethylcellulose calcium, croscarmellose sodium, croscarmellose calcium, carmellose calcium, cellulose polacrilin potassium, magnesium aluminum silicate (Veegum), sweeteners, clays, bentonite, alginic acid, sodium alginate, alginates, gums, agar, guar, locust bean, karaya, pectin, tragacanth, citrus pulp, crospovidone and other materials known to one of ordinary skill in the art. In some embodiments, the disintegrant is a cellulose derivative. In some embodiments, the cellulose derivative is croscarmellose sodium.

In some embodiments, the solid formulations comprise one or more lubricants or lubricating agents. As used herein, "lubricant" or "lubricating agent" means a substance used in solid dosage formulations to reduce friction during compression. Exemplary lubricants include, but are not limited to, a stearate, such as zinc stearate, sodium stearate, calcium stearate, magnesium stearate, stearic acid, talc, mineral oil, a silica, malt, glyceryl behenate, hydrogenated vegetable oils, polyethylene glycol, sodium benzoate, sodium acetate, sodium chloride, leucine, magnesium lauryl sulfate, and sodium lauryl sulfate. In some embodiments, the lubricant is a stearate. In some embodiments, the lubricant is magnesium stearate.

In some embodiments, the solid formulation includes a lubricant in an amount of about 0.1 wt % to about 5 wt %; about 0.1 wt % to about 3 wt %; about 0.1 wt % to about 1 wt %; or about 0.1 wt % to about 0.5 wt %. In some embodiments, the solid formulation includes a lubricant in an amount of about 0.1 wt %; about 0.2 wt %; about 0.3 wt %; about 0.4 wt %; about 0.5 wt %; about 0.6 wt %; about 0.7 wt %; about 0.8 wt %; about 0.9 wt %; or about 1 wt %.

In some embodiments, the solid formulations comprise one or more glidants. As used herein, the term "glidant" is intended to mean an agent used in solid dosage formulations to promote flowability of the solid mass. Such compounds include, but are not limited to, colloidal silica, colloidal silicon dioxide, fumed silica, cornstarch, talc, calcium silicate, magnesium silicate, tribasic calcium phosphate, silicon hydrogel and other materials known to one of ordinary skill in the art. In some embodiments, the glidant is silicon dioxide. In some embodiments, the glidant is fumed silica.

In some embodiments, the solid formulation includes a glidant in an amount of about 0.1 wt % to about 5 wt %; about 0.1 wt % to about 3 wt %; about 0.1 wt % to about 1 wt %; or about 0.1 wt % to about 0.5 wt %. In some embodiments, the solid formulation includes a glidant in an amount of about 0.1 wt %; about 0.2 wt %; about 0.3 wt %; about 0.4 wt %; about 0.5 wt %; about 0.6 wt %; about 0.7 wt %; about 0.8 wt %; about 0.9 wt %; or about 1 wt %.

In some embodiments, the solid formulation includes one or more dispersing agents. Examples of dispersing agents include, but are not limited to, hydrophilic polymers, electrolytes, Tween® 60 or 80, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropyl methylcellulose acetate succinate (HPMC-AS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamines and poloxamers (also denoted polyoxypropylene-polyoxyethylene block copolymers), including poloxamer 188, poloxamer 237, poloxamer 338, poloxamer 407, or other block copolymers of ethylene oxide and propylene oxide, polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol (PEG), e.g., the polyethylene glycol has a molecular weight of about 300 to about 6000, or about 3350 to about 4000, or about 7000 to about 5400, polysorbate-80, sodium alginate, gums, such as, e.g., gum tragacanth and gum acacia, guar gum, xanthans, including xanthan gum, sugars, cellulosics, polysorbate-80, sodium alginate, polyethoxylated sorbitan monolaurate, povidone, carbomers, alginates, chitosans and combinations thereof. Plasticizers such as cellulose or triethyl cellulose can also be used as dispersing agents.

In some embodiments, the dispersing agent is hydroxypropyl methylcellulose acetate succinate (HPMC-AS). In some embodiments, the dispersing agent is a poloxamer. In some embodiments, the dispersing agent is poloxamer 188, which has an average molecular weight of about 8400 and a melting point of about 50-54° C. In some embodiments, the dispersing agent is a combination of HPMC-AS and poloxamer 188.

In some embodiments, the solid formulation includes one or more dispersing agents in an amount of about 0.1 wt % to about 5 wt %; about 0.1 wt % to about 3 wt %; about 0.1 wt % to about 1 wt %; or about 0.1 wt % to about 0.5 wt %. In some embodiments, the solid formulation includes one or more dispersing agents in an amount of about 0.1 wt %; about 0.2 wt %; about 0.3 wt %; about 0.4 wt %; about 0.5 wt %; about 0.6 wt %; about 0.7 wt %; about 0.8 wt %; about 0.9 wt %; or about 1 wt %.

In some embodiments, a surfactant is included in the solid formulation. Surfactants include both non-ionic and ionic (cationic, anionic and zwitterionic) surfactants suitable for use in pharmaceutical dosage forms. These include, for example, polyethoxylated fatty acids and their derivatives, such as polyethylene glycol 400 distearate, polyethylene glycol-20 dioleate, polyethylene glycol 4-150 mono dilaurate, and polyethylene glycol-20 glyceryl stearate; alcohol-oil transesterification products, for example, polyethylene glycol-6 corn oil; polyglycerized fatty acids, for example, polyglyceryl-6 pentaoleate; propylene glycol fatty acid esters, for example, propylene glycol monocaprylate; mono and diglycerides, for example, glyceryl ricinoleate; sterol and sterol derivatives; sorbitan fatty acid esters and its derivatives, for example, polyethylene glycol-20 sorbitan monooleate and sorbitan monolaurate; polyethylene glycol alkyl ether or phenols, for example, polyethylene glycol-20 cetyl ether and polyethylene glycol-10-100 nonyl phenol; sugar esters, for example, sucrose monopalmitate; polyoxyethylene-polyoxypropylene block copolymers known as poloxamer; ionic surfactants, for example sodium caproate, sodium glycocholate, soy lecithin, sodium stearyl fumarate, propylene glycol alginate, octyl sulfosuccinate disodium, and palmitoyl carnitine.

In some embodiments, the solid formulation includes a binder. Suitable examples of binders include, but are not limited to, acacia, sodium alginate, starch, gelatin, saccharides (including glucose, sucrose, dextrose and lactose), molasses, extract of Irish moss, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone such as PVP K90, or mixtures thereof.

Provided herein is a solid formulation including 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I):

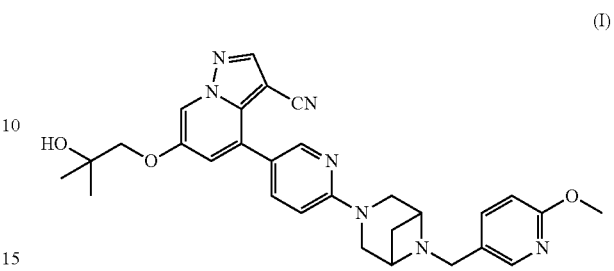

or a pharmaceutically acceptable salt, amorphous form, or polymorph form thereof, a diluent or filler, and a glidant. In some embodiments, the compound of Formula (I) is present in the solid formulation in an amount from about 5 wt % to about 35 wt %. In some embodiments, the compound of Formula (I) is present in the solid formulation in an amount of about 20 wt %. In some embodiments, the compound of Formula (I) is present in the solid formulation in an amount of about 30 wt %.

In some embodiments, the diluent or filler includes microcrystalline cellulose.

In some embodiments, the glidant includes fumed silica.

In some embodiments, the solid formulation is a powder. In some embodiments, the powder is encapsulated. In some embodiments, the powder is encapsulated in a gelatin capsule. In some embodiments, the gelatin capsule is a hard gelatin capsule.

Provided herein is a solid formulation including 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I):

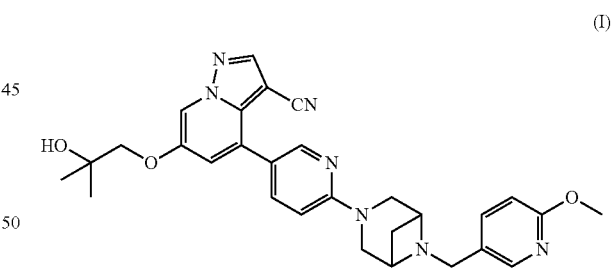

or a pharmaceutically acceptable salt, amorphous form, or polymorph form thereof, a diluent or filler, and a glidant. In some embodiments, the compound of Formula (I) is present in the solid formulation in an amount from about 5 wt % to about 35 wt %. In some embodiments, the compound of Formula (I) is present in the solid formulation in an amount of about 20 wt %. In some embodiments, the diluent or filler is present in the solid formulation in an amount from about 70 wt % to about 90 wt %. In some embodiments, the diluent or filler is present in the solid formulation in an amount of about 79%. In some embodiments, the glidant is present in the solid formulation in an amount from about 0.5 wt % to about 1.5 wt %. In some embodiments, the glidant is present in the solid formulation in an amount of about 1%.

In some embodiments, the diluent or filler includes microcrystalline cellulose.

In some embodiments, the glidant includes fumed silica.

In some embodiments, the solid formulation is a powder. In some embodiments, the powder is encapsulated. In some embodiments, the powder is encapsulated in a gelatin capsule. In some embodiments, the gelatin capsule is a hard gelatin capsule.

Provided herein is a solid formulation including 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I):

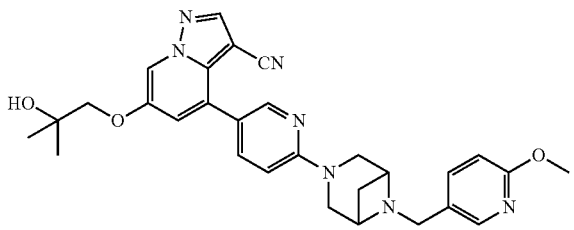

(I)

or a pharmaceutically acceptable salt, amorphous form, or polymorph form thereof, a diluent or filler, and a glidant. In some embodiments, the compound of Formula (I) is present in the solid formulation in an amount from about 5 wt % to about 35 wt %. In some embodiments, the compound of Formula (I) is present in the solid formulation in an amount of about 30 wt %. In some embodiments, the diluent or filler is present in the solid formulation in an amount from about 60 wt % to about 90 wt %. In some embodiments, the diluent or filler is present in the solid formulation in an amount of about 69%. In some embodiments, the glidant is present in the solid formulation in an amount from about 0.5 wt % to about 1.5 wt %. In some embodiments, the glidant is present in the solid formulation in an amount of about 1%.

In some embodiments, the diluent or filler includes microcrystalline cellulose.

In some embodiments, the glidant includes fumed silica.

In some embodiments, the solid formulation is a powder. In some embodiments, the powder is encapsulated. In some embodiments, the powder is encapsulated in a gelatin capsule. In some embodiments, the gelatin capsule is a hard gelatin capsule.

Provided herein is a solid formulation including 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile having the Formula (I):

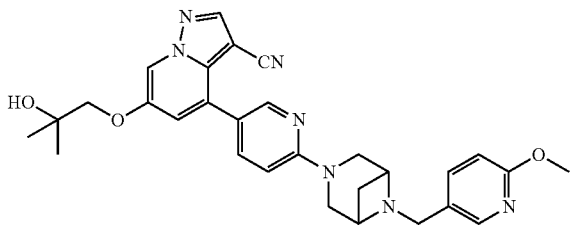

(I)

or a pharmaceutically acceptable salt, amorphous form, or polymorph form thereof, a diluent or filler, a dispersing agent, a disintegrant, and a binder. In some embodiments, the compound of Formula (I) is present in the solid formulation in an amount from about 5 wt % to about 35 wt %. In some embodiments, the compound of Formula (I) is present in the solid formulation in an amount of about 5 wt % to about 15 wt %. In some embodiments, the compound of Formula (I) is present in the solid formulation in an amount of about 6.7 wt %.

In some embodiments, the diluent or filler includes microcrystalline cellulose and mannitol.

In some embodiments, the dispersing agent includes hydroxypropyl methylcellulose acetate succinate (HPMC-AS) and a poloxamer. In some embodiments, the poloxamer is poloxamer 188.

In some embodiments, the disintegrant includes a cellulose derivative. In some embodiments, the disintegrant includes croscarmellose sodium.

In some embodiments, the binder includes magnesium stearate.

In some embodiments, the solid formulation is a spray dried dispersion.

In some embodiments, the solid formulation including the compound of Formula (I) or a pharmaceutically acceptable salt, amorphous form, or polymorph form thereof, and one or more excipients is selected from the group consisting of a tablet, capsule, sachet, powder, granules, coated particle, coated tablet, enterocoated tablet, enterocoated capsule, melting strip, and melting film. In some embodiments, the solid formulation is a powder. In some embodiments, the powder is spray dried. In some embodiments, the powder is encapsulated.

In some embodiments, solid dosage forms, e.g., tablets, effervescent tablets, and capsules, are prepared by mixing the compound of Formula (I) with one or more pharmaceutical excipients to form a bulk blend composition. When referring to these bulk blend compositions as homogeneous, it is meant that the particles of the compound of Formula (I) are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., "*The Theory and Practice of Industrial Pharmacy*" (1986). Other methods include, e.g., spray drying, pan coating, melt granulation, granulation, fluidized bed spray drying or coating (e.g., wurster coating), tangential coating, top spraying, tableting, extruding and the like.

In some embodiments, the solid formulation including the compound of Formula (I) or a pharmaceutically acceptable salt, amorphous form, or polymorph form thereof, and one or more excipients is a powder. Methods of producing powders are well known to one of skill in the art. Exemplary processes for producing powders include, but are not limited to, spray drying, freeze drying, evaporation, lyophilization, or absorption plating.

In some embodiments, the methods for forming the powders include spray drying. Spray drying processes and spray drying equipment are described generally in Perry's Chemical Engineers' Handbook, pp. 20-57 (Sixth Edition 1984).

More details on spray drying processes and equipment are reviewed by Marshall (1954) "Atomization and Spray-Drying," *Chem. Eng. Prog. Monogr.* 50:Series 2 and Masters, "*Spray Drying Handbook*" (Fourth Edition 1985). Methods for spray drying are well known (see, e.g. U.S. Pat. Nos. 5,430,021 and 6,534,085 and U.S. Publication No. US 2007/0184117). In general, spray drying is used to dry a heated liquid by passing it through hot gas. One or more spray nozzles is used to atomize the liquid in a cooling tower or chamber. As the material is atomized (sprayed), the surface tension causes a uniform spherical particle to form, which is passed through the cooling chamber and hardens into a solid intact sphere. The spray dried particles can be between about 0.5 microns and about 100 microns, and typically are less than about 10 microns, typically less than about 5 microns, and typically less than about 1 micron.

In some embodiments, the solid formulations disclosed herein are in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In some embodiments, the solid formulation is in the form of a powder. In still other embodiments, the solid formulation is in the form of a capsule, including but not limited to, a hard capsule. Additionally, the solid formulations described herein can be administered as a single capsule or in multiple capsule dosage form. In some embodiments, the solid formulation is administered in two, or three, or four, capsules or tablets.

The pharmaceutical solid dosage forms described herein include the compound of Formula (I) and one or more pharmaceutically acceptable excipients, including, but not limited to a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or combinations thereof. In some embodiments, using standard coating procedures, such as those described in *Remington's Pharmaceutical Sciences*, 20th Edition (2000), a film coating is provided around the solid formulation, e.g., powder, that includes the compound of Formula (I), or a pharmaceutically acceptable salt, amorphous form, or polymorph form thereof, and one or more excipients. In some embodiments, the powder is encapsulated.

In some embodiments, a capsule is prepared by placing the bulk blend of the solid formulation inside of a capsule. In some embodiments, the solid formulation is placed in a soft gelatin capsule. In some embodiments, the formulation is placed in a hard gelatin capsule. In some embodiments, the solid formulation is placed in standard gelatin capsules or non-gelatin capsules such as capsules comprising HPMC. In some embodiments, the solid formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

The capsule can be any shape or size. The shape and size of the capsule can vary in accordance with the method of preparation and the planned use of the capsule. Hard shell capsule sizes are designated by convention as (000), (00), (0), (1), (2), (3), (4), and (5), with a larger number corresponding to a smaller size. For example, one teaspoon can fill approximately seven size "0" capsules and about five size "00" capsules. Size "00" capsules are generally the largest size utilized for human consumption. Soft gel capsule sizes range from 1 to 120, with the particular size depending on the desired shape and other characteristics of the product. Typically, shapes include, but are not limited to, round, oval, oblong, tube, and special shapes, for example, animals, stars, hearts, or squares. For example, capsules can be oval-shaped and be size 2, 3, 4, 5, 6, 7, 7.5, 8.5, 10, 12, 16, 20, 30, 40, 60, 65, 80, or more. Capsules can be, for example, oblong-shaped and be size 3, 4, 5, 6, 8, 9.5, 11, 12, 14, 16, 20, 22, 24, or more. Other exemplary capsules include round capsules, for example, size 1, 2, 3, 4, 5, 6, 7, 9, 15, 20, 28, 40, 90, or more, and tube capsules, for example, size 5, 6, 8, 17.5, 30, 45, 55, or 120. Capsules can be any color and have any amount of transparency, for example, the capsules can be, but are not limited to, opaque, translucent, or pearlescent capsules. In some embodiments, the solid formulation is filled into a hard gelatin capsule. In some embodiments, the capsule is a two-piece hard gelatin capsule. In some embodiments, the capsule is sealed. In some embodiments, the capsule is unsealed.

In some embodiments, the solid formulation including the compound of Formula (I), or a pharmaceutically acceptable salt, amorphous form, or polymorph form thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In some embodiments, the solid formulation including the compound of Formula (I), or a pharmaceutically acceptable salt, amorphous form, or polymorph form thereof, can be administered by a variety of routes, depending upon the treatment desired and upon the area to be treated. In some embodiments, administration is oral. Oral administration can include a dosage form formulated for once-daily or twice-daily (BID) administration.

The compositions comprising the compound of Formula (I) or a pharmaceutically acceptable salt, amorphous form, or polymorph form thereof can be formulated in a unit dosage form, each dosage containing from about 1 to about 1,000 mg (1 g), more usually about 5 mg to about 100 mg, of the active ingredient. The term "unit dosage form" refers to physically discrete units suitable as unitary dosages for human subjects and other patients, each unit containing a predetermined quantity of active material (i.e., the compound of Formula (I) or a pharmaceutically acceptable salt, amorphous form, or polymorph form thereof) calculated to produce the desired therapeutic effect, in association with a suitable pharmaceutical excipient.

In some embodiments, the solid formulation is formulated as a 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg dosage form. In some embodiments, the solid formulation is formulated as a 10 mg, 20 mg, or 80 mg dosage form.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient. In some embodiments, the compositions provided herein contain about 10 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The daily dosage of the compound of Formula (I) or a pharmaceutically acceptable salt, amorphous form, or polymorph form thereof can be varied over a wide range from 1.0 to 10,000 mg per adult human per day, or higher, or any range therein. In some embodiments, for oral administration, the compositions can be provided in the form of tablets containing about 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.1 mg/kg to about 1000 mg/kg of body weight per day, or any range therein. In some embodiments, the range is from about 0.5 to about 500 mg/kg of body weight per day, or any range therein. In some embodiments, from about 1.0 to about 250 mg/kg of body weight per day, or any range therein. In some embodiments, from about 0.1 to about 100 mg/kg of body weight per day, or any range therein. In some embodiments, the range is from about 0.1 to about 50.0 mg/kg of body weight per day, or any amount or range therein. In some embodiments, the range is from about 0.1 to about 15.0 mg/kg of body weight per day, or any range therein. In some embodiments, the range is from about 0.5 to about 7.5 mg/kg of body weight per day, or any amount or range therein. Pharmaceutical compositions containing the compound of Formula (I) or a pharmaceutically acceptable salt, amorphous form, or polymorph form thereof can be administered on a regimen of 1 to 4 times per day or in a single daily dose.

The active compound may be effective over a wide dosage range and is generally administered in a pharmaceutically effective amount. Optimal dosages to be administered can be readily determined by those skilled in the art. It will be understood, therefore, that the amount of the compound actually administered will usually be determined by a physician, and will vary according to the relevant circumstances, including the mode of administration, the actual compound administered, the strength of the preparation, the condition to be treated, and the advancement of the disease condition. In addition, factors associated with the particular patient being treated, including; patient response, age, weight, diet, time of administration and severity of the patient's symptoms, will result in the need to adjust dosages.

Polymorph Forms of the Compound of Formula (I)

In some embodiments, the solid formulation includes a polymorph form of the compound of Formula (I). The forms include, e.g., free bases, solvates, hydrates, salts, and nonsolvated forms of the compound of Formula (I), including, for example, polymorph Forms 1, 2, 7, and 8. In some embodiments, the polymorph form of the compound of Formula (I) is a pharmaceutically acceptable salt. In some embodiments, the compound of Formula (I) is a phosphate salt.

Form 1

One such polymorph is a polymorph known as Form 1. Form 1 is an anhydrous polymorph of the compound of Formula (I). In some embodiments, Form 1 has an X-ray powder diffraction (XRPD or XRD) pattern, obtained with CuKα1-radiation, with at least peaks at °2θ values of 16.5±0.2, 18.9±0.2, and 26.0±0.2. In some embodiments, Form 1 has an XRPD pattern with at least peaks at °2θ values of 16.5±0.2, 18.9±0.2, 23.8±0.2, 25.3±0.2, and 26.0±0.2. In some embodiments, Form 1 has an XRPD pattern with at least peaks at °2θ values of 16.5±0.2, 17.8±0.2, 18.9±0.2, 23.8±0.2, 25.3±0.2, 25.6±0.2, 26.0±0.2, and 28.3±0.2. For example, in some embodiments, Form 1 has an XRPD pattern with at least peaks at °2θ values of 9.8±0.2, 16.5±0.2, 17.8±0.2, 18.9±0.2, 23.8±0.2, 25.0±0.2, 25.3±0.2, 25.6±0.2, 26.0±0.2, and 28.3±0.2.

In some embodiments, provided herein is a composition comprising polymorph Form 1. In some embodiments, the composition can be substantially pure. For example, the composition has a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than about 15% by weight of other forms of the compound of Formula (I). For example, the composition can contain less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 2, Form 7, Form 8, or a combination of two or more thereof.

In some embodiments, provided herein is polymorph Form 1 that exhibits an endotherm that is observed between about 185-200° C., e.g., around 195° C., as measured by differential scanning calorimetry (DSC) related to sorbed water. In some embodiments, polymorph Form 1 exhibits an endothermic event that is observed between about 200-210° C., e.g., around 207° C. In some embodiments, the endotherms are observed when using a scan rate of 10° C. per minute.

In some embodiments, provided herein is polymorph Form 1 that exhibits an endothermic event observed at an onset of around 190° C., as measured by thermogravimetric/differential thermal analysis (TG/DTA). In some embodiments, polymorph Form 1 undergoes a mass loss of about 0.4% before around 200° C., e.g., from about 190° C. to about 200° C. In some embodiments, polymorph Form 1 exhibits an endothermic event from an onset of around 204° C. In some embodiments, the endothermic event is accompanied by a corresponding weight loss of about 0.2%.

Provided herein are methods of preparing polymorph Form 1. In some embodiments, the method comprises slurrying a composition comprising the compound of Formula (I) in a solvent selected from the group consisting of 1,4-dioxane, 1-butanol, 1-propanol, acetone, anisole, chloroform, cyclohexane, cyclohexanone, dichloromethane, DMSO, ethanol, ethyl acetate, isopropyl alcohol, methyl ethyl ketone, methyl acetate, 2-ethoxyethanol, 2-methyl THF, methyl isobutyl ketone (MIBK), nitromethane, and THF to generate polymorph Form 1 as a residual solid. In some embodiments, the solvent is ethyl acetate. In some embodiments, the solvent is in a mixture with water, for example the solvent can be a mixture of water and acetone or water and acetonitrile. In some embodiments, the water is present in an amount of about 20% by weight. In some embodiments, the water is present in an amount of about 50% by weight. In some embodiments, the slurry is temperature cycled between around 40° C. and RT. In some embodiments, the temperature cycling occurs between about 60 hours and 84 hours, such as, e.g., around 72 hours. In some embodiments, the method further comprises collecting the residual solid. In some embodiments, the residual solid is collected by filtration. In some embodiments, the method further comprises drying the residual solid, for example, under vacuum. In some embodiments, the drying is at a temperature of between about 30° C. and 50° C., such as, e.g., around 40° C.

In some embodiments, a method of preparing a polymorph of Form 1 is provided. The method comprises providing a composition comprising the compound of Formula (I) in a solvent. In some embodiments, polymorph Form 1 can be prepared by evaporating the solvent from the composition comprising the compound of Formula (I) to generate polymorph Form 1 as a residual solid, where the solvent is selected from the group consisting of dichloromethane, DMSO, methyl acetate, 2-ethoxyethanol, nitromethane, and a mixture of acetonitrile and water (20%). In some embodiments, the method comprises evaporating the solvent from a composition comprising the compound of Formula (I) to generate a mixture of polymorph Form 1 and another polymorph form as a residual solid, where the solvent is selected from the group consisting of acetone, chloroform, and THF. In some embodiments, the residual solid is a mixture of Form 1 and Form 8.

In some embodiments, polymorph Form 1 can be prepared by cooling a solution comprising the compound of Formula (I) in acetone to a temperature of about 5° C. to precipitate polymorph Form 1 as a residual solid. In some embodiments, the residual solid is a mixture of Form 1 and Form 8.

In some embodiments, polymorph Form 1 can be prepared by recrystallizing a composition comprising the compound of Formula (I) to generate polymorph Form 1, where the recrystallizing solvent is selected from the group consisting of a mixture of DMSO and water and a mixture of dichloromethane and heptane.

Form 2

Also provided herein is a polymorph known as Form 2. Form 2 is a hydrated polymorph form of the compound of Formula (I). In some embodiments, Form 2 has an XRPD pattern, obtained with CuKα1-radiation, with at least peaks at °2θ values of 15.1±0.2, 17.8±0.2, and 24.2±0.2. In some embodiments, Form 2 has an XRPD pattern with at least peaks at °2θ values of 15.1±0.2, 17.8±0.2, 20.4±0.2, 21.1±0.2, and 24.2±0.2. In some embodiments, Form 2 has an XRPD pattern with at least peaks at °2θ values of 15.1±0.2, 17.8±0.2, 18.1±0.2, 20.4±0.2, 21.1±0.2, 23.4±0.2, 24.2±0.2, and 24.6±0.2. For example, in some embodiments, Form 2 has an XRPD pattern with at least peaks at °2θ values of 6.2±0.2, 15.1±0.2, 17.8±0.2, 18.1±0.2, 20.4±0.2, 21.1±0.2, 23.4±0.2, 24.2±0.2, 24.6±0.2, and 31.2±0.2.

In some embodiments, provided herein is a composition comprising polymorph Form 2. In some embodiments, the composition can be substantially pure. For example, the composition has a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). In some embodiments, the composition contains less than about 15% by weight of other forms of the compound of Formula (I). For example, the composition can contain less than 14%, 13%, 12%, 11%, 10%, 9%, 8%, 7%, 6%, 5%, 4%, 3%, 2%, 1% by weight of one or more other forms of the compound of Formula (I). For example, the composition can contain less than about 15% of Form 1, Form 7, Form 8, or a combination of two or more thereof.

In some embodiments, provided herein is polymorph Form 2 that exhibits an endotherm that is observed between about 190-200° C., e.g., around 197.5° C., as measured by DSC related to sorbed water. In some embodiments, polymorph Form 2 exhibits an endothermic event that is observed between about 200-210° C., e.g., around 207.5° C. In some embodiments, the endotherms are observed when using a scan rate of 10° C. per minute.

In some embodiments, provided herein is polymorph Form 2 that exhibits a weight loss of about 0.7% from the onset of heating to about 165° C., as measured by TG/DTA. In some embodiment, polymorph Form 2 exhibits an endothermic event observed at an onset of around 194° C. In some embodiments, polymorph Form 2 undergoes a mass loss of about 0.2% before around 200° C., e.g., from about 194° C. to about 200° C. In some embodiments, polymorph Form 2 exhibits an endothermic event from an onset of around 205° C.

Provided herein are methods of preparing polymorph Form 2. In some embodiments, the method comprises slurrying a composition comprising the compound of Formula (I) in a mixture of ethanol and water to generate polymorph Form 2 as a residual solid. In some embodiments, the water is present in an amount of about 10% by weight. In some embodiments, the slurry is temperature cycled between around 40° C. and RT. In some embodiments, the temperature cycling occurs between about 60 hours and 84 hours, such as, e.g., around 72 hours. In some embodiments, the method further comprises collecting the residual solid. In some embodiments, the residual solid is collected by filtration. In some embodiments, the residual solid is dried. In some embodiments, the residual solid is dried on the filter bed.

Form 7

Provided herein is a polymorph known as Form 7. Form 7 is a hydrated polymorph form of the compound of Formula (I). In some embodiments, Form 7 has an XRPD pattern, obtained with CuKα1-radiation, with at least peaks at °2θ values of 16.6±0.2, 18.0±0.2, and 19.9±0.2. In some embodiments, Form 7 has an XRPD pattern with at least peaks at °2θ values of 16.6±0.2, 18.0±0.2, 19.3±0.2, 19.9±0.2, and 23.3±0.2. In some embodiments, Form 7 has an XRPD pattern with at least peaks at °2θ values of 16.6±0.2, 17.3±0.2, 18.0±0.2, 19.0±0.2, 19.3±0.2, 19.9±0.2, 23.3±0.2, and 25.1±0.2. For example, in some embodiments, Form 7 has an XRPD pattern with at least peaks at °2θ values of 15.8±0.2, 16.6±0.2, 17.3±0.2, 18.0±0.2, 19.0±0.2, 19.3±0.2, 19.91±0.2, 21.4±0.2, 23.3±0.2, and 25.1±0.2.

In some embodiments, provided herein is a composition comprising polymorph Form 7. In some embodiments, the composition can be substantially pure. For example, the composition has a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). In some embodiments, the composition contains less than about 15% by weight of other forms of the compound of Formula (I). For example, the composition can contain less than 14%, 13%, 12%, 11%, 10%, 9%, 8%, 7%, 6%, 5%, 4%, 3%, 2%, 1% by weight of one or more other forms of the compound of Formula (I). For example, the composition can contain less than about 15% of Form 1, Form 2, Form 8, or a combination of two or more thereof.

In some embodiments, provided herein is polymorph Form 7 that exhibits an endotherm that is observed between about 145-155° C., e.g., around 150° C., as measured by DSC related to sorbed water. In some embodiments, polymorph Form 7 exhibits an endotherm that is observed between about 190-205° C., e.g., around 201° C. In some embodiments, polymorph Form 7 exhibits an endothermic event that is observed between about 205-210° C., e.g., around 207° C. In some embodiments, the endotherms are observed when using a scan rate of 10° C. per minute.

In some embodiments, provided herein is polymorph Form 7 that exhibits an endothermic event observed at an onset of around 147° C., as measured by TG/DTA. In some embodiments, polymorph Form 7 undergoes a weight loss of about 7% before around 150° C., e.g., from about 145° C. to about 155° C. In some embodiments, the weight loss is the loss of solvent. In some embodiments, the weight loss is equal to about two equivalents of solvent as compared to the amount of compound present in the sample. In some embodiments, the solvent is water. In some embodiments, polymorph Form 7 exhibits an endothermic event observed from an onset of around 196° C. In some embodiments, polymorph Form 7 dehydrates upon heating to become polymorph Form 1. In some embodiments, the endothermic event relates to the transition observed in Form 1. In some embodiments, the transition relates to the endothermic event of Form 1 observed from an onset of around 206° C.

Provided herein are methods of preparing polymorph Form 7. In some embodiments, the method comprises slurrying a composition comprising the compound of Formula (I) in a mixture of 1,4-dioxane and water to generate polymorph Form 7 as a residual solid. In some embodiments, the water is present in an amount of about 10% by weight. In some embodiments, the slurry is temperature cycled between around 40° C. and RT. In some embodiments, the temperature cycling occurs between about 60 hours and 84 hours, such as, e.g., around 72 hours. In some embodiments, the method further comprises collecting the residual solid. In some embodiments, the residual solid is collected by filtration. In some embodiments, the residual solid is dried. In some embodiments, the residual solid is dried on the filter bed.

Form 8

Provided herein is a polymorph known as Form 8. Form 8 is a solvated polymorph form of the compound of Formula (I). Polymorph Form 8 is an isopropyl alcohol solvate polymorph form of the compound of Formula (I). In some embodiments, Form 8 has an XRPD pattern, obtained with CuKα1-radiation, with at least peaks at °2θ values of 15.1±0.2, 17.8±0.2, and 24.2±0.2. In some embodiments, Form 8 has an XRPD pattern with at least peaks at °2θ values of 15.1±0.2, 17.8±0.2, 20.4±0.2, 21.1±0.2, and 24.2±0.2. In some embodiments, Form 8 has an XRPD pattern with at least peaks at °2θ values of 15.1±0.2, 17.8±0.2, 18.1±0.2, 20.4±0.2, 21.1±0.2, 23.4±0.2, 24.2±0.2, and 24.6±0.2. For example, in some embodiments, Form 8 has an XRPD pattern with at least peaks at °2θ values of 6.2±0.2, 15.1±0.2, 17.8±0.2, 18.1±0.2, 20.4±0.2, 21.1±0.2, 23.4±0.2, 24.2±0.2, 24.6±0.2, and 31.2±0.2.

In some embodiments, provided herein is a composition comprising polymorph Form 8. In some embodiments, the composition can be substantially pure. For example, the composition has a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). In some embodiments, the composition contains less than about 15% by weight of other forms of the compound of Formula (I). For example, the composition can contain less than 14%, 13%, 12%, 11%, 10%, 9%, 8%, 7%, 6%, 5%, 4%, 3%, 2%, 1% by weight of one or more other forms of the compound of Formula (I). For example, the composition can contain less than about 15% of Form 1, Form 2, Form 7, or a combination of two or more thereof.

In some embodiments, provided herein is polymorph Form 8 that exhibits an endotherm that is observed between about 165-175° C., e.g., around 172° C., as measured by DSC related to sorbed water. In some embodiments, polymorph Form 8 exhibits an endotherm that is observed between about 185-200° C., e.g., around 196° C. In some embodiments, polymorph Form 8 exhibits an endothermic event that is observed between about 200-210° C., e.g., around 206° C. In some embodiments, the endotherms are observed when using a scan rate of 10° C. per minute.

In some embodiments, provided herein is polymorph Form 8 that exhibits an endothermic event observed at around 165° C., as measured by TG/DTA. In some embodiments, polymorph Form 8 undergoes a weight loss of about 4% before around 165° C. In some embodiments, the weight loss is the loss of solvent. In some embodiments, the weight loss is equal to about 0.5 equivalents of solvent. In some embodiments, the solvent is IPA. In some embodiments, polymorph Form 8 exhibits an endothermic event observed from an onset of around 191° C. In some embodiments, the endothermic event relates to the transition observed in Form 1. In some embodiments, the transition relates to the endothermic event of Form 1 observed from an onset of around 205° C.

Provided herein are methods of preparing polymorph Form 8. In some embodiments, the method comprises slurrying a composition comprising the compound of Formula (I) in a solvent selected from the group consisting of IPA and 1-propanol to generate polymorph Form 8 as a residual solid. In some embodiments, the slurry is temperature cycled between around 40° C. and RT. In some embodiments, the temperature cycling occurs between about 60 hours and 84 hours, such as, e.g., around 72 hours. In some embodiments, the method further comprises collecting the residual solid. In some embodiments, the residual solid is collected by filtration. In some embodiments, the method further comprises drying the residual solid, for example, under vacuum. In some embodiments, the drying is at a temperature of between about 30° C. and 50° C., such as, e.g., around 40° C.

In some embodiments, a method of preparing a polymorph of Form 8 is provided. The method comprises providing a composition comprising the compound of Formula (I) in a solvent. In some embodiments, the method comprises evaporating the solvent from the composition comprising the compound of Formula (I), including amorphous and polymorph forms thereof to generate a mixture of polymorph Form 8 and another polymorph form as a residual solid. In some embodiments, the residual solid is a mixture of polymorph Form 8 and polymorph Form 1. In some embodiments, the solvent is acetone. In some embodiments, the solvent is chloroform. In some embodiments, the solvent is THF.

Salts of Formula (I)

In some embodiments, the compound of Formula (I) is a pharmaceutically acceptable salt. For example, pharmaceutically acceptable salts of the compound of Formula (I) can include, but are not limited to, sulfate, tosylate, naphthalene-2-sulfonate, oxalate, phosphate, tartrate, and fumarate salts. In some embodiments, the compound of Formula (I) is a sulfate salt. In some embodiments, the sulfate salt is prepared in a mixture of solvents. In some embodiments, the solvent is a mixture of IPA and water. In some embodiments, the water is present in an amount of 10% by weight. In some embodiments, the compound of Formula (I) is a tosylate salt. In some embodiments, the tosylate salt is prepared in a mixture of solvents. In some embodiments, the solvent is a mixture of acetone and water. In some embodiments, the water is present in an amount of 10% by weight. In some embodiments, the compound of Formula (I) is a naphthalene-2-sulfonate salt. In some embodiments, the naphthalene-2-sulfonate salt is prepared in a mixture of solvents. In some embodiments, the solvent is a mixture of THF and water. In some embodiments, the water is present in an amount of 10% by weight. In some embodiments, the compound of Formula (I) is an oxalate salt. In some embodiments, the oxalate salt is prepared in a mixture of solvents. In some embodiments, the solvent is a mixture of 1,4-dioxane and water. In some embodiments, the water is present in an amount of 10% by weight. In some embodiments, the oxalate salt is prepared from evaporation from a mixture of solvents. In some embodiments, the solvent is a mixture of THF and water. In some embodiments, the compound of Formula (I) is a tartrate salt. In some embodiments, the tartrate salt is prepared in a mixture of solvents. In some embodiments, the solvent is a mixture of IPA and water. In some embodiments, the water is present in an amount of 10% by weight. In some embodiments, the compound of Formula (I) is a fumarate salt. In some embodiments, the fumarate salt is prepared in a mixture of solvents. In some embodiments, the solvent is a mixture of THF and water. In some embodiments, the compound of Formula (I) is a phosphate salt. In some embodiments, the phosphate salt is prepared in a mixture of solvents. In some embodiments, the solvent is a mixture of acetone and water. In some embodiments, the solvent is a mixture of IPA and water. In some embodiments, the water is present in an amount of 10% by weight.

Provided herein is a phosphate salt of the compound of Formula (I). In some embodiments, the phosphate salt has a ratio of 1.4:1, $PO_4$:free base. In some embodiments, the phosphate salt has an XRPD pattern, obtained with $CuK\alpha 1$-radiation, with at least peaks at °2θ values of 3.6±0.2, 16.7±0.2, and 18.2±0.2. In some embodiments, the phosphate salt has an XRPD pattern with at least peaks at °2θ values of 3.6±0.2, 15.9±0.2, 16.7±0.2, 17.8±0.2, and 18.2±0.2. In some embodiments, the phosphate salt has an XRPD pattern with at least peaks at °2θ values of 3.6±0.2, 6.2±0.2, 15.9±0.2, 16.7±0.2, 17.8±0.2, 18.2±0.2, 20.3±0.2, and 25.5±0.2. For example, in some embodiments, the phosphate salt has an XRPD pattern with at least peaks at °2θ values of 3.6±0.2, 6.2±0.2, 15.9±0.2, 16.7±0.2, 17.8±0.2, 18.2±0.2, 19.1±0.2, 20.3±0.2, 20.9±0.2, and 25.5±0.2.

In some embodiments, provided herein is a composition comprising the phosphate salt of the compound of Formula (I). In some embodiments, the composition can be substantially pure. For example, the composition has a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). In some embodiments, the composition contains less than about 15% by weight of other forms of the compound of Formula (I). For example, the composition can contain less than 14%, 13%, 12%, 11%, 10%, 9%, 8%, 7%, 6%, 5%, 4%, 3%, 2%, 1% by weight of one or more other forms of the compound of Formula (I).

In some embodiments, provided herein is a phosphate salt of the compound of Formula (I) that exhibits an endotherm that is observed between about 165-175° C., e.g., around 170° C., as measured by DSC related to sorbed water. In some embodiments, the endotherm is observed when using a scan rate of 10° C. per minute.

In some embodiments, provided herein is a phosphate salt of the compound of Formula (I) that exhibits a melting point of around 167° C., as measured by TG/DTA. In some embodiments, the phosphate salt of the compound of Formula (I) undergoes a mass loss of about 1.3% from the onset of heating to before around 150° C. In some embodiments, the phosphate salt of the compound of Formula (I) exhibits a second weight loss of about 1.2% from an onset of around 167° C.

Provided herein are methods of preparing a phosphate salt of the compound of Formula (I). In some embodiments, the method comprises slurrying a composition comprising the compound of Formula (I) in a mixture of water and IPA and adding a phosphoric acid solution to the mixture to generate the phosphate salt as a residual solid. In some embodiments, the water is present in an amount of about 10% by weight. In some embodiments, the acid is a 1M solution of phosphoric acid. In some embodiments, the slurry is temperature cycled between around 40° C. and RT. In some embodiments, the temperature cycling occurs between about 12 hours and 48 hours, such as, e.g., around 24 hours. In some embodiments, the method further comprises centrifuging the composition and collecting the residual solid. In some embodiments, the residual solid is washed with a solvent. In some embodiments, the solvent is IPA. In some embodiments, the method further comprises drying the residual solid. In some embodiments, the residual solid is dried under vacuum. In some embodiments, the drying is at a temperature of between about 30° C. and 50° C., such as, e.g., around 40° C.

It will be understood that the 2-theta values of the XRPD patterns for the crystalline forms of the compound of Formula (I), e.g., Forms 1, 2, 7, and 8, and pharmaceutically acceptable salts thereof, e.g., phosphate salt, can vary slightly from one instrument to another and also depending on variations in sample preparation and batch to batch variation, and so the values quoted are not to be construed as absolute. It will be understood that the peak positions in an XRPD pattern are reported in terms of angular positions (two theta) with an allowable variability of ±0.2° 2θ. The variability of ±0.2° 2θ is intended to be used when comparing two powder XRPD patterns. In practice, if a diffraction pattern peak from one pattern is assigned a range of angular positions (two theta) which is the measured peak position±0.2° and if those ranges of peak positions overlap, then the two peaks are considered to have the same angular position. For example, if a peak from one pattern is determined to have a position of 11.0° 2θ, for comparison purposes the allowable variability allows the peak to be assigned a position in the range of 10.8°-11.2° 2θ. It will also be understood that the relative intensities of peaks can vary depending on orientation effects so that the intensities shown in the XRPD traces included herein are illustrative and not intended to be used for absolute comparison. It is to be further understood that for comparison purposes some variability in peak intensities from those shown in XRPD traces is allowed. Accordingly, it is to be understood that the phrase "substantially the same XRPD pattern as shown in FIG. 1" means that for comparison purposes, at least 90% of the peaks shown in FIG. 1 are present. Compounds provided herein can also contain unnatural proportions of atomic isotopes at one or more of the atoms that constitute such compounds. That is, an atom, in particular when mentioned in relation to a compound according to Formula (I), comprises all isotopes and isotopic mixtures of that atom, such as naturally occurring isotopes with natural abundance. For example, when hydrogen is mentioned, it is understood to refer to $^1H$, $^2H$, $^3H$ or mixtures thereof; when carbon is mentioned, it is understood to refer to $^{12}C$, $^{13}C$, $^{14}C$ or mixtures thereof; when nitrogen is mentioned, it is understood to refer to $^{14}N$, $^{15}N$ or mixtures thereof; and when oxygen is mentioned, it is understood to refer to $^{16}O$, $^{17}O$, $^{18}O$ or mixtures thereof. All isotopic variations of the compounds provided herein are intended to be encompassed within the scope of the present invention.

In some embodiments, the solid formulations provided herein include a polymorph form of the compound of Formula (I). In some embodiments, the polymorph form is selected from among a free base, solvate, hydrate, salt, and non-solvated form of the compound of Formula (I), including, for example, polymorph Forms 1, 2, 7, and 8. In some embodiments, the polymorph form of the compound of Formula (I) is a pharmaceutically acceptable salt. In some embodiments, the compound of Formula (I) is a phosphate salt.

Liquid Formulations of the Compound of Formula (I)

In some embodiments, provided herein is a pharmaceutical composition comprising any one of the crystalline forms, solid forms, solvates, hydrates or salts of the compound of Formula (I) described herein, and a compounding agent as disclosed herein.

In some embodiments, provided herein is a pharmaceutical composition comprising the compound of Formula (I) and a compounding agent, wherein at least some of the compound of Formula (I) is present as any one of the crystalline forms, solid forms, solvates, hydrates, or salts described herein.

In some embodiments, provided herein is a pharmaceutical composition prepared by a process comprising mixing a compounding agent with the compound of Formula (I), to form the pharmaceutical composition.

In some embodiments, provided herein is a pharmaceutical composition prepared by a process comprising mixing a compounding agent with any of the crystalline forms of the compound of Formula (I) (e.g., Form 1, Form 2, Form 7, or Form 8), to form the pharmaceutical composition.

In some embodiments, provided herein is a pharmaceutical composition prepared by a process comprising mixing a compounding agent with any one of the crystalline forms, solid forms, solvates, hydrates, or salts described herein, to form the pharmaceutical composition.

In some embodiments, provided herein is a process for preparing a pharmaceutical composition comprising the compound of Formula (I), comprising mixing a compounding agent as disclosed herein with the compound of Formula (I), to form the pharmaceutical composition.

In some embodiments, provided herein is a process for preparing a pharmaceutical composition, comprising mixing a compounding agent as disclosed herein with any one of the crystalline forms, solid forms, solvates, hydrates, or salts described herein, to form the pharmaceutical composition.

In some embodiments, the pharmaceutical composition is a liquid oral pharmaceutical composition.

Pharmaceutical compositions comprising the compound of Formula (I), or pharmaceutical compositions comprising any one of the crystalline forms, solid forms, solvates, hydrates or salts described herein, can be prepared by intimately mixing, respectively, the compound of Formula (I) or the crystalline form, solid form, solvate, hydrate or salt described herein with a compounding agent as disclosed herein according to conventional pharmaceutical compounding techniques. For liquid oral compositions such as suspensions, elixirs and solutions, suitable compounding agents and additives comprise one or more of water, glycols, oils, alcohols, flavoring agents, preservatives, stabilizers, coloring agents, and the like. In some embodiments, of liquid oral compositions, the compounding agent is a compounding agent as disclosed hereinbelow.

In some embodiments, the compositions disclosed herein can further contain components that are conventional in pharmaceutical preparations, e.g., diluents, carriers, pH modifiers, sweeteners, bulking agents, and further active agents. Such compositions form a further aspect of the present disclosure.

In preparing liquid oral compositions, such as, for example, suspensions, elixirs, and solutions, suitable compounding agents comprise one or more of water, glycols, glycerols, oils, cyclodextrins, alcohols, e.g., ethanol, flavoring agents, preservatives, coloring agents, and the like.

In some embodiments, the compounding agent is an aqueous compounding agent.

In some embodiments, the compounding agent is an aqueous compounding agent comprising microcrystalline cellulose, carboxymethylcellulose sodium, xanthan gum, carrageenan, or a combination thereof. In some embodiments, the aqueous compounding agent comprises microcrystalline cellulose. In some embodiments, the aqueous compounding agent comprises colloidal microcrystalline cellulose. In some embodiments, the aqueous compounding agent comprises carboxymethylcellulose sodium. In some embodiments, the aqueous compounding agent comprises xanthan gum. In some embodiments, the aqueous compounding agent comprises carrageenan. In some embodiments, the aqueous compounding agent comprises microcrystalline cellulose and carboxymethylcellulose sodium. In some embodiments, the aqueous compounding agent comprises microcrystalline cellulose and carrageenan. In some embodiments, the aqueous compounding agent comprises microcrystalline cellulose and xanthan gum. In some embodiments, the aqueous compounding agent comprises carboxymethylcellulose sodium and carrageenan. In some embodiments, the aqueous compounding agent comprises carboxymethylcellulose sodium and xanthan gum. In some embodiments, the aqueous compounding agent comprises xanthan gum and carrageenan. In some embodiments, the aqueous compounding agent comprises microcrystalline cellulose, carboxymethylcellulose sodium, and xanthan gum. In some embodiments, the aqueous compounding agent comprises microcrystalline cellulose, carboxymethylcellulose sodium, and carrageenan. In some embodiments, the aqueous compounding agent comprises microcrystalline cellulose, xanthan gum, and carrageenan. In some embodiments, the aqueous compounding agent comprises carboxymethylcellulose sodium, xanthan gum, and carrageenan. In some embodiments, the aqueous compounding agent comprises microcrystalline cellulose, carboxymethylcellulose sodium, xanthan gum, and carrageenan. In some embodiments, the aqueous compounding agent comprises colloidal microcrystalline cellulose, carboxymethylcellulose sodium, xanthan gum, and carrageenan.

In some embodiments, the compounding agent is an aqueous compounding agent comprising microcrystalline cellulose, xanthan gum, carrageenan, calcium sulfate, or a combination thereof. In some embodiments, the aqueous compounding agent comprises calcium sulfate. In some embodiments, the compounding agent comprises microcrystalline cellulose and calcium sulfate. In some embodiments, the compounding agent comprises xanthan gum and calcium sulfate. In some embodiments, the compounding agent comprises carrageenan and calcium sulfate. In some embodiments, the compounding agent comprises microcrystalline cellulose, xanthan gum, and calcium sulfate. In some embodiments, the compounding agent comprises microcrystalline cellulose, carrageenan, and calcium sulfate. In some embodiments, the compounding agent comprises xanthan gum, carrageenan, and calcium sulfate. In some embodiments, the compounding agent comprises microcrystalline cellulose, xanthan gum, carrageenan, and calcium sulfate. In some embodiments, the compounding agent comprises colloidal microcrystalline cellulose, xanthan gum, carrageenan, and calcium sulfate.

In some embodiments, an aqueous compounding agent can be present in an amount of about 1 wt % to about 98 wt % of a pharmaceutical composition (e.g, about 1 wt % to about 10 wt %, about 1 wt % to about 30 wt %, about 1 wt % to about 50 wt %, about 1 wt % to about 70 wt %, about 1 wt % to about 90 wt %, about 10 wt % to about 98 wt %, about 30 wt % to about 98 wt % about 70 wt % to about 98 wt %, about 30 wt % to about 50 wt %, about 40 wt % to about 60 wt %, or about 45 wt % to about 55 wt %).

The pharmaceutical composition comprising the compounding agent can further comprise at least one of citric acid, a citrate, a lactate, a phosphate, a maleate, a tartrate, a succinate, a sulfate, or an acetate. In some embodiments, the pharmaceutical composition comprises at least one of lithium lactate, sodium lactate, potassium lactate, calcium lactate, lithium phosphate, trisodium phosphate, sodium phosphate, potassium phosphate, calcium phosphate, lithium maleate, sodium maleate, potassium maleate, calcium maleate, lithium tartarate, sodium tartarate, potassium tartarate, calcium tartarate, lithium succinate, sodium succinate, potassium succinate, calcium succinate, lithium acetate, sodium acetate, potassium acetate, or calcium acetate. The composition can comprise a citrate. The citrate can be at least one of lithium citrate monohydrate, sodium citrate monohydrate, potassium citrate monohydrate, calcium citrate monohydrate, lithium citrate dihydrate, sodium citrate dihydrate, potassium citrate dihydrate, calcium citrate dihydrate, lithium citrate trihydrate, sodium citrate trihydrate, potassium citrate trihydrate, calcium citrate trihydrate, lithium citrate tetrahydrate, sodium citrate tetrahydrate, potassium citrate tetrahydrate, calcium citrate tetrahydrate, lithium citrate pentahydrate, sodium citrate pentahydrate, potassium citrate pentahydrate, calcium citrate pentahydrate, lithium citrate hexahydrate, sodium citrate hexahydrate, potassium citrate hexahydrate, calcium citrate hexahydrate, lithium citrate heptahydrate, sodium citrate heptahydrate, potassium citrate heptahydrate, or calcium citrate heptahydrate. In some embodiments, the pharmaceutical composition comprises at least one of sodium citrate monohydrate, potassium citrate monohydrate, calcium citrate monohydrate, sodium citrate dihydrate, potassium citrate dihydrate, calcium citrate dihydrate, sodium citrate trihydrate, potassium citrate trihydrate, calcium citrate trihydrate, sodium citrate tetrahydrate, potassium citrate tetrahydrate, calcium citrate tetrahydrate, sodium citrate pentahydrate, potassium citrate pentahydrate, calcium citrate pentahydrate, sodium citrate hexahydrate, potassium citrate hexahydrate, calcium citrate hexahydrate, sodium citrate heptahydrate, potassium citrate heptahydrate, or calcium citrate heptahydrate. In some embodiments, the pharmaceutical composition includes sodium citrate dihydrate.

In some embodiments, the pharmaceutical composition comprises citric acid.

In some embodiments, the pharmaceutical composition comprises sulfate. In some embodiments, the sulfate can be lithium sulfate, sodium sulfate, potassium sulfate, magnesium sulfate, or calcium sulfate. In some embodiments, the sulfate can be calcium sulfate.

In some embodiments, the pharmaceutical composition comprises trisodium phosphate, sodium phosphate, citric acid, calcium sulfate, or a combination thereof. In some embodiments, the pharmaceutical composition comprises trisodium phosphate. In some embodiments, the pharmaceutical composition comprises sodium phosphate. In some embodiments, the pharmaceutical composition comprises citric acid. In some embodiments, the pharmaceutical composition comprises calcium sulfate. In some embodiments, the pharmaceutical composition comprises trisodium phosphate and sodium phosphate. In some embodiments, the pharmaceutical composition comprises trisodium phosphate and citric acid. In some embodiments, the pharmaceutical composition comprises sodium phosphate and citric acid. In some embodiments, the pharmaceutical composition comprises calcium sulfate and sodium phosphate. In some embodiments, the pharmaceutical composition comprises calcium sulfate and trisodium phosphate. In some embodiments, the pharmaceutical composition comprises calcium sulfate and citric acid. In some embodiments, the pharmaceutical composition comprises trisodium phosphate, sodium phosphate, and citric acid. In some embodiments, the pharmaceutical composition comprises calcium sulfate, sodium phosphate, and citric acid. In some embodiments, the pharmaceutical composition comprises calcium sulfate, trisodium phosphate, and citric acid. In some embodiments, the pharmaceutical composition comprises calcium sulfate, trisodium phosphate, and sodium phosphate. In some embodiments, the pharmaceutical composition comprises calcium sulfate, trisodium phosphate, sodium phosphate, and citric acid.

In some embodiments, the pharmaceutical composition comprises an antifoam. In some embodiments, an antifoam can include dimethicone, simethicone, an organic antifoam (e.g., one or more polyols, oils, or a combination thereof), or a combination thereof. In some embodiments, an antifoam can be an emulsion of dimethicone or simethicone.

In some embodiments, the pharmaceutical composition further comprises a preservative. In some embodiments, the preservative is selected from methylparaben, potassium sorbate, and a combination thereof.

In some embodiments, an aqeuous compounding agent can be Ora-Plus®. In some embodiments, an aqueous compounding agent in a pharmaceutical composition can be Ora-Plus®.

In some embodiments, a pharmaceutical composition comprising the compound of Formula (I) can further comprise Ora-Plus®.

In some embodiments of a pharmaceutical composition comprising the compound of Formula (I) and a compounding agent, the compound of Formula (I) is present in a concentration of about 5 mg/mL to about 40 mg/mL (e.g, about 5 mg/mL to about 10 mg/mL, about 5 mg/mL to about 20 mg/mL, about 5 mg/mL to about 30 mg/mL, about 10 mg/mL to about 40 mg/mL, about 20 mg/mL to about 40 mg/mL, about 30 mg/mL to about 40 mg/mL, about 5 mg/mL, about 10 mg/mL, about 20 mg/mL, about 30 mg/mL, or about 40 mg/mL).

In some embodiments, the pharmaceutical composition comprising the compounding agent can further comprise a sweetener.

In some embodiments, the pharmaceutical composition comprising the compounding agent and the sweetener is an aqueous composition.

In some embodiments, provided herein is a pharmaceutical composition comprising the compound of Formula (I) and a sweetener.

In some embodiments, provided herein is a pharmaceutical composition comprising any one of the crystalline forms, solid forms, solvates, hydrates, or salts described herein, and a sweetener.

In some embodiments, provided herein is a pharmaceutical composition comprising the compound of Formula (I) and a sweetener, wherein at least some of the compound of Formula (I) is present as any one of the crystalline forms, solid forms, solvates, hydrates, or salts described herein.

In some embodiments, provided herein is a pharmaceutical composition prepared by a process comprising mixing a sweetener with any of the crystalline forms of the compound of Formula (I) (e.g., Form 1, Form 2, Form 7, or Form 8), to form the pharmaceutical composition.

In some embodiments, the pharmaceutical composition comprising the sweetener is an aqueous pharmaceutical composition.

In some embodiments, the sweetener in a composition as disclosed herein comprises a sugar or a sugar substitute. In some embodiments, the sweetener comprises sucrose, saccharin, mannitol, sorbitol, dextrose, acesulfame, aspartame, fructose, maltitol, sucralose, or a combination thereof, wherein the sweetener or at least one sweetener in a combination of sweeteners is optionally in a salt form. In some embodiments, the sweetener comprises sucrose. In some embodiments, the sweetener comprises saccharin. In some embodiments, the sweetener comprises saccharin sodium (also called sodium saccharin). In some embodiments, the sweetener comprises saccharin sodium dihydrate. In some embodiments, the sweetener comprises saccharin calcium. In some embodiments, the sweetener comprises mannitol. In some embodiments, the sweetener comprises sorbitol. In some embodiments, the sweetener comprises dextrose. In some embodiments, the sweetener comprises anhydrous dextrose. In some embodiments, the sweetener comprises dextrose monohydrate. In some embodiments, the sweetener comprises acesulfame. In some embodiments, the sweetener comprises acesulfame potassium. In some embodiments, the sweetener comprises aspartame. In some embodiments, the sweetener comprises fructose. In some embodiments, the sweetener comprises maltitol. In some embodiments, the sweetener comprises sucralose.

In some embodiments, the sweetener is present in an amount of about 0.01 wt. % to about 1 wt. % in the pharmaceutical composition. In some embodiments, the sweetener is present in an amount of about 0.05 wt. % to about 0.75 wt. % in the pharmaceutical composition. In some embodiments, the sweetener is present in an amount of about 0.1 wt. % to about 0.5 wt. % in the pharmaceutical composition. In some embodiments, the sweetener is present in an amount of about 0.2 wt. % to about 0.4 wt. % in the pharmaceutical composition. In some embodiments, the sweetener is present in an amount of about 0.3 wt. % in the pharmaceutical composition.

In some embodiments, the sweetener is an aqueous sweetener.

In some embodiments, the sweetener is an aqueous sweetener comprising sucrose, glycerin (also called glycerine or glycerol), sorbitol, or a combination thereof. In some embodiments, the aqueous sweetener comprises sucrose. In some embodiments, the aqueous sweetener comprises glycerin. In some embodiments, the aqueous sweetener comprises sorbitol. In some embodiments, the aqueous sweetener comprises sucrose and glycerin. In some embodiments, the aqueous sweetener comprises sucrose and sorbitol. In some embodiments, the aqueous sweetener comprises glycerin and sorbitol. In some embodiments, the aqueous sweetener comprises sucrose, glycerin, and sorbitol.

In some embodiments, the sweetener is an aqueous sweetener that does not comprise sucrose. In some embodiments, the sweetener is an aqueous sweetener comprising glycerin, sorbitol, sodium saccharin, xanthan gum, or a combination thereof. In some embodiments, the aqueous sweetener comprises glycerin. In some embodiments, the aqueous sweetener comprises sorbitol. In some embodiments, the aqueous sweetener comprises sodium saccharin. In some embodiments, the aqueous sweetener comprises xanthan gum. In some embodiments, the aqueous sweetener comprises glycerin and sorbitol. In some embodiments, the aqueous sweetener comprises glycerin and sodium saccharin. In some embodiments, the aqueous sweetener comprises glycerin and xanthan gum. In some embodiments, the aqueous sweetener comprises sorbitol and sodium saccharin. In some embodiments, the aqueous sweetener comprises sorbitol and xanthan gum. In some embodiments, the aqueous sweetener comprises sodium saccharin and xanthan gum. In some embodiments, the aqueous sweetener comprises glycerin, sorbitol, and sodium saccharin. In some embodiments, the aqueous sweetener comprises glycerin, sorbitol, and xanthan gum. In some embodiments, the aqueous sweetener comprises glycerin, sodium saccharin, and xanthan gum. In some embodiments, the aqueous sweetener comprises sorbitol, sodium saccharin, and xanthan gum.

In some embodiments, the aqueous sweetener can further comprise a flavoring agent. In some embodiments, the flavoring agent can be a fruit flavoring agent. In some embodiments, the flavoring agent can be a citrus-berry flavoring agent.

In some embodiments, the aqueous sweetener can further comprise a buffer. In some embodiments, the buffer is can be selected from citric acid, sodium citrate, sodium phosphate, and combinations thereof.

In some embodiments, the aqueous sweetener can further comprise a preservative. In some embodiments, the preservative can be selected from methyparaben, potassium sorbate, propylparaben, and combinations thereof.

In some embodiments, an aqueous sweetener can be present in an amount of about 1 wt % to about 98 wt % of a pharmaceutical composition (e.g, about 1 wt % to about 10 wt %, about 1 wt % to about 30 wt %, about 1 wt % to about 50 wt %, about 1 wt % to about 70 wt %, about 1 wt % to about 90 wt %, about 10 wt % to about 98 wt %, about 30 wt % to about 98 wt % about 70 wt % to about 98 wt %, about 30 wt % to about 50 wt %, about 40 wt % to about 60 wt %, or about 45 wt % to about 55 wt %).

In some embodiments, the aqueous sweetener can be Ora-Sweet®. In some embodiments, the aqueous sweetener can be Ora-Sweet® SF.

In some embodiments, a sweetener in a pharmaceutical composition comprising can include Ora-Sweet®. In some embodiments, a sweetener in a pharmaceutical composition comprising can include Ora-Sweet® SF.

In some embodiments of a pharmaceutical composition comprising the compound of Formula (I) and a sweetener, the compound of Formula (I) is present in a concentration of about 5 mg/mL to about 40 mg/mL (e.g, about 5 mg/mL to about 10 mg/mL, about 5 mg/mL to about 20 mg/mL, about 5 mg/mL to about 30 mg/mL, about 10 mg/mL to about 40 mg/mL, about 20 mg/mL to about 40 mg/mL, about 30 mg/mL to about 40 mg/mL, about 5 mg/mL, about 10 mg/mL, about 20 mg/mL, about 30 mg/mL, or about 40 mg/mL).

Accordingly, in some embodiments, provided herein is a pharmaceutical composition comprising the compound of Formula (I), a compounding agent, and a sweetener.

In some embodiments, provided herein is a pharmaceutical composition comprising any one of the crystalline forms, solid forms, solvates, hydrates, or salts described herein, a compounding agent, and a sweetener.

In some embodiments, provided herein is a pharmaceutical composition comprising the compound of Formula (I), a compounding agent, and a sweetener, wherein at least some of the compound of Formula (I) is present as any one of the crystalline forms, solid forms, solvates, hydrates, or salts described herein.

In some embodiments, provided herein is a pharmaceutical composition prepared by a process comprising mixing a compounding agent and a sweetener with any of the crystalline forms of the compound of Formula (I) (e.g., Form 1, Form 2, Form 7, or Form 8), to form the pharmaceutical composition.

In some embodiments, the pharmaceutical composition has a pH of about 3 to about 8. In some embodiments, the composition has a pH of about 4 to about 7. In some embodiments, the composition has a pH of about 3 to about 5. In some embodiments, the composition has a pH of about 4 to about 5. In some embodiments, the composition has a pH of about 4.0 to about 4.5. In some embodiments, the composition has a pH of about 5 to 6. In some embodiments, the composition has a pH of about 5.3. In some embodiments, the composition has a pH of about 5.4. In some embodiments, the composition has a pH of about 5.5. In some embodiments, the composition has a pH of about 4.1. In some embodiments, the composition has a pH of about 5.6. In some embodiments, the composition has a pH of about 4.2. In some embodiments, the composition has a pH of about 4.3. In some embodiments, the composition has a pH of about 4.4. In some embodiments, the composition has a pH of about 4.5.

In some embodiments, a compounding agent (e.g., an aqueous compounding agent) can be used in a fixed ratio with a sweetener (e.g., an aqueous sweetener). For example, in some embodiments, a compounding agent (e.g., an aqueous compounding agent) and a sweetener (e.g., an aqueous sweetener) can be used in a ratio of about 1:1 (v/v). In some embodiments, Ora-Plus® and Ora-Sweet® can be used in a ratio of about 1:1 (v/v). In some embodiments, Ora-Plus® and Ora-Sweet® SF can be used in a ratio of about 1:1 (v/v).

In some embodiments of a pharmaceutical composition comprising the compound of Formula (I), a compounding agent, and a sweetener, the compound of Formula (I) is present in a concentration of about 5 mg/mL to about 40 mg/mL (e.g, about 5 mg/mL to about 10 mg/mL, about 5 mg/mL to about 20 mg/mL, about 5 mg/mL to about 30 mg/mL, about 10 mg/mL to about 40 mg/mL, about 20 mg/mL to about 40 mg/mL, about 30 mg/mL to about 40 mg/mL, about 5 mg/mL, about 10 mg/mL, about 20 mg/mL, about 30 mg/mL, or about 40 mg/mL).

In some embodiments, a compounding agent as described herein (e.g., an aqueous compounding agent as described herein) and a sweetener as described herein (e.g., an aqueous sweetener as described herein) can be provided in the form of an excipient blend. In some embodiments, an excipient blend can be an aqueous excipient blend. For example, in some embodiments, the aqueous excipient blend can be Ora-Blend®. For example, in some embodiments, the aqueous excipient blend can be Ora-Blend® SF.

In some embodiments, an excipient blend can be present in an amount of about 1 wt % to about 98 wt % of a pharmaceutical composition (e.g, about 1 wt % to about 10 wt %, about 1 wt % to about 30 wt %, about 1 wt % to about 50 wt %, about 1 wt % to about 70 wt %, about 1 wt % to about 90 wt %, about 10 wt % to about 98 wt %, about 30 wt % to about 98 wt % about 70 wt % to about 98 wt %, about 80 wt % to about 98 wt %, or about 90 wt % to about 98 wt %).

Accordingly, in some embodiments, provided herein is a pharmaceutical composition comprising the compound of Formula (I) and an excipient blend.

In some embodiments, provided herein is a pharmaceutical composition comprising any one of the crystalline forms, solid forms, solvates, hydrates, or salts described herein, and an excipient blend.

In some embodiments, provided herein is a pharmaceutical composition comprising the compound of Formula (I) and an excipient blend, wherein at least some of the compound of Formula (I) is present as any one of the crystalline forms, solid forms, solvates, hydrates, or salts described herein.

In some embodiments, provided herein is a pharmaceutical composition prepared by a process comprising mixing an excipient blend with any of the crystalline forms of the compound of Formula (I) (e.g., Form 1, Form 2, Form 7, or Form 8), to form the pharmaceutical composition.

In some embodiments of a pharmaceutical composition comprising the compound of Formula (I) and an excipient blend, the compound of Formula (I) is present in a concentration of about 5 mg/mL to about 40 mg/mL (e.g, about 5 mg/mL to about 10 mg/mL, about 5 mg/mL to about 20 mg/mL, about 5 mg/mL to about 30 mg/mL, about 10 mg/mL to about 40 mg/mL, about 20 mg/mL to about 40 mg/mL, about 30 mg/mL to about 40 mg/mL, about 5 mg/mL, about 10 mg/mL, about 20 mg/mL, about 30 mg/mL, or about 40 mg/mL).

In some embodiments, provided herein is a kit comprising:
- a) the compound of Formula (I);
- b) a compounding agent; and
- c) a sweetener.

In some embodiments, provided herein is a kit comprising:
- a) any one of the crystalline forms, solid forms, solvates, hydrates, or salts of Formula (I) described herein;
- b) a compounding agent; and
- c) a sweetener.

In some embodiments, provided herein is a kit comprising:
- a) the compound of Formula (I);
- b) an aqueous compounding agent; and
- c) a sweetener.

In some embodiments, provided herein is a kit comprising:
- a) any one of the crystalline forms, solid forms, solvates, hydrates, or salts of Formula (I) described herein;
- b) an aqueous compounding agent; and
- c) a sweetener.

In some embodiments, provided herein is a kit comprising:
- a) the compound of Formula (I);
- b) a compounding agent; and
- c) an aqueous sweetener.

In some embodiments, provided herein is a kit comprising:
- a) any one of the crystalline forms, solid forms, solvates, hydrates, or salts of Formula (I) described herein;
- b) a compounding agent; and
- c) an aqueous sweetener.

In some embodiments, provided herein is a kit comprising:
- d) the compound of Formula (I);
- e) an aqueous compounding agent; and
- f) an aqueous sweetener.

In some embodiments, provided herein is a kit comprising:
- a) any one of the crystalline forms, solid forms, solvates, hydrates, or salts of Formula (I) described herein;
- b) an aqueous compounding agent; and
- c) an aqueous sweetener.

In some embodiments, provided herein is a kit comprising:
- a) the compound of Formula (I); and
- b) an excipient blend.

In some embodiments, provided herein is a kit comprising:
- a) any one of the crystalline forms, solid forms, solvates, hydrates, or salts of Formula (I) described herein; and
- b) an excipient blend.

In some embodiments, provided herein is a kit comprising
1. a pharmaceutical composition comprising the compound of Formula (I) and a compounding agent; and
2. a pharmaceutical composition comprising the compound of Formula (I) and a sweetener.

In some embodiments, provided herein is a kit comprising
- a) a pharmaceutical composition comprising any one of the crystalline forms, solid forms, solvates, hydrates, or salts described herein, and a compounding agent; and
- b) a pharmaceutical composition comprising any one of the crystalline forms, solid forms, solvates, hydrates, or salts described herein, and a sweetener.

In some embodiments, provided herein is a pharmaceutical composition comprising:
the compound of Formula (I);
a compounding agent comprising microcrystalline cellulose, carboxymethylcellulose sodium, xanthan gum, carrageenan, or a combination thereof;
at least one of citric acid, a citrate, a lactate, a phosphate, a maleate, a tartrate, a succinate, a sulfate, or an acetate; and optionally a sweetener;
wherein the composition has a pH of about 3 to about 8.

In some embodiments, the pharmaceutical composition comprises:
the compound of Formula (I);
about 0.1 wt. % to about 2.0 wt. % of microcrystalline cellulose;
about 0.1 wt. % to about 1.0 wt. % of xanthan gum;
about 0.01 wt. % to about 1.0 wt. % of carrageenan; and
about 0.01 wt. % to about 1.0 wt. % of $CaSO_4$.

In some embodiments, provided herein is a pharmaceutical composition comprising: Form I of the compound of Formula (I);
a compounding agent comprising microcrystalline cellulose, carboxymethylcellulose sodium, xanthan gum, carrageenan, or a combination thereof;
at least one of citric acid, a citrate, a lactate, a phosphate, a maleate, a tartrate, a succinate, a sulfate, or an acetate; and optionally a sweetener;
wherein the composition has a pH of about 3 to about 8.

In some embodiments, the pharmaceutical composition comprises: Form I of the compound of Formula (I);
about 0.1 wt. % to about 2.0 wt. % of microcrystalline cellulose;
about 0.1 wt. % to about 1.0 wt. % of xanthan gum;
about 0.01 wt. % to about 1.0 wt. % of carrageenan; and
about 0.01 wt. % to about 1.0 wt. % of $CaSO_4$.

Methods for Preparing the Compound of Formula (I)

For illustrative purposes, Schemes 1 and 2 show general methods for preparing the compounds provided herein as well as key intermediates. For a more detailed description of the individual reaction steps, see, e.g., U.S. Provisional App. Ser. Nos. 62/406,252 and 62/447,850, both of which are incorporated by reference in their entirety herein. Those skilled in the art will appreciate that other synthetic routes can be used to synthesize the compounds. Although specific starting materials and reagents are depicted in the Schemes and discussed below, other starting materials and reagents can be easily substituted to provide a variety of derivatives and/or reaction conditions.
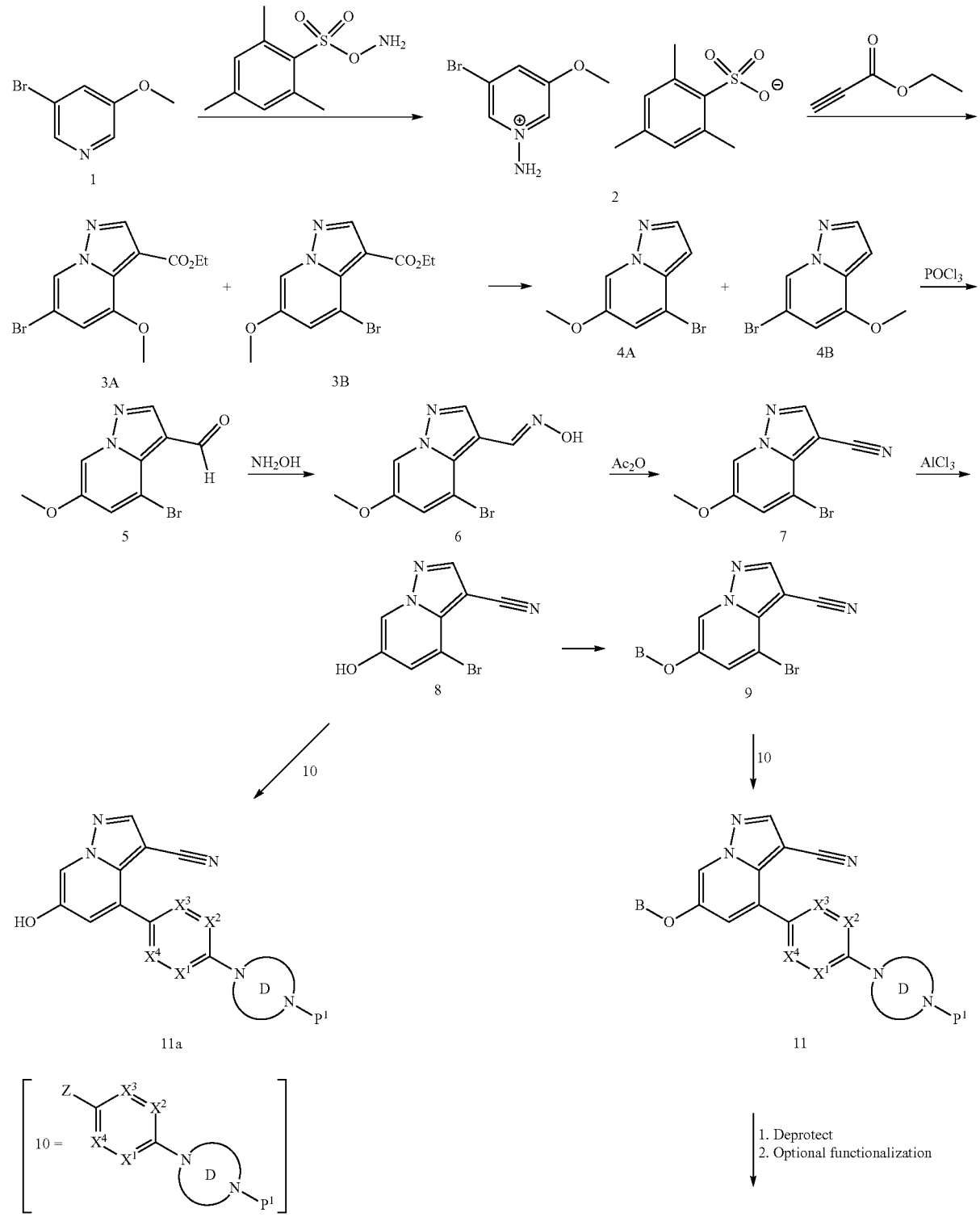
Scheme 1

-continued

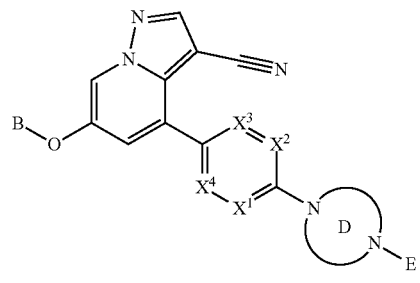

Scheme 1 shows a general scheme for the synthesis of the compound of Formula (I) (shown as compound 12 in scheme 1), where B is —CH$_2$C(CH$_3$)$_2$OH; X$^1$ is N; X$^2$, X$^3$, and X$^4$ are CH; and D and E are represented by

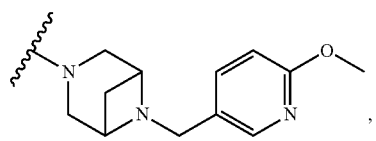 [SMILES: *N1CC2CC(C1)N2Cc1ccc(OC)nc1]

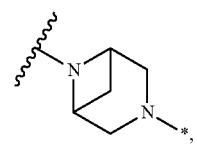

where the wavy line indicates the point of attachment to the ring comprising X$^1$, X$^2$, X$^3$, and X$^4$.

Compound 2 is obtained by treating commercially available 3-bromo-5-methoxypyridine (compound 1) with O-(mesitylsulfonyl)hydroxylamine. The O-mesitylsulfonylhydroxylamine can be prepared as described in Mendiola et al., Org. Process Res. Dev. (2009) 13(2):263-267. Compound 2 can be reacted with ethyl propiolate to provide a mixture of compounds 3A and 3B, which typically are obtained in a ratio of approximately 2:1 to 9:1, respectively. The mixture of compounds 3A and 3B can be treated with 48% HBr at elevated temperatures, followed by recrystallization or chromatography purifications, to isolate compound 4A as the minor isomer and compound 4B as the major isomer. After isolation, compound 4A can be treated with POCl$_3$ to provide compound 5. The formyl group can be converted to an oxime group using NH$_2$OH to provide compound 6. The oxime group can be converted to a nitrile group using acetic anhydride to provide compound 7. The methoxy group of compound 7 can be converted to a hydroxy group by treating compound 7 with aluminum trichloride to provide compound 8.

In some embodiments, to prepare compound 9, compound 8 can be reacted with a reagent such as

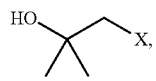

where X is a leaving atom or group (such as a halide or triflate), in the presence of a suitable base (e.g., a metal alkali carbonate, such as potassium carbonate). In some embodiments, compound 9 can be prepared by reacting compound 8 with an epoxide reagent, such as an alkylated epoxide, in the presence of a suitable base. Compound 11 can then be prepared by coupling compound 9 with the corresponding boronic ester compound 10 (where Ring D is wherein the wavy line indicates the point of attachment of Ring D to the ring comprising X$^1$, X$^2$, X$^3$ and X$^4$, and the asterisk indicates the point of attachment to P$^1$; X$^1$, X$^2$, X$^3$ and X$^4$ are as defined above; P$^1$ is an amino protecting group; Z is —B(OR$^x$)(OR$^y$) and R$^z$ and R$^y$ are H or (1-6C) alkyl, or R$^x$ and R$^y$ together with the atoms to which they are connected form a 5-6 membered ring optionally substituted with 1-4 substituents selected from (C1-C3 alkyl)) using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures). Compound 12 can then be prepared from compound 11 by removing the protecting group P$^1$ under standard conditions (for example, a Boc group can be removed by treating compound 11 under acidic conditions, e.g., HCl), followed by functionalization (i.e., reacting or treating compound 11 with the appropriate reagent) to introduce the E group

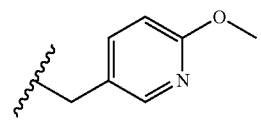 [SMILES: *Cc1ccc(OC)nc1]

under standard conditions.

Alternatively, compound 8 can be coupled with the corresponding boronic ester compound 10 to provide compound 11a using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures). Compound 11a can then be reacted with a reagent such as

where X is a leaving atom or group (such as a halide or triflate), under Mitsunobu reaction conditions (e.g., PPh$_3$ and diisopropyl azodicarboxylate) to provide compound 11. Compound 12 can then be prepared from compound 11 as described above.

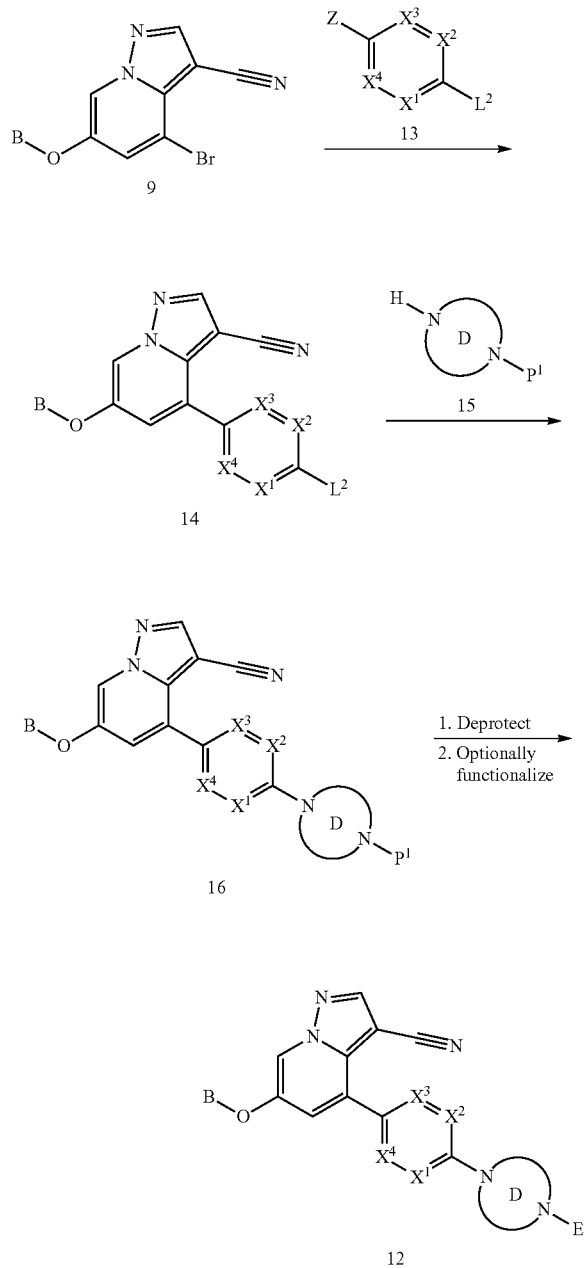

Scheme 2 shows another general scheme for the synthesis of compound 12 where and B, X$^1$, X$^2$, X$^3$, X$^4$, Ring D and E are as defined above for Scheme 1.

Compound 9 (prepared, e.g., as described in Scheme 1) in which B is as defined above, can be coupled with the corresponding boronic ester 13 (where X$^1$, X$^2$, X$^3$ and X$^4$ are as defined above; L$^2$ is a leaving group such as a triflate or halide); Z is —B(OR$^x$)(OR$^y$) and R$^x$ and R$^y$ are H or (1-6C)alkyl, or R$^x$ and R$^y$ together with the atoms to which they are connected form a 5-6 membered ring optionally substituted with 1-4 substituents selected from (C1-C3 alkyl)), using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures) to provide compound 14. Compound 16 can be prepared by coupling compound 14 with compound 15 where Ring D is as defined above and P$^1$ is an amino protecting group, under appropriate S$_N$Ar conditions (for example, optionally in the presence of a base such as K$_2$CO$_3$ and at elevated temperature).

The protecting group P$^1$ on Ring D of compound 16 can be removed under standard conditions (for example, a Boc group can be removed by treating compound 16 under acidic conditions, e.g., HCl) to provide compound 12 where E is H (i.e., Ring D is deprotected). The deprotected Ring D can then be functionalized (i.e., reacted or treated with an appropriate reagent) to introduce the E group under standard conditions such as described below to provide compound 12 where E is as defined above.

The term "amino protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives which can be removed to regenerate the desired amine group. Non-limiting examples of amino protecting groups are acetyl, trifluoroacetyl, t-butyloxycarbonyl ("Boc"), benzyloxycarbonyl ("CBz") and 9-fluorenylmethyleneoxycarbonyl ("Fmoc"). Further examples of these groups, and other protecting groups, are found in T. W. Greene et al., Greene's Protective Groups in Organic Synthesis. New York: Wiley Interscience, 2006.

Hydroxy groups can be protected with any convenient hydroxy protecting group, for example as described in T. W. Greene et al., Greene's Protective Groups in Organic Synthesis. New York: Wiley Interscience, 2006. Examples include benzyl, trityl, silyl ethers, and the like.

Nitrogen atoms in compounds described in any of the above methods can be protected with any convenient nitrogen protecting group, for example as described in Greene & Wuts, eds., "Protecting Groups in Organic Synthesis," 2$^{nd}$ ed. New York; John Wiley & Sons, Inc., 1991. Examples of nitrogen protecting groups include acyl and alkoxycarbonyl groups, such as t-butoxycarbonyl (BOC), phenoxycarbonyl, and [2-(trimethylsilyl)ethoxy]methyl (SEM).

In some embodiments, the synthesis of the compound of Formula (I) includes using compound A. In some embodiments, compound A is prepared as shown in Scheme 3 below.

Scheme 3
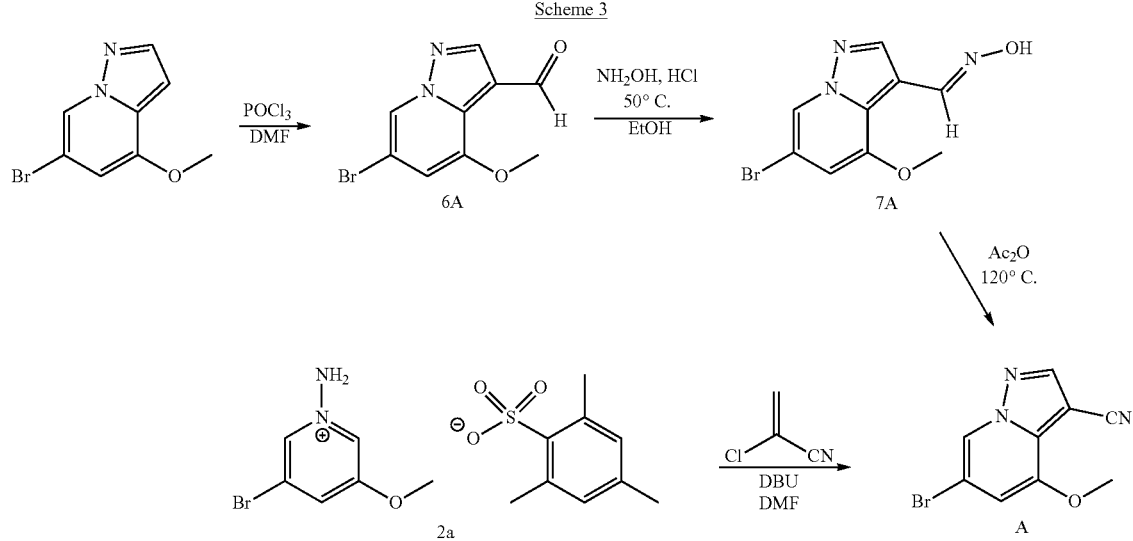
In some embodiments, the compound of Formula (I) is prepared from compound A as shown in Scheme 4 below, wherein X represents a halogen and $R^1$ is an amine protecting group.
Scheme 4
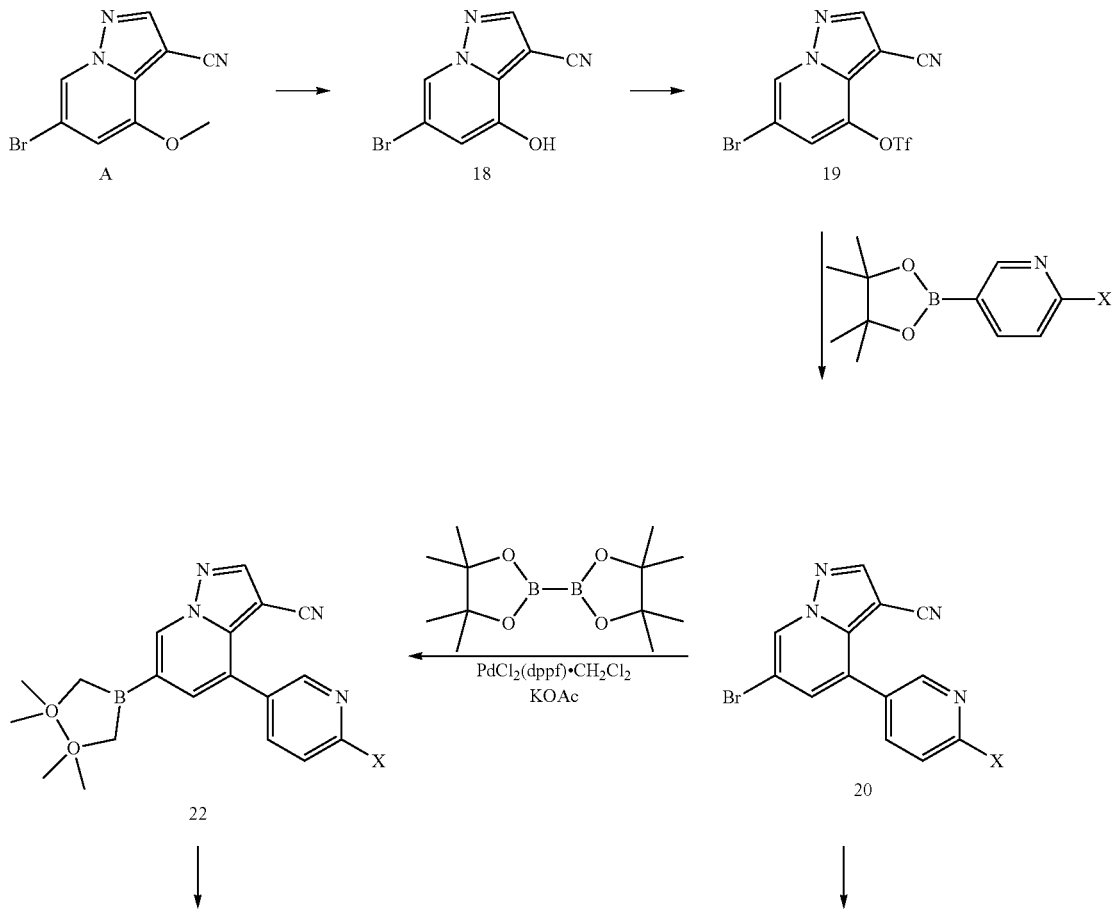

53

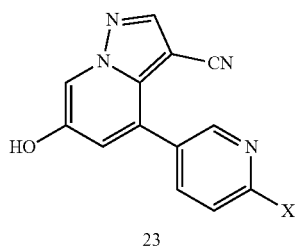

23

54

-continued

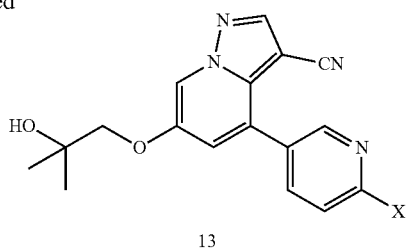

13

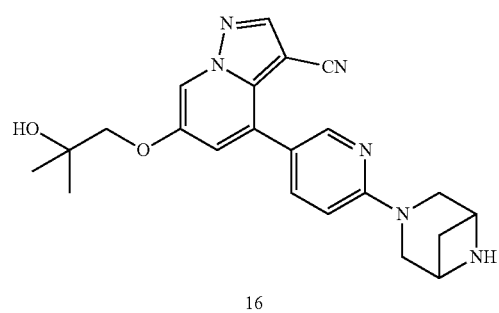

16

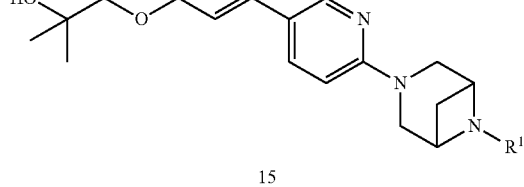

15

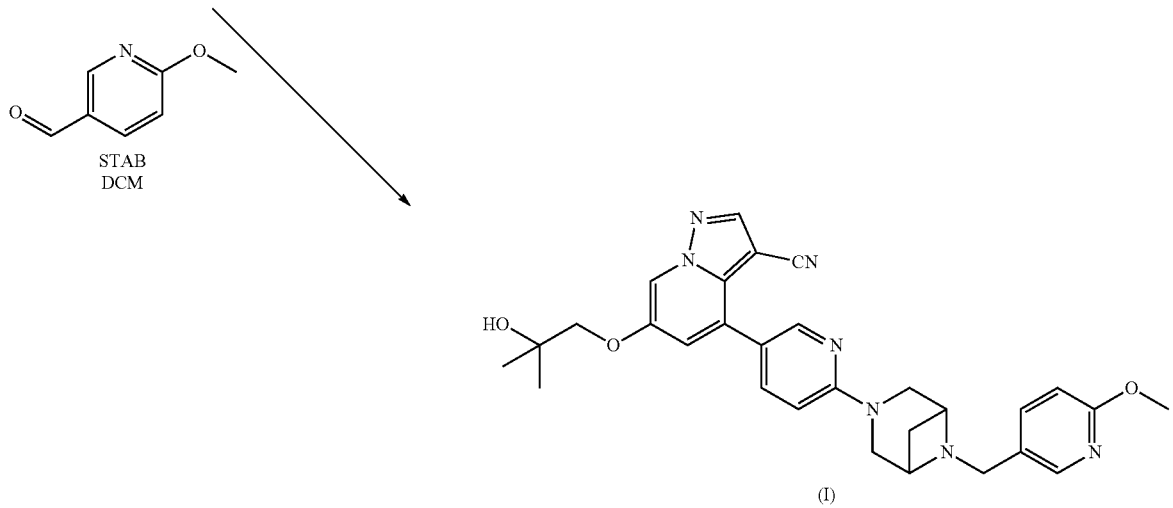

(I)

In some embodiments, X is a halogen that is selected from F, Cl, Br, and I. In some embodiments, X is F.

In some embodiments, $R^1$ is an amine protecting group that is selected from formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenylmethyloxycarbonyl, nitroveratryloxycarbonyl, p-methoxybenzyl and tosyl. In some embodiments, $R^1$ is tert-butyloxycarbonyl (Boc).

In some embodiments, the synthesis of the compound of Formula (I) includes using compound B. In some embodiments, compound B is prepared as shown in Scheme 5 below.

Scheme 5

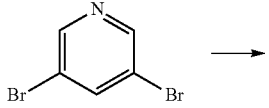

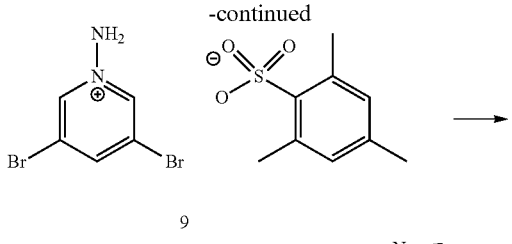

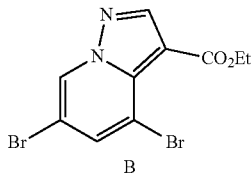

In some embodiments, the compound of Formula (I) is prepared from compound B as shown in Scheme 6 below, wherein R¹ is an amine protecting group and R² represents a boronic acid or ester with the boron atom as the point of attachment to the pyridine ring of the compound.

In some embodiments, $R^1$ is an amine protecting group that is selected from formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenylmethyloxycarbonyl, nitroveratryloxycarbonyl, p-methoxybenzyl and tosyl. In some embodiments, $R^1$ is tert-butyloxycarbonyl (Boc).

In some embodiments, $R^2$ is a boronic acid or ester that is boronic acid pinacol ester. In some embodiments, the boronic acid or ester is represented by the formula

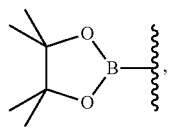 [SMILES: *B1OC(C)(C)C(C)(C)O1]

wherein the wavy line indicates the point of attachment to the pyridine ring of the compound.

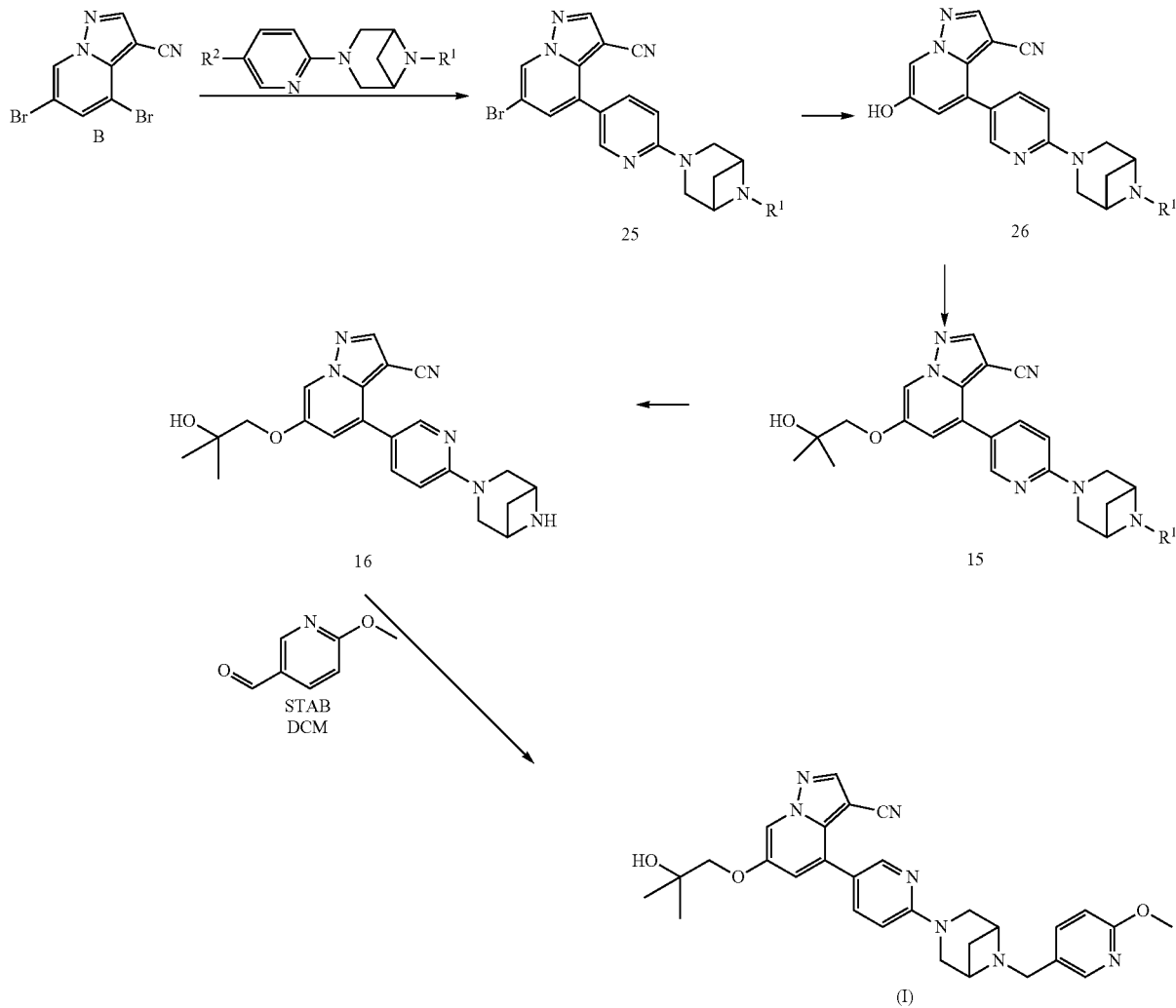

Methods of Treatment

The ability of the compound of Formula (I) or a pharmaceutically acceptable salt, amorphous form, polymorph form, or pharmaceutical composition (e.g., any of the solid or liquid formulations described herein) thereof, to act as a RET can be demonstrated by the assays described in, e.g., PCT Publication No. WO2018/071447 and U.S. Patent Application Publication No. US 20180134702, each of which is incorporated by reference in its entirety.

In some embodiments, the compounds provided herein exhibit potent and selective RET inhibition. For example, the compounds provided herein exhibit nanomolar potency against wild type RET and a RET kinase encoded by a RET gene including an activating mutation or a RET kinase inhibitor resistance mutation, including, for example, the KIF5B-RET fusion, G810R and G810S ATP cleft front mutations, M918T activating mutation, and V804M, V804L, and V804E gatekeeper mutations, with minimal activity against related kinases.

In some embodiments, the compound of Formula (I) or a pharmaceutically acceptable salt, amorphous form, polymorph form, or pharmaceutical composition (e.g., any of the solid or liquid formulations described herein) thereof selectively target a RET kinase. For example, the compound of Formula (I) or a pharmaceutically acceptable salt, amorphous form, polymorph form, or pharmaceutical composition (e.g., any of the solid or liquid formulations described herein) thereof can selectively target a RET kinase over another kinase or non-kinase target. In some embodiments, the compound of Formula (I) or a pharmaceutically acceptable salt, amorphous form, polymorph form, or pharmaceutical composition (e.g., any of the solid or liquid formulations described herein) thereof exhibit nanomolar potency against an altered RET fusion protein encoded by a RET gene encoding the RET fusion protein (e.g. any of the RET fusion proteins described herein including, without limitation, CCDC6-RET or KIF5B-RET) which RET gene includes a RET kinase inhibitor resistance mutation (e.g., any of the RET mutations described herein including, without limitation, V804M, V804L, or V804E) such that the altered RET protein is a RET fusion protein that exhibits RET kinase resistance due to the presence of a RET kinase inhibitor resistance amino acid substitution or deletion. Non-limiting examples include CCDC6-RET-V804M and KIF5B-RET-V804M. In some embodiments, the compounds provided herein exhibit nanomolar potency against an altered RET protein encoded by a RET gene that that includes a RET mutation (e.g. any of the RET mutations described herein including, without limitation, C634W or M918T) and that includes a RET kinase inhibitor resistance mutation (e.g., any of the RET kinase inhibitor resistance mutations described herein including, without limitation, V804M, V804L, or V804E) such that the altered RET protein includes a RET substitution caused by the RET mutation (e.g., a RET primary mutation) and the altered RET protein exhibits RET kinase resistance due to the presence of a RET kinase inhibitor resistance amino acid substitution or deletion.

In some embodiments, the compound of Formula (I) or a pharmaceutically acceptable salt, amorphous form, polymorph form, or pharmaceutical composition (e.g., any of the solid or liquid formulations described herein) thereof, exhibits at least a 30-fold selectivity for a RET kinase over another kinase. For example, the compound of Formula (I) or a pharmaceutically acceptable salt, amorphous form, polymorph form, or pharmaceutical composition (e.g., any of the solid or liquid formulations described herein) thereof, exhibits at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 200-fold selectivity; at least 300-fold selectivity; at least 400-fold selectivity; at least 500-fold selectivity; at least 600-fold selectivity; at least 700-fold selectivity; at least 800-fold selectivity; at least 900-fold selectivity; or at least 1000-fold selectivity for a RET kinase over another kinase. In some embodiments, selectivity for a RET kinase over another kinase is measured in a cellular assay (e.g., a cellular assay as provided herein).

In some embodiments, the compounds provided herein can exhibit selectivity for a RET kinase over a KDR kinase (e.g., VEGFR2). In some embodiments, the selectivity for a RET kinase over a KDR kinase is observed without loss of potency for a RET kinase encoded by a RET gene including an activating mutation or a RET kinase inhibitor resistance mutation (e.g., a gatekeeper mutant). In some embodiments, the selectivity over a KDR kinase is at least 10-fold (e.g., at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 150-fold selectivity; at least 200-fold selectivity; at least 250-fold selectivity; at least 300-fold selectivity; at least 350-fold selectivity; or at least 400-fold selectivity) as compared to the inhibition of KIF5B-RET (e.g., the compounds are more potent against KIF5B-RET than KDR). In some embodiments, the selectivity for a RET kinase over a KDR kinase is about 30-fold. In some embodiments, the selectivity for a RET kinase over a KDR kinase is at least 100-fold. In some embodiments, the selectivity for a RET kinase over a KDR kinase is at least 150-fold. In some embodiments, the selectivity for a RET kinase over a KDR kinase is at least 400-fold. Without being bound by any theory, potent KDR kinase inhibition is believed to be a common feature among multikinase inhibitors (MKIs) that target RET and may be the source of the dose-limiting toxicities observed with such compounds.

In some embodiments, inhibition of V804M is similar to that observed for wild-type RET. For example, inhibition of V804M is within about 2-fold (e.g., about 5-fold, about 7-fold, about 10-fold) of inhibition of wild-type RET (e.g., the compounds were similarly potent against wild-type RET and V804M). In some embodiments, selectivity for a wild-type or V804M RET kinase over another kinase is measured in an enzyme assay (e.g., an enzyme assay as provided herein). In some embodiments, the compounds provided herein exhibit selective cytotoxicity to RET-mutant cells.

In some embodiments, inhibition of G810S and/or G810R is similar to that observed for wild-type RET. For example, inhibition of G810S and/or G810R is within about 2-fold (e.g., about 5-fold, about 7-fold, about 10-fold) of inhibition of wild-type RET (e.g., the compounds were similarly potent against wild-type RET and G810S and/or G810R). In some embodiments, selectivity for a wildtype or G810S and/or G810R RET kinase over another kinase is measured in an enzyme assay (e.g., an enzyme assay as provided herein). In some embodiments, the compounds provided herein exhibit selective cytotoxicity to RET-mutant cells.

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor. For example, a RET-associated primary brain tumor or metastatic brain tumor.

In some embodiments, the compounds of Formula (I) or a pharmaceutically acceptable salt, amorphous form, polymorph form, or pharmaceutical composition (e.g., any of the solid or liquid formulations described herein) thereof, exhibit one or more of high GI absorption, low clearance, and low potential for drug-drug interactions.

Compounds of Formula (I) or a pharmaceutically acceptable salt, amorphous form, polymorph form, or pharmaceutical composition (e.g., any of the solid or liquid formulations described herein) thereof are useful for treating diseases and disorders which can be treated with a RET kinase inhibitor, such as RET-associated diseases and disorders, e.g., proliferative disorders such as cancers, including hematological cancers and solid tumors (e.g., advanced solid tumors and/or RET-fusion positive solid tumors), and gastrointestinal disorders such as IBS.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the terms "subject," "individual," or "patient," are used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer with a dysregulation of a RET gene, a RET protein, or expression or activity, or level of any of the same (a RET-associated cancer) (e.g., as determined using a regulatory agency-approved, e.g., FDA-approved, assay or kit). In some embodiments, the subject has a tumor that is positive for a dysregulation of a RET gene, a RET protein, or expression or activity, or level of any of the same (e.g., as determined using a regulatory agency-approved assay or kit). The subject can be a subject with a tumor(s) that is positive for a dysregulation of a RET gene, a RET protein, or expression or activity, or level of any of the same (e.g., identified as positive using a regulatory agency-approved, e.g., FDA-approved, assay or kit). The subject can be a subject whose tumors have a dysregulation of a RET gene, a RET protein, or expression or activity, or a level of the same (e.g., where the tumor is identified as such using a regulatory agency-approved, e.g., FDA-approved, kit or assay). In some embodiments, the subject is suspected of having a RET-associated cancer. In some embodiments, the subject has a clinical record indicating that the subject has a tumor that has a dysregulation of a RET gene, a RET protein, or expression or activity, or level of any of the same (and optionally the clinical record indicates that the subject should be treated with any of the compositions provided herein). In some embodiments, the patient is a pediatric patient.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula (I) or a pharmaceutically acceptable salt, amorphous form, polymorph form, or pharmaceutical composition (e.g., any of the solid or liquid formulations described herein) thereof are useful for preventing diseases and disorders as defined herein (for example, autoimmune diseases, inflammatory diseases, and cancer). The term "preventing" as used herein means the prevention of the onset, recurrence or spread, in whole or in part, of the disease or condition as described herein, or a symptom thereof.

The term "RET-associated disease or disorder" as used herein refers to diseases or disorders associated with or having a dysregulation of a RET gene, a RET kinase (also called herein RET kinase protein), or the expression or activity or level of any (e.g., one or more) of the same (e.g., any of the types of dysregulation of a RET gene, a RET kinase, a RET kinase domain, or the expression or activity or level of any of the same described herein). Non-limiting examples of a RET-associated disease or disorder include, for example, cancer and gastrointestinal disorders such as irritable bowel syndrome (IBS).

The term "RET-associated cancer" as used herein refers to cancers associated with or having a dysregulation of a RET gene, a RET kinase (also called herein RET kinase protein), or expression or activity, or level of any of the same. Non-limiting examples of a RET-associated cancer are described herein.

The phrase "dysregulation of a RET gene, a RET kinase, or the expression or activity or level of any of the same" refers to a genetic mutation (e.g., a chromosomal translocation that results in the expression of a fusion protein including a RET kinase domain and a fusion partner, a mutation in a RET gene that results in the expression of a RET protein that includes a deletion of at least one amino acid as compared to a wildtype RET protein, a mutation in a RET gene that results in the expression of a RET protein with one or more point mutations as compared to a wildtype RET protein, a mutation in a RET gene that results in the expression of a RET protein with at least one inserted amino acid as compared to a wildtype RET protein, a gene duplication that results in an increased level of RET protein in a cell, or a mutation in a regulatory sequence (e.g., a promoter and/or enhancer) that results in an increased level of RET protein in a cell), an alternative spliced version of a RET mRNA that results in a RET protein having a deletion of at least one amino acid in the RET protein as compared to the wild-type RET protein), or increased expression (e.g., increased levels) of a wildtype RET kinase in a mammalian cell due to aberrant cell signaling and/or dysregulated autocrine/paracrine signaling (e.g., as compared to a control non-cancerous cell). As another example, a dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains a first portion of RET that includes a functional kinase domain, and a second portion of a partner protein (i.e., that is not RET). In some examples, dysregulation of a RET gene, a RET protein, or expression or activity or level of any of the same can be a result of a gene translocation of one RET gene with another non-RET gene. Non-limiting examples of fusion proteins are described in Table 1. Non-limiting examples of RET kinase protein point mutations/insertions/deletions are described in Tables 2 and 2a. Additional examples of RET kinase protein mutations (e.g., point mutations) are RET inhibitor resistance mutations. Non-limiting examples of RET inhibitor resistance mutations are described in Tables 3 and 4.

In some embodiments, dysregulation of a RET gene, a RET kinase, or the expression or activity or level of any of the same can be caused by an activating mutation in a RET gene (see, e.g., chromosome translocations that result in the expression of any of the fusion proteins listed in Table 1). In some embodiments, dysregulation of a RET gene, a RET kinase, or the expression or activity or level of any of the same can be caused by a genetic mutation that results in the expression of a RET kinase that has increased resistance to inhibition by a RET kinase inhibitor and/or a multi-kinase inhibitor (MKI), e.g., as compared to a wildtype RET kinase (see, e.g., the amino acid substitutions in Tables 3 and 4). In some embodiments, dysregulation of a RET gene, a RET kinase, or the expression or activity or level of any of the same can be caused by a mutation in a nucleic acid encoding an altered RET protein (e.g., a RET fusion protein or a RET protein having a mutation (e.g., a primary mutation)) that results in the expression of an altered RET protein that has increased resistance to inhibition by a RET kinase inhibitor and/or a multi-kinase inhibitor (MKI), e.g., as compared to a wildtype RET kinase (see, e.g., the amino acid substitutions in Tables 3 and 4). The exemplary RET kinase point mutations, insertions, and deletions shown in Tables 2 and 2a can be caused by an activating mutation and/or can result in the expression of a RET kinase that has increased resistance to inhibition by a RET kinase inhibitor and/or a multi-kinase inhibitor (MKI).

The term "activating mutation" describes a mutation in a RET kinase gene that results in the expression of a RET kinase that has an increased kinase activity, e.g., as compared to a wildtype RET kinase, e.g., when assayed under identical conditions. For example, an activating mutation can result in the expression of a fusion protein that includes a RET kinase domain and a fusion partner. In another example, an activating mutation can be a mutation in a RET kinase gene that results in the expression of a RET kinase that has one or more (e.g., two, three, four, five, six, seven, eight, nine, or ten) amino acid substitutions (e.g., any combination of any of the amino acid substitutions described herein) that has increased kinase activity, e.g., as compared to a wildtype RET kinase, e.g., when assayed under identical conditions. In another example, an activating mutation can be a mutation in a RET kinase gene that results in the expression of a RET kinase that has one or more (e.g., two, three, four, five, six, seven, eight, nine, or ten) amino acids deleted, e.g., as compared to a wildtype RET kinase, e.g., when assayed under identical conditions. In another example, an activating mutation can be a mutation in a RET kinase gene that results in the expression of a RET kinase that has at least one (e.g., at least 2, at least 3, at least 4, at least 5, at least 6, at least 7, at least 8, at least 9, at least 10, at least 12, at least 14, at least 16, at least 18, or at least 20) amino acid inserted as compared to a wildtype RET kinase, e.g., the exemplary wildtype RET kinase described herein, e.g., when assayed under identical conditions. Additional examples of activating mutations are known in the art.

The term "wildtype" or "wild-type" describes a nucleic acid (e.g., a RET gene or a RET mRNA) or protein (e.g., a RET protein) that is found in a subject that does not have a RET-associated disease, e.g., a RET-associated cancer (and optionally also does not have an increased risk of developing a RET-associated disease and/or is not suspected of having a RET-associated disease), or is found in a cell or tissue from a subject that does not have a RET-associated disease, e.g., a RET-associated cancer (and optionally also does not have an increased risk of developing a RET-associated disease and/or is not suspected of having a RET-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating cancer (e.g., a RET-associated cancer) in a patient in need of such treatment, the method comprising administering to the patient a therapeutically effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof. For example, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of the compound of Formula (I) or a pharmaceutically acceptable salt, amorphous form, or polymorph form thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions. Non-limiting examples of RET kinase protein point mutations/insertions/deletions are described in Tables 2 and 2a. In some embodiments, the RET kinase protein point mutations/insertions/deletions are selected from the group consisting of M918T, M918V, C634W, V804L, V804M, G810S, and G810R. In some embodiments, the RET kinase protein point mutations/insertions/deletions occur in a RET fusion protein (e.g., any of the RET gene fusion proteins described in Table 1).

In some embodiments of any of the methods or uses described herein, the cancer (e.g., RET-associated cancer) is a hematological cancer. In some embodiments of any of the methods or uses described herein, the cancer (e.g., RET-associated cancer) is a solid tumor (e.g., an advanced solid tumor and/or a RET-fusion positive solid tumor). In some embodiments of any of the methods or uses described herein, the cancer (e.g., RET-associated cancer) is a lung cancer (e.g., small cell lung carcinoma or non-small cell lung carcinoma), thyroid cancer (e.g., papillary thyroid cancer, medullary thyroid cancer (e.g., sporadic medullary thyroid cancer or hereditary medullary thyroid cancer), differentiated thyroid cancer, recurrent thyroid cancer, or refractory differentiated thyroid cancer), thyroid ademoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., RET-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are RET-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a RET-associated cancer) is AML or CMML.

In some embodiments, the cancer (e.g., the RET-associated cancer) is a solid tumor. Examples of solid tumors (e.g., solid tumors that are RET-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

In some embodiments, the patient is a human.

Compounds of Formula (I) or a pharmaceutically acceptable salt, amorphous form, polymorph form, or pharmaceutical composition (e.g., any of the solid or liquid formulations described herein) thereof are also useful for treating a RET-associated cancer. In any of the methods disclosed herein, the compound of Formula (I) can be administered in the form of any of the solid or liquid formulations described herein.

Accordingly, also provided herein is a method for treating a patient diagnosed with or identified as having a RET-associated cancer, e.g., any of the exemplary RET-associated cancers disclosed herein, comprising administering to the patient a therapeutically effective amount of the compound of Formula (I) or a pharmaceutically acceptable salt, amorphous form, polymorph form, or pharmaceutical composition (e.g., any of the solid or liquid formulations described herein) thereof, or a pharmaceutical composition thereof as defined herein.

Also provided herein is a method of treating cancer in a patient in need thereof. The method includes administering to the patient a therapeutically effective amount of a liquid formulation provided herein.

In the methods of treatment described herein the liquid formulations provided herein can be especially useful in treating a subject with dysphagia (e.g., difficulty swallowing). For example, the liquid formulations provided herein can be useful in a method of treating cancer in a subject with an oropharyngeal dysphagia.

In some embodiments, a cancer results in dysphagia or difficulty swallowing. For example, a cancer can be a head and neck cancer, a mouth cancer, a throat cancer, or an esophageal cancer. In some embodiments, a patient having cancer develops difficulty swallowing due to one or more of fibrosis in the throat, esophagus, or mouth; infections of the mouth or esophagus (e.g., from radiation therapy or chemotherapy), swelling or narrowing of the throat or esophagus (e.g., from radiation therapy or surgery); physical changes to the mouth, jaws, throat, or esophagus from surgery; muscositis, which is soreness, pain or inflammation in the throat, esophagus, or mouth; xerostomia, commonly referred to as dry mouth (e.g., from radiation therapy or chemotherapy).

In some embodiments, the patient is a pediatric patient (e.g., an infant, a child, an adolescent), or an elderly patient.

In some embodiments, the patient has a dysphagia. The dysphagia can be an oropharyngeal dysphagia. Oropharyngeal dysphagia can arise due to cancer (e.g., certain cancers and some cancer treatments, such as radiation, can cause difficulty swallowing), neurological disorders (e.g., certain disorders, such as multiple sclerosis, muscular dystrophy and Parkinson's disease, can cause dysphagia), neurological damage (e.g., sudden neurological damage, such as from a stroke or brain or spinal cord injury, that effects one's ability to swallow), and pharyngeal diverticula.

In some embodiments, the patient has a neurological disorders (e.g., certain disorders, such as multiple sclerosis, muscular dystrophy and Parkinson's disease, can cause dysphagia), neurological damage (e.g., sudden neurological damage, such as from a stroke or brain or spinal cord injury, that effects one's ability to swallow), and pharyngeal diverticula.

Also provided herein is a method of treating cancer in a patient in need thereof with dysphagia (e.g., difficulty swallowing). The method includes identifying a patient in need thereof with dysphagia. The method further includes administering to the patient a therapeutically effective amount of a liquid formulation described herein.

In some embodiments, the dysphagia is an oropharyngeal dysphagia.

Also provided herein is a method of treating cancer in a patient in need thereof with dysphagia. The method includes identifying a patient in need thereof with dysphagia. The method further includes determining if the cancer is a RET-associated cancer. If the cancer is determined to be a RET-associated cancer, the method further includes administering to the patient a therapeutically effective amount of a liquid formulation described herein. Also provided herein is a method of treating cancer in a patient in need thereof with dysphagia. The method includes identifying a patient in need thereof with dysphagia. The method further includes identifying the cancer as a RET-associated cancer, and administering to the patient a therapeutically effective amount of a liquid formulation described herein.

In some embodiments, the dysphagia is an oropharyngeal dysphagia. Oropharyngeal dysphagia can arise due to cancer (e.g., certain cancers and some cancer treatments, such as radiation, can cause difficulty swallowing), neurological disorders (e.g., certain disorders, such as multiple sclerosis, muscular dystrophy and Parkinson's disease, can cause dysphagia), neurological damage (e.g., sudden neurological damage, such as from a stroke or brain or spinal cord injury, that effects one's ability to swallow), and pharyngeal diverticula.

Dysregulation of a RET kinase, a RET gene, or the expression or activity or level of any (e.g., one or more) of the same can contribute to tumorigenesis. For example, a dysregulation of a RET kinase, a RET gene, or expression or activity or level of any of the same can be a translocation, overexpression, activation, amplification, or mutation of a RET kinase, a RET gene, or a RET kinase domain. Translocation can include a gene translocation resulting in the expression of a fusion protein that includes a RET kinase domain and a fusion partner. For example, a fusion protein can have increased kinase activity as compared to a wildtype RET protein. In some embodiments, a mutation in a RET gene can involve mutations in the RET ligand-binding site, extracellular domains, kinase domain, and in regions involved in protein:protein interactions and downstream signaling. In some embodiments, a mutation (e.g., an activating mutation) in a RET gene can result in the expression of a RET kinase having one or more (e.g., two, three, four, five, six, seven, eight, nine, or ten) amino acid substitutions (e.g., one or more amino acid substitutions in the kinase domain (e.g., amino acid positions 723 to 1012 in a wildtype RET protein), a gatekeeper amino acid (e.g., amino acid position 804 in a wildtype RET protein), the P-loop (e.g., amino acid positions 730-737 in a wildtype RET protein), the DFG motif (e.g., amino acid positions 892-894 in a wildtype RET protein), ATP cleft solvent front amino acids (e.g., amino acid positions 758, 811, and 892 in a wildtype RET protein), the activation loop (e.g., amino acid positions 891-916 in a wildtype RET protein), the C-helix and loop preceeding the C-helix (e.g., amino acid positions 768-788 in a wildtype RET protein), and/or the ATP binding site (e.g., amino acid positions 730-733, 738, 756, 758, 804, 805, 807, 811, 881, and 892 in a wildtype RET protein). In some embodiments, a mutation can be a gene amplification of a RET gene. In some embodiments, a mutation (e.g., an activating mutation) in a RET gene can result in the expression of a RET kinase or RET receptor that lacks at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) as compared to a wildtype RET protein. In some embodiments, dyregulation of a RET kinase can be increased expression (e.g., increased levels) of a wildtype RET kinase in a mammalian cell due to aberrant cell signaling and/or dysregulated autocrine/paracrine signaling (e.g., as compared to a control non-cancerous cell). In some embodiments, a mutation (e.g., an activating mutation) in a RET gene can result in the expression of a RET kinase or RET receptor that has at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) inserted as compared to a wildtype RET protein. In some embodiments, dyregulation of a RET kinase can be increased expression (e.g., increased levels) of a wildtype RET kinase in a mammalian cell (e.g., as compared to a control non-cancerous cell), e.g., due to aberrant cell signaling and/or dysregulated autocrine/paracrine signaling. Other dysregulations can include RET mRNA splice variants. In some embodiments, the wildtype RET protein is the exemplary wildtype RET protein described herein.

In some embodiments, the dysregulation of a RET gene, a RET kinase, or expression or activity or level of any of the same, includes overexpression of wild-type RET kinase (e.g., leading to autocrine activation). In some embodiments, the dysregulation of a RET gene, a RET kinase protein, or expression or activity or level of any of the same, includes overexpression, activation, amplification, or mutation in a chromosomal segment comprising the RET gene or a portion thereof, including, for example, the kinase domain portion, or a portion capable of exhibiting kinase activity.

In some embodiments, the dysregulation of a RET gene, a RET kinase protein, or expression or activity or level of any of the same, includes one or more chromosome translocations or inversions resulting in a RET gene fusion. In some embodiments, the dysregulation of a RET gene, a RET kinase protein, or expression or activity or level of any of the same, is a result of genetic translocations in which the expressed protein is a fusion protein containing residues from a non-RET partner protein, and includes a minimum of a functional RET kinase domain.

Non-limiting examples of RET fusion proteins are shown in Table 1.

TABLE 1

Exemplary RET Fusion Partners and Cancers

| Fusion Partner | Non-limiting Exemplary RET-Associated Cancer(s) |
|---|---|
| BCR | Chronic Myelomonocytic Leukemia (CMML) |
| CLIP1 | Adenocarcinoma |
| KIF5B | NSCLC, Ovarian Cancer, Spitzoid Neoplasms; Lung Adenocarcinoma[3, 4, 14, 28]; Adenosquamous Carcinomas[15] |
| CCDC6 (also called PTC1, D10S170, or H4) | NSCLC, Colon Cancer, Papillary Thyroid Cancer; Adenocarcinomas; Lung Adenocarcinoma; Metastatic Colorectal Cancer[5]; Adenosquamous Carcinomas[15], Breast Cancer[30] |
| PTC1ex9 (a novel CCDC6 rearrangement) | Metastatic papillary thyroid cancer[2] |
| NCOA4 (also called PTC3, ELE1, and RFG) | Papillary Thyroid Cancer[21], NSCLC, Colon Cancer, Salivary Gland Cancer, Metastatic Colorectal Cancer[5]; Lung Adenocarcinoma[15]; Adenosquamous Carcinomas[15] Diffuse Sclerosing Variant of Papillary Thyroid Cancer[16], Breast Cancer[30], Acinic Cell Carcinoma[32], Mammary Analog Secretory Carcinoma[33] |
| TRIM33 (also called PTC7, RFG7, and TIF1G) | NSCLC, Papillary Thyroid Cancer, Lung Adenocarcinoma[46], Various[22] |
| ERC1 (also called ELKS and RAB61P2) | Papillary Thyroid Cancer, Breast Cancer |
| FGFR1OP | CMML, Primary Myelofibrosis with secondary Acute Myeloid Leukemia |
| MBD1(also known as PCM1) | Papillary Thyroid Cancer |
| PRKAR1A (also called PTC2) | Papillary Thyroid Cancer |
| TRIM24 (also called PTC6) | Papillary Thyroid Cancer |
| KTN1 (also called PTC8) | Papillary Thyroid Cancer |
| GOLGA5 (also called PTC5) | Papillary Thyroid Cancer, Spitzoid Neoplasms |
| HOOK3 | Papillary Thyroid Cancer |
| KIAA1468 (also called PTC9 and RFG9) | Papillary Thyroid Cancer, Lung Adenocarcinoma[8, 12] |
| TRIM27 (also called RFP) | Papillary Thyroid Cancer |
| AKAP13 | Papillary Thyroid Cancer |
| FKBP15 | Papillary Thyroid Cancer, Acute Myeloid Leukemia[46] |
| SPECC1L | Papillary Thyroid Cancer; Thyroid Gland Carcinoma |
| TBL1XR1 | Papillary Thyroid Cancer; Thyroid Gland Carcinoma |
| CEP55 | Diffuse Gastric Cancer[7] |
| CUX1 | Lung Adenocarcinoma |
| ACBD5 | Papillary Thyroid Carcinoma |
| MYH13 | Medullary Thyroid Carcinoma[1] |
| Uncharacterized | Inflammatory Myofibroblastic Tumor[6] |
| PIBF1 | Bronchiolus Lung Cell Carcinoma[9] |

TABLE 1-continued

Exemplary RET Fusion Partners and Cancers

| Fusion Partner | Non-limiting Exemplary RET-Associated Cancer(s) |
|---|---|
| KIAA1217 (also called SKT) | Papillary Thyroid Cancer[10, 13] Lung Adenocarcinoma[14] NSCLC[14] |
| MPRIP | NSCLC[11] |
| HRH4-RET | Thyroid Cancer and/or Paillary Thyroid Carcinoma[17] |
| Ria-RET | Thyroid Cancer and/or Papillary Thyroid Carcinoma[17] |
| RFG8 | Papillary Thyroid Carcinoma[18] |
| FOXP4 | Lung Adenocarcinoma[19] |
| MYH10 | Infantile Myofibromatosis[20] |
| HTIF1 | Various[22] |
| H4L | Various[22] |
| PTC4 (a novel NCO4/ELE1 rearrangement) | Papillary Thyroid Cancer[23] |
| FRMD4A | NSCLC[24] |
| SQSTM1 | Papillary Thyroid Carcinoma[25] |
| AFAP1L2 | Papillary Thyroid Carcinoma[25] |
| AFAP1 | NSCLC[31] |
| PPFIBP2 | Papillary Thyroid Carcinoma[25] |
| EML4 | NSCLC |
| PARD3 | NSCLC[27] |
| RASGEF1A | Breast Cancer[30] |
| TEL (also called ETV6) | In vitro[34], secretory carcinoma[51] |
| RUFY1 | Colorectal Cancer[35] |
| OLFM4 | Small-Bowel Cancer[36] |
| UEVLD | Papillary Thyroid Carcinoma[29] |
| DLG5 | Non-Anaplastic Thyroid (NAT) Cancer[37] |
| RRBP1 | Colon Cancer[38] |
| ANK3 | Papillary Thyroid Carcinoma[39] |
| PICALM | NSCLC[40] |
| MYO5C | NSCLC[41] |
| EPHA5 | NSCLC[40] |
| RUFY2 | Lung Cancer[42] |
| KIF13A | Lung Adenocarcinoma[43], NSCLC[45] |
| TNIP1 | Colorectal Cancer[44] |
| SNRNP70 | Colorectal Cancer[44] |
| MRLN | Thyroid Carcinoma[46] |
| LMNA | Spitzoid Melanoma[47] |
| RUFY3 | Papillary Thyroid Carcinoma |
| TFG | |
| MYO5A | Pigmented spindle cell nevus (PSCN) of Reed[48] |
| ADD3 | Lung adenocarcinoma[49] |
| JMJD1C | NSCLC[50] |
| RBPMS | |
| DOCK1 | |
| TAF3 | |
| NCOA1 | NSCLC[52] |

[1] Grubbs et al., *J. Clin. Endocrinol. Metab.* 100: 788-793, 2015.
[2] Halkova et al., *Human Pathology* 46: 1962-1969, 2015.
[3] U.S. Pat. No. 9,297,011
[4] U.S. Pat. No. 9,216,172
[5] Le Rolle et al., *Oncotarget.* 6(30): 28929-37, 2015.
[6] Antonescu et al., *Am J Surg Pathol.* 39(7): 957-67, 2015.
[7] U.S. Patent Application Publication No. 2015/0177246.
[8] U.S. Patent Application Publication No. 2015/0057335.
[9] Japanese Patent Application Publication No. 2015/109806A.
[10] Chinese Patent Application Publication No. 105255927A.
[11] Fang, et al. *Journal of Thoracic Oncology* 11.2 (2016): S21-S22.
[12] European Patent Application Publication No. EP3037547A1.
[13] Lee et al., *Oncotarget.* DOI: 10.18632/oncotarget.9137, e-published ahead of printing, 2016.
[14] Saito et al., *Cancer Science* 107: 713-720, 2016.
[15] Pirker et al., *Transl. Lung Cancer Res.* 4(6): 797-800, 2015.
[16] Joung et al., *Histopathology* 69(1): 45-53, 2016.
[17] PCT Patent Application Publication No. WO 2016/141169.
[18] Klugbauer et al., Cancer Res., 60(24): 7028-32, 2000.
[19] Bastien et al., *Journal of Molecular Diagnostics*, 18(6): 1027, Abstract Number: S120, 2016 Annual Meeting of the Association for Molecular Pathology, Charlotte, NC, 2016.
[20] Rosenzweig et al., *Pediatr Blood Cancer*, doi: 10.1002/pbc.26377, 2016.
[21] Su et al., *PLoS One*, 11(111): e0165596, 2016.
[22] U.S. Pat. No. 9,487,491.
[23] Fugazzola et al., *Oncogene*, 13(5): 1093-7, 1996.
[24] Velcheti et al., *J Thorac Oncol.*, 12(2): e15-e16. doi: 10.1016/j.jtho.2016.11.274, 2017.
[25] Kato et al, Clin Cancer Res. 2017 Apr 15; 23(8): 1988-1997. doi: 10.1158/1078-0432.CCR-16-1679. Epub 2016 Sep 28.
[26] Drilon, Alexander, et al. "A phase 1/1b study of RXDX-105, an oral RET and BRAF inhibitor, in patients with advanced solid tumors." Aug 8 (2016): 7.
[27] Sabari et al., *Oncoscience*, Advance Publications, www.impactjournals.com/oncoscience/files/papers/1/345/345.pdf, 2017.
[28] U.S. Patent Application Publication No. 2017/0014413.
[29] Lu et al., Oncotarget, 8(28): 45784-45792, doi: 10.18632/oncotarget.17412, 2017.
[30] Hirshfield et al al., *Cancer Research*, (February 2017) Vol. 77, No. 4, Supp. 1. Abstract Number: P3-07-02. Meeting Info: 39th Annual CTRC-AACR San Antonio Breast Cancer Symposium. San Antonio, TX, United States. 6 Dec 2016-10 Dec 2016.
[31] Morgensztern et al., *Journal of Thoracic Oncology*, (January 2017) Vol. 12, No. 1, Supp. 1, pp. S717-S718, Abstract Number: P1.07-035, Meeting Info: 17th World Conference of the International Association for the Study of Lung Cancer, IASLC 2016. Vienna, Austria. 4 Dec 2016.
[32] Dogan et al., *Laboratory Investigation*, (February 2017) Vol. 97, Supp. 1, pp. 323A. Abstract Number: 1298, Meeting Info: 106th Annual Meeting of the United States and Canadian Academy of Pathology, USCAP 2017. San Antonio, TX, United States.
[33] Dogan et al., MODERN PATHOLOGY, Vol. 30, Supp. [2], pp. 323A-323A. MA 1298, 2017.
[34] PCT Patent Application Publication No. WO 2017/146116.
[35] PCT Patent Application Publication No. WO 2017/122815.
[36] Reeser et al., *J. Mol. Diagn.*, 19(5): 682-696, doi: 10.1016/j.jmoldx.2017.05.006, 2017.
[37] Ibrahimpasic et al., *Clin. Cancer Res.*, doi: 10.1158/1078-0432.CCR-17-1183, 2017.
[38] Kloosterman et al., *Cancer Res.*, 77(14): 3814-3822. doi: 10.1158/0008-5472.CAN-16-3563, 2017.
[39] Chai et al., *Oncology Reports*, 35(2): 962-970. doi: 10.3892/or.2015.4466, 2015.
[40] Gautschi et al. *Journal of Clinical Oncology*, 35(13) 1403-1410. doi: 10.1200/JCO.2016.70.9352, 2017.
[41] Lee et al., *Annals of Oncology*, 28(2), 292-297. doi: 10.1093/annonc/mdw559, 2016.
[42] Zheng et al. *Nature Medicine*, 20(12), 1479-1484. doi: 10.1038/nm.3729, 2014.
[43] Zhang et al. *Lung Cancer*, 118, 27-29. doi: 10.1016/j.lungcan.2017.08.019, 2018.
[44] Morano et al. *Molecular Cancer Therapeutics*, (January 2018) Vol. 17, No. 1, Supp. Supplement 1. Abstract Number: B049. Meeting Info: AACR-NCI-EORTC International Conference: Molecular Targets and Cancer Therapeutics 2017.
[45] Wang et al. *Journal of Thoracic Oncology*, (November 2017) Vol. 12, No. 11, Supp. Supplement 2, pp. S2105. Abstract Number: P2.02-018. Meeting Info: 18th World Conference on Lung Cancer of the International Association for the Study of Lung Cancer, IASLC 2017. Yokohama, Japan. 15 Oct 2017-18 Oct 2017.
[46] Gao et al. *Cell Reports*, 23(1), 227-238. doi: 10.1016/j.celrep.2018.03.050, 2018.
[47] U.S. Patent Application Publication No. 2016/0010068.
[48] VandenBoom, et al. *Am. J. Surg. Pathol.* 42(8): 1042-1051, 2018. doi: 10.1097/PAS.0000000000001074
[49] Cao, et al. *Onco. Targets. Ther.* 2018(11): 2637-2646, 2018. doi: 10.2147/OTT.S155995
[50] Luo, et al. *Int. J. Cancer*, 2018. epub ahead of print. doi: 10.1002/ijc.31542
[51] Guilmette, et al. *Hum Pathol.* pii: S0046-8177(18)30316-2, 2018. doi: 10.1016/j.humpath.2018.08.011
[52] Zhao, et al. *Journal of Clinical Oncology* Vol 36, No. 15, Supp. [S], MA e21139.

In some embodiments, the dysregulation of a RET gene, a RET kinase, or expression or activity or level of any of the same, includes one or more deletions (e.g., deletion of an amino acid at position 4), insertions, or point mutation(s) in a RET kinase. In some embodiments, the dysregulation of a RET gene, a RET kinase, or expression or activity or level of any of the same, includes a deletion of one or more residues from the RET kinase, resulting in constitutive activity of the RET kinase domain.

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2).

TABLE 2

| RET Kinase Protein Amino Acid Substitutions/Insertions/Deletions[4] |
| --- |
| Amino acid position 2 |
| Amino acid position 3 |
| Amino acid position 4 |
| Amino acid position 5 |
| Amino acid position 6 |
| Amino acid position 7 |
| Amino acid position 8 |
| Amino acid position 11 |
| Amino acid position 12 |
| Amino acid position 13 |
| Amino acid position 20 |
| Amino acid position 32 (e.g., S32L) |
| Amino acid position 34 (e.g., D34S) |
| Amino acid position 40 (e.g., L40P) |
| Amino acid position 45 (e.g., A45A)[39] |
| Amino acid position 56 (e.g., L56M)[30] |
| Amino acid position 64 (e.g., P64L) |
| Amino acid position 67 (e.g., R67H) |
| Amino acid position 77 (e.g., R77C)[65] |
| Amino acid position 114 (e.g., R114H) |
| Amino acid position 136 (e.g., glutamic acid to stop codon) |
| Amino acid position 145 (e.g., V145G) |
| Amino acid position 177 (e.g., R177L)[67] |
| Amino acid position 180 (e.g., arginine to stop codon) |
| Amino acid position 200 |
| Amino acid position 270 (e.g., P270L)[65] |
| Amino acid position 278 (e.g., T278N)[57] |
| Amino acid position 292 (e.g., V292M) |
| Amino acid position 294 |
| Amino acid position 321 (e.g., G321R) |
| Amino acid position 330 (e.g., R330Q) |
| Amino acid position 338 (e.g., T338I) |
| Amino acid position 360 (e.g., R360W) |
| Amino acid position 373 (e.g., alanine to frameshift) |
| Δ Amino acid positions 378-385 with insertion of one amino acid (e.g., D378-G385 > E) |
| Amino acid position 393 (e.g., F393L) |
| Amino acid position 423 (e.g., G423R)[27] |
| Amino acid position 428 (e.g., E428K)[57] |
| Amino acid position 432 (e.g., A432A[39]) |
| Amino acid position 446 (e.g., G446R)[28] |
| Δ Amino acid positions 505-506 (6-Base Pair In-Frame Germline Deletion in Exon 7)[3] |
| Amino acid position 510 (e.g., A510V) |
| Amino acid position 511 (e.g., E511K) |
| Amino acid position 513 (e.g., G513D)[7*] |
| Amino acid position 515 (e.g., C515S, C515W[4]) |
| Amino acid position 525 (e.g., R525W)[7*] |
| Amino acid position 531 (e.g., C531R, or 9 base pair duplication[2]) |
| Amino acid position 532 (e.g., duplication)[2] |
| Amino acid position 533 (e.g., G533C, G533S) |
| Amino acid position 534 (e.g., L534L)[6] |
| Amino acid position 550 (e.g., G550E) |
| Amino acid position 591 (e.g., V591I) |
| Amino acid position 593 (e.g., G593E) |

TABLE 2-continued

| RET Kinase Protein Amino Acid Substitutions/Insertions/Deletions[4] |
| --- |
| Amino acid position 595 (e.g., E595D and E595A)[18] |
| Amino acid position 600 (e.g., R600Q) |
| Amino acid position 602 (e.g., I602V)[6] |
| Amino acid position 603 (e.g., K603Q, K603E[2]) |
| Amino acid position 606 (e.g., Y606C) |
| Amino acid position 609 (e.g., C609Y, C609S, C609G, C609R, C609F, C609W, C609C[32]) |
| Amino acid position 611 (e.g., C611R, C611S, C611G, C611Y, C611F, C611W) |
| Amino acid position 616 (e.g., E616Q)[23] |
| Δ Amino acid position 616[64] |
| Amino acid position 618 (e.g., C618S, C618Y, C618R, C618G, C618F, C618W, stop[56]) |
| Amino acid position 619 (e.g., F619F) |
| Amino acid position 620 (e.g., C620S, C620W, C620R, C620G, C620L, C620Y, C620F, C620A[47]) |
| Δ Amino acid positions 612-620[74] |
| Amino acid position 622 (e.g., P622L)[68] |
| Amino acid position 623 (e.g., E623K) |
| Amino acid position 624 (e.g., D624N) |
| Amino acid position 628 (e.g., P628N)[73] |
| Amino acid positions 629-631 (e.g., L629-D631delinsH)[80] |
| Amino acid position 630 (e.g., C630A, C630R, C630S, C630Y, C630F, C630W) |
| Δ Amino acid position 630[56] |
| Amino acid position 631 (e.g., D631N, D631Y, D631A, D631G, D631V, D631E,) |
| Δ Amino acid position 631[69] |
| Amino acid positions 631-633 > V (i.e., residues 631-633 are replaced with a single valine residue) |
| Amino acid positions 631-633 > A (i.e., residues 631-633 are replaced with a single alanine residue) |
| Amino acid positions 631-633 > E (i.e., residues 631-633 are replaced with a single glutamic acid residue) |
| Δ Amino acid positions 631-633 (e.g., D631-L633) |
| Δ Amino acid positions 631-634 (e.g., D631-C634) |
| Amino acid position 632 (e.g., E632K, E632G[5, 11], E632V[62], 632 to frameshift[47]) |
| Amino acid positions 632-633 > V (i.e., residues 632 and 633 are replaced with a single valine residue)[74] |
| Δ Amino acid positions 632-633 (e.g., E632-L633 in either the somatic cells, or a 6-Base Pair In-Frame Germline Deletion in Exon 11[9]) |
| Amino acid positions 632-639 > HR (i.e., residues 632-639 are replaced with two residues, histidine and arginine) |
| Amino acid position 633 (e.g., L633R[62], 9 base pair duplication[2], L633delinsLCR[71]) |
| Amino acid position 634 (e.g., C634W, C634Y, C634S, C634R, C634F, C634G, C634L, C634A, or C634T, a 9 base pair deletion[62], a 9 base pair duplication[56], or a 12 base pair duplication[2]) (e.g., causing MTC) |
| Δ Amino acid position 634[56] |
| Amino acid position 632/633/634 (E632V/L633R/634 9 base pair deletion)[62] |
| Amino acid position 635 (e.g., R635G or an insertion ELCR[2]) |
| Amino acid position 636 (e.g., T636P[2], T636M[4]) |
| Amino acid positions 636-637 (e.g., T636-V637insCRT)[80] |
| Amino acid position 638 (e.g., isoleucine to frameshift[47]) |
| Amino acid position 640 (e.g., A640G) |
| Amino acid position 634/640 (e.g., C634R/A640G)[56] |
| Amino acid position 641 (e.g., A641S, A641T[8]) |
| Amino acid position 634/641 (e.g., C634S/A641S)[56] |
| Amino acid position 639/641 (e.g., A639G/A641R)[56] |
| Amino acid position 644 (e.g., T644M)[59] |
| Amino acid position 648 (e.g., V648I) |
| Amino acid positions 634/648 (e.g., C634R/V648I)[77] |
| Amino acid position 649 (e.g., S649L)[28] |
| Amino acid position 661 (e.g., H661H)[6] |
| Amino acid position 664 (e.g., A664D) |
| Amino acid position 665 (e.g., H665Q) |
| Amino acid position 666 (e.g., K666E, K666M, K666N, K666R) |
| Amino acid position 675 (T675T, silent nucleotide change)[18] |

TABLE 2-continued

RET Kinase Protein Amino Acid Substitutions/Insertions/Deletions[4]

Amino acid position 679 (e.g., P679P)[6]
Amino acid position 680 (e.g., A680T, alanine to frameshift)[6]
Amino acid position 686 (e.g., S686N)
Amino acid position 689 (e.g., S689T)[18]
Amino acid position 691 (e.g., G691S)
Amino acid position 694 (e.g., R694Q)
Amino acid position 700 (e.g., M700L)
Amino acid position 706 (e.g., V706M, V706A)
Amino acid position 713 splice variant (e.g., E713K (e.g., a splice variant))[6]
Amino acid position 714 (e.g., D714Y)[57]
Amino acid position 727 (e.g., G727E)[6]
Amino acid position 732 (e.g., E732K)[20]
Amino acid position 734 (e.g., E734K)[48]
Amino acid position 736 (e.g., G736R)[6]
Amino acid position 738 (e.g., V738V)[6]
Amino acid position 742 (e.g., T742M)[51]
Amino acid position 748 (e.g., G748C)
Amino acid position 749 (e.g., R749T[36])
Amino acid position 750 (e.g., A750P, A750G[6])
Amino acid position 752 (e.g., Y752Y)[6]
Amino acid position 751 (e.g., G751G)[6]
Amino acid position 762 (e.g., E762Q[36])
Amino acid position 765 (e.g., S765P, S765F)
Amino acid position 766 (e.g., P766S, P766M[6])
Amino acid position 768 (e.g., E768Q, E768D, E768N[46], E768G[72])
Amino acid position 769 (e.g., L769L)[6]
Amino acid position 770 (e.g., R770Q)
Amino acid position 771 (e.g., D771N)
Amino acid position 777 (e.g., N777S)
Amino acid position 778 (e.g., V778I)
Amino acid position 781 (e.g., Q781R)
Amino acid position 788 (e.g., I788I[32], I788N[78])
Amino acid position 790 (e.g., L790F)
Amino acid position 768/790 (e.g., E768D/L790T)[40]
Amino acid position 791 (e.g., Y791F, Y791N[24])
Amino acid position 634/791 (e.g., C634Y/Y791F)[55]
Amino acid position 790/791 (e.g., L790F/Y791F)[55]
Amino acid position 802
Amino acid position 804 (e.g., V804L[15, 16], V804M[15, 16], V804E[12]) (e.g., causing MTC)
Amino acid position 778/804[50] (e.g., V778I/V804M[54])
Amino acid position 781/804 (e.g., Q781R/V804M)[41]
Amino acid position 805 (e.g., E805K)
Amino acid position 804/805 (e.g., V804M/E805K)[17]
Amino acid position 806 (e.g., Y806F, Y806S[12], Y806G, Y806C[2, 12, 14], Y806E[14], Y806H[12], Y806N[12], Y806Y[32])
Amino acid position 804/806 (e.g., V804M/Y806C)[38]
Amino acid position 810 (e.g., G810R[12], G810S[12], G810A[13], G810C, G810V, and G810D)
Amino acid position 818 (e.g., E818K)
Amino acid position 819 (e.g., S819I)
Amino acid position 820 (e.g., R820L)[57]
Amino acid position 823 (e.g., G823E)
Amino acid position 826 (e.g., Y826M, Y826S)[10]
Amino acid position 828 (e.g., G828R)[57]
Amino acid position 833 (e.g., R833C)
Amino acid position 836 (e.g., S836S)[19]
Amino acid position 841 (e.g., P841L, P841P)
Amino acid position 843 (e.g., E843D)
Amino acid position 844 (e.g., R844W, R844Q, R844L)
Amino acid position 804/844 (e.g., V804M/R844L)[76]
Amino acid position 845 (e.g., A845A)[63]
Amino acid position 848 (e.g., M848T)
Amino acid position 852 (e.g., I852M)
Amino acid position 853 (e.g., S853T)[57]
Amino acid position 865 (e.g., L865V)[12]
Amino acid position 866 (e.g., A866W)[33]
Amino acid position 867 (e.g., E867K)[37]
Amino acid position 870 (e.g., L870F)[12]
Amino acid position 873 (e.g., R873W, R873Q[42])
Amino acid position 876 (e.g., A876V)
Amino acid position 881 (e.g., L881V)
Amino acid position 882
Amino acid position 883 (e.g., A883F, A883S, A883T, A883Y[53], A883V)
Amino acid position 884 (e.g., E884K, E884V[35])
Amino acid position 886 (e.g., R886W)
Amino acid position 891 (e.g., S891A, S891S[32], S891L[35])
Amino acid position 893 (e.g., F893L)[42]
Amino acid position 894 (e.g., G894S)[43]
Amino acid position 897 (e.g., R897Q, R897P)
Amino acid position 898 (e.g., D898V, D898Y[66])
Δ Amino acid position 898
Δ Amino acid positions 898-902[58]
Δ Amino acid positions 899-902[47]
Δ Amino acid positions 898-901[47]
Δ Amino acid positions 632-633/Δ Amino acid positions 898-901[47]
Amino acid position 900 (e.g., Y900F)[22]
Amino acid position 901 (e.g., E901K)
Amino acid position 904 (e.g., S904F, S904S, S904C[2], S904T[57])
Amino acid position 691/904 (e.g., G691S/S904S)[49]
Amino acid position 804/904 (e.g., V804M/S904C)[38]
Amino acid position 905 (e.g., Y905F)[22]
Amino acid position 907 (e.g., K907E, K907M)
Amino acid position 908 (e.g., R908K)
Amino acid position 911 (e.g., G911D, G911G (e.g., a splice variant))[6]
Amino acid position 912 (e.g., R912P, R912Q)
Amino acid position 918 (e.g., M918T[2], M918V, M918L[6]) (e.g., causing MTC)
Amino acid position 591/918 (e.g., V591I/M918T)[61]
Amino acid position 620/918 (e.g., C620F/M918T)[47]
Amino acid position 891/918 (e.g., S891A/M918T)[47]
Δ Amino acid position 898-901/M918T[47]
Amino acid position 919 (e.g., A919V, A919P[52])
Amino acid position 768/919[54]
Amino acid position 921 (e.g., E921K, E921D)
Amino acid position 911/918/921 (e.g., G911E/M918T/E921K)[61]
Amino acid position 922 (e.g., S922P, S922Y)
Amino acid position 924 (e.g., F924S)[6]
Amino acid position 930 (e.g., T930M)
Amino acid position 961 (e.g., F961L)
Amino acid position 972 (e.g., R972G)
Amino acid position 973 (e.g., P973T)[57]
Amino acid position 977 (e.g., S977R)[37]
Amino acid position 981 (e.g., Y981F)[22]
Amino acid position 982 (e.g., R982C)[70]
Amino acid position 634/691/982 (e.g., C634R/G691S/R982C)[45]
Amino acid position 292/67/982 (e.g., V292M/R67H/R982C)[75]
Amino acid position 634/292/67/982 (e.g., C634R/V292M/R67H/R982C)[75]
Amino acid position 1009 (e.g., M1009V)
Amino acid position 1015 (e.g., Y1015F)[22]
Amino acid position 1017 (e.g., D1017N)
Amino acid position 1024 (e.g., S1024F)[79]
Amino acid position 1041 (e.g., V1041G)
Amino acid position 1047 (e.g., P1047S)[65]
Amino acid position 1051 (e.g., A1051T)[57]
Δ Amino acid position 1059[57]
Amino acid position 1064 (e.g., M1064T)
Amino acid position 1096 (e.g., Y1096F)[21]
Amino acid position 1105 (e.g., A1105V)[57]
Amino acid position 1109 (e.g., M1109T)[34]
RET + 3[1]

TABLE 2-continued

RET Kinase Protein Amino Acid Substitutions/Insertions/Deletions[A]

(In-Frame Deletion in Exons 6 and 11)[25]
(3bp In-Frame Deletion in Exon 15)[26]
Nucleotide position 2136 + 2 (e.g., 2136 + 2T > G)[29]
(del632-636 ins6)[31]
Amino acid positions 791 and 852 (e.g., Y791F + I852M)[31]
Amino acid positions 634 and 852 (e.g., C634R + I852M)[31]
c.1893_1895del[44]

[A]The RET kinase mutations shown may be activating mutations and/or confer increased resistance of the RET kinase to a RET kinase inhibitor and/or a multi-kinase inhibitor (MKI), e.g., as compared to a wildtype RET kinase.
[1]U.S. Patent Application Publication No. 2014/0272951.
[2]Krampitz et al., Cancer 120: 1920-1931, 2014.
[3]Latteyer, et al., *J. Clin. Endocrinol. Metab.* 101(3): 1016-22, 2016.
[4]Silva, et al. Endocrine 49.2: 366-372, 2015.
[5]Scollo, et al., *Endocr. J.* 63(1): 87-91, 2016.
[6]Jovanovic, et al., *Prilozi* 36(1): 93-107, 2015.
[7]Qi, et al., *Oncotarget.* 6(32): 33993-4003, 2015. * R525W and G513D appear to act in combination with S891A to enhance oncogenic activity.
[8]Kim, et al. ACTA ENDOCRINOLOGICA-BUCHAREST 11.2, 189-194, 2015.
[9]Cecchirini, et al. *Oncogene*, 14, 2609-2612, 1997.
[10]Karrasch, et al. *Eur. Thyroid J.*, 5(1): 73-7, 2016.
[11]Scollo et al., *Endocr. J.* 63: 87-91, 2016.
[12]PCT Patent Application Publication No. WO 2016/127074.
[13]Huang et al., Mol. Cancer Ther., 2016 Aug. 5. pii: molcanther.0258.2016. [Epub ahead of print].
[14]Carlomagno, et al., *Endocr. Rel. Cancer* 16(1): 233-41, 2009.
[15]Yoon et al., *J. Med. Chem.* 59(1): 358-73, 2016.
[16]U.S. Pat. No. 8,629,135.
[17]Cranston, et al., *Cancer Res.* 66(20): 10179-87, 2006.
[18]Kheiroddin et al., *Clin. Lab.* 62(5): 871-6, 2016.
[19]Ceolin et al., PLoS One. 11(2): e0147840, doi: 10.1371/journal.pone.0147840, 2016.
[20]Mamedova et al., Summer Undergraduate Research Programs (SURP) Student Abstracts, University of Oklahoma Health Sciences Center, 2016.
[21]Liu et al., *J. Biol. Chem.*, 271(10): 5309-12, 1995.
[22]Kato et al., *Cancer Res.*, 62: 2414-22, 2002.
[23]Grey et al., *Endocrine Pathology*, doi: 10.1007/s12022-016-9451-6, 2016.
[24]De Almeida et al., *Endocrine Reviews*, 2016, Vol. 37, No. 2, Supp. Supplement 1. Abstract Number: SUN-068; 98th Annual Meeting and Expo of the Endocrine Society, ENDO 2016. Boston, MA, US. 01 Apr 2016-04 Apr 2016.
[25]Vanden et al., *Annals of Oncology*, 2016, Vol. 27, Supp. Supplement 6. Abstract Number: 427PD; 41st European Society for Medical Oncology Congress, ESMP 2016. Copenhagen, Denmark. 07 Oct 2016-11 Oct 2016.
[26]Romei et al., *European Thyroid Journal* (August 2016) Vol. 5, Supp. Supplement 1, pp. 75; 39th Annual Meeting of the European Thyroid Association, ETA 2016. Copenhagen, Denmark. 03 Sep 2016-06 Sep 2016.
[27]Lee et al., *Oncotarget*, 8(4): 6579-6588, doi: 10.18632/oncotarget.14172, 2017.
[28]Zhang et al., *Laboratory Investigation*, (February 2017) Vol. 97, Supp. 1, pp. 209A. Abstract Number: 840, Meeting Info: 106th Annual Meeting of the United States and Canadian Academy of Pathology, USCAP 2017. San Antonio, TX, United States.
[29]Borecka et al., *European Journal of Cancer*, (July 2016) Vol. 61, No. 1, pp. S26, Abstract Number: 162, Meeting Info: 24th Biennial Congress of the European Association for Cancer Research, EACR 2016. Manchester, United Kingdom.
[30]Corsello et al., *Endocrine Reviews*, (JUN 2014) Vol. 35, No. 3, Suppl. S, pp. SUN-0322, Meeting Info.: 96th Annual Meeting and Expo of the Endocrine-Society, Chicago, IL, USA, June 21-24, 2014.
[31]Gazizova et al., *Endocrine Reviews*, (JUN 2014) Vol. 35, No. 3, Suppl. S, pp. SAT-0304, Meeting Info.: 96th Annual Meeting and Expo of the Endocrine-Society, Chicago, IL, USA, June 21-24, 2014.
[32]Sromek et al., *Endocr Pathol.*, doi: 10.1007/s12022-017-9487-2, 2017.
[33]U.S. Patent Application Publication No. 2017/0267661.
[34]Davila et. al., *Rare Tumors*, 2017; 9(2): 6834. doi: 10.4081/rt.2017.6834.
[35]U.S. Patent Application Publication No. 2018/0009818.
[36]PCT Patent Application Publication No. WO 2017/197051
[37]European Patent Application Publication No. 3271848
[38]Roskoski and Sadeghi-Nejad, *Pharmacol. Res.*, 128, 1-17. doi: 10.1016/j.phrs.2017.12.021, 2018.
[39]Kaczmarek-Rys, et al. *Endocrine-related cancer* 25(4): 421-436. doi: 10.1530/ERC-17-0452, 2018.
[40]Raue, et al. *J. Clin Endocrinol Metab*, 103(1): 235-243. doi: 10.1210/jc.2017-01884, 2018.
[41]Nakao, et al. *Head and Neck*, 35: E363-E368. doi: 10.1002/hed.23241, 2013.
[42]Attie, et al. *Human Molecular Genetics* 4(8): 1381-1386. doi: 10.1093/hmg/4.8.1381, 1995.
[43]Fitze, et al. *Lancet*, 393(9313): 1200-1205. doi: 10.1016/S0140-6736(02)08218-1, 2002.
[44]Weng, et al. *Zhonghua Nei Ke Za Zhi*, 57(2): 134-137. doi: 10.3760/cma.j.issn.0578-1426.2018.02.010, 2018.
[45]Chen, et al. *Medical Journal of Chinese People's Liberation Army* 38.4 (2013): 308-312.
[46]Gudernova, et al. eLife, 6: e21536. doi: 10.7554/eLife.21536, 2017.
[47]Romei, et al. *Oncotarget*, 9(11): 9875-9884. doi: 10.18632/oncotarget.23986, 2018.
[48]Plaza-Menacho. *Endocr Relat Cancer*, 25(2): T79-T90. doi: 10.1530/ERC-17-0354, 2017.
[49]Guerin, et al. *Endocr Relat Cancer*, 25(2): T15-T28. doi: 10.1530/ERC-17-0266, 2017.
[50]Roy et al. Oncologist, 18(10): 1093-1100. doi: 10.1634/theoncologist.2013-0053, 2013
[51]U.S. Patent Application Publication No. 2017/0349953
[52]Santoro, et al. *Endocrinology*, 145(12), 5448-5451, 2004. doi: 10.1210/en.2004-0922

TABLE 2-continued

RET Kinase Protein Amino Acid Substitutions/Insertions/Deletions[A]

[53]U.S. Pat. No. 9,006,256
[54]Yeganeh, et al. *Asian Pac J Cancer Prev*, 16(6), 2107-17. doi: 10.7314/APJCP.2015.16.6.2107
[55]Mulligan, L. M, *Nature Reviews Cancer*, 14(3), 173, 2014, doi: 10.1038/nrc368
[56]Arighi, et al, *Cytokine & Growth Factor Reviews*, 16(4-5), 441-467, 2005. doi: 10.1016/j.cytogfr.2005.05.010
[57]Dabir, et al, *Journal of Thoracic Oncology*, 9(9), 1316-1323, 2014. doi: 10.1097/JTO.0000000000000234
[58]Uchino, et al, *Cancer Science*, 90(11), 1231-1237, 1999. doi: 10.1111/j.1349-7006.1999.tb00701.x
[59]Krampitz. *Cancer*, 120(13), 1920-1931, 2014: 10.1002/cncr.28661
[60]Jhiang et al, Thyroid 6(2), 1996. doi: 10.1089/thy.1996.6.115
[61]Dvorakova, et al. *Thyroid*, 16(3), 311-316, 2006. doi: 0.1089/thy.2006.16.311
[62]Severskaya et al, *Genomics Transcriptomics Proteomics*, 40(3) 425-435.
[63]Elisei, et al, *Journal of Genetic Syndromes & Gene Therapy*, 5(1), 1, 2014. doi: 10.4172/2157-7412.1000214
[64]Ahmed et al. The Journal of Molecular Diagnostics, 7(2), 283-288, 2005. doi: 10.1016/S1525-1578(10)60556-9
[65]Oliveira, et al. *J. Exp. Clin. Cancer Res.* 37(84), 2018. doi: 10.1186/s13046-018-0746-y
[66]Yi, et al. *Case Rep. Endocrinol.* 2018: 8657314, 2018. doi: 10.1155/2018/8657914
[67]Huang, et al. Cell. 173(2): 355-370, 2018. doi: 10.1016/j.cell.2018.03.039
[68]Bosic, et al. *Pathology.* 50(3): 327-332, 2018. doi: 10.1016/j.pathol.2017.10.011
[69]Yao, et al. *Zhonghua Yi Xue Za Zhi.* 87(28): 1962-1965, 2007. PMID: 17923033
[70]Quintela-Fandino, et al. Mol. Oncol. 8(8): 1719-1728, 2014. doi: 10.1016/j.molonc.2014.07.005
[71]Urbini, et al. *Int J Genomics* 2018: 6582014. doi: 10.1155/2018/6582014
[72]Yu, et al. *Clin Lung Cancer*, pii: S1525-7304(18)30204-3, 2018. doi: 10.1016/j.cllc.2018.08.010
[73]Soca-Chafre, et al. *Oncotarget* 9(55): 30499-30512, 2018. doi: 10.18632/oncotarget.25369
[74]Kim, et al. BMC Urol 18(1): 68, 2018. doi: 10.1186/s12894-018-0380-1
[75]Qi, et al. PLoS One 6(5): e20353, 2011. doi: 10.1371/journal.pone.0020353
[76]Bartsch, et al *Exp Clin Endocrinol Diabetes* 108(2): 128-132, 2000. doi: 10.1055/s-2000-5806
[77]Nunes, et al. *J Clin Endocrinol Metab.* 87(12): 5658-5661, 2002. doi: 10.1210/jc.2002-020345
[78]Plenker et al., Sci. Transl. Med., 9(394), doi: 10.1126/scitranslmed.aah6144, 2017
[79]Romei, et al., *European Thyroid Journal*, Vol. 7, Supp. 1, pp 63. Abstract No: P1-07-69. Meeting Info: 41st Annual Meeting of the European Thyroid Association, ETA 2018. 15 Sep 2018-18 Sep 2018. doi: 10.1159/000491542
[80]Ciampi, et al., *European Thyroid Journal*, Vol. 7, Supp. 1, pp 63. Abstract No: OP-09-66. Meeting Info: 41st Annual Meeting of the European Thyroid Association, ETA 2018. 15 Sep 2018-18 Sep 2018. doi: 10.1159/000491542

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2a).

TABLE 2a

RET Kinase Protein Amino Acid Substitutions/Insertions/Deletions[A]

Amino acid position 20
Amino acid position 32 (e.g., S32L)
Amino acid position 34 (e.g., D34S)
Amino acid position 40 (e.g., L40P)
Amino acid position 64 (e.g., P64L)
Amino acid position 67 (e.g., R67H)
Amino acid position 114 (e.g., R114H)
Amino acid position 145 (e.g., V145G)
Amino acid position 200
Amino acid position 292 (e.g., V292M)
Amino acid position 294
Amino acid position 321 (e.g., G321R)
Amino acid position 330 (e.g., R330Q)
Amino acid position 338 (e.g., T338I)
Amino acid position 360 (e.g., R360W)
Amino acid position 393 (e.g., F393L)
Amino acid position 432
Δ Amino acid residues 505-506 (6-Base Pair In-Frame Germline Deletion in Exon 7)
Amino acid position 510 (e.g., A510V)
Amino acid position 511 (e.g., E511K)
Amino acid position 513 (e.g., G513D)
Amino acid position 515 (e.g., C515S, C515W[4])
Amino acid position 525 (e.g., R525W)
Amino acid position 531 (e.g., C531R, or 9 base pair duplication)

TABLE 2a-continued

RET Kinase Protein Amino Acid Substitutions/Insertions/Deletions[A]

Amino acid position 532 (e.g., duplication)
Amino acid position 533 (e.g., G533C, G533S)
Amino acid position 550 (e.g., G550E)
Amino acid position 591 (e.g., V591I)
Amino acid position 593 (e.g., G593E)
Amino acid position 595 (e.g., E595D and E595A)
Amino acid position 600 (e.g., R600Q)
Amino acid position 602 (e.g., I602V)
Amino acid position 603 (e.g., K603Q, K603E)
Amino acid position 606 (e.g., Y606C)
Amino acid position 609 (e.g., C609Y, C609S, C609G, C609R, C609F, C609W)
Amino acid position 611 (e.g., C611R, C611S, C611G, C611Y, C611F, C611W)
Amino acid position 616 (e.g., E616Q)
Amino acid position 618 (e.g., C618S, C618Y, C618R, C618G, C618F, C618W)
Amino acid position 620 (e.g., C620S, C620W, C620R, C620G, C620L, C620Y, C620F)
Amino acid position 623 (e.g., E623K)
Amino acid position 624 (e.g., D624N)
Amino acid position 630 (e.g., C630A, C630R, C630S, C630Y, C630F, C630W)
Amino acid position 631 (e.g., D631N, D631Y, D631A, D631G, D631V, D631E,)
Amino acid position 632 (e.g., E632K, E632G)
Δ Amino acid residues 632-633 (6-Base Pair In-Frame Germline Deletion in Exon 11)
Amino acid position 633 (e.g., 9 base pair duplication)
Amino acid position 634 (e.g., C634W, C634Y, C634S, C634R, C634F, C634G, C634L, C634A, or C634T, or an insertion ELCR, or a 12 base pair duplication) (e.g., causing MTC)
Amino acid position 635 (e.g., R635G)
Amino acid position 636 (e.g., T636P, T636M)
Amino acid position 640 (e.g., A640G)
Amino acid position 641 (e.g., A641S, A641T)
Amino acid position 648 (e.g., V648I)
Amino acid position 649 (e.g., S649L)
Amino acid position 664 (e.g., A664D)
Amino acid position 665 (e.g., H665Q)
Amino acid position 666 (e.g., K666E, K666M, K666N, K666R)
Amino acid position 686 (e.g., S686N)
Amino acid position 689 (e.g., S689T)
Amino acid position 691 (e.g., G691S)
Amino acid position 694 (e.g., R694Q)
Amino acid position 700 (e.g., M700L)
Amino acid position 706 (e.g., V706M, V706A)
Amino acid position 713 splice variant (e.g., E713K)
Amino acid position 732 (e.g., E732K)
Amino acid position 736 (e.g., G736R)
Amino acid position 748 (e.g., G748C)
Amino acid position 750 (e.g., A750P)
Amino acid position 765 (e.g., S765P)
Amino acid position 766 (e.g., P766S, P766M)
Amino acid position 768 (e.g., E768Q, E768D)
Amino acid position 769 (e.g., L769L)
Amino acid position 770 (e.g., R770Q)
Amino acid position 771 (e.g., D771N)
Amino acid position 777 (e.g., N777S)
Amino acid position 778 (e.g., V778I)
Amino acid position 781 (e.g., Q781R)
Amino acid position 790 (e.g., L790F)
Amino acid position 791 (e.g., Y791F, Y791N)
Amino acid position 802
Amino acid position 804 (e.g., V804L, V804M, V804E) (e.g., causing MTC)
Amino acid position 805 (e.g., E805K)
Amino acid position 804/805 (e.g., V804M/E805K)
Amino acid position 806 (e.g., Y806F, Y806S, Y806G, Y806C, Y806E, Y806H, Y806N)
Amino acid position 810 (e.g., G810R, G810S, G810A, G810C, G810V, and G810D)
Amino acid position 818 (e.g., E818K)
Amino acid position 819 (e.g., S819I)
Amino acid position 823 (e.g., G823E)
Amino acid position 826 (e.g., Y826M, Y826S)
Amino acid position 833 (e.g., R833C)
Amino acid position 836 (e.g., S836S)
Amino acid position 841 (e.g., P841L, P841P)
Amino acid position 843 (e.g., E843D)
Amino acid position 844 (e.g., R844W, R844Q, R844L)
Amino acid position 848 (e.g., M848T)
Amino acid position 852 (e.g., I852M)
Amino acid position 865 (e.g., L865V)
Amino acid position 870 (e.g., L870F)
Amino acid position 873 (e.g., R873W)
Amino acid position 876 (e.g., A876V)
Amino acid position 881 (e.g., L881V)
Amino acid position 882
Amino acid position 883 (e.g., A883F, A883S, A883T)
Amino acid position 884 (e.g., E884K)
Amino acid position 886 (e.g., R886W)
Amino acid position 891 (e.g., S891A)
Amino acid position 897 (e.g., R897Q)
Amino acid position 898 (e.g., D898V)
Amino acid position 900 (e.g., Y900F)
Amino acid position 901 (e.g., E901K)
Amino acid position 904 (e.g., S904F, S904S, S904C)
Amino acid position 907 (e.g., K907E, K907M)
Amino acid position 908 (e.g., R908K)
Amino acid position 911 (e.g., G911D)
Amino acid position 912 (e.g., R912P, R912Q)
Amino acid position 918 (e.g., M918T, M918V, M918L) (e.g., causing MTC)
Amino acid position 919 (e.g., A919V)
Amino acid position 921 (e.g., E921K)
Amino acid position 922 (e.g., S922P, S922Y)
Amino acid position 930 (e.g., T930M)
Amino acid position 961 (e.g., F961L)
Amino acid position 972 (e.g., R972G)
Amino acid position 982 (e.g., R982C)
Amino acid position 1009 (e.g., M1009V)
Amino acid position 1015 (e.g., Y1015F)
Amino acid position 1017 (e.g., D1017N)
Amino acid position 1041 (e.g., V1041G)
Amino acid position 1064 (e.g., M1064T)
Amino acid position 1096 (e.g., Y1096F)
RET + 3
(In-Frame Deletion in Exons 6 and 11)
(3 bp In-Frame Deletion in Exon 15)

[A]The RET kinase mutations shown above may be activating mutations and/or may confer increased resistance of the RET kinase to a RET inhibitor and/or a multi-kinase inhibitor (MKI), e.g., as compared to a wildtype RET kinase.

In some embodiments, the dysregulation of a RET gene, a RET kinase, or expression or activity or level of any of the same, includes a splice variation in a RET mRNA which results in an expressed protein that is an alternatively spliced variant of RET having at least one residue deleted (as compared to the wild-type RET kinase) resulting in a constitutive activity of a RET kinase domain.

A "RET kinase inhibitor" as defined herein includes any compound exhibiting RET inhibition activity. In some embodiments, a RET kinase inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitor can exhibit inhibition activity ($IC_{50}$) against a RET kinase of less than about 25 nM, less than about 10 nM, less than about 5 nM, or less than about 1 nM as measured in an assay as provided herein.

As used herein, a "first RET kinase inhibitor" or "first RET inhibitor" is a RET kinase inhibitor as defined herein, but which does not include the compound of Formula (I) or a pharmaceutically acceptable salt, amorphous form, polymorph form, or pharmaceutical composition (e.g., any of the solid or liquid formulations described herein) thereof as defined herein. As used herein, a "second RET kinase inhibitor" or a "second RET inhibitor" is a RET kinase inhibitor as defined herein, but which does not include the compound of Formula (I) or a pharmaceutically acceptable salt, amorphous form, polymorph form, or pharmaceutical composition (e.g., any of the solid or liquid formulations described herein) thereof as defined herein. When both a first and a second RET inhibitor are present in a method provided herein, the first and second RET kinase inhibitor are different.

In some embodiments, the dysregulation of a RET gene, a RET kinase, or expression or activity or level of any of the same, includes at least one point mutation in a RET gene that results in the production of a RET kinase that has one or more amino acid substitutions or insertions or deletions in a RET gene that results in the production of a RET kinase that has one or more amino acids inserted or removed, as compared to the wild-type RET kinase. In some cases, the resulting RET kinase is more resistant to inhibition of its phosphotransferase activity by one or more first RET kinase inhibitor(s), as compared to a wildtype RET kinase or a RET kinase not including the same mutation. Such mutations, optionally, do not decrease the sensitivity of the cancer cell or tumor having the RET kinase to treatment with the compound of Formula (I) or a pharmaceutically acceptable salt, amorphous form, polymorph form, or pharmaceutical composition (e.g., any of the solid or liquid formulations described herein) thereof (e.g., as compared to a cancer cell or a tumor that does not include the particular RET inhibitor resistance mutation). In such embodiments, a RET inhibitor resistance mutation can result in a RET kinase that has one or more of an increased $V_{max}$, a decreased $K_m$ for ATP, and an increased $K_D$ for a first RET kinase inhibitor, when in the presence of a first RET kinase inhibitor, as compared to a wildtype RET kinase or a RET kinase not having the same mutation in the presence of the same first RET kinase inhibitor.

In other embodiments, the dysregulation of a RET gene, a RET kinase, or expression or activity or level of any of the same, includes at least one point mutation in a RET gene that results in the production of a RET kinase that has one or more amino acid substitutions as compared to the wild-type RET kinase, and which has increased resistance to the compound of Formula (I) or a pharmaceutically acceptable salt, amorphous form, polymorph form, or pharmaceutical composition (e.g., any of the solid or liquid formulations described herein) thereof as compared to a wildtype RET kinase or a RET kinase not including the same mutation. In such embodiments, a RET inhibitor resistance mutation can result in a RET kinase that has one or more of an increased $V_{max}$, a decreased $K_m$, and a decreased $K_D$ in the presence of the compound of Formula (I) or a pharmaceutically acceptable salt, amorphous form, polymorph form, or pharmaceutical composition (e.g., any of the solid or liquid formulations described herein) thereof, as compared to a wildtype RET kinase or a RET kinase not having the same mutation in the presence of the same compound of Formula (I) or a pharmaceutically acceptable salt, amorphous form, polymorph form, or pharmaceutical composition (e.g., any of the solid or liquid formulations described herein) thereof.

Examples of RET inhibitor resistance mutations can, e.g., include point mutations, insertions, or deletions in and near the ATP binding site in the tertiary structure of RET kinase (e.g., amino acid positions 730-733, 738, 756, 758, 804, 805, 807, 810, 811, 881, and 892 of a wildtype RET kinase, e.g., the exemplary wildtype RET kinase described herein), including but not limited to a gatekeeper residue (e.g., amino acid position 804 in a wildtype RET kinase), P-loop residues (e.g., amino acid positions 730-737 in a wildtype RET kinase), residues in or near the DFG motif (e.g., amino acid positions 888-898 in a wildtype RET kinase), and ATP cleft solvent front amino acid residues (e.g., amino acid positions 758, 811, and 892 of a wildtype RET kinase). Additional examples of these types of mutations include changes in residues that may affect enzyme activity and/or drug binding including but are not limited to residues in the activation loop (e.g., amino acid positions 891-916 of a wildtype RET kinase), residues near or interacting with the activation loop, residues contributing to active or inactive enzyme conformations, changes including mutations, deletions, and insertions in the loop proceeding the C-helix and in the C-helix (e.g., amino acid positions 768-788 in a wildtype RET protein). In some embodiments, the wildtype RET protein is the exemplary wildtype RET kinase described herein. Specific residues or residue regions that may be changed (and are RET inhibitor resistance mutations) include but are not limited to those listed in Table 3, with numbering based on the human wildtype RET protein sequence (e.g., SEQ ID NO: 1). As can be appreciated by those skilled in the art, an amino acid position in a reference protein sequence that corresponds to a specific amino acid position in SEQ ID NO: 1 can be determined by aligning the reference protein sequence with SEQ ID NO: 1 (e.g., using a software program, such as ClustalW2). Additional examples of RET inhibitor resistance mutation positions are shown in Table 4. Changes to these residues may include single or multiple amino acid changes, insertions within or flanking the sequences, and deletions within or flanking the sequences. See also J. Kooistra, G. K. Kanev, O. P. J. Van Linden, R. Leurs, I. J. P. De Esch, and C. De Graaf, "KLIFS: A structural kinase-ligand interaction database," *Nucleic Acids Res.*, vol. 44, no. D1, pp. D365-D371, 2016, which is incorporated by reference in its entirety herein.

Exemplary Sequence of Mature Human RET Protein (SEQ ID NO: 1)

```
MAKATSGAAG  LRLLLLLLLP  LLGKVALGLY  FSRDAYWEKL

YVDQAAGTPL  LYVHALRDAP  EEVPSFRLGQ  HLYGTYRTRL

HENNWICIQE  DTGLLYLNRS  LDHSSWEKLS  VRNRGFPLLT

VYLKVFLSPT  SLREGECQWP  GCARVYFSFF  NTSFPACSSL

KPRELCFPET  RPSFRIRENR  PPGTFHQFRL  LPVQFLCPNI

SVAYRLLEGE  GLPFRCAPDS  LEVSTRWALD  REQREKYELV

AVCTVHAGAR  EEVVMVPFPV  TVYDEDDSAP  TFPAGVDTAS

AVVEFKRKED  TVVATLRVFD  ADVVPASGEL  VRRYTSTLLP

GDTWAQQTFR  VEHWPNETSV  QANGSFVRAT  VHDYRLVLNR

NLSISENRTM  QLAVLVNDSD  FQGPGAGVLL  LHFNVSVLPV

SLHLPSTYSL  SVSRRARRFA  QIGKVCVENC  QAFSGINVQY

KLHSSGANCS  TLGVVTSAED  TSGILFVNDT  KALRRPKCAE

LHYMVVATDQ  QTSRQAQAQL  LVTVEGSYVA  EEAGCPLSCA

VSKRRLECEE  CGGLGSPTGR  CEWRQGDGKG  ITRNFSTCSP
```

-continued

```
STKTCPDGHC DVVETQDINI CPQDCLRGSI VGGHEPGEPR

GIKAGYGTCN CFPEEEKCFC EPEDIQDPLC DELCRTVIAA

AVLFSFIVSV LLSAFCIHCY HKFAHKPPIS SAEMTFRRPA

QAFPVSYSSS GARRPSLDSM ENQVSVDAFK ILEDPKWEFP

RKNLVLGKTL GEGEFGKVVK ATAFHLKGRA GYTTVAVKML

KENASPSELR DLLSEFNVLK QVNHPHVIKL YGACSQDGPL

LLIVEYAKYG SLRGFLRESR KVGPGYLGSG GSRNSSSLDH

PDERALTMGD LISFAWQISQ GMQYLAEMKL VHRDLAARNI

LVAEGRKMKI SDFGLSRDVY EEDSYVKRSQ GRIPVKWMAI

ESLFDHIYTT QSDVWSFGVL LWEIVTLGGN PYPGIPPERL

FNLLKTGHRM ERPDNCSEEM YRLMLQCWKQ EPDKRPVFAD

ISKDLEKMMV KRRDYLDLAA STPSDSLIYD DGLSEEETPL

VDCNNAPLPR ALPSTWIENK LYGMSDPNWP GESPVPLTRA

DGTNTGFPRY PNDSVYANWM LSPSAAKLMD TFDS
```

In some embodiments, a RET inhibitor resistance mutation can include a dysregulation of a MET gene, a MET kinase, or the expression or activity or level of any of the same.

The phrase "dysregulation of a MET gene, a MET kinase, or the expression or activity or level of any of the same" refers to a genetic mutation (e.g., a MET gene translocation that results in the expression of a fusion protein, a deletion in a MET gene that results in the expression of a RET protein that includes a deletion of at least one amino acid as compared to the wild-type RET protein, or a mutation in a MET gene that results in the expression of a RET protein with one or more point mutations, or an alternative spliced version of a MET mRNA that results in a MET protein that results in the deletion of at least one amino acid in the MET protein as compared to the wild-type MET protein), or a MET gene amplification that results in overexpression of a MET protein or an autocrine activity resulting from the overexpression of a MET gene a cell, that results in a pathogenic increase in the activity of a kinase domain of a MET protein (e.g., a constitutively active kinase domain of a MET protein) in a cell. As another example, a dysregulation of a MET gene, a MET protein, or expression or activity, or level of any of the same, can be a mutation in a MET gene that encodes a MET protein that is constitutively active or has increased activity as compared to a protein encoded by a MET gene that does not include the mutation. For example, a dysregulation of a MET gene, a MET protein, or expression or activity, or level of any of the same, can be the result of a gene or chromosome translocation which results in the expression of a fusion protein that contains a first portion of MET that includes a functional kinase domain, and a second portion of a partner protein (i.e., that is not MET). In some examples, dysregulation of a MET gene, a MET protein, or expression or activity, can be a result of a gene translocation of one MET gene with another non-MET gene.

The term "wildtype MET" or "wild-type MET" describes a nucleic acid (e.g., a MET gene or a MET mRNA) or protein (e.g., a MET protein) that is found in a subject that does not have a MET-associated cancer (and optionally also does not have an increased risk of developing a MET-associated cancer and/or is not suspected of having a MET-associated cancer), or is found in a cell or tissue from a subject that does not have a MET-associated cancer (and optionally also does not have an increased risk of developing a MET-associated cancer and/or is not suspected of having a MET-associated cancer). The term "MET-associated cancer" as used herein refers to cancers associated with or having a dysregulation of a MET gene, a MET kinase, or expression or activity, or level of any of the same.

In some embodiments, compounds of Formula (I) or a pharmaceutically acceptable salt, amorphous form, polymorph form, or pharmaceutical composition (e.g., any of the solid or liquid formulations described herein) thereof are useful in treating patients that develop cancers with RET inhibitor resistance mutations (e.g., that result in an increased resistance to a first RET inhibitor, e.g., a substitution at amino acid position 804, e.g., V804M, V804L, or V804E, a substitution at amino acid position 810, e.g., G810S, G810R, G810C, G810A, G810V, and G810D, and/or one or more RET inhibitor resistance mutations listed in Tables 3 and 4) by either dosing in combination or as a subsequent or additional (e.g., follow-up) therapy to existing drug treatments (e.g., other RET kinase inhibitors; e.g., first and/or second RET kinase inhibitors). Exemplary first and second RET kinase inhibitors are described herein. In some embodiments, a first or second RET kinase inhibitor can be selected from the group consisting of cabozantinib, vandetanib, alectinib, apatinib, sitravatinib, sorafenib, lenvatinib, ponatinib, dovitinib, sunitinib, foretinib, BLU667, and BLU6864.

In some embodiments, compounds of Formula (I) or a pharmaceutically acceptable salt, amorphous form, polymorph form, or pharmaceutical composition (e.g., any of the solid or liquid formulations described herein) thereof are useful for treating a cancer that has been identified as having one or more RET inhibitor resistance mutations (that result in an increased resistance to a first or second RET inhibitor, e.g., a substitution at amino acid position 804, e.g., V804M, V804L, or V804E, or e.g., a substitution at amino acid position 810, e.g., G810S, G810R, G810C, G810A, G810V, and G810D). In some embodiments, the one or more RET inhibitor resistance mutations occur in a nucleic acid sequence encoding a RET fusion protein (e.g. any of the RET gene fusion proteins described in Table 1) resulting in a RET fusion protein that exhibits RET kinase inhibitor resistance. In some embodiments, the one or more RET inhibitor resistance mutations occurs in a nucleic acid sequence encoding a mutant RET protein (e.g. a mutant RET protein having any of the mutations described in Table 2) resulting in a mutant RET protein that exhibits RET kinase resistance. Non-limiting examples of RET inhibitor resistance mutations are listed in Tables 3 and 4.

TABLE 3

RET Inhibitor Resistance Mutations
Exemplary RET Resistance Mutations

Amino acid position 634 (e.g., C634W)[10]
Amino acid position 732 (e.g., E732K)[7]
Amino acid position 788 (e.g., I788N)[8]
Amino acid position 790 (e.g., L790F)[9]
Amino acid position 804 (e.g., V804M[1,2], V804L[1,2], V804E[6])
Amino acid position 778/804[13]
Amino acid position 804/805 (e.g., V804M/E805K)[3]
Amino acid position 806 (e.g., Y806C[4,6], Y806E[4], Y806S[6], Y806H[6], Y806N[6])
Amino acid position 804/806 (e.g., V804M/Y806C)[11]

TABLE 3-continued

RET Inhibitor Resistance Mutations
Exemplary RET Resistance Mutations

Amino acid position 810 (e.g., G810A[5], G810R[6], G810S[6], G810C, G810V, and G810D)
Amino acid position 865 (e.g., L865V[6])
Amino acid position 870 (e.g., L870F[6])
Amino acid position 891 (e.g., S891A)[10]
Amino acid position 904 (e.g., S904F)[12]
Amino acid position 804/904 (e.g., V804M/S904C)[11]
Amino acid position 918 (e.g., M918T)[10]

[1]Yoon et al., *J. Med. Chem.* 59(1): 358-73, 2016.
[2]U.S. Pat. No. 8,629,135.
[3]Cranston, et al., *Cancer Res.* 66(20): 10179-87, 2006.
[4]Carlomagno, et al., *Endocr. Rel. Cancer* 16(1): 233-41, 2009.
[5]Huang et al., Mol. Cancer Ther., 2016 Aug. 5. pii: molcanther.0258.2016. [Epub ahead of print].
[6]PCT Patent Application Publication No. WO 2016/127074.
[7]Mamedova et al., Summer Undergraduate Research Programs (SURP) Student Abstracts, University of Oklahoma Health Sciences Center, 2016.
[8]Plenker et al., *Sci. Transl. Med.*, 9(394), doi: 10.1126/scitranslmed.aah6144, 2017.
[9]Kraft et al, *Cancer Research*, 2017, Vol. 77, No. 13, Supp. Supplement 1. Abstract Number: 4882; American Association for Cancer Research Annual Meeting 2017. Washington, DC, United States. 1 Apr. 2017-5 Apr. 2017.
[10]U.S. Patent Application Publication No. 2018/0022732.
[11]Roskoski and Sadeghi-Nejad, *Pharmacol. Res.*, 128, 1-17. doi: 10.1016/j.phrs.2017.12.021, 2018.
[12]Nakaoku, et al. *Nat Commun*, 9(1), 625. doi: 10.1038/s41467-018-02994-7, 2018.
[13]Roy et al. *Oncologist*, 18(10): 1093-1100. doi: 10.1634/theoncologist.2013-0053, 2013.

TABLE 4

Additional Exemplary Amino Acid Positions of RET Inhibitor Resistance Mutations

| RET Amino Acid and Position | Exemplary Mutation | Mechanistic Resistance Rationale |
|---|---|---|
| L730 | P | Steric hindrance and/or active conformational effect |
| G731 | V | Steric hindrance and/or active conformational effect |
| E732 | K | Steric hindrance and/or active conformational effect |
| G733 | V | Steric hindrance and/or active conformational effect |
| E734 | K | Steric hindrance and/or active conformational effect |
| L760 | M | Active conformational effect |
| K761 | E | Active conformational effect |
| E762 | K | Active conformational effect |
| N763 | D | Active conformational effect |
| A764 | V | Active conformational effect |
| S765 | N | Active conformational effect |
| P766 | A | Active conformational effect |
| S767 | C | Active conformational effect |
| E768 | K | Active conformational effect |
| L779 | M | Steric hindrance and/or active conformational effect |
| I788 | M | Steric hindrance and/or active conformational effect |
| M868 | R | Steric hindrance and/or active conformational effect |
| K869 | E | Steric hindrance and/or active conformational effect |
| L870 | Q | Steric hindrance and/or active conformational effect |
| V871 | M | Steric hindrance and/or active conformational effect |
| H872 | R | Steric hindrance and/or active conformational effect |
| R873 | P | Steric hindrance and/or active conformational effect |
| D874 | Y | Steric hindrance and/or active conformational effect |
| L881 | R | Steric hindrance and/or active conformational effect |
| L895 | M | Active conformational effect |
| S896 | N | Active conformational effect |
| R897 | C | Active conformational effect |
| D898 | Y | Active conformational effect |
| V899 | G | Active conformational effect |
| Y900 | D | Active conformational effect |
| E901 | K | Active conformational effect |
| E902 | K | Active conformational effect |
| D903 | Y | Active conformational effect |
| S904 | C | Active conformational effect |
| Y905 | D | Active conformational effect |
| V906 | M | Active conformational effect |
| K907 | E | Active conformational effect |
| R908 | P | Active conformational effect |
| S909 | C | Active conformational effect |
| Q910 | R | Active conformational effect |
| G911 | C | Active conformational effect |
| R912 | P | Active conformational effect |

The oncogenic role of RET was first described in papillary thyroid carcinoma (PTC) (Grieco et al., *Cell*, 1990, 60, 557-63), which arises from follicular thyroid cells and is the most common thyroid malignancy. Approximately 20-30% of PTC harbor somatic chromosomal rearrangements (translocations or inversions) linking the promoter and the 5' portions of constitutively expressed, unrelated genes to the RET tyrosine kinase domain (Greco et al., Q. *J. Nucl. Med. Mol. Imaging*, 2009, 53, 440-54), therefore driving its ectopic expression in thyroid cells. Fusion proteins generated by such rearrangements are termed "RET/PTC" proteins. For example, RET/PTC 1 is a fusion between CCDD6 and RET that is commonly found in papillary thyroid carcinomas. Similarly, both RET/PTC3 and RET/PTC4 are fusions of ELE1 and RET that are commonly found in papillary thyroid carcinomas, although the fusion events resulting RET/PTC3 and RET/PTC4 lead to different proteins with different molecular weights (see e.g., Fugazzola et al., *Oncogene*, 13(5):1093-7, 1996). Some RET fusions associated with PTC are not referred to as "RET/PTC", but instead are referred to as the fusion protein inself. For example, fusion between RET and both ELKS and PCM1 are found in PTCs, but the fusion proteins are referred to as ELKS-RET and PCM1-RET (see e.g., Romei and Elisei, *Front. Endocrinol. (Lausanne)*, 3:54, doi: 10.3389/fendo.2012.00054, 2012). The role of RET-PTC rearrangements in the pathogenesis of PTC has been confirmed in transgenic mice (Santoro et al., *Oncogene*, 1996, 12, 1821-6). To date, a variety of fusion partners have been identified, from PTC and other cancer types, all providing a protein/protein interaction domain that induces ligand-independent RET dimerization and constitutive kinase activity (see, e.g., Table 1). Recently, a 10.6 Mb pericentric inversion in chromosome 10, where RET gene maps, has been identified in about 2% of lung adenocarcinoma patients, generating different variants of the chimeric gene KIF5B-RET (Ju et al., *Genome Res.*, 2012, 22, 436-45; Kohno et al., 2012, *Nature Med.*, 18, 375-7; Takeuchi et al., *Nature Med.*, 2012, 18, 378-81; Lipson et al., 2012, *Nature Med.*, 18, 382-4). The fusion transcripts are highly expressed and all the resulting chimeric proteins contain the N-terminal portion of the coiled-coil region of KIF5B, which mediates homodimerization, and the entire RET kinase domain. None of RET positive patients harbor other known oncogenic alterations (such as EGFR or K-Ras mutation, ALK translocation), supporting the possibility that KIF5B-RET fusion could be a driver mutation of lung adenocarcinoma. The oncogenic potential of KIF5B-RET has been confirmed by transfecting the fusion gene into cultured cell lines: similarly to what has been observed with RET-PTC fusion proteins, KIF5B-RET is constitutively phosphorylated and induces NIH-3T3 transformation and IL-3 independent growth of BA-F3 cells. However, other RET fusion proteins have been identified in lung adenocarcinoma patients, such as the CCDC6-RET fusion protein, which has been found to play a key role in the proliferation of the human lung adenocarcinoma cell line LC-2/ad (*Journal of Thoracic Oncology*, 2012, 7(12):1872-1876). RET inhibitors have been shown to be useful in treating lung cancers involving RET rearrangements (Drilon, A. E. et al. *J Clin Oncol* 33, 2015 (suppl; abstr 8007)). RET fusion proteins have also been identified in patients having colorectal cancer (Song Eun-Kee, et al. *International Journal of Cancer,* 2015, 136: 1967-1975).

Besides rearrangements of the RET sequence, gain of function point mutations of RET proto-oncogene are also driving oncogenic events, as shown in medullary thyroid carcinoma (MTC), which arises from parafollicular calcitonin-producing cells (de Groot, et al., *Endocrine Rev.,* 2006, 27, 535-60; Wells and Santoro, *Clin. Cancer Res.,* 2009, 15, 7119-7122). Around 25% of MTC are associated with multiple endocrine neoplasia type 2 (MEN2), a group of inherited cancer syndromes affecting neuroendocrine organs caused by germline activating point mutations of RET. In MEN2 subtypes (MEN2A, MEN2B and Familial MTC/FMTC) RET gene mutations have a strong phenotype-genotype correlation defining different MTC aggressiveness and clinical manifestations of the disease. In MEN2A syndrome mutations involve one of the six cysteine residues (mainly C634) located in the cysteine-rich extracellular region, leading to ligand-independent homodimerization and constitutive RET activation. Patients develop MTC at a young age (onset at 5-25 years) and may also develop pheochromocytoma (50%) and hyperparathyroidism. MEN2B is mainly caused by M918T mutation, which is located in the kinase domain. This mutation constitutively activates RET in its monomeric state and alters substrate recognition by the kinase. MEN2B syndrome is characterized by an early onset (<1 year) and very aggressive form of MTC, pheochromocytoma (50% of patients) and ganglioneuromas. In FMTC the only disease manifestation is MTC, usually occurring at an adult age. Many different mutations have been detected, spanning the entire RET gene. The remaining 75% of MTC cases are sporadic and about 50% of them harbor RET somatic mutations: the most frequent mutation is M918T that, as in MEN2B, is associated with the most aggressive phenotype. Somatic point mutations of RET have also been described in other tumors such as colorectal cancer (Wood et al., *Science,* 2007, 318, 1108-13) and small cell lung carcinoma (*Jpn. J Cancer Res.,* 1995, 86, 1127-30). In some embodiments, the MTC is RET-fusion positive MTC.

RET signaling components have been found to be expressed in primary breast tumors and to functionally interact with estrogen receptor-cc pathway in breast tumor cell lines (Boulay et al., *Cancer Res.* 2008, 68, 3743-51; Plaza-Menacho et al., *Oncogene,* 2010, 29, 4648-57), while RET expression and activation by GDNF family ligands could play an important role in perineural invasion by different types of cancer cells (Ito et al., *Surgery,* 2005, 138, 788-94; Gil et al., J. Natl. Cancer Inst., 2010, 102, 107-18; Iwahashi et al., Cancer, 2002, 94, 167-74).

RET is also expressed in 30-70% of invasive breast cancers, with expression being relatively more frequent in estrogen receptor-positive tumors (Plaza-Menacho, I., et al., *Oncogene,* 2010, 29, 4648-4657; Esseghir, S., et al., *Cancer Res.,* 2007, 67, 11732-11741; Morandi, A., et al., *Cancer Res.,* 2013, 73, 3783-3795; Gattelli, A., *EMBO Mol. Med.,* 2013, 5, 1335-1350).

The identification of RET rearrangements has been reported in a subset of (patient-derived xenograft) PDX established from colorectal cancer. Although the frequency of such events in colorectal cancer patients remains to be defined, these data suggest a role of RET as a target in this indication (Gozgit et al., AACR Annual Meeting 2014). Studies have shown that the RET promoter is frequently methylated in colorectal cancers, and heterozygous missense mutations, which are predicted to reduce RET expression, are identified in 5-10% of cases, which suggests that RET might have some features of a tumor suppressor in sporadic colon cancers (Luo, Y., et al., *Oncogene,* 2013, 32, 2037-2047; Sjoblom, T., et al., *Science,* 2006, 268-274; Cancer Genome Atlas Network, *Nature,* 2012, 487, 330-337).

An increasing number of tumor types are now being shown to express substantial levels of wild-type RET kinase that could have implications for tumor progression and spread. RET is expressed in 50-65% of pancreatic ductal carcinomas, and expression is more frequent in metastatic and higher grade tumors (Ito, Y, et al., *Surgery,* 2005, 138, 788-794; Zeng, Q., et al., *Int. Med. Res.* 2008, 36, 656-664).

In neoplasms of hematopoietic lineages, RET is expressed in acute myeloid leukemia (AML) with monocytic differentiation, as well as in CMML (Gattei, V. et al., *Blood,* 1997, 89, 2925-2937; Gattei, V., et al., *Ann. Hematol,* 1998, 77, 207-210; Camos, M., *Cancer Res.* 2006, 66, 6947-6954). Recent studies have identified rare chromosomal rearrangements that involve RET in patients with chronic myelomonocytic leukemia (CMML). CMML is frequently associated with rearrangements of several tyrosine kinases, which result in the expression of chimeric cytosolic oncoproteins that lead to activation of RAS pathways (Kohlmann, A., et al., *J. Clin. Oncol.* 2010, 28, 2858-2865). In the case of RET, gene fusions that link RET with BCR (BCR-RET) or with fibroblast growth factor receptor 1 oncogene partner (FGFR1OP-RET) were transforming in early hematopoietic progenitor cells and could shift maturation of these cells towards monocytic paths, probably through the initiation of RET-mediated RAS signaling (Ballerini, P., et al., *Leukemia,* 2012, 26, 2384-2389).

RET expression has also been shown to occur in several other tumor types, including prostate cancer, small-cell lung carcinoma, melanoma, renal cell carcinoma, and head and neck tumors (Narita, N., et al., *Oncogene,* 2009, 28, 3058-3068; Mulligan, L. M., et al., *Genes Chromosomes Cancer,* 1998, 21, 326-332; Flavin, R., et al., *Urol. Oncol.,* 2012, 30, 900-905; Dawson, D. M., *J Natl Cancer Inst,* 1998, 90, 519-523).

In neuroblastoma, RET expression and activation by GFLs has roles in tumor cell differentiation, potentially collaborating with other neurotrophic factor receptors to down regulate N-Myc, the expression of which is a marker of poor prognosis (Hofstra, R. M., W., et al., *Hum. Genet.* 1996, 97, 362-364; Petersen, S. and Bogenmann, E., *Oncogene,* 2004, 23, 213-225; Brodeur, G. M., *Nature Ref. Cancer,* 2003, 3, 203-216).

Multitargeted inhibitors which cross react with RET are known (Borrello, M. G., et al., *Expert Opin. Ther. Targets,* 2013, 17(4), 403-419; International Patent Application Nos. WO 2014/141187, WO 2014/184069, and WO 2015/079251). Such multitargeted inhibitors (or multikinase inhibitors or MKIs) can also be associated with development of RET inhibitor resistance mutations. See, for example, Q. Huang et al., "Preclinical Modeling of KIF5B-RET Fusion Lung Adenocarcinoma.," *Mol. Cancer Ther.*, no. 18, pp. 2521-2529, 2016; Yasuyuki Kaneta et al., Abstract B173: Preclinical characterization and antitumor efficacy of DS-5010, a highly potent and selective RET inhibitor, *Mol Cancer Ther* Jan. 1, 2018 (17) (1 Supplement) B173; DOI:10.1158/1535-7163.TARG-17-B173, both of which are incorporated by reference in their entirety herein.

Accordingly, provided herein are methods for treating a patient diagnosed with (or identified as having) a cancer that include administering to the patient a therapeutically effective amount of the compound of Formula (I) or a pharmaceutically acceptable salt, amorphous form, polymorph form, or pharmaceutical composition (e.g., any of the solid or liquid formulations described herein) thereof. Also provided herein are methods for treating a patient identified or diagnosed as having a RET-associated cancer that include administering to the patient a therapeutically effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof. In some embodiments, the patient that has been identified or diagnosed as having a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods for treating cancer in a patient in need thereof, the method comprising: (a) detecting a RET-associated cancer in the patient; and (b) administering to the patient a therapeutically effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof. Some embodiments of these methods further include administering to the subject another anticancer agent (e.g., a second RET inhibitor or an immunotherapy). In some embodiments, the subject was previously treated with a first RET inhibitor or previously treated with another anticancer treatment, e.g., at least partial resection of the tumor or radiation therapy. In some embodiments, the patient is determined to have a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods of treating a patient that include performing an assay on a sample obtained from the patient to determine whether the patient has a dysregulation of a RET gene, a RET kinase, or expression or activity or level of any of the same, and administering (e.g., specifically or selectively administering) a therapeutically effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof to the patient determined to have a dysregulation of a RET gene, a RET kinase, or expression or activity or level of any of the same. Some embodiments of these methods further include administering to the subject another anticancer agent (e.g., a second RET inhibitor or immunotherapy). In some embodiments of these methods, the subject was previously treated with a first RET inhibitor or previously treated with another anticancer treatment, e.g., at least partial resection of a tumor or radiation therapy. In some embodiments, the patient is a patient suspected of having a RET-associated cancer, a patient presenting with one or more symptoms of a RET-associated cancer, or a patient having an elevated risk of developing a RET-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a RET gene, a RET kinase, or expression or activity or level of any of the same includes one or more RET inhibitor resistance mutations.

Also provided is the compound of Formula (I) or a pharmaceutically acceptable salt, amorphous form, polymorph form, or pharmaceutical composition (e.g., any of the solid or liquid formulations described herein) thereof or a pharmaceutical composition thereof for use in treating a RET-associated cancer in a patient identified or diagnosed as having a RET-associated cancer through a step of performing an assay (e.g., an in vitro assay) on a sample obtained from the patient to determine whether the patient has a dysregulation of a RET gene, a RET kinase, or expression or activity or level of any of the same, where the presence of a dysregulation of a RET gene, a RET kinase, or expression or activity or level of any of the same, identifies that the patient has a RET-associated cancer. Also provided is the use of the compound of Formula (I) or a pharmaceutically acceptable salt, amorphous form, polymorph form, or pharmaceutical composition (e.g., any of the solid or liquid formulations described herein) thereof for the manufacture of a medicament for treating a RET-associated cancer in a patient identified or diagnosed as having a RET-associated cancer through a step of performing an assay on a sample obtained from the patient to determine whether the patient has a dysregulation of a RET gene, a RET kinase, or expression or activity or level of any of the same where the presence of dysregulation of a RET gene, a RET kinase, or expression or activity or level of any of the same, identifies that the patient has a RET-associated cancer. Some embodiments of any of the methods or uses described herein further include recording in the patient's clinical record (e.g., a computer readable medium) that the patient is determined to have a dysregulation of a RET gene, a RET kinase, or expression or activity or level of any of the same, through the performance of the assay, should be administered the compound of Formula (I) or a pharmaceutically acceptable salt, amorphous form, polymorph form, or pharmaceutical composition (e.g., any of the solid or liquid formulations described herein) thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. In some embodiments, the dysregulation of a RET gene, a RET kinase, or expression or activity or level of any of the same includes one or more RET inhibitor resistance mutations.

Also provided is the compound of Formula (I) or a pharmaceutically acceptable salt, amorphous form, polymorph form, or pharmaceutical composition (e.g., any of the solid or liquid formulations described herein) thereof, for use in the treatment of a cancer in a patient in need thereof or a patient identified or diagnosed as having a RET-associated cancer. Also provided is the use of the compound of Formula (I) or a pharmaceutically acceptable salt, amorphous form, polymorph form, or pharmaceutical composition (e.g., any of the solid or liquid formulations described herein) thereof for the manufacture of a medicament for treating a cancer in a patient identified or diagnosed as having a RET-associated cancer. In some embodiments, the cancer is a RET-associated cancer, for example, a RET-associated cancer having one or more RET inhibitor resistance mutations. In some embodiments, a patient is identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the patient. As provided herein, a RET-associated cancer includes those described herein and known in the art.

Also provided herein are methods for treating a pediatric patient diagnosed with (or identified as having) a cancer that include administering to the pediatric patient a therapeutically effective amount of the compound of Formula (I) or a pharmaceutically acceptable salt, amorphous form, polymorph form, or pharmaceutical composition (e.g., any of the solid or liquid formulations described herein) thereof. Also provided herein are methods for treating a pediatric patient identified or diagnosed as having a RET-associated cancer that include administering to the pediatric patient a therapeutically effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof. In some embodiments, the pediatric patient that has been identified or diagnosed as having a RET-associated cancer through the use of a regulatory agency-approved, e.g., FDA-approved test or assay for identifying dysregulation of a RET gene, a RET kinase, or expression or activity or level of any of the same, in a pediatric patient or a biopsy sample from the pediatric patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods for treating cancer in a pediatric patient in need thereof, the method comprising: (a) determining if the cancer in the pediatric patient is a RET-associated cancer; and (b) if the cancer is determined to be a RET-associated cancer, administering to the pediatric patient a therapeutically effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof. Some embodiments of these methods further include administering to the subject another anticancer agent (e.g., a second RET inhibitor or immunotherapy). In some embodiments, the subject was previously treated with a first RET inhibitor or previously treated with another anticancer treatment, e.g., resection of the tumor or radiation therapy. In some embodiments, the pediatric patient is determined to have a RET-associated cancer through the use of a regulatory agency-approved, e.g., FDA-approved test or assay for identifying dysregulation of a RET gene, a RET kinase, or expression or activity or level of any of the same, in a pediatric patient or a biopsy sample from the pediatric patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods of treating a pediatric patient that include performing an assay on a sample obtained from the pediatric patient to determine whether the pediatric patient has a dysregulation of a RET gene, a RET kinase, or expression or activity or level of any of the same, and administering (e.g., specifically or selectively administering) a therapeutically effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof to the pediatric patient determined to have a dysregulation of a RET gene, a RET kinase, or expression or activity or level of any of the same. Some embodiments of these methods further include administering to the subject another anticancer agent (e.g., a second RET inhibitor or immunotherapy). In some embodiments of these methods, the subject was previously treated with a first RET inhibitor or previously treated with another anticancer treatment, e.g., resection of a tumor or radiation therapy. In some embodiments, the pediatric patient is a pediatric patient suspected of having a RET-associated cancer, a pediatric patient presenting with one or more symptoms of a RET-associated cancer, or a pediatric patient having an elevated risk of developing a RET-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. Additional, non-limiting assays that may be used in these methods are described herein. Additional assays are also known in the art. In some embodiments, the dysregulation of a RET gene, a RET kinase, or expression or activity or level of any of the same includes one or more RET inhibitor resistance mutations.

Also provided is the compound of Formula (I) or a pharmaceutically acceptable salt, amorphous form, polymorph form, or pharmaceutical composition (e.g., any of the solid or liquid formulations described herein) thereof or a pharmaceutical composition thereof for use in treating a RET-associated cancer in a pediatric patient identified or diagnosed as having a RET-associated cancer through a step of performing an assay (e.g., an in vitro assay) on a sample obtained from the pediatric patient to determine whether the pediatric patient has a dysregulation of a RET gene, a RET kinase, or expression or activity or level of any of the same, where the presence of a dysregulation of a RET gene, a RET kinase, or expression or activity or level of any of the same, identifies that the pediatric patient has a RET-associated cancer. Also provided is the use of the compound of Formula (I) or a pharmaceutically acceptable salt, amorphous form, polymorph form, or pharmaceutical composition (e.g., any of the solid or liquid formulations described herein) thereof for the manufacture of a medicament for treating a RET-associated cancer in a pediatric patient identified or diagnosed as having a RET-associated cancer through a step of performing an assay on a sample obtained from the pediatric patient to determine whether the pediatric patient has a dysregulation of a RET gene, a RET kinase, or expression or activity or level of any of the same where the presence of dysregulation of a RET gene, a RET kinase, or expression or activity or level of any of the same, identifies that the pediatric patient has a RET-associated cancer. Some embodiments of any of the methods or uses described herein further include recording in the pediatric patient's clinical record (e.g., a computer readable medium) that the pediatric patient is determined to have a dysregulation of a RET gene, a RET kinase, or expression or activity or level of any of the same, through the performance of the assay, should be administered the compound of Formula (I) or a pharmaceutically acceptable salt, amorphous form, polymorph form, or pharmaceutical composition (e.g., any of the solid or liquid formulations described herein) thereof. In some embodiments, the assay utilizes next generation sequencing, pyro-sequencing, immunohistochemistry, or break apart FISH analysis. In some embodiments, the assay is a regulatory agency-approved assay, e.g., FDA-approved kit. In some embodiments, the dysregulation of a RET gene, a RET kinase, or expression or activity or level of any of the same includes one or more RET inhibitor resistance mutations.

Also provided is the compound of Formula (I) or a pharmaceutically acceptable salt, amorphous form, polymorph form, or pharmaceutical composition (e.g., any of the solid or liquid formulations described herein) thereof for use in the treatment of a cancer in a pediatric patient in need thereof or a pediatric patient identified or diagnosed as having a RET-associated cancer. Also provided is the use of the compound of Formula (I) or a pharmaceutically acceptable salt, amorphous form, polymorph form, or pharmaceutical composition (e.g., any of the solid or liquid formulations described herein) thereof for the manufacture of a medicament for treating a cancer in a pediatric patient identified or diagnosed as having a RET-associated cancer. In some embodiments, the cancer is a RET-associated cancer, for example, a RET-associated cancer having one or more RET inhibitor resistance mutations. In some embodiments, a pediatric patient is identified or diagnosed as having a RET-associated cancer through the use of a regulatory agency-approved, e.g., FDA-approved, kit for identifying dysregulation of a RET gene, a RET kinase, or expression or activity or level of any of the same, in a pediatric patient or a biopsy sample from the pediatric patient. As provided herein, a RET-associated cancer includes those described herein and known in the art.

In some embodiments of any of the methods or uses described herein, the patient has been identified or diagnosed as having a cancer with a dysregulation of a RET gene, a RET kinase, or expression or activity or level of any of the same. In some embodiments of any of the methods or uses described herein, the patient has a tumor that is positive for a dysregulation of a RET gene, a RET kinase, or expression or activity or level of any of the same. In some embodiments of any of the methods or uses described herein, the patient can be a patient with a tumor(s) that is positive for a dysregulation of a RET gene, a RET kinase, or expression or activity or level of any of the same. In some embodiments of any of the methods or uses described herein, the patient can be a patient whose tumors have a dysregulation of a RET gene, a RET kinase, or expression or activity or level of any of the same. In some embodiments of any of the methods or uses described herein, the patient is suspected of having a RET-associated cancer (e.g., a cancer having one or more RET inhibitor resistance mutations). In some embodiments, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions/deletions. Non-limiting examples of RET kinase protein point mutations/insertions/deletions are described in Tables 2 and 2a. In some embodiments, the RET kinase protein point mutations/insertions/deletions are selected from the group consisting of M918T, M918V, C634W, V804L, V804M, G810S, and G810R. In some embodiments, the dysregulation of a RET gene, a RET kinase, or the expression or activity or level of any of the same includes one or more RET inhibitor resistance mutations. Non-limiting examples of RET inhibitor resistance mutations are described in Tables 3 and 4. In some embodiments, the RET inhibitor resistance mutation is V804M. In some embodiments, the RET inhibitor resistance mutation is G810S. In some embodiments, the RET inhibitor resistance mutation is G810R. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

In some embodiments of any of the methods or uses described herein, the patient has a clinical record indicating that the patient has a tumor that has a dysregulation of a RET gene, a RET kinase, or expression or activity or level of any of the same (e.g., a tumor having one or more RET inhibitor resistance mutations). In some embodiments, the clinical record indicates that the patient should be treated with one or more of the compound of Formula (I) or a pharmaceutically acceptable salt, amorphous form, polymorph form, or pharmaceutical composition (e.g., any of the solid or liquid formulations described herein) thereof. In some embodiments, the cancer with a dysregulation of a RET gene, a RET kinase, or expression or activity or level of any of the same is a cancer having one or more RET inhibitor resistance mutations. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

Also provided are methods of treating a patient that include administering a therapeutically effective amount of the compound of Formula (I) or a pharmaceutically acceptable salt, amorphous form, polymorph form, or pharmaceutical composition (e.g., any of the solid or liquid formulations described herein) thereof to a patient having a clinical record that indicates that the patient has a dysregulation of a RET gene, a RET kinase, or expression or activity or level of any of the same. Also provided is the use of the compound of Formula (I) or a pharmaceutically acceptable salt, amorphous form, polymorph form, or pharmaceutical composition (e.g., any of the solid or liquid formulations described herein) thereof for the manufacture of a medicament for treating a RET-associated cancer in a patient having a clinical record that indicates that the patient has a dysregulation of a RET gene, a RET kinase, or expression or activity or level of any of the same. Some embodiments of these methods and uses can further include: a step of performing an assay (e.g., an in vitro assay) on a sample obtained from the patient to determine whether the patient has a dysregulation of a RET gene, a RET kinase, or expression or activity or level of any of the same, and recording the information in a patient's clinical file (e.g., a computer readable medium) that the patient has been identified to have a dysregulation of a RET gene, a RET kinase, or expression or activity or level of any of the same. In some embodiments, the assay is an in vitro assay. For example, an assay that utilizes next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the dysregulation of a RET gene, RET kinase, or expression or activity or level of any of the same includes one or more RET inhibitor resistance mutations.

Also provided herein is a method of treating a subject. In some embodiments, the method includes performing an assay on a sample obtained from the subject to determine whether the subject has a dysregulation of a RET gene, a RET protein, or expression or level of any of the same. In some such embodiments, the method also includes administering to a subject determined to have a dysregulation of a RET gene, a RET protein, or expression or activity, or level of any of the same a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the dysregulation in a RET gene, a RET kinase protein, or expression or activity of the same is a gene or chromosome translocation that results in the expression of a RET fusion protein (e.g., any of the RET fusion proteins described herein). In some embodiments, the RET fusion can be selected from a KIF5B-RET fusion and a CCDC6-RET fusion. In some embodiments, the dysregulation in a RET gene, a RET kinase protein, or expression or activity or level of any of the same is one or more point mutation in the RET gene (e.g., any of the one or more of the RET point mutations described herein). The one or more point mutations in a RET gene can result, e.g., in the translation of a RET protein having one or more of the following amino acid substitutions: M918T, M918V, C634W, V804L, V804M, G810S, and G810R. In some embodiments, the dysregulation in a RET gene, a RET kinase protein, or expression or activity or level of any of the same is one or more RET inhibitor resistance mutations (e.g., any combination of the one or more RET inhibitor resistance mutations described herein). Some embodiments of these methods further include administering to the subject another anticancer agent (e.g., a second RET inhibitor or immunotherapy).

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and craniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the patient has previously been treated with another anticancer agent, e.g., another RET inhibitor (e.g., a compound that is not the compound of Formula (I) or a pharmaceutically acceptable salt, amorphous form, polymorph form, or pharmaceutical composition (e.g., any of the solid or liquid formulations described herein) thereof) or a multi-kinase inhibitor. In some embodiments, the brain tumor is a metastatic brain tumor. In some embodiments, the patient has previously been treated with another anticancer agent, e.g., another RET inhibitor (e.g., a compound that is not a compound of Formula (I) or a pharmaceutically acceptable salt, amorphous form, polymorph form, or pharmaceutical composition (e.g., any of the solid or liquid formulations described herein) thereof) or a multi-kinase inhibitor.

Also provided are methods (e.g., in vitro methods) of selecting a treatment for a patient identified or diagnosed as having a RET-associated cancer. Some embodiments can further include administering the selected treatment to the patient identified or diagnosed as having a RET-associated cancer. For example, the selected treatment can include administration of a therapeutically effective amount of the compound of Formula (I) or a pharmaceutically acceptable salt, amorphous form, polymorph form, or pharmaceutical composition (e.g., any of the solid or liquid formulations described herein) thereof. Some embodiments can further include a step of performing an assay on a sample obtained from the patient to determine whether the patient has a dysregulation of a RET gene, a RET kinase, or expression or activity or level of any of the same, and identifying and diagnosing a patient determined to have a dysregulation of a RET gene, a RET kinase, or expression or activity or level of any of the same, as having a RET-associated cancer. In some embodiments, the cancer is a RET-associated cancer having one or more RET inhibitor resistance mutations. In some embodiments, the patient has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the patient. In some embodiments, the RET-associated cancers is a cancer described herein or known in the art. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided herein are methods of selecting a treatment for a patient, wherein the methods include a step of performing an assay on a sample obtained from the patient to determine whether the patient has a dysregulation of a RET gene, a RET kinase, or expression or activity or level of any of the same (e.g., one or more RET inhibitor resistance mutations), and identifying or diagnosing a patient determined to have a dysregulation of a RET gene, a RET kinase, or expression or activity or level of any of the same, as having a RET-associated cancer. Some embodiments further include administering the selected treatment to the patient identified or diagnosed as having a RET-associated cancer. For example, the selected treatment can include administration of a therapeutically effective amount of the compound of Formula (I) or a pharmaceutically acceptable salt, amorphous form, polymorph form, or pharmaceutical composition (e.g., any of the solid or liquid formulations described herein) thereof to the patient identified or diagnosed as having a RET-associated cancer. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided are methods of selecting a patient for treatment, wherein the methods include selecting, identifying, or diagnosing a patient having a RET-associated cancer, and selecting the patient for treatment including administration of a therapeutically-effective amount of the compound of Formula (I) or a pharmaceutically acceptable salt, amorphous form, polymorph form, or pharmaceutical composition (e.g., any of the solid or liquid formulations described herein) thereof. In some embodiments, identifying or diagnosing a patient as having a RET-associated cancer can include a step of performing an assay on a sample obtained from the patient to determine whether the patient has a dysregulation of a RET gene, a RET kinase, or expression or activity or level of any of the same, and identifying or diagnosing a patient determined to have a dysregulation of a RET gene, a RET kinase, or expression or activity or level of any of the same, as having a RET-associated cancer. In some embodiments, the method of selecting a patient for treatment can be used as a part of a clinical study that includes administration of various treatments of a RET-associated cancer. In some embodiments, a RET-associated cancer is a cancer having one or more RET inhibitor resistance mutations. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the dysregulation of the RET gene, the RET kinase, or expression or activity or level of any of the same includes one or more RET inhibitor resistance mutations.

In some embodiments of any of the methods or uses described herein, an assay used to determine whether the patient has a dysregulation of a RET gene, or a RET kinase, or expression or activity or level of any of the same, using a sample from a patient can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a RET gene, a RET kinase, or expression or activity or levels of any of the same (see, e.g., the references cited herein). In some embodiments, the dysregulation of the RET gene, the RET kinase, or expression or activity or level of any of the same includes one or more RET inhibitor resistance mutations. In some embodiments, the sample is a biological sample or a biopsy sample (e.g., a paraffin-embedded biopsy sample) from the patient. In some embodiments, the patient is a patient suspected of having a RET-associated cancer, a patient having one or more symptoms of a RET-associated cancer, and/or a patient that has an increased risk of developing a RET-associated cancer).

In some embodiments, dysregulation of a RET gene, a RET kinase, or the expression or activity or level of any of the same can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.,* 3(3):36, 2016. Liquid biopsy methods can be used to detect total tumor burden and/or the dysregulation of a RET gene, a RET kinase, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a RET gene, a RET kinase, or the expression or activity or level of any of the same. In some embodiments, liquid biopsies can be used to detect the presence of dysregulation of a RET gene, a RET kinase, or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a RET gene, a RET kinase, or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially-available testing panels designed to detect dysregulation of a RET gene, a RET kinase, or the expression or activity or level of any of the same). Liquid biopsies can be used to detect dysregulation of a RET gene, a RET kinase, or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a liquid biopsy can be used to detect a genetic mutation that develops after development of the primary genetic mutation (e.g., a resistance mutation that arises in response to a treatment administered to a subject). In some embodiments, a dysregulation of a RET gene, a RET kinase, or the expression or activity or level of any of the same identified using a liquid biopsy is also present in a cancer cell that is present in the subject (e.g., in a tumor). In some embodiments, any of the types of dysregulation of a RET gene, a RET kinase, or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a RET gene, a RET kinase, or the expression or activity or level of any of the same in the subject can indicate that the subject will be responsive to a treatment that includes administration of a compound of Formula (I) or a pharmaceutically acceptable salt, amorphous form, polymorph form, or pharmaceutical composition (e.g., any of the solid or liquid formulations described herein) thereof.

Liquid biopsies can be performed at multiple times during a course of diagnosis, a course of monitoring, and/or a course of treatment to determine one or more clinically relevant parameters including, without limitation, progression of the disease, efficacy of a treatment, or development of resistance mutations after administering a treatment to the subject. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable) or to determine the presence of a resistance mutation that has arisen as a result of the treatment. In some embodiments, a treatment to be administered to a subject can include a compound of Formula (I) or a pharmaceutically acceptable salt, amorphous form, polymorph form, or pharmaceutical composition (e.g., any of the solid or liquid formulations described herein) thereof.

In some embodiments, the efficacy of the compound of Formula (I) or a pharmaceutically acceptable salt, amorphous form, polymorph form, or pharmaceutical composition (e.g., any of the solid or liquid formulations described herein) thereof, can be determined by assessing the allele frequency of a dysregulation of a RET gene in cfDNA obtained from a patient at different time points, e.g., cfDNA obtained from the patient at a first time point and cfDNA obtained from the patient at a second time point, where at least one dose of a compound of Formula (I) or a pharmaceutically acceptable salt, amorphous form, polymorph form, or pharmaceutical composition (e.g., any of the solid or liquid formulations described herein) thereof is administered to the patient between the first and second time points. Some embodiments of these methods can further include administering to the patient the at least one dose of the compound of Formula (I) or a pharmaceutically acceptable salt, amorphous form, polymorph form, or pharmaceutical composition (e.g., any of the solid or liquid formulations described herein) thereof, between the first and second time points. For example, a reduction (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction) in the allele frequency (AF) of the dysregulation of a RET gene in the cfDNA obtained from the patient at the second time point as compared to the allele frequency (AF) of the dysregulation of a RET gene in the cfDNA obtained from the patient at the first time point indicates that the compound of Formula (I) or a pharmaceutically acceptable salt, amorphous form, polymorph form, or pharmaceutical composition (e.g., any of the solid or liquid formulations described herein) thereof, was effective in the subject. In some embodiments, the AF is reduced such that the level is below the detection limit of the instrument. Alternatively, an increase in the allele frequency (AF) of the dysregulation of a RET gene in the cfDNA obtained from the patient at the second time point as compared to the allele frequency (AF) of the dysregulation of a RET gene in the cfDNA obtained from the patient at the first time point indicates that the compound of Formula (I) or a pharmaceutically acceptable salt, amorphous form, polymorph form, or pharmaceutical composition (e.g., any of the solid or liquid formulations described herein) thereof, was not effective in the subject (e.g., the subject has developed a resistance mutation to the compound of Formula (I) or a pharmaceutically acceptable salt, amorphous form, polymorph form, or pharmaceutical composition (e.g., any of the solid or liquid formulations described herein) thereof). Some embodiments of these methods can further include, administering additional doses of a compound of Formula (I) or a pharmaceutically acceptable salt, amorphous form, polymorph form, or pharmaceutical composition (e.g., any of the solid or liquid formulations described herein) thereof, to a patient in which a compound of Formula (I) or a pharmaceutically acceptable salt, amorphous form, polymorph form, or pharmaceutical composition (e.g., any of the solid or liquid formulations described herein) thereof, was determined to be effective. Some embodiments of these methods can further include, administering a different treatment (e.g., a treatment that does not include the administration of Formula (I) or a pharmaceutically acceptable salt, amorphous form, polymorph form, or pharmaceutical composition (e.g., any of the solid or liquid formulations described herein) thereof, as a monotherapy) to a patient in which a compound of Formula (I) or a pharmaceutically acceptable salt, amorphous form, polymorph form, or pharmaceutical composition (e.g., any of the solid or liquid formulations described herein) thereof, was determined not to be effective.

In some examples of these methods, the time difference between the first and second time points can be about 1 day to about 1 year, about 1 day to about 11 months, about 1 day to about 10 months, about 1 day to about 9 months, about 1 day to about 8 months, about 1 day to about 7 months, about 1 day to about 6 months, about 1 day to about 5 months, about 1 day to about 4 months, about 1 day to about 3 months, about 1 day to about 10 weeks, about 1 day to about 2 months, about 1 day to about 6 weeks, about 1 day to about 1 month, about 1 day to about 25 days, about 1 day to about 20 days, about 1 day to about 15 days, about 1 day to about 10 days, about 1 day to about 5 days, about 2 days to about 1 year, about 5 days to about 1 year, about 10 days to about 1 year, about 15 days to about 1 year, about 20 days to about 1 year, about 25 days to about 1 year, about 1 month to about 1 year, about 6 weeks to about 1 year, about 2 months to about 1 year, about 3 months to about 1 year, about 4 months to about 1 year, about 5 months to about 1 year, about 6 months to about 1 year, about 7 months to about 1 year, about 8 months to about 1 year, about 9 months to about 1 year, about 10 months to about 1 year, about 11 months to about 1 year, about 1 day to about 7 days, about 1 day to about 14 days, about 5 days to about 10 days, about 5 day to about 20 days, about 10 days to about 20 days, about 15 days to about 1 month, about 15 days to about 2 months, about 1 week to about 1 month, about 2 weeks to about 1 month, about 1 month to about 3 months, about 3 months to about 6 months, about 4 months to about 6 months, about 5 months to about 8 months, or about 7 months to about 9 months. In some embodiments of these methods, the patient can be previously identified as having a cancer having a dysregulated RET gene (e.g., any of the examples of a dysregulated RET gene described herein). In some embodiments of these methods, a patient can have been previously diagnosed as having any of the types of cancer described herein. In some embodiments of these methods, the patient can have one or more metastases (e.g., one or more brain metastases).

In some of the above embodiments, the cfDNA comprises ctDNA such as RET-associated ctDNA. For example, the cfDNA is ctDNA such as RET-associated ctDNA. In some embodiments, at least some portion of cfDNA is determined to be RET-associated ctDNA, for example, a sequenced and/or quantified amount of the total cfDNA is determined to have a RET fusion and/or a RET resistance mutation.

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as other kinase inhibitors, signal transduction inhibitors and/or monoclonal antibodies. For example, a surgery may be open surgery or minimally invasive surgery. Compounds of Formula (I) or a pharmaceutically acceptable salt, amorphous form, polymorph form, or pharmaceutical composition (e.g., any of the solid or liquid formulations described herein) thereof therefore may also be useful as adjuvants to cancer treatment, that is, they can be used in combination with one or more additional therapies or therapeutic agents, for example a chemotherapeutic agent that works by the same or by a different mechanism of action. In some embodiments, a compound of Formula (I) or a pharmaceutically acceptable salt, amorphous form, polymorph form, or pharmaceutical composition (e.g., any of the solid or liquid formulations described herein) thereof, can be used prior to administration of an additional therapeutic agent or additional therapy. For example, a patient in need thereof can be administered one or more doses of a compound of Formula (I) or a pharmaceutically acceptable salt, amorphous form, polymorph form, or pharmaceutical composition (e.g., any of the solid or liquid formulations described herein) thereof for a period of time and then under go at least partial resection of the tumor. In some embodiments, the treatment with one or more doses of a compound of Formula (I) or a pharmaceutically acceptable salt, amorphous form, polymorph form, or pharmaceutical composition (e.g., any of the solid or liquid formulations described herein) thereof reduces the size of the tumor (e.g., the tumor burden) prior to the at least partial resection of the tumor. In some embodiments, a patient in need thereof can be administered one or more doses of a compound of Formula (I) or a pharmaceutically acceptable salt, amorphous form, polymorph form, or pharmaceutical composition (e.g., any of the solid or liquid formulations described herein) thereof for a period of time and under one or more rounds of radiation therapy. In some embodiments, the treatment with one or more doses of a compound of Formula (I) or a pharmaceutically acceptable salt, amorphous form, polymorph form, or pharmaceutical composition (e.g., any of the solid or liquid formulations described herein) thereof reduces the size of the tumor (e.g., the tumor burden) prior to the one or more rounds of radiation therapy.

In some embodiments, a patient has a cancer (e.g., a locally advanced or metastatic tumor) that is refractory or intolerant to standard therapy (e.g., administration of a chemotherapeutic agent, such as a first RET inhibitor or a multikinase inhibitor, immunotherapy, or radiation (e.g., radioactive iodine)). In some embodiments, a patient has a cancer (e.g., a locally advanced or metastatic tumor) that is refractory or intolerant to prior therapy (e.g., administration of a chemotherapeutic agent, such as a first RET inhibitor or a multikinase inhibitor, immunotherapy, or radiation (e.g., radioactive iodine)). In some embodiments, a patient has a cancer (e.g., a locally advanced or metastatic tumor) that has no standard therapy. In some embodiments, a patient is RET-kinase inhibitor naïve. For example, the patient is naïve to treatment with a selective RET-kinase inhibitor. In some embodiments, a patient is not RET-kinase inhibitor naïve.

In some embodiments, a patient has undergone prior therapy. In some embodiments, a patient having NSCLC (e.g, a RET-fusion positive NSCLS) has received treatment with a platinum-based chemotherapy, PD-1/PDL1 immunotherapy, or both prior to treatment with a compound of Formula (I) or a pharmaceutically acceptable salt, amorphous form, polymorph form, or pharmaceutical composition (e.g., any of the solid or liquid formulations described herein) thereof. In some embodiments, a patient having a thyroid cancer (e.g., a RET-fusion positive thyroid cancer) has received treatment with one or more of sorafenib, lenvatinib, and radioactive iodine prior to treatment with a compound of Formula (I) or a pharmaceutically acceptable salt, amorphous form, polymorph form, or pharmaceutical composition (e.g., any of the solid or liquid formulations described herein) thereof. In some embodiments, a patient having a colorectal cancer (e.g., a RET-fusion positive colorectal cancer) has received treatment with a fluoropyrimidine-based chemotherapy, with or without ant-VEGF-directed therapy or anti-EGFR-directed therapy, prior to treatment with a compound of Formula (I) or a pharmaceutically acceptable salt, amorphous form, polymorph form, or pharmaceutical composition (e.g., any of the solid or liquid formulations described herein) thereof. In some embodiments, a patient having a pancreatic cancer (e.g., a RET-fusion positive pancreatic cancer) has received treatment with one or more of a fluoropyrimidine-based chemotherapy, a gemcitabine-based chemotherapy, and a S-1 chemotherapy prior to treatment with a compound of Formula (I) or a pharmaceutically acceptable salt, amorphous form, polymorph form, or pharmaceutical composition (e.g., any of the solid or liquid formulations described herein) thereof. In some embodiments, a patient having a breast cancer (e.g., a RET-fusion positive breast cancer) has received treatment with one or more of anthracycline, taxane, HER2-directed therapy, and hormonal therapy prior to treatment with a compound of Formula (I) or a pharmaceutically acceptable salt, amorphous form, polymorph form, or pharmaceutical composition (e.g., any of the solid or liquid formulations described herein) thereof. In some embodiments, a patient having a MTC (e.g., a RET-fusion positive MTC cancer) has received treatment with one or more of caboxantinib and vandetanib prior to treatment with a compound of Formula (I) or a pharmaceutically acceptable salt, amorphous form, polymorph form, or pharmaceutical composition (e.g., any of the solid or liquid formulations described herein) thereof.

In some embodiments of any the methods described herein, the compound of Formula (I) or a pharmaceutically acceptable salt, amorphous form, polymorph form, or pharmaceutical composition (e.g., any of the solid or liquid formulations described herein) thereof is administered in combination with a therapeutically effective amount of at least one additional therapeutic agent selected from one or more additional therapies or therapeutic (e.g., chemotherapeutic) agents.

Non-limiting examples of additional therapeutic agents include: other RET-targeted therapeutic agents (i.e. a first or second RET kinase inhibitor), other kinase inhibiors (e.g., receptor tyrosine kinase-targeted therapeutic agents (e.g., Trk inhibitors or EGFR inhibitors)), signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy.

In some embodiments, the other RET-targeted therapeutic is a multikinase inhibitor exhibiting RET inhibition activity. In some embodiments, the other RET-targeted therapeutic inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitors can exhibit inhibition activity ($IC_{50}$) against a RET kinase of less than about 25 nM, less than about 10 nM, less than about 5 nM, or less than about 1 nM as measured in an assay as provided herein.

Non-limiting examples of RET-targeted therapeutic agents (e.g., a first RET inhibitor or a second RET inhibitor) include alectinib (9-Ethyl-6,6-dimethyl-8-[4-(morpholin-4-yl)piperidin-1-yl]-11-oxo-6,11-dihydro-5H-benzo[b]carbazole-3-carbonitrile); amuvatinib (MP470, HPK56) (N-(1,3-benzodioxol-5-ylmethyl)-4-([1]benzofuro[3,2-d]pyrimidin-4-yl)piperazine-1-carbothioamide); apatinib (YN968D1) (N-[4-(1-cyanocyclopentyl)phenyl-2-(4-picolyl)amino-3-Nicotinamide methanesulphonate); cabozantinib (Cometriq XL-184) (N-(4-((6,7-Dimethoxyquinolin-4-yl)oxy)phenyl)-N'-(4-fluorophenyl)cyclopropane-1,1-dicarboxamide); dovitinib (TKI258; GFKI-258; CHIR-258) ((3Z)-4-amino-5-fluoro-3-[5-(4-methylpiperazin-1-yl)-1,3-dihydrobenzimidazol-2-ylidene]quinolin-2-one); famitinib (5-[2-(diethylamino)ethyl]-2-[(Z)-(5-fluoro-2-oxo-1H-indol-3-ylidene) methyl]-3-methyl-6,7-dihydro-1H-pyrrolo[3,2-c]pyridin-4-one); fedratinib (SAR302503, TG101348) (N-(2-Methyl-2-propanyl)-3-{[5-methyl-2-({4-[2-(1-pyrrolidinyl)ethoxy] phenyl}amino)-4-pyrimidinyl] amino}benzenesulfonamide); foretinib (XL880, EXEL-2880, GSK1363089, GSK089) (N1'-[3-fluoro-4-[[6-methoxy-7-(3-morpholinopropoxy)-4-quinolyl]oxy] phenyl]-N1-(4-fluorophenyl)cyclopropane-1,1-dicarboxamide); fostamantinib (R788) (2H-Pyrido[3,2-b]-1, 4-oxazin-3(4H)-one, 6-[[5-fluoro-2-[(3,4,5-trimethoxyphenyl)amino]-4-pyrimidinyl]amino]-2,2-dimethyl-4-[(phosphonooxy)methyl]-, sodium salt (1:2)); ilorasertib (ABT-348) (1-(4-(4-amino-7-(1-(2-hydroxyethyl)-1H-pyrazol-4-yl)thieno[3,2-c]pyridin-3-yl)phenyl)-3-(3-fluorophenyl)urea); lenvatinib (E7080, Lenvima) (4-[3-chloro-4-(cyclopropylaminocarbonyl)aminophenoxy]-7-methoxy-6-quinolinecarboxamide); motesanib (AMG 706) (N-(3,3-Dimethyl-2,3-dihydro-1H-indol-6-yl)-2-[(pyridin-4-ylmethyl)amino]pyridine-3-carboxamide); nintedanib (3-Z-[1-(4-(N-((4-methyl-piperazin-1-yl)-methylcarbonyl)-N-methyl-amino)-anilino)-1-phenyl-methylene]-6-methyoxycarbonyl-2-indolinone); ponatinib (AP24534) (3-(2-Imidazo[1,2-b]pyridazin-3-ylethynyl)-4-methyl-N-[4-[(4-methylpiperazin-1-yl)methyl]-3-(trifluoromethyl) phenyl]benzamide); PP242 (a TORKinib) (2-[4-Amino-1-(1-methylethyl)-1H-pyrazolo[3,4-d]pyrimidin-3-yl]-1H-indol-5-ol); quizartinib (1-(5-(tert-Butyl)isoxazol-3-yl)-3-(4-(7-(2-morpholinoethoxy)benzo[d]imidazo[2,1-b]thiazol-2-yl)phenyl)urea); regorfenib (BAY 73-4506, stivarga) (4-

[4-({[4-Chloro-3-(trifluoromethyl)phenyl]carbamoyl}amino)-3-fluorophenoxy]-N-methylpyridine-2-carboxamide hydrate); RXDX-105 (CEP-32496, agerafenib) (1-(3-((6,7-dimethoxyquinazolin-4-yl)oxy)phenyl)-3-(5-(1,1,1-trifluoro-2-methylpropan-2-yl)isoxazol-3-yl)urea); semaxanib (SU5416) ((3Z)-3-[(3,5-dimethyl-1H-pyrrol-2-yl)methylidene]-1,3-dihydro-2H-indol-2-one); sitravatinib (MGCD516, MG516) (N-(3-Fluoro-4-{[2-(5-{[(2-methoxyethyl)amino]methyl}-2-pyridinyl)thieno[3,2-b]pyridin-7-yl]oxy}phenyl)-N?-(4-fluorophenyl)-1,1-cyclopropanedicarboxamide); sorafenib (BAY 43-9006) (4-[4-[[[[4-chloro-3-(trifluoromethyl)phenyl]amino]carbonyl]amino]phenoxy]-N-methyl-2-pyridinecarboxamide); vandetanib (N-(4-bromo-2-fluorophenyl)-6-methoxy-7-[(1-methylpiperidin-4-yl)methoxy]quinazolin-4-amine); vatalanib (PTK787, PTK/ZK, ZK222584) (N-(4-chlorophenyl)-4-(pyridin-4-ylmethyl)phthalazin-1-amine); AD-57 (N-[4-[4-amino-1-(1-methylethyl)-1H-pyrazolo[3,4-d]pyrimidin-3-yl]phenyl]-N'-[3-(trifluoromethyl)phenyl]-urea); AD-80 (1-[4-(4-amino-1-propan-2-ylpyrazolo[3,4-d]pyrimidin-3-yl)phenyl]-3-[2-fluoro-5-(trifluoromethyl)phenyl]urea); AD-81 (1-(4-(4-amino-1-isopropyl-1H-pyrazolo[3,4-d]pyrimidin-3-yl)phenyl)-3-(4-chloro-3-(trifluoromethyl)phenyl)urea); ALW-II-41-27 (N-(5-((4-((4-ethylpiperazin-1-yl)methyl)-3-(trifluoromethyl)phenyl)carbamoyl)-2-methylphenyl)-5-(thiophen-2-yl)nicotinamide); BPR1K871 (1-(3-chlorophenyl)-3-(5-(2-((7-(3-(dimethylamino)propoxy)quinazolin-4-yl)amino)ethyl)thiazol-2-yl)urea); CLM3 (1-phenethyl-N-(1-phenylethyl)-1H-pyrazolo[3,4-d]pyrimidin-4-amine); EBI-907 (N-(2-chloro-3-(1-cyclopropyl-8-methoxy-3H-pyrazolo[3,4-c]isoquinolin-7-yl)-4-fluorophenyl)-3-fluoropropane-1-sulfonamide); NVP-AST-487 (N-[4-[(4-ethyl-1-piperazinyl)methyl]-3-(trifluoromethyl)phenyl]-N'-[4-[[6-(methylamino)-4-pyrimidinyl]oxy]phenyl]-urea); NVP-BBT594 (BBT594) (5-((6-acetamidopyrimidin-4-yl)oxy)-N-(4-((4-methylpiperazin-1-yl)methyl)-3-(trifluoromethyl)phenyl)indoline-1-carboxamide); PD173955 (6-(2,6-dichlorophenyl)-8-methyl-2-(3-methylsulfanylanilino)pyrido[2,3-d]pyrimidin-7-one); PP2 (4-amino-5-(4-chlorophenyl)-7-(dimethylethyl)pyrazolo[3,4-d]pyrimidine); PZ-1 (N-(5-(tert-butyl)isoxazol-3-yl)-2-(4-(5-(1-methyl-1H-pyrazol-4-yl)-1Hbenzo[d]imidazol-1-yl)phenyl)acetamide); RPI-1 (1,3-dihydro-5,6-dimethoxy-3-[(4-hydroxyphenyl)methylene]-H-indol-2-one; (3E)-3-[(4-hydroxyphenyl)methylidene]-5,6-dimethoxy-1H-indol-2-one); SGI-7079 (3-[2-[[3-fluoro-4-(4-methyl-1-piperazinyl)phenyl]amino]-5-methyl-7H-pyrrolo[2,3-d]pyrimidin-4-yl]-benzeneacetonitrile); SPP86 (1-Isopropyl-3-(phenylethynyl)-1H-pyrazolo[3,4-d]pyrimidin-4-amine); SU4984 (4-[4-[(E)-(2-oxo-1H-indol-3-ylidene)methyl]phenyl]piperazine-1-carbaldehyde); sunitinb (SU11248) (N-(2-Diethylaminoethyl)-5-[(Z)-(5-fluoro-2-oxo-1H-indol-3-ylidene)methyl]-2,4-dimethyl-1H-pyrrole-3-carboxamide); TG101209 (N-tert-butyl-3-(5-methyl-2-(4-(4-methylpiperazin-1-yl)phenylamino)pyrimidin-4-ylamino)benzenesulfonamide); Withaferin A ((4β,5β,6β,22R)-4,27-Dihydroxy-5,6:22,26-diepoxyergosta-2,24-diene-1,26-di one); XL-999 ((Z)-5-((1-ethylpiperidin-4-yl)amino)-3-((3-fluorophenyl)(5-methyl-1H-imidazol-2-yl)methylene)indolin-2-one); BPR1J373 (a 5-phenylthiazol-2-ylamine-pyriminide derivative); CG-806 (CG'806); DCC-2157; GTX-186; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); SW-01 (Cyclobenzaprine hydrochloride); XMD15-44 (N-(4-((4-ethylpiperazin-1-yl)methyl)-3-(trifluoromethyl)phenyl)-4-methyl-3-(pyridin-3-ylethynyl)benzamide (generated from structure)); Y078-DM1 (an antibody drug conjugate composed of a RET antibody (Y078) linked to a derivative of the cytotoxic agent maytansine); Y078-DM4 (an antibody drug conjugate composed of a RET antibody (Y078) linked to a derivative of the cytotoxic agent maytansine); ITRI-305 (D0N5TB, DIB003599); BLU-667 (((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide); BLU6864; DS-5010; GSK3179106; GSK3352589; NMS-E668; and TAS0286/HM05.

Further examples of RET-targeted therapeutics (e.g., a first RET kinase inhibitor aor a second RET kinase inhibitor) include 5-amino-3-(5-cyclopropylisoxazol-3-yl)-1-isopropyl-1H-pyrazole-4-carboxamide; 3-(5-cyclopropylisoxazol-3-yl)-1-isopropyl-1H-pyrazolo[3,4-d]pyrimidin-4-amine; 3-((6,7-Dimethoxyquinazolin-4-yl)amino)-4-fluoro-2-methylphenol; N-(5-(tert-butyl)isoxazol-3-yl)-2-(4-(imidazo[1,2-a]pyridin-6-yl)phenyl)acetamide; N-(5-(tert-butyl)isoxazol-3-yl)-2-(3-(imidazo[1,2-b]pyridazin-6-yloxy)phenyl)acetamide; N-(2-fluoro-5-trifluoromethylphenyl)-N'-{4'-[(2"-benzamido)pyridin-4"-ylamino]phenyl}urea; 2-amino-6-{[2-(4-chlorophenyl)-2-oxoethyl]sulfanyl}-4-(3-thienyl)pyridine-3,5-dicarbonitrile; and 3-arylureidobenzylidene-indolin-2-ones.

Additional examples of other RET kinase inhibitors include those described in U.S. Pat. Nos. 9,150,517 and 9,149,464, and International Publication No. WO 2014075035, all of which are hereby incorporated by reference. For example, in some embodiments the other RET inhibitor is a compound of formula I:

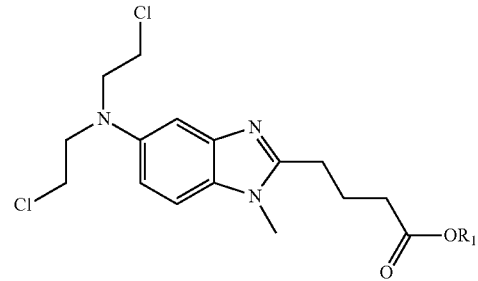

wherein $R_1$ is C6-C24alkyl or polyethylene glycol; or a pharmaceutically acceptable salt form thereof. In some embodiments, the other RET inhibitor is 4-{5-[bis-(chloroethyl)-amino]-1-methyl-1H-benzimidazol-2-yl}butyric acid dodecyl ester.

Additional examples of other RET kinase inhibitors include those described in International Publication No. WO 2016127074, which is hereby incorporated by reference. For example, in some embodiments, the other RET inhibitor is a compound of Formula (I) or a pharmaceutically acceptable salt thereof, wherein:

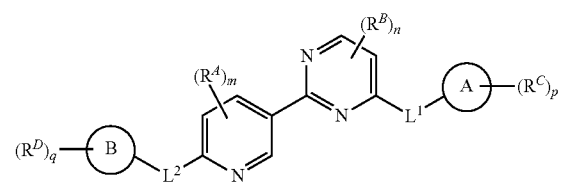

wherein Rings A and B are each independently selected from aryl, heteroaryl, cycloalkyl and heterocyclyl;

each $L^1$ and $L^2$ is independently selected from a bond, —(C1-C6 alkylene)-, —(C2-C6alkenylene)-, —(C2-C6 alkynylene)-, —(C1-C6 haloalkylene)-, —(C1-C6 heteroalkylene)-, —C(O)—, —O—, —S—, —S(O), —S(O)$_2$—, —N(R$^1$)—, —O—(C1-C6 alkylene)-, —(C1-C6 alkylene)-O—, —N(R$^1$)—C(O)—, —C(O)N(R$^1$)—, —(C1-C6 alkylene)-N(R$^1$)—, —N(R$^1$)—(C1-C6 alkylene)-, —N(R$^1$)—C(O)—(C1-C6 alkylene)-, —(C1-C6 alkylene)-N(R$^1$)—C(O)—, —C(O)—N(R$^1$)—(C1-C6 alkylene)-, —(C1-C6 alkylene)-C(O)—N(R$^1$)—, —N(R$^1$)—S(O)$_2$—, —S(O)$_2$—N(R$^1$)—, —N(R$^1$)—S(O)$_2$—(C1-C6 alkylene)-, and —S(O)$_2$—N(R$^1$)—(C1-C6 alkylene)-; wherein each alkylene, alkenylene, alkynylene, haloalkylene, and heteroalkylene is independently substituted with 0-5 occurrences of R';

each $R^A$ and $R^B$ is independently selected from C1-C6 alkyl, C1-C6 alkoxy, halo, C1-C6 haloalkyl, C1-C6 hydroxyalkyl, C1-C6 heteroalkyl, and —N(R$^1$)(R$^1$); wherein each alkyl, alkoxy, haloalkyl, hydroxyalkyl, and hydroxyalkyl is independently substituted with 0-5 occurrences of Ra;

each $R^C$ and $R^D$ is independently selected from C1-C6 alkyl, C2-C6 alkenyl, C2-C6 alkynyl, C1-C6 alkoxy, halo, C1-C6 heteroalkyl, C1-C6 haloalkyl, C1-C6 haloalkoxy, C1-C6 hydroxyalkyl, cycloalkyl, aryl, heteroaryl, aryloxy, aralkyl, heterocyclyl, heterocyclylalkyl, nitro, cyano, —C(O)R$^1$, —OC(O)R$^1$, —C(O)OR$^1$, —(C1-C6 alkylene)-C(O)R$^1$, —SR$^1$, —S(O)$_2$R$^1$, —S(O)$_2$—N(R$^1$)(R$^1$), —(C1-C6 alkylene)-S(O)$_2$R$^1$, —(C1-C6 alkylene)-S(O)$_2$—N(R$^1$)(R$^1$), —N(R$^1$)(R$^1$)—C(O)—N(R$^1$)(R$^1$)—N(R$^1$)—C(O)R$^1$, —N(R$^1$)—C(O)OR$^1$, —(C1-C6 alkylene)-N(R$^1$)—C(O)R$^1$, —N(R$^1$)S(O)$_2$R$^1$, and —P(O)(R$^1$)(R$^1$); wherein each of alkyl, alkenyl, alkynyl, alkoxy, heteroalkyl, haloalkyl, haloalkoxy, hydroxyalkyl, cycloalkyl, aryl, heteroaryl, aryloxy, aralkyl, heterocyclyl, and heterocyclylalkyl is independently substituted with 0-5 occurrences of R$^a$; or 2 R$^C$ or 2 R$^D$ together with the carbon atom(s) to which they are attached form a cycloalkyl or heterocyclyl ring independently substituted with 0-5 occurrences of R$^a$;

each R$^1$ is independently selected from hydrogen, hydroxyl, halo, thiol, C1-C6 alkyl, C1-C6 thioalkyl, C1-C6 alkoxy, C1-C6 haloalkyl, C1-C6 hydroxyalkyl, C1-C6 heteroalkyl, cycloalkyl, cycloalkylalkyl, heteroarylalkyl, heterocyclyl, and heterocyclylalkyl, wherein each of alkyl, thioalkyl, alkoxy, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of R$^b$, or 2 R$^1$ together with the atom(s) to which they are attached form a cycloalkyl or heterocyclyl ring independently substituted with 0-5 occurrences of R$^b$;

each R$^a$ and R$^b$ is independently C1-C6 alkyl, halo, hydroxyl, C1-C6 haloalkyl, C1-C6 heteroalkyl, C1-C6 hydroxyalkyl, C1-C6 alkoxy, cycloalkyl, heterocyclyl, or cyano, wherein each of alkyl, haloalkyl, heteroalkyl, hydroxyalkyl, alkoxy, cycloalkyl and heterocyclyl is independently substituted with 0-5 occurrences of R';

each R' is C1-C6 alkyl, C1-C6 heteroalkyl, halo, hydroxyl, C1-C6 haloalkyl, C1-C6 hydroxyalkyl, cycloalkyl or cyano; or 2 R', together with the atom(s) to which they are attached form a cycloalkyl or heterocyclyl ring;

m is 0, 1, 2, or 3;

n is 0, 1, or 2; and p and q are each independently 0, 1, 2, 3, or 4. For example, a RET inhibitor can be selected from the group consisting of:

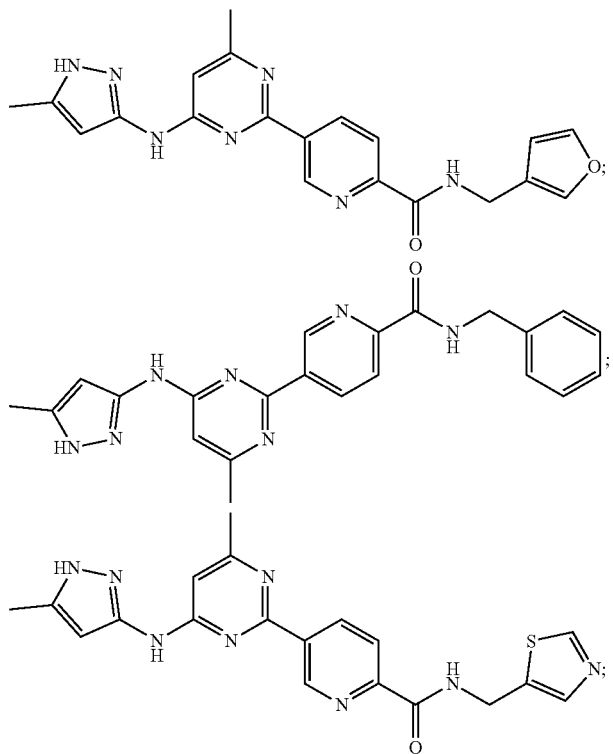

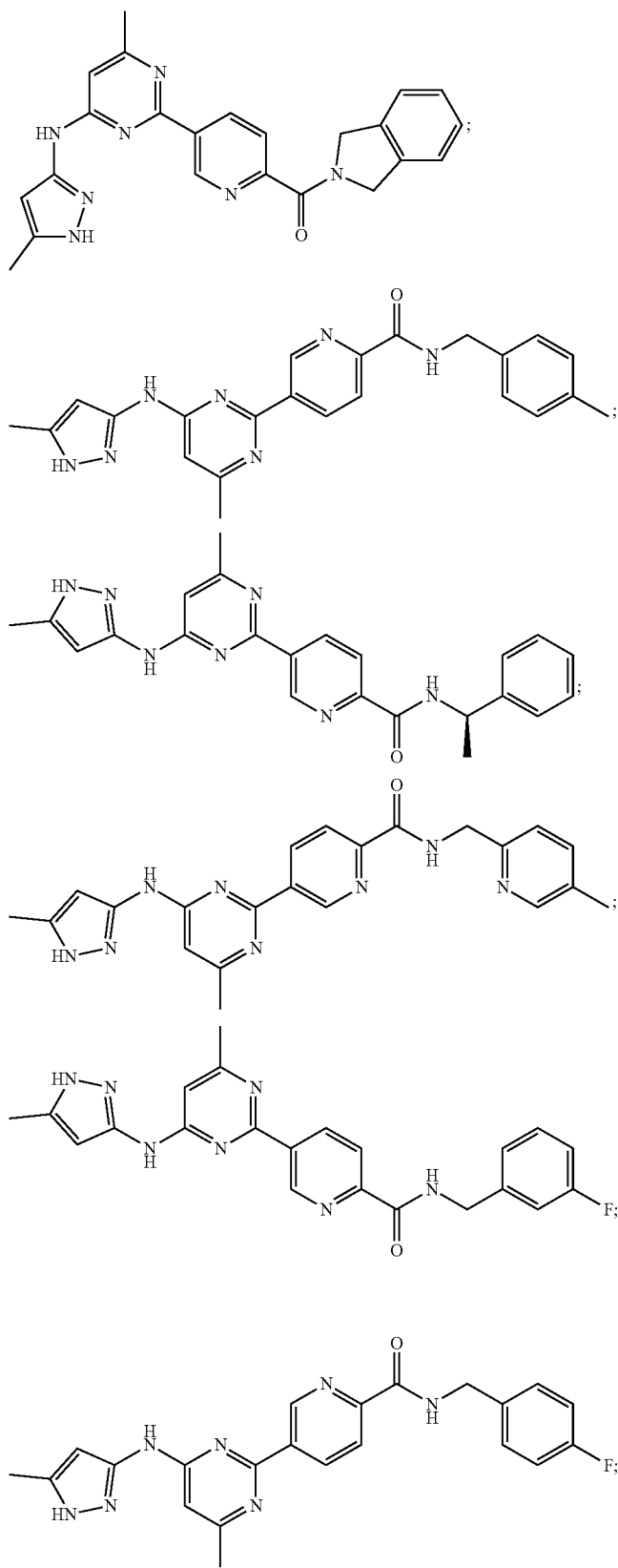

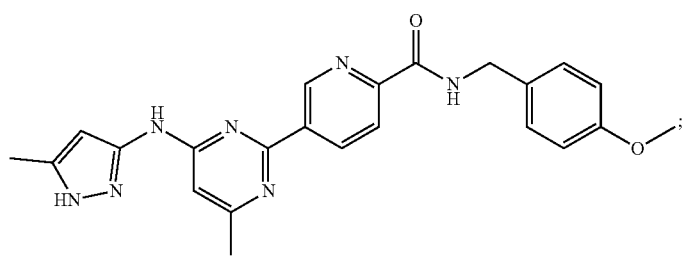
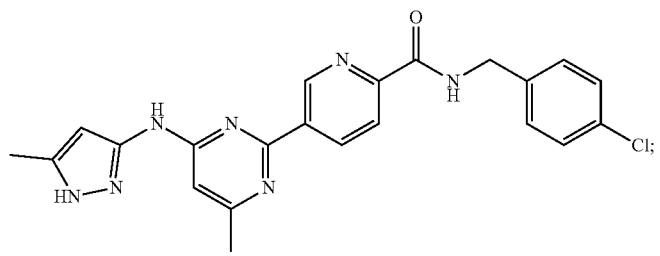
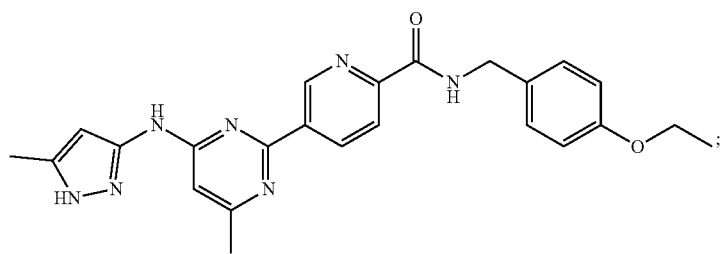
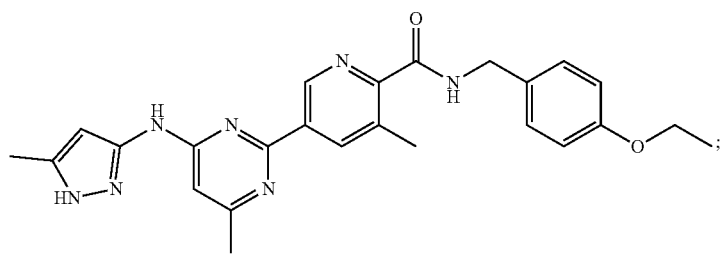
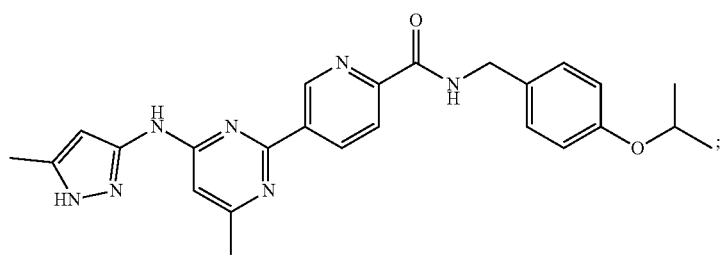
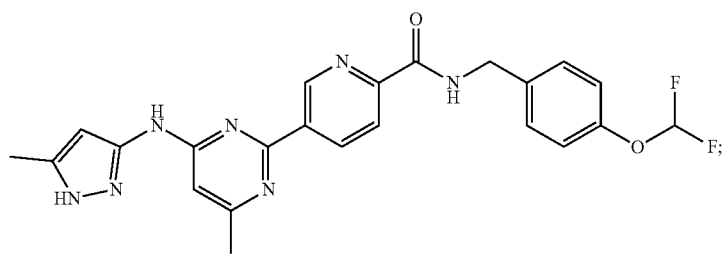

-continued
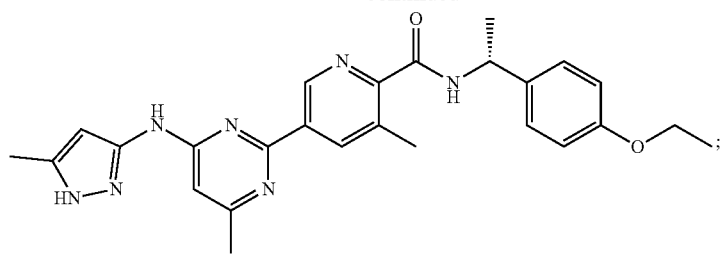
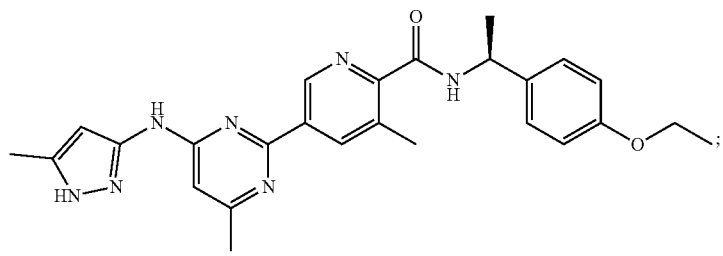
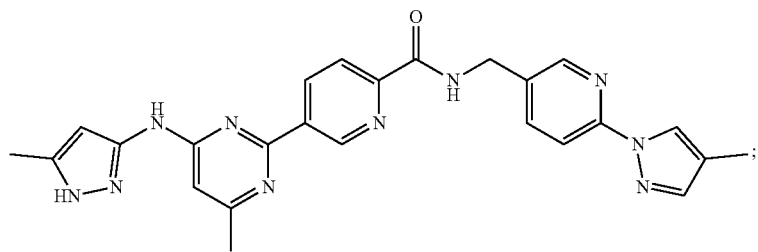
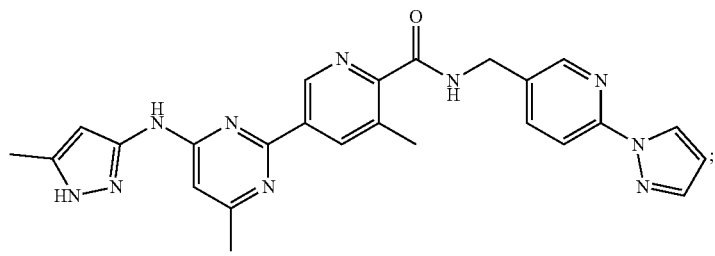
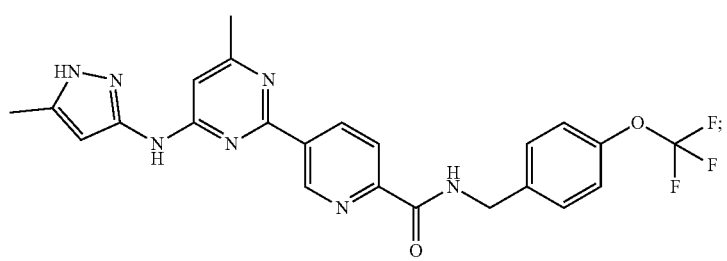
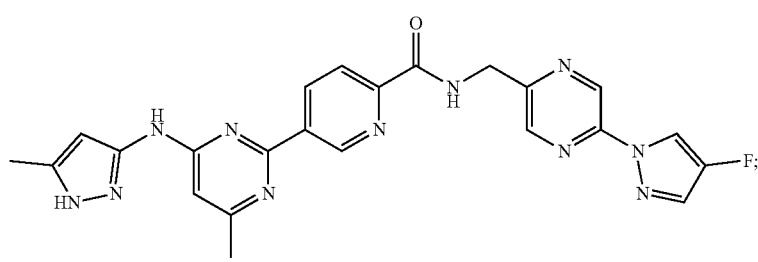

-continued
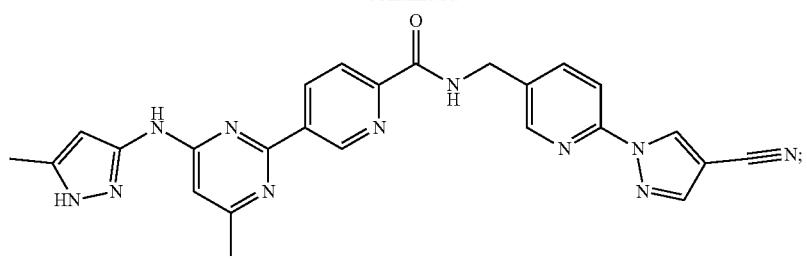
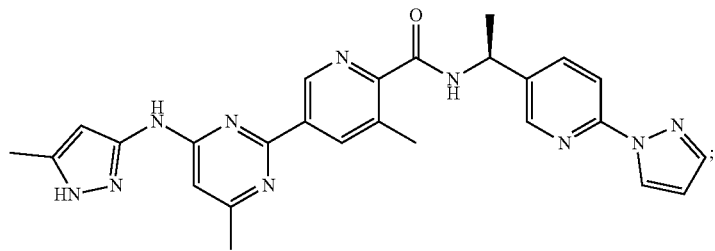
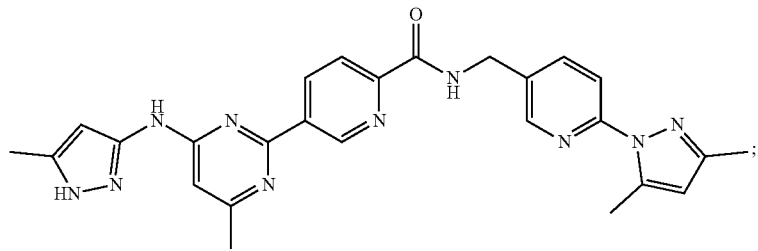
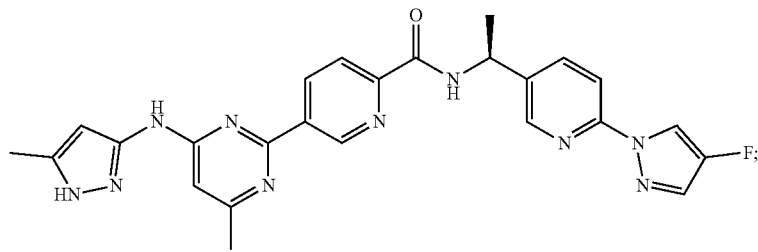
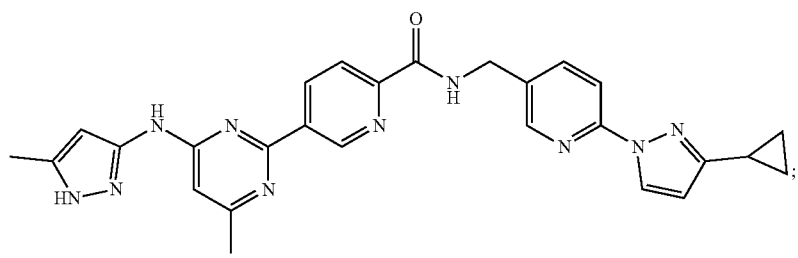
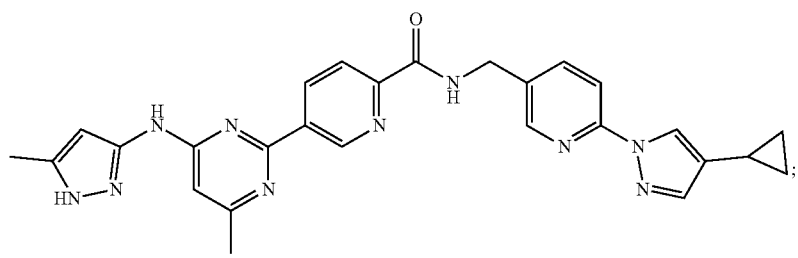

-continued
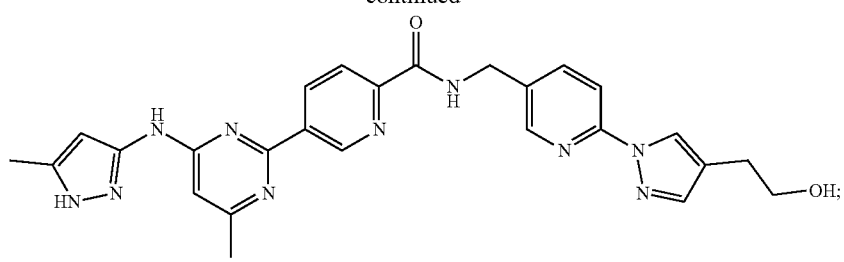
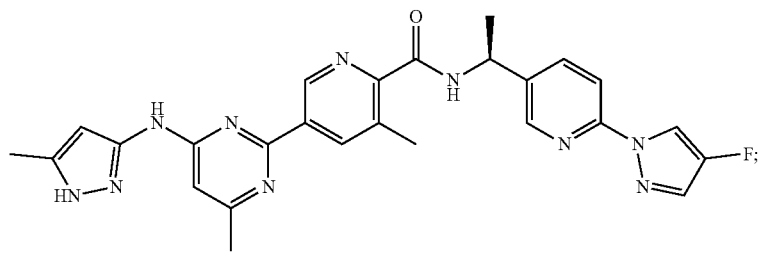 [SMILES: Cc1cc(Nc2cc(C)[nH]n2)nc(-c2ccc(C(=O)N[C@@H](C)c3cnc(-n4cc(F)cn4)cn3)nc2)n1]
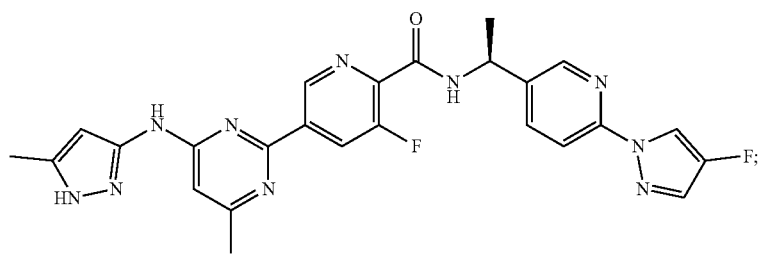
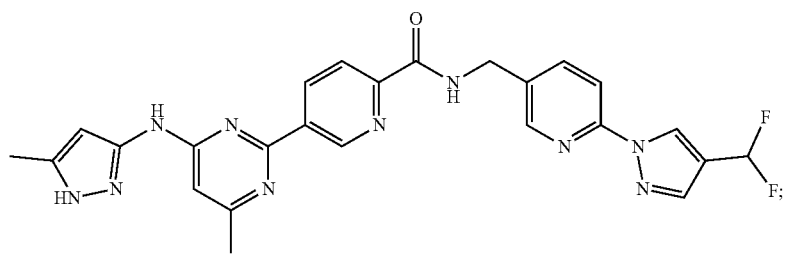
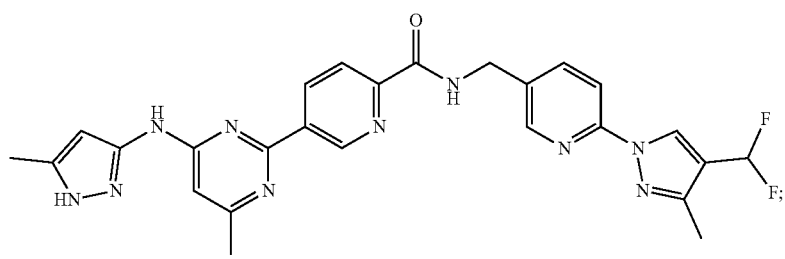
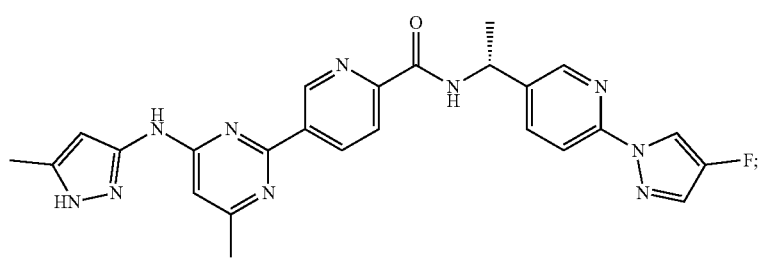

-continued

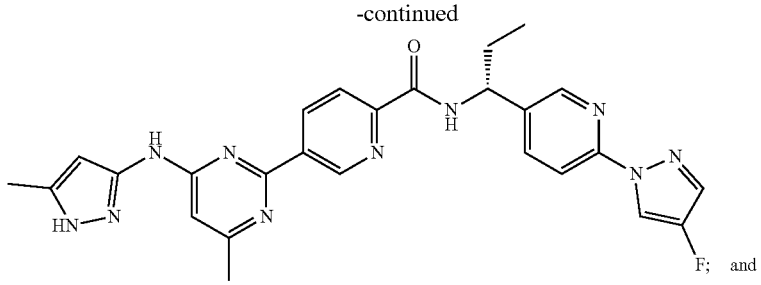

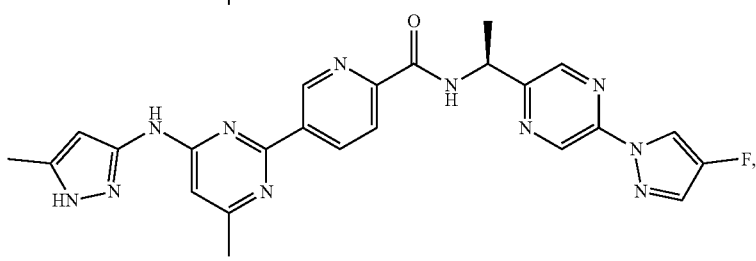

or a pharmaceutically acceptable salt thereof.

Additional examples of other RET kinase inhibitors include those described in International Publication No. WO 2016075224, which is hereby incorporated by reference. For example, in some embodiments, the other RET inhibitor is a compound of Formula (II) or a pharmaceutically acceptable salt thereof, wherein:

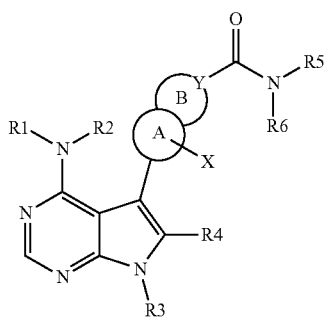

(II)

R1 and R2 are independently hydrogen or an optionally substituted group selected from straight or branched (C1-C6) alkyl, (C3-C6) cycloalkyl and COR', wherein R' is an optionally substituted group selected from straight or branched (C1-C6) alkyl and (C3-C6) cycloalkyl;

R3 is hydrogen or an optionally substituted group selected from straight or branched (C1-C6) alkyl, (C2-C6) alkenyl, (C2-C6) alkynyl, (C3-C6) cycloalkyl, aryl, heteroaryl and a 3- to 7-membered heterocyclyl ring;

R4 is hydrogen or an optionally substituted group selected from straight or branched (C1-C6) alkyl, (C2-C6) alkenyl, aryl, heteroaryl or heterocyclyl;

A is a 5- or 6-membered heteroaryl ring or a phenyl ring;

B is a 5- or 6-membered ring selected from heteroaryl, (C5-C6) cycloalkyl and heterocyclyl ring or a phenyl ring; wherein ring A and ring B are fused together to form a bicyclic system comprising a 6-membered aromatic or 5- to 6-membered heteroaromatic ring fused with a 6-membered aromatic or 5- to 6-membered heteroaromatic, (C5-C6) cycloalkyl or heterocyclyl ring;

Y is carbon or nitrogen;

X is hydrogen, halogen, hydroxyl, cyano or an optionally substituted group selected from straight or branched (C1-C6) alkyl and (C1-C6) alkoxyl; and R5 and R6 are independently hydrogen or an optionally substituted group selected from straight or branched (C1-C6) alkyl, (C3-C6) cycloalkyl, heterocyclyl, aryl and heteroaryl.

Additional examples of other RET kinase inhibitors include those described in International Publication No. WO 2015079251, which is hereby incorporated by reference. For example, in some embodiments, the other RET inhibitor is a compound of Formula (III) or a pharmaceutically acceptable salt or solvate thereof, wherein:

(III)

X is NH, $NR_x$, O or S, wherein $R_x$ is (1-3C)alkyl;

$R_1$ is selected from halo (e.g., fluoro, chloro, or bromo), trifluoromethyl, (1-4C)alkyl (e.g., methyl), (1-4C) alkoxy or (3-6C)cycloalkyl, wherein an alkyl, alkoxy or cycloalkyl group is optionally substituted with one or more fluoro;

$R_2$ is selected from hydrogen, halo (e.g., fluoro, chloro or bromo), hydroxyl, cyano, trifluoromethyl, trifluoromethoxy, (1-6C)alkyl (e.g., methyl), (3-8C)cycloalkyl, or (1-4C)alkoxy (e.g., OMe), wherein an alkyl, cycloalkyl or alkoxy group is optionally substituted with one or more fluoro;

$R_3$ is selected from hydrogen, halo (e.g. fluoro, chloro or bromo), hydroxyl, cyano, trifluoromethyl, trifluoromethoxy, (1-6C)alkyl (e.g., methyl), (3-8C)cycloalkyl, or (1-4C)alkoxy (e.g., OMe), wherein an alkyl, cycloalkyl or alkoxy group is optionally substituted with one or more fluoro;

$R_4$ is selected from hydrogen, halo (e.g., fluoro, chloro or bromo), hydroxyl, cyano, trifluoromethyl, trifluoromethoxy, (1-6C)alkyl (e.g., methyl), (3-8C)cycloalkyl, or (1-4C)alkoxy (e.g., OMe), wherein an alkyl, cycloalkyl or alkoxy group is optionally substituted with one or more fluoro;

$R_5$ is selected from hydrogen or a group defined by the formula:

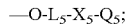
—O-L$_5$-X$_5$-Q$_5$;

wherein $L_5$ is absent or a linear or branched (1-4C)alkylene;

$X_5$ is absent or —C(O)O—, —O—, —C(O)—, —OC(O)—, —CH(QR$_{5L}$)—, —N(R')—, —N(R$_{5L}$)—C(O)—, —N(R$_{5L}$)—C(O)O—, —C(O)—N(R$_{5L}$)—, —S—, —SO—, —SO$_2$—, —S(O)$_2$N(R$_{5L}$)—, or —N(R$_{5L}$)SO$_2$— wherein R$_{5L}$ is selected from hydrogen or methyl; and $Q_5$ is (1-6C)alkyl, (2-6C)alkenyl, (2-6C)alkynyl, (3-8C)cycloalkyl, (3-8C)cycloalkyl-(1-4C)alkyl, aryl, aryl-(1-4C)alkyl, heteroaryl, heteroaryl-(1-4C)alkyl, heterocyclyl or heterocyclyl-(1-4C)alkyl;

$R_6$ is selected from hydrogen, or a group defined by the formula:

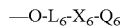
—O-L$_6$-X$_6$-Q$_6$ wherein $L_6$ is absent or a linear or branched (1-4C)alkylene;

$X_6$ is absent or selected from —O—, —C(O)—, —C(O)O—, —OC(O)—, —CH(OR$_{6L}$)—, —N(R$_{6L}$), —N(R$_{6L}$)—C(O)—, —N(R$_{6L}$)—C(O)O—, —C(O)—N(R$_{6L}$)—, —S—, —SO—, —SO$_2$—, —S(O)$_2$N(R$_{6L}$)—, or —N(R$_{6L}$)SO$_2$— wherein R$_{6L}$ is selected from hydrogen or (1-3C)alkyl;

$Q_6$ is hydrogen, (1-8C)alkyl, (2-8C)alkenyl, (2-8C)alkynyl, (3-8C)cycloalkyl, (3-8C)cycloalkyl-(1-6C)alkyl, aryl, aryl-(1-6C)alkyl, heteroaryl, heteroaryl-(1-6C)alkyl, heterocyclyl, heterocyclyl-(1-6C)alkyl, or $Q_6$ and $R_{L6}$ are linked such that, together with the nitrogen atom to which they are attached, they form a heterocyclic ring;

wherein $R_6$ is optionally substituted (e.g. substituted on $L_6$ and/or $Q_6$) with one or more (1-6C)alkyl, (1-6C)alkanoyl, OR$_{6X}$, SR$_{6X}$, S(O)R$_{6X}$, S(O)$_2$R$_{6X}$, C(O)OR$_{6X}$ or C(O)NR$_{6X}$R'$_{6X}$, wherein R$_{6X}$ and R'$_{6X}$ are independently hydrogen, (1-8C)alkyl, or R$_{6X}$ and R'$_{6X}$ are linked such that, together with the nitrogen atom to which they are attached, they form a heterocyclic ring; and $R_7$ is selected from hydrogen, (1-6C)alkoxy, or a group defined by the formula:

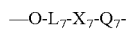
—O-L$_7$-X$_7$-Q$_7$- wherein $L_7$ is absent or a linear or branched (1-4C)alkylene;

$X_7$ is absent or selected from —O—, —C(O)—, —C(O)O—, —OC(O)—, —CH(OR$_{6L}$)—, —N(R$_{7L}$)—, —N(R$_{7L}$)—C(O)—, —N(R$_{7L}$)—C(O)O—, —C(O)—N(R$_{7L}$)—, —S—, —SO—, —SO$_2$—, —S(O)$_2$N(R$_{7L}$)—, or —N(R$_{7L}$)SO$_2$— wherein R$_{7L}$ is selected from hydrogen or (1-3C)alkyl;

$Q_7$ is hydrogen, (1-8C)alkyl, (2-8C)alkenyl, (2-8C)alkynyl, (3-8C)cycloalkyl, (3-8C)cycloalkyl-(1-6C)alkyl, aryl, aryl-(1-6C)alkyl, heteroaryl, heteroaryl-(1-6C)alkyl, heterocyclyl, heterocyclyl-(1-6C)alkyl, or $Q_7$ and $R_{7L}$ are linked such that, together with the nitrogen atom to which they are attached, they form a heterocyclic ring;

wherein $R_7$ is optionally substituted (e.g., substituted on $L_7$ and/or $Q_7$) with one or more halo, hydroxyl, nitro, cyano, (1-8C)alkyl, (1-8C)alkanoyl, OR$_{7X}$, SR$_{7X}$, S(O)R$_{7X}$, S(O)$_2$R$_{7X}$, C(O)OR$_{7X}$ or C(O)NR$_{7X}$R'$_{7X}$, wherein R$_{7X}$ and R'$_{7X}$ are independently hydrogen, (1-8C)alkyl, or R$_{7X}$ and R'$_{7X}$ are linked such that, together with the nitrogen atom to which they are attached, they form a heterocyclic ring; or $R_7$ is optionally substituted with one or more groups selected from oxo, (1-4C)haloalkyl, (1-4C)hydroxyalkyl, C(O)R$_{7y}$ or NR$_{7y}$R$_{7y}$, wherein R$_{7y}$ and R'$_{7y}$ are independently hydrogen or (1-8C)alkyl.

Additional examples of other RET kinase inhibitors include those described in International Publication No. WO2017178845, which is hereby incorporated by reference. For example, in some embodiments, the other RET inhibitor is a compound of Formula (IV) or a pharmaceutically acceptable salt thereof, wherein:

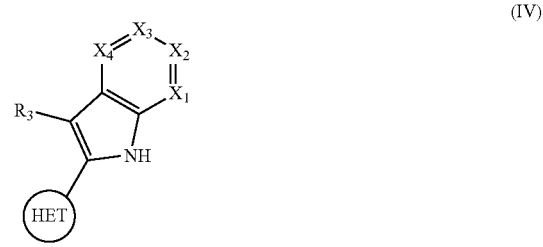

HET is selected from one of the following:

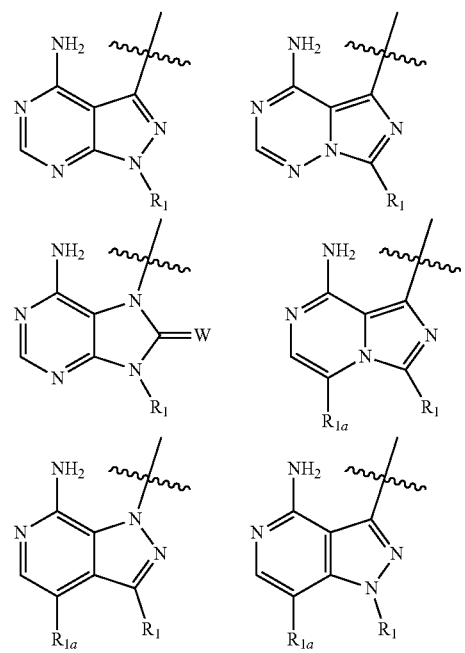

-continued

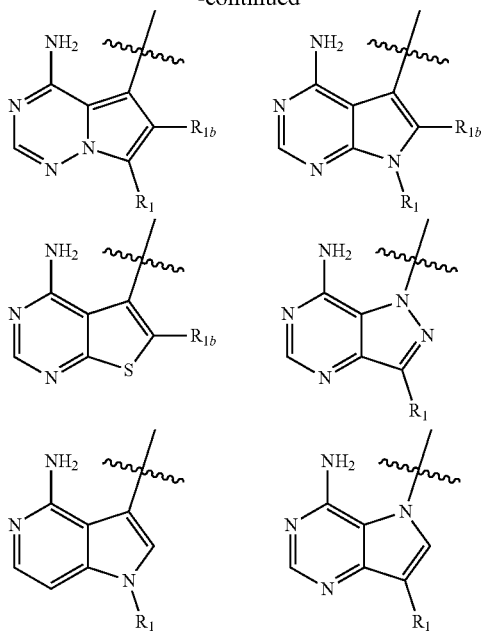

wherein

denotes the point of attachment;
R₁ is selected from hydrogen, (1-4C)haloalkyl, (1-4C)haloalkoxy or a group of the formula:

-L-Y-Q wherein:
L is absent or (1-5C)alkylene optionally substituted by one or more substituents selected from (1-2C)alkyl or oxo;
Y is absent or O, S, SO, SO₂, N(R$_a$), C(O), C(O)O, OC(O), C(O)N(R$_a$), N(R$_a$)C(O), N(R$_a$)C(O)N(R$_b$), N(R$_a$)C(O)O, OC(O)N(R$_a$), S(O)₂N(R$_a$), or N(R$_a$)SO₂, wherein R$_a$ and R$_b$ are each independently selected from hydrogen or (1-4C)alkyl; and
Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$_c$R$_d$, OR$_c$, C(O)R$_c$, C(O)OR$_c$, OC(O)R$_c$, C(O)N(R$_d$)R$_c$, N(R$_d$)C(O)R$_c$, S(O)$_p$R$_c$ (where p is 0, 1 or 2), SO₂N(R$_d$)R$_c$, N(R$_d$)SO₂R$_c$, Si(R$_e$)(R$_d$)R$_c$ or (CH₂)$_q$NR$_c$R$_d$ (where q is 1, 2 or 3); wherein R$_c$, R$_d$ and R$_e$ are each independently selected from hydrogen, (1-6C)alkyl or (3-6C)cycloalkyl; or R$_c$ and R$_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy; or
Q is optionally substituted by a group of the formula:

-L₁-L$_{Q1}$-W₁ wherein:
L₁ is absent or (1-3C)alkylene optionally substituted by one or more substituents selected from (1-2C)alkyl or oxo;
L$_{Q1}$ is absent or selected from O, S, SO, SO₂, N(R$_f$), C(O), C(O)O, OC(O), C(O)N(R$_f$), N(R$_f$)C(O), N(R$_f$)C(O)N(R$_g$), N(R$_f$)C(O)O, OC(O)N(R$_f$), S(O)₂N(R$_f$), or N(R$_f$)SO₂, wherein R$_f$ and R$_g$ are each independently selected from hydrogen or (1-2C)alkyl; and
W₁ is hydrogen, (1-6C)alkyl, aryl, aryl(1-2C)alkyl, (3-8C)cycloalkyl, (3-8C)cycloalkenyl, heteroaryl or heterocyclyl; wherein W₁ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, NR$_h$R$_i$, OR$_h$, C(O)R$_h$, C(O)OR$_h$, OC(O)R$_h$, C(O)N(R$_i$)R$_h$, N(R)C(O)R$_h$, S(O)$_r$R$_h$ (where r is 0, 1 or 2), SO₂N(R$_i$)R$_h$, N(R$_i$)SO₂R$_h$ or (CH₂)$_s$NR$_i$R$_h$ (where s is 1, 2 or 3); wherein R$_h$ and R$_i$ are each independently selected from hydrogen, (1-4C)alkyl or (3-6C)cycloalkyl;
R$_{1a}$ and R$_{1b}$ are each selected from H, (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl or mercapto;
W is selected from O, S or NR$_{W1}$, wherein R$_{W1}$ is selected from H or (1-2C)alkyl;
X₁, X₂, X₃ and X₄ are independently selected from CH, CR₂ or N;
R₂ is selected from hydrogen, halo, (1-4C)alkyl, (1-4C)alkoxy, (1-4C)haloalkyl, (1-4C)haloalkoxy, amino, cyano, nitro, aryl, heteroaryl, heterocyclyl, cycloalkyl, (2-4C)alkynyl, NR$_j$R$_k$, OR$_j$, C(O)R$_j$, C(O)OR$_j$, OC(O)R$_j$, C(O)N(R$_k$)R$_j$, N(R$_k$)C(O)R$_j$, N(R$_k$)C(O)N(R$_j$), S(O)$_{r1}$R$_k$ (where r₁ is 0, 1 or 2), SO₂N(R$_j$)R$_k$, N(R$_j$)SO₂R$_k$ or (CH₂)$_v$NR$_j$R$_k$ (where v is 1, 2 or 3); wherein and R$_k$ are each independently selected from hydrogen or (1-4C)alkyl; and wherein said (1-4C)alkyl, aryl, heteroaryl, heterocycyl or cycloalkyl is optionally substituted by one or more substituents selected from halo, (1-4C)alkyl, (1-4C)alkoxy, (1-4C)haloalkyl, (1-4C)haloalkoxy, amino, cyano, nitro, phenyl, (2-4C)alkynyl, NR$_{j1}$R$_{k1}$, OR$_{j1}$, C(O)R$_{j1}$, C(O)OR$_{j1}$, OC(O)R$_{j1}$, C(O)N(R$_{k1}$)R$_{j1}$, N(R$_{k1}$)C(O)R$_{j1}$, S(O)$_{r2}$R$_h$ (where r₂ is 0, 1 or 2), SO₂N(R$_{j1}$)R$_{k1}$, N(R$_{j1}$)SO₂R$_{k1}$ or (CH₂)$_{v1}$NR$_{j1}$R$_{k1}$ (where v₁ is 1, 2 or 3); and wherein R$_{j1}$ and R$_{k1}$ are each independently selected from hydrogen or (1-4C)alkyl; and
R₃ is selected from halo, (1-4C)alkyl, (1-4C)alkoxy, (1-4C)haloalkyl, (1-4C)haloalkoxy, amino, cyano, nitro, (2-4C)alkynyl, NR$_l$R$_m$, OR$_l$, C(O)R$_l$, C(O)OR$_l$, OC(O)R$_l$, C(O)N(R$_m$)R$_l$, N(R$_m$)C(O)R$_l$, or (CH₂)$_y$NR$_l$R$_m$ (where y is 1, 2 or 3); wherein said (1-4C)alkyl is optionally substituted by one or more substituents selected from amino, hydroxy, (1-2C)alkoxy or halo; and wherein R$_l$ and R$_m$ are each independently selected from hydrogen or (1-4C)alkyl.
Additional examples of other RET kinase inhibitors include those described in International Publication No.

WO2017178844, which is hereby incorporated by reference. For example, in some embodiments, the other RET inhibitor is a compound of Formula (V) or a pharmaceutically acceptable salt thereof, wherein:

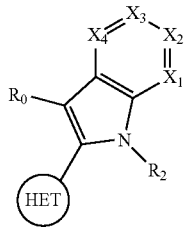

(V)

HET is selected from one of the following:

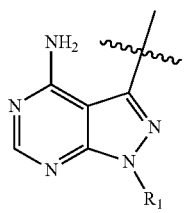 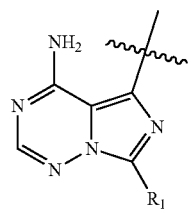

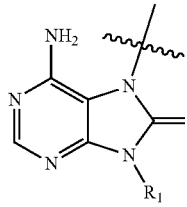 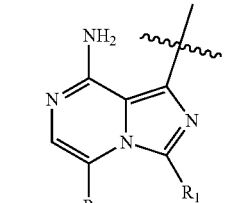

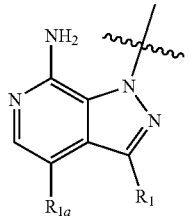 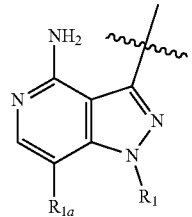

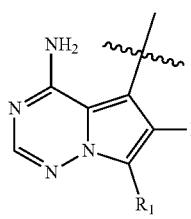 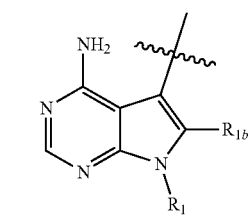

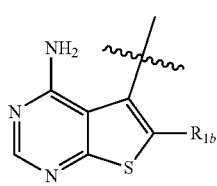 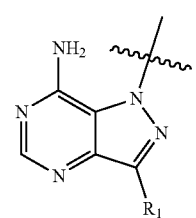

-continued

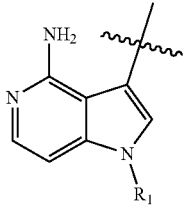 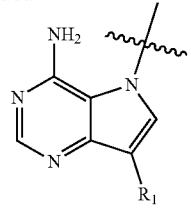

wherein

denotes the point of attachment;

R$_1$ is selected from hydrogen, (1-4C)haloalkyl, (1-4C)haloalkoxy or a group of the formula:

-L-Y-Q wherein:

L is absent or (1-5C)alkylene optionally substituted by one or more substituents selected from (1-2C)alkyl or oxo;

Y is absent or O, S, SO, SO$_2$, N(R$_a$), C(O), C(O)O, OC(O), C(O)N(R$_a$), N(R$_a$)C(O), N(R$_a$)C(O)N(R$_b$), N(R$_a$)C(O)O, OC(O)N(R$_a$), S(O)$_2$N(R$_a$), or N(R$_a$)SO$_2$, wherein R$_a$ and R$_b$ are each independently selected from hydrogen or (1-4C)alkyl; and Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$_c$R$_d$, OR$_c$, C(O)R$_c$, C(O)OR$_c$, OC(O)R$_c$, C(O)N(R$_d$)R$_c$, N(R$_d$)C(O)R$_c$, S(O)$_y$R$_c$ (where y is 0, 1 or 2), SO$_2$N(R$_d$)R$_c$, N(R$_d$)SO$_2$R$_c$, Si(R$_d$)(R$_c$)R$_e$ or (CH$_2$)$_z$NR$_c$R$_d$ (where z is 1, 2 or 3); wherein R$_c$, R$_d$ and R$_e$ are each independently selected from hydrogen, (1-6C)alkyl or (3-6C)cycloalkyl; or R$_c$ and R$_d$ can be linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxyl; or Q is optionally substituted by a group of the formula:

-L$_1$-L$_{Q1}$-Z$_1$ wherein:

L$_1$ is absent or (1-3C)alkylene optionally substituted by one or more substituents selected from (1-2C)alkyl or oxo;

L$_{Q1}$ is absent or selected from O, S, SO, SO$_2$, N(R$_f$), C(O), C(O)O, OC(O), C(O)N(R$_f$), N(R$_f$)C(O), N(R$_g$)C(O)N(R$_f$), N(R$_f$)C(O)O, OC(O)N(R$_f$), S(O)$_2$N(R$_f$), or N(R$_f$)SO$_2$, wherein R$_f$ and R$_g$ are each independently selected from hydrogen or (1-2C)alkyl; and Z$_1$ is hydrogen, (1-6C)alkyl, aryl, aryl(1-2C)alkyl, (3-8C)cycloalkyl, (3-8C)cycloalkenyl, heteroaryl or heterocyclyl; wherein $Z_1$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, $NR_hR_i$, $OR_h$, $C(O)R_h$, $C(O)OR_h$, $OC(O)R_h$, $C(O)N(R_i)R_h$, $N(R)C(O)R_h$, $S(O)_{ya}R_h$ (where $y^a$ is 0, 1 or 2), $SO_2N(R_i)R_h$, $N(R_i)SO_2R_h$ or $(CH_2)_{za}NR_iR_h$ (where $z^a$ is 1, 2 or 3); wherein $R_h$ and $R_i$ are each independently selected from hydrogen, (1-4C)alkyl or (3-6C)cycloalkyl;

$R_{1a}$ and $R_{1b}$ are each selected from hydrogen, (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl or mercapto;

W is selected from O, S or $NR_j$, wherein $R_j$ is selected from H or (1-2C)alkyl;

$X_1$ and $X_2$ are each independently selected from N or $CR_k$; wherein $R_k$ is selected from hydrogen, halo, (1-4C)alkyl, (1-4C)alkoxy, amino, (1-4C)alkylamino, (1-4C)dialkylamino, cyano, (2C)alkynyl, $C(O)R_{k1}$, $C(O)OR_{k1}$, $OC(O)R_{k1}$, $C(O)N(R_{k2})R_{k1}$, $N(R_{k2})C(O)R_{k1}$, $S(O)_{yb}R_{k1}$ (where $y^b$ is 0, 1 or 2), $SO_2N(R_{k2})R_{k1}$, $N(R_{k2})SO_2R_{k1}$ or $(CH_2)_{zb}NR_{k1}R_{k2}$ (where $z^b$ is 1, 2 or 3); wherein said (1-4C)alkyl is optionally substituted by one or more substituents selected from amino, hydroxy, (1-2C)alkoxy or halo; and $R_{k1}$ and $R_{k2}$ are each independently selected from hydrogen or (1-4C)alkyl;

$X_3$ is selected from N or $CR_m$; wherein $R_m$ is selected from hydrogen, halo, (1-4C)alkyl, (1-4C)alkoxy, amino, (1-4C)alkylamino, (1-4C)dialkylamino, cyano, (2C)alkynyl, $C(O)R_{m1}$, $C(O)OR_{m1}$, $OC(O)R_{m1}$, $C(O)N(R_{m2})R_{m1}$, $N(R_{m2})C(O)R_{m1}$, $S(O)_{yc}R_{m1}$ (where $y^c$ is 0, 1 or 2), $SO_2N(R_{m2})R_{m1}$, $N(R_{m2})SO_2R_{m1}$ or $(CH_2)_{zc}NR_{m1}R_{m2}$ (where $z^c$ is 1, 2 or 3); wherein said (1-4C)alkyl is optionally substituted by one or more substituents selected from amino, hydroxy, (1-2C)alkoxy or halo; and $R_{m1}$ and $R_{m2}$ are each independently selected from hydrogen or (1-4C)alkyl;

$R_o$ is selected from halo, (1-4C)alkyl, (1-4C)alkoxy, amino, (1-4C)alkylamino, (1-4C)dialkylamino, cyano, (2C)alkynyl, $C(O)R_{o1}$, $C(O)OR_{o1}$, $OC(O)R_{o1}$, $C(O)N(R_{o2})R_{o1}$, $N(R_{o2})C(O)R_{o1}$, $S(O)_{yd}R_{o1}$ (where $y^d$ is 0, 1 or 2), $SO_2N(R_{o2})R_{o1}$, $N(R_{o2})SO_2R_{o1}$ or $(CH_2)_{zd}NR_{o1}R_{o2}$ (where $z^d$ is 1, 2 or 3); wherein said (1-4C)alkyl is optionally substituted by one or more substituents selected from amino, hydroxy, (1-2C)alkoxy or halo; and $R_{o1}$ and $R_{o2}$ are each independently selected from hydrogen or (1-4C)alkyl;

$R_2$ is selected from hydrogen, (1-4C)alkyl or a group of the formula:

-$L_2$-$Y_2$-$Q_2$ wherein:
$L_2$ is absent or (1-3C)alkylene optionally substituted by one or more substituents selected from (1-2C)alkyl or oxo;
$Y_2$ is absent or C(O), C(O)O, C(O)N($R_p$), wherein $R_p$ is selected from hydrogen or (1-4C)alkyl; and $Q_2$ is hydrogen, (1-6C)alkyl, aryl, (3-8C)cycloalkyl, (3-8C)cycloalkenyl, heteroaryl or heterocyclyl; wherein $Q_2$ is optionally further substituted by one or more substituent groups independently selected from (1-4C)alkyl, halo, (1-4C)haloalkyl, (1-4C)haloalkoxy, amino, cyano, hydroxy, carboxy, carbamoyl, sulphamoyl, $NR_qR_r$, $OR_q$, wherein $R_q$ and $R_r$ are each independently selected from hydrogen, (1-4C)alkyl or (3-6C)cycloalkyl;

$R_3$ is selected from a group of the formula:

—$Y_3$-$Q_3$ wherein:
$Y_3$ is C(O), C(O)N($R_y$), C(O)N($R_y$)O, N($R_y$)(O)C, C(O)O, OC(O), N($R_y$)C(O)N($R_{y1}$), $SO_2$N($R_y$), N($R_y$)$SO_2$, oxazolyl, triazolyl, oxadiazolyl, thiazolyl, imidazolyl, thiadiazolyl, pyridinyl, pyrazolyl, pyrrolyl or tetrazolyl, wherein $R_y$ and $R_{y1}$ are independently selected from hydrogen or (1-2C)alkyl; and $Q_3$ is hydrogen, (1-6C)alkyl, aryl, aryl(1-2C)alkyl, (3-8C)cycloalkyl, (3-8C)cycloalkenyl, heteroaryl or heterocyclyl; wherein $Q_3$ is optionally further substituted by one or more substituent groups independently selected from (1-4C)alkyl, halo, (1-4C)haloalkyl, (1-4C)haloalkoxy, amino, cyano, hydroxy, carboxy, carbamoyl, sulphamoyl, $NR_zR_{aa}$, $OR_z$, wherein $R_z$ and $R_{aa}$ are each independently selected from hydrogen, (1-4C)alkyl or (3-6C)cycloalkyl; or $Q_3$ is optionally substituted by a group of the formula:

-$L_4$-$L_{Q4}$-$Z_4$ wherein:
$L_4$ is absent or (1-3C)alkylene optionally substituted by one or more substituents selected from (1-2C)alkyl or oxo;
$L_{Q4}$ is absent or selected from or O, S, SO, $SO_2$, N($R_{ab}$), C(O), C(O)O, OC(O), C(O)N($R_{ab}$), N($R_{ab}$)C(O), N($R_{ac}$)C(O)N($R_{ab}$), N($R_{ab}$)C(O)O, OC(O)N($R_{ab}$), $S(O)_2$N($R_{ab}$), or N($R_{ab}$)$SO_2$, wherein $R_{ab}$ and $R_{ac}$ are each independently selected from hydrogen or (1-2C)alkyl; and
$Z_4$ is hydrogen, (1-6C)alkyl, aryl, aryl(1-2C)alkyl, (3-8C)cycloalkyl, (3-8C)cycloalkenyl, heteroaryl or heterocyclyl; wherein $Z_4$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, $NR_{ad}R_{ae}$, $OR_{ad}$, $C(O)R_{ad}$, $C(O)OR_{ad}$, $OC(O)R_{ad}$, $C(O)N(R_{ae})R_{ad}$, $N(R_{ae})C(O)R_{ad}$, $S(O)_{ye}R_{ad}$ (where $y^e$ is 0, 1 or 2), $SO_2N(R_{ae})R_{ad}$, $N(R_{ae})SO_2R_{ad}$ or $(CH_2)_{ze}NR_{ad}R_{ae}$ (where $z^e$ is 1, 2 or 3); wherein $R_{ad}$ and $R_{ae}$ are each independently selected from hydrogen, (1-4C)alkyl or (3-6C)cycloalkyl; or
$Q_3$ and $R_y$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxyl;

with the proviso that only one or two of $X_1$, $X_2$ or $X_3$ can be N.

Additional examples of other RET kinase inhibitors include those described in International Publication No. WO 2017145050, which is hereby incorporated by reference. For example, in some embodiments, the other RET has the Formula (VI) or is a pharmaceutically acceptable salt thereof.

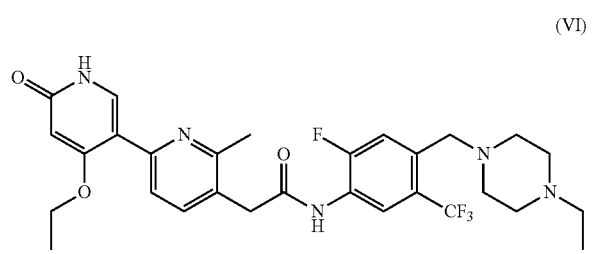 [SMILES: CCOc1cc(=O)[nH]cc1-c1ccc(CC(=O)Nc2cc(C(F)(F)F)c(CN3CCN(CC)CC3)cc2F)c(C)n1]

(VI)

Additional examples of other RET kinase inhibitors include those described in International Publication No. WO 2016038552 is hereby incorporated by reference. For example, in some embodiments, the other RET has the Formula (VII), or the Formula (VIII), or is a pharmaceutically acceptable salt thereof

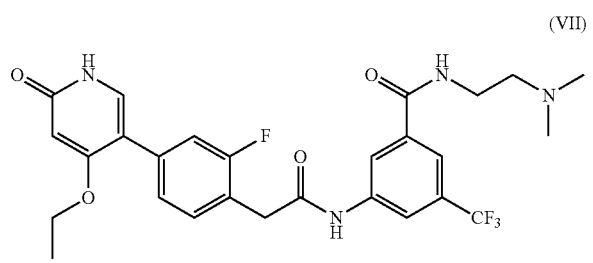

(VII)

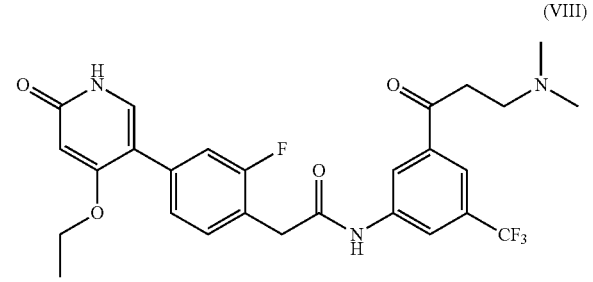

(VIII)

Yet other therapeutic agents include RET inhibitors such as those described, for example, in U.S. Pat. Nos. 10,030, 005; 9,738,660; 9,801,880; 9,682,083; 9,789,100; 9,550, 772; 9,493,455; 9,758,508; 9,604,980; 9,321,772; 9,522, 910; 9,669,028; 9,186,318; 8,933,230; 9,505,784; 8,754, 209; 8,895,744; 8,629,135; 8,815,906; 8,354,526; 8,741, 849; 8,461,161; 8,524,709; 8,129,374; 8,686,005; 9,006, 256; 8,399,442; 7,795,273; 7,863,288; 7,465,726; 8,552, 002; 8,067,434; 8,198,298; 8,106,069; 6,861,509; 8,299, 057; 9,150,517; 9,149,464; 8,299,057; and 7,863,288; U.S. Publication Nos. 2018/0009818; 2018/0009817; 2017/ 0283404; 2017/0267661; 2017/0298074; 2017/0114032; 2016/0009709; 2015/0272958; 2015/0238477; 2015/ 0099721; 2014/0371219; 2014/0137274; 2013/0079343; 2012/0283261; 2012/0225057; 2012/0065233; 2013/ 0053370; 2012/0302567; 2011/0189167; 2016/0046636; 2013/0012703; 2011/0281841; 2011/0269739; 2012/ 0271048; 2012/0277424; 2011/0053934; 2011/0046370; 2010/0280012; 2012/0070410; 2010/0081675; 2010/ 0075916; 2011/0212053; 2009/0227556; 2009/0209496; 2009/0099167; 2010/0209488; 2009/0012045; 2013/ 0303518; 2008/0234267; 2008/0199426; 2010/0069395; 2009/0312321; 2010/0173954; 2011/0195072; 2010/ 0004239; 2007/0149523; 2017/0281632; 2017/0226100; 2017/0121312; 2017/0096425; 2017/0044106; 2015/ 0065468; 2009/0069360; 2008/0275054; 2007/0117800; 2008/0234284; 2008/0234276; 2009/0048249; 2010/ 0048540; 2008/0319005; 2009/0215761; 2008/0287427; 2006/0183900; 2005/0222171; 2005/0209195; 2008/ 0262021; 2008/0312192; 2009/0143399; 2009/0130229; 2007/0265274; 2004/0185547; and 2016/0176865; and International Publication Nos. WO 2018/149382; WO 2018/ 136796; WO 2017/079140; WO 2017/145050; WO 2017/ 097697; WO 2017/049462; WO 2017/043550; WO 2017/ 027883; WO 2017/013160; WO 2017/009644; WO 2016/ 168992; WO 2016/137060; WO 2016/127074; WO 2016/ 075224; WO 2016/038552; WO 2015/079251; WO 2014/ 086284; WO 2013/042137; WO 2013/036232; WO 2013/ 016720; WO 2012/053606; WO 2012/047017; WO 2007/ 109045; WO 2009/042646; WO 2009/023978; WO 2009/ 017838; WO 2017/178845; WO 2017/178844; WO 2017/ 146116; WO 2017/026718; WO 2016/096709; WO 2007/ 057397; WO 2007/057399; WO 2007/054357; WO 2006/ 130613; WO 2006/089298; WO 2005/070431; WO 2003/ 020698; WO 2001/062273; WO 2001/016169; WO 1997/ 044356; WO 2007/087245; WO 2005/044835; WO 2014/ 075035; and WO 2016/038519; and *J. Med. Chem.* 2012, 55 (10), 4872-4876, all of which are hereby incorporated by reference in their entireties.

In some embodiments, a RET inhibitor (e.g., a first RET inhibitor or a second RET inhibitor) is a compound of the Formula II:

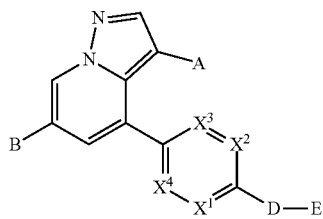

II or a pharmaceutically acceptable salt or solvate thereof, wherein:
$X^1$ is CH, CCH$_3$, CF, CCl or N;
$X^2$ is CH, CF or N;
$X^3$ is CH, CF or N;
$X^4$ is CH, CF or N;
wherein zero, one or two of $X^1$, $X^2$, $X^3$ and $X^4$ is N;
A is H, Cl, CN, Br, CH$_3$, CH$_2$CH$_3$ or cyclopropyl;
B is hetAr$^1$;
hetAr$^1$ is a 5-membered heteroaryl ring having 1-3 ring heteroatoms independently selected from N, S and O, wherein said heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl, (R$^a$R$^b$N)C(=O)C1-C6 alkyl, (C1-C6 alkylSO$_2$)C1-C6 alkyl, hetCyc$^a$, and 4-methoxybenzyl;

$R^a$ and $R^b$ are independently H or C1-C6 alkyl;

hetCyc$^a$ is a 4-6 membered heterocyclic ring having a ring heteroatom selected from N and O, wherein said heterocyclic ring is optionally substituted with halogen, C1-C6 alkyl, fluoroC1-C6 alkyl, difluoroC1-C6 alkyl, trifluoroC1-C6 alkyl, (C1-C6 alkoxy)C1-C6 alkyl, di(C1-C3 alkyl)NCH$_2$C(=O), (C1-C6 alkoxy)C(=O) or (C1-C6 alkoxy)CH$_2$C(=O);

D is hetCyc$^a$, hetCyc$^2$, hetCyc$^3$ or hetCyc$^9$;

hetCyc$^a$ is a 4-6 membered heterocyclic ring having 1-2 ring atoms selected from N and O, wherein said heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or said heterocyclic ring is substituted with a C3-C6 cycloalkylidene ring, or said heterocyclic ring is substituted with an oxo group;

hetCyc$^2$ is a 7-8 membered bridged heterocyclic ring having 1-3 ring heteroatoms independently selected from N and O, wherein said heterocyclic ring is optionally substituted with C1-C3 alkyl;

hetCyc$^3$ is a 7-11 membered heterospirocyclic ring having 1-2 ring heteroatoms independently selected from N and O, wherein said ring is optionally substituted with C1-C3 alkyl;

hetCyc$^9$ is a fused 9-10 membered heterocyclic ring having 1-3 ring nitrogen atoms and optionally substituted with oxo;

E is
 (a) hydrogen,
 (b) OH,
 (c) $R^aR^bN$—, wherein $R^a$ is H or C1-C6 alkyl and $R_b$ is H, C1-C6 alkyl or phenyl;
 (d) C1-C6 alkyl optionally substituted with one to three fluoros,
 (e) hydroxyC1-C6 alkyl- optionally substituted with one to three fluoros,
 (f) C1-C6 alkoxy optionally substituted with one to three fluoros,
 (g) hydroxy(C1-C6 alkoxy) optionally substituted with one to three fluoros,
 (h) (C1-C6 alkoxy)hydroxy C1-C6 alkyl- optionally substituted with one to three fluoros,
 (i) (C1-C6 alkyl)C(=O)— optionally substituted with one to three fluoros,
 (j) (hydroxy C1-C6 alkyl)C(=O)— optionally substituted with one to three fluoros,
 (k) (C1-C6 alkoxy)C(=O)—,
 (l) (C1-C6 alkoxy)(C1-C6 alkyl)C(=O)—,
 (m) HC(=O)—,
 (n) Cyc$^1$,
 (o) Cyc$^1$C(=O)—,
 (p) Cyc$^1$(C1-C6 alkyl)C(=O)— wherein said alkyl portion is optionally substituted with one or more groups independently selected from the group consisting of OH, fluoro, C1-C3 alkoxy and $R^cR^dN$—, where $R^c$ and $R^d$ are independently H or C1-C6 alkyl,
 (q) hetCyc$^4$,
 (r) hetCyc$^4$C(=O)—,
 (s) hetCyc$^4$(C1-C3 alkyl)C(=O)—,
 (t) (hetCyc$^4$)C(=O)C1-C2 alkyl-,
 (u) hetCyc$^4$C(=O)NH—,
 (v) Ar$^2$,
 (w) Ar$^2$C(=O)—,
 (x) Ar$^2$C1-C6 alkyl-,
 (y) (Ar$^2$)hydroxy C2-C6 alkyl-,
 (z) Ar$^2$(C1-C3 alkyl)C(=O)— wherein said alkyl portion is optionally substituted with one or two groups independently selected from the group consisting of OH, C1-C6 alkyl (optionally substituted with 1-3 fluoros), hydroxyC1-C6 alkyl, C1-C6 alkoxy and $R^eR^fN$—, where $R^e$ and $R^f$ are independently H or C1-C6 alkyl, or $R^e$ and $R^f$ together with the nitrogen to which they are attached form a 5-6 membered azacyclic ring optionally having an additional ring heteroatom selected from N and O,
 (aa) hetAr$^2$C(=O)—,
 (bb) (hetAr$^2$)hydroxyC2-C6 alkyl-,
 (cc) hetAr$^2$(C1-C3 alkyl)C(=O)—, wherein said alkyl portion is optionally substituted with one or two groups independently selected from the group consisting of OH, C1-C6 alkyl, hydroxyC1-C6 alkyl, C1-C6 alkoxy and $R^eR^fN$—, wherein $R^e$ and $R^f$ are independently H or C1-C6 alkyl or $R^e$ and $R^f$ together with the nitrogen to which they are attached form a 5-6 membered azacyclic ring optionally having an additional ring heteroatom selected from N and O,
 (dd) $R^1R^2NC(=O)$—,
 (ee) $R^1R^2N$(C1-C3 alkyl)C(=O)—, wherein said alkyl portion is optionally substituted with phenyl,
 (ff) $R^1R^2NC(=O)$C1-C2 alkyl-,
 (gg) $R^1R^2NC(=O)NH$—,
 (hh) CH$_3$SO$_2$(C1-C6 alkyl)C(=O)—,
 (ii) (C1-C6 alkyl)SO$_2$—,
 (jj) (C3-C6 cycloalkyl)CH$_2$SO$_2$—,
 (kk) hetCyc$^5$-SO$_2$—,
 (ll) $R^4R^5NSO_2$—,
 (mm) $R^6C(=O)NH$—,
 (nn) hetCyc$^6$,
 (oo) hetAr$^2$C1-C6 alkyl-,
 (pp) (hetCyc$^4$)C1-C6 alkyl-,
 (qq) (C1-C6 alkoxy)C1-C6 alkyl- optionally substituted with 1-3 fluoros,
 (rr) (C3-C6 cycloalkoxy)C1-C6 alkyl-,
 (ss) (C3-C6 cycloalkyl)C1-C6 alkyl-, wherein said cycloalkyl is optionally substituted with 1-2 fluoros,
 (tt) ($R^gR^hN$)C1-C6 alkyl-, wherein $R^g$ and $R^h$ are independently H or C1-C6 alkyl,
 (uu) Ar$^2$—O—,
 (vv) (C1-C6 alkylSO$_2$)C1-C6 alkyl-,
 (ww) (C1-C6 alkoxy)C(=O)NHC1-C6 alkyl-,
 (xx) (C3-C6 cycloalkoxy)C(=O)—,
 (yy) (C3-C6 cycloalkyl)SO$_2$—, wherein said cycloalkyl is optionally substituted with C1-C6 alkyl,
 (zz) Ar$^4$CH$_2$OC(=O)—,
 (aaa) (N—(C1-C3 alkyl)pyridinonyl)C1-C3 alkyl-, and
 (bbb) (Ar$^4$SO$_2$)C1-C6 alkyl-;

Cyc$^1$ is a C3-C6 cycloalkyl, wherein (a) said cycloalkyl is optionally substituted with one or more substituents independently selected from the group consisting of OH, halogen, C1-C6 alkoxy, CN, hydroxyC1-C6 alkyl, (C1-C6 alkoxy)C1-C6 alkyl, and C1-C6 alkyl optionally substituted with 1-3 fluoros, or (b) said cycloalkyl is substituted with phenyl, wherein said phenyl is optionally substituted with one or more substituents independently selected from the group consisting of halogen, C1-C3 alkyl, C1-C3 alkoxy and CF, or (c) said cycloalkyl is substituted with a 5-6 membered heteroaryl ring having 1-3 ring heteroatoms independently selected from N and O, wherein said heteroaryl ring is optionally substituted with one or more substituents independently selected from the group consisting of halogen, C1-C3 alkyl, C1-C3 alkoxy and CF$_3$;

$Ar^2$ is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and $R^iR^jN$— wherein $R^i$ and $R^j$ are independently H or C1-C6 alkyl;

hetAr$^2$ is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN, OH, and R'R"N—, wherein R' and R" are independently H or C1-C3 alkyl;

hetCyc$^4$ is (a) a 4-6 membered heterocyclic ring having 1-2 ring heteroatoms independently selected from N, O and S wherein said S is optionally oxidized to SO$_2$, (b) a 7-8 membered bridged heterocyclic ring having 1-2 ring heteroatoms independently selected from N and O, (c) a 6-12 membered fused bicyclic heterocyclic ring having 1-2 ring heteroatoms independently selected from N and O and optionally independently substituted with 1-2 C1-C6 alkyl substitutents, or (d) a 7-10 membered spirocyclic heterocyclic ring having 1-2 ring heteroatoms independently selected from N and O, wherein each of said heterocyclic rings is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, (C1-C6 alkyl)C(=O)—, a 5-6 membered heterocyclic ring having 1-2 ring heteroatoms independently selected from N and O, and phenyl wherein said phenyl is optionally substituted with one or more substituents selected from halogen, C1-C6 alkyl and C1-C6 alkoxy;

hetCyc$^5$ is a 5-6 membered heterocyclic ring having a ring heteroatom selected from 0 and N;

hetCyc$^6$ is a 5 membered heterocyclic ring having one or two ring heteroatoms independently selected from N and O, wherein said ring is substituted with oxo and wherein said ring is further optionally substituted with one or more substituents independently selected from the group consisting of OH and C1-C6 alkyl;

$R^1$ is H, C1-C6 alkyl or (C1-C6 alkoxy)C1-C6 alkyl;

$R^2$ is H, C1-C6 alkyl (optionally substituted with 1-3 fluoros), (C1-C6 alkoxy)C1-C6 alkyl (optionally substituted with 1-3 fluoros), Cyc$^3$, hydroxyC1-C6 alkyl (optionally substituted with 1-3 fluoros), C1-C6 alkoxy (optionally substituted with 1-3 fluoros), (C1-C6 alkoxy)C(=O), hetCyc$^7$, Ar$^3$, Ar$^3$C1-C3 alkyl-, hydroxyC1-C6 alkoxy or (3-6C cycloalkyl)CH$_2$O—;

Cyc$^3$ is a 3-6 membered carbocyclic ring optionally substituted with 1-2 groups independently selected from the group consisting of C1-C6 alkoxy, OH and halogen;

hetCyc$^7$ is a 5-6 membered heterocyclic ring having a ring heteroatom selected from O and N wherein said ring is optionally substituted with C1-C6 alkyl;

Ar$^3$ is phenyl optionally substituted with one or more substituents independently selected from halogen, C1-C3 alkyl, C1-C3 alkoxy, fluoroC1-C3 alkyl, difluoroC1-C3 alkyl and trifluoroC1-C3 alkyl;

$R^4$ and $R^5$ are independently H or C1-C6 alkyl;

$R^6$ is C1-C6 alkyl, hydroxyC1-C6 alkyl, C1-C6 alkoxy, (C1-C6 alkoxy)C1-C6 alkyl, phenyl or hetCyc$^8$;

hetCyc$^8$ is a 5-6 membered heterocyclic ring having a ring heteroatom selected from O and N, wherein said heterocyclic ring is optionally substituted with C1-C6 alkyl; and Ar$^4$ is phenyl optionally substituted with one or more halogens.

In some embodiments, a RET inhibitor (e.g., a first RET inhibitor or a second RET inhibitor) is a compound of the Formula III:

III or a pharmaceutically acceptable salt or solvate thereof, wherein:

$X^1$ is CH or N;
$X^2$ is CH or N;
$X^3$ is CH or N;
$X^4$ is CH or N;

wherein one or two of $X^1$, $X^2$, $X^3$ and $X^4$ is N;

A is CN;

B is hetAr$^1$;

hetAr$^1$ is a 5-membered heteroaryl ring having 1-3 ring nitrogen atoms, wherein said heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl, (R$^a$R$^b$N)C(=O)C1-C6 alkyl, (C1-C6 alkylSO$_2$)C1-C6 alkyl, and 4-methoxybenzyl;

R$^a$ and R$^b$ are independently H or C1-C6 alkyl;

D is hetCyc$^1$;

hetCyc$^1$ is a 4-6 membered heterocyclic ring having 1-2 ring nitrogen atoms, wherein said heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or said heterocyclic ring is substituted with a C3-C6 cycloalkylidene ring, or said heterocyclic ring is substituted with an oxo group;

E is
(w) Ar$^2$C(=O)—,
(x) Ar$^2$C1-C6 alkyl-,
(z) Ar$^2$(C1-C3 alkyl)C(=O)— wherein said alkyl portion is optionally substituted with one or two groups independently selected from the group consisting of OH, C1-C6 alkyl (optionally substituted with 1-3 fluoros), hydroxyC1-C6 alkyl, C1-C6 alkoxy and R$^e$R$^f$N—, where R$^e$ and R$^f$ are independently H or C1-C6 alkyl, or R$^e$ and R$^f$ together with the nitrogen to which they are attached form a 5-6 membered azacyclic ring optionally having an additional ring heteroatom selected from N and O, (cc) hetAr$^2$(C1-C3 alkyl)C(=O)—, wherein said alkyl portion is optionally substituted with one or two groups independently selected from the group consisting of OH, C1-C6 alkyl, hydroxyC1-C6 alkyl, C1-C6 alkoxy and R$^e$R$^f$N—, wherein R$^e$ and R$^f$ are independently H or C1-C6 alkyl or R$^e$ and R$^f$ together with the nitrogen to which they are attached form a 5-6 membered azacyclic ring optionally having an additional ring heteroatom selected from N and O, (dd) R$^1$R$^2$NC(=O)—, (oo) hetAr$^2$C1-C6 alkyl-, Ar$^2$ is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and wherein R$^i$ and R$^j$ are independently H or C1-C6 alkyl;

hetAr$^2$ is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN, OH, and R'R"N—, wherein R' and R" are independently H or C1-C3 alkyl;

R$^1$ is H, C1-C6 alkyl or (C1-C6 alkoxy)C1-C6 alkyl; and

R$^2$ is H, C1-C6 alkyl (optionally substituted with 1-3 fluoros), (C1-C6 alkoxy)C1-C6 alkyl (optionally substituted with 1-3 fluoros), hydroxyC1-C6 alkyl (optionally substituted with 1-3 fluoros), C1-C6 alkoxy (optionally substituted with 1-3 fluoros), (C1-C6 alkoxy)C(=O), hydroxyC1-C6 alkoxy or (3-6C cycloalkyl)CH$_2$O.

In some embodiments, a RET inhibitor (e.g., a first RET inhibitor or a second RET inhibitor) is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazol[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof.

In some embodiments, a RET inhibitor (e.g., a first RET inhibitor or a second RET inhibitor) is a compound of the Formula IV:

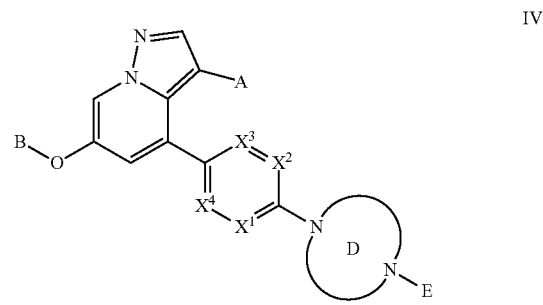

or a pharmaceutically acceptable salt or solvate thereof, wherein:

X$^1$, X$^2$, X$^3$ and X$^4$ are independently CH, CF, CCH$_3$ or N, wherein zero, one or two of X$^1$, X$^2$, X$^3$ and X$^4$ is N;

A is H, CN, Cl, CH$_3$—, CH$_3$CH$_2$—, cyclopropyl, —CH$_2$CN or —CH(CN)CH$_3$;

B is
  (a) hydrogen,
  (b) C1-C6 alkyl optionally substituted with 1-3 fluoros,
  (c) hydroxyC2-C6 alkyl-, wherein the alkyl portion is optionally substituted with 1-3 fluoros or a C3-C6 cycloalkylidene ring,
  (d) dihydroxyC3-C6 alkyl-, wherein the alkyl portion is optionally substituted with a C3-C6 cycloalkylidene ring,
  (e) (C1-C6 alkoxy)C1-C6 alkyl- optionally substituted with 1-3 fluoros,
  (f) (R$^1$R$^2$N)C1-C6 alkyl- wherein said alkyl portion is optionally substituted with OH and wherein R$^1$ and R$^2$ are independently H or C1-C6 alkyl (optionally substituted with 1-3 fluoros);
  (g) hetAr$^1$C1-C3 alkyl-, wherein hetAr$^1$ is a 5-6 membered heteroaryl ring having 1-3 ring heteroatoms independently selected from N, O and S and is optionally substituted with one or more independently selected C1-C6 alkyl substituents;
  (h) (C3-C6 cycloalkyl)C1-C3 alkyl-, wherein said cycloalkyl is optionally substituted with OH,
  (i) (hetCyc$^a$)C1-C3 alkyl-,
  (j) hetCyc$^a$-,
  (k) C3-C6 cycloalkyl-, wherein said cycloalkyl is optionally substituted with OH,
  (l) (C1-C4 alkyl)C(=O)O—C1-C6 alkyl-, wherein each of the C1-C4 alkyl and C1-C6 alkyl portions is optionally and independently substituted with 1-3 fluoros, or
  (m) (R$^1$R$^2$N)C(=O)C1-C6 alkyl-, wherein R$^1$ and R$^2$ are independently H or C1-C6 alkyl (optionally substituted with 1-3 fluoros);

hetCyc$^a$- is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(=O)—, (C1-

C6 alkoxy)C1-C6 alkyl-, and fluoro, or wherein het-Cyc$^a$ is substituted with oxo;

Ring D is (i) a saturated 4-7 membered heterocyclic ring having two ring nitrogen atoms, (ii) a saturated 7-8 membered bridged heterocyclic ring having two ring nitrogen atoms and optionally having a third ring heteroatom which is oxygen, (iii) a saturated 7-11 membered heterospirocyclic ring having two ring nitrogen atoms, or (iv) a saturated 9-10 membered bicyclic fused heterocyclic ring having two ring nitrogen atoms, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group;

E is
(a) hydrogen,
(b) C1-C6 alkyl optionally substituted with 1-3 fluoros,
(c) (C1-C6 alkoxy)C1-C6 alkyl- optionally substituted with 1-3 fluoros,
(d) (C1-C6 alkyl)C(=O)—, wherein said alkyl portion is optionally substituted with 1-3 fluoros or with a R$^g$R$^h$N— substituent wherein R$^g$ and R$^h$ are independently H or C1-C6 alkyl,
(e) (hydroxyC2-C6 alkyl)C(=O)— optionally substituted with 1-3 fluoros,
(f) (C1-C6 alkoxy)C(=O)—,
(g) (C3-C6 cycloalkyl)C(=O)—, wherein said cycloalkyl is optionally substituted with one or more substituents independently selected from C1-C6 alkyl, C1-C6 alkoxy, OH, and (C1-C6 alkoxy)C1-C6 alkyl-, or said cycloalkyl is substituted with a 5-6 membered heteroaryl ring having 1-3 ring heteroatoms independently selected from N and O,
(h) Ar$^1$C1-C6 alkyl-,
(i) Ar$^1$(C1-C6 alkyl)C(=O)—, wherein said alkyl portion is optionally substituted with OH, hydroxyC1-C6 alkyl-, C1-C6 alkoxy, R$^m$R$^n$N— or R$^m$R$^n$N—CH$_2$—, wherein each R$_m$ and R$^n$ is independently H or C1-C6 alkyl,
(j) hetAr$^2$C1-C6 alkyl-, wherein said alkyl portion is optionally substituted with 1-3 fluoros,
(k) hetAr$^2$(C1-C6 alkyl)C(=O)— wherein said alkyl portion is optionally substituted with OH, hydroxyC1-C6 alkyl- or C1-C6 alkoxy,
(l) hetAr$^2$C(=O)—,
(m) hetCyc$^1$C(=O)—,
(n) hetCyc$^1$C1-C6 alkyl-,
(o) R$^3$R$^4$NC(=O)—,
(p) Ar$^1$N(R$^3$)C(=O)—,
(q) hetAr$^2$N(R$^3$)C(=O)—,
(r) (C1-C6 alkyl)SO$_2$—, wherein the alkyl portion is optionally substituted with 1-3 fluoros,
(s) Ar$^1$SO$_2$—,
(t) hetAr$^2$SO$_2$—,
(u) N—(C1-C6 alkyl)pyridinonyl,
(v) Ar$^1$C(=O)—;
(w) Ar$^1$O—C(=O)—,
(x) (C3-C6 cycloalkyl)(C1-C6 alkyl)C(=O)—,
(y) (C3-C6 cycloalkyl)(C1-C6 alkyl)SO$_2$—, wherein the alkyl portion is optionally substituted with 1-3 fluoros,
(z) Ar$^1$(C1-C6 alkyl)SO$_2$—,
(aa) hetCyc$^1$-O—C(=O)—,
(bb) hetCyc$^1$CH$_2$C(=O)—,
(cc) hetAr$^2$, or
(dd) C3-C6 cycloalkyl;

Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), R$^e$R$^f$N— wherein R$^e$ and R$^f$ are independently H, C1-C6 alkyl, (R$^p$R$^q$N)C1-C6 alkoxy- wherein R$^p$ and R$^q$ are independently H or C1-C6 alkyl, and (hetAr$^a$)C1-C6 alkyl- wherein hetAr$^a$ is a 5-6 membered heteroaryl ring having 1-2 ring nitrogen atoms, or Ar$^1$ is a phenyl ring fused to a 5-6 membered heterocyclic ring having 1-2 ring heteroatoms independently selected from N and 0;

hetAr$^2$ is a 5-6 membered heteroaryl ring having 1-3 ring heteroatoms independently selected from N, O and S or a 9-10 membered bicyclic heteroaryl ring having 1-3 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), R$^e$R$^f$N— wherein R$^e$ and R$^f$ are independently H or C1-C6 alkyl, OH, (C1-C6 alkoxy)C1-C6 alkoxy- and C3-C6 cycloalkyl;

hetCyc$^1$ is a 4-6 membered saturated heterocyclic ring having 1-2 ring heteroatoms independently selected from N, O and S wherein said heterocyclic ring is optionally substituted with one or more substituents independently selected from C1-C6 alkoxy and halogen;

R$^3$ is H or C1-C6 alkyl; and
R$^4$ is C1-C6 alkyl.

In some embodiments, a RET inhibitor (e.g., a first RET inhibitor or a second RET inhibitor) is a compound of the Formula V:

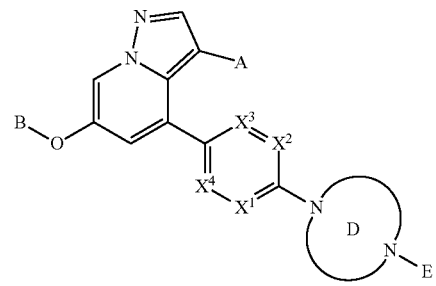

or a pharmaceutically acceptable salt and solvate thereof, wherein:

X$^1$, X$^2$, X$^3$ and X$^4$ are independently CH or N, wherein zero, one or two of X$^1$, X$^2$, X$^3$ and X$^4$ is N;

A is CN;

B is
(b) C1-C6 alkyl optionally substituted with 1-3 fluoros,
(c) hydroxyC2-C6 alkyl-, wherein the alkyl portion is optionally substituted with 1-3 fluoros or a C3-C6 cycloalkylidene ring,
(e) (C1-C6 alkoxy)C1-C6 alkyl- optionally substituted with 1-3 fluoros,
(f) (R$^1$R$^2$N)C1-C6 alkyl-, wherein said alkyl portion is optionally substituted with OH and wherein R$^1$ and R$^2$ are independently H or C1-C6 alkyl (optionally substituted with 1-3 fluoros);

(g) hetAr¹C1-C3 alkyl-, wherein hetAr¹ is a 5-6 membered heteroaryl ring having 1-3 ring heteroatoms independently selected from N, O and S and is optionally substituted with one or more independently selected C1-C6 alkyl substituents; or
(i) (hetCyc^a)C1-C3 alkyl-,
hetCyc^a- is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(=O)—, (C1-C6 alkoxy)C1-C6 alkyl- and fluoro, or wherein hetCyc^a is substituted with oxo;
Ring D is (i) a saturated 4-7 membered heterocyclic ring having two ring nitrogen atoms, or (ii) a saturated 7-9 membered bridged heterocyclic ring having two ring nitrogen atoms and optionally having a third ring heteroatom which is oxygen, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group;
E is
(h) Ar¹C1-C6 alkyl-,
(j) hetAr²C1-C6 alkyl-, wherein the alkyl portion is optionally substituted with 1-3 fluoros, or
(l) hetAr²C(=O)—,
Ar¹ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), R^eR^fN— wherein R^e and R^f are independently H or C1-C6 alkyl, (R^pR^qN)C1-C6 alkoxy- wherein R^p and R^q are independently H or C1-C6 alkyl, and (hetAr^a)C1-C6 alkyl- wherein hetAr^a is a 5-6 membered heteroaryl ring having 1-2 ring nitrogen atoms, or Ar¹ is a phenyl ring fused to a 5-6 membered heterocyclic ring having 1-2 ring heteroatoms independently selected from N and O; and
hetAr² is a 5-6 membered heteroaryl ring having 1-3 ring heteroatoms independently selected from N, O and S or a 9-10 membered bicyclic heteroaryl ring having 1-3 ring nitrogen atoms, wherein hetAr² is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), R^eR^fN— wherein R^e and R^f are independently H or C1-C6 alkyl, OH, (C1-C6 alkoxy) C1-C6 alkoxy- and C3-C6 cycloalkyl.

In some embodiments, a RET inhibitor (e.g., a first RET inhibitor or a second RET inhibitor) is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-methoxy ethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof.

In some embodiments, a RET inhibitor (e.g., a first RET inhibitor or a second RET inhibitor) is a compound of Formula VI:

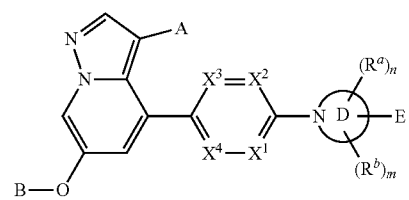

VI or a pharmaceutically acceptable salt or solvate thereof, wherein:
X¹, X², X³ and X⁴ are independently CH, CCH₃, CF or N, wherein zero, one or two of X¹, X², X³ and X⁴ is N;
A is H, CN, Cl, methyl, ethyl or cyclopropyl;
B is:
(a) hydrogen,
(b) C1-C6 alkyl optionally substituted with 1-3 fluoros,
(c) hydroxyC2-C6 alkyl- wherein the alkyl portion is optionally substituted with a C3-C6 cycloalkylidene ring,
(d) dihydroxyC3-C6 alkyl- wherein the alkyl portion is optionally substituted with a C3-C6 cycloalkylidene ring,
(e) (C1-C6 alkoxy)C1-C6 alkyl- optionally substituted with 1-3 fluoros,
(f) (R¹R²N)C1-C6 alkyl- where R¹ and R² are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—;
(g) hetAr¹C1-C3 alkyl-, where hetAr¹ is a 5-6 membered heteroaryl ring having 1-3 ring heteroatoms independently selected from N, O and S and is optionally substituted with one or more independently selected C1-C6 alkyl substituents;
(h) (C3-C6 cycloalkyl)C1-C3 alkyl-, wherein said cycloalkyl is optionally substituted with OH,
(i) (hetCyc^a)C1-C3 alkyl-,
(j) hetCyc^a,
(k) (R¹R²N)C(=O)C1-C6 alkyl-, where R¹ and R² are independently selected from H and C1-C6 alkyl;
(l) (R¹R²N)C(=O)—, where R¹ and R² are independently selected from H and C1-C6 alkyl, or
(m) hetCyc^aC(=O)C1-C6 alkyl-;
hetCyc^a is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—;

Ring D is (i) a saturated monocyclic 4-7 membered heterocyclic ring having one ring heteroatom which is nitrogen, (ii) a saturated 7-8 membered bridged heterocyclic ring having one ring heteroatom which is nitrogen, or (iii) a saturated 7-11 membered heterospirocyclic ring system having one ring heteroatom which is nitrogen;

each $R^a$ is independently C1-C6 alkyl (optionally substituted with 1-3 fluoros), hydroxyC1-C6 alkyl or (C1-C6 alkoxy)C1-C6 alkyl-;

$R^b$ is (a) hydroxy, (b) cyclopropyl, (c) hetCyc$^b$CH$_2$—, (d) R$^i$R$^j$NC(=O)CH$_2$OCH$_2$— where R$^i$ and W are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, (j) hetCyc$^b$(C1-C3 alkyl)OCH$_2$—, (k) hetCyc$^b$C(=O)NH— or (l) hetAr$^a$C(=O)NH—;

hetCyc$^b$ is a 4-6 membered heterocyclic ring, a 7-8 membered bridged heterocyclic ring, or a 7-10 membered heterospirocyclic ring, each ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), (C1-C6 alkoxy)C1-C6 alkyl-, (C1-C6 alkoxy)C(=O)—, C1-C6 alkoxy, and R'R"N— where R' and R" are independently hydrogen or C1-C6 alkyl;

hetAr$^a$ is a 5-6 membered heteroaryl ring having 1-3 ring heteroatoms independently selected from N, O and S wherein hetAr$^a$ is optionally substituted with one or more substituents independently selected from the group consisting of halogen, CN, C1-C6 alkyl (optionally substituted with 1-3 fluoros), and C1-C6 alkoxy (optionally substituted with 1-3 fluoros), $R^c$ is hydrogen or C1-C6 alkyl;

$R_d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$— wherein the phenyl is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO$_2$—, R$^e$R$^f$N— and (R$^e$R$^f$N)C1-C6 alkyl- where each R$^e$ and R$^f$ is independently H or C1-C6 alkyl, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl;

n is 0, 1, 2, 3, 4, 5 or 6;

m is 0 or 1;

E is:
(a) hydrogen,
(b) hydroxy,
(c) C1-C6 alkyl optionally substituted with 1-3 fluoros,
(d) Ar$^1$C1-C6 alkyl- wherein said alkyl portion is optionally substituted with 1-3 fluoros, (e) hetAr$^2$C1-C6 alkyl-,
(f) (C1-C6 alkoxy)C1-C6 alkoxy-,
(g) Ar$^1$O—,
(h) hetAr$^2$—O—,
(i) Ar$^1$NR$^g$— where R$^g$ is H or C1-C6 alkyl,
(j) hetAr$^2$NR$^g$— where R$^g$ is H or C1-C6 alkyl,
(k) R$^3$C(=O)NR$^g$— where R$^g$ is H or C1-C6 alkyl;
(l) Ar$^1$C(=O)NR$^g$— where R$^g$ is H or C1-C6 alkyl,
(m) hetAr$^2$C(=O)NR$^g$(CH$_2$)$_p$— where p is 0 or 1 and R$^g$ is H or C1-C6 alkyl,
(n) R$^4$R$^5$NC(=O)—,
(o) Ar$^1$NR$^g$C(=O)—, where R$^g$ is H or C1-C6 alkyl,
(p) hetAr$^2$NR$^g$C(=O)—, where R$^g$ is H or C1-C6 alkyl,
(q) Ar$^1$(C1-C6 alkyl)C(=O)— wherein said alkyl portion is optionally substituted with OH, hydroxy(C1-C6 alkyl), C1-C6 alkoxy or NH$_2$,
(r) hetCyc$^5$C(=O)—,
(s) R$^4$R$^5$NC(=O)NR$^g$— where R$^g$ is H or C1-C6 alkyl, or
(t) (C1-C6 alkyl)SO$_2$—;
(u) Ar$^1$(C1-C6 alkyl)C(=O)NR$^g$— where R$^g$ is H or C1-C6 alkyl,
(v) hetAr$^4$C(=O)NR$^g$— where R$^g$ is H or C1-C6 alkyl,
(w) hetAr$^2$—S(=O)—,
(x) (C3-C6 cycloalkyl)CH$_2$SO$_2$—,
(y) Ar$^1$(C1-C6 alkyl)SO$_2$—,
(z) hetAr$^2$SO$_2$—,
(aa) Ar$^1$,
(bb) hetAr$^2$,
(cc) hetCyc$^5$,
(dd) C1-C6 alkoxy,
(ee) Ar$^1$(C1-C6 alkyl)-O—,
(ff) hetAr$^2$(C1-C6 alkyl)-O—,
(gg) hetAr$^2$—O—C1-C6 alkyl-,
(hh) Ar$^1$(C1-C6 alkyl)NR$^g$— where R$^g$ is H or C1-C6 alkyl,
(ii) hetAr$^2$—S—,
(jj) Ar$^2$SO$_2$NR$^g$(CH$_2$)$_p$— where p is 0 or 1 and R$^g$ is H or C1-C6 alkyl,
(kk) (C1-C6 alkoxy)C(=O)—,
(ll) (C1-C6 alkyl)NR$^g$C(=O)O— where R$^g$ is H or C1-C6 alkyl,
(mm) (C1-C6 alkyl)NR$^g$SO$_2$— where R$^g$ is H or C1-C6 alkyl,
(nn) hetCyc$^5$C(=O)NR$^g$— where R$^g$ is H or C1-C6 alkyl,
(oo) Q-NR$^h$(C1-C3 alkyl)C(=O)NR$^g$— where R$^g$ and R$^h$ are independently H or C1-C6 alkyl and Q is H, C1-C6 alkyl or (C1-C6 alkyl)OC(=O)—,
(pp)

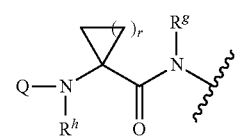

where $R^g$ and $R^h$ are independently H or C1-C6 alkyl, Q is H, C1-C6 alkyl or (C1-C6 alkyl)OC(=O)— and r is 1, 2, 3 or 4, (qq)

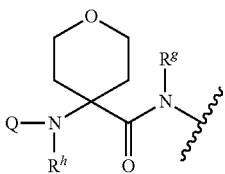

where $R^g$ and $R^h$ are independently H or C1-C6 alkyl and Q is H, C1-C6 alkyl or (C1-C6 alkyl)OC(=O)—, (rr)

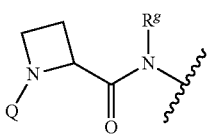

where $R^g$ is H or C1-C6 alkyl and Q is H, C1-C6 alkyl or (C1-C6 alkyl)OC(=O)—, or (ss) $R^g R^h N$— where $R^g$ and $R^h$ are independently H or C1-C6 alkyl, (tt) (C3-C6 cycloalkyl)C(=O)$NR^g$— where the cycloalkyl is optionally and independently substituted with one or more halogens, (uu) (C1-C6 alkyl)C(=O)$NR^g CH_2$— where $R^g$ is H or C1-C6 alkyl, or (vv) C1-C6 alkyl)$SO_2 NR^g$— where $R^g$ is H or C1-C6 alkyl;

$Ar^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)$SO_2$—, $R^e R^f N$— and ($R^e R^f N$)C1-C6 alkyl- where each $R^e$ and $R^f$ is independently H or C1-C6 alkyl;

$hetAr^2$ is a 5-6 membered heteroaryl ring having 1-3 ring heteroatoms independently selected from N, O and S, or a 9-10 membered bicyclic heteroaryl having 1-2 ring nitrogen atoms, wherein $hetAr^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-;

$hetCyc^5$ is a 4-6 membered saturated heterocyclic ring having 1-2 ring heteroatoms independently selected from N, O and S wherein said heterocyclic ring is optionally substituted with one or more substituents independently selected from C1-C6 alkoxy and oxo;

$R^3$ is C1-C6 alkyl (optionally substituted with 1-3 fluoros), hydroxyC1-C6 alkyl-, C1-C6 alkoxy, C3-C6 cycloalkyl, (C3-C6 cycloalkyl)$CH_2$—, (C3-C6 cycloalkyl)O—, (C3-C6 cycloalkyl)$CH_2 O$—, $hetCyc^7 O$—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH or R'R"N— where R' and R" are independently hydrogen or C1-C6 alkyl;

$R^4$ is H or C1-C6 alkyl;

$R^5$ is $Ar^2$, $hetAr^3$, $Ar^2 CH_2$—, $hetCyc^6$-$CH_2$—, hydroxyC1-C6 alkyl-, (C3-C6 cycloalkyl)$CH_2$—, or C1-C6 alkyl optionally substituted with 1-3 fluoros;

$Ar^2$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, and $R^g R^h N$— where $R^g$ and $R^h$ are independently H or C1-C6 alkyl, or $Ar^2$ is phenyl fused to a 6 membered heterocyclic ring having a ring nitrogen atom and optionally substituted with C1-C6 alkyl;

$hetAr^3$ is a 5-6 membered heteroaryl ring having 1-3 ring heteroatoms independently selected from N, O and S and optionally substituted with one or more substituents independently selected from the group consisting of halogen, CN, C1-C6 alkyl (optionally substituted with 1-3 fluoros), C1-C6 alkoxy (optionally substituted with 1-3 fluoros), and (C1-C6 alkoxy)C1-C6 alkyl- (optionally substituted with 1-3 fluoros);

$hetAr^4$ is pyridin-4(1H)-onyl or pyridin-2(1H)-onyl optionally substituted with one or more substituents independently selected from C1-C6 alkyl and halogen;

$hetCyc^6$ is a 5-7 membered heterocyclic ring having 1-3 ring heteroatoms independently selected from N, O and S; and $hetCyc^7$ is a 5-7 membered heterocyclic ring having 1-3 ring heteroatoms independently selected from N, O and S.

In some embodiments, a RET inhibitor (e.g., a first RET inhibitor or a second RET inhibitor) is a compound of the Formula VII:

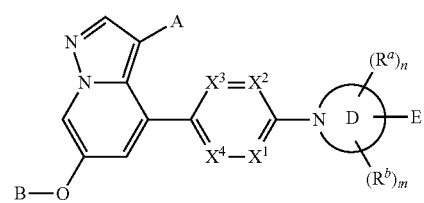

VII or a pharmaceutically acceptable salt or solvate thereof, wherein:

$X^1$, $X^2$, $X^3$ and $X^4$ are independently CH or N, wherein zero, one or two of $X^1$, $X^2$, $X^3$ and $X^4$ is N;

A is CN;

B is:

(b) C1-C6 alkyl optionally substituted with 1-3 fluoros, (c) hydroxyC2-C6 alkyl- wherein the alkyl portion is optionally substituted with a C3-C6 cycloalkylidene ring, or (i) ($hetCyc^a$)C1-C3 alkyl-;

$hetCyc^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo, and (C1-C6 alkoxy)C(=O)—;

Ring D is a saturated monocyclic 4-7 membered heterocyclic ring having one ring heteroatom which is nitrogen;

each $R^a$ is independently C1-C6 alkyl (optionally substituted with 1-3 fluoros);

$R^b$ is (a) hydroxy;

n is 0 or 1;

m is 0 or 1;

E is:
- (e) hetAr$^2$C1-C6 alkyl-,
- (h) hetAr$^2$—O—,
- (k) $R^3C(=O)NR^g$— where $R^g$ is H or C1-C6 alkyl,
- (l) Ar$^1$C(=O)NR$^g$— where $R^g$ is H or C1-C6 alkyl, or
- (m) hetAr$^2$C(=O)NR$^g$(CH$_2$)$_p$— where p is 0 or 1 and $R^g$ is H or C1-C6 alkyl;

Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO$_2$—, $R^eR^fN$— and $(R^eR^fN)$C1-C6 alkyl- where each $R^e$ and $R^f$ is independently H or C1-C6 alkyl;

hetAr$^2$ is a 5-6 membered heteroaryl ring having 1-3 ring heteroatoms independently selected from N, O and S, or a 9-10 membered bicyclic heteroaryl having 1-2 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-; and $R^3$ is C1-C6 alkyl (optionally substituted with 1-3 fluoros), hydroxyC1-C6 alkyl-, C1-C6 alkoxy, C3-C6 cycloalkyl, (C3-C6 cycloalkyl)CH$_2$—, (C3-C6 cycloalkyl)O—, (C3-C6 cycloalkyl)CH$_2$O—, hetCyc$^7$O—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH, or R'R"N— where R' and R" are independently hydrogen or C1-C6 alkyl.

In some embodiments, a RET inhibitor (e.g., a first RET inhibitor or a second RET inhibitor) is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl) pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOXO-101, MGCD516, PLX7486, RXDX101, VM-902A, TPX-0005, and TSR-011. Additional Trk targeted therapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in *Cancer Chemother. Pharmacol.* 75(1): 131-141, 2015; and GNF-5837 (N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl) phenyl]-urea), described in *ACS Med. Chem. Lett.* 3(2):140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in *Cancer* 117(6):1321-1391, 2011; AZD6918, described in *Cancer Biol. Ther.* 16(3):477-483, 2015; AZ64, described in *Cancer Chemother. Pharmacol.* 70:477-486, 2012; AZ-23 ((S)-5-Chloro-N2-(1-(5-fluoropyridin-2-yl)ethyl)-N4-(5-isopropoxy-1H-pyrazol-3-yl)pyrimidine-2,4-diamine), described in *Mol. Cancer Ther.* 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025, 166; 5,910,574; 5,877,016; and 5,844,092, each of which is incorporated by reference in its entirety.

Further examples of Trk inhibitors include CEP-751, described in *Int. J. Cancer* 72:672-679, 1997; CT327, described in *Acta Derm. Venereol.* 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in *PLoS One* 9:e95628, 2014; compounds described in International Publication No. WO 2011/133637; compounds described in U.S. Pat. No. 8,637,256; compounds described in *Expert. Opin. Ther. Pat.* 24(7):731-744, 2014; compounds described in *Expert Opin. Ther. Pat.* 19(3):305-319, 2009; (R)-2-phenylpyrrolidine substituted imidazopyridazines, e.g., GNF-8625, (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol as described in ACS Med. Chem. Lett. 6(5):562-567, 2015; GTx-186 and others, as described in *PLoS One* 8(12):e83380, 2013; K252a ((9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one), as described in *Mol. Cell Biochem.* 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in *J Med. Chem.* 51(15):4672-4684, 2008; PHA-739358 (danusertib), as described in *Mol. Cancer Ther.* 6:3158, 2007; Gö 6976 (5,6,7,13-tetrahydro-13-methyl-5-oxo-12H-indolo[2,3-a]pyrrolo[3,4-c]carbazole-12-propanenitrile), as described in *J Neurochem.* 72:919-924, 1999; GW441756 ((3Z)-3-[(1-methylindol-3-yl)methylidene]-1H-pyrrolo[3,2-b]pyridin-2-one), as described in *IJAE* 115:117, 2010; milciclib (PHA-848125AC), described in *J. Carcinog.* 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5S,6S,8R)-6-Hydroxy-6-(hydroxymethyl)-5-methyl-7,8,14,15-tetrahydro-5H-16-oxa-4b,8a,14-triaza-5,8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2 (1H)-one mono 2-hydroxypropanoate hydrate); sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl)phenyl]carbamoyl}amino)-3-fluorophenoxy]-N-methylpyridine-2-carboxamide hydrate); and VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, the receptor tyrosine kinase inhibitor is an epidermal growth factor receptor typrosine kinase inhibitor (EGFR). For example, EGFR inhibitors can include osimertinib (merelectinib, Tagrisso), erlotinib (Tarceva), gefitinib (Iressa), cetuximab (Erbitux), necitumumab (Portrazza), neratinib (Nerlynx), lapatinib (Tykerb), panitumumab (Vectibix), and vandetanib (Caprelsa). In some embodiments, the EGFR inhibitor is osimertinib.

In some embodiments, signal transduction pathway inhibitors include Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3]benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™) cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is bacillus Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) *OncoImmunology* 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; and WO 2016/075224 all of which are hereby incorporated by reference in their entireties.

Further examples of kinase inhibitors include those described in, for example, WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Further examples of kinase inhibitors include luminespib (AUY-922, NVP-AUY922) (5-(2,4-dihydroxy-5 sopropyl-phenyl)-N-ethyl-4-(4-(morpholinomethyl)phenyl)isoxazole-3-carboxamide) and doramapimod (BIRB-796) (1-[5-tert-butyl-2-(4-methylphenyl)pyrazol-3-yl]-3-[4-(2-morpholin-4-ylethoxy)naphthalen-1-yl]urea).

Accordingly, also provided herein is a method of treating cancer, comprising administering to a patient in need thereof a pharmaceutical combination for treating cancer which comprises (a) the compound of Formula (I) or a pharmaceutically acceptable salt, amorphous form, polymorph form, or pharmaceutical composition (e.g., any of the solid or liquid formulations described herein) thereof, (b) an additional therapeutic agent, and (c) optionally at least one pharmaceutically acceptable carrier for simultaneous, separate or sequential use for the treatment of cancer, wherein the amounts of the compound of Formula (I) or a pharmaceutically acceptable salt, amorphous form, polymorph form, or pharmaceutical composition (e.g., any of the solid or liquid formulations described herein) thereof and the additional therapeutic agent are together effective in treating the cancer.

In some embodiments, the additional therapeutic agent(s) includes any one of the above listed therapies or therapeutic agents which are standards of care in cancers wherein the cancer has a dysregulation of a RET gene, a RET protein, or expression or activity, or level of any of the same.

These additional therapeutic agents may be administered with one or more doses of the compound of Formula (I) or a pharmaceutically acceptable salt, amorphous form, polymorph form, or pharmaceutical composition (e.g., any of the solid or liquid formulations described herein) thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer in a patient in need thereof, which comprises (a) the compound of Formula (I) or a pharmaceutically acceptable salt, amorphous form, polymorph form, or pharmaceutical composition (e.g., any of the solid or liquid formulations described herein) thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula (I) or a pharmaceutically acceptable salt, amorphous form, polymorph form, or pharmaceutical composition (e.g., any of the solid or liquid formulations described herein) thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a patient in need thereof. In one embodiment the patient is a human. In some embodiments, the cancer is a RET-associated cancer. For example, a RET-associated cancer having one or more RET inhibitor resistance mutations.

The term "pharmaceutical combination", as used herein, refers to a pharmaceutical therapy resulting from the mixing or combining of more than one active ingredient and includes both fixed and non-fixed combinations of the active ingredients. The term "fixed combination" means that the compound of Formula (I) or a pharmaceutically acceptable salt, amorphous form, polymorph form, or pharmaceutical composition (e.g., any of the solid or liquid formulations described herein) thereof and at least one additional therapeutic agent (e.g., a chemotherapeutic agent), are both administered to a patient simultaneously in the form of a single composition or dosage. The term "non-fixed combination" means that the compound of Formula (I) or a pharmaceutically acceptable salt, amorphous form, polymorph form, or pharmaceutical composition (e.g., any of the solid or liquid formulations described herein) thereof and at least one additional therapeutic agent (e.g., chemotherapeutic agent) are formulated as separate compositions or dosages such that they may be administered to a patient in need thereof simultaneously, concurrently or sequentially with variable intervening time limits, wherein such administration provides effective levels of the two or more compounds in the body of the patient. These also apply to cocktail therapies, e.g. the administration of three or more active ingredients Accordingly, also provided herein is a method of treating a cancer, comprising administering to a patient in need thereof a pharmaceutical combination for treating cancer which comprises (a) the compound of Formula (I) or a pharmaceutically acceptable salt, amorphous form, polymorph form, or pharmaceutical composition (e.g., any of the solid or liquid formulations described herein) thereof, (b) an additional therapeutic agent, and (c) optionally at least one pharmaceutically acceptable carrier for simultaneous, separate or sequential use for the treatment of cancer, wherein the amounts of compound of Formula (I) or a pharmaceutically acceptable salt, amorphous form, polymorph form, or pharmaceutical composition (e.g., any of the solid or liquid formulations described herein) thereof and the additional therapeutic agent are together effective in treating the cancer. In one embodiment, the compound of Formula (I) or a pharmaceutically acceptable salt, amorphous form, polymorph form, or pharmaceutical composition (e.g., any of the solid or liquid formulations described herein) thereof and the additional therapeutic agent are administered simultaneously as separate dosages. In one embodiment, the compound of Formula (I) or a pharmaceutically acceptable salt, amorphous form, polymorph form, or pharmaceutical composition (e.g., any of the solid or liquid formulations described herein) thereof, and the additional therapeutic agent are administered as separate dosages sequentially in any order, in jointly therapeutically effective amounts, e.g. in daily or intermittently dosages. In one embodiment, the compound of Formula (I) or a pharmaceutically acceptable salt, amorphous form, polymorph form, or pharmaceutical composition (e.g., any of the solid or liquid formulations described herein) thereof, and the additional therapeutic agent are administered simultaneously as a combined dosage. In some embodiments, the cancer is a RET-associated cancer. For example, a RET-associated cancer having one or more RET inhibitor resistance mutations. In some embodiments, the additional therapeutic agent is crizotinib. In some embodiments, the additional therapeutic agent is osimertinib. In some embodiments, the patient has been administered one or more doses of a compound of Formula (I) or a pharmaceutically acceptable salt, amorphous form, polymorph form, or pharmaceutical composition (e.g., any of the solid or liquid formulations described herein) thereof, prior to administration of the pharmaceutical composition. In some embodiments, the cancer is a lung cancer (e.g., a RET-associated lung cancer).

Also provided herein is a method of treating a disease or disorder mediated by RET in a patient in need of such treatment, the method comprising administering to the patient a therapeutically effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof. In some embodiments, the disease or disorder mediated by RET is a dysregulation of RET gene, a RET kinase, or expression or activity or level of any of the same. For example the dysregulation of a RET gene, a RET kinase, or expression or activity or level of any of the same includes one or more RET inhibitor resistance mutations. A disease or disorder mediated by RET can include any disease, disorder or condition that is directly or indirectly linked to expression or activity of RET, including overexpression and/or abnormal activity levels. In one embodiment, the disease is cancer (e.g., a RET-associated cancer). In one embodiment, the cancer is any of the cancers or RET-associated cancers described herein. In some embodiments, the additional therapeutic agent is crizotinib. In some embodiments, the additional therapeutic agent is osimertinib. In some embodiments, the patient has been administered one or more doses of a compound of Formula (I) or a pharmaceutically acceptable salt, amorphous form, polymorph form, or pharmaceutical composition (e.g., any of the solid or liquid formulations described herein) thereof, prior to administration of the pharmaceutical composition. In some embodiments, the cancer is a lung cancer (e.g., a RET-associated lung cancer).

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. For example, overexpression of glial cell-derived neurotrophic factor (GDNF) and its RET receptor tyrosine kinase have been correlated with cancer proliferation and metastasis. See, e.g., Zeng, Q. et al. *J. Int. Med. Res.* (2008) 36(4): 656-64.

Accordingly, also provided herein are methods for inhibiting, preventing, aiding in the prevention, or decreasing the symptoms of metastasis of a cancer in a patient in need thereof, the method comprising administering to the patient a therapeutically effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. See also, e.g., Hezam K et al., *Rev Neurosci* 2018 Jan. 26; 29:93-98; Gao L, et al., *Pancreas* 2015 January; 44:134-143; Ding K et al., *J Biol Chem* 2014 Jun. 6; 289:16057-71; and Amit Metal., *Oncogene* 2017 Jun. 8; 36:3232-3239. In some embodiments, the cancer is a RET-associated cancer. In some embodiments, the compound of Formula (I) or a pharmaceutically acceptable salt, amorphous form, polymorph form, or pharmaceutical composition (e.g., any of the solid or liquid formulations described herein) thereof is used in combination with an additional therapy or another therapeutic agent, including a chemotherapeutic agent, such as a kinase inhibitor. For example, a first or second RET kinase inhibitor. In some embodiments, the additional therapeutic agent is crizotinib. In some embodiments, the additional therapeutic agent is osimertinib. In some embodiments, the patient has been administered one or more doses of a compound of Formula (I) or a pharmaceutically acceptable salt, amorphous form, polymorph form, or pharmaceutical composition (e.g., any of the solid or liquid formulations described herein) thereof, prior to administration of the pharmaceutical composition. In some embodiments, the cancer is a lung cancer (e.g., a RET-associated lung cancer).

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a patient having a RET-associated cancer that include: selecting, identifying, or diagnosing a patient as having a RET-associated cancer, and administering a therapeutically effective amount of the compound of Formula (I) or a pharmaceutically acceptable salt, amorphous form, polymorph form, or pharmaceutical composition (e.g., any of the solid or liquid formulations described herein) thereof to the patient selected, identified, or diagnosed as having a RET-associated cancer. Also provided are methods of decreasing the risk of developing a metastasis or an additional metastasis in a patient having a RET-associated cancer that includes administering a therapeutically effective amount of the compound of Formula (I) or a pharmaceutically acceptable salt, amorphous form, polymorph form, or pharmaceutical composition (e.g., any of the solid or liquid formulations described herein) thereof to a patient having a RET-associated cancer. The decrease in the risk of developing a metastasis or an additional metastasis in a patient having a RET-associated cancer can be compared to the risk of developing a metastasis or an additional metastasis in the patient prior to treatment, or as compared to a patient or a population of patients having a similar or the same RET-associated cancer that has received no treatment or a different treatment. In some embodiments, the RET-associated cancer is a RET-associated cancer having one or more RET inhibitor resistance mutations. In some embodiments, the additional therapeutic agent is crizotinib. In some embodiments, the additional therapeutic agent is osimertinib. In some embodiments, the patient has been administered one or more doses of a compound of Formula (I) or a pharmaceutically acceptable salt, amorphous form, polymorph form, or pharmaceutical composition (e.g., any of the solid or liquid formulations described herein) thereof, prior to administration of the pharmaceutical composition. In some embodiments, the cancer is a lung cancer (e.g., a RET-associated lung cancer).

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject a compound of Formula (I) or a pharmaceutically acceptable salt, amorphous form, polymorph form, or pharmaceutical composition (e.g., any of the solid or liquid formulations described herein) thereof. In some embodiments, the compound of Formula (I) or a pharmaceutically acceptable salt, amorphous form, polymorph form, or pharmaceutical composition (e.g., any of the solid or liquid formulations described herein) thereof is administered in combination with the first RET inhibitor. Also provided are methods of treating a subject identified as having a cancer cell that has one or more RET inhibitor resistance mutations that include administering to the subject the compound of Formula (I) or a pharmaceutically acceptable salt, amorphous form, polymorph form, or pharmaceutical composition (e.g., any of the solid or liquid formulations described herein) thereof. In some embodiments, the compound of Formula (I) or a pharmaceutically acceptable salt, amorphous form, polymorph form, or pharmaceutical composition (e.g., any of the solid or liquid formulations described herein) thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668. In some embodiments, the methods further comprise (after (b)) (c) determining whether a cancer cell in a sample obtained from the subject has at least one RET inhibitor resistance mutation; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668. In some embodiments, the methods further comprise (after (b)) (c) determining whether a cancer cell in a sample obtained from the subject has at least one RET inhibitor resistance mutation; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668. In some embodiments, the methods further comprise (after (b)) (c) determining whether a cancer cell in a sample obtained from the subject has at least one RET inhibitor resistance mutation of Tables 3 or 4; and (d) administering the compound of Formula (I) or a pharmaceutically acceptable salt, amorphous form, polymorph form, or pharmaceutical composition (e.g., any of the solid or liquid formulations described herein) thereof, as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668. In some embodiments, the methods further comprise (after (b)) (c) determining whether a cancer cell in a sample obtained from the subject has the RET inhibitor resistance mutation V804M, G810S, or G810R; and (d) administering the compound of Formula (I) or a pharmaceutically acceptable salt, amorphous form, polymorph form, or pharmaceutical composition (e.g., any of the solid or liquid formulations described herein) thereof selected from the group consisting of the compound of Formula (I) or a pharmaceutically acceptable salt, amorphous form, polymorph form, or pharmaceutical composition (e.g., any of the solid or liquid formulations described herein) thereof, as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has the RET inhibitor resistance mutation V804M, G810S, or G810R; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a second therapeutic agent, wherein the second therapeutic agent is selected from the group consisting of crizotinib and osimertinib, as a monotherapy or in conjunction with the compound of Formula (I) or a pharmaceutically acceptable salt, amorphous form, polymorph form, or pharmaceutical composition (e.g., any of the solid or liquid formulations described herein) thereof to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions of Table 2 in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation of Tables 3 or 4; and (d) administering a second therapeutic agent, wherein the second therapeutic agent is selected from the group consisting of crizotinib and osimertinib, as a monotherapy or in conjunction with the compound of Formula (I) or a pharmaceutically acceptable salt, amorphous form, polymorph form, or pharmaceutical composition (e.g., any of the solid or liquid formulations described herein) thereof to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments of the above, the RET-associated cancer is a lung cancer.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject the compound of Formula (I) or a pharmaceutically acceptable salt, amorphous form, polymorph form, or pharmaceutical composition (e.g., any of the solid or liquid formulations described herein) thereof. In some embodiments, the compound of Formula (I) or a pharmaceutically acceptable salt, amorphous form, polymorph form, or pharmaceutical composition (e.g., any of the solid or liquid formulations described herein) thereof is administered in combination with the first RET inhibitor. Also provided are methods of treating a subject identified as having a cancer cell that has one or more RET inhibitor resistance mutations that include administering to the subject the compound of Formula (I) or a pharmaceutically acceptable salt, amorphous form, polymorph form, or pharmaceutical composition (e.g., any of the solid or liquid formulations described herein) thereof. In some embodiments, the compound of Formula (I) or a pharmaceutically acceptable salt, amorphous form, polymorph form, or pharmaceutical composition (e.g., any of the solid or liquid formulations described herein) thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzoyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl) piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzoyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)

pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering the compound of Formula (I) or a pharmaceutically acceptable salt, amorphous form, polymorph form, or pharmaceutical composition (e.g., any of the solid or liquid formulations described herein) thereof selected from the group consisting of the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridin-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering the compound of Formula (I) or a pharmaceutically acceptable salt, amorphous form, polymorph form, or pharmaceutical composition (e.g., any of the solid or liquid formulations described herein) thereof selected from the group consisting of the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-methoxy ethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-methoxy ethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)

methyl)-3,6-diazabicyclo[3.1.1]heptan-3-yl)pyridin-3-yl) pyrazolo[1,5-a]pyridine-3-carbonitrile; 4-(6-(6-((6-methoxypyridin-3-yl)methyl)-3,6-diazabicyclo[3.1.1] heptan-3-yl)pyridin-3-yl)-6-(2-morpholinoethoxy)pyrazolo [1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1] heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has the RET inhibitor resistance mutation V804M, G810S, or G810R; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo [3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo [3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl) methyl)-3,6-diazabicyclo[3.1.1]heptan-3-yl)pyrazin-2-yl) pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo [1,5-a]pyridin-4-yl)pyridin-2-yl)-4-methylpiperidin-4-yl) benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a] pyridine-3-carbonitrile; 6-(2-hydroxy-2-methylpropoxy)-4-(6-(4-((6-methoxypyridazin-3-yl)oxy)piperidin-1-yl) pyridin-3-yl)pyrazolo[1,5-a]pyridine-3-carbonitrile; (S)-6-(2-hydroxy-2-methylpropoxy)-4-(6-(3-(pyridin-2-yloxy) pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl) pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl) pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo [1,5-a]pyridin-4-yl)pyridin-2-yl)-4-methylpiperidin-4-yl) benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a] pyridine-3-carbonitrile; 6-(2-hydroxy-2-methylpropoxy)-4-(6-(4-((6-methoxypyridazin-3-yl)oxy)piperidin-1-yl) pyridin-3-yl)pyrazolo[1,5-a]pyridine-3-carbonitrile; (S)-6-(2-hydroxy-2-methylpropoxy)-4-(6-(3-(pyridin-2-yloxy) pyrrolidin-1-yl)pyridin-3-yl)pyrazolo[1,5-a]pyridine-3- carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl) pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl) pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl) pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl) pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering the compound of Formula (I) or a pharmaceutically acceptable salt, amorphous form, polymorph form, or pharmaceutical composition (e.g., any of the solid or liquid formulations described herein) thereof selected from the group consisting of the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has the RET inhibitor resistance mutation V804M, G810S, or G810R; and (d) administering a second RET inhibitor, wherein the second RET inhibitor is selected from the group consisting of: N-(1-(5-(3-cyano-6-(2-hydroxy-2-methyl-propoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation.

In some embodiments provided herein, circulating tumor DNA can be used to monitor the responsiveness of a patient to a particular therapy (e.g., a first RET inhibitor, a second RET inhibitor, or the compound of Formula (I) or a pharmaceutically acceptable salt, amorphous form, polymorph form, or pharmaceutical composition (e.g., any of the solid or liquid formulations described herein) thereof). For example, prior to starting treatment with a therapy as described herein (e.g., a first RET inhibitor, a second RET inhibitor, or the compound of Formula (I) or a pharmaceutically acceptable salt, amorphous form, polymorph form, or pharmaceutical composition (e.g., any of the solid or liquid formulations described herein) thereof), a biological sample can be obtained from the subject and the level of circulating tumor DNA determined in the biological sample. This sample can be considered a base-line sample. The subject can then be administered one or more doses of a therapy as described herein (e.g., a first RET inhibitor, a second RET inhibitor, or the compound of Formula (I) or a pharmaceutically acceptable salt, amorphous form, polymorph form, or pharmaceutical composition (e.g., any of the solid or liquid formulations described herein) thereof) and the levels of circulating tumor DNA can be monitored (e.g., after the first dose, second dose, third dose, etc. or after one week, two weeks, three weeks, four weeks, etc.). If the level of circulating tumor DNA is lower than the baseline sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction etc.), this is indicative of responsiveness to the therapy. In some embodiments, the level of circulating tumor DNA is reduced such that it is below the detection limit of the instrument. In some embodiments, the level of circulating tumor DNA in a biological sample obtained from the patient (n) is compared to the sample taken just previous (n-1). If the level of circulating tumor DNA in the n sample is lower than the n-1 sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to the therapy. In some embodiments, the level of circulating tumor DNA is reduced such that it is below the detection limit of the instrument. In the case of responsiveness to therapy, the subject can to be administered one or more doses of the therapy and the circulating tumor DNA can be continued to be monitored.

If the level of circulating tumor DNA in the sample is higher than the baseline (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of resistance to the therapy. If the level of circulating tumor DNA in the n sample is higher than the n−1 sample (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase etc.), this can be indicative of resistance to the therapy. When resistance to therapy is suspected, the subject can undergo one or more of imaging, biopsy, surgery, or other diagnostic tests. In some embodiments, when resistance to the therapy is suspected, the subject can be administered (either as a monotherapy or in combination with the previous therapy) a compound capable of treating a RET inhibitor resistance (e.g., the compound of Formula (I) or a pharmaceutically acceptable salt, amorphous form, polymorph form, or pharmaceutical composition (e.g., any of the solid or liquid formulations described herein) thereof, as provided herein). See, for example, Cancer Discov; 7(12); 1368-70 (2017); and Cancer Discov; 7(12); 1394-403 (2017).

In some embodiments provided herein, a protein biomarker can be used to monitor the responsiveness of a patient to a particular therapy (e.g., a first RET inhibitor, a second RET inhibitor, or the compound of Formula (I) or a pharmaceutically acceptable salt, amorphous form, polymorph form, or pharmaceutical composition (e.g., any of the solid or liquid formulations described herein) thereof). For example, prior to starting treatment with a therapy as described herein (e.g., a first RET inhibitor, a second RET inhibitor, or the compound of Formula (I) or a pharmaceutically acceptable salt, amorphous form, polymorph form, or pharmaceutical composition (e.g., any of the solid or liquid formulations described herein) thereof), a biological sample can be obtained from the subject and the level of a protein biomarker can be determined in the biological sample. This sample can be considered a base-line sample. The subject can then be administered one or more doses of a therapy as described herein (e.g., a first RET inhibitor, a second RET inhibitor, or the compound of Formula (I) or a pharmaceutically acceptable salt, amorphous form, polymorph form, or pharmaceutical composition (e.g., any of the solid or liquid formulations described herein) thereof) and the levels of the protein biomarker can be monitored (e.g., after the first dose, second dose, third dose, etc. or after one week, two weeks, three weeks, four weeks, etc.). If the level of the protein biomarker is lower than the baseline sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction etc.), this is indicative of responsiveness to the therapy. In some embodiments, the level of the protein biomarker is reduced such that it is below the detection limit of the instrument. In some embodiments, the level of the protein biomarker in a biological sample obtained from the patient (n) is compared to the sample taken just previous (n−1). If the level of the protein biomarker in the n sample is lower than the n−1 sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to the therapy. In some embodiments, the level of the protein biomarker is reduced such that it is below the detection limit of the instrument. In the case of responsiveness to therapy, the subject can to be administered one or more doses of the therapy and the protein biomarker can be continued to be monitored.

If the level of the protein biomarker in the sample is higher than the baseline (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of resistance to the therapy. If the level of the protein biomarker in the n sample is higher than the n−1 sample (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase etc.), this can be indicative of resistance to the therapy. When resistance to therapy is suspected, the subject can undergo one or more of imaging, biopsy, surgery, or other diagnostic tests. In some embodiments, when resistance to the therapy is suspected, the subject can be administered (either as a monotherapy or in combination with the previous therapy) a compound capable of treating a RET inhibitor resistance (e.g., the compound of Formula (I) or a pharmaceutically acceptable salt, amorphous form, polymorph form, or pharmaceutical composition (e.g., any of the solid or liquid formulations described herein) thereof, as provided herein).

In some embodiments, one or more protein biomarkers are monitored. The particular protein biomarkers to be monitored can depend on the type of cancer and can be readily identified by one having ordinary skill in the art. Non-limiting examples of protein biomarkers include: CA 125, carcinoembryonic antigen (CEA), calcitonin, thyroglobulin, adrenocorticotropic hormone (ACTH), cortisol, CA 19-9, prolactin, hepatocyte growth factor, osteopontin, myeloperoxidase, tissue inhibitor of metalloproteinases 1, angiopoietin-1 (Ang-1), cytokeratin 19 (CK-19), tissue inhibitor of metalloproteinase-1 (TIMP-1), chitinase 3 like-1 (YKL-40), galectin-3 (GAL-3), CYFRA 21-1 (cytokeratins), EPCAM (epithelial cell adhesion molecule), ProGRP (pro-gastrin-releasing peptide), and CEACAM (carcinoembryonic antigen). See, for example, Cohen J D, Li L, Wang Y, et al. Detection and localization of surgically resectable cancers with a multi-analyte blood test. *Science*; Published online 18 Jan. 2018. pii: eaar3247. DOI: 10.1126/science.aar3247; Fawaz M Makki et al. Serum biomarkers of papillary thyroid cancer. *J Otolaryngol Head Neck Surg.* 2013; 42(1): 16; and Tatiana N. Zamay et al. Current and Prospective Protein Biomarkers of Lung Cancer. *Cancers* (Basel). 2017 November; 9(11): 155. In some embodiments, the biomarkers include one or more of CEA, calcitonin, thyroglobulin, ACTH, and cortisol. In some embodiments, the cancer is medullary thyroid cancer and the protein biomarkers include CEA and calcitonin. In some embodiments, the cancer is non-medullary thyroid cancer and the protein biomarker include thyroglobulin. In some embodiments, the biomarkers are ACTH and cortisol (e.g., when a patient as Cushing's disease related to their cancer).

Also provided herein are methods of treating a RET-associated cancer in a subject that include (a) administering one or more (e.g., two or more, three or more, four or more, five or more, or ten or more) doses of a first RET kinase inhibitor to a subject identified or diagnosed as having a RET-associated cancer (e.g., any of the types of RET-associated cancers described herein)(e.g., identified or diagnosed as having a RET-associated cancer using any of the exemplary methods described herein or known in the art); (b) after step (a), determining a level of circulating tumor DNA in a biological sample (e.g., a biological sample comprising blood, serum, or plasma) obtained from the subject; (c) administering a therapeutically effective amount of a second RET inhibitor or the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to a subject identified as having about the same or an elevated level of circulating tumor DNA as compared to a reference level of circulating tumor DNA (e.g., any of the reference levels of circulating tumor DNA described herein). In some examples of these methods, the reference level of circulating tumor DNA is a level of circulating tumor DNA in a biological sample obtained from the subject prior to step (a). Some embodiments of these methods further include determining the level of circulating tumor DNA in the biological sample obtained from the subject prior to step (a). In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some examples of these methods, the first RET inhibitor is selected from the group of: cabozantinib, vandetanib, alectinib, apatinib, sitravatinib, sorafenib, lenvatinib, ponatinib, dovitinib, sunitinib, foretinib, BLU667, and BLU6864.

Also provided herein are methods of treating a RET-associated cancer in a subject that include administering a therapeutically effective amount of the compound of Formula (I) or a pharmaceutically acceptable salt, amorphous form, polymorph form, or pharmaceutical composition (e.g., any of the solid or liquid formulations described herein) thereof, to a subject (i) identified or diagnosed as having a RET-associated cancer (e.g., any of the types of RET-associated cancers described herein) (e.g., identified or diagnosed as having a RET-associated cancer using any of the exemplary methods described herein or known in the art), (ii) previously administered one or more (e.g., two or more, three or more, four or more, five or more, or ten or more) doses of a second RET kinase inhibitor, and (iii) after the prior administration of the one or more doses of the second RET kinase inhibitor, identified as having about the same or an elevated level of circulating tumor DNA as compared to a reference level of circulating tumor DNA (e.g., any of the reference levels of circulating tumor DNA described herein or known in the art). In some embodiments of these methods, the reference level of circulating tumor DNA is a level of circulating tumor DNA in a biological sample (e.g., a biological sample comprising blood, plasma, or serum) obtained from the subject prior to the administration of the one or more doses of the second RET kinase inhibitor. Some embodiments of these methods further include determining the level of circulating tumor DNA in the biological sample obtained from the subject prior to administration of the one or more doses of the second RET kinase inhibitor. In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some embodiments of these methods, the second RET kinase inhibitor is selected from the group consisting of:

cabozantinib, vandetanib, alectinib, apatinib, sitravatinib, sorafenib, lenvatinib, ponatinib, dovitinib, sunitinib, foretinib, BLU667, and BLU6864.

Also provided herein are methods of treating a RET-associated cancer in a subject that include: (a) administering one or more doses of the compound of Formula (I) or a pharmaceutically acceptable salt, amorphous form, polymorph form, or pharmaceutical composition (e.g., any of the solid or liquid formulations described herein) thereof, as a monotherapy to a subject identified or diagnosed as having a RET-associated cancer (e.g., any of the types of RET-associated cancer described herein) (e.g., a subject identified or diagnosed as having a RET-associated cancer using any of the methods described herein or known in the art); (b) after step (a), determining a level of circulating tumor DNA in a biological sample (e.g., a biological sample comprising blood, serum, or plasma) obtained from the subject; (c) administering a therapeutically effective amount of the compound of Formula (I) or a pharmaceutically acceptable salt, amorphous form, polymorph form, or pharmaceutical composition (e.g., any of the solid or liquid formulations described herein) thereof, and an additional therapeutic agent or treatment (e.g., any of the additional therapeutic agents or treatments of a RET-associated cancer described herein or known in the art) to a subject identified as having about the same or an elevated level of circulating tumor DNA as compared to a reference level of circulating tumor DNA (e.g., any of the exemplary reference levels of circulating tumor DNA described herein or known in the art). In some embodiments of these methods, the additional therapeutic agent is a second RET kinase inhibitor (e.g., a RET kinase inhibitor selected from the group of: cabozantinib, vandetanib, alectinib, apatinib, sitravatinib, sorafenib, lenvatinib, ponatinib, dovitinib, sunitinib, foretinib, BLU667, and BLU6864. In some examples of any of these methods, the additional therapeutic agent or treatment comprises one or more of: radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor) and one or more other kinase inhibitors (e.g., any of the exemplary kinase inhibitors described herein or known in the art). In some examples of these methods, the reference level of circulating tumor DNA is a level of circulating tumor DNA in a biological sample (e.g., a biological sample comprising blood, serum, or plasma) obtained from the subject prior to step (a). In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment).

Also provided herein are methods of treating a RET-associated cancer in a subject that include: administering a therapeutically effective amount of the compound of Formula (I) or a pharmaceutically acceptable salt, amorphous form, polymorph form, or pharmaceutical composition (e.g., any of the solid or liquid formulations described herein) thereof, and an additional therapeutic agent or treatment to a subject (i) identified or diagnosed as having a RET-associated cancer (e.g., any of the types of RET-associated cancer described herein) (e.g., a subject identified or diagnosed as having a RET-associated cancer using any of the methods described herein or known in the art), (ii) previously administered one or more doses of the compound of Formula (I) or a pharmaceutically acceptable salt, amorphous form, polymorph form, or pharmaceutical composition (e.g., any of the solid or liquid formulations described herein) thereof, as a monotherapy, and (ii) after administration of the one or more (e.g., two or more, three or more, four or more, five or more, or ten or more) doses of the compound of Formula (I) or a pharmaceutically acceptable salt, amorphous form, polymorph form, or pharmaceutical composition (e.g., any of the solid or liquid formulations described herein) thereof, as a monotherapy, identified as having about the same or an elevated level of circulating tumor DNA as compared to a reference level of circulating tumor DNA (e.g., any of the exemplary reference levels of circulating tumor DNA described herein). In some embodiments of these methods, the reference level of circulating tumor DNA is a level of circulating tumor DNA in a biological sample obtained from the subject prior to administration of the one or more (e.g., two or more, three or more, four or more, five or more, or ten or more) doses of the compound of Formula (I) or a pharmaceutically acceptable salt, amorphous form, polymorph form, or pharmaceutical composition (e.g., any of the solid or liquid formulations described herein) thereof, as a monotherapy. Some embodiments of these methods further include determining the level of circulating tumor DNA in the biological sample obtained from the subject prior to administration of the one or more doses of the compound of Formula (I) or a pharmaceutically acceptable salt, amorphous form, polymorph form, or pharmaceutical composition (e.g., any of the solid or liquid formulations described herein) thereof, as a monotherapy. In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some embodiments of this method, the additional therapeutic agent is a second RET kinase inhibitor (e.g., a second RET kinase inhibitor selected from the group of cabozantinib, vandetanib, alectinib, apatinib, sitravatinib, sorafenib, lenvatinib, ponatinib, dovitinib, sunitinib, foretinib, BLU667, and BLU6864. In some embodiments of these methods, the additional therapeutic agent or treatment includes one or more of radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor), and one or more other kinase inhibitors (e.g., any of the kinase inhibitors described herein or known in the art).

Also provided herein are methods of selecting a treatment for a subject that include: selecting a therapeutically effective amount of the compound of Formula (I) or a pharmaceutically acceptable salt, amorphous form, polymorph form, or pharmaceutical composition (e.g., any of the solid or liquid formulations described herein) thereof, for a subject (i) identified or diagnosed as having a RET-associated cancer (e.g., any of the RET-associated cancers described herein) (e.g., a subject identified or diagnosed as having a RET-associated cancer using any of the methods described herein or known in the art), (ii) previously administered one or more (e.g., two or more, three or more, four or more, five or more, or ten or more) doses of a second RET kinase inhibitor (e.g., any of the RET kinase inhibitors described herein or known in the art), and (ii) after administration of the one or more doses of the second RET kinase inhibitor, identified as having about the same or an elevated level of circulating tumor DNA as compared to a reference level of circulating tumor DNA. In some embodiments of any of these methods, the reference level of circulating tumor DNA is a level of circulating tumor DNA in a biological sample (e.g., a biological sample comprising blood, serum, or plasma) obtained from the subject prior to administration of the one or more doses of the second RET kinase inhibitor. Some embodiments of these methods further include determining the level of circulating tumor DNA in the biological sample obtained from the subject prior to administration of the one or more doses of the second RET kinase inhibitor. In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some embodiments of any these methods, the second RET kinase inhibitor is selected from the group of cabozantinib, vandetanib, alectinib, apatinib, sitravatinib, sorafenib, lenvatinib, ponatinib, dovitinib, sunitinib, foretinib, BLU667, and BLU6864.

Also provided herein are methods of selecting a treatment for a subject that include selecting a therapeutically effective amount of the compound of Formula (I) or a pharmaceutically acceptable salt, amorphous form, polymorph form, or pharmaceutical composition (e.g., any of the solid or liquid formulations described herein) thereof, and an additional therapeutic agent or treatment for a subject (i) identified or diagnosed as having a RET-associated cancer (e.g., any of the RET-associated cancers described herein or known in the art) (e.g., a subject diagnosed or identified as having a RET-associated cancer using any of the methods described herein or known in the art), (ii) previously administered one or more doses (e.g., two or more, three or more, four or more, five or more, or ten or more) of the compound of Formula (I) or a pharmaceutically acceptable salt, amorphous form, polymorph form, or pharmaceutical composition (e.g., any of the solid or liquid formulations described herein) thereof, as a monotherapy, and (ii) after administration of the one or more doses of the compound of Formula (I) or a pharmaceutically acceptable salt, amorphous form, polymorph form, or pharmaceutical composition (e.g., any of the solid or liquid formulations described herein) thereof, identified as having about the same or an elevated level of circulating tumor DNA as compared to a reference level of circulating tumor DNA. In some embodiments of these methods, the reference level of circulating tumor DNA is a level of circulating tumor DNA in a biological sample (e.g., a biological sample comprising blood, serum, or plasma) obtained from the subject prior to administration of the one or more doses of the compound of Formula (I) or a pharmaceutically acceptable salt, amorphous form, polymorph form, or pharmaceutical composition (e.g., any of the solid or liquid formulations described herein) thereof, as a monotherapy. Some embodiments further include determining the level of circulating tumor DNA in the biological sample obtained from the subject prior to administration of the one or more doses of the compound of Formula (I) or a pharmaceutically acceptable salt, amorphous form, polymorph form, or pharmaceutical composition (e.g., any of the solid or liquid formulations described herein) thereof, as a monotherapy. In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some embodiments of any of these methods, the additional therapeutic agent is a second RET kinase inhibitor (e.g., a second RET kinase inhibitor selected from the group of: cabozantinib, vandetanib, alectinib, apatinib, sitravatinib, sorafenib, lenvatinib, ponatinib, dovitinib, sunitinib, foretinib, BLU667, and BLU6864. In some embodiments of any of the methods described herein, the additional therapeutic agent or treatment includes one or more of radiation therapy, a chemotherapeutic agent (e.g., any of the examples of a chemotherapeutic agent described herein or known in the art), a checkpoint inhibitor (e.g., any of the checkpoint inhibitors described herein or known in the art), surgery (e.g., at least partial resection of the tumor), and one or more other kinase inhibitors (e.g., any of the other kinase inhibitors described herein or known in the art).

Also provided herein are methods of determining the efficacy of a treatment in a subject that include: (a) determining a first level of circulating tumor DNA in a biological sample (e.g., a biological sample including blood, serum, or plasma) obtained from a subject identified or diagnosed as having a RET-associated cancer at a first time point; (b) administering a treatment including one or more doses of the compound of Formula (I) or a pharmaceutically acceptable salt, amorphous form, polymorph form, or pharmaceutical composition (e.g., any of the solid or liquid formulations described herein) thereof to the subject, after the first time point and before a second time point; (c) determining a second level of circulating tumor DNA in a biological sample (e.g., a biological sample comprising blood, serum, or plasma) obtained from the subject at the second time point; and (d) identifying that the treatment is effective in a subject determined to have a decreased second level of circulating tumor DNA as compared to the first level of circulating tumor DNA; or identifying the treatment is not effective in a subject determined to have about the same or an elevated second level of circulating tumor DNA as compared to the first level of circulating tumor DNA. In some embodiments of these methods, the first time point and the second time point are about 1 week to about 1 year apart (e.g., about 1 week to about 10 months, about 1 week to about 8 months, about 1 week to about 6 months, about 1 week to about 4 months, about 1 week to about 3 months, about 1 week to about 2 months, about 1 week to about 1 month, or about 1 week to about 2 weeks).

Also provided herein are methods of determining whether a subject has developed resistance to a treatment that include: (a) determining a first level of circulating tumor DNA in a biological sample (e.g., a biological sample comprising blood, serum, or plasma) obtained from a subject identified or diagnosed as having a RET-associated cancer at a first time point; (b) administering a treatment including one or more (e.g., two or more, three or more, four or more, five or more, or ten or more) doses of the compound of Formula (I) or a pharmaceutically acceptable salt, amorphous form, polymorph form, or pharmaceutical composition (e.g., any of the solid or liquid formulations described herein) thereof to the subject, after the first time point and before a second time point; (c) determining a second level of circulating tumor DNA in a biological sample obtained from the subject at the second time point; and (d) determining that a subject having a decreased second level of circulating tumor DNA as compared to the first level of circulating tumor DNA has not developed resistance to the treatment; or determining that a subject having about the same or an elevated second level of circulating tumor DNA as compared to the first level of circulating tumor DNA has developed resistance to the treatment. In some embodiments of these methods, the first time point and the second time point are about 1 week to about 1 year apart (e.g., about 1 week to about 10 months, about 1 week to about 8 months, about 1 week to about 6 months, about 1 week to about 4 months, about 1 week to about 3 months, about 1 week to about 2 months, about 1 week to about 1 month, or about 1 week to about 2 weeks).

Exemplary methods for detecting circulating tumor DNA are described in Moati et al., *Clin. Res. Hepatol. Gastroenterol.* Apr. 4, 2018; Oussalah et al., *EBioMedicine* Mar. 28, 2018; Moon et al., *Adv. Drug Deliv. Rev.* Apr. 4, 2018; Solassaol et al., *Clin. Chem. Lab. Med.* Apr. 7, 2018; Arriola et al., *Clin. Transl. Oncol.* Apr. 5, 2018; Song et al., *J Circ. Biomark.* Mar. 25, 2018; Aslibekyan et al., *JAMA Cardiol.* Apr. 4, 2018; Isbell et al., *J. Thorac. Cardiovasc. Surg.* Mar. 13, 2018; Boeckx et al., *Clin. Colorectal Cancer* Feb. 22, 2018; Anunobi et al., *J Surg. Res.* Mar. 28, 2018; Tan et al., *Medicine* 97(13):e0197, 2018; Reithdorf et al., *Transl. Androl. Urol.* 6(6):1090-1110, 2017; Volckmar et al., *Genes Chromosomes Cancer* 57(3):123-139, 2018; and Lu et al., *Chronic Dis. Transl. Med.* 2(4):223-230, 2016. Additional methods for detecting circulating tumor DNA are known in the art.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a multikinase inhibitor, wherein the multikinase inhibitor is selected from vandetanib or cabozantinib; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first multikinase inhibitor, wherein the mulitkinase inhibitor is selected from the group consisting of: vandetanib or cabozantinib; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a multikinase inhibitor, wherein the multikinase inhibitor is selected from the group consisting of: vandetanib or cabozantinib; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a multikinase inhibitor, wherein the multikinase inhibitor is selected from the group consisting of vandetanib or cabozantinib; or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering the compound of Formula (I) or a pharmaceutically acceptable salt, amorphous form, polymorph form, or pharmaceutical composition (e.g., any of the solid or liquid formulations described herein) thereof selected from the group consisting of the compound of Formula (I)

or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a multikinase inhibitor (e.g., vandetanib or cabozantinib, as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering a multikinase inhibitor (e.g., vandetanib or cabozantinib), as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation of Tables 3 or 4; and (d) administering a multikinase inhibitor (e.g., vandetanib or cabozantinib), as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has the RET inhibitor resistance mutation V804M, G810S, or G810R; and (d) administering a multikinase inhibitor (e.g., vandetanib or cabozantinib) as a monotherapy or in conjunction with another anticancer agent to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation.

Also, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering additional doses of the compound of Formula (I) or a pharmaceutically acceptable salt, amorphous form, polymorph form, or pharmaceutical composition (e.g., any of the solid or liquid formulations described herein) thereof of step (b) to the subject as a monotherapy or in conjunction with another anticancer agent (e.g., a second RET inhibitor or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation; and (d) administering additional doses of the compound of Formula (I) or a pharmaceutically acceptable salt, amorphous form, polymorph form, or pharmaceutical composition (e.g., any of the solid or liquid formulations described herein) thereof of step (b) to the subject as a monotherapy or in conjunction with another anticancer agent (e.g., a second RET inhibitor or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof selected from the group consisting of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has at least one RET inhibitor resistance mutation of Tables 3 or 4; and (d) administering additional doses of the compound of Formula (I) or a pharmaceutically acceptable salt, amorphous form, polymorph form, or pharmaceutical composition (e.g., any of the solid or liquid formulations described herein) thereof of step (b) to the subject as a monotherapy or in conjunction with another anticancer agent (e.g., a second RET inhibitor or immunotherapy) or anticancer therapy (e.g., surgery or radiation) if the subject has a cancer cell that has at least one RET inhibitor resistance mutation. In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668 is administered in step (d). In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) determining whether a cancer cell in a sample obtained from the subject has the RET inhibitor resistance mutation V804M, G810S, or G810R; and (d) administering additional doses of the compound of Formula (I) or a pharmaceutically acceptable salt, amorphous form, polymorph form, or pharmaceutical composition (e.g., any of the solid or liquid formulations described herein) thereof of step (b) to the subject as a monotherapy or in conjunction with another anticancer agent (e.g., a second RET inhibitor, or immunotherapy) or anticancer therapy (e.g., surgery or radiation) if the subject has a cancer cell that has at least one RET inhibitor resistance mutation. In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668 is administered in step (d).

Also, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) detecting at least one RET inhibitor resistance mutation in a cancer cell in a sample obtained from the subject; and (d) administering additional doses of the compound of Formula (I) or a pharmaceutically acceptable salt, amorphous form, polymorph form, or pharmaceutical composition (e.g., any of the solid or liquid formulations described herein) thereof of step (b) to the subject as a monotherapy or in conjunction with another anticancer agent (e.g., a second RET inhibitor, or immunotherapy) or anticancer therapy (e.g., surgery or radiation). In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) detecting at least one RET inhibitor resistance mutation in a cancer cell in a sample obtained from the subject; and (d) administering additional doses of the compound of Formula (I) or a pharmaceutically acceptable salt, amorphous form, polymorph form, or pharmaceutical composition (e.g., any of the solid or liquid formulations described herein) thereof of step (b) to the subject as a monotherapy or in conjunction with another anticancer agent (e.g., a second RET inhibitor, or immunotherapy) or anticancer therapy (e.g., surgery or radiation). In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof selected from the group consisting of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) detecting at least one RET inhibitor resistance mutation of Tables 3 or 4 in a cancer cell in a sample obtained from the subject; and (d) administering additional doses of the compound of Formula (I) or a pharmaceutically acceptable salt, amorphous form, polymorph form, or pharmaceutical composition (e.g., any of the solid or liquid formulations described herein) thereof of step (b) to the subject as a monotherapy or in conjunction with another anticancer agent (e.g., a second RET inhibitor, or immunotherapy) or anticancer therapy (e.g., surgery or radiation). In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668 is administered in step (d). In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprise (after (b)) (c) detecting the RET inhibitor resistance mutation V804M, G810S, or G810R in a cancer cell in a sample obtained from the subject; and (d) administering additional doses of the compound of Formula (I) or a pharmaceutically acceptable salt, amorphous form, polymorph form, or pharmaceutical composition (e.g., any of the solid or liquid formulations described herein) thereof of step (b) to the subject as a monotherapy or in conjunction with another anticancer agent (e.g., a second RET inhibitor, or immunotherapy) or anticancer therapy (e.g., surgery or radiation). In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668 is administered in step (d).

Further provided herein is a method for treating lung cancer in a patient in need thereof, the method comprising administering to the patient a therapeutically effective amount of the compound of Formula (I) or a pharmaceutically acceptable salt, amorphous form, polymorph form, or pharmaceutical composition (e.g., any of the solid or liquid formulations described herein) thereof, crizotinib, osimertinib, or any combination thereof.

In some embodiments, the lung cancer is a RET-associated cancer. For example, the method can include: (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the methods further comprises (after (b)) (c) determining whether a cancer cell in a sample obtained from the subject has at least one RET inhibitor resistance mutation (e.g., a MET dysregulation such as a MET gene amplification); and (d) administering a second therapeutic agent, wherein the second therapeutic agent is crizotinib, as a monotherapy or in conjunction with the compound of Formula (I) or a pharmaceutically acceptable salt, amorphous form, polymorph form, or pharmaceutical composition (e.g., any of the solid or liquid formulations described herein) thereof to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation. In some such embodiments, the method comprises (a) detecting one or more fusion proteins of Table 1 and/or one or more RET kinase protein point mutations/insertions of Table 2 in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In further embodiments, the methods further comprise (after (b)) (c) determining whether a cancer cell in a sample obtained from the subject has at least one RET inhibitor resistance mutation (e.g., a MET dysregulation such as a MET gene amplification); and (d) administering a second therapeutic agent, wherein the second therapeutic agent is crizotinib, as a monotherapy or in conjunction with the compound of Formula (I) or a pharmaceutically acceptable salt, amorphous form, polymorph form, or pharmaceutical composition (e.g., any of the solid or liquid formulations described herein) thereof to the subject if the subject has a cancer cell that has at least one RET inhibitor resistance mutation; or (e) administering additional doses of the compound of Formula (I) or a pharmaceutically acceptable salt, amorphous form, polymorph form, or pharmaceutical composition (e.g., any of the solid or liquid formulations described herein) thereof of step (b) to the subject if the subject has a cancer cell that does not have a RET inhibitor resistance mutation.

In some embodiments, the lung cancer is an EGFR-associated cancer. For example, the method can include: (a) detecting a dysregulation of an EGFR gene, an EGFR kinase, or the expression or activity or level of any of the same in a sample from the subject; and (b) administering to the subject a therapeutically effective amount of an EGFR inhibitor (e.g., osimertinib). In some embodiments, the methods further comprises (after (b)) (c) determining whether a cancer cell in a sample obtained from the subject has at least one dysregulation of a RET gene, a RET kinase, or the expression or activity or level of any of the same (e.g., a RET gene fusion); and (d) administering the compound of Formula (I) or a pharmaceutically acceptable salt, amorphous form, polymorph form, or pharmaceutical composition (e.g., any of the solid or liquid formulations described herein) thereof, as a monotherapy or in conjunction with the EGFR inhibitor (e.g., osimertinib) to the subject if the subject has a cancer cell that has at least one dysregulation of a RET gene, a RET kinase, or the expression or activity or level of any of the same (e.g., a RET gene fusion); or (e) administering additional doses of the EGFR inhibitor (e.g., osimertinib) of step (b) to the subject if the subject has a cancer cell that does not have a dysregulation of a RET gene, a RET kinase, or the expression or activity or level of any of the same (e.g., a RET gene fusion). In some such embodiments, the method comprises (a) detecting a dysregulation of an EGFR gene, an EGFR kinase, or the expression or activity or level of any of the same in a sample from the subject; and (b) administering to the subject a therapeutically effective amount of osimertinib. In further embodiments, the methods further comprise (after (b)) (c) determining whether a cancer cell in a sample obtained from the subject has one or more fusion proteins of Table 1 and/or one or more RET kinase protein point mutations/insertions of Table 2; and (d) administering the compound of Formula (I) or a pharmaceutically acceptable salt, amorphous form, polymorph form, or pharmaceutical composition (e.g., any of the solid or liquid formulations described herein) thereof, as a monotherapy or in conjunction with osimertinib to the subject if the subject has a cancer cell that has one or more fusion proteins of Table 1 and/or one or more RET kinase protein point mutations/insertions of Table 2; or (e) administering additional doses of the osimertinib of step (b) to the subject if the subject has a cancer cell that does not have one or more fusion proteins of Table 1 and/or one or more RET kinase protein point mutations/insertions of Table 2.

The term "EGFR-associated cancer" as used herein refers to cancers associated with or having a dysregulation of a EGFR gene, a EGFR kinase, or expression or activity, or level of any of the same.

The phrase "dysregulation of a EGFR gene, a EGFR kinase, or the expression or activity or level of any of the same" refers to a genetic mutation (e.g., a EGFR gene translocation that results in the expression of a fusion protein, a deletion in a EGFR gene that results in the expression of a EGFR protein that includes a deletion of at least one amino acid as compared to the wild-type EGFR protein, or a mutation in a EGFR gene that results in the expression of a EGFR protein with one or more point mutations, or an alternative spliced version of a EGFR mRNA that results in a EGFR protein that results in the deletion of at least one amino acid in the EGFR protein as compared to the wild-type EGFR protein), or a EGFR gene amplification that results in overexpression of a EGFR protein or an autocrine activity resulting from the overexpression of a EGFR gene a cell, that results in a pathogenic increase in the activity of a kinase domain of a EGFR protein (e.g., a constitutively active kinase domain of a EGFR protein) in a cell. As another example, a dysregulation of a EGFR gene, a EGFR protein, or expression or activity, or level of any of the same, can be a mutation in a EGFR gene that encodes a EGFR protein that is constitutively active or has increased activity as compared to a protein encoded by a EGFR gene that does not include the mutation. For example, a dysregulation of a EGFR gene, a EGFR protein, or expression or activity, or level of any of the same, can be the result of a gene or chromosome translocation which results in the expression of a fusion protein that contains a first portion of EGFR that includes a functional kinase domain, and a second portion of a partner protein (i.e., that is not EGFR). In some examples, dysregulation of a EGFR gene, a EGFR protein, or expression or activity, can be a result of a gene translocation of one EGFR gene with another non-EGFR gene. In some embodiments, the EGFR mutation is a T790M mutation. In some embodiments, the EGFR mutation is a C797S mutation.

The term "wildtype EGFR" or "wild-type EGFR" describes a nucleic acid (e.g., a EGFR gene or a EGFR mRNA) or protein (e.g., a EGFR protein) that is found in a subject that does not have a EGFR-associated cancer (and optionally also does not have an increased risk of developing a EGFR-associated cancer and/or is not suspected of having a EGFR-associated cancer), or is found in a cell or tissue from a subject that does not have a EGFR-associated cancer (and optionally also does not have an increased risk of developing a EGFR-associated cancer and/or is not suspected of having a EGFR-associated cancer).

Also provided are methods of selecting a treatment for a subject having a cancer that include: identifying a subject having a cancer cell that has one or more RET inhibitor resistance mutations; and selecting a treatment that includes administration of the compound of Formula (I) or a pharmaceutically acceptable salt, amorphous form, polymorph form, or pharmaceutical composition (e.g., any of the solid or liquid formulations described herein) thereof. In some embodiments, the one or more RET inhibitor resistance mutations confer increased resistance to a cancer cell or tumor to treatment with a first RET inhibitor. In some embodiments, the compound of Formula (I) or a pharmaceutically acceptable salt, amorphous form, polymorph form, or pharmaceutical composition (e.g., any of the solid or liquid formulations described herein) thereof is administered in combination with the first RET inhibitor. Also provided are methods of selecting a treatment for a subject having a cancer that include: selecting a treatment that includes administration of the compound of Formula (I) or a pharmaceutically acceptable salt, amorphous form, polymorph form, or pharmaceutical composition (e.g., any of the solid or liquid formulations described herein) thereof for a subject identified as having a cancer cell that has one or more RET inhibitor resistance mutations. Also provided are methods of selecting a subject having a cancer for a treatment that does not include a first RET inhibitor as a monotherapy that include: identifying a subject having a cancer cell that has one or more RET inhibitor resistance mutations; and selecting the identified subject for a treatment that includes the compound of Formula (I) or a pharmaceutically acceptable salt, amorphous form, polymorph form, or pharmaceutical composition (e.g., any of the solid or liquid formulations described herein) thereof. Also provided are methods of selecting a subject having a cancer for a treatment that does not include a first RET inhibitor as a monotherapy that include: selecting a subject identified as having a cancer cell that has one or more RET inhibitor resistance mutations for a treatment that includes administration of the compound of Formula (I) or a pharmaceutically acceptable salt, amorphous form, polymorph form, or pharmaceutical composition (e.g., any of the solid or liquid formulations described herein) thereof. In some embodiments, the one or more RET inhibitor resistance mutations include one or more RET inhibitor resistance mutations listed in Tables 3 and 4. In some embodiments, the one or more RET inhibitor resistance mutations can include a substitution at amino acid position 804, e.g., V804M, V804L, or V804E, or a substitution amino acid position 810, e.g., G810S, G810R, G810C, G810A, G810V, and G810D.

Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject having a cancer cell that has one or more RET inhibitor resistance mutations has a decreased likelihood of having a positive response (i.e. an increased likelihood of having a negative response) to treatment with a first RET inhibitor as a monotherapy. Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject not having a cancer cell that has one or more RET inhibitor resistance mutations has an increased likelihood of having a positive response to treatment with a first RET inhibitor as a monotherapy as compared to a subject having a cancer cell that has one or more RET inhibitor resistance mutations. Also provided are methods of predicting the efficacy of treatment with a first RET inhibitor as a monotherapy in a subject having cancer that include: determining whether a cancer cell in a sample obtained from the subject has one or more RET inhibitor resistance mutations; and determining that treatment with a first RET inhibitor as a monotherapy is less likely to be effective in a subject having a cancer cell in a sample obtained from the subject that has one or more RET inhibitor resistance mutations. Also provided are methods of predicting the efficacy of treatment with a first RET inhibitor as a monotherapy in a subject having cancer that include: determining that treatment with a first RET inhibitor as a monotherapy is less likely to be effective in a subject having a cancer cell in a sample obtained from the subject that has one or more RET inhibitor resistance mutations. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering the compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (d) administering additional doses of the first RET inhibitor of step (a) to the subject if the subject has a cancer cell that does not have a RET inhibitor resistance mutation. In some embodiments, where the subject is administered additional doses of the first RET inhibitor of step (a), the subject can also be administered another anticancer agent (e.g., a second RET inhibitor or a compound of Formula (I) or a pharmaceutically acceptable salt, amorphous form, polymorph form, or pharmaceutical composition (e.g., any of the solid or liquid formulations described herein) thereof, or immunotherapy). In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering a second RET inhibitor as a monotherapy or in conjunction with another anticancer agent to the subject if the subject has a cancer cell that has at least one RET inhibitor resistance mutation; or (d) administering additional doses of the first RET inhibitor step (a) to the subject if the subject has a cancer cell that does not have a RET inhibitor resistance mutation. In some embodiments, where the subject is administered additional doses of the first RET inhibitor of step (a), the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., the compound of Formula (I) or a pharmaceutically acceptable salt, amorphous form, polymorph form, or pharmaceutical composition (e.g., any of the solid or liquid formulations described herein) thereof). In some embodiments, the additional anticancer agent is an immunotherapy.

Also provided are methods of treating a subject having a cancer (e.g., a RET-associated cancer) that include: (a) determining whether a cancer cell in a sample obtained from a subject having a cancer and previously administered one or more doses of a first RET inhibitor, has one or more RET inhibitor resistance mutations; and (b) administering a compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent to the subject if the subject has a cancer cell that has at least one RET inhibitor resistance mutation; or (c) administering additional doses of the first RET inhibitor previously administered to the subject if the subject has a cancer cell that does not have a RET inhibitor resistance mutation. In some embodiments, where the subject is administered additional doses of the first RET inhibitor previously administered to the subject, the subject can also be administered another anticancer agent (e.g., a compound of Formula (I) or a pharmaceutically acceptable salt, amorphous form, polymorph form, or pharmaceutical composition (e.g., any of the solid or liquid formulations described herein) thereof, or immunotherapy). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (b), another anticancer agent can be the first RET inhibitor administered in step (a).

Also provided are methods of treating a subject having a cancer that include: (a) determining whether a cancer cell in a sample obtained from a subject having a cancer and previously administered one or more doses of a first RET inhibitor has one or more RET inhibitor resistance mutations; and (b) administering a second RET inhibitor as a monotherapy or in conjunction with another anticancer agent to the subject if the subject has a cancer cell that has at least one RET inhibitor resistance mutation; or (c) administering additional doses of the first RET inhibitor previously administered to the subject if the subject has a cancer cell that does not have a RET inhibitor resistance mutation. In some embodiments, where the subject is administered additional doses of the first RET inhibitor previously administered to the subject, the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., the compound of Formula (I) or a pharmaceutically acceptable salt, amorphous form, polymorph form, or pharmaceutical composition (e.g., any of the solid or liquid formulations described herein) thereof). In some embodiments, the additional anticancer agent is an immunotherapy. In some embodiments of (b), another anticancer agent can be the first RET inhibitor administered in step (a).

In some embodiments, a RET-associated cancer as described herein can occur in a subject along with a dysregulation of another gene, another protein, or the expression or activity or level of any of the same.

For example, a RET-associated cancer that exhibits a RET fusion can occur in a subject along with one or more of: a dysregulation of a MET gene, a MET protein, or the expression or activity or level of any of the same; a dysregulation of a PIK3CA gene, a PIK3CA protein, or the expression or activity or level of any of the same; a dysregulation of a KRAS gene, a KRAS protein, or the expression or activity or level of any of the same; a dysregulation of a EGFR gene, a EGFR protein, or the expression or activity or level of any of the same (e.g., an amplification of a EGFR gene); a dysregulation of a FGFR2 gene, a FGFR2 protein, or the expression or activity or level of any of the same (eg., a fusion of an FGFR2 gene or an FGFR2 protein); a dysregulation of a CDK4 gene, a CDK4 protein, or the expression or activity or level of any of the same (e.g., an amplication of a CDK4 gene); a dysregulation of a mTOR gene, a mTOR protein, or the expression or activity or level of any of the same; a dysregulation of a CDKN2A gene, a CDKN2A protein, or the expression or activity or level of any of the same (e.g., a deletion in a CDKN2A gene or a CDKN2A protein); a dysregulation of a CDKN2B gene, a CDKN2B protein, or the expression or activity or level of any of the same (e.g., a deletion in a CDKN2B gene or a CDKN2B protein); a dysregulation of a NF1 gene, a NF1 protein, or the expression or activity or level of any of the same; a dysregulation of a MYC gene, a MYC protein, or the expression or activity or level of any of the same (e.g., an amplification in a MYC gene); a dysregulation of a MDM2 gene, a MDM2 protein, or the expression or activity or level of any of the same (e.g., an amplification in a MDM2 gene); a dysregulation of a GNAS gene, a GNAS protein, or the expression or activity or level of any of the same; a dysregulation of a BRCA2 gene, a BRCA2 protein, or the expression or activity or level of any of the same.

In some embodiments, a RET-associated cancer that exhibits a mutation of a RET gene and/or a RET protein can occur in a subject along with one or more of: a dysregulation of a PIK3CA gene, a PIK3CA protein, or the expression or activity or level of any of the same; a dysregulation of a KRAS gene, a KRAS protein, or the expression or activity or level of any of the same; a dysregulation of a EGFR gene, a EGFR protein, or the expression or activity or level of any of the same; a dysregulation of a FGFR1 gene, a FGFR1 protein, or the expression or activity or level of any of the same (e.g, an amplification of a FGFR1 gene); a dysregulation of a FGFR2 gene, a FGFR2 protein, or the expression or activity or level of any of the same (e.g., an amplification of a FGFR2 gene); a dysregulation of a FGFR3 gene, a FGFR3 protein, or the expression or activity or level of any of the same (e.g., a fusion of a FGFR3 gene or a FGFR3 protein); a dysregulation of a ERBB2 gene, a ERBB2 protein, or the expression or activity or level of any of the same (e.g., an amplification of ERBB2 gene); and a dysregulation of a KIT gene, a KIT protein, or the expression or level of any of the same.

In some embodiments, a RET-associated cancer that exhibits an amplification of a RET gene can occur in a patient along with one or more additional kinase amplifications. For example, am amplification in a FGFR1 gene; an amplification in a FGFR2 gene; an amplification in a FGFR3 gene; an amplification of a FGFR4 gene; an amplification of a CDK4 gene; and an amplification in a CDK6 gene.

In some embodiments, wherein a RET-associated cancer as described herein can occur in a subject along with a dysregulation in another kinase, the methods described herein can further comprise administration of an additional therapeutic agent that targets and/or treats the dysregulation in the other kinase. For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the method further comprises (c) detecting a dysregulation in another kinase in a sample from the subject; and (d) administering to the subject a therapeutic agent that targets and/or treats the dysregulation in the other kinase. In some embodiments, the administration of the compound of Formula (I) or a pharmaceutically acceptable salt, amorphous form, polymorph form, or pharmaceutical composition (e.g., any of the solid or liquid formulations described herein) thereof is done concurrently, sequentially, or serially. In some embodiments, the detecting steps (a) and (c) can be done simultaneously or sequentially in any order.

Additional therapeutic agents that target and/or treat the dysregulation of the other kinase can include any known inhibitor of the other kinase. Examples of such agents are as follows:

Exemplary PARP inhibitors include: 3-aminobenzamide (INO-1001), 5-aminoisoquinoline, ABT472, ABT767, AG140361, AG14032, ANG2864, ANG3186, AZD2281, AZD2461, BGP-15, BSI101, BSI401, CEP6800, CEP8983, CK102, CEP9722 (prodrug of CEP8983), CPH101 with CPH102, DR2313, E7016 (GPI-21016), E7449, GP16150, IMP4297, IMP04149, INO1002, INO1003, JPI283, JPI289, KU0687, KU58948, niraparib (MK-4827), NT125, olaparib (AZD2281), ONO-1924H, ONO2231, pamiparib (BGB-290), PJ-34, rucaparib (AG014699), SC10914, SOMCL9112, talazoparib (BMN-673), and veliparib (ABT-888).

Exemplary CDK 4/6 inhibitors include: palbociclib (PD0332991), abemaciclib (LY2835219), ribociclib (LEE011), trilaciclib (G1T28), voruciclib, and G1T38.

Exemplary ERBB2 (HER2/neu) inhibitors include: afatinib, afatinib, dacomitinib (PF-00299804), DS8201-a, erlontinib, gefitinib, KU004, lapatinib, laptinib ditosylate, MM-111, mubritinib (TAK-165), neratinib, pyrotinib (HTI-1001), tucatinib (ONT-380, ARRY-380), 7C3, cetuximab, HER2-BsAb, hersintuzumab, margetuximab, MI130004, NeuVax, paitumumab, pertuzumab, SYD985, trastuzumab, and trastuzumab emtansine.

Exemplary inhibitors of amplified ERBB2 (HER2/neu) include dacomitinib (PF-00299804), lapatinib, neratinib, pertuzumab, trastuzumab, and trastuzumab emtansine.

Exemplary EGFR inhibitors include: AC0010, afatinib, AP26113, ASP8273, avatinib, avitinib, AZD3759, BMS-690514, brigatinib, canertinib, Cap-701, CHMFL-EGFR-202, CUDC-101, dacomitinib, EAI045, EGF816, erlontinib, erlotinib, gefitinib, GNS-1481, GNS-1486, Gö6976, HS-10296, icotinib, KU004, lapatinib, nazartinib, neratinib, olmutinib (HM61713, BI 1482694), osimertinib, osimertinib (AZD9291), pelitinib, PF-06747775, PKC412, pyrotinib (HTI-1001), rocilentinib, vandetanib, varlitinib, XL647, 7C3, cetuximab, depatuxizumab mafodotin (ABT-414), matuzumab, nimotuzumab, panitumumab, and zalutumumab.

Exemplary wild-type EGFR inhibitors include: afatinib, BMS-690514, canertinib, CUDC-101, dacomitinib, erlotinib, gefitinib, lapatinib, neratinib, pelitinib, vandetanib, varlitinib, XL647, cetuximab, matuzumab, nimotuzumab, panitumumab, and zalutumumab.

Exemplary inhibitors of mutated EGFR include: AC0010, afatinib, AP26113, ASP8273, avatinib, avitinib, AZD3759, BMS-690514, brigatinib, canertinib, Cap-701, CHMFL-EGFR-202, CUDC-101, dacomitinib, EAI045, EGF816, GNS-1481, GNS-1486, Gö6976, HS-10296, icotinib, nazartinib, neratinib, olmutinib (HM61713, BI 1482694), osimertinib (AZD9291), PF-06747775, PKC412, rocilentinib, vandetanib, varlitinib, and cetuximab.

An exemplary inhibitor of amplified EGFR is depatuxizumab mafodotin (ABT-414).

Exemplary inhibitors of FGFR include: ASP5878, AZD4547, BGJ398, BLU9931, brivatinib, cediranib, DEBIO 1347, derazantinib (ARQ-087), dovitinib (CHIR258), E7090, ENMD-2076, erdafitinib (JNJ-42756293), FGF 401, FIIN-1, FRIN-1, INCB054828, $L_{16}H50$, lenvatinib, lucitanib, LY2874455, nintedanib, NP603, orantinib (SU6668), pazopanib, PBI05204, PD173074, ponatinib, PRN1371, regorafenib, rogaratinib (BAY-1163877), 549076, SOMCL-085, SU5402, sunitinib, TAS-120, FP-1039, GAL-F2, GAL-FR21, GAL-FR22, GAL-FR23, GP369, hLD1.vb, LD1, MFGR1877S, MM-161, PRO-001, and R3Mab.

Exemplary inhibitors of FGFR fusions include: BGJ398, DEBIO 1347, derazantinib (ARQ-087), E7090, erdafitinib (JNJ-42756293), lucitanib, and TAS-120.

Exemplary inhibitors of FGFR1, FGFR2, and FGFR3 include: AZD4547, BGJ398, DEBIO 1347, E7090, INCB054828, 549076, SOMCL-085, and TAS-120.

Exemplary inhibitors of FGF4 include: BLU-554, BLU9931, NVP-FGF401, and hLD1.vb.

Exemplary inhibitors of amplified FGFR1 include: AZD4547, BGJ398, DEBIO 1347, derazantinib (ARQ-087), erdafitinib (JNJ-42756293), INCB054828, and lucitanib.

Exemplary inhibitors of amplified FGFR2 include: AZD4547, DEBIO 1347, derazantinib (ARQ-087), lucitanib, regorafenib, and TAS-120.

An exemplary inhibitor of amplified FGFR3 is AZD4547.

Exemplary MEK inhibitors include: AZD8330 (ARRY-424704), AZD6244 (ARRY-142866), BI-847325, binimetinib, BIX02188, BIX02189, CH4987655, CH5126766, CI-1040, cobemetinib (GDC-0973), EBI-1051, G-573, G8935, GDC-0623, Myricetin, nobiletin, PD0325901, PD184161, PD318088, PD98059, PD334581, pimasertib (AS-703026), refametinib (RDEA119, BAY 869766), selumentinib (AZD6244), SL-327, TAK-733, trametinib, and U0126.

Exemplary KRAS inhibitors include: 0375-0604, a covalent quinazoline-based switch II pocket (SIIP) compound, ARS-1620, AZD4785, and LP1.

Exemplary PI3K inhibitors include: 3-methyladenine, A66, alpelisib (BYL719), AMG319, apitolisib (GDC-0980, RG7422), AS-252424, AS-604850, AS-605240, AZD6842, AZD8186, AZD8835, BGT226 (NVP-BGT226), buparlisib (BKM120), CAY10505, CH5132799, copanlisib (BAY 80-6946), CUDC-907, CZC24832, dactolisib (BEZ235, NVP-BEZ235), DS7423, duvelisib (IPI-145, INK1197), GDC-0032, GDC-0084, GDC-0326, gedatolisib (PF-05212384, PKI-5587), GNE-317, GS-9820, GSK1059615, GSK2292767, GSK2636771, HS-173, IC-87114, Idelalisib (CAL-101, GS-1101), IPI-145, IPI-3063, IPI-549, LY294002, LY3023414, nemiralisib (GSK2269557), omipalisib (GSK2126458, GSK458), PF-04691502, PF-4989216, PI-103, PI-3065, pictilisib (GDC-0941), PIK-293, PIK-294, PIK-75, PIK-90, PIK-93, PIK-III, pilaralisib (XL147), PKI-587, PP-110, PQR309, PQR309, PW-12, PX-866, quercetin, 514161, SAR245409 (XL765), SAR260301, SAR405, serabelisib (INK-1117, MLN-1117, TAK-1117), SF-1126, SF-2523, SN32976, taselisib (GDC-0032), TB101110, TG100-115, TG100-713, TGR-1202, TGX-221, umbralisib (TGR-1202), voxtalisib (XL765, SAR245409), VPS34-IN1, VS-5584 (SB2343), WJD008, wortmannin, and ZSTK474.

Exemplary KIT inhibitors include: AMG 706, amuvatinib (MP-470), APcK110, axitinib (AG-013736), AZD2932, dasatinib (BMS-354825), dovitinib (TKI-258, CHIR-258), EXEL-0862, imatinib, KI-328, masitinib (AB1010), midostaurin, MLN518, motesanib, N3-(6-aminopyridin-3- yl)-N1-(2-cyclopentylethyl)-4-methylisophthalamide, nilotinib, OSI-930, pazopanib (GW786034), pexidartinib (PLX3397), PKC412, PLX647, PP1, quizartinib (AC220), regorafenib (BAY 73-4506), semaxinib (SU 5416), sitravatinib (MGCD516), sorafenib, STI571, SU11248, SU9529, sunitinib, telatinib, tivozanib (AV-951), tyrphostin AG 1296, VX-322, and WBZ_4.

Exemplary MDM2 inhibitors include: (−)-parthenolide, ALRN6924, AM-8553, AMG232, CGM-097, DS-3032b, GEM240, HDM201, H1198, idasanutlin (RG-7338), JapA, MI-219, MI-219, MI-319, MI-77301 (SAR405838), MK4828, MK-8242, MX69, NSC 207895 (XI-006), Nutlin-3, Nutlin-3a, Nutlin-3b, NVP-CFC218, NVP-CGM097, PXn727/822, RG7112, RO2468, RO5353, RO5503781, serdemetan (JNJ-26854165), SP-141, and YH239-EE.

Exemplary inhibitors of amplified MDM2 include: AM-8553, AMG232, DS-3032b, MI-77301 (SAR405838), NSC 207895 (XI-006), Nutlin-3a, NVP-CFC218, NVP-CGM097, and RG7112.

Exemplary inhibitors of MET include: (−)-Oleocanthal, ABBV-399, AMG-208, AMG-337, AMG-458, BAY-853474, BMS-754807, BMS-777607, BMS-794833, cabozantinib (XL184, BMS-907351), capmatinib (INCB28060), crizotinib (PF-02341066), DE605, foretinib (GSK1363089, XL880), glesatinib (MGCD265), golvatinib (E7050), INCB028060, JNJ-38877605, KRC-408, merestinib (LY2801653), MK-2461, MK8033, NPS-1034, NVP-BVU972, PF-04217903, PHA-665752, 549076, savolitinib (AZD6094, HMPL-504), SGX-523, SU11274, TAS-115, tepotinib (EMD 1214063, MSC2156119J), volitinib, CE-355621, and Onartuzumab.

Exemplary inhibitors of mTOR include: anthracimycin, apitolisib (GDC-0980, RG7422), AZD-8055, BGT226 (NVP-BGT226), CC-223, CZ415, dactolisib (BEZ235, NVP-BEZ235), DS7423, everolimus (RAD001), GDC-0084, GDC-0349, gedatolisib (PF-05212384, PKI-5587), GSK1059615, INK128, KU-0063794, LY3023414, MLN0128, omipalisib (GSK2126458, GSK458), OSI-027, OSU-53, Palomid 529 (P529), PF-04691502, PI-103, PKI-587, PP242, PQR309, ridaforolimus (AP-23573), sapanisertib (INK 128, MLN0128), SAR245409 (XL765), SF-1126, SF2523, sirolimus (rapamycin), SN32976, TAK228, temsirolimus (CCI-779, NSC 683864), Torin 1, Torin 2, torkinib (PP242), umirolimus, vistusertib (AZD2014), voxtalisib (XL765, SAR245409), VS-5584, VS-5584 (SB2343), WAY-600, WYE-125132 (WYE-132), WYE-354, WYE-687, XL388, and zotarolimus (ABT-578).

Exemplary inhibitors of MYC include: 10058-F4, 10074-G5, and KSI-3716.

The phrase "dysregulation of a gene, a protein, or the expression or activity or level of any of the same" refers to a genetic mutation (e.g., a chromosomal translocation that results in the expression of a fusion protein including a kinase domain and a fusion partner, a mutation in a gene that results in the expression of a protein that includes a deletion of at least one amino acid as compared to a wildtype protein, a mutation in a gene that results in the expression of a protein with one or more point mutations as compared to a wildtype protein, a mutation in a gene that results in the expression of a protein with at least one inserted amino acid as compared to a wildtype protein, a gene duplication that results in an increased level of protein in a cell, or a mutation in a regulatory sequence (e.g., a promoter and/or enhancer) that results in an increased level of protein in a cell), an alternative spliced version of a mRNA that results in a protein having a deletion of at least one amino acid in the protein as compared to the wild-type protein), or increased expression (e.g., increased levels) of a wildtype protein in a mammalian cell due to aberrant cell signaling and/or dysregulated autocrine/paracrine signaling (e.g., as compared to a control non-cancerous cell). As another example, a dysregulation of a gene, a protein, or expression or activity, or level of any of the same, can be a mutation in a gene that encodes a protein that is constitutively active or has increased activity as compared to a protein encoded by a gene that does not include the mutation. For example, a dysregulation of a gene, a protein, or expression or activity, or level of any of the same, can be the result of a gene or chromosome translocation which results in the expression of a fusion protein that contains a first portion of a protein that includes a functional kinase domain, and a second portion of a partner protein (i.e., that is not the primary protein). In some examples, dysregulation of a gene, a protein, or expression or activity or level of any of the same can be a result of a gene translocation of one gene with a different gene.

Treatment of a patient having a cancer with a multi-kinase inhibitor (MKI) or target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) can result in dysregulation of a RET gene, a RET kinase, or the expression or activity or level of the same in the cancer, and/or resistance to a RET inhibitor. See, e.g., Bhinge et al., *Oncotarget* 8:27155-27165, 2017; Chang et al., *Yonsei Med. J.* 58:9-18, 2017; and Lopez-Delisle et al., doi: 10.1038/s41388-017-0039-5, *Oncogene* 2018.

Treatment of a patient having a cancer with a RET inhibitor in combination with a multi-kinase inhibitor or a target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) can have increased therapeutic efficacy as compared to treatment of the same patient or a similar patient with the RET inhibitor as a monotherapy, or the multi-kinase inhibitor or the target-specific kinase inhibitor as a monotherapy. See, e.g., Tang et al., doi: 10.1038/modpathol.2017.109, *Mod. Pathol.* 2017; Andreucci et al., *Oncotarget* 7:80543-80553, 2017; Nelson-Taylor et al., *Mol. Cancer Ther.* 16:1623-1633, 2017; and Kato et al., *Clin. Cancer Res.* 23:1988-1997, 2017.

Provided herein are methods of treating a patient having a cancer (e.g., any of the cancers described herein) and previously administered a multi-kinase inhibitor (MKI) or a target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) (e.g., as a monotherapy) that include: administering to the patient (i) a therapeutically effective dose of the compound of Formula (I) or a pharmaceutically acceptable salt, amorphous form, polymorph form, or pharmaceutical composition (e.g., any of the solid or liquid formulations described herein) thereof as a monotherapy, or (ii) a therapeutically effective dose of the compound of Formula (I) or a pharmaceutically acceptable salt, amorphous form, polymorph form, or pharmaceutical composition (e.g., any of the solid or liquid formulations described herein) thereof, and a therapeutically effective dose of the previously administered MKI or the previously administered target-specific kinase inhibitor.

Provided herein are methods of treating a patient having a cancer (e.g., any of the cancers described herein) previously administered a MKI or a target specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) (e.g., as a monotherapy) that include: identifying a patient having a cancer cell that has a dysregulation of a RET gene, a RET kinase, or the expression or activity or level of the same; and administering to the identified patient (i) a therapeutically effective dose of the compound of Formula (I) or a pharmaceutically acceptable salt, amorphous form, polymorph form, or pharmaceutical composition (e.g., any of the solid or liquid formulations described herein) thereof as a monotherapy, or (ii) a therapeutically effective dose of the compound of Formula (I) or a pharmaceutically acceptable salt, amorphous form, polymorph form, or pharmaceutical composition (e.g., any of the solid or liquid formulations described herein) thereof, and a therapeutically effective dose of the previously administered MKI or the previously administered target-specific kinase inhibitor.

Provided herein are methods of treating a patient having a cancer (e.g., any of the cancers described herein) that include: administering to a patient a therapeutically effective amount of a MKI or a target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) (e.g., as a monotherapy) for a first period of time; after the period of time, identifying a patient having a cancer cell that has a dysregulation of a RET gene, a RET kinase, or the expression or activity or level of the same; and administering to the identified patient (i) a therapeutically effective dose of the compound of Formula (I) or a pharmaceutically acceptable salt, amorphous form, polymorph form, or pharmaceutical composition (e.g., any of the solid or liquid formulations described herein) thereof as a monotherapy, or (ii) a therapeutically effective dose of the compound of Formula (I) or a pharmaceutically acceptable salt, amorphous form, polymorph form, or pharmaceutical composition (e.g., any of the solid or liquid formulations described herein) thereof, and a therapeutically effective dose of the previously administered MKI or the previously administered target-specific kinase inhibitor.

Provided herein are methods of treating a patient having a cancer (e.g., any of the cancers described herein) that has dysregulation of a BRAF gene, a BRAF kinase, or the expression or activity or level of the same that include administering to the patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of a BRAF inhibitor (e.g., any of the BRAF inhibitors described herein or known in the art).

Provided herein are methods of treating a patient having a cancer (e.g., any of the cancers described herein) that include: identifying a patient having a cancer cell that has dysregulation of a BRAF gene, a BRAF kinase, or the expression or activity or level of the same; and administering to the identified patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of a BRAF inhibitor (e.g., any of the BRAF inhibitors described herein or known in the art).

Provided herein are methods of treating a patient having a cancer (e.g., any of the cancers described herein) that has dysregulation of an EGFR gene, an EGFR protein, or the expression or activity or level of the same that include administering to the patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of an EGFR inhibitor (e.g., any of the EGFR inhibitors described herein or known in the art).

Provided herein are methods of treating a patient having a cancer (e.g., any of the cancers described herein) that include: identifying a patient having a cancer cell that has dysregulation of an EGFR gene, an EGFR protein, or the expression or activity or level of the same; and administering to the identified patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of an EGFR inhibitor (e.g., any of the EGFR inhibitors described herein or known in the art).

Provided herein are methods of treating a patient having a cancer (e.g., any of the cancers described herein) that has dysregulation of a MEK gene, a MEK protein, or the expression or activity or level of the same that include administering to the patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of a MEK inhibitor (e.g., any of the MEK inhibitors described herein or known in the art).

Provided herein are methods of treating a patient having a cancer (e.g., any of the cancers described herein) that include: identifying a patient having a cancer cell that has dysregulation of a MEK gene, a MEK protein, or the expression or activity or level of the same; and administering to the identified patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of a MEK inhibitor (e.g., any of the MEK inhibitors described herein or known in the art).

Provided herein are methods of treating a patient having a cancer (e.g., any of the cancers described herein) that has dysregulation of an ALK gene, an ALK protein, or the expression or activity or level of the same that include administering to the patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of an ALK inhibitor (e.g., any of the ALK inhibitors described herein or known in the art).

Provided herein are methods of treating a patient having a cancer (e.g., any of the cancers described herein) that include: identifying a patient having a cancer cell that has dysregulation of an ALK gene, an ALK protein, or the expression or activity or level of the same; and administering to the identified patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount an ALK inhibitor (e.g., any of the ALK inhibitors described herein or known in the art).

Provided herein are methods of treating a patient having a cancer (e.g., any of the cancers described herein) that has dysregulation of a ROS gene, a ROS protein, or the expression or activity or level of the same that include administering to the patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of a ROS inhibitor (e.g., any of the ROS inhibitors described herein or known in the art).

Provided herein are methods of treating a patient having a cancer (e.g., any of the cancers described herein) that include: identifying a patient having a cancer cell that has dysregulation of a ROS gene, a ROS protein, or the expression or activity or level of the same; and administering to the identified patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount a ROS inhibitor (e.g., any of the ROS inhibitors described herein or known in the art).

Provided herein are methods of treating a patient having a cancer (e.g., any of the cancers described herein) that has dysregulation of a MET gene, a MET protein, or the expression or activity or level of the same that include administering to the patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of a MET inhibitor (e.g., any of the MET inhibitors described herein or known in the art).

Provided herein are methods of treating a patient having a cancer (e.g., any of the cancers described herein) that include: identifying a patient having a cancer cell that has dysregulation of a MET gene, a MET protein, or the expression or activity or level of the same; and administering to the identified patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount a MET inhibitor (e.g., any of the MET inhibitors described herein or known in the art).

Provided herein are methods of treating a patient having a cancer (e.g., any of the cancers described herein) that has dysregulation of an aromatase gene, an aromatase protein, or the expression or activity or level of the same that include administering to the patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of an aromatase inhibitor (e.g., any of the aromatase inhibitors described herein or known in the art).

Provided herein are methods of treating a patient having a cancer (e.g., any of the cancers described herein) that include: identifying a patient having a cancer cell that has dysregulation of an aromatase gene, an aromatase protein, or the expression or activity or level of the same; and administering to the identified patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount an aromatase inhibitor (e.g., any of the aromatase inhibitors described herein or known in the art).

Provided herein are methods of treating a patient having a cancer (e.g., any of the cancers described herein) that has dysregulation of a RAF gene, a RAF protein, or the expression or activity or level of the same that include administering to the patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of a RAF inhibitor (e.g., any of the RAF inhibitors described herein or known in the art).

Provided herein are methods of treating a patient having a cancer (e.g., any of the cancers described herein) that include: identifying a patient having a cancer cell that has dysregulation of a RAF gene, a RAF protein, or the expression or activity or level of the same; and administering to the identified patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount a RAF inhibitor (e.g., any of the RAF inhibitors described herein or known in the art).

Provided herein are methods of treating a patient having a cancer (e.g., any of the cancers described herein) that has dysregulation of a RAS gene, a RAS protein, or the expression or activity or level of the same that include administering to the patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount of a RAS inhibitor (e.g., any of the RAS inhibitors described herein or known in the art).

Provided herein are methods of treating a patient having a cancer (e.g., any of the cancers described herein) that include: identifying a patient having a cancer cell that has dysregulation of a RAS gene, a RAS protein, or the expression or activity or level of the same; and administering to the identified patient (i) a therapeutically effective amount of the compound of Formula (I) or a pharmaceutically acceptable salt, amorphous form, polymorph form, or pharmaceutical composition (e.g., any of the solid or liquid formulations described herein) thereof and (ii) a therapeutically effective amount a RAS inhibitor (e.g., any of the RAS inhibitors described herein or known in the art).

The phrase "dysregulation of a BRAF gene, a BRAF protein, or the expression or activity or level of any of the same" refers to a genetic mutation (e.g., a chromosomal translocation that results in the expression of a fusion protein including a BRAF kinase domain and a fusion partner, a mutation in a BRAF gene that results in the expression of a BRAF protein that includes a deletion of at least one amino acid as compared to a wildtype BRAF protein, a mutation in a BRAF gene that results in the expression of a BRAF protein with one or more point mutations as compared to a wildtype BRAF protein, a mutation in a BRAF gene that results in the expression of a BRAF protein with at least one inserted amino acid as compared to a wildtype BRAF protein, a gene duplication that results in an increased level of BRAF protein in a cell, or a mutation in a regulatory sequence (e.g., a promoter and/or enhancer) that results in an increased level of BRAF protein in a cell), an alternative spliced version of a BRAF mRNA that results in a BRAF protein having a deletion of at least one amino acid in the BRAF protein as compared to the wild-type BRAF protein), or increased expression (e.g., increased levels) of a wildtype BRAF protein in a mammalian cell due to aberrant cell signaling and/or dysregulated autocrine/paracrine signaling (e.g., as compared to a control non-cancerous cell). As another example, a dysregulation of a BRAF gene, a BRAF protein, or expression or activity, or level of any of the same, can be a mutation in a BRAF gene that encodes a BRAF protein that is constitutively active or has increased activity as compared to a protein encoded by a BRAF gene that does not include the mutation. For example, a dysregulation of a BRAF gene, a BRAF protein, or expression or activity, or level of any of the same, can be the result of a gene or chromosome translocation which results in the expression of a fusion protein that contains a first portion of a BRAF protein that includes a functional kinase domain, and a second portion of a partner protein (i.e., that is not BRAF). In some examples, dysregulation of a BRAF gene, a BRAF protein, or expression or activity or level of any of the same can be a result of a gene translocation of one BRAF gene with another non-BRAF gene.

Non-limiting examples of a BRAF inhibitor include dabrafenib, vemurafenib (also called RG7204 or PLX4032), sorafenib tosylate, PLX-4720, GDC-0879, BMS-908662 (Bristol-Meyers Squibb), LGX818 (Novartis), PLX3603 (Hofmann-LaRoche), RAF265 (Novartis), RO5185426 (Hofmann-LaRoche), and GSK2118436 (GlaxoSmithKline). Additional examples of a BRAF inhibitor are known in the art.

The phrase "dysregulation of an EGFR gene, an EGFR protein, or the expression or activity or level of any of the same" refers to a genetic mutation (e.g., a chromosomal translocation that results in the expression of a fusion protein including an EGFR kinase domain and a fusion partner, a mutation in an EGFR gene that results in the expression of an EGFR protein that includes a deletion of at least one amino acid as compared to a wildtype EGFR protein, a mutation in an EGFR gene that results in the expression of an EGFR protein with one or more point mutations as compared to a wildtype EGFR protein, a mutation in an EGFR gene that results in the expression of an EGFR protein with at least one inserted amino acid as compared to a wildtype EGFR protein, a gene duplication that results in an increased level of EGFR protein in a cell, or a mutation in a regulatory sequence (e.g., a promoter and/or enhancer) that results in an increased level of EGFR protein in a cell), an alternative spliced version of a EGFR mRNA that results in an EGFR protein having a deletion of at least one amino acid in the EGFR protein as compared to the wild-type EGFR protein), or increased expression (e.g., increased levels) of a wildtype EGFR protein in a mammalian cell due to aberrant cell signaling and/or dysregulated autocrine/paracrine signaling (e.g., as compared to a control non-cancerous cell). As another example, a dysregulation of an EGFR gene, an EGFR protein, or expression or activity, or level of the same, can be a mutation in an EGFR gene that encodes an EGFR protein that is constitutively active or has increased activity as compared to a protein encoded by an EGFR gene that does not include the mutation. For example, a dysregulation of an EGFR gene, an EGFR protein, or expression or activity, or level of any of the same, can be the result of a gene or chromosome translocation which results in the expression of a fusion protein that contains a first portion of a EGFR protein that includes a functional kinase domain, and a second portion of a partner protein (i.e., that is not EGFR). In some examples, dysregulation of an EGFR gene, an EGFR protein, or expression or activity or level of any of the same can be a result of a gene translocation of one EGFR gene with another non-EGFR gene.

Non-limiting examples of an EGFR inhibitor include gefitinib, erlotinib, brigatinib, lapatinib, neratinib, icotinib, afatinib, dacomitinib, poziotinib, vandetanib, afatinib, AZD9291, CO-1686, HM61713, AP26113, CI-1033, PKI-166, GW-2016, EKB-569, PDI-168393, AG-1478, CGP-59326A. Additional examples of an EGFR inhibitor are known in the art.

The phrase "dysregulation of a MEK gene, a MEK protein, or the expression or activity or level of any of the same" refers to a genetic mutation (e.g., a chromosomal translocation that results in the expression of a fusion protein including a MEK kinase domain and a fusion partner, a mutation in a MEK gene that results in the expression of a MEK protein that includes a deletion of at least one amino acid as compared to a wildtype MEK protein, a mutation in a MEK gene that results in the expression of a MEK protein with one or more point mutations as compared to a wildtype MEK protein, a mutation in a MEK gene that results in the expression of a MEK protein with at least one inserted amino acid as compared to a wildtype MEK protein, a gene duplication that results in an increased level of MEK protein in a cell, or a mutation in a regulatory sequence (e.g., a promoter and/or enhancer) that results in an increased level of MEK protein in a cell), an alternative spliced version of a MEK mRNA that results in a MEK protein having a deletion of at least one amino acid in the MEK protein as compared to the wild-type MEK protein), or increased expression (e.g., increased levels) of a wildtype MEK protein in a mammalian cell due to aberrant cell signaling and/or dysregulated autocrine/paracrine signaling (e.g., as compared to a control non-cancerous cell). As another example, a dysregulation of a MEK gene, a MEK protein, or expression or activity, or level of any of the same, can be a mutation in a MEK gene that encodes a MEK protein that is constitutively active or has increased activity as compared to a protein encoded by a MEK gene that does not include the mutation. For example, a dysregulation of a MEK gene, a MEK protein, or expression or activity, or level of any of the same, can be the result of a gene or chromosome translocation which results in the expression of a fusion protein that contains a first portion of a MEK protein that includes a functional kinase domain, and a second portion of a partner protein (i.e., that is not MEK). In some examples, dysregulation of a MEK gene, a MEK protein, or expression or activity or level of any of the same can be a result of a gene translocation of one MEK gene with another non-MEK gene.

Non-limiting examples of a MEK inhibitor include mekinist, trametinib (GSK1120212), cobimetinib (XL518), binimetinib (MEK162), selumetinib, PD-325901, CI-1040, PD035901, TAK-733, PD098059, U0126, AS703026/MSC1935369, XL-518/GDC-0973, BAY869766/RDEA119, and GSK1120212. Additional examples of a MEK inhibitor are known in the art.

The phrase "dysregulation of an ALK gene, an ALK protein, or the expression or activity or level of any of the same" refers to a genetic mutation (e.g., a chromosomal translocation that results in the expression of a fusion protein including an ALK kinase domain and a fusion partner, a mutation in an ALK gene that results in the expression an ALK protein that includes a deletion of at least one amino acid as compared to a wildtype ALK protein, a mutation in an ALK gene that results in the expression of an ALK protein with one or more point mutations as compared to a wildtype ALK protein, a mutation in an ALK gene that results in the expression of an ALK protein with at least one inserted amino acid as compared to a wildtype ALK protein, a gene duplication that results in an increased level of ALK protein in a cell, or a mutation in a regulatory sequence (e.g., a promoter and/or enhancer) that results in an increased level of ALK protein in a cell), an alternative spliced version of an ALK mRNA that results in an ALK protein having a deletion of at least one amino acid in the ALK protein as compared to the wild-type ALK protein), or increased expression (e.g., increased levels) of a wildtype ALK protein in a mammalian cell due to aberrant cell signaling and/or dysregulated autocrine/paracrine signaling (e.g., as compared to a control non-cancerous cell). As another example, a dysregulation of an ALK gene, an ALK protein, or expression or activity, or level of any of the same, can be a mutation in an ALK gene that encodes an ALK protein that is constitutively active or has increased activity as compared to a protein encoded by an ALK gene that does not include the mutation. For example, a dysregulation of an ALK gene, an ALK protein, or expression or activity, or level of any of the same, can be the result of a gene or chromosome translocation which results in the expression of a fusion protein that contains a first portion of an ALK protein that includes a functional kinase domain, and a second portion of a partner protein (i.e., that is not ALK). In some examples, dysregulation of an ALK gene, an ALK protein, or expression or activity or level of any of the same can be a result of a gene translocation of one ALK gene with another non-ALK gene.

Non-limiting examples of an ALK inhibitor include crizotinib (Xalkori), ceritinib (Zykadia), alectinib (Alecensa), dalantercept, ACE-041 (Brigatinib) (AP26113), entrectinib (NMS-E628), PF-06463922 (Pfizer), TSR-011 (Tesaro), CEP-37440 (Teva), CEP-37440 (Teva), X-396 (Xcovery), and ASP-3026 (Astellas). Additional examples of an ALK inhibitor are known in the art.

The phrase "dysregulation of a ROS1 gene, a ROS1 protein, or the expression or activity or level of any of the same" refers to a genetic mutation (e.g., a chromosomal translocation that results in the expression of a fusion protein including a ROS1 kinase domain and a fusion partner, a mutation in a ROS1 gene that results in the expression a ROS1 protein that includes a deletion of at least one amino acid as compared to a wildtype ROS1 protein, a mutation in a ROS1 gene that results in the expression of a ROS1 protein with one or more point mutations as compared to a wildtype ROS1 protein, a mutation in a ROS1 gene that results in the expression of a ROS1 protein with at least one inserted amino acid as compared to a wildtype ROS1 protein, a gene duplication that results in an increased level of ROS1 protein in a cell, or a mutation in a regulatory sequence (e.g., a promoter and/or enhancer) that results in an increased level of ROS1 protein in a cell), an alternative spliced version of a ROS1 mRNA that results in a ROS1 protein having a deletion of at least one amino acid in the ROS1 protein as compared to the wild-type ROS1 protein), or increased expression (e.g., increased levels) of a wildtype ROS1 protein in a mammalian cell due to aberrant cell signaling and/or dysregulated autocrine/paracrine signaling (e.g., as compared to a control non-cancerous cell). As another example, a dysregulation of a ROS1 gene, a ROS1 protein, or expression or activity, or level of any of the same, can be a mutation in a ROS1 gene that encodes a ROS1 protein that is constitutively active or has increased activity as compared to a protein encoded by a ROS1 gene that does not include the mutation. For example, a dysregulation of a ROS1 gene, a ROS1 protein, or expression or activity, or level of any of the same, can be the result of a gene or chromosome translocation which results in the expression of a fusion protein that contains a first portion of a ROS1 protein that includes a functional kinase domain, and a second portion of a partner protein (i.e., that is not ROS1). In some examples, dysregulation of a ROS1 gene, a ROS1 protein, or expression or activity or level of any of the same can be a result of a gene translocation of one ROS1 gene with another non-ROS1 gene.

Non-limiting examples of a ROS1 inhibitor include crizotinib, entrectinib (RXDX-101), lorlatinib (PF-06463922), certinib, TPX-0005, DS-605, and cabozantinib. Additional examples of a ROS1 inhibitor are known in the art.

The phrase "dysregulation of a MET gene, a MET protein, or the expression or activity or level of any of the same" refers to a genetic mutation (e.g., a chromosomal translocation that results in the expression of a fusion protein including a MET kinase domain and a fusion partner, a mutation in a MET gene that results in the expression a MET protein that includes a deletion of at least one amino acid as compared to a wildtype MET protein, a mutation in a MET gene that results in the expression of a MET protein with one or more point mutations as compared to a wildtype MET protein, a mutation in a MET gene that results in the expression of a MET protein with at least one inserted amino acid as compared to a wildtype MET protein, a gene duplication that results in an increased level of MET protein in a cell, or a mutation in a regulatory sequence (e.g., a promoter and/or enhancer) that results in an increased level of MET protein in a cell), an alternative spliced version of a MET mRNA that results in a MET protein having a deletion of at least one amino acid in the MET protein as compared to the wild-type MET protein), or increased expression (e.g., increased levels) of a wildtype MET protein in a mammalian cell due to aberrant cell signaling and/or dysregulated autocrine/paracrine signaling (e.g., as compared to a control non-cancerous cell). As another example, a dysregulation of a MET gene, a MET protein, or expression or activity, or level of any of the same, can be a mutation in a MET gene that encodes a MET protein that is constitutively active or has increased activity as compared to a protein encoded by a MET gene that does not include the mutation. For example, a dysregulation of a MET gene, a MET protein, or expression or activity, or level of any of the same, can be the result of a gene or chromosome translocation which results in the expression of a fusion protein that contains a first portion of a MET protein that includes a functional kinase domain, and a second portion of a partner protein (i.e., that is not MET). In some examples, dysregulation of a MET gene, a MET protein, or expression or activity or level of any of the same can be a result of a gene translocation of one MET gene with another non-MET gene.

Non-limiting examples of a MET inhibitor include crizotinib, cabozantinib, JNJ-38877605, PF-04217903 (Pfizer), MK-2461, GSK 1363089, AMG 458 (Amgen), tivantinib, INCB28060 (Incyte), PF-02341066 (Pfizer), E7050 (Eisai), BMS-777607 (Bristol-Meyers Squibb), JNJ-38877605 (Johnson & Johnson), ARQ197 (ArQule), GSK/1363089/ XL880 (GSK/Exeilixis), and XL174 (BMS/Exelixis). Additional examples of a MET inhibitor are known in the art.

The phrase "dysregulation of a aromatase gene, an aromatase protein, or the expression or activity or level of any of the same" refers to a genetic mutation (e.g., a mutation in an aromatase gene that results in the expression an aromatase protein that includes a deletion of at least one amino acid as compared to a wildtype aromatase protein, a mutation in an aromatase gene that results in the expression of an aromatase protein with one or more point mutations as compared to a wildtype aromatase protein, a mutation in an aromatase gene that results in the expression of an aromatase protein with at least one inserted amino acid as compared to a wildtype aromatase protein, a gene duplication that results in an increased level of aromatase protein in a cell, or a mutation in a regulatory sequence (e.g., a promoter and/or enhancer) that results in an increased level of aromatase protein in a cell), an alternative spliced version of an aromatase mRNA that results in an aromatase protein having a deletion of at least one amino acid in the aromatase protein as compared to the wild-type aromatase protein), or increased expression (e.g., increased levels) of a wildtype aromatase in a mammalian cell due to aberrant cell signaling and/or dysregulated autocrine/paracrine signaling (e.g., as compared to a control non-cancerous cell). As another example, a dysregulation of an aromatase gene, an aromatase protein, or expression or activity, or level of any of the same, can be a mutation in an aromatase gene that encodes an aromatase protein that is constitutively active or has increased activity as compared to a protein encoded by an aromatase gene that does not include the mutation.

Non-limiting examples of an aromatase inhibitor include Arimidex (anastrozole), Aromasin (exemestane), Femara (letrozole), Teslac (testolactone), and formestane. Additional examples of an aromatase inhibitor are known in the art.

The phrase "dysregulation of a RAF gene, a RAF protein, or the expression or activity or level of any of the same" refers to a genetic mutation (e.g., a chromosomal translocation that results in the expression of a fusion protein including a RAF kinase domain and a fusion partner, a mutation in a RAF gene that results in the expression a RAF protein that includes a deletion of at least one amino acid as compared to a wildtype RAF protein, a mutation in a RAF gene that results in the expression of a RAF protein with one or more point mutations as compared to a wildtype RAF protein, a mutation in a RAF gene that results in the expression of a RAF protein with at least one inserted amino acid as compared to a wildtype RAF protein, a gene duplication that results in an increased level of RAF protein in a cell, or a mutation in a regulatory sequence (e.g., a promoter and/or enhancer) that results in an increased level of RAF protein in a cell), an alternative spliced version of a RAF mRNA that results in a RAF protein having a deletion of at least one amino acid in the RAF protein as compared to the wild-type RAF protein), or increased expression (e.g., increased levels) of a wildtype RAF protein in a mammalian cell due to aberrant cell signaling and/or dysregulated autocrine/paracrine signaling (e.g., as compared to a control non-cancerous cell). As another example, a dysregulation of a RAF gene, a RAF protein, or expression or activity, or level of any of the same, can be a mutation in a RAF gene that encodes a RAF protein that is constitutively active or has increased activity as compared to a protein encoded by a RAF gene that does not include the mutation. For example, a dysregulation of a RAF gene, a RAF protein, or expression or activity, or level of any of the same, can be the result of a gene or chromosome translocation which results in the expression of a fusion protein that contains a first portion of a RAF protein that includes a functional kinase domain, and a second portion of a partner protein (i.e., that is not RAF). In some examples, dysregulation of a RAF gene, a RAF protein, or expression or activity or level of any of the same can be a result of a gene translocation of one RAF gene with another non-RAF gene.

Non-limiting examples of a RAF inhibitor include sorafenib, vemurafenib, dabrafenib, BMS-908662/XL281, GSK2118436, RAF265, RO5126766, and RO4987655. Additional examples of a RAF inhibitor are known in the art.

The phrase "dysregulation of a RAS gene, a RAS protein, or the expression or activity or level of any of the same" refers to a genetic mutation (e.g., a chromosomal translocation that results in the expression of a fusion protein including a RAS kinase domain and a fusion partner, a mutation in a RAS gene that results in the expression a RAS protein that includes a deletion of at least one amino acid as compared to a wildtype RAS protein, a mutation in a RAS gene that results in the expression of a RAS protein with one or more point mutations as compared to a wildtype RAS protein, a mutation in a RAS gene that results in the expression of a RAS protein with at least one inserted amino acid as compared to a wildtype RAS protein, a gene duplication that results in an increased level of RAS protein in a cell, or a mutation in a regulatory sequence (e.g., a promoter and/or enhancer) that results in an increased level of RAS protein in a cell), an alternative spliced version of a RAS mRNA that results in a RAS protein having a deletion of at least one amino acid in the RAS protein as compared to the wild-type RAS protein), or increased expression (e.g., increased levels) of a wildtype RAS protein in a mammalian cell due to aberrant cell signaling and/or dysregulated autocrine/paracrine signaling (e.g., as compared to a control non-cancerous cell). As another example, a dysregulation of a RAS gene, a RAS protein, or expression or activity, or level of any of the same, can be a mutation in a RAS gene that encodes a RAS protein that is constitutively active or has increased activity as compared to a protein encoded by a RAS gene that does not include the mutation. For example, a dysregulation of a RAS gene, a RAS protein, or expression or activity, or level of any of the same, can be the result of a gene or chromosome translocation which results in the expression of a fusion protein that contains a first portion of a RAS protein that includes a functional kinase domain, and a second portion of a partner protein (i.e., that is not RAS). In some examples, dysregulation of a RAS gene, a RAS protein, or expression or activity or level of any of the same can be a result of a gene translocation of one RAS gene with another non-RAS gene.

Non-limiting examples of a RAS inhibitor include Kobe0065 and Kobe2602. Additional examples of a RAS inhibitor are known in the art.

Non-limiting examples of multi-kinase inhibitors (MKIs) include dasatinib and sunitinib.

In some embodiments, provided herein are methods of treating a subject having a cancer that include: (a) administering one or more doses of a first RET inhibitor or the compound of Formula (I) or a pharmaceutically acceptable salt, amorphous form, polymorph form, or pharmaceutical composition (e.g., any of the solid or liquid formulations described herein) thereof to the subject for a period of time; (b) after (a), determining whether a cancer cell in a sample obtained from the subject has at least one dysregulation of a gene, a protein, or the expression or activity or level of any of the same, wherein the gene or protein is selected from the group consisting of EGFR, MET, ALK, ROS1, KRAS, BRAF, RAS, PIK3CA, and HER2; and (c) administering 1) a second RET inhibitor as a monotherapy or in conjunction with another anticancer agent, 2) administering additional doses of the first RET inhibitor or the compound of Formula (I) or a pharmaceutically acceptable salt, amorphous form, polymorph form, or pharmaceutical composition (e.g., any of the solid or liquid formulations described herein) thereof in combination with an inhibitor targeting the gene or protein (e.g., an inhibitor of EGFR, MET, ALK, ROS1, KRAS, BRAF, RAS, PIK3CA, and HER2), or 3) stop administration of the RET inhibitor of step a) and administer an inhibitor targeting the gene or protein (e.g., an inhibitor of EGFR, MET, ALK, ROS1, KRAS, BRAF, RAS, PIK3CA, and HER2) to the subject if the subject has a cancer cell that has at least one dysregulation of a gene, a protein, or the expression or activity or level of the same, wherein the gene or protein is selected from the group consisting of EGFR, MET, ALK, ROS1, KRAS, BRAF, RAS, PIK3CA, and HER2; or (d) administering additional doses of the first RET inhibitor step (a) to the subject if the subject has a cancer cell that does not have a RET inhibitor resistance mutation. In some embodiments, the one or more dysregulations of a gene, a protein, or the expression or activity or level of any of the same, wherein the gene or protein is selected from the group consisting of EGFR, MET, ALK, ROS1, KRAS, BRAF, RAS, PIK3CA, and HER2 confer increased resistance to a cancer cell or tumor to treatment with the first RET inhibitor or the compound of Formula (I) or a pharmaceutically acceptable salt, amorphous form, polymorph form, or pharmaceutical composition (e.g., any of the solid or liquid formulations described herein) thereof. In some embodiments, the tumor is a NSCLC tumor and the one or more dysregulations of a gene, a protein, or the expression or activity or level of any of the same are selected from targetable mutations in EGFR or MET, targetable rearrangements involving ALK or ROS1, or activating mutations in KRAS. In some embodiments, the tumor is a thyroid (non-MTC) tumor and the one or more dysregulations of a gene, a protein, or the expression or activity or level of any of the same are selected from targetable mutations in BRAF or activating mutations in RAS. In some embodiments, the tumor is a MTC tumor and the one or more dysregulations of a gene, a protein, or the expression or activity or level of any of the same are selected from targetable mutations in ALK or activating mutations in RAS. In some embodiments, the tumor is a pancreatic tumor and the one or more dysregulations of a gene, a protein, or the expression or activity or level of any of the same is an activating mutations in KRAS. In some embodiments, the tumor is a colorectal tumor and the one or more dysregulations of a gene, a protein, or the expression or activity or level of any of the same are selected from targetable mutations in BRAF or PIK3CA or an activating mutation in RAS. In some embodiments, the tumor is a breast tumor and the one or more dysregulations of a gene, a protein, or the expression or activity or level of any of the same are selected from targetable mutations in PIK3CA or alteration in HER2.

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a compound of Formula (I) or a pharmaceutically acceptable salt, amorphous form, polymorph form, or pharmaceutical composition (e.g., any of the solid or liquid formulations described herein) thereof as a monotherapy or in conjunction with another anticancer agent for the subject if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., the compound of Formula (I) or a pharmaceutically acceptable salt, amorphous form, polymorph form, or pharmaceutical composition (e.g., any of the solid or liquid formulations described herein) thereof). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a second RET inhibitor as a monotherapy or in conjunction with another anticancer agent if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent (e.g., the compound of Formula (I) or a pharmaceutically acceptable salt, amorphous form, polymorph form, or pharmaceutical composition (e.g., any of the solid or liquid formulations described herein) thereof) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET inhibitor can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a second RET inhibitor as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., the compound of Formula (I) or a pharmaceutically acceptable salt, amorphous form, polymorph form, or pharmaceutical composition (e.g., any of the solid or liquid formulations described herein) thereof or an immunotherapy) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a second RET inhibitor as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., a compound of Formula (I) or a pharmaceutically acceptable salt, amorphous form, polymorph form, or pharmaceutical composition (e.g., any of the solid or liquid formulations described herein) thereof). In some embodiments, the additional anticancer agent is an immunotherapy. In some embodiments, another RET can be the first RET inhibitor administered in step (a).

Also provided are methods of determining a subject's risk for developing a cancer that has some resistance to a first RET inhibitor that include: determining whether a cell in a sample obtained from the subject has one or more RET inhibitor resistance mutations; and identifying a subject having a cell that has one or more RET inhibitor resistance mutations, as having an increased likelihood of developing a cancer that has some resistance to the first RET inhibitor. Also provided are methods of determining a subject's risk for developing a cancer that has some resistance to a first RET inhibitor that include: identifying a subject having a cell that has one or more RET inhibitor resistance mutations, as having an increased likelihood of developing a cancer that has some resistance to the first RET inhibitor. Also provided are methods of determining the presence of a cancer that has some resistance to a first RET inhibitor that include: determining whether a cancer cell in a sample obtained from the subject has one or more RET inhibitor resistance mutations; and determining that the subject having a cancer cell that has one or more RET inhibitor resistance mutations has a cancer that has some resistance to the first RET inhibitor. Also provided are methods of determining the presence of a cancer that has some resistance to a first RET inhibitor in a subject that include: determining that a subject having a cancer cell that has one or more RET inhibitor resistance mutations, has a cancer that has some resistance to the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

In some embodiments of any of the methods described herein, a RET inhibitor resistance mutation that confers increased resistance to a cancer cell or tumor to treatment with a first RET inhibitor can be any of the RET inhibitor resistance mutations listed in Table 3 or 4 (e.g., a substitution at amino acid position 804, e.g., V804M, V804L, or V804E, or a substitution at amino acid position 810, e.g., G810S, G810R, G810C, G810A, G810V, and G810D).

In some embodiments, the presence of one or more RET inhibitor resistance mutations in a tumor causes the tumor to be more resistant to treatment with the compound of Formula (I) or a pharmaceutically acceptable salt, amorphous form, polymorph form, or pharmaceutical composition (e.g., any of the solid or liquid formulations described herein) thereof. Methods useful when a RET inhibitor resistance mutation causes the tumor to be more resistant to treatment with the compound of Formula (I) or a pharmaceutically acceptable salt, amorphous form, polymorph form, or pharmaceutical composition (e.g., any of the solid or liquid formulations described herein) thereof are described below. For example, provided herein are methods of treating a subject having a cancer that include: identifying a subject having a cancer cell that has one or more RET inhibitor resistance mutations; and administering to the identified subject a treatment that does not include the compound of Formula (I) or a pharmaceutically acceptable salt, amorphous form, polymorph form, or pharmaceutical composition (e.g., any of the solid or liquid formulations described herein) thereof as a monotherapy (e.g., a second RET kinase inhibitor). Also provided are methods of treating a subject identified as having a cancer cell that has one or more RET inhibitor resistance mutations that include administering to the subject a treatment that does not include the compound of Formula (I) or a pharmaceutically acceptable salt, amorphous form, polymorph form, or pharmaceutical composition (e.g., any of the solid or liquid formulations described herein) thereof as a monotherapy (e.g., a second RET kinase inhibitor). In some embodiments, the one or more RET inhibitor resistance mutations confer increased resistance to a cancer cell or tumor to treatment with the compound of Formula (I) or a pharmaceutically acceptable salt, amorphous form, polymorph form, or pharmaceutical composition (e.g., any of the solid or liquid formulations described herein) thereof.

Also provided are methods of selecting a treatment for a subject having a cancer that include: identifying a subject having a cancer cell that has one or more RET inhibitor resistance mutations; and selecting a treatment that does not include the compound of Formula (I) or a pharmaceutically acceptable salt, amorphous form, polymorph form, or pharmaceutical composition (e.g., any of the solid or liquid formulations described herein) thereof as a monotherapy for the identified subject (e.g., a second RET kinase inhibitor). Also provided are methods of selecting a treatment for a subject having a cancer that include: selecting a treatment that does not include the compound of Formula (I) or a pharmaceutically acceptable salt, amorphous form, polymorph form, or pharmaceutical composition (e.g., any of the solid or liquid formulations described herein) thereof as a monotherapy (e.g., a second RET kinase inhibitor) for a subject identified as having a cancer cell that has one or more RET inhibitor resistance mutations. Also provided are methods of selecting a subject having a cancer for a treatment that does not include the compound of Formula (I) or a pharmaceutically acceptable salt, amorphous form, polymorph form, or pharmaceutical composition (e.g., any of the solid or liquid formulations described herein) thereof as a monotherapy (e.g., a second RET kinase inhibitor) that include: identifying a subject having a cancer cell that has one or more RET inhibitor resistance mutations; and selecting the identified subject for a treatment that does not include the compound of Formula (I) or a pharmaceutically acceptable salt, amorphous form, polymorph form, or pharmaceutical composition (e.g., any of the solid or liquid formulations described herein) thereof as a monotherapy (e.g., a second RET kinase inhibitor). Also provided are methods of selecting a subject having a cancer for a treatment that does not include the compound of Formula (I) or a pharmaceutically acceptable salt, amorphous form, polymorph form, or pharmaceutical composition (e.g., any of the solid or liquid formulations described herein) thereof as a monotherapy (e.g., a second RET kinase inhibitor) that include: selecting a subject identified as having a cancer cell that has one or more RET inhibitor resistance mutations for a treatment that does not include the compound of Formula (I) or a pharmaceutically acceptable salt, amorphous form, polymorph form, or pharmaceutical composition (e.g., any of the solid or liquid formulations described herein) thereof as a monotherapy. In some embodiments, the one or more RET inhibitor resistance mutations confer increased resistance to a cancer cell or tumor to treatment with the compound of Formula (I) or a pharmaceutically acceptable salt, amorphous form, polymorph form, or pharmaceutical composition (e.g., any of the solid or liquid formulations described herein) thereof.

Also provided are methods of determining the likelihood that a subject having a cancer will have a positive response to treatment with the compound of Formula (I) or a pharmaceutically acceptable salt, amorphous form, polymorph form, or pharmaceutical composition (e.g., any of the solid or liquid formulations described herein) thereof as a monotherapy that include: determining whether a cancer cell in a sample obtained from the subject has one or more RET inhibitor resistance mutations; and determining that the subject having the cancer cell that has one or more RET inhibitor resistance mutations has a decreased likelihood of having a positive response to treatment with the compound of Formula (I) or a pharmaceutically acceptable salt, amorphous form, polymorph form, or pharmaceutical composition (e.g., any of the solid or liquid formulations described herein) thereof as a monotherapy. Also provided are methods of determining the likelihood that a subject having cancer will have a positive response to treatment with the compound of Formula (I) or a pharmaceutically acceptable salt, amorphous form, polymorph form, or pharmaceutical composition (e.g., any of the solid or liquid formulations described herein) thereof as a monotherapy that include: determining that a subject having a cancer cell that has one or more RET inhibitor resistance mutations has a decreased likelihood of having a positive response to treatment with the compound of Formula (I) or a pharmaceutically acceptable salt, amorphous form, polymorph form, or pharmaceutical composition (e.g., any of the solid or liquid formulations described herein) thereof as a monotherapy. Also provided are methods of predicting the efficacy of treatment with the compound of Formula (I) or a pharmaceutically acceptable salt, amorphous form, polymorph form, or pharmaceutical composition (e.g., any of the solid or liquid formulations described herein) thereof as a monotherapy in a subject having cancer that include: determining whether a cancer cell in a sample obtained from the subject has one or more RET inhibitor resistance mutations; and determining that treatment with the compound of Formula (I) or a pharmaceutically acceptable salt, amorphous form, polymorph form, or pharmaceutical composition (e.g., any of the solid or liquid formulations described herein) thereof as a monotherapy is less likely to be effective in a subject having a cancer cell in a sample obtained from the subject that has one or more RET inhibitor resistance mutations. Also provided are methods of predicting the efficacy of treatment with the compound of Formula (I) or a pharmaceutically acceptable salt, amorphous form, polymorph form, or pharmaceutical composition (e.g., any of the solid or liquid formulations described herein) thereof as a monotherapy in a subject having cancer that include: determining that treatment with the compound of Formula (I) or a pharmaceutically acceptable salt, amorphous form, polymorph form, or pharmaceutical composition (e.g., any of the solid or liquid formulations described herein) thereof as a monotherapy is less likely to be effective in a subject having a cancer cell in a sample obtained from the subject that has one or more RET inhibitor resistance mutations.

Also provided are methods of treating a subject having a cancer that include: (a) administering one or more doses of the compound of Formula (I) or a pharmaceutically acceptable salt, amorphous form, polymorph form, or pharmaceutical composition (e.g., any of the solid or liquid formulations described herein) thereof for a period of time; (b) after (a), determining whether a cancer cell in a sample obtained from the subject has one or more RET inhibitor resistance mutations; and (c) administering a second RET inhibitor as a monotherapy or in conjunction with another anticancer agent to a subject having a cancer cell that has one or more RET inhibitor resistance mutations; or (d) administering additional doses of the compound of Formula (I) or a pharmaceutically acceptable salt, amorphous form, polymorph form, or pharmaceutical composition (e.g., any of the solid or liquid formulations described herein) thereof of step (a) are selected for the subject, the method can also include further selecting another anticancer agent. In some embodiments, the one or more RET inhibitor resistance mutations confer increased resistance to a cancer cell or tumor to treatment with the compound of Formula (I) or a pharmaceutically acceptable salt, amorphous form, polymorph form, or pharmaceutical composition (e.g., any of the solid or liquid formulations described herein) thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the Formula (I) or a pharmaceutically acceptable salt, amorphous form, polymorph form, or pharmaceutical composition (e.g., any of the solid or liquid formulations described herein) thereof.

Also provided are methods of treating a subject having a cancer that include: (a) determining whether a cancer cell in a sample obtained from a subject having a cancer and previously administered one or more doses of the compound of Formula (I) or a pharmaceutically acceptable salt, amorphous form, polymorph form, or pharmaceutical composition (e.g., any of the solid or liquid formulations described herein) thereof, has one or more RET inhibitor resistance mutations; (b) administering a second RET inhibitor as a monotherapy or in conjunction with another anticancer agent to a subject having a cancer cell that has one or more RET inhibitor resistance mutations; or (c) administering additional doses of the compound of Formula (I) or a pharmaceutically acceptable salt, amorphous form, polymorph form, or pharmaceutical composition (e.g., any of the solid or liquid formulations described herein) thereof previously administered to a subject having a cancer cell that does not have a RET inhibitor resistance mutation. In some embodiments, where the subject is administered additional doses of the compound of Formula (I) or a pharmaceutically acceptable salt, amorphous form, polymorph form, or pharmaceutical composition (e.g., any of the solid or liquid formulations described herein) thereof of step (a), the subject can also be administered another anticancer agent. In some embodiments, the one or more RET inhibitor resistance mutations confer increased resistance to a cancer cell or tumor to treatment with the compound of Formula (I) or a pharmaceutically acceptable salt, amorphous form, polymorph form, or pharmaceutical composition (e.g., any of the solid or liquid formulations described herein) thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula (I) or a pharmaceutically acceptable salt, amorphous form, polymorph form, or pharmaceutical composition (e.g., any of the solid or liquid formulations described herein) thereof administered in step (a).

Also provided are methods of selecting a treatment for a subject having a cancer that include: (a) administering one or more doses of the compound of Formula (I) or a pharmaceutically acceptable salt, amorphous form, polymorph form, or pharmaceutical composition (e.g., any of the solid or liquid formulations described herein) thereof to the subject for a period of time; (b) after (a), determining whether a cancer cell in a sample obtained from the subject has one or more RET inhibitor resistance mutations; and (c) selecting a second RET inhibitor as a monotherapy or in conjunction with another anticancer agent for the subject if the subject has a cancer cell that has a RET inhibitor resistance mutation; or (d) selecting additional doses of the compound of Formula (I) or a pharmaceutically acceptable salt, amorphous form, polymorph form, or pharmaceutical composition (e.g., any of the solid or liquid formulations described herein) thereof of step (a) for the subject if the subject has a cancer cell that does not have a RET inhibitor resistance mutation. In some embodiments, where additional doses of the compound of Formula (I) or a pharmaceutically acceptable salt, amorphous form, polymorph form, or pharmaceutical composition (e.g., any of the solid or liquid formulations described herein) thereof of step (a) are selected for the subject, the method can also include further selecting another anticancer agent. In some embodiments, the one or more RET inhibitor resistance mutations confer increased resistance to a cancer cell or tumor to treatment with the compound of Formula (I) or a pharmaceutically acceptable salt, amorphous form, polymorph form, or pharmaceutical composition (e.g., any of the solid or liquid formulations described herein) thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula (I) or a pharmaceutically acceptable salt, amorphous form, polymorph form, or pharmaceutical composition (e.g., any of the solid or liquid formulations described herein) thereof administered in step (a).

Also provided are methods of selecting a treatment for a subject having a cancer that include: (a) determining whether a cancer cell in a sample obtained from a subject having a cancer and previously administered one or more doses of the compound of Formula (I) or a pharmaceutically acceptable salt, amorphous form, polymorph form, or pharmaceutical composition (e.g., any of the solid or liquid formulations described herein) thereof, has one or more RET inhibitor resistance mutations; (b) selecting a second RET inhibitor as a monotherapy or in conjunction with another anticancer agent for the subject if the subject has a cancer cell that has a RET inhibitor resistance mutation; or (c) selecting additional doses of the compound of Formula (I) or a pharmaceutically acceptable salt, amorphous form, polymorph form, or pharmaceutical composition (e.g., any of the solid or liquid formulations described herein) thereof previously administered to the subject if the subject has a cancer cell that does not have a RET inhibitor resistance mutation. In some embodiments, where additional doses of the compound of Formula (I) or a pharmaceutically acceptable salt, amorphous form, polymorph form, or pharmaceutical composition (e.g., any of the solid or liquid formulations described herein) thereof of step (a) are selected for the subject, the method can also include further selecting another anticancer agent. In some embodiments, the one or more RET inhibitor resistance mutations confer increased resistance to a cancer cell or tumor to treatment with the compound of Formula (I) or a pharmaceutically acceptable salt, amorphous form, polymorph form, or pharmaceutical composition (e.g., any of the solid or liquid formulations described herein) thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula (I) or a pharmaceutically acceptable salt, amorphous form, polymorph form, or pharmaceutical composition (e.g., any of the solid or liquid formulations described herein) thereof administered in step (a).

Also provided are methods of determining a subject's risk for developing a cancer that has some resistance to the compound of Formula (I) or a pharmaceutically acceptable salt, amorphous form, polymorph form, or pharmaceutical composition (e.g., any of the solid or liquid formulations described herein) thereof that include: determining whether a cell in a sample obtained from the subject has one or more RET inhibitor resistance mutations; and identifying the subject if the subject has a cell that has one or more RET inhibitor resistance mutations as having an increased likelihood of developing a cancer that has some resistance to the compound of Formula (I) or a pharmaceutically acceptable salt, amorphous form, polymorph form, or pharmaceutical composition (e.g., any of the solid or liquid formulations described herein) thereof. Also provided are methods of determining a subject's risk for developing a cancer that has some resistance to the compound of Formula (I) or a pharmaceutically acceptable salt, amorphous form, polymorph form, or pharmaceutical composition (e.g., any of the solid or liquid formulations described herein) thereof that include: identifying a subject having a cell that has one or more RET inhibitor resistance mutations as having an increased likelihood of developing a cancer that has some resistance to the compound of Formula (I) or a pharmaceutically acceptable salt, amorphous form, polymorph form, or pharmaceutical composition (e.g., any of the solid or liquid formulations described herein) thereof. Also provided are methods of determining the presence of a cancer that has some resistance to the compound of Formula (I) or a pharmaceutically acceptable salt, amorphous form, polymorph form, or pharmaceutical composition (e.g., any of the solid or liquid formulations described herein) thereof that includes: determining whether a cancer cell in a sample obtained from the subject has one or more RET inhibitor resistance mutations; and determining that the subject having the cancer cell that has one or more RET inhibitor resistance mutations has a cancer that has some resistance to the compound of Formula (I) or a pharmaceutically acceptable salt, amorphous form, polymorph form, or pharmaceutical composition (e.g., any of the solid or liquid formulations described herein) thereof. Also provided are methods of determining the presence of a cancer that has some resistance to the compound of Formula (I) or a pharmaceutically acceptable salt, amorphous form, polymorph form, or pharmaceutical composition (e.g., any of the solid or liquid formulations described herein) thereof in a subject that include: determining that a subject having a cancer cell that has one or more RET inhibitor resistance mutations has a cancer that has some resistance to the compound of Formula (I) or a pharmaceutically acceptable salt, amorphous form, polymorph form, or pharmaceutical composition (e.g., any of the solid or liquid formulations described herein) thereof. In some embodiments, the one or more RET inhibitor resistance mutations confer increased resistance to a cancer cell or tumor to treatment with the compound of Formula (I) or a pharmaceutically acceptable salt, amorphous form, polymorph form, or pharmaceutical composition (e.g., any of the solid or liquid formulations described herein) thereof.

In some embodiments of any of the methods described herein, a RET inhibitor resistance mutation that confers increased resistance to a cancer cell or tumor to treatment with the compound of Formula (I) or a pharmaceutically acceptable salt, amorphous form, polymorph form, or pharmaceutical composition (e.g., any of the solid or liquid formulations described herein) thereof can be any of the RET inhibitor resistance mutations listed in Table 3 or 4.

Methods of determining the level of resistance of a cancer cell or a tumor to a RET inhibitor (e.g., any of the RET inhibitors described herein or known in the art) can be determined using methods known in the art. For example, the level of resistance of a cancer cell to a RET inhibitor can be assessed by determining the $IC_{50}$ of a RET inhibitor (e.g., any of the RET inhibitors described herein or known in the art) on the viability of a cancer cell. In other examples, the level of resistance of a cancer cell to a RET inhibitor can be assessed by determining the growth rate of the cancer cell in the presence of a RET inhibitor (e.g., any of the RET inhibitors described herein). In other examples, the level of resistance of a tumor to a RET inhibitor can be assessed by determining the mass or size of one or more tumors in a subject over time during treatment with a RET inhibitor (e.g., any of the RET inhibitors described herein). In other examples, the level of resistance of a cancer cell or a tumor to a RET inhibitor can be indirectly assessed by determining the activity of a RET kinase including one or more of the RET inhibitor resistance mutations (i.e., the same RET kinase expressed in a cancer cell or a tumor in a subject). The level of resistance of a cancer cell or tumor having one or more RET inhibitor resistance mutations to a RET inhibitor is relative to the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein). For example, the determined level of resistance of a cancer cell or a tumor having one or more RET inhibitor resistance mutations can be greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, greater than about 200%, greater than about 210%, greater than about 220%, greater than about 230%, greater than about 240%, greater than about 250%, greater than about 260%, greater than about 270%, greater than about 280%, greater than about 290%, or greater than about 300% of the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein).

RET is thought to play an important role in the development and survival of afferent nociceptors in the skin and gut. RET kinase knock-out mice lack enteric neurons and have other nervous system anomalies suggesting that a functional RET kinase protein product is necessary during development (Taraviras, S. et al., *Development*, 1999, 126:2785-2797). Moreover population studies of patients with Hirschsprung's disease characterized by colonic obstruction due to lack of normal colonic enervation have a higher proportion of both familial and sporadic loss of function RET mutations (Butler Tjaden N., et al., *Transl. Res.*, 2013, 162: 1-15). Irritable bowel syndrome (IBS) is a common illness affecting 10-20% of individuals in developed countries and is characterized by abnormal bowel habits, bloating and visceral hypersensitivity (Camilleri, M., *N. Engl. J. Med.*, 2012, 367: 1626-1635). While the etiology of IBS is unknown it is thought to result from either a disorder between the brain and gastrointestinal tract, a disturbance in the gut microbiome or increased inflammation. The resulting gastrointestinal changes affect normal bowel transit resulting in either diarrhea or constipation. Furthermore in many IBS patients the sensitization of the peripheral nervous system results in visceral hypersensitivity or allodynia (Keszthelyi, D., *Eur. J. Pain,* 2012, 16: 1444-1454). See, e.g., U.S. Publication No. 2015/0099762.

Accordingly, provided herein are methods for treating a patient diagnosed with (or identified as having) an irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, and inflammatory bowel disease that include administering to the patient a therapeutically effective amount of the compound of Formula (I) or a pharmaceutically acceptable salt, amorphous form, polymorph form, or pharmaceutical composition (e.g., any of the solid or liquid formulations described herein) thereof.

Also provided herein are methods for treating a patient identified or diagnosed as having a RET-associated irritable bowel syndrome (IBS) (e.g., a patient that has been identified or diagnosed as having a RET-associated irritable bowel syndrome (IBS) through the use of a regulatory agency-approved, e.g., FDA-approved, kit for identifying dysregulation of a RET gene, a RET kinase, or expression or activity or level of any of the same, in a patient or a biopsy sample from the patient) that include administering to the patient a therapeutically effective amount of the compound of Formula (I) or a pharmaceutically acceptable salt, amorphous form, polymorph form, or pharmaceutical composition (e.g., any of the solid or liquid formulations described herein) thereof.

Also provided herein are methods for treating pain associated with IBS that include administering to the patient a therapeutically effective amount of the compound of Formula (I) or a pharmaceutically acceptable salt, amorphous form, polymorph form, or pharmaceutical composition (e.g., any of the solid or liquid formulations described herein) thereof. In some embodiments, the compound of Formula (I) or a pharmaceutically acceptable salt, amorphous form, polymorph form, or pharmaceutical composition (e.g., any of the solid or liquid formulations described herein) thereof is administered in combination with another therapeutic agent useful for treating one or more symptoms of IBS.

Also provided are methods for treating an irritable bowel syndrome (IBS) in a patient in need thereof, the method comprising: (a) determining if the irritable bowel syndrome (IBS) in the patient is a RET-associated IBS (e.g., using a regulatory-agency approved, e.g., FDA-approved, kit for identifying dysregulation of a RET gene, a RET kinase, or expression or activity or level of any of the same, in a patient or a biopsy sample from the patient, or by performing any of the non-limiting examples of assays described herein); and (b) if the IBS is determined to be a RET-associated IBS, administering to the patient a therapeutically effective amount of the compound of Formula (I) or a pharmaceutically acceptable salt, amorphous form, polymorph form, or pharmaceutical composition (e.g., any of the solid or liquid formulations described herein) thereof.

In some embodiments, the compounds of the present invention are useful for treating irritable bowel syndrome (IBS) in combination with one or more additional therapeutic agents or therapies effective in treating the irritable bowel syndrome that work by the same or a different mechanism of action. The at least one additional therapeutic agent may be administered with the compound of Formula (I) or a pharmaceutically acceptable salt, amorphous form, polymorph form, or pharmaceutical composition (e.g., any of the solid or liquid formulations described herein) thereof as part of the same or separate dosage forms, via the same or different routes of administration, and on the same or different administration schedules according to standard pharmaceutical practice known to one skilled in the art.

Non-limiting examples of additional therapeutics for the treatment of irritable bowel syndrome (IBS) include probiotics, fiber supplements (e.g., psyllium, methylcellulose), anti-diarrheal medications (e.g., loperamide), bile acid binders (e.g., cholestyramine, colestipol, colesevelam), anticholinergic and antispasmodic medications (e.g., hyoscyamine, dicyclomine), antidepressant medications (e.g., tricyclic antidepressant such as imipramine or notriptyline or a selective serotonin reuptake inhibitor (SSRI) such as fluoxetine or paroxetine), antibiotics (e.g., rifaximin), alosetron, and lubiprostone.

Accordingly, also provided herein are methods of treating irritable bowel syndrome (IBS), comprising administering to a patient in need thereof a pharmaceutical combination for treating IBS which comprises (a) the compound of Formula (I) or a pharmaceutically acceptable salt, amorphous form, polymorph form, or pharmaceutical composition (e.g., any of the solid or liquid formulations described herein) thereof, (b) an additional therapeutic agent, and (c) optionally at least one pharmaceutically acceptable carrier for simultaneous, separate or sequential use for the treatment of IBS, wherein the amounts of the compound of Formula (I) or a pharmaceutically acceptable salt, amorphous form, polymorph form, or pharmaceutical composition (e.g., any of the solid or liquid formulations described herein) thereof and the additional therapeutic agent are together effective in treating the IBS. In one embodiment, the compound of Formula (I) or a pharmaceutically acceptable salt, amorphous form, polymorph form, or pharmaceutical composition (e.g., any of the solid or liquid formulations described herein) thereof, and the additional therapeutic agent are administered simultaneously as separate dosages. In one embodiment, the compound of Formula (I) or a pharmaceutically acceptable salt, amorphous form, polymorph form, or pharmaceutical composition (e.g., any of the solid or liquid formulations described herein) thereof, and the additional therapeutic agent are administered as separate dosages sequentially in any order, in jointly therapeutically effective amounts, e.g. in daily or intermittently dosages. In one embodiment, the compound of Formula (I) or a pharmaceutically acceptable salt, amorphous form, polymorph form, or pharmaceutical composition (e.g., any of the solid or liquid formulations described herein) thereof, and the additional therapeutic agent are administered simultaneously as a combined dosage.

Also provided herein is (i) a pharmaceutical combination for treating irritable bowel syndrome in a patient in need thereof, which comprises (a) the compound of Formula (I) or a pharmaceutically acceptable salt, amorphous form, polymorph form, or pharmaceutical composition (e.g., any of the solid or liquid formulations described herein) thereof, (b) at least one additional therapeutic agent (e.g., any of the exemplary additional therapeutic agents described herein for treating irritable bowel syndrome or known in the art), and (c) optionally at least one pharmaceutically acceptable carrier for simultaneous, separate or sequential use for the treatment of irritable bowel syndrome, wherein the amounts of the compound of Formula (I) or a pharmaceutically acceptable salt, amorphous form, polymorph form, or pharmaceutical composition (e.g., any of the solid or liquid formulations described herein) thereof and of the additional therapeutic agent are together effective in treating the irritable bowel syndrome; (ii) a pharmaceutical composition comprising such a combination; (iii) the use of such a combination for the preparation of a medicament for the treatment of irritable bowel syndrome; and (iv) a commercial package or product comprising such a combination as a combined preparation for simultaneous, separate or sequential use; and to a method of treatment of irritable bowel syndrome in a patient in need thereof. In one embodiment the patient is a human.

The term "pharmaceutical combination", as used herein, refers to a pharmaceutical therapy resulting from the mixing or combining of more than one active ingredient and includes both fixed and non-fixed combinations of the active ingredients. The term "fixed combination" means that the compound of Formula (I) or a pharmaceutically acceptable salt, amorphous form, polymorph form, or pharmaceutical composition (e.g., any of the solid or liquid formulations described herein) thereof and at least one additional therapeutic agent (e.g., an agent effective in treating irritable bowel syndrome), are both administered to a patient simultaneously in the form of a single composition or dosage. The term "non-fixed combination" means that the compound of Formula (I) or a pharmaceutically acceptable salt, amorphous form, polymorph form, or pharmaceutical composition (e.g., any of the solid or liquid formulations described herein) thereof and at least one additional therapeutic agent (e.g., an agent effective in treating irritable bowel syndrome) are formulated as separate compositions or dosages, such that they may be administered to a patient in need thereof simultaneously, concurrently or sequentially with variable intervening time limits, wherein such administration provides effective levels of the two or more compounds in the body of the patient. In one embodiment, the compound of Formula (I) or a pharmaceutically acceptable salt, amorphous form, polymorph form, or pharmaceutical composition (e.g., any of the solid or liquid formulations described herein) thereof and the additional therapeutic agent are formulated as separate unit dosage forms, wherein the separate dosages forms are suitable for either sequential or simultaneous administration. These also apply to cocktail therapies, e.g. the administration of three or more active ingredients.

In some embodiments, a compound provided herein can be used as an agent for supportive care for a patient undergoing cancer treatment. For example, the compound of Formula (I) or a pharmaceutically acceptable salt, amorphous form, polymorph form, or pharmaceutical composition (e.g., any of the solid or liquid formulations described herein) thereof, can be useful to reduce one or more symptoms associated with treatment with one or more cancer therapies such as diarrheal or constipations complications and/or abdominal pain. See, for example, U.S. Publication No. 2015/0099762 and Hoffman, J. M. et al. *Gastroenterology* (2012) 142:844-854. Accordingly, a compound, or a pharmaceutically acceptable salt thereof, or composition provided herein can be administered to a patient to address one or more complications associated with cancer treatment (e.g., gastrointestinal complications such as diarrhea, constipation, or abdominal pain).

In some embodiments, a therapeutically effective amount of the compound of Formula (I) or a pharmaceutically acceptable salt, amorphous form, polymorph form, or pharmaceutical composition (e.g., any of the solid or liquid formulations described herein) thereof can be administered to a patient undergoing cancer treatment (e.g., a patient experiencing an adverse event associated with cancer treatment such as an immune-related adverse event or a gastrointestinal complication including diarrhea, constipation, and abdominal pain). For example, a compound provided herein, or a pharmaceutically acceptable salt thereof, can be used in the treatment of colitis or IBS associated with administration of a checkpoint inhibitor; see, e.g., Postow, M. A. et al. *Journal of Clinical Oncology* (2015) 33: 1974-1982. In some such embodiments, a compound provided herein, or a pharmaceutically acceptable salt thereof, can be formulated to exhibit low bioavailability and/or be targeted for delivery in the gastrointestinal tract. See, for example, U.S. Pat. No. 6,531,152.

Also provided is a method for inhibiting RET kinase activity in a cell, comprising contacting the cell with the compound of Formula (I) or a pharmaceutically acceptable salt, amorphous form, polymorph form, or pharmaceutical composition (e.g., any of the solid or liquid formulations described herein) thereof. In one embodiment, the contacting is in vitro. In one embodiment, the contacting is in vivo. In one embodiment, the contacting is in vivo, wherein the method comprises administering an effective amount of the compound of Formula (I) or a pharmaceutically acceptable salt, amorphous form, polymorph form, or pharmaceutical composition (e.g., any of the solid or liquid formulations described herein) thereof to a subject having a cell having RET kinase activity. In some embodiments, the cell is a cancer cell. In one embodiment, the cancer cell is any cancer as described herein. In some embodiments, the cancer cell is a RET-associated cancer cell. In some embodiments, the cell is a gastrointestinal cell.

Also provided is a method for inhibiting RET kinase activity in a mammalian cell, comprising contacting the cell with the compound of Formula (I) or a pharmaceutically acceptable salt, amorphous form, polymorph form, or pharmaceutical composition (e.g., any of the solid or liquid formulations described herein) thereof. In one embodiment, the contacting is in vitro. In one embodiment, the contacting is in vivo. In one embodiment, the contacting is in vivo, wherein the method comprises administering an effective amount of the compound of Formula (I) or a pharmaceutically acceptable salt, amorphous form, polymorph form, or pharmaceutical composition (e.g., any of the solid or liquid formulations described herein) thereof to a mammal having a cell having RET kinase activity. In some embodiments, the mammalian cell is a mammalian cancer cell. In one embodiment, the mammalian cancer cell is any cancer as described herein. In some embodiments, the mammalian cancer cell is a RET-associated cancer cell. In some embodiments, the mammalian cell is a gastrointestinal cell.

As used herein, the term "contacting" refers to the bringing together of indicated moieties in an in vitro system or an in vivo system. For example, "contacting" a RET kinase with a compound provided herein includes the administration of a compound provided herein to an individual or patient, such as a human, having a RET kinase, as well as, for example, introducing a compound provided herein into a sample containing a cellular or purified preparation containing the RET kinase.

Also provided herein is a method of inhibiting cell proliferation, in vitro or in vivo, the method comprising contacting a cell with an effective amount of the compound of Formula (I) or a pharmaceutically acceptable salt, amorphous form, polymorph form, or pharmaceutical composition (e.g., any of the solid or liquid formulations described herein) thereof or a pharmaceutical composition thereof as defined herein.

The phrase "effective amount" means an amount of compound that, when administered to a patient in need of such treatment, is sufficient to (i) treat a RET kinase-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of the compound of Formula (I) or a pharmaceutically acceptable salt, amorphous form, polymorph form, or pharmaceutical composition (e.g., any of the solid or liquid formulations described herein) thereof that will correspond to such an amount will vary depending upon factors such as the particular compound, disease condition and its severity, the identity (e.g., weight) of the patient in need of treatment, but can nevertheless be routinely determined by one skilled in the art.

EXAMPLES

Example 1: Synthesis of the Compound of Formula (I) Via Intermediates 1-4

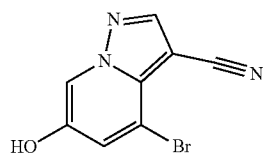

Intermediate 1

4-Bromo-6-hydroxypyrazolo[1,5-a]pyridine-3-carbonitrile

Part A: Preparation of O-(mesitylsulfonyl)hydroxylamine

Step 1: Tert-butyl (mesitylsulfonyl)oxycarbamate

To a 0° C. solution of 2,4,6-trimethylbenzene-1-sulfonyl chloride (10.0 g, 45.72 mmol) and tert-butyl hydroxycarbamate (6.088 g, 45.72 mmol) in MTBE (100 mL) was added TEA (14.46 mL, 48.01 mmol) dropwise while stirring. The resulting suspension was stirred at 0° C. for an additional 30 min and then warmed to ambient temperature. The reaction was then diluted with water (100 mL) and adjusted to pH 4 with 1 N HCl(aq). The organic layer was dried ($Na_2SO_4$), filtered, and concentrated to yield the title compound initially as a yellowish oil, which upon drying overnight under high vacuum became a white solid (12.89 g, 89% yield). $^1$H NMR ($CDCl_3$): δ 7.66 (br s, 1H), 6.98 (s, 2H), 2.67 (s, 6H), 2.32 (s, 3H), 1.31 (s, 9H).

Step 2: O-(mesitylsulfonyl)hydroxylamine

To TFA (117 mL, 1521 mmol) at 0° C. was slowly added tert-butyl (mesitylsulfonyl)oxycarbamate (39.0 g, 124 mmol) over 25 min. The reaction mixture was stirred at 0° C. for 1.5 h and then quenched with the sequential addition of crushed ice and water. The resulting thick suspension was vigorously stirred at ambient temperature for 5 min. Without allowing the filter cake to run dry, the solids were collected by careful vacuum filtration, followed by subsequent rinsing with water (4 L) until the filtrate reached pH 6 (Caution: explosion risk exists with dry compound at ambient temperature). The wet filter cake was taken up in dichloromethane (150 mL) and the resulting biphasic solution was separated. The dichloromethane layer was dried over $MgSO_4$ for 30 min and then filtered and rinsed with dichloromethane (420 mL) to provide the title compound as a 0.22 M solution in dichloromethane.

Part B: Preparation of 4-bromo-6-hydroxypyrazolo [1,5-a]pyridine-3-carbonitrile

Step 1: 1-amino-3-bromo-5-methoxypyridin-1-ium-2,4,6-trimethylbenzenesulfonate

To a solution of O-(mesitylsulfonyl)hydroxylamine (Part A, 26.6 g, 117 mmol) in dichloromethane (570 mL) cooled to 0° C. was added 3-bromo-5-methoxypyridine (22.1 g, 117 mmol) in portions. The reaction mixture was stirred for 1 h at 0° C. then treated with additional 3-bromo-5-methoxypyridine (250 mg, 1.39 mmol) and stirred for an additional 2 h at 0° C. The reaction mixture was diluted with $Et_2O$ (600 mL), stirred at 0° C. for 10 min and then vacuum filtered, and rinsed with $Et_2O$ (3×250 mL). Upon reduction in volume by about ⅓, the filtrate yielded additional precipitate which was collected by filtration. Both filter cakes were dried in vacuo to provide the title compound (39.3 g, 83% yield). $^1$H NMR ($CDCl_3$): δ 9.25 (br s, 1H), 8.99 (m, 1H), 8.74 (m, 1H), 7.46 (m, 1H), 6.83 (s, 2H), 3.92 (s, 3H), 2.65 (s, 6H), 2.22 (s, 3H).

Step 2: Ethyl-6-bromo-4-methoxypyrazolo[1,5-a] pyridine-3-carboxylate and ethyl-4-bromo-6-methoxypyrazolo[1,5-a]pyridine-3-carboxylate To a magnetically stirred white suspension of 1-amino-3-bromo-5-methoxypyridin-1-ium-2,4,6-trimethylbenzenesulfonate (33.24 g, 82.42 mmol) in DMF (82 mL) at ambient temperature was added TEA (22.98 mL, 164.8 mmol), followed by dropwise addition of ethyl propiolate (16.71 mL, 164.8 mmol). After vigorous stirring for 2 d, the reaction was slowly quenched via portion-wise addition to rapidly stirring ice water (820 mL). The mixture was stirred at ambient temperature for 10 min and then vacuum filtered. Solids collected were rinsed with water and air-dried, yielding the title compounds as an orange solid in an isomeric ratio of about 4:1 (by $^1$H NMR) with the 6-Br isomer as the major isomer (21 g). The wet solid isomeric mixture (about 75% w/w) was directly used in Step 3 without further purification. MS (apci) m/z=298.9, 300.9 (M+H). Regioisomeric ratio was determined by MeO chemical shift in $^1$H NMR ($CDCl_3$) δ 3.98 (6-Br isomer) vs. 3.83 (4-Br isomer).

Step 3: 6-bromo-4-methoxypyrazolo[1,5-a]pyridine (Intermediate 1) and 4-bromo-6-methoxypyrazolo [1,5-a]pyridine The isomeric mixture of ethyl-6-bromo-4-methoxypyrazolo[1,5-a]pyridine-3-carboxylate and ethyl-4-bromo-6-methoxypyrazolo[1,5-a]pyridine-3-carboxylate from Step 2 (15 g, 50.1 mmol) was added to 48% HBr (114 mL) while stirring, then heated at 80° C. for 90 min, followed by stirring at ambient temperature overnight. The resulting suspension was vacuum filtered and rinsed with water. The aqueous filtrate and the filter cake were treated independently. The filter cake was taken up in MTBE and vacuum filtered to remove insoluble impurities. The MTBE filtrate was dried over anhydrous $Na_2SO_4$, filtered and concentrated in vacuo to yield 6-bromo-4-methoxypyrazolo[1,5-a]pyridine as a beige solid (about 98:2 6-/4-Br; 5.08 g). MS (apci) m/z=226.9, 228.9 (M+H). $^1$H NMR (CDCl$_3$): δ 8.26 (m, 1H), 7.82 (d, 1H), 6.61 (m, 1H), 6.43 (m, 1H), 3.94 (s, 3H). Independently, the original aqueous reaction mixture filtrate was extracted with EtOAc (2×500 mL). The combined organic extracts were dried (Na$_2$SO$_4$), filtered and concentrated in vacuo. The crude residue was taken up in DCM (50 mL) and then filtered to remove insoluble solids. Concentration of the DCM filtrate under vacuum followed by silica chromatography (0 to 50% EtOAc/hexanes) yielded a second batch of 6-bromo-4-methoxypyrazolo[1,5-a]pyridine (Intermediate 1) as a white solid (upper R$_f$ spot, 2.06 g), as well as the minor isomer title compound 4-bromo-6-methoxypyrazolo[1,5-a]pyridine also as a white solid (lower R$_f$ spot, 1.32 g). MS (apci) m/z=226.9, 228.9 (M+H). $^1$H NMR (CDCl$_3$): δ 8.02 (m, 1H), 7.85 (d, 1H), 7.17 (d, 1H), 6.55 (m, 1H), 3.80 (s, 3H).

Step 4: 4-bromo-6-methoxypyrazolo[1,5-a]pyridine-3-carbaldehyde

A solution of 4-bromo-6-methoxypyrazolo[1,5-a]pyridine (5.0 g, 22 mmol) in DMF (220 mL) was cooled to 0° C. and then slowly treated with POCl$_3$ (6.2 mL, 66 mmol). The reaction was warmed to ambient temperature and stirred overnight. The reaction mixture was cooled to 0° C., quenched with water (220 mL), and basified with 6 M NaOH$_{(aq)}$ to pH 9-10. The reaction mixture was stirred for 1 h and then vacuum filtered. The solids were rinsed sequentially with water (3×50 mL) and MTBE (3×50 mL). The collected solid was suspended in DCM (500 mL) and stirred in a sonicating bath for 30 min and then vacuum filtered. The filtrate was retained, while the filter cake was taken up in water (300 mL) and extracted with DCM. The organic extracts, along with the retained DCM filtrate, were combined and dried over anhydrous Na$_2$SO$_4$, then filtered and concentrated in vacuo to provide the title compound (4.84 g, 86% yield). MS (apci), m/z=256.9 (M+H).

Step 5: 4-bromo-6-methoxypyrazolo[1,5-a]pyridine-3-carbaldehyde Oxime

To a suspension of 4-bromo-6-methoxypyrazolo[1,5-a]pyridine-3-carbaldehyde (4.84 g, 19.0 mmol) in EtOH (253 mL) at ambient temperature was added water (127 mL) and hydroxylamine hydrochloride (1.98 g, 28.5 mmol). After stirring at 50° C. overnight, the reaction mixture was cooled to ambient temperature and concentrated in vacuo. The residue was suspended in water (150 mL) and then quenched slowly with saturated NaHCO$_{3(aq)}$ (30 mL). After stirring for 1 hour at ambient temperature, the suspension was vacuum filtered and the filter cake rinsed sequentially with H$_2$O (500 mL) and MTBE (100 mL) to yield the title compound as a 2:1 E/Z mixture (5.13 g, quantitative yield), which was used in the next step without further purification. MS (apci) m/z=271.9 (M+H).

Step 6: 4-bromo-6-methoxypyrazolo[1,5-a]pyridine-3-carbonitrile

The E/Z mixture of 4-bromo-6-methoxypyrazolo[1,5-a]pyridine-3-carbaldehyde oxime (4.95 g, 18.33 mmol) in acetic anhydride (172.9 mL, 1833 mmol) was stirred at 140° C. for 25 h, and then cooled to ambient temperature. The resulting suspension was further cooled in an ice bath for 15 min and then vacuum filtered and rinsed sequentially with water (200 mL) and MTBE (300 mL) to provide the title compound (3.74 g, 81% yield). $^1$H NMR (d$^6$-DMSO): δ 8.70 (s, 1H), 8.60 (s, 1H), 7.78 (s, 1H), 3.83 (s, 3H).

Step 7: 4-bromo-6-hydroxypyrazolo[1,5-a]pyridine-3-carbonitrile

A slurry of 4-bromo-6-methoxypyrazolo[1,5-a]pyridine-3-carbonitrile (50.0 g, 198.4 mmol) in DCE (500 mL) was treated with AlCl$_3$ (79.34 g, 595.1 mmol). Under an N$_{2(g)}$ atmosphere, the resulting mixture was stirred 19 h at 76° C., before cooling to room temperature. Using THF (1750 mL) as a rinse solvent, the reaction mixture was poured into a mechanically stirred suspension of sodium sulfate decahydrate (10 eq, 639 g) in THF (1000 mL). After stirring overnight at ambient temperature, the resulting suspension was filtered, and the solids were rinsed with additional THF (2×250 mL). The filtrate was concentrated in vacuo, and the resulting solid was dried under high vacuum for 3 days to afford the title compound (46.18 g, 98% yield) in sufficient purity for subsequent use. $^1$H NMR (d$^6$-DMSO): δ 10.48 (s, 1H), 8.58 (s, 1H), 8.38 (d, 1H), 7.64 (3, 1H).

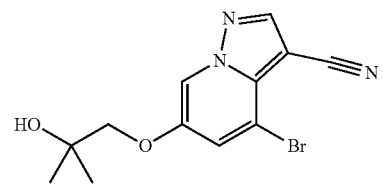

Intermediate 2

4-bromo-6-(2-hydroxy-2-methylpropoxy)pyrazolo[1,5-a]pyridine-3-carbonitrile

In a pressure vessel, a mixture of 4-bromo-6-hydroxypyrazolo[1,5-a]pyridine-3-carbonitrile (Intermediate 1; 10.0 g, 42.0 mmol) and K$_2$CO$_{3(s)}$ (17.4 g, 126 mmol) in DMF (50 mL) was treated with 2,2-dimethyloxirane (36.9 mL, 420 mmol). After sealing the vessel, the reaction mixture was stirred for 12 h at 60° C., then for 12 h at 85° C. The mixture was allowed to cool to ambient temperature. The room temperature mixture was poured into water (400 mL), then stirred for 1 hour at ambient temperature. The resultant suspension was vacuum filtered and the filter cake was rinsed with water. The solids were collected and dried in vacuo to cleanly provide the title compound (11 g, 84% yield).

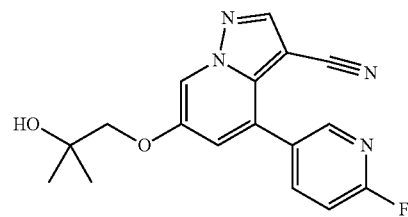

Intermediate 3

4-(6-fluoropyridin-3-yl)-6-(2-hydroxy-2-methylpropoxy)pyrazolo[1,5-a]pyridine-3-carbonitrile A mixture of 4-bromo-6-(2-hydroxy-2-methylpropoxy)pyrazolo[1,5-a]pyridine-3-carbonitrile (Intermediate 2; 10.0 g, 32.2 mmol), 2-fluoro-5-(4,4,5,5-tetramethyl-1,3,2-dioxaborolan-2-yl)pyridine (10.8 g, 48.4 mmol) and Pd(PPh$_3$)$_4$ (1.12 g, 0.967 mmol) in dioxane (200 mL) was treated with 2 M Na$_2$CO$_{3(aq)}$ (64.5 mL, 129 mmol). The resulting mixture was sparged with Ar$_{(g)}$, then stirred for 12 h at 85° C. under an atmosphere of N$_{2(g)}$. After cooling to ambient temperature, the resultant mixture was poured into cold water (1.5 L). The pH of the mixture was adjusted to about pH 6 with the addition of 10% citric acid. After stirring for 1 hour at ambient temperature, the resultant suspension was vacuum filtered. The solids were collected and dried in vacuo to cleanly provide the title compound (10 g, 95% yield).

Intermediate 4

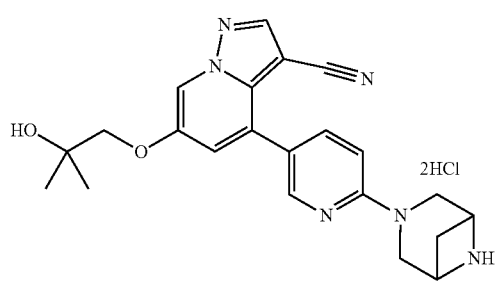

4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile Dihydrochloride Step 1: Tert-butyl-3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate A mixture of 4-(6-fluoropyridin-3-yl)-6-(2-hydroxy-2-methylpropoxy)pyrazolo[1,5-a]pyridine-3-carbonitrile (Intermediate 3; 1.70 g, 8.55 mmol), 3,6-diaza-bicyclo[3.1.1]heptane-6-carboxylic acid tert-butyl ester (1.70 g, 8.55 mmol) and K$_2$CO$_{3(s)}$ (7.88 g, 57.0 mmol) in DMSO (7 mL) was stirred 12 h at 90° C. The resultant thick slurry was diluted with additional DMSO (2 mL) and stirred for 12 h at 90° C. The mixture was cooled to ambient temperature and diluted with water (100 mL). The aqueous mixture was washed with DCM. The combined organic extracts were dried over anhydrous MgSO$_{4(s)}$, filtered and concentrated in vacuo. The crude residue was purified by silica chromatography (30-80% EtOAc/hexanes as the gradient eluent system) to cleanly provide the title compound (2.87 g, 100% yield). MS (apci) m/z=505.2 (M+H).

Step 2: 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile Dihydrochloride A solution of tert-butyl-3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (see step 1; 3.05 g, 6.04 mmol) in DCM (20 mL) was treated with 4 N HCl in dioxanes (15.1 mL, 60.4 mmol). The resulting mixture was stirred for 12 hours at ambient temperature, and then concentrated in vacuo. The crude residue was diluted with DCM and toluene, and then sonicated before concentrating in vacuo to afford the title compound as the dihydrochloride salt (2.44 g, quantitative yield). MS (apci) m/z=405.2 (M+H).

Formula (I)

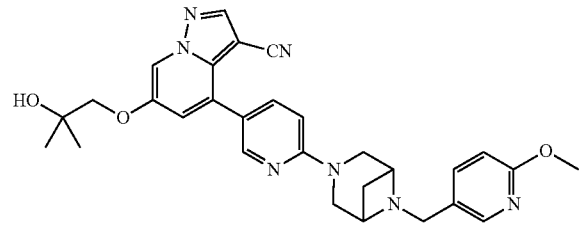

6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile Method A:

A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate 4; 12.2 mg, 0.0277 mmol) in DCE (513 µL) was treated sequentially with 6-methoxynicotinaldehyde (7.59 mg, 0.0553 mmol) and NaBH(AcO)$_3$ (17.6 mg, 0.0830 mmol), then stirred overnight at ambient temperature. The mixture was concentrated in vacuo, and the residue was purified by silica chromatography (0-20% MeOH in DCM as the gradient eluent) to yield 13.59 mg (93% yield) of the title compound. The purified material was then recrystallized in either DCM/heptane or DMSO/water.

Method B:

To a mixture of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate 4, 6.0 g, 12.6 mmol) in DCM (30 mL) was added triethylamine (5.3 mL, 37.7 mmol), followed by 6-methoxynicotinaldehyde (2.59 g, 18.9 mmol) and then sodium triacetoxyborohydride (5.33 g, 25.1 mmol) in one portion while stirring. Additional DCM (30 mL) was added and the reaction was stirred at ambient temperature overnight. The reaction mixture was poured into water (200 mL) and extracted with DCM (200 mL). After phase-separation, the organic layer was washed with water (2×200 mL). The combined aq washes was back-extracted with DCM (200 mL). The combined organic extracts was washed with brine (250 mL), passed through a Phase Separator frit and treated with activated charcoal (Darco G-60, 6 g). After stirred at ambient temperature for 2 h, the mixture was vacuum-filtered, rinsed with DCM (3×10 mL). The filtrate was treated with 3-(trimethoxysilyl)propane-1-thiol (11 g, 7.4 mmol) and magnetically stirred overnight. The mixture was vacuum-filtered and concentrated on rotovap to ca. 200 mL. n-Heptanes (150 mL) was added portion-wise to the above DCM solution while stirring until cloudy. After 90 min stirring, the white slurry was vacuum-filtered, rinsed with heptane (200 mL), yielding the title product as fine crystalline white powder (3.9 g, 59%).

Recrystallization of the Compound of Formula (I) Prepared by Method A or Method B:

Recrystallization of the compound of Formula (I) in DMSO/water was performed as follows. To a reaction flask was charged the compound of Formula (I) (10.1 g) and DMSO (110 mL). The mixture was heated to 50° C. until all of the solid was in solution. The mixture was cooled to 25° C. and polish filtered. DMSO (10 mL) was charged through the filter as a wash. The resulting solution was heated to 45° C. and water (5 mL) was slowly added. The mixture was stirred for 30 minutes and a seed bed formed. Water (25 mL) was added over 1 h and the slurry was aged at 45° C. for an additional 1 hour. The slurry was then allowed to cool to 25° C. and stir for 2 hours. The slurry was filtered and the cake was washed with water (20 mL×3), MeOH (20 mL×2) and MTBE (20 mL×2). The cake was dried at room temperature in a vacuum oven to give 9.35 g (74%) of the title compound. MS (apci) m/z=526.2 (M+H). $^1$H NMR (400 MHz, DMSO-d$_6$) δ: 8.64 (d, 1H, J=2.3 Hz), 8.55 (s, 1H), 8.38 (d, 1H, J=2.3 Hz), 8.04 (d, 1H, J=2.3 Hz), 7.80 (dd, 1H, J=8.6, 2.3 Hz), 7.64 (dd, 1H, J=8.6, 2.3 Hz), 7.27 (d, 1H, J=2.0 Hz), 6.76 (d, 1H, J=8.6 Hz), 6.73 (d, 1H, J=8.2 Hz), 4.67 (s, 1H), 3.85 (s, 2H), 3.79 (s, 3H), 3.72 (d, 2H, J=12.5 Hz), 3.64 (d, 2H, J=5.9 Hz), 3.51 (br d, 2H), 3.47 (s, 2H), 2.47 (m, 1H), 1.55 (d, 1H), 1.20 (s, 6H).

Example 2: Synthesis of the Compound of Formula (I) Via Compound A

1. Preparation of Compound A

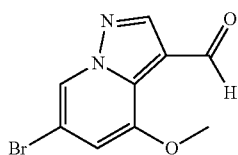

6-bromo-4-methoxypyrazolo[1,5-a]pyridine-3-carbaldehyde (6A)

To a 0° C. solution of 6-bromo-4-methoxypyrazolo[1,5-a]pyridine (0.75 g, 3.303 mmol) in DMF (33 mL) was slowly added POCl$_3$ (0.92 mL, 9.909 mmol). The reaction was warmed to ambient temperature and stirred for 4 h and then diluted with H$_2$O (30 mL). The resulting suspension was basified to pH 9-10 with 1 M NaOH$_{(aq)}$, then stirred for 1 h and vacuum filtered, then rinsed sequentially with H$_2$O (25 mL) and MTBE (50 mL) to yield the title compound (0.76 g, 90% yield). MS (apci) m/z=256.9 (M+H).

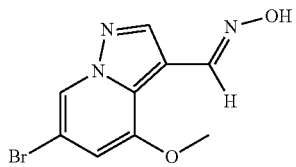

(E)-6-bromo-4-methoxypyrazolo[1,5-a]pyridine-3-carbaldehyde Oxime (7A)

To a suspension of 6-bromo-4-methoxypyrazolo[1,5-a]pyridine-3-carbaldehyde (6A) (0.76 g, 3.0 mmol) and hydroxylamine hydrochloride (0.31 g, 4.5 mmol) in EtOH (40 mL) was added water (20 mL), and the reaction was stirred at 50° C. for 4 h. After cooling to ambient temperature the reaction mixture was concentrated in vacuo. The residue was suspended in water, then treated with saturated NaHCO$_{3(aq)}$ and vacuum filtered. The solids were rinsed sequentially with H$_2$O (25 mL) and MTBE (50 mL) to yield the title compound (0.68 g, 84% yield). MS (apci) m/z=271.9 (M+H).

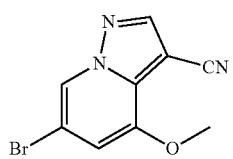

6-bromo-4-methoxypyrazolo[1,5-a]pyridine-3-carbonitrile (A)

A solution of (E)-6-bromo-4-methoxypyrazolo[1,5-a]pyridine-3-carbaldehyde oxime (7A) (17.15 g, 63.50 mmol) in acetic anhydride (707 mL, 7.49 mol) was heated at 120° C. overnight. Following subsequent distillation to remove the acetic anhydride, the remaining residue was dried in vacuo to yield the title compound (15.92 g, 99.4% yield). $^1$H NMR (CDCl$_3$): δ 8.32 (m, 1H), 8.12 (s, 1H), 6.74 (m, 1H), 4.03 (s, 3H).

Compound A can also be prepared according to the method described below.

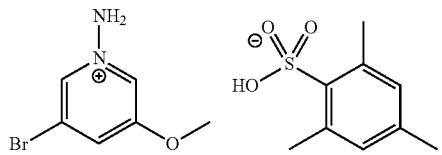

1-amino-3-bromo-5-methoxypyridin-1-ium 2,4,6-trimethylbenzenesulfonate (2a)

To a solution of O-(mesitylsulfonyl)hydroxylamine (146 moles) in DCM (200 kg), was added 3-bromo-5-methoxypyridine (24.6 kg, 131 mol) dropwise at 0-5° C. The reaction was stirred for 16 h at 0-5° C. HPLC indicated that the reaction was complete. To the reaction n-heptanes (130 kg) was added and the mixture was stirred at 0-5° C. for 1 h. The suspension was filtered and the filter cake was washed with n-heptane (20 kg×2) and dried to give compound 2 (40 kg) as a white solid. $^1$H NMR (400 MHz, DMSO-d$_6$), δ (ppm): 8.71 (s, 1H), 8.62 (s, 1H), 8.57 (s, 2H), 8.26 (s, 1H), 6.75 (s, 2H), 3.975 (s, 3H), 2.176 (s, 3H).

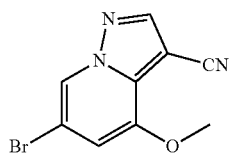

6-bromo-4-methoxypyrazolo[1,5-a]pyridine-3-carbonitrile (A)

To a solution of 1-amino-3-bromo-5-methoxypyridin-1-ium 2,4,6-trimethylbenzenesulfonate (2a) (40 kg, 100 mol) in acetonitrile (300 kg) was added 2-chloroacrylonitrile (13 kg, 150 mol) in one portion at −5° C. DBU (56 kg, 370 mol) was added dropwise at −10-0° C. to the solution. The reaction mixture was stirred at 25-30° C. for 16 h. HPLC showed the reaction was complete. The reaction mixture was quenched with H$_2$O (900 L), the suspension was filtered, and the solid was washed with H$_2$O (100 L). The resulting solid was combined with another lot of compound A. To the combined solids was added DCM (400 L), and the remaining solid was washed with DCM (4×400 L). The combined organic layers were concentrated under vacuum. The residue was suspended in n-heptanes (80 kg), filtered, and dried to give compound A (20.8 kg, 39.1%) as a yellow solid. $^1$H NMR (400 MHz, DMSO-d$_6$) δ (ppm): 8.92 (s, 1H), 8.58 (s, 1H), 7.23 (s, 1H). 4.036 (s, 3H).

2. Preparation of the Compound of Formula (I) from Compound A

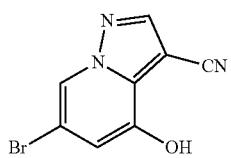

6-bromo-4-hydroxypyrazolo[1,5-a]pyridine-3-carbonitrile (18)

To a solution of 6-bromo-4-methoxypyrazolo[1,5-a]pyridine-3-carbonitrile (A) (20.8 kg, 82.5 mol) in DMF (200 kg) was added an aqueous solution of NaOH (6.6 kg in 13.5 H$_2$O) in one portion at 40° C. 1-dodecanethiol (33.5 kg, 165 mol) was added to the solution at 40-45° C. and the reaction mixture was stirred at 50° C. for 16 h. HPLC showed the reaction was complete. The reaction mixture was poured into water (900 kg) at 0-5° C., followed by 10% aqueous citric acid monohydrate, which was used to adjust the pH to 5-6. The mixture was extracted with ethyl acetate (400 L×3). The combined organic layers were washed with brine and concentrated under reduced pressure. The residue was suspended in n-heptanes (80 kg) and filtered, and the filter cake was washed with n-heptanes (20 kg×2) and dried to give 18 (17.8 kg, 90.8%) as a yellow solid. $^1$H NMR (400 MHz, DMSO-d$_6$) δ (ppm): 8.75 (s, 1H), 8.51 (s, 1H), 6.84 (d, 1H).

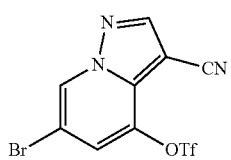

6-bromo-3-cyanopyrazolo[1,5-a]pyridin-4-yl trifluoromethanesulfonate (19)

To a solution of 6-bromo-4-hydroxypyrazolo[1,5-a]pyridine-3-carbonitrile (18) (17.8 kg, 74.8 mol) in DMF (170 kg) was added DIPEA (19.0 kg, 147 mol) in portions at −5-5° C. N,N-bis(trifluoromethylsulfonyl)aniline (26.2 kg, 73.5 mol) was added in portions to the above solution at −5-0° C. The reaction mixture was stirred at 0° C. for 1 h. TLC (pet. Ether:ethyl acetate, 2:1, R$_F$=0.5) showed the reaction was complete. The reaction was quenched by the addition of H$_2$O (500 kg) and a suspension formed. The solid was obtained by filtration and then dissolved in ethyl acetate (300 L) and brine (70 L). The organic layer was concentrated to 30 L and n-heptanes (80 kg) was added. The suspension was stirred at 30° C. for 0.5 h, then filtered. The solid was washed with n-heptanes (20 kg×2), dried to give 19 (22.5 kg, 81.0%) as a white solid. $^1$H NMR (400 MHz, CDCl$_3$) δ (ppm): 8.768 (s, 1H), 8.321 (s, 1H), 7.60 (s, 1H), 3.84 (s, 3H).

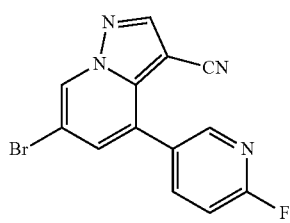

6-bromo-4-(6-fluoropyridin-3-yl)pyrazolo[1,5-a]pyridine-3-carbonitrile (20a)

To a solution of 6-bromo-3-cyanopyrazolo[1,5-a]pyridin-4-yl trifluoromethanesulfonate (19) (21.5 kg, 58 mol), 2-fluoro-5-(tetramethyl-1,3,2-dioxaborolan-2-yl)pyridine (12) (12.9 kg, 58 mol) and Pd(dppf)Cl$_2$.DCM (1.4 kg, 1.7 mol) in THF (400 kg) under an N2 atmosphere was added an aqueous solution of potassium acetate (11.5 kg in 100 kg of water) at 10° C. The reaction mixture was stirred at 25-30° C. for 48 h. HPLC showed the reaction was complete. The reaction was quenched by the addition of water (150 kg) and the suspension was filtered. The solid was suspended in MeOH (200 L) and the suspension was stirred at 25-30° C. for 0.5 h and filtered. The filter cake was washed with MeOH (50 L) and dried to give the crude product (17 kg), which was purified by re-crystallization to give 20a (15.03 kg, 81.6%) as a white solid.

The recrystallization process was as follows: To a solution of the crude product 20a (17 kg) in THF (600 L) at 60° C. was added DMF (36 kg). The mixture was stirred at 60° C. for 0.5 h. The mixture was cooled to 20° C. and water (300 L) was added, followed by filtration. The filter cake was washed with water (100 L) and dried to give compound 20a (15.0 kg, 82%). $^1$H NMR (DMSO-d$_6$, 40 MHz) δ (ppm): 9.48 (s, 1H), 8.73 (s, 1H), 8.51 (s, 1H), 8.25-8.29 (m, 1H), 7.86 (d, 1H), 7.38-7.41 (m, 1H). HPLC: 99.33%. MS: [M]=316.8, [M+2]=318.8.

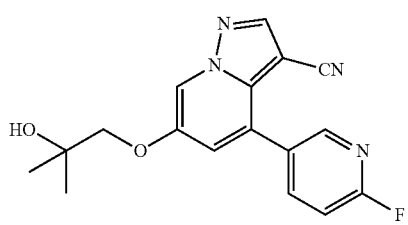

4-(6-fluoropyridin-3-yl)-6-(2-hydroxy-2-methylpropoxy)pyrazolo[1,5-a]pyridine-3-carbonitrile (13a)

Direct Synthesis:

To a reaction vessel was charged 6-bromo-4-(6-fluoropyridin-3-yl)pyrazolo[1,5-a]pyridine-3-carbonitrile (20a) (7.8 kg, 5.68 mol), p-dioxane (28 L), water (9.5 L) and Cs$_2$CO$_3$ (5.55 kg, 17.03 mol). The mixture was agitated and purged with N2 for not less than 30 min. To the flask was charged di-tert-butyl(2',4',6'-triisopropyl-3,4,5,6-tetramethyl-[1,1'-biphenyl]-2-yl)phosphane (436 g, 908 mmol), Pd$_2$(dba)$_3$ (208 g, 227 mmol) and p-dioxane (0.8 L). The mixture was agitated and purged with N2 for not less than 30 min and then 2,2-diimethyloxirane (5.04 L, 56.8 mol) was charged and the reaction was heated to 72° C. overnight and the next day. The reaction was sampled to show the reaction was complete. The heating was terminated and the reaction was allowed to cool. When the internal temperature was ~40° C., Darco G60 (180 g) was added. The reaction was stirred (while continuing to cool) for not less than 1 h. When the reaction mixture was ~30° C. it was filtered over Celite (2.7 kg). The Celite cake was rinsed with ethyl acetate (7.2 L×5). The mixture was diluted with water (18 L) and the phases were separated. The organic layer was washed with 1:1 water/brine (36 L). The layers were separated. The aqueous layers were combined and extracted with ethyl acetate (18 L). The layers were separated and the organic layers were concentrated to 18 L (bath temperature 35° C.). To the organic layer was charged Silicycle (2.3 kg) and charcoal (1.8 kg). The mixture was heated to 50° C. and stirred overnight. The reaction was cooled to ambient temperature and then filtered over Celite (2.2 kg). The Celite cake was rinsed with ethyl acetate (10.8 L and then 14.4 L). The solvent was removed under vacuum until there was a total of ~3.6 L. A charge of MTBE (3.6 L) was made and the solvent was concentrated to 3.6 L. This step was repeated two more times and the mixture stirred at ambient temperature overnight. The mixture was filtered and the filter cake was rinsed with MTBE (3.6 L×2). The solids were transferred to a vacuum oven and dried to give 13a (1085 g, 89 wt %, 56% corrected yield).

Step-Wise Synthesis:

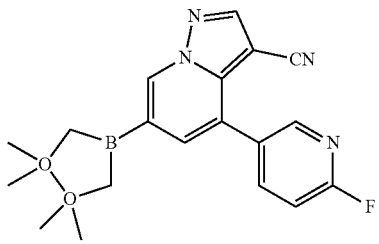

4-(6-fluoropyridin-3-yl)-6-(4,4,5,5-tetramethyl-1,3,2-dioxaborolan-2-yl)pyrazolo[1,5-a]pyridine-3-carbonitrile (22a)

A reaction flask charged with 6-bromo-4-(6-fluoropyridin-3-yl)pyrazolo[1,5-a]pyridine-3-carbonitrile (20a) (50.2 g, 153 mmol), bis(pinacolato)diboron (40.9 g, 161 mmol), and potassium acetate (45.2 g, 460 mmol) were slurried in DMSO (395 mL, 0.4 M) and then sparged with argon for 10 minutes. The reaction mixture was then treated with Pd(dppf)Cl$_2$.DCM (1.25 g, 1.54 mmol) and sparged with argon for an additional 10 minutes. The reaction mixture was heated to 70° C. for 16 h under a backflow of N2 and then cooled to room temperature. The mixture was then diluted with ethyl acetate (2 L) and water (2 L). The biphasic mixture was stirred for 1 h and then the solids were removed by filtration and the cake was washed with ethyl acetate (250 mL). The layers were separated and the aqueous layer was extracted with ethyl acetate (1 L). The combined organic layers were washed with water (1 L×2) and then brine (1×250 mL). The organic layer was dried with Na$_2$SO$_4$ and filtered. The filtrate was treated with 15 g of Si-Thiol resin and stirred for 16 h. The solids were removed by filtration and the cake was washed with ethyl acetate. The organic layers were concentrated under vacuum to give 22a (54.1 g, 85.8 wt %). Compound 22a was used directly in the next step.

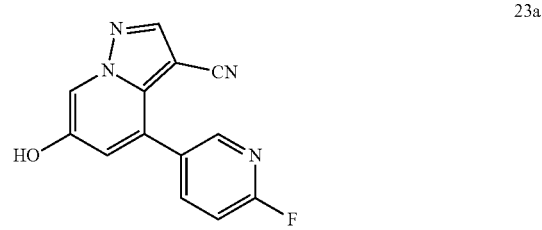 [SMILES: N#Cc1cnn2cc(O)cc(-c3ccc(F)nc3)c12]

4-(6-fluoropyridin-3-yl)-6-hydroxypyrazolo[1,5-a]pyridine-3-carbonitrile (23a)

4-(6-fluoropyridin-3-yl)-6-(4,4,5,5-tetramethyl-1,3,2-dioxaborolan-2-yl)pyrazolo[1,5-a]pyridine-3-carbonitrile (22a) (54.1 g, 127.5 mmol) was dissolved in THF (750 mL, 0.2 M) and cooled to ~3° C. under a backflow of N2. The reaction mixture was then treated with sodium hydroxide (319 mL, 637 mmol) and allowed to cool back to ~3° C. The mixture was treated dropwise with chilled (~2° C.) 35% hydrogen peroxide (89 mL, 1.02 mol) at a rate of ~1 drop every 2 seconds. The mixture was stirred for 4 h after complete addition of peroxide. To drive the reaction to completion an additional 1.0 equiv. of H$_2$O$_2$ was added and the mixture stirred at ~3° C. for an additional 1 h. The reaction mixture was then treated dropwise at a rate of ~2 drops per second with sodium thiosulfate (382 mL, 1.1 mol) at 3° C. and then allowed to slowly warm to room temp and stir for 16 h. The mixture was diluted with MTBE (1.5 L) and water (500 mL) and stirred at room temperature for 30 minutes. The layers were separated and the organic layer was washed with 0.1 M NaOH (200 mL). The combined aqueous layers were extracted with MTBE (500 mL). The aqueous layer was then acidified to pH~5 using solid citric acid and then diluted with water (1 L) and allowed to stir for 1 h. The solids were filtered, rinsed with additional water (~200 mL), and dried under vacuum for ~60 h to give 23a (25.6 g, 81%).

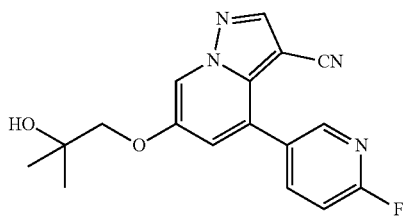

4-(6-fluoropyridin-3-yl)-6-(2-hydroxy-2-methyl-propoxy)pyrazolo[1,5-a]pyridine-3-carbonitrile (13a)

4-(6-fluoropyridin-3-yl)-6-hydroxypyrazolo[1,5-a]pyridine-3-carbonitrile (23a) (2.46 g, 9.68 mmol) was dissolved in DMF (48 mL, 0.2 M) and cooled to 0° C. The mixture was then treated with sodium hydroxide (4.98 ml, 9.97 mmol) and stirred at 0° C. for 15 minutes and then treated with isobutylene oxide (8.50 ml, 96.8 mmol), sealed, and heated to 80° C. for 48 h. The mixture was cooled to room temperature, diluted with water (500 mL) and acidified to pH~5 using solid citric acid and stirred for 30 minutes. The mixture was extracted with ethyl acetate (500 mL×2). The combined organic layers were washed with water (250 mL×2), brine (100 mL) and dried over $Na_2SO_4$, filtered, and concentrated. The concentrate was purified by silica gel chromatography (1 to 50% DCM/acetone) to give 13a (1.94 g, 61%).

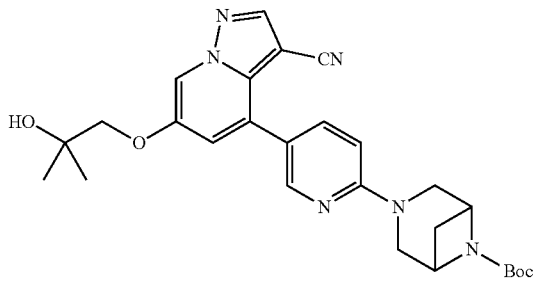

Tert-butyl-3-(5-(3-cyano-6-(2-hydroxy-2-methyl-propoxy)pyrazolo[1,5-a]pyridin-4-yl)pyridin-2-yl)-3,6-diazabicyclo[3.1.1]heptane-6-carboxylate (15a)

A reactor was charged with 4-(6-fluoropyridin-3-yl)-6-(2-hydroxy-2-methylpropoxy)pyrazolo[1,5-a]pyridine-3-carbonitrile (13a) (50 g, 153 mmol), tert-butyl 3,6-diazabicyclo[3.1.1]heptane-6-carboxylate (14a) (42.5 g, 215 mmol), DMSO (200 mL), and KOAc (30.1 g, 306 mmol). The reaction was heated to 75° C. with agitation for 24 h. The batch was cooled to ~15° C., and water (50 mL) was added at a rate to keep the internal temperature<35° C. and the mixture was stirred for 30 min. The suspension was filtered and the cake was washed with 30% DMSO/water (200 mL) and then water (200 mL). Acetone (200 mL) was charged to the cake and after 2 h the solid was transferred to a vacuum oven and dried at 45° C. to give 15a (66.2 g, 87%).

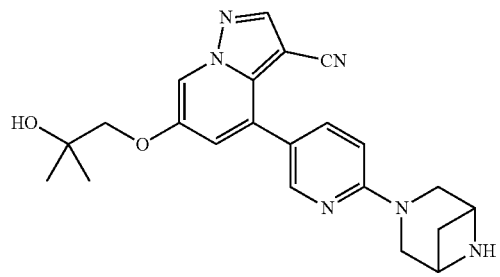

4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile (16)

To a reactor was charged tert-butyl-3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (15a) (80 g, 159 mmol) and 5% IPA/water (320 mL). The reaction was heated to 45° C. To the reaction was charged $H_2SO_4$ (35 mL, 634 mol) at a rate to keep the internal temperature below 60° C. The reaction mixture was aged at 45° C. for 2 h and then cooled to <30° C. Isopropyl alcohol (IPA, 720 mL) was slowly added over 5 minutes and the reaction stirred for not less than 1 h. The suspension was filtered and the cake was rinsed with IPA (160 mL), then 1:1 IPA/MTBE (160 mL) and then MTBE (160 mL×2). The cake was dried in a vacuum oven at 45° C. to give 16 as an off-white solid (70.4 g, 92 wt %, 74% adjusted yield).

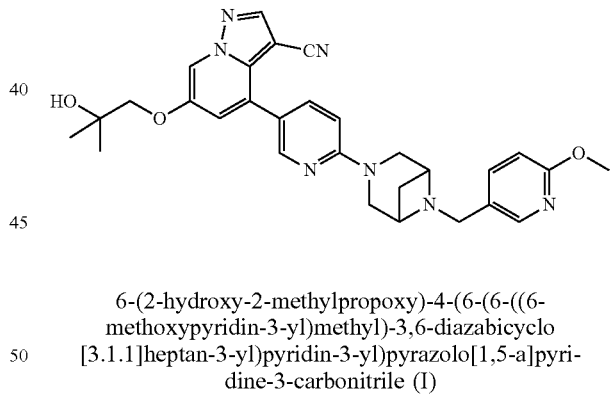

6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (I)

To a reactor was charged 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile (16) (15 g, 25 mmol), 6-methoxynicotinaldehyde (5.14 g, 25.0 mmol), DCM (150 mL), and TEA (12.2 mL, 87.4 mmol). To the reaction mixture was charged (in two portions) sodium triacetoxy borohydride (STAB) (10.6 g, 50.0 mmol). The reaction was stirred at room temperature overnight. To the reaction was charged an additional portion of STAB (2.65 g, 12.5 mmol). The reaction was stirred for an additional 2 h at ambient temperature and was judged complete by HPLC analysis. The reaction mixture was diluted with water (150 mL) and DCM (225 mL) and the layers were separated. The organic layer was washed with 1:1 water/sat. $NaHCO_3$ (2×150 mL) and 1:1 water/brine (150 mL). The organic layer was concentrated under vacuum to ~300 mL and then heated to ~32° C. to produce a homogenous solution. n-Heptanes (105 mL) was slowly added and the suspension was allowed to cool to 25° C. An additional charge of n-heptanes (195 mL) was made and the suspension was stirred at room temperature for 3 h. The solids were collected by filtration and the cake was rinsed with n-heptanes (30 mL×2) and MTBE (30 mL×2). The cake was dried in a vacuum oven at 45° C. to give the compound of Formula (I) as an off-white solid (10.5 g).

The compound of Formula (I) was recrystallized as follows. To a reaction flask was charged (I) (10.1 g) and DMSO (110 mL). The mixture was heated to 50° C. until all of the solid was in solution. The mixture was cooled to 25° C. and polish filtered. DMSO (10 mL) was charged through the filter as a wash. The resulting solution was heated to 45° C. and water (5 mL) was slowly added. The mixture was stirred for 30 minutes and a seed bed formed. Water (25 mL) was added over 1 h and the slurry was aged at 45° C. for an additional 1 h. The slurry was then allowed to cool to 25° C. and stir for 2 h. The slurry was filtered and the cake was washed with water (20 mL×3), MeOH (20 mL×2) and MTBE (20 mL×2). The cake was dried at room temperature in a vacuum oven to give 9.35 g (74%) of the compound of Formula (I). MS (apci) m/z=526.2 (M+H). $^1$H NMR (400 MHz, DMSO-$d_6$) δ: 8.64 (d, 1H, J=2.3 Hz), 8.55 (s, 1H), 8.38 (d, 1H, J=2.3 Hz), 8.04 (d, 1H, J=2.3 Hz), 7.80 (dd, 1H, J=8.6, 2.3 Hz), 7.64 (dd, 1H, J=8.6, 2.3 Hz), 7.27 (d, 1H, J=2.0 Hz), 6.76 (d, 1H, J=8.6 Hz), 6.73 (d, 1H, J=8.2 Hz), 4.67 (s, 1H), 3.85 (s, 2H), 3.79 (s, 3H), 3.72 (d, 2H, J=12.5 Hz), 3.64 (d, 2H, J=5.9 Hz), 3.51 (br d, 2H), 3.47 (s, 2H), 2.47 (m, 1H), 1.55 (d, 1H), 1.20 (s, 6H).

3. Preparation of the Compound of Formula (I) from Compound A

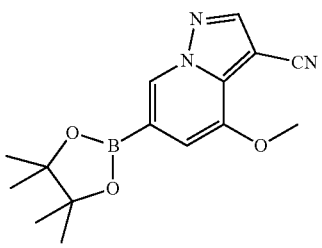

4-methoxy-6-(4,4,5,5-tetramethyl-1,3,2-dioxaborolan-2-yl)pyrazolo[1,5-a]pyridine-3-carbonitrile (32a)

To a reaction vessel was charged 6-bromo-4-methoxypyrazolo[1,5-a]pyridine-3-carbonitrile (A) (200 g, 793.4 mmol), KOAc (233.6 g, 2.38 mol), 4,4,4',4',5,5,5',5'-octamethyl-2,2'-bi(1,3,2-dioxaborolane) (261.9 g, 1.03 mol), and p-dioxane (3000 mL). The reaction was degassed for 20 minutes at ambient temperature. To the reaction was charged Pd(dppf)DCM (12.96 g, 15.87 mmol). The reaction was degassed for 20 minutes at ambient temperature and then heated to 75° C. overnight. The reaction was cooled to ambient temperature, charcoal (20 g) was charged and the suspension stirred at ambient temperature for ≥2 hours. The mixture was filtered over celite (200 g) and the cake was rinsed with EtOAc (7×400 mL). The mixture was added to a reactor and then washed with water (2000 mL). The aqueous layer was removed and the organic layer was washed with 3:1 water/brine (2000 mL) and then 1:1 water/brine (2000 mL). The first aqueous layer was back extracted with EtOAc (1000 mL). The combined organic layers were added to a flask and silicycle-thiol (240 g) and charcoal (100 g) were added. The suspension was heated to 50° C. and stirred overnight. The reaction was cooled to below 30° C. and was filtered over celite (250 g). The cake was rinsed with EtOAc (6×400 mL). The filtrate was distilled under vacuum with heating to a set volume and a thick slurry formed. n-Heptanes was slowly added over ~10 minutes (400 mL) to the slurry and the mixture was distilled back down to a set volume. An additional charge of n-heptanes (400 mL) was made and the distillation continued until a set volume was reached. The vacuum was removed and the heating discontinued. n-Heptanes (200 mL) and MTBE (50 mL) were added and the suspension was stirred overnight. After stirring overnight, it appeared that solvent was lost and n-heptanes (1250 mL) was slowly added. The suspension was aged at ambient temperature for ~10 minutes and was then filtered. The cake was rinsed with n-heptanes (2×200 mL) and dried at ambient temperature by pulling air through it to give 32a (168.2 g, 87 wt %, 62% corrected yield).

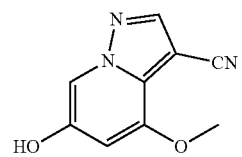

6-Hydroxy-4-methoxypyrazolo[1,5-a]pyridine-3-carbonitrile (33)

To a flask was charged 4-methoxy-6-(4,4,5,5-tetramethyl-1,3,2-dioxaborolan-2-yl)pyrazolo[1,5-a]pyridine-3-carbonitrile (32a) (100.0 g, 334.3 mmol), NMO (78.3 g, 668.6 mmol, 2 eq), and THF (1000 mL, 10 vol). The reaction was heated to 50° C. for 1 hour and then additional NMO (19.5 g, 167 mmol, 0.5 eq) was charged. After 1 hour, an additional charge of NMO (19.5 g, 167 mmol, 0.5 eq) was made and the reaction was heated to 45° C. overnight. After stirring overnight, the reaction was heated back to 50° C. and NMO (40 g, 334 mmol, 1 eq) was charged. After heating for 5 hours, the reaction was distilled to a total volume of 600 mL (internal temperature was held between 42° C. and 50° C. during distillation). The mixture was cooled to 40° C. and water (1800 mL total, 18 vol) was added. A suspension was produced and additional water (500 mL) was added. The thick slurry was aged at ambient temperature overnight and then the suspension was filtered. The cake was washed with water (250 mL) and n-heptanes (250 mL) and the solid dried under vacuum at 50° C. overnight to give 33 (49.6 g, 95.3 wt %, 85.9% corrected yield based on 87 wt % 32a).

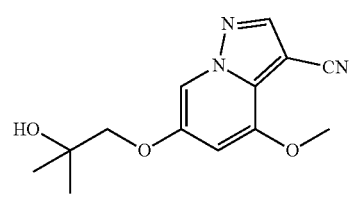

6-(2-Hydroxy-2-methylpropoxy)-4-methoxypyrazolo[1,5-a]pyridine-3-carbonitrile (34)

To a flask was charged 6-hydroxy-4-methoxypyrazolo[1,5-a]pyridine-3-carbonitrile (33) (10.00 g, 52.86 mmol) and THF (50.0 mL, 5 vol). NaOH (28 mL, 2M) was added in one portion and after stirring for ~5 minutes, 2,2-dimethyloxirane (23.5 mL, 264.3 mmol) was added, the reaction was heated to 60° C., and then stirred overnight. The reaction was cooled to room temperature, THF (10.0 mL) was added, and then water (200 mL) was slowly added. A suspension was produced and additional water (25 mL) was added. The solid was filtered, the cake was washed with water (3×20 mL), n-heptanes (20 mL), and dried under vacuum at 50° C. to give 34 (10.273 g, 96.2 wt %, 75.1% corrected yield based on 95 wt % 33).

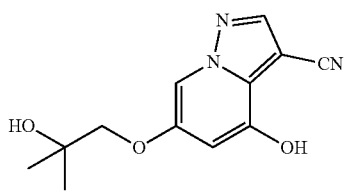

4-Hydroxy-6-(2-hydroxy-2-methylpropoxy)pyrazolo[1,5-a]pyridine-3-carbonitrile (35)

To flask was charged 6-(2-hydroxy-2-methylpropoxy)-4-methoxypyrazolo[1,5-a]pyridine-3-carbonitrile (34) (8.00 g, 30.62 mmol) and DMA (40 mL, 5 vol). NaOH (2.40 mL, 50 wt %) was added and the mixture heated to 30° C. Dodecane-1-thiol (11.1 mL, 45.93 mmol) was added and the mixture was heated to 60° C. The reaction was called complete and the heating was discontinued. Water (24 mL, 3 vol) was added to the reaction (~60° C.) and the mixture was allowed to cool to room temperature. The reaction mixture was slowly added (temperature<20° C. during addition) to 15 wt % citric acid (160 mL), precooled to 10° C. The solids were filtered, the cake was washed with water (2×16 mL), n-heptanes (3×16 mL) and dried under vacuum at 50° C. overnight to give 35 (6.333 g, 93 wt %, 81% corrected yield based on 96 wt % 34).

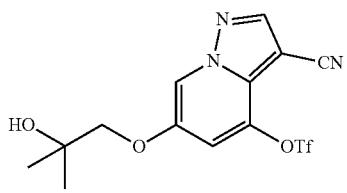

3-Cyano-6-(2-hydroxy-2-methylpropoxy)pyrazolo[1,5-a]pyridin-4-yl trifluoromethanesulfonate (36)

To a flask was charged 4-hydroxy-6-(2-hydroxy-2-methylpropoxy)pyrazolo[1,5-a]pyridine-3-carbonitrile (35) (3.31 g), 1,1,1-trifluoro-N-phenyl-N-((trifluoromethyl)sulfonyl)methanesulfonamide (4.79 g), and DMA (33 mL, 10 vol). DIEA (4.67 mL) was added and after 10 minutes the reaction judged complete. The reaction mixture was slowly (maintaining the temperature<20° C.) added to HOAc (0.92 mL, 1.2 eq) in water (33 mL) that was precooled to 15° C. (ice/water bath). The slurry was stirred for 15 minutes and the solids were filtered, the cake was washed with water (3×7 mL), n-heptanes (2×7 mL), and then dried under vacuum at 50° C. to give 36 (3.517 g, 99.4 wt %, 68.9% yield (uncorrected)).

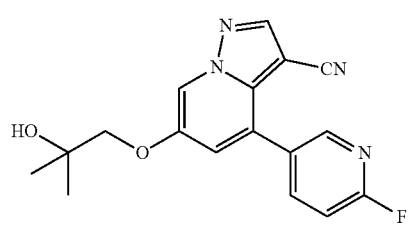

4-(6-fluoropyridin-3-yl)-6-(2-hydroxy-2-methylpropoxy)pyrazolo[1,5-a]pyridine-3-carbonitrile (13)

To a flask was charged 3-cyano-6-(2-hydroxy-2-methylpropoxy)pyrazolo[1,5-a]pyridin-4-yl trifluoromethanesulfonate (36) (3.00 g. 7.91 mmol), 2-fluoro-5-(4,4,5,5-tetramethyl-1,3,2-dioxaborolan-2-yl)pyridine (1.85 g, 8.30 mmol), and THF (60 mL, 20 vol). The solution was purged with nitrogen for 15 minutes and PdCl$_2$(dppf)DCM (452 mg, 0.553 mmol) was charged and the mixture was purged with nitrogen for an additional 5 minutes. To a separate flask was added KOAc (1.55 g, 15.82 mmol) and water (15 mL). This mixture was purged with nitrogen for 2 minutes and then added to the reaction mixture, which was purged with nitrogen for an additional 5 minutes. The reaction stirred overnight at ambient temperature. The reaction mixture was poured onto MTBE (60 mL) and water (45 mL). The layers were separated and the organic layer was washed with water (30 mL) followed by 3:1 water/brine (30 mL). The first and second aqueous layers were combined and back extracted with MTBE (30 mL). The organic layers were combined and concentrated to a solid. The solid was taken up in MTBE (30 mL) and after stirring for 2 hours at ambient temperature the suspension was filtered, the cake washed with n-heptanes (3×6 mL) and the solids dried under vacuum to give 13 (1.69 g, 65% yield). Compound 13 was converted to the compound of Formula I as described above.

Example 3: Synthesis of the Compound of Formula (I) Via Compound B

1. Preparation of Compound B

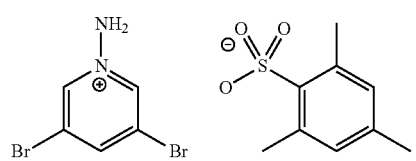

1-amino-3,5-dibromo-pyridin-1-ium 2,4,6-trimethylbenzenesulfonate (9)

To a solution of O-(mesitylsulfonyl)hydroxylamine in DCM (2 L) was added a solution of 3,5-dibromopyridine (320 g, 1.35 mol) in DCM (2.5 L) at 0-5° C. The reaction was stirred for 16 h at this temperature before ether (5 L) was added at 0-5° C. The suspension was then filtered and the cake was washed with Et₂O (4 L) to give compound 9 (500 g crude).

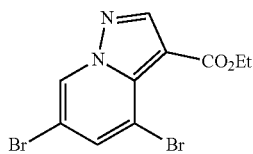

B 4,6-dibromopyrazolo[1,5-a]pyridine-3-carbonitrile (B)

To a mixture of compound 9 (40 g, 88.5 mmol) in p-dioxane (400 mL) was added acrylonitrile (10.72 g, 202 mmol) and DIPEA (14.8 g, 11.5 mmol). The mixture stirred at room temperature for 3 h, then DDQ (41.8 g, 184 mmol) was added and the mixture was stirred at room temperature for 3 additional hours. The reaction was monitored by TLC (eluent: ethyl acetate/petroleum ether, 1:2) and showed that compound 9 was consumed. The reaction mixture was poured into water (1.6 L) and the resulting solid was filtered. The solid was collected and then purified with column chromatography (silica-gel column eluting with ethyl acetate/petroleum ether (1:2)) to afford compound B (13.8 g, 56.5 mmol, 52.1%).

2. Preparation of the Compound of Formula (I) from Compound B

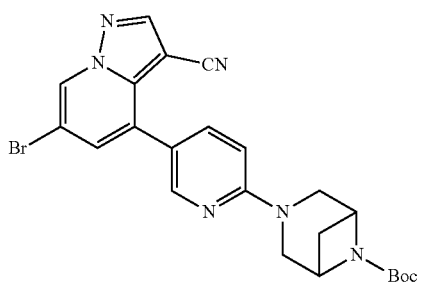

25a

Tert-butyl 3-(5-(6-bromo-3-cyanopyrazolo[1,5-a] pyridin-4-yl)pyridin-2-yl)-3,6-diazabicyclo[3.1.1] heptane-6-carboxylate (25a)

A solution of 4,6-dibromopyrazolo[1,5-a]pyridine-3-carbonitrile (B) (0.295 g, 0.980 mmol) and tert-butyl 3-(5-(4,4,5,5-tetramethyl-1,3,2-dioxaborolan-2-yl)pyridin-2-yl)-3,6-diazabicyclo[3.1.1]heptane-6-carboxylate (24a) (0.413 g, 1.03 mmol) in DMF (9.8 mL, 0.980 mmol) was heated to 50° C. to solubilize all of the solids. The mixture was then cooled to room temperature. Aqueous K₂CO₃ (0.980 mL, 1.96 mmol) was slowly added and the mixture was purged with Ar gas for 5 min. Pd(dppf)Cl₂.CH₂Cl₂ (60 mg, 0.0735 mmol) was then added and the reaction stirred at room temperature over 48 h. LCMS indicated that the reaction was complete. Ethyl acetate and water were added to the mixture. The layers were separated and the organic layer was washed with water and brine and dried with Na₂SO₄. The organic layer was concentrated under vacuum and then purified using column chromatography (hexanes/ethyl acetate, 10-90%) to give 25a (0.332 g, 0.670 mmol, 68.4% yield).

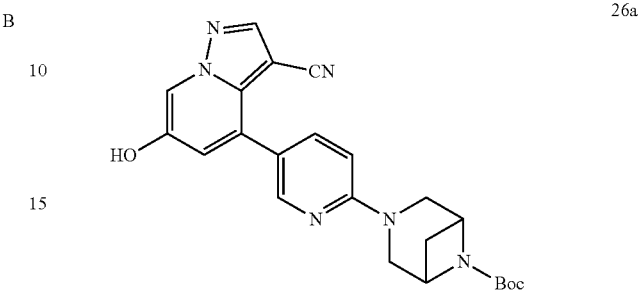

26a

Tert-butyl 3-(5-(3-cyano-6-hydroxypyrazolo[1,5-a] pyridin-4-yl)pyridin-2-yl)-3,6-diazabicyclo[3.1.1] heptane-6-carboxylate (26a)

Tert-butyl 3-(5-(6-bromo-3-cyanopyrazolo[1,5-a]pyridin-4-yl)pyridin-2-yl)-3,6-diazabicyclo[3.1.1]heptane-6-carboxylate (25a) (475 mg, 0.959 mmol) was dissolved in THF (10 mL, 0.1 M) and treated with bis(pinacolato)diboron (255 mg, 1.00 mmol), dichloro[1,1'-bis(diphenylphosphino) ferrocene]palladium (II).dichloromethane (39 mg, 0.0479 mmol), and potassium acetate (282 mg, 2.88 mmol). The reaction mixture was sparged with argon, sealed, and heated to 70° C. for 16 h. The reaction was judged complete and the mixture was then cooled to 0° C. and treated with sodium hydroxide (4.8 mL, 4.79 mmol) then portion-wise treatment with hydrogen peroxide (0.49 mL×15, 7.35 mL) every 15 minutes. After complete addition of hydrogen peroxide the reaction mixture was allowed to slowly warm to room temperature and stir for 16 h. The reaction mixture was diluted with water and extracted with 4:1 DCM:IPA (2×). The aqueous layer was then acidified to pH~5 using AcOH and extracted with 4:1 DCM:IPA (2×). The combined organic layers were washed with water, dried over Na₂SO₄, filtered, and concentrated. The concentrate was purified by silica gel chromatography (5 to 75% DCM/acetone) to give 26a (314 mg, 75.7%).

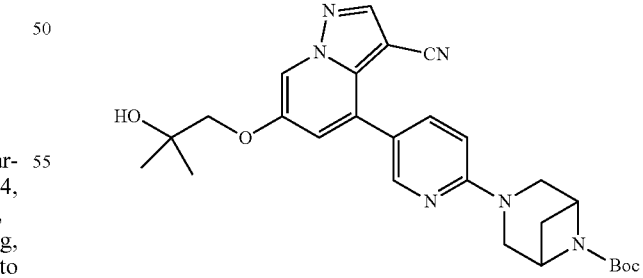

15a

Tert-butyl-3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (15a)

Tert-butyl-3-(5-(3-cyano-6-hydroxypyrazolo[1,5-a]pyridin-4-yl)pyridin-2-yl)-3,6-diazabicyclo[3.1.1]heptane-6- carboxylate (26a) (312 mg, 0.721 mmol) was dissolved in DMF (4.8 mL, 0.15 M) and treated with sodium hydroxide (794 μL, 0.794 mmol). The reaction mixture was stirred for 10 minutes then treated with isobutylene oxide (634 μL, 7.21 mmol), sealed, and heated to 80° C. for 16 h. The reaction mixture was cooled to room temperature, diluted with water (100 mL) and stirred for 30 minutes. The solid was filtered and rinsed with water to give 15a (304 mg, 84%) as a light tan solid. Compound 15a was converted to the compound of Formula (I) as described above in Example 3 (from compound A).

Example 4: Synthesis of the Compound of Formula (I) Via Compound C

1. Preparation of Compound C

Compound C can be prepared according to the method described in U.S. Provisional Appl. No. 62/406,252. Briefly:

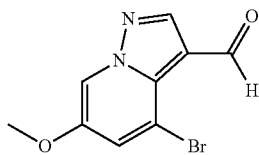

4-bromo-6-methoxypyrazolo[1,5-a]pyridine-3-carbaldehyde (6C)

A solution of 4-bromo-6-methoxypyrazolo[1,5-a]pyridine (5C) (5.0 g, 22 mmol) in DMF (220 mL) was cooled to 0° C. and then slowly treated with POCl$_3$ (6.2 mL, 66 mmol). The reaction was warmed to ambient temperature and stirred overnight. The reaction mixture was cooled to 0° C., quenched with water (220 mL), and basified with 6 M NaOH$_{(aq)}$ to pH 9-10. The reaction mixture was stirred for 1 h and then vacuum filtered. The solids were rinsed sequentially with water (3×50 mL) and MTBE (3×50 mL). The collected solid was suspended in DCM (500 mL) and stirred in a sonicating bath for 30 min and then vacuum filtered. The filtrate was retained, while the filter cake was taken up in water (300 mL) and extracted with DCM. The organic extracts, along with the retained DCM filtrate, were combined and dried over anhydrous Na$_2$SO$_4$, then filtered and concentrated in vacuo to provide the title compound (4.84 g, 86% yield). MS (apci), m/z=256.9 (M+H).

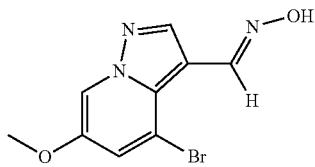

4-bromo-6-methoxypyrazolo[1,5-a]pyridine-3-carbaldehyde Oxime (7C)

To a suspension of 4-bromo-6-methoxypyrazolo[1,5-a]pyridine-3-carbaldehyde (6C) (4.84 g, 19.0 mmol) in EtOH (253 mL) at ambient temperature was added water (127 mL) and hydroxylamine hydrochloride (1.98 g, 28.5 mmol). After stirring at 50° C. overnight, the reaction mixture was cooled to ambient temperature and concentrated in vacuo. The residue was suspended in water (150 mL) and then quenched slowly with saturated NaHCO$_{3(aq)}$ (30 mL). After stirring for 1 hour at ambient temperature the suspension was vacuum filtered and the filter cake rinsed sequentially with H$_2$O (500 mL) and MTBE (100 mL) to yield the title compound as a 2:1 E/Z mixture (5.13 g, quantitative yield), which was used in the next step without further purification. MS (apci) m/z=271.9 (M+H).

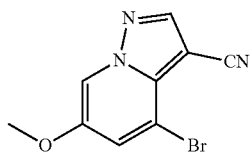

4-bromo-6-methoxypyrazolo[1,5-a]pyridine-3-carbonitrile (C)

The E/Z mixture of 4-bromo-6-methoxypyrazolo[1,5-a]pyridine-3-carbaldehyde oxime (7C) (4.95 g, 18.33 mmol) in acetic anhydride (172.9 mL, 1833 mmol) was stirred at 140° C. for 25 h, and then cooled to ambient temperature. The resulting suspension was further cooled in an ice bath for 15 min and then vacuum filtered and rinsed sequentially with water (200 mL) and MTBE (300 mL) to provide the title compound (3.74 g, 81% yield). $^1$H NMR (d$_6$-DMSO): δ 8.70 (s, 1H), 8.60 (s, 1H), 7.78 (s, 1H), 3.83 (s, 3H).

2. Preparation of the Compound of Formula (I) from Compound C

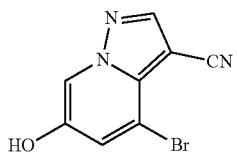

4-Bromo-6-hydroxypyrazolo[1,5-a]pyridine-3-carbonitrile (10)

A slurry of 4-bromo-6-methoxypyrazolo[1,5-a]pyridine-3-carbonitrile (C) (50.0 g, 198.4 mmol) in DCE (500 mL) was treated with AlCl$_3$ (79.34 g, 595.1 mmol). Under an N$_{2(g)}$ atmosphere, the resulting mixture was stirred for 19 h at 76° C. before cooling to room temperature. Using THF (1750 mL) as a rinse solvent, the reaction mixture was poured into a mechanically stirred suspension of sodium sulfate decahydrate (10 eq, 639 g) in THF (1000 mL). After stirring overnight at ambient temperature, the resulting suspension was filtered, and the solids were rinsed with additional THF (2×250 mL). The filtrate was concentrated in vacuo, and the resulting solid was dried under high vacuum for 3 days to afford the title compound (46.18 g, 98% yield) in sufficient purity for subsequent use. $^1$H NMR (d$^6$-DMSO): δ 10.48 (s, 1H), 8.58 (s, 1H), 8.38 (d, 1H), 7.64 (3, 1H).

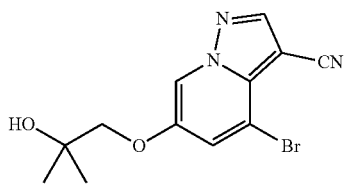

4-Bromo-6-(2-hydroxy-2-methylpropoxy)pyrazolo[1,5-a]pyridine-3-carbonitrile (11)

In a pressure vessel, a mixture of 4-bromo-6-hydroxypyrazolo[1,5-a]pyridine-3-carbonitrile (10) (10.0 g, 42.0 mmol) and $K_2CO_{3(s)}$ (17.4 g, 126 mmol) in DMF (50 mL) was treated with 2,2-dimethyloxirane (36.9 mL, 420 mmol). After sealing the vessel, the reaction mixture was stirred for 12 h at 60° C., then for 12 h at 85° C. The mixture was allowed to cool to ambient temperature. The room temperature mixture was poured into water (400 mL), then stirred for 1 hour at ambient temperature. The resultant suspension was vacuum filtered and the filter cake was rinsed with water. The solids were collected and dried in vacuo to cleanly provide the title compound (11 g, 84% yield).

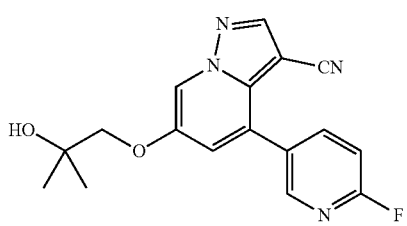

4-(6-fluoropyridin-3-yl)-6-(2-hydroxy-2-methylpropoxy)pyrazolo[1,5-a]pyridine-3-carbonitrile (13a)

A mixture of 4-bromo-6-(2-hydroxy-2-methylpropoxy)pyrazolo[1,5-a]pyridine-3-carbonitrile (11) (10.0 g, 32.2 mmol), 2-fluoro-5-(4,4,5,5-tetramethyl-1,3,2-dioxaborolan-2-yl)pyridine (10.8 g, 48.4 mmol) and Pd(PPh$_3$)$_4$ (1.12 g, 0.967 mmol) in dioxane (200 mL) was treated with 2 M Na$_2$CO$_{3(aq)}$ (64.5 mL, 129 mmol). The resulting mixture was sparged with Ar$_{(g)}$, then stirred for 12 h at 85° C. under an atmosphere of N$_{2(g)}$. After cooling to ambient temperature, the resultant mixture was poured into cold water (1.5 L). The pH of the mixture was adjusted to about pH 6 with the addition of 10% citric acid. After stirring for 1 hour at ambient temperature, the resultant suspension was vacuum filtered. The solids were collected and dried in vacuo to cleanly provide the title compound (10 g, 95% yield).

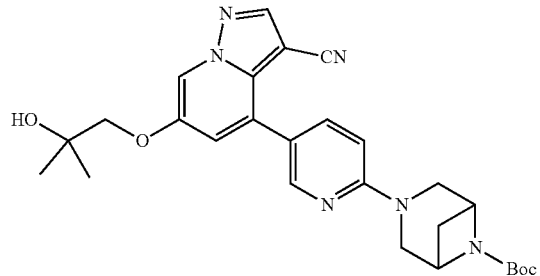

Tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (15a)

A mixture of 4-(6-fluoropyridin-3-yl)-6-(2-hydroxy-2-methylpropoxy)pyrazolo[1,5-a]pyridine-3-carbonitrile (13a) (1.70 g, 8.55 mmol), 3,6-diaza-bicyclo[3.1.1]heptane-6-carboxylic acid tert-butyl ester (1.70 g, 8.55 mmol) and K$_2$CO$_{3(s)}$ (7.88 g, 57.0 mmol) in DMSO (7 mL) was stirred for 12 h at 90° C. The resultant thick slurry was diluted with additional DMSO (2 mL) and stirred for 12 h at 90° C. The mixture was cooled to ambient temperature and diluted with water (100 mL). The aqueous mixture was washed with DCM. The combined organic extracts were dried over anhydrous MgSO$_{4(s)}$, filtered and concentrated in vacuo. The crude residue was purified by silica chromatography (30-80% EtOAc/hexanes as the gradient eluent system) to cleanly provide the title compound (2.87 g, 100% yield). MS (apci) m/z=505.2 (M+H).

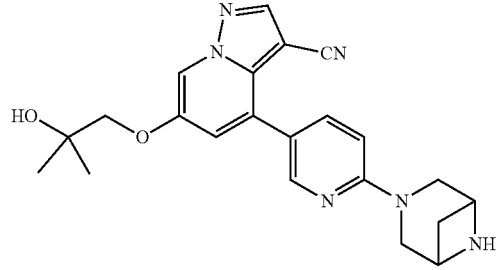

4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile Dihydrochloride (16)

A solution of tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (15a) (3.05 g, 6.04 mmol) in DCM (20 mL) was treated with 4 N HCl in dioxanes (15.1 mL, 60.4 mmol). The resulting mixture was stirred for 12 h at ambient temperature, and then concentrated in vacuo. The crude residue was diluted with DCM and toluene, and then sonicated before concentrating in vacuo to afford the title compound as the dihydrochloride salt (2.44 g, quantitative yield). MS (apci) m/z=405.2 (M+H).

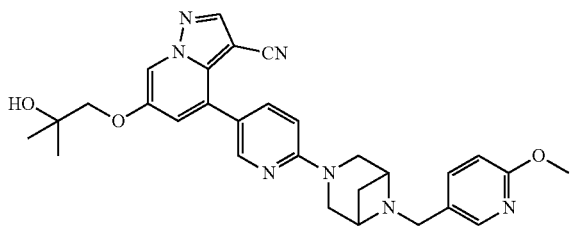

6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (I)

A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (16) (12.2 mg, 0.0277 mmol) in DCE (513 µL) was treated sequentially with 6-methoxynicotinaldehyde (7.59 mg, 0.0553 mmol) and NaBH(AcO)$_3$ (17.6 mg, 0.0830 mmol), then stirred overnight at ambient temperature. The mixture was concentrated in vacuo, and the residue was purified by silica chromatography (0-20% MeOH in DCM as the gradient eluent) to cleanly provide the title compound (13.59 mg, 93% yield). MS (apci) m/z=526.2 (M+H). $^1$H NMR (400 MHz, DMSO-d$_6$) δ: 8.64 (d, 1H, J=2.3 Hz), 8.55 (s, 1H), 8.38 (d, 1H, J=2.3 Hz), 8.04 (d, 1H, J=2.3 Hz), 7.80 (dd, 1H, J=8.6, 2.3 Hz), 7.64 (dd, 1H, J=8.6, 2.3 Hz), 7.27 (d, 1H, J=2.0 Hz), 6.76 (d, 1H, J=8.6 Hz), 6.73 (d, 1H, J=8.2 Hz), 4.67 (s, 1H), 3.85 (s, 2H), 3.79 (s, 3H), 3.72 (d, 2H, J=12.5 Hz), 3.64 (d, 2H, J=5.9 Hz), 3.51 (br d, 2H), 3.47 (s, 2H), 2.47 (m, 1H), 1.55 (d, 1H), 1.20 (s, 6H).

Example 5: Polymorph Salt Screens

A. Instrumentation and Methods of Analysis

The instruments and methods of analysis used in the polymorph screens described in the examples below are as follows.

X-Ray Powder Diffraction (XRPD)

XRPD analysis was carried out on a Panalytical X'pert pro, scanning the samples between 3 and 35° 2θ. The material was gently ground and loaded onto a multi-well plate with Kapton or mylar polymer film to support the sample. The multi-well plate was then loaded into a Panalytical diffractometer running in transmission mode and analyzed, using the following experimental conditions.

Raw Data Origin: XRD measurement (*.XRDML)
Scan Axis: Gonio
Start Position [°2θ]: 3.0066
End Position [°2θ]: 34.9866
Step Size [°2θ]: 0.0130
Scan Step Time [s]: 18.8700
Scan Type: Continuous
PSD Mode: Scanning
PSD Length [°2θ]: 3.35
Offset [°2θ]: 0.0000
Divergence Slit Type: Fixed
Divergence Slit Size [°]: 1.0000
Measurement Temperature [°C.]: 25.00
Anode Material: Cu
K-Alpha1 [Å]: 1.54060
K-Alpha2 [Å]: 1.54443
K-Beta [Å]: 1.39225
K-A2/K-A1 Ratio: 0.50000
Generator Settings: 40 mA, 40 kV
Goniometer Radius [mm]: 240.00
Dist. Focus-Diverg. Slit [mm]: 91.00
Incident Beam Monochromator: No
Spinning: No Polarized Light Microscopy (PLM)

The presence of crystallinity (birefringence) was determined using an Olympus BX50 polarizing microscope, equipped with a Motic camera and image capture software (Motic Images Plus 2.0). All images were recorded using the 20× objective, unless otherwise stated.

Thermogravimetric Analysis (TGA)

Approximately 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm$^3$/min.

Differential Scanning Calorimetry (DSC)

Approximately 5 mg of material was weighed into an aluminum DSC pan and sealed nonhermetically with a pierced aluminum lid. The sample pan was then loaded into a Seiko DSC6200 (equipped with a cooler), cooled, and held at 20° C. Once a stable heat-flow response was obtained, the sample and reference were heated at scan rate of 10° C./min and the resulting heat flow response monitored.

Nuclear Magnetic Resonance (NMR)

NMR experiments were performed on a Bruker AVIIIHD spectrometer equipped with a DCH cryoprobe operating at 500.12 MHz for protons. Experiments were performed in deuterated solvents and each sample was prepared to approximately 10 mM concentration.

Dynamic Vapor Sorption (DVS)

Approximately 10 mg of sample was placed into a mesh vapor sorption balance pan and loaded into a DVS-1 dynamic vapor sorption balance by Surface Measurement Systems. The sample was subjected to a ramping profile from 40-90% relative humidity (RH) at 10% increments, maintaining the sample at each step until a stable weight had been achieved (99.5% step completion). After completion of the sorption cycle, the sample was dried using the same procedure to 0% RH and then a second sorption cycle back to 40% RH. The weight change during the sorption/desorption cycles were plotted, allowing for the hygroscopic nature of the sample to be determined. XRPD analysis was then carried out on any solid retained.

Gravimetric Vapor Sorption (GVS)

Approximately 10-20 mg of sample was placed into a mesh vapor sorption balance pan and loaded into an IGAS-orp Moisture Sorption Analyzer balance by Hiden Analytical. The sample was subjected to a ramping profile from 40-90% RH at 10% increments, maintaining the sample at each step until a stable weight had been achieved (98% step completion). After completion of the sorption cycle, the sample was dried using the same procedure to 0% RH, and finally taken back to the starting point of 40% RH. The weight change during the sorption/desorption cycles were plotted, allowing for the hygroscopic nature of the sample to be determined.

High Performance Liquid Chromatography-Ultraviolet Detection (HPLC-UV)
　Instrument: HPLC with UV detector.
　Column: ACE Excel 3 Super C18 75 mm×4.6 mm column
　Column Temperature: 40° C.
　Autosampler Temperature: 25° C.
　UV wavelength: 235 nm
　Injection Volume: 5.0 QL
　Flow Rate: 1.0 mL/min
　Mobile Phase A: 0.1% TFA in water
　Mobile Phase B: 0.1% TFA in acetonitrile
　Gradient program:

| Time (minutes) | Solvent B (%) |
|---|---|
| 0.00 | 10 |
| 15.00 | 90 |
| 15.10 | 10 |
| 20.00 | 10 |

Charged Aerosol Detection (CAD)
　Instrument: HPLC with charged aerosol detection
　Column: Thermo Acclaim P2 50×2.1 mm 3.0 QL
　Temperature: 30° C.
　Autosampler Temperature: Ambient
　Injection Volume: 10 QL
　Flow Rate: 0.5 mL/min
　Mobile Phase A: Deionized water
　Mobile Phase B: 100 mM, pH3.65 ammonium formate buffer
　Gradient program:

| Time (minutes) | Solvent B (%) |
|---|---|
| 0.00 | 35 |
| 2 | 35 |
| 12 | 65 |
| 15.3 | 65 |
| 18.6 | 40 |
| 19.3 | 35 |
| 23 | 35 |

B. Initial Characterization

Figure 44A:
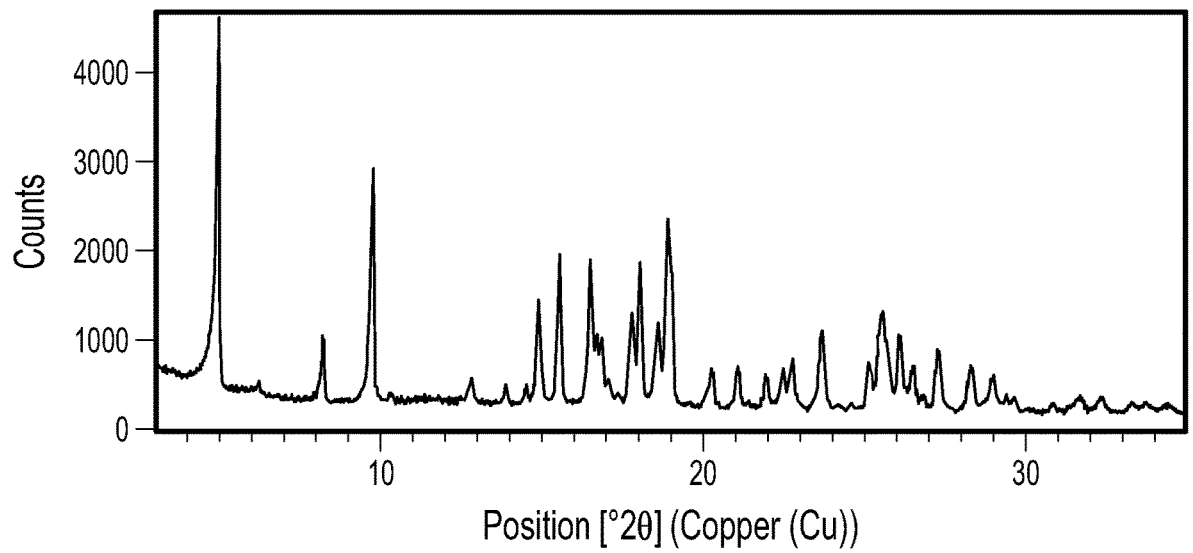
FIGS. 44A-44F are scans of the compound of Formula (I).
Figure 44B:
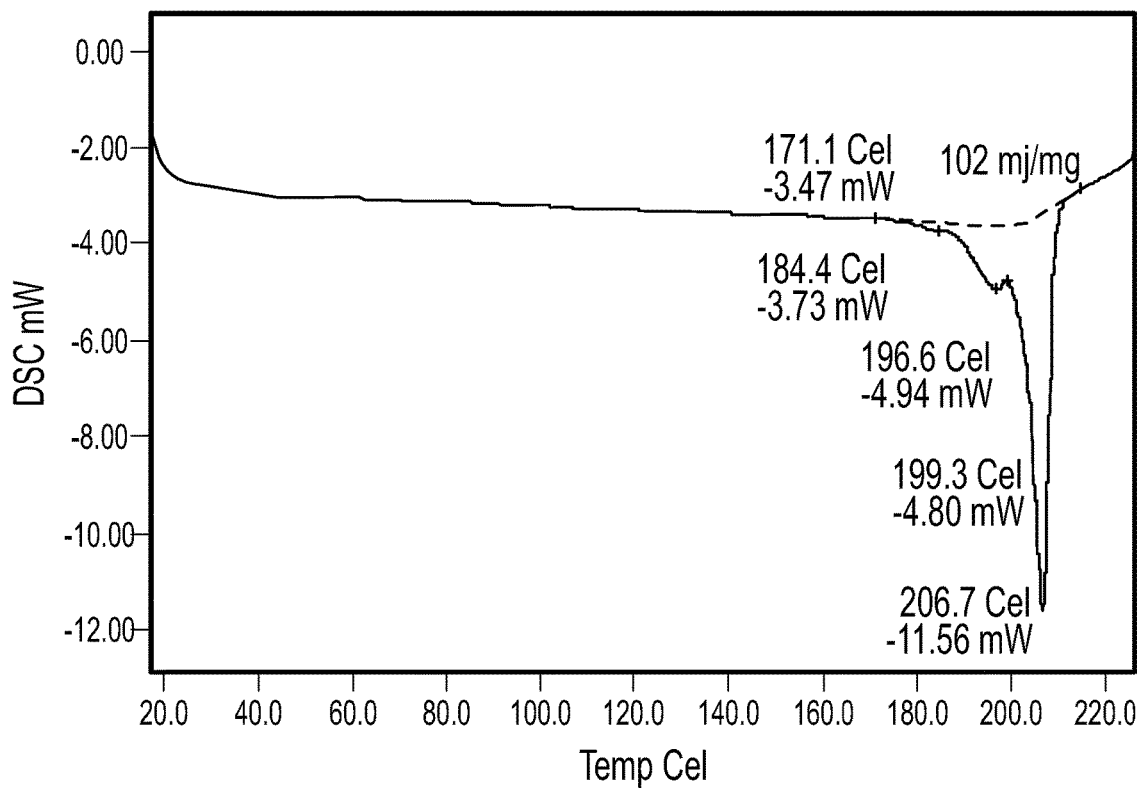
Figure 44C:
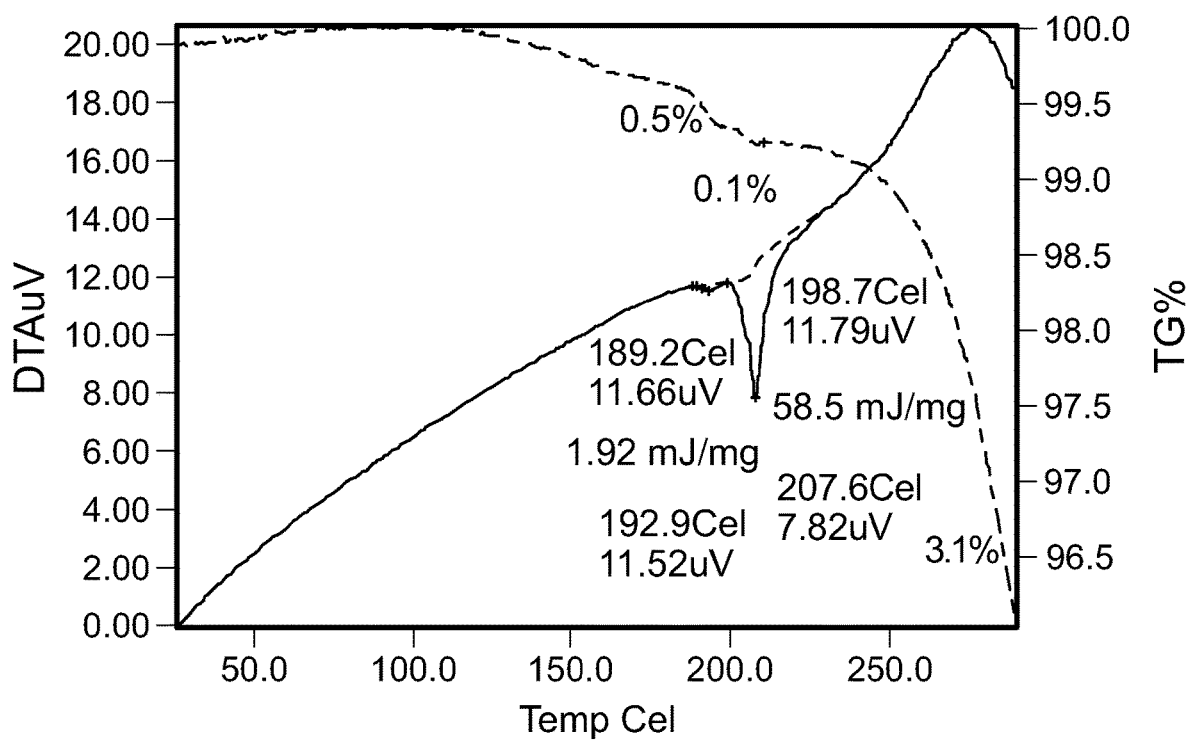
Figure 44D:
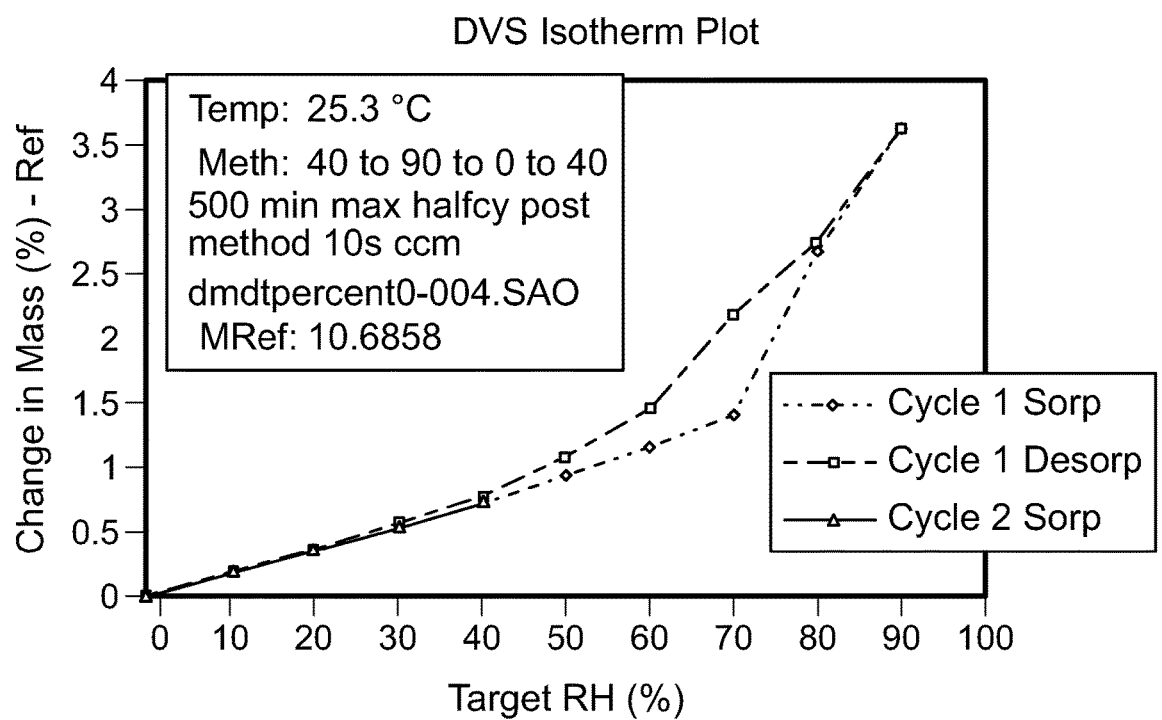
Figure 44E:
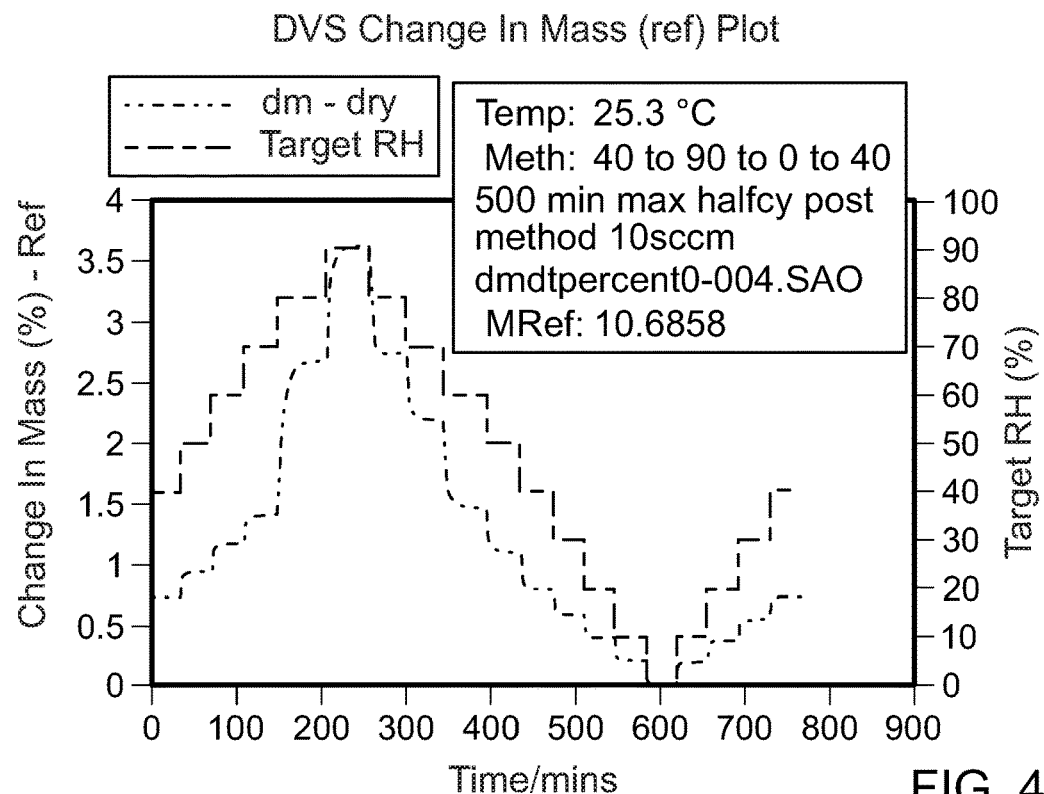
Figure 44F:
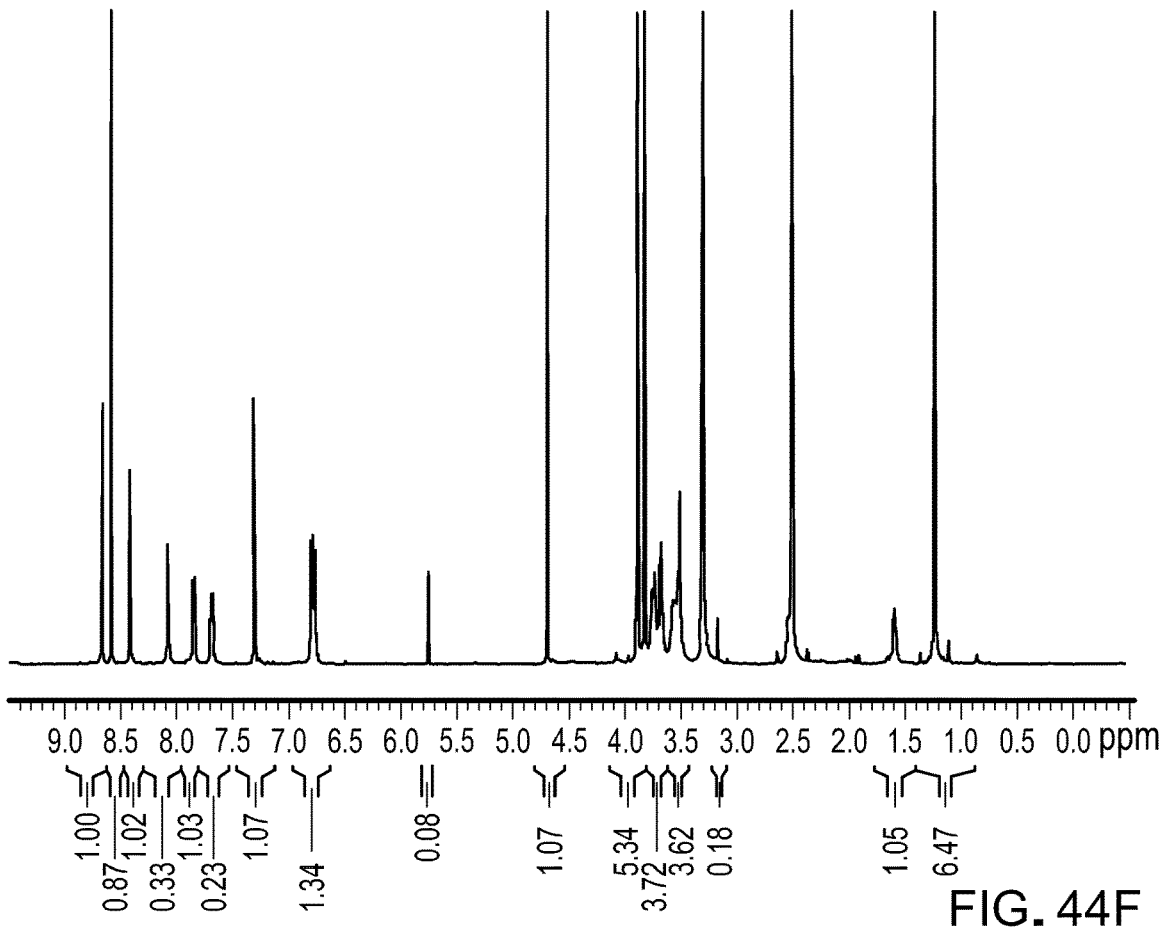

The compound of Formula (I), prepared as described in Example 1, above, was analyzed by XRPD, TG/DTA, DSC, DVS, PLM, $^1$H NMR, and HPLC and identified as Form 1. The material appeared highly crystalline by XRPD (FIG. 44A). PLM analysis showed agglomerates of small, needle-like crystals. A small endotherm with an onset of around 189° C. was observed by TG/DTA (FIG. 44C) followed by a sharp endotherm from an onset of around 199° C., relating to a melting transition. This event was followed by thermal degradation. The initial endotherm was potentially a solid-solid transition followed by melting of the more stable solid Form. A small endotherm was observed in the DSC data from an onset of around 184° C. followed by a sharp endotherm observed from an onset of around 199° C. (FIG. 44B). The material appeared moderately hygroscopic by DVS (FIGS. 44D and 44E) with a weight increase of around 3.6% at 90% RH. No change in Form was observed post-DVS. The material was 99.2% pure by HPLC. $^1$H NMR in $d_6$-DMSO showed trace DCM (0.04 eq.) and MeOH (0.06 eq.) were present in the material (FIG. 44F).

C. Primary Salt Screen

A primary salt screen was conducted on the compound of Formula (I) using the acid counterions and solvent systems shown in Tables 5 and 6, below.

TABLE 5

| Acids screened | | |
|---|---|---|
| Hydrochloric acid | Sulfuric Acid | 1,2-Ethanedisulfonic acid |
| Methanesulfonic acid | Naphthalene-2-sulfonic acid | Benzenesulfonic acid |
| 2-Hydroxyethanesulfonic acid | L-Aspartic acid | Maleic acid |
| Ethanesulfonic acid | L-Glutamic acid | L-Tartaric acid |
| Citric Acid | D-Glucuronic acid | L-Malic Acid |
| D-Gluconic acid | L-Lactic Acid | L-Ascorbic acid |
| Succinic Acid | Oxalic acid | Phosphoric acid |
| p-Toluenesulfonic acid | Fumaric Acid | Hippuric acid |
| Benzoic Acid | | |

TABLE 6

| Solvent systems |
|---|
| Solvent system |
| THF/water (1%) |
| 1,4 Dioxane/water (10%) |
| MeCN/water (20%) |
| Acetone/water (10%) |
| IPA/water (10%) |
| EtOH/water (10%) |

The salt screen was performed as follows. A stock aqueous solution of acid was added to approximately 30 mg of the compound of Formula (I) in each of the solvent systems listed in Table 6 above. In cases where stock solutions could not be attained, the acid was added neat to the solution of the compound of Formula (I). Acid weights and volumes used in the preparation of the stock solutions are shown in Table 7 below.

TABLE 7

| Primary salt screen counterion stock solutions | | | | | |
|---|---|---|---|---|---|
| | Acid Stock Solution | | Known | Acid Stock | |
| Acid | Amount of Acid | Volume of Solvent (mL) | Suitable Stock Solvent | Addition Amount Per Vial/Well | Other |
| Hydrochloric acid | 83.5 μL | 1 | Water | 57.1 μL | |
| Sulfuric acid | 56.1 μL | 1 | Water | 57.1 μL | |
| 1,2-Ethanedisulfonic acid | 234.2 mg | 1 | EtOH | 57.1 μL | Add 1 eqv. HCl |
| p-Toluenesulfonic acid | 190.2 mg | 1 | Water | 57.1 μL | |
| Methanesulfonic acid | 64.9 μL | 1 | Water | 57.1 μL | |
| Naphthalene-2-sulfonic acid | 255.8 mg | 1 | EtOH | 57.1 μL | Add 1 eqv. HCl |

TABLE 7-continued

Primary salt screen counterion stock solutions

| Acid | Acid Stock Solution Amount of Acid | Volume of Solvent (mL) | Known Suitable Stock Solvent | Acid Stock Addition Amount Per Vial/Well | Other |
|---|---|---|---|---|---|
| Benzenesulfonic acid | 168.3 mg | 1 | Water | 57.1 μL | |
| Oxalic acid | 90.0 mg | 1 | Water | 57.1 μL | |
| 2-Hydroxyethanesulfonic acid | 148.1 mg | 1 | Water | 57.1 μL | Add 1 eqv. HCl |
| L-Aspartic acid | N/A | N/A | N/A | 7.7 mg | Added neat |
| Maleic acid | 116.1 mg | 1 | Water | 57.1 μL | |
| Phosphoric acid | 98.0 mg | 1 | Water | 57.1 μL | |
| Ethanesulfonic acid | 81.6 | 1 | Water | 57.1 μL | |
| L-Glutamic acid | N/A | N/A | N/A | 8.5 mg | Added neat |
| L-Tartaric acid | 150.1 mg | 1 | Water | 57.1 μL | |
| Fumaric acid | N/A | N/A | N/A | 6.5 mg | Added neat |
| Citric acid | 192.1 mg | 1 | Water | 57.1 μL | |
| D-Glucuronic acid | 194.1 mg | 1 | Water | 57.1 μL | |
| L-Malic acid | 134.1 mg | 1 | Water | 57.1 μL | |
| Hippuric acid | N/A | N/A | N/A | 10.3 mg | Added neat |
| D-Gluconic acid | 319.0 μL | 1 | Water | 57.1 μL | |
| L-Lactic acid | 76.0 μL | 1 | Water | 57.1 μL | |
| L-Ascorbic acid | 176.1 mg | 1 | Water | 57.1 μL | |
| Benzoic acid | 122.1 mg | 1 | IPA | 57.1 μL | |
| Succinic acid | 118.1 mg | 1 | MeOH | 57.1 μL | |

The samples were then temperature cycled between ambient (RT) and 40° C. in 4-hour cycles over 24 hours. Each mixture was filtered and isolated solids were analyzed (wet) by XRPD to determine crystallinity and form. Samples in which solid was not observed were stored uncapped to allow solvent evaporation. The remaining samples were placed in an oven at 40° C. and 75% RH overnight. The samples were then reanalyzed by XRPD to determine any changes in form or crystallinity. The observations and results, including the different diffractogram patterns observed during the screen, are shown in Tables 8-32, below, and FIGS. 6A-6B through 29A-29B.

TABLE 8

Hydrochloric acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | White solid | Pale orange solid | White solid | White solid | White solid | Pale yellow solid |
| XRPD post-cycling | Form 2 | Form 2 | Form 2 | Form 2 | Form 2 | Form 2 |
| XRPD post-stability | Form 2 | Form 2 | Form 2 | Form 2 | Form 2 | Form 2 |

Figure 6A:
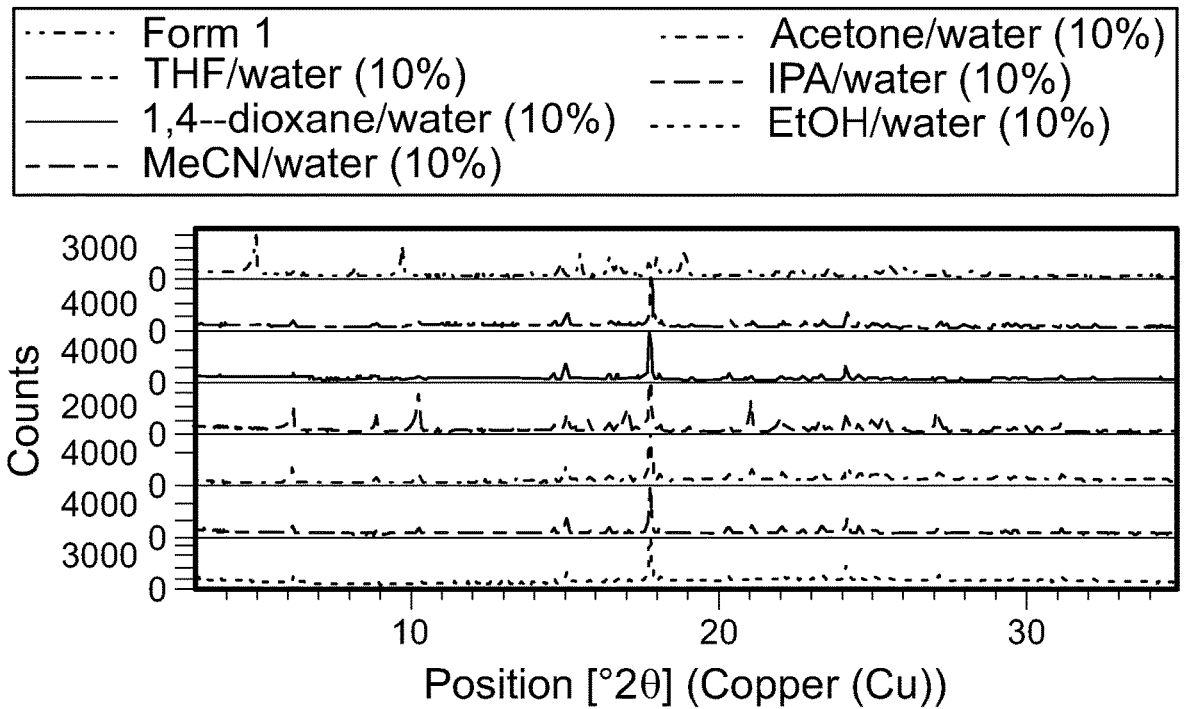
FIGS. 6A-6B are x-ray powder diffraction scans from a salt screen of the compound of Formula (I) with hydrochloric acid.
Figure 6B:
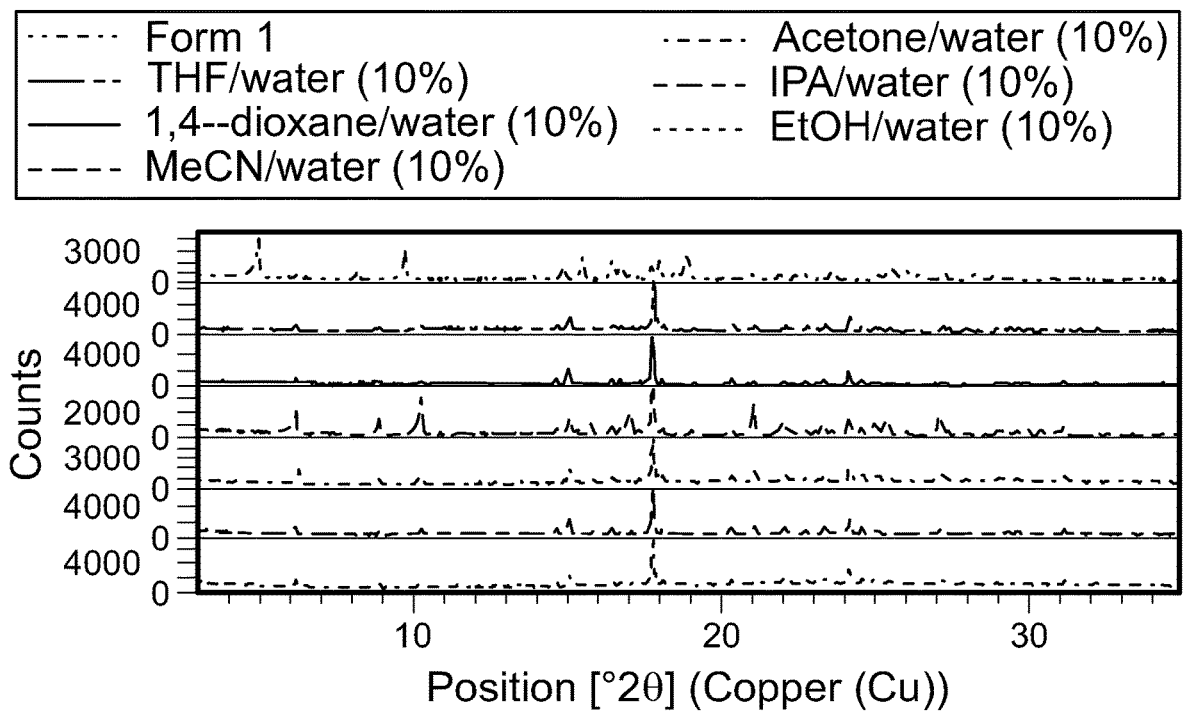

The post-cycling and post-stability XRPD scans for hydrochloric acid are shown in FIGS. 6A and 6B, respectively.

TABLE 9

Sulfuric acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow gum | Pale yellow solution | Colorless solution | Pale yellow solution | White solid in yellow solution | Pale yellow solution |
| XRPD post-cycling | No solid | No solid | No solid | No solid | Form 3 | No solid |
| XRPD post-stability | No solid | No solid | No solid | No solid | Form 5 | No solid |

Figure 7A:
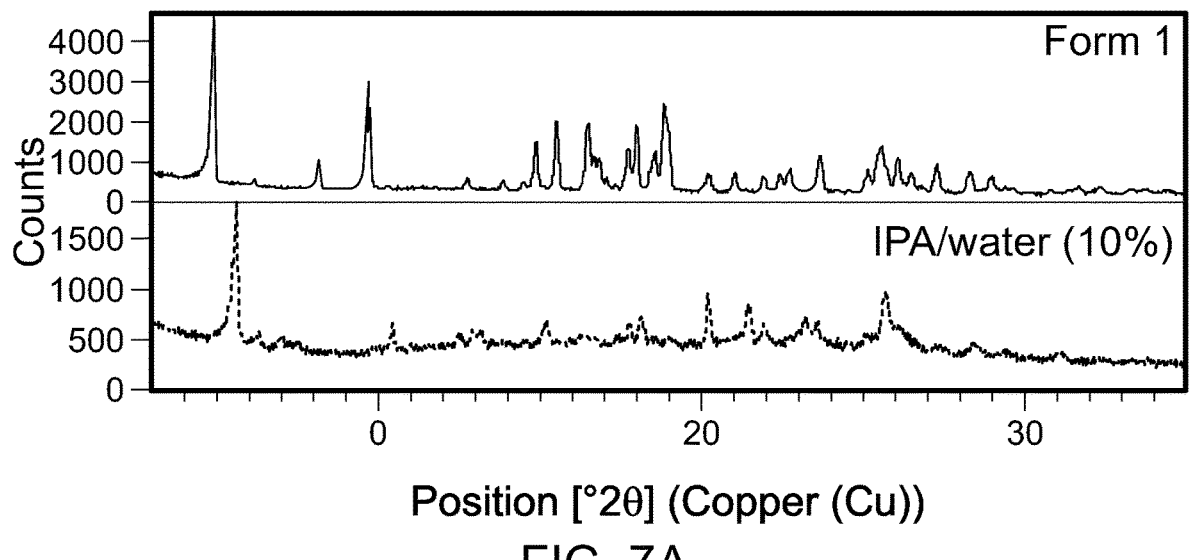
FIGS. 7A-7B are x-ray powder diffraction scans from a salt screen of the compound of Formula (I) with sulfuric acid.
Figure 7B:
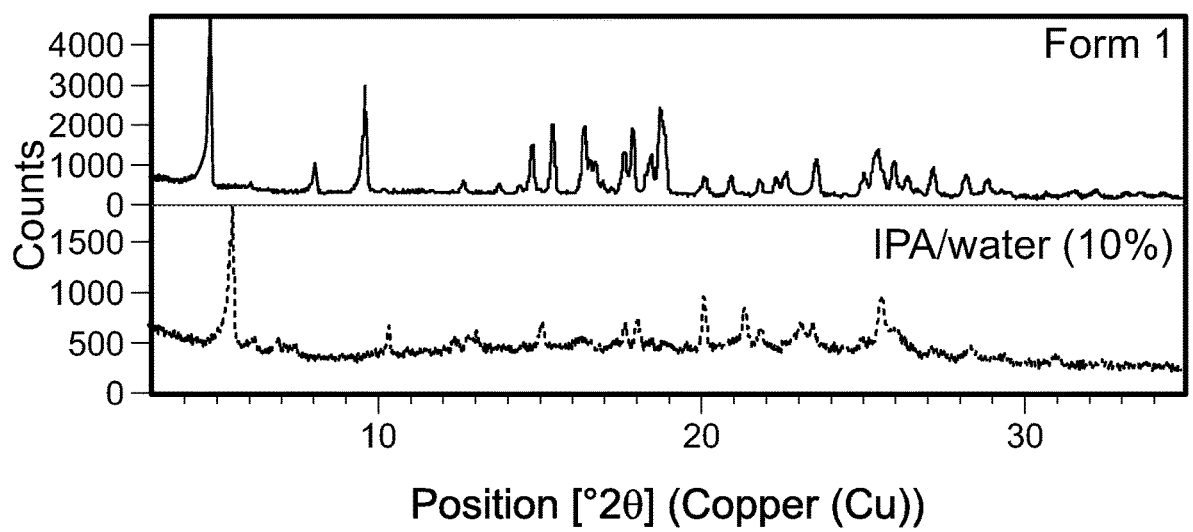

The post-cycling and post-stability XRPD scans for sulfuric acid are shown in FIGS. 7A and 7B, respectively.

TABLE 10

1,2-Ethane disulfonic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Pale yellow solution | Pale yellow solution | Colorless solution | Pale yellow solution | Colorless solution | Pale yellow solution |
| XRPD post-cycling | No solid | No solid | No solid | No solid | No solid | No solid |
| XRPD post-stability | No solid | No solid | No solid | No solid | No solid | No solid |

TABLE 11 p-Toluene sulfonic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow solution | Yellow solution | White solid | White solid in yellow solution | White solid in yellow solution | White solid in yellow solution |
| XRPD post-cycling | Weak diffraction | No solid | No solid | Form 4 | Amorphous | Amorphous |
| XRPD post-stability | Form 4 | No solid | No solid | Form 4 | Form 4 | Amorphous |

Figure 8A:
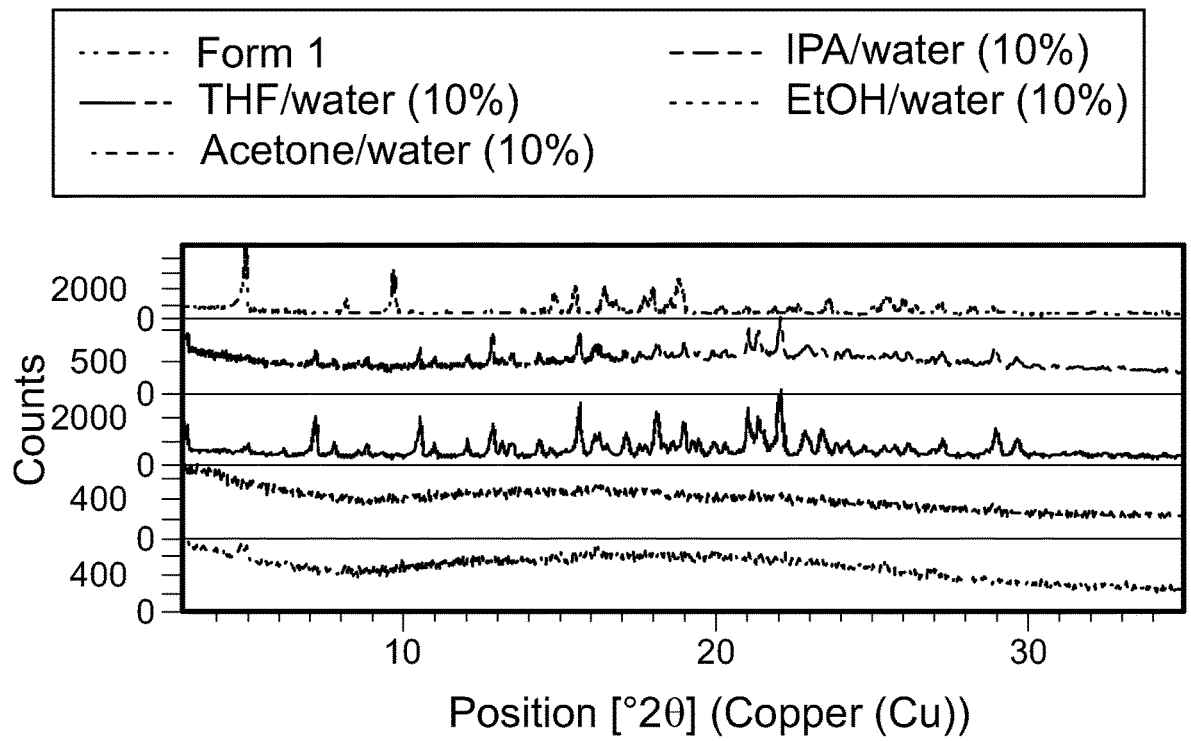
FIGS. 8A-8B are x-ray powder diffraction scans from a salt screen of the compound of Formula (I) with p-toluene sulfonic acid.
Figure 8B:
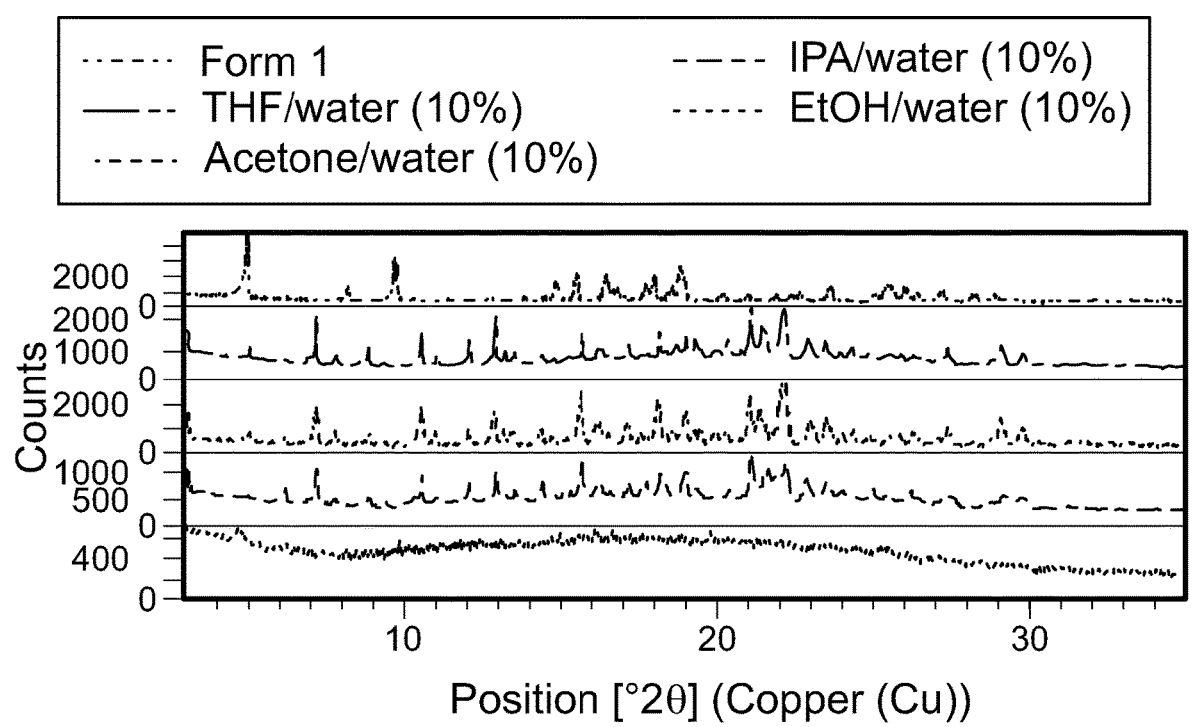

The post-cycling and post-stability XRPD scans for p-toluene sulfonic acid are shown in FIGS. 8A and 8B, respectively.

TABLE 12

Methane sulfonic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow solution | Yellow solution | Yellow solution | White solid | White solid | White solid |
| XRPD post-cycling | No solid | No solid | No solid | Amorphous | Form 2 | Amorphous |
| XRPD post-stability | No solid | No solid | No solid | Amorphous | Form 2 | Amorphous |

Figure 9A:
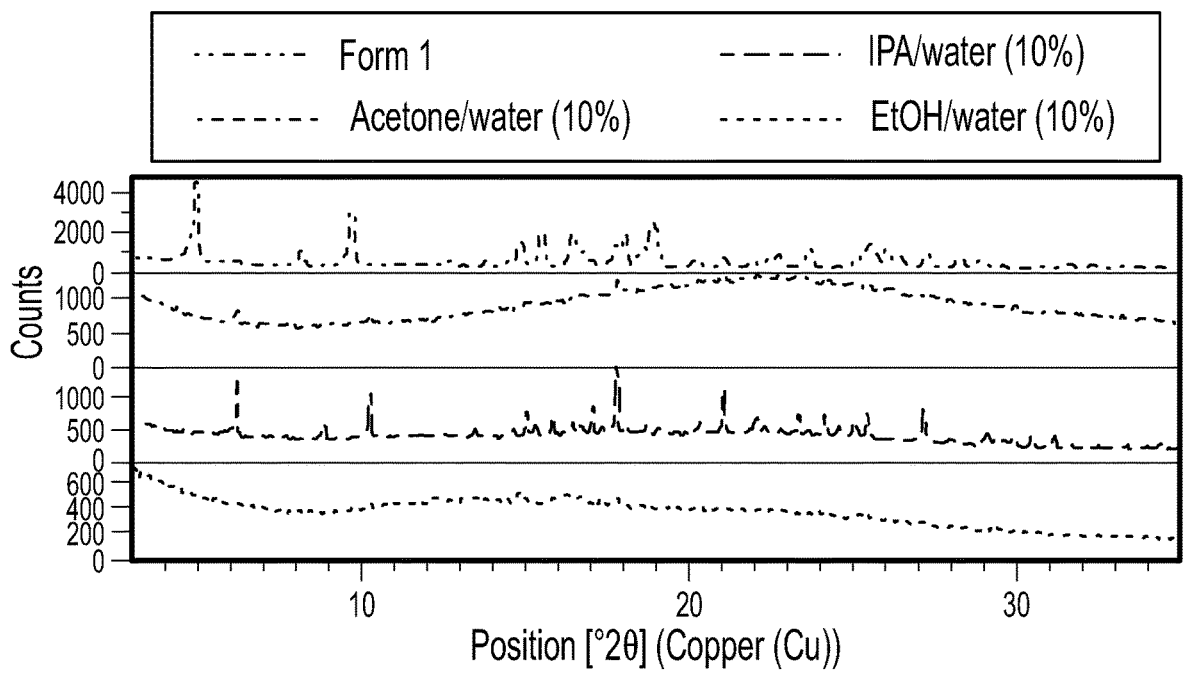
FIGS. 9A-9B are x-ray powder diffraction scans from a salt screen of the compound of Formula (I) with methane sulfonic acid.
Figure 9B:
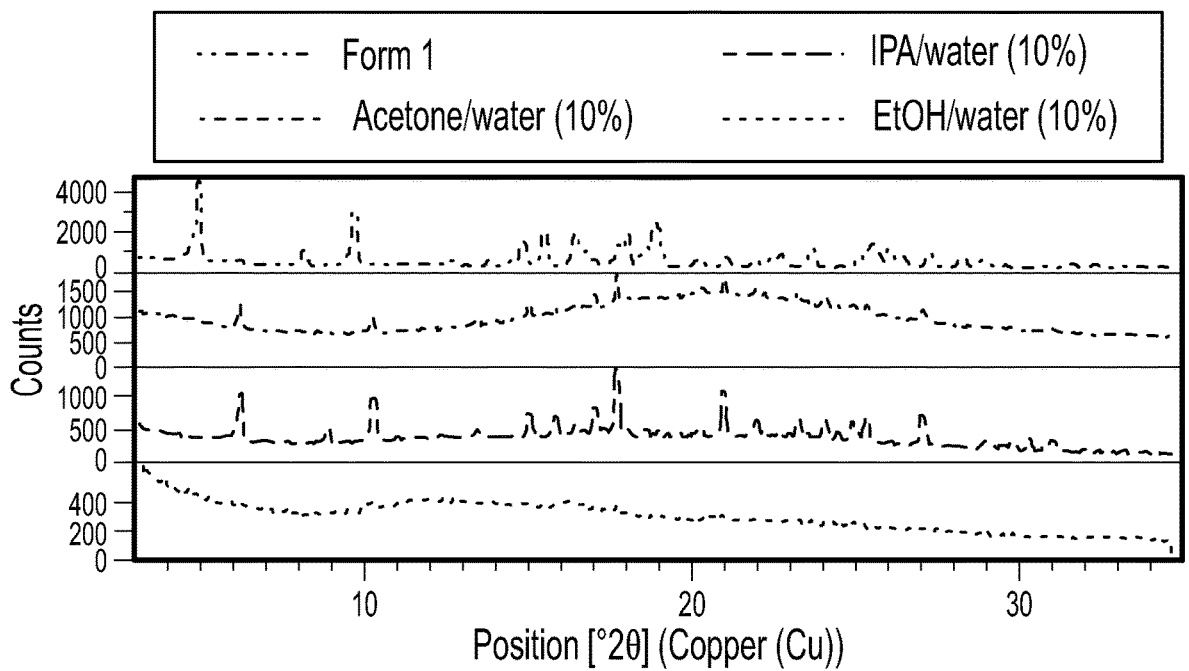

The post-cycling and post-stability XRPD scans for methane sulfonic acid are shown in FIGS. 9A and 9B, respectively.

TABLE 13

Naphthalene-2-sulfonic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow solution | Yellow solution | Pale yellow solution | White solid | White solid in yellow solution | White solid in yellow solution |
| XRPD post-cycling | Form 5 | Form 2/ Form 5 | Form 2/ Form 5 | Form 2/ Form 5 | Form 2/ Form 5 | Form 2 |
| XRPD post-stability | Form 2/ Form 5 | Form 2/ Form 5 | Form 2/ Form 5 | Form 2/ Form 5 | Form 2/ Form 5 | Form 2 |

Figure 10A:
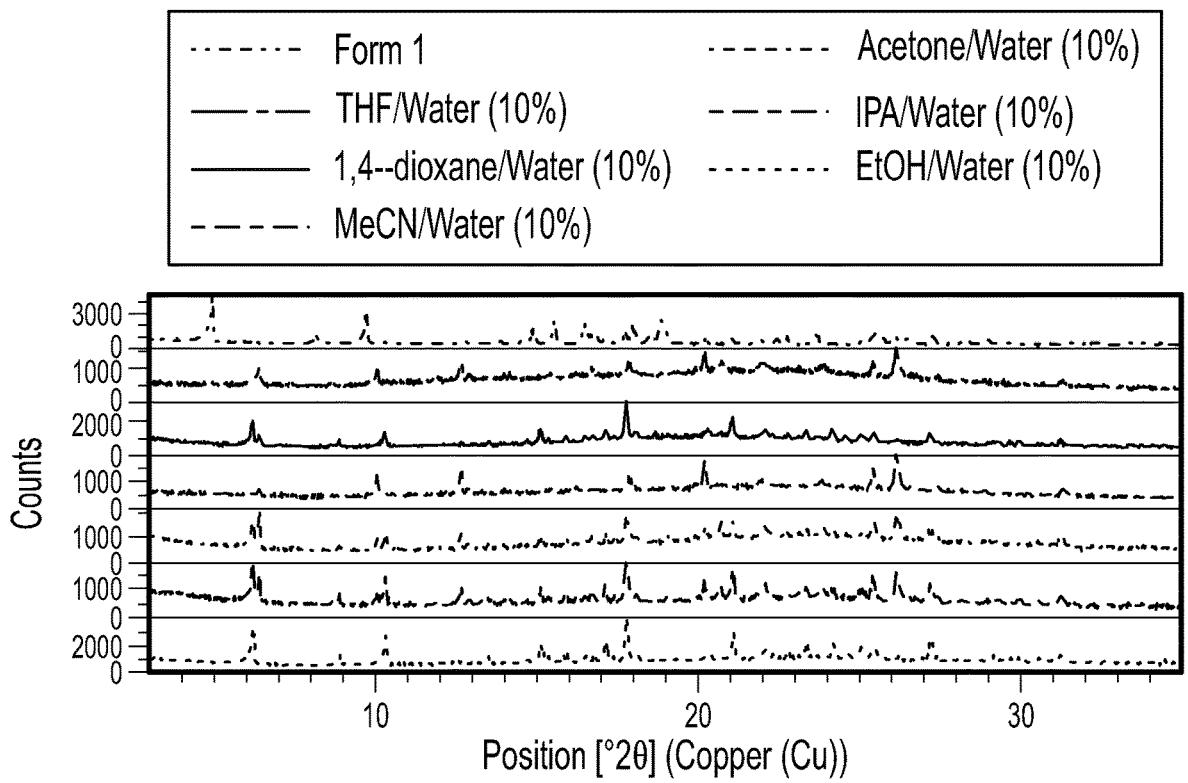
FIGS. 10A-10B are x-ray powder diffraction scans from a salt screen of the compound of Formula (I) with naphthalene-2-sulfonic acid.
Figure 10B:
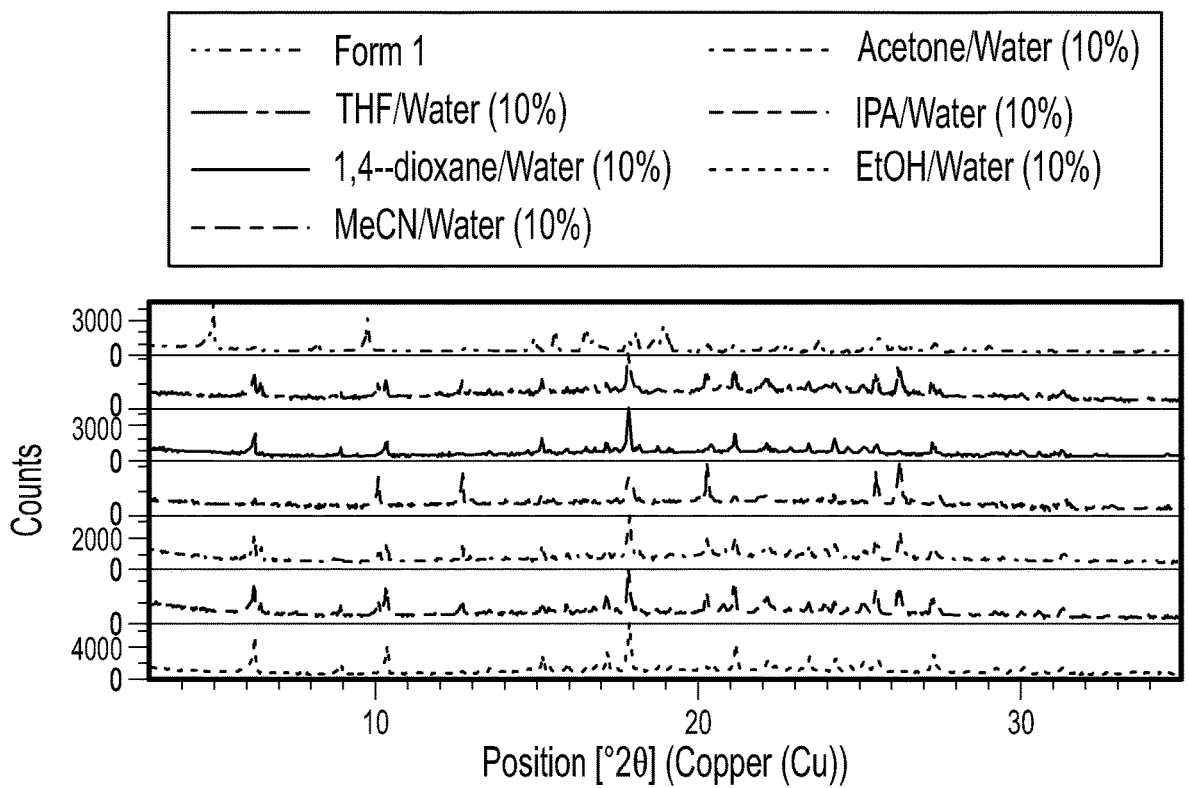

The post-cycling and post-stability XRPD scans for natphthalene-2-sulfonic acid are shown in FIGS. 10A and 10B, respectively.

TABLE 14

Benzene sulfonic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Pale yellow solution | White solid | Pale yellow solution | White solid | White solid | White solid |
| XRPD post-cycling | No solid | No solid | No solid | Weak diffraction | Form 2 | Form 2 |
| XRPD post-stability | No solid | No solid | No solid | Weak diffraction | Form 2 | Form 2 |

Figure 11A:
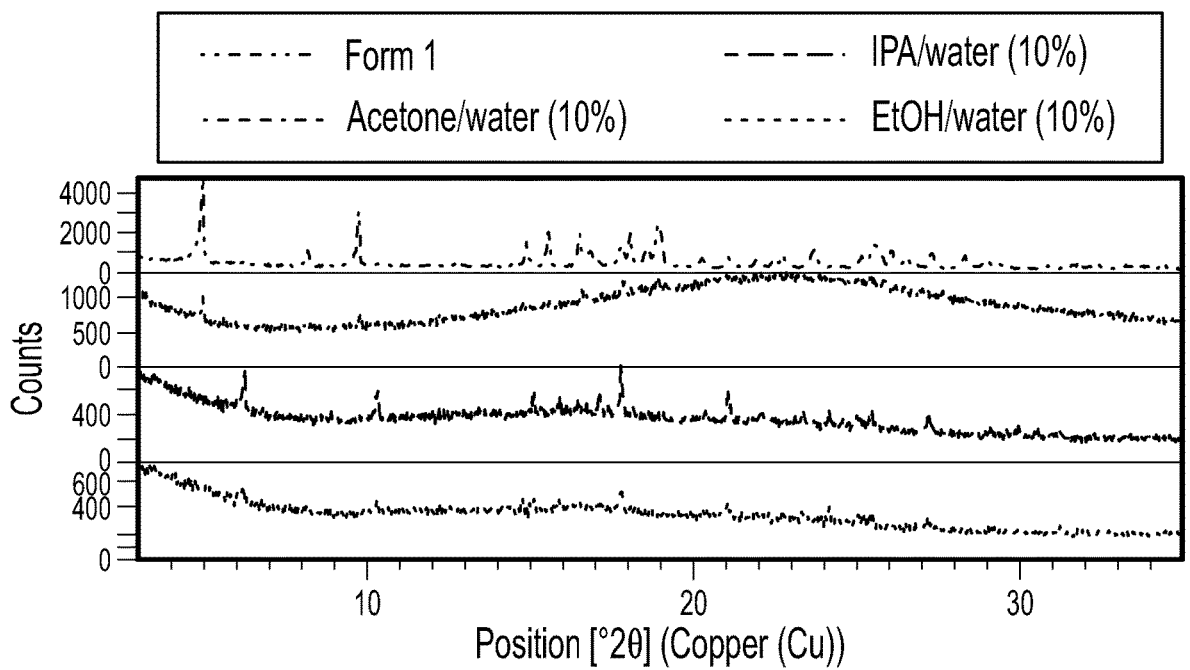
FIGS. 11A-11B are x-ray powder diffraction scans from a salt screen of the compound of Formula (I) with benzene sulfonic acid.
Figure 11B:
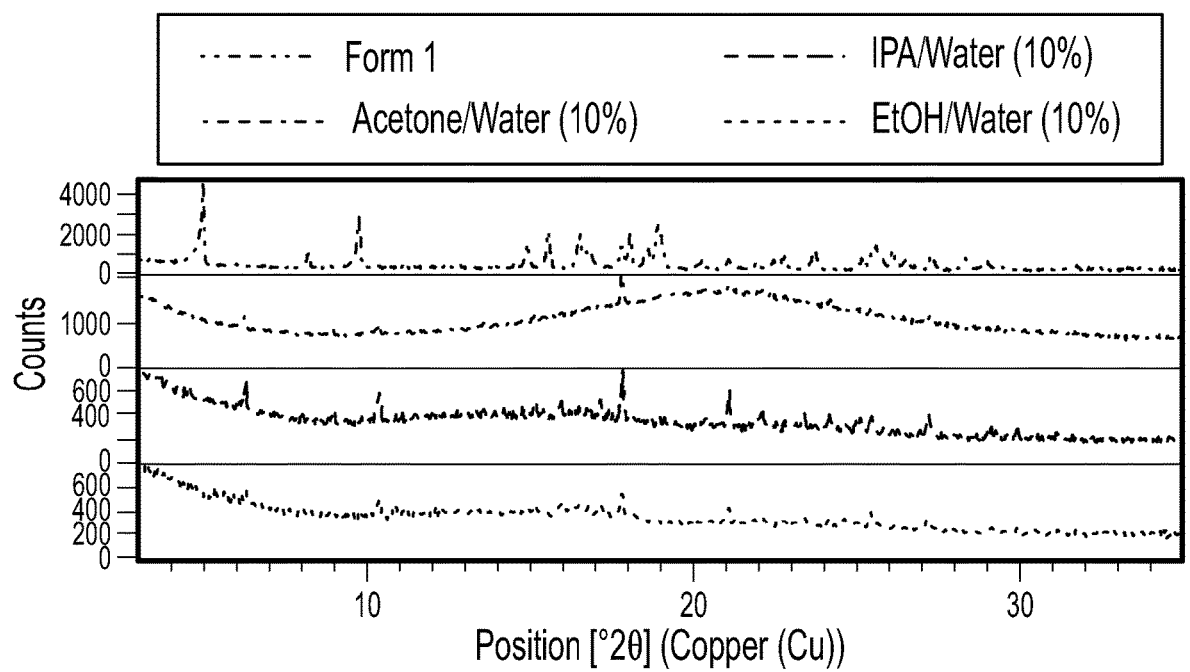

The post-cycling and post-stability XRPD scans for benzene sulfonic acid are shown in FIGS. 11A and 11B, respectively.

TABLE 15

Oxalic acid observations and XRPD results

| | Solvent | | | | | |
|---|---|---|---|---|---|---|
| | THF/water (1%) | Dioxane/water (10%) | MeCN/water (20%) | Acetone/water (10%) | IPA/water (10%) | EtOH/water (10%) |
| Pre-cycling | Slurry | Slurry | Slurry | Slurry | Slurry | Slurry |
| Post-cycling | Pale yellow solid | White solid in yellow solution | White solid | White solid | White solid | White solid |
| XRPD post-cycling | No solid | Form 6 | No solid | Amorphous | Amorphous | Amorphous |
| XRPD post-stability | No solid | Form 6 | No solid | Form 2/Form 6 | Form 6 | Form 6 |

Figure 12A:
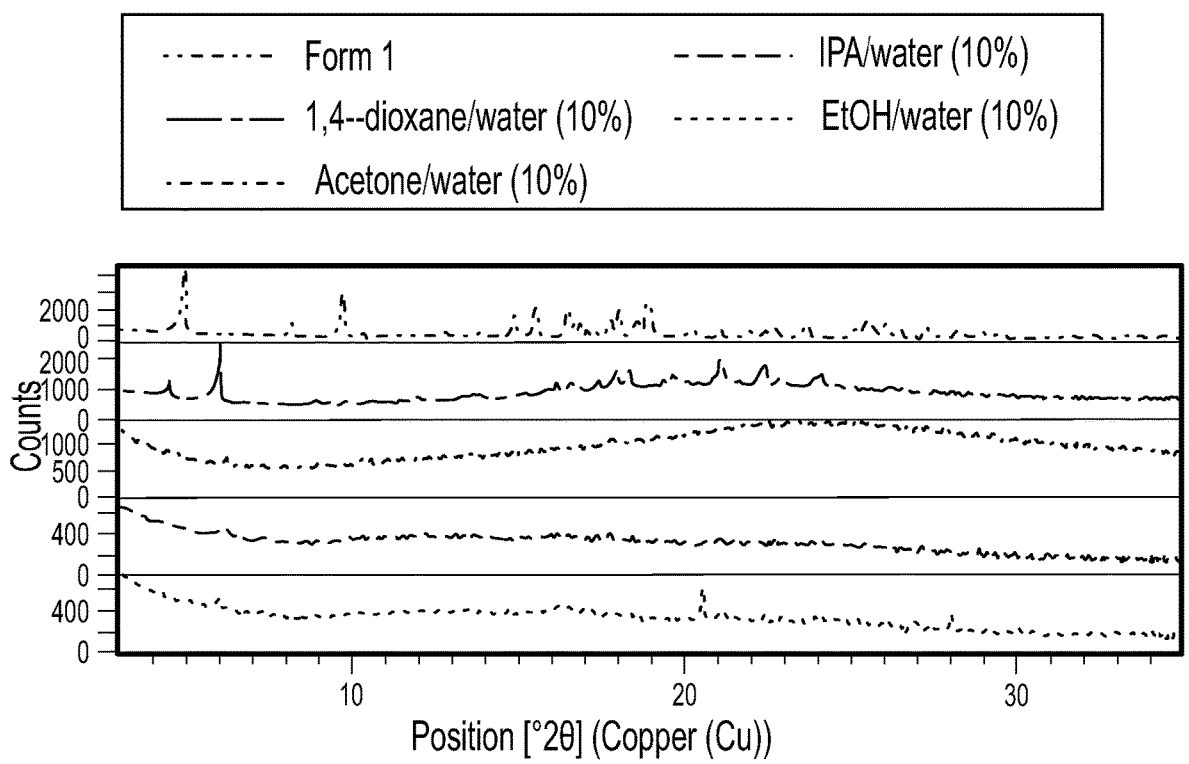
FIGS. 12A-12B are x-ray powder diffraction scans from a salt screen of the compound of Formula (I) with oxalic acid.
Figure 12B:
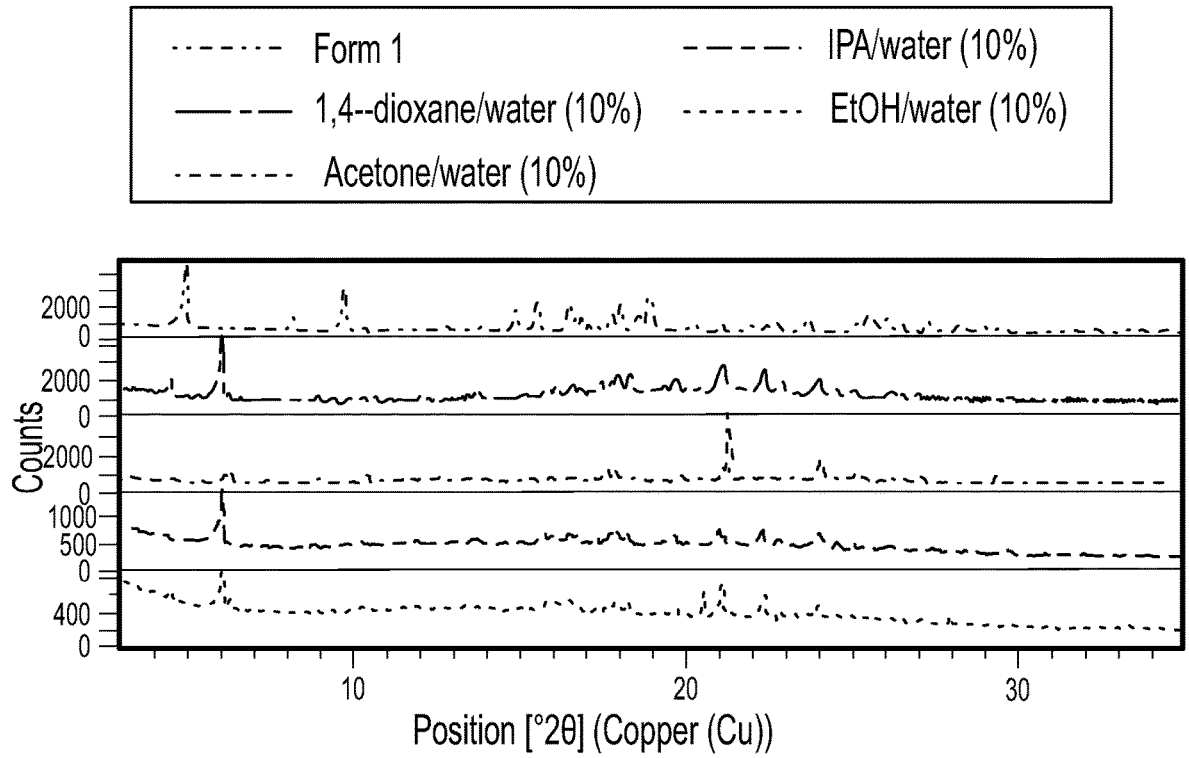

The post-cycling and post-stability XRPD scans for oxalic acid are shown in FIGS. 12A and 12B, respectively.

TABLE 16

2-Hydroxy ethanesulfonic acid observations and XRPD results

| | Solvent | | | | | |
|---|---|---|---|---|---|---|
| | THF/water (1%) | Dioxane/water (10%) | MeCN/water (20%) | Acetone/water (10%) | IPA/water (10%) | EtOH/water (10%) |
| Pre-cycling | Slurry | Slurry | Slurry | Slurry | Slurry | Slurry |
| Post-cycling | White solid | White solid | White solid | White solid | White solid | White solid |
| XRPD post-cycling | Form 1 (freebase)/Form 2 | Form 7 | Form 1 (freebase) | Form 1 (freebase) | Form 2/Form 7 | Form 7 |
| XRPD post-stability | Form 1 (freebase)/Form 2 | Form 7 | Form 1 (freebase)/Form 8 | Form 1 (freebase)/Form 8 | Form 2/Form 7 | Form 7 |

Figure 13A:
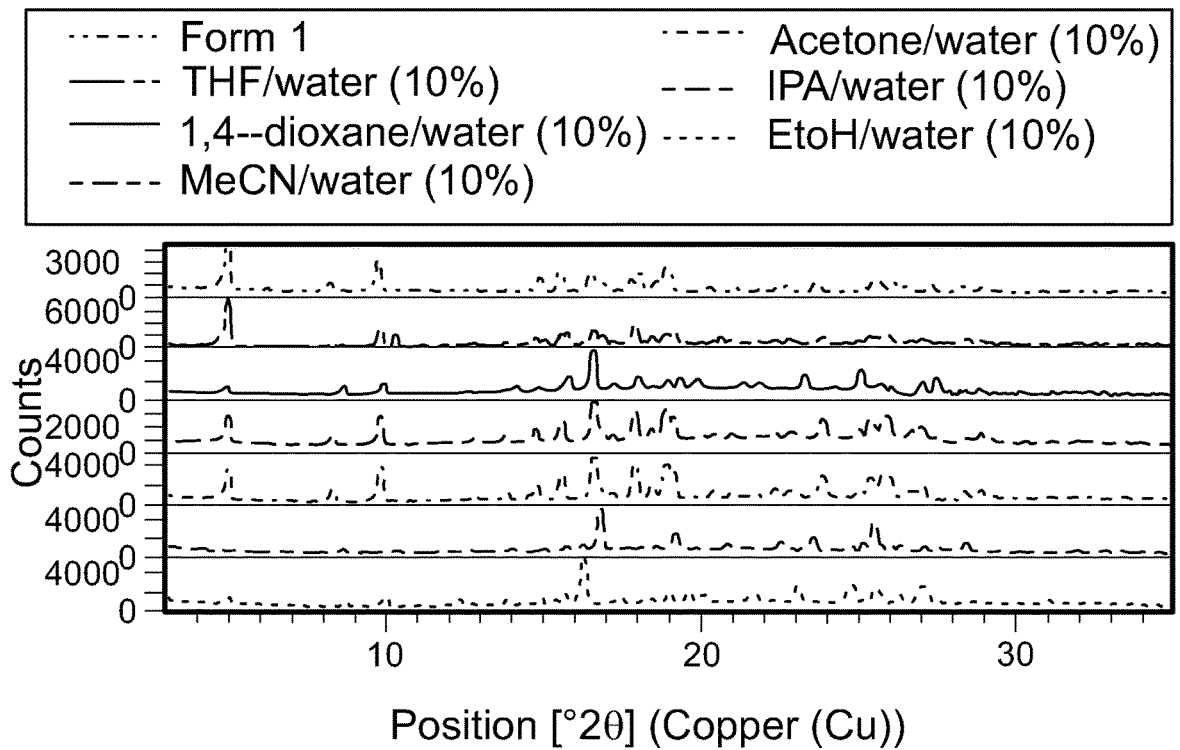
FIGS. 13A-13B are x-ray powder diffraction scans from a salt screen of the compound of Formula (I) with 2-hydroxyethanesulfonic acid.
Figure 13B:
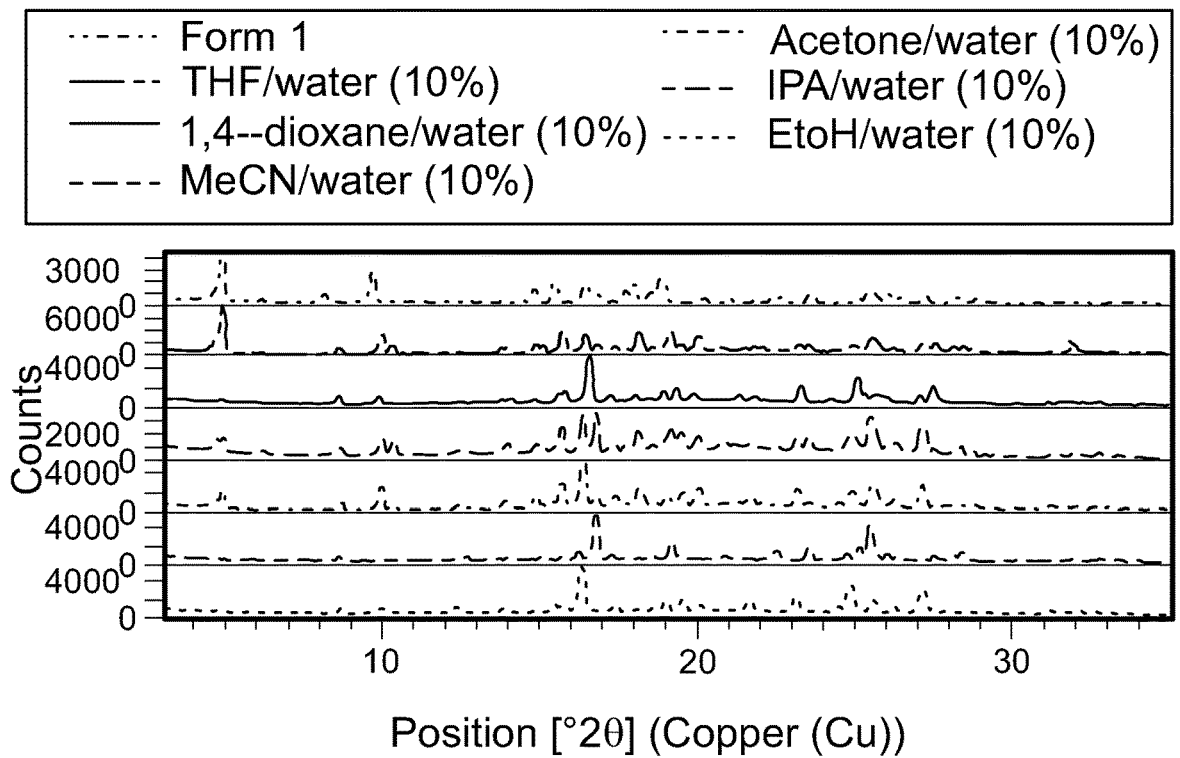

The post-cycling and post-stability XRPD scans for 2-hydroxy ethanesulfonic acid are shown in FIGS. 13A and 13B, respectively.

TABLE 17

L-Aspartic acid observations and XRPD results

| | Solvent | | | | | |
|---|---|---|---|---|---|---|
| | THF/water (1%) | Dioxane/water (10%) | MeCN/water (20%) | Acetone/water (10%) | IPA/water (10%) | EtOH/water (10%) |
| Pre-cycling | Slurry | Slurry | Slurry | Slurry | Slurry | Slurry |
| Post-cycling | Yellow solid | Pale yellow solution | Colorless solution | White solid | White solid | White solid |
| XRPD post-cycling | Form 8 | Form 1 (freebase)/Form 8 | Form 1 (freebase)/Form 8 | Form 1 (freebase)/Form 8 | Form 8 | Form 1 (freebase)/Form 8 |
| XRPD post-stability | Form 8 | Form 1 (freebase)/Form 8 | Form 8 | Form 14 | Form 8 | Form 1 (freebase)/Form 8 |

Figure 14A:
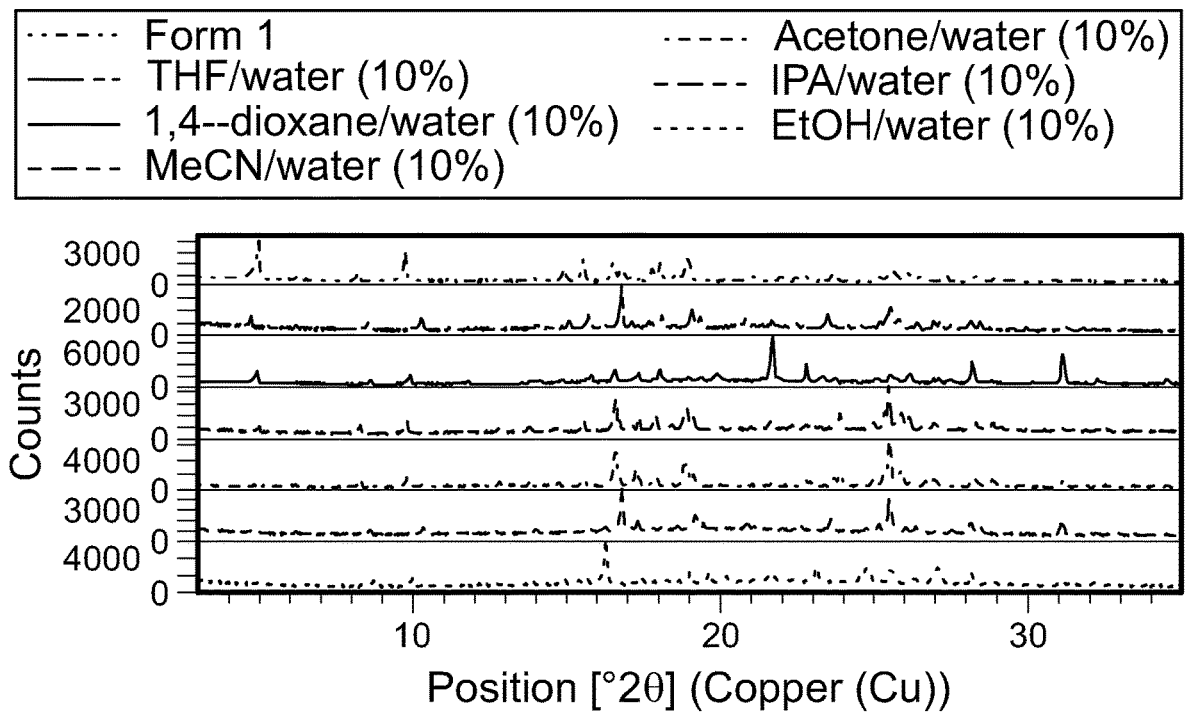
FIGS. 14A-14B are x-ray powder diffraction scans from a salt screen of the compound of Formula (I) with L-aspartic acid.
Figure 14B:
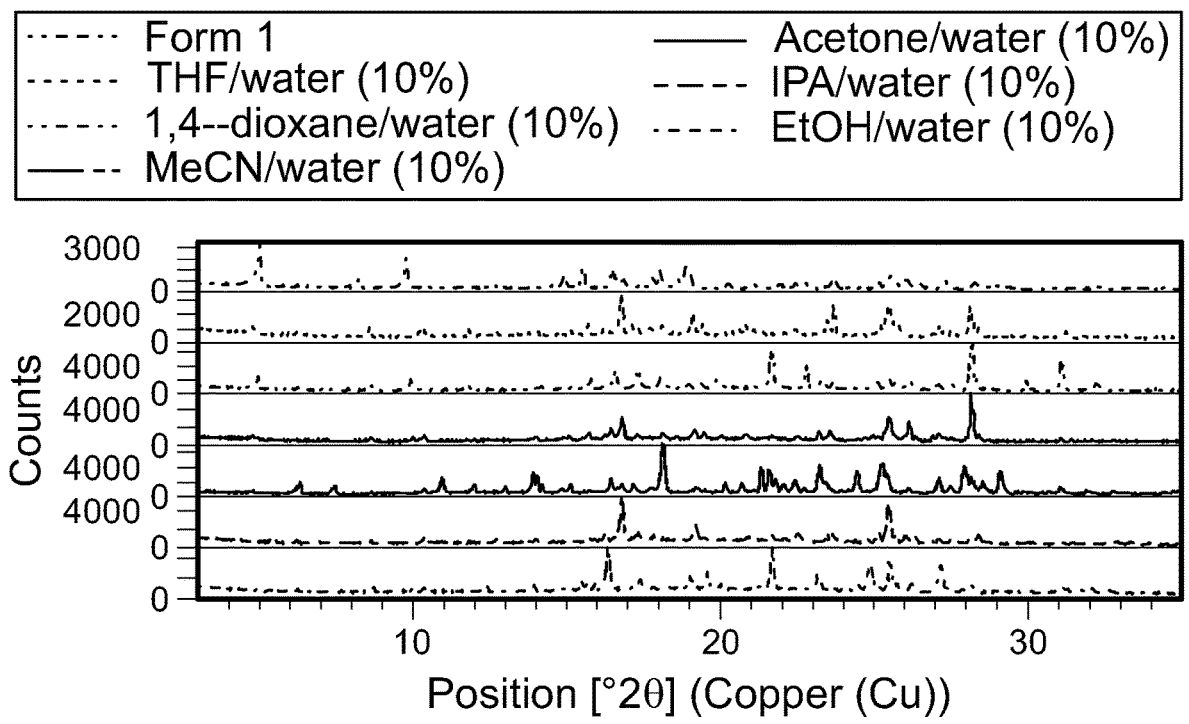

The post-cycling and post-stability XRPD scans for L-aspartic acid are shown in FIGS. 14A and 14B, respectively.

TABLE 18

Maleic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow solid | Colorless solution | Colorless solution | White solid | White solid | White solid |
| XRPD post-cycling | Weak diffraction | No solid | No solid | Amorphous | Amorphous | Amorphous |
| XRPD post-stability | Form 15 | No solid | No solid | Amorphous | Amorphous | Amorphous |

Figure 15A:
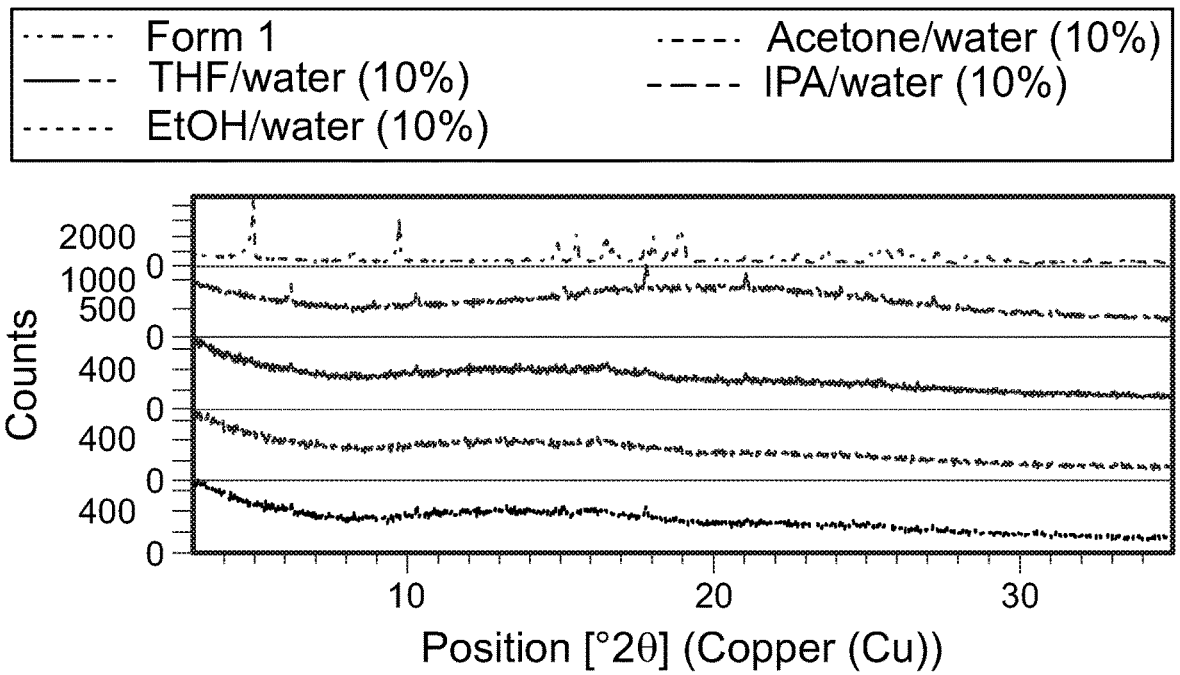
FIGS. 15A-15B are x-ray powder diffraction scans from a salt screen of the compound of Formula (I) with maleic acid.
Figure 15B:
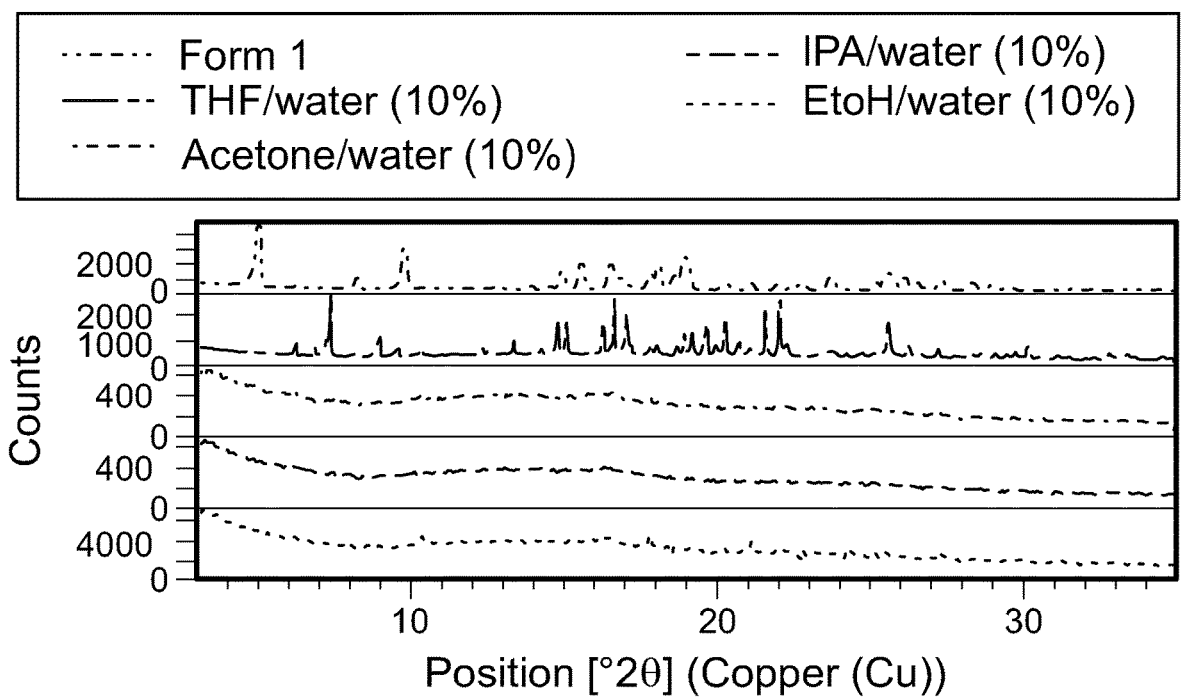

The post-cycling and post-stability XRPD scans for maleic acid are shown in FIGS. 15A and 15B, respectively.

TABLE 19

Phosphoric acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow gum | Yellow solution | Pale yellow gum | Pale yellow gum | White solid | Yellow gum |
| XRPD post-cycling | Amorphous | No solid | No solid | Form 9 | Form 10 | Weak diffraction |
| XRPD post-stability | Form 10 | No solid | No solid | Form 9/ Form 10 | Form 10 | Form 10 |

Figure 16A:
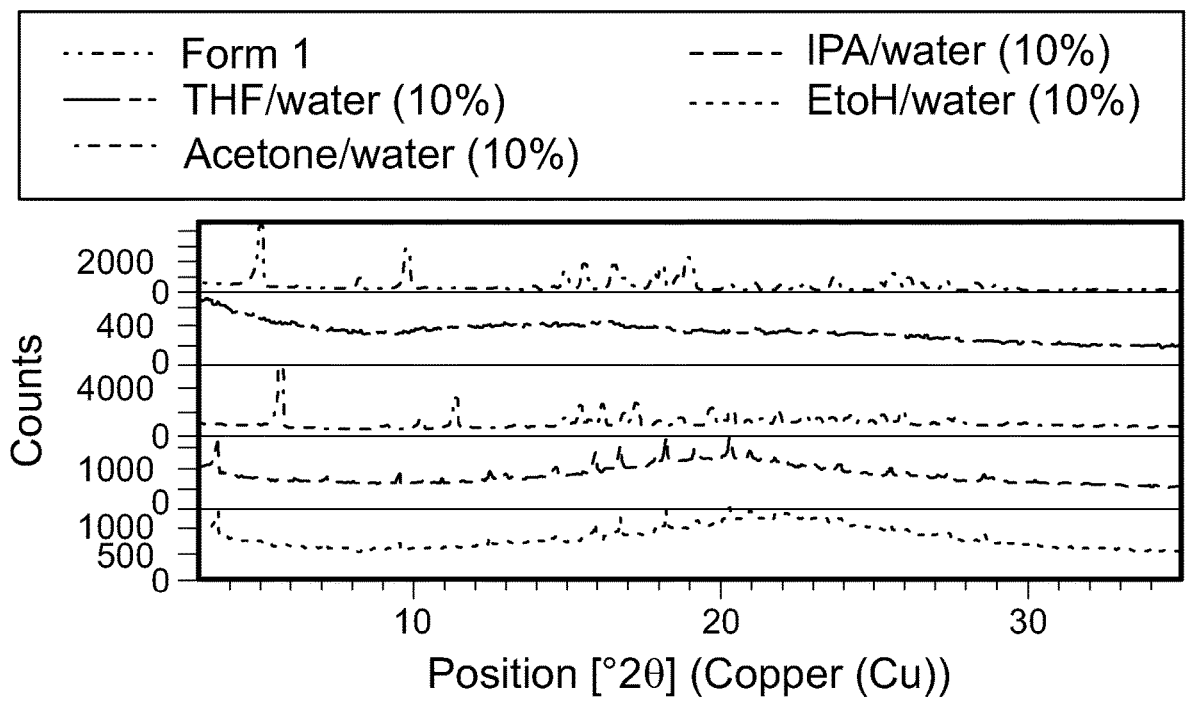
FIGS. 16A-16B are x-ray powder diffraction scans from a salt screen of the compound of Formula (I) with phosphoric acid.
Figure 16B:
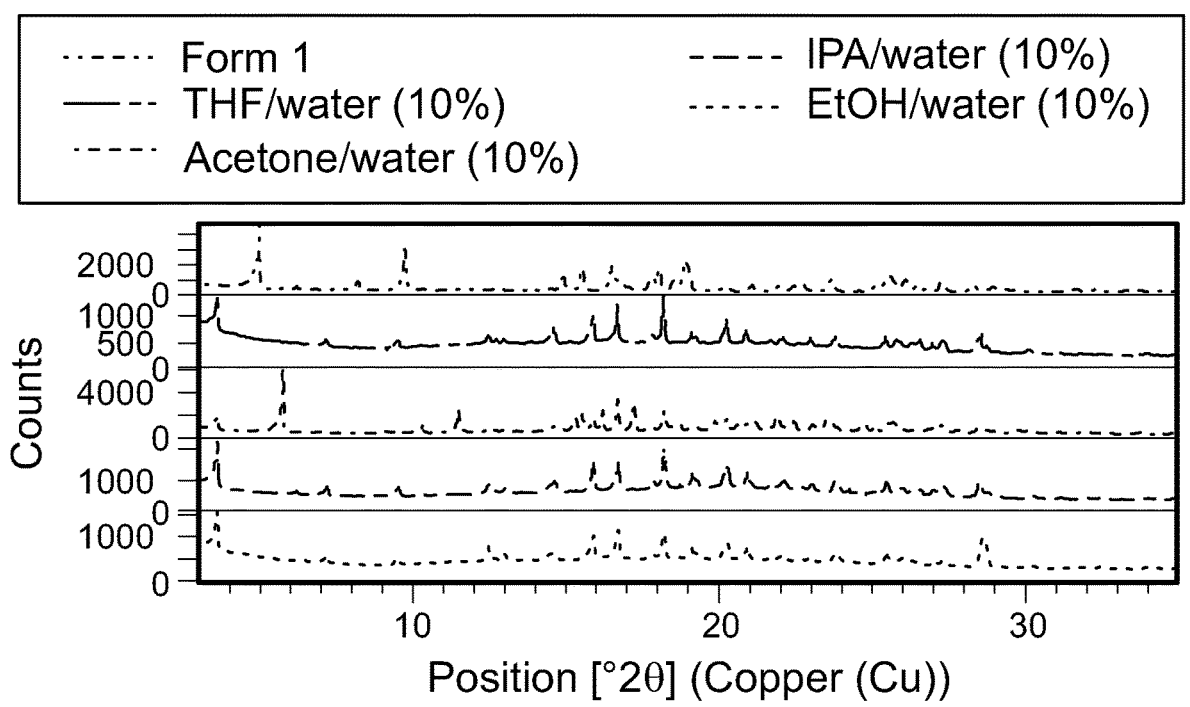

The post-cycling and post-stability XRPD scans for phosphoric acid are shown in FIGS. 16A and 16B, respectively.

TABLE 20

Ethane sulfonic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow solution | Yellow gum | Pale yellow gum | Pale yellow gum | White solid | Yellow solution |
| XRPD post-cycling | No solid | No solid | No solid | No solid | Amorphous | No solid |
| XRPD post-stability | No solid | No solid | No solid | No solid | Amorphous | No solid |

Figure 17A:
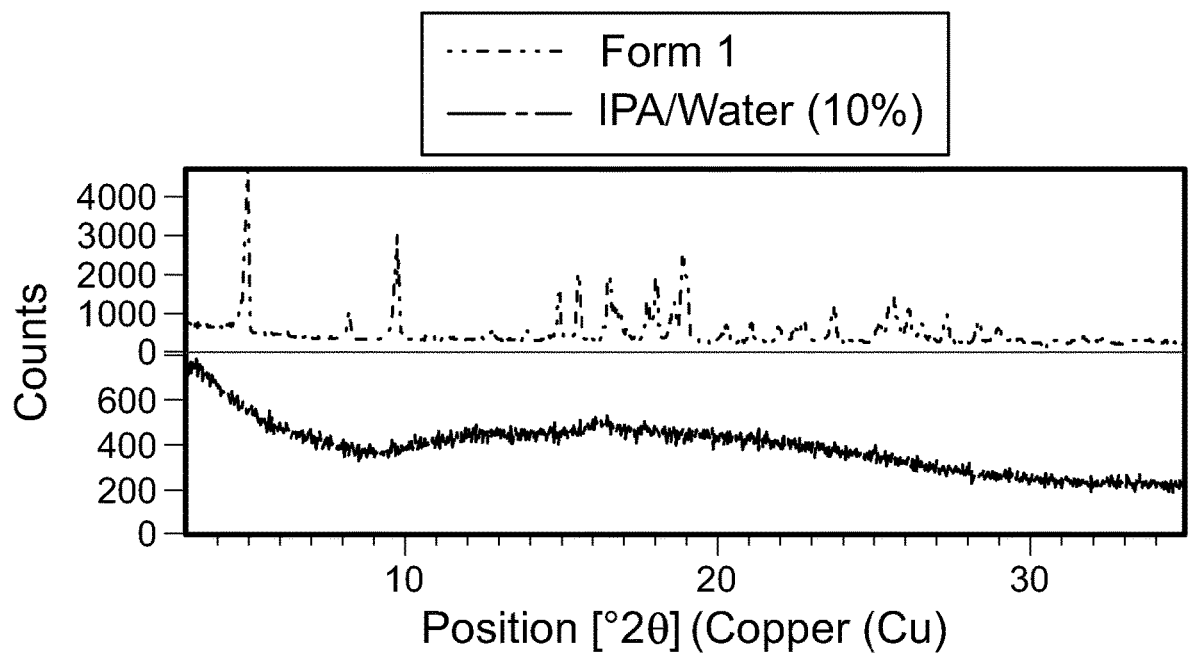
FIGS. 17A-17B are x-ray powder diffraction scans from a salt screen of the compound of Formula (I) with ethanesulfonic acid.
Figure 17B:
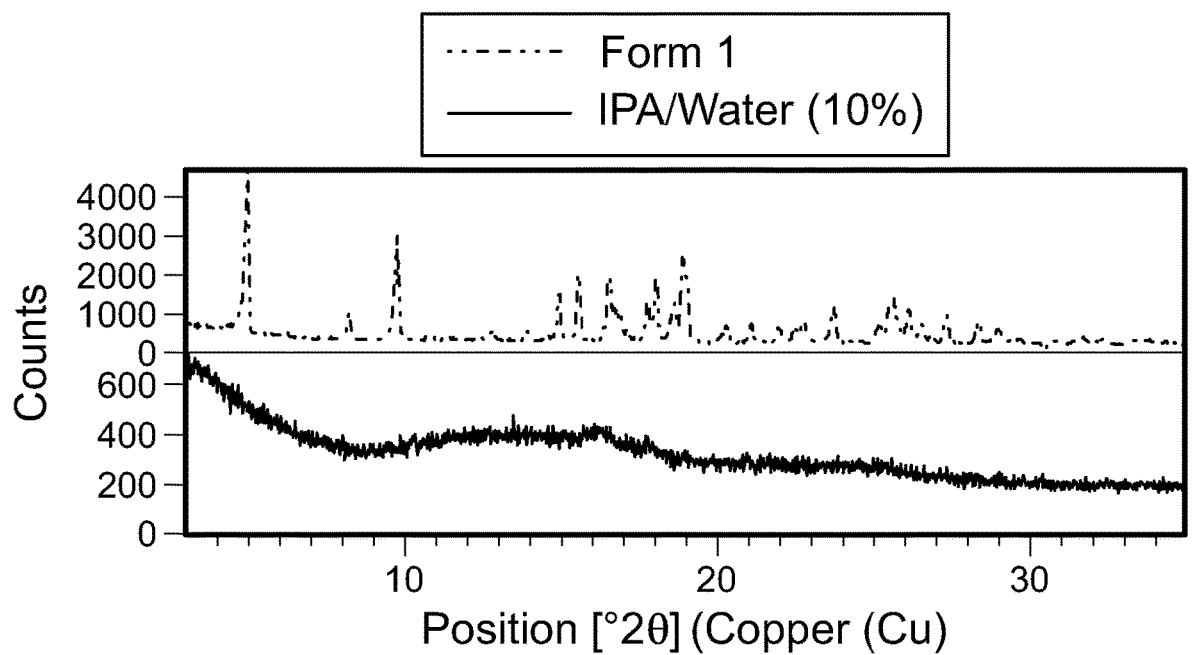

The post-cycling and post-stability XRPD scans for ethane sulfonic acid are shown in FIGS. 17A and 17B, respectively.

TABLE 21

| | \multicolumn{6}{c}{Solvent} | | | | | |
|---|---|---|---|---|---|---|
| | THF/water (1%) | Dioxane/water (10%) | MeCN/water (20%) | Acetone/water (10%) | IPA/water (10%) | EtOH/water (10%) |
| Pre-cycling | Slurry | Slurry | Slurry | Slurry | Slurry | Slurry |
| Post-cycling | White solid in yellow solution | White solid | White solid | White solid | White solid | White solid |
| XRPD post-cycling | Form 8 | Form 7 | Form 1 (freebase) | Form 1 (freebase) | Form 1 (freebase)/ Form 2 | Form 1 (freebase)/ Form 2 |
| XRPD post-stability | Form 8 | Form 7 | Form 1 (freebase) | Form 1 (freebase) | Form 1 (freebase)/ Form 2 | Form 1 (freebase) |

L-Glutamic acid observations and XRPD results

Figure 18A:
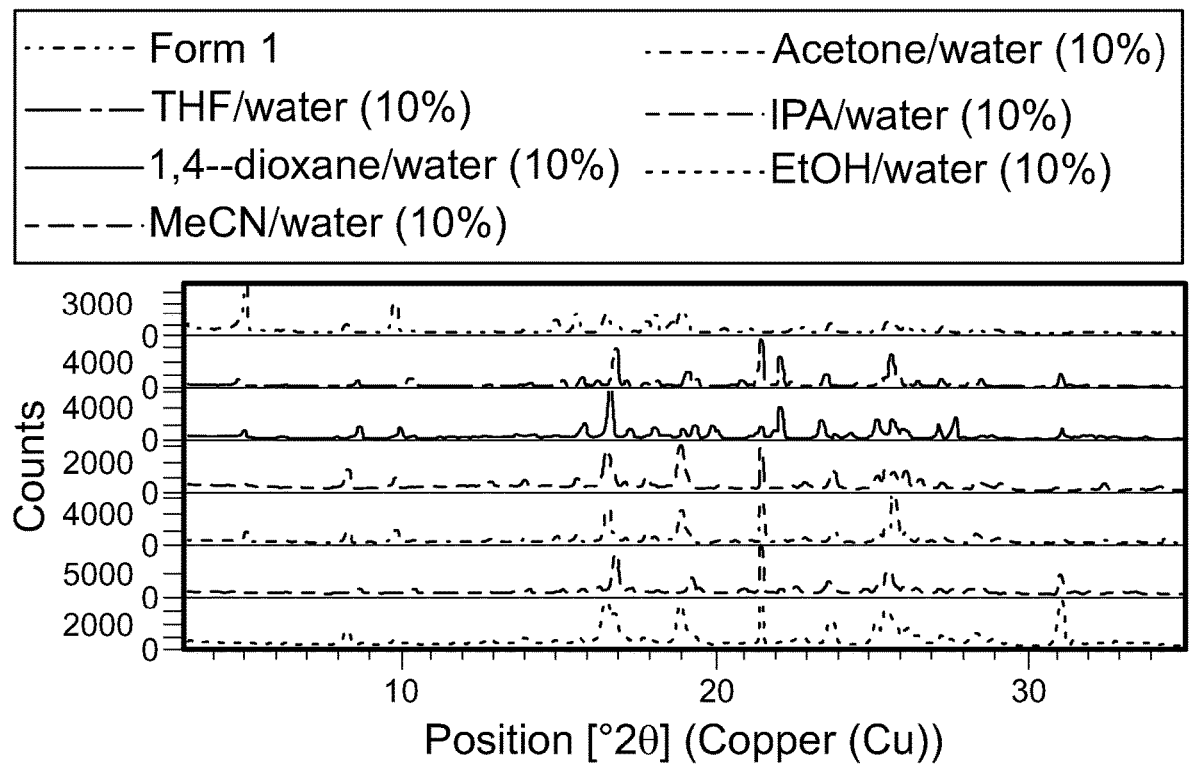
FIGS. 18A-18B are x-ray powder diffraction scans from a salt screen of the compound of Formula (I) with L-glutamic acid.
Figure 18B:
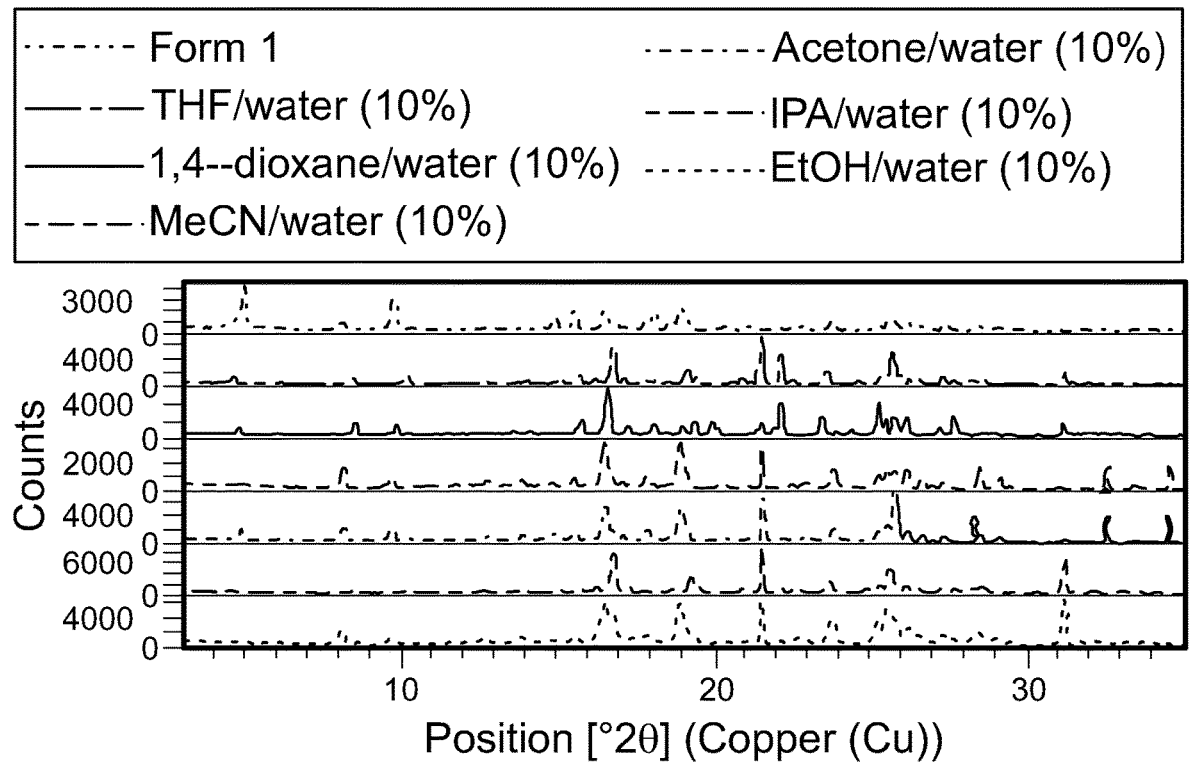

The post-cycling and post-stability XRPD scans for L-glutamic acid are shown in FIGS. 18A and 18B, respectively.

TABLE 22

L-Tartaric acid observations and XRPD results

| | \multicolumn{6}{c}{Solvent} | | | | | |
|---|---|---|---|---|---|---|
| | THF/water (1%) | Dioxane/water (10%) | MeCN/water (20%) | Acetone/water (10%) | IPA/water (10%) | EtOH/water (10%) |
| Pre-cycling | Slurry | Slurry | Slurry | Slurry | Slurry | Slurry |
| Post-cycling | White solid in yellow solution | White solid | White solid | White solid | White solid | White solid |
| XRPD post-cycling | Weak diffraction | Weak diffraction | No solid | Weak diffraction | Form 11 | Weak diffraction |
| XRPD post-stability | Weak diffraction | Weak diffraction | No solid | Weak diffraction | Form 11 | Weak diffraction |

Figure 19A:
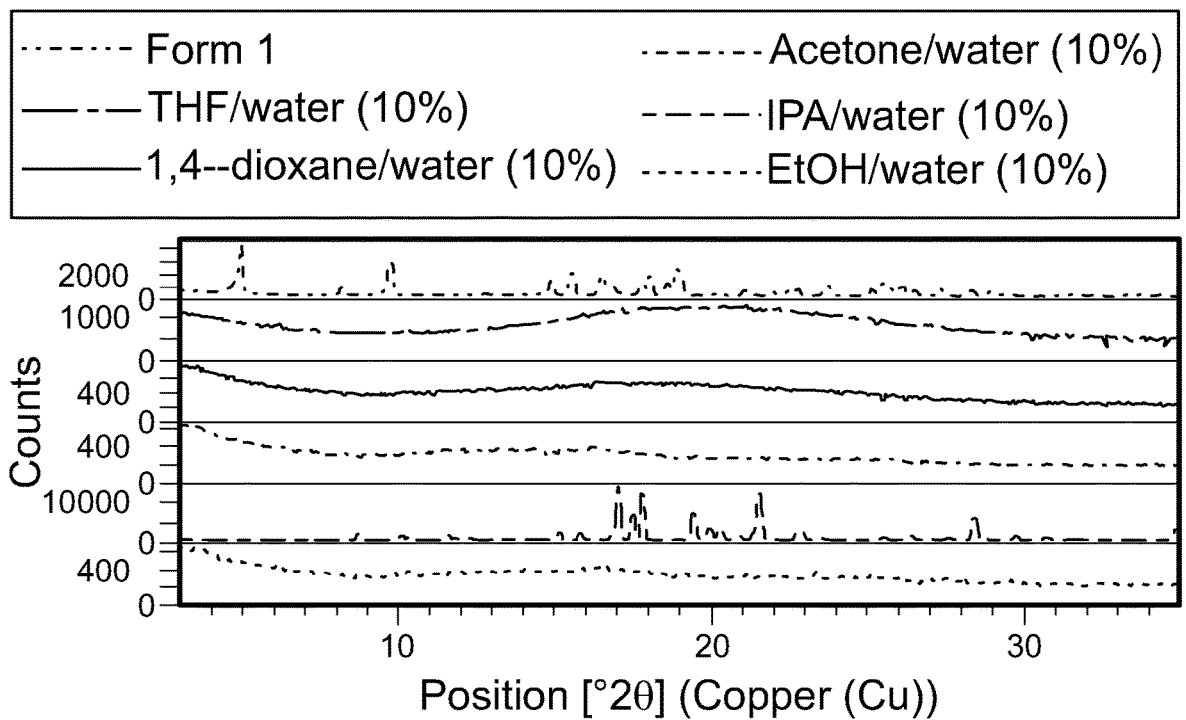
FIGS. 19A-19B are x-ray powder diffraction scans from a salt screen of the compound of Formula (I) with L-tartaric acid.
Figure 19B:
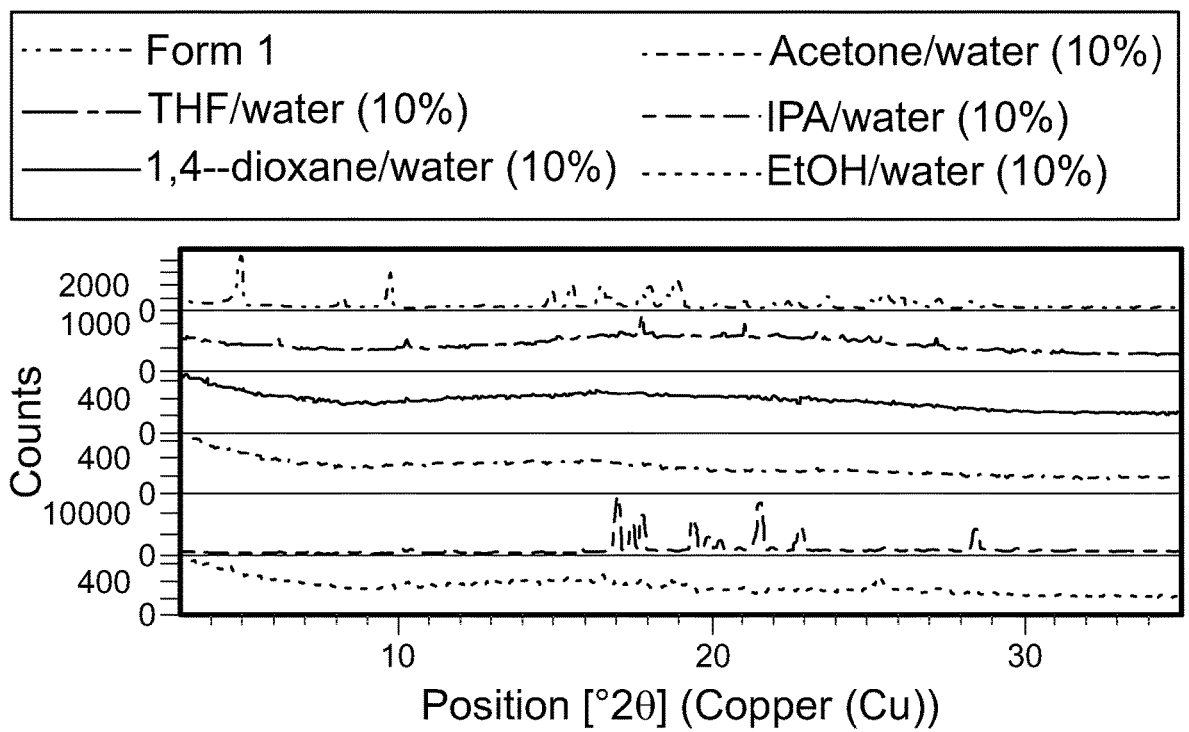

The post-cycling and post-stability XRPD scans for L-tartaric acid are shown in FIGS. 19A and 19B, respectively.

TABLE 23

Fumaric acid observations and XRPD results

| | \multicolumn{6}{c}{Solvent} | | | | | |
|---|---|---|---|---|---|---|
| | THF/water (1%) | Dioxane/water (10%) | MeCN/water (20%) | Acetone/water (10%) | IPA/water (10%) | EtOH/water (10%) |
| Pre-cycling | Slurry | Slurry | Slurry | Slurry | Slurry | Slurry |
| Post-cycling | Pale yellow solid | White solid | Colorless solution | White solid | White solid | White solid |
| XRPD post-cycling | Form 12 | No solid | No solid | No solid | Form 8 | Form 8 |
| XRPD post-stability | Form 12 | No solid | No solid | No solid | Form 8 | Form 8 |

Figure 20A:
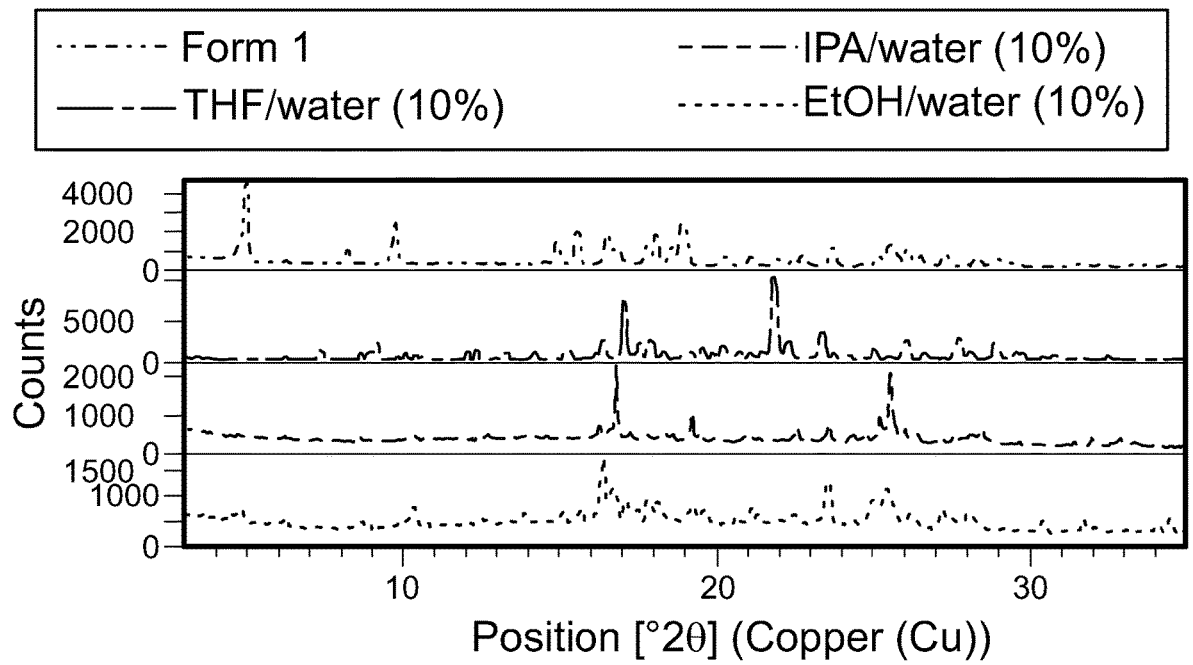
FIGS. 20A-20B are x-ray powder diffraction scans from a salt screen of the compound of Formula (I) with fumaric acid.
Figure 20B:
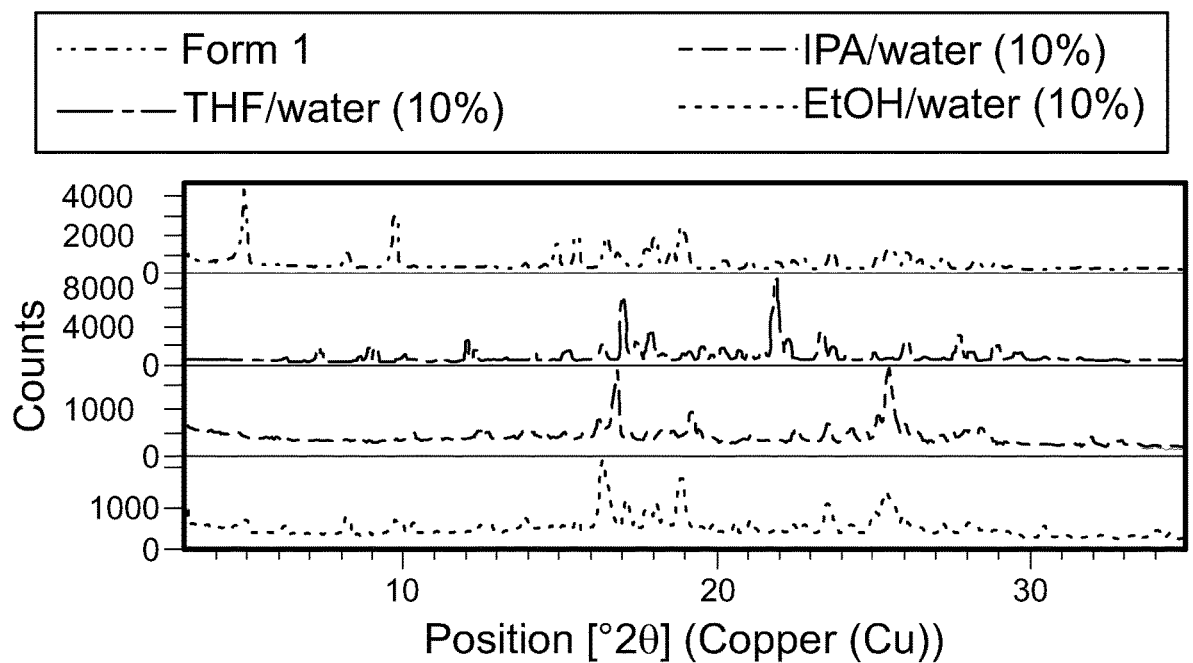

The post-cycling and post-stability XRPD scans for fumaric acid are shown in FIGS. 20A and 20B, respectively.

TABLE 24

Citric acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow solid | Pale yellow solution | Colorless solution | Pale yellow gum | White solid | White solid |
| XRPD post-cycling | Weak diffraction | No solid | No solid | Weak diffraction | Form 1 (freebase) | No solid |
| XRPD post-stability | Weak diffraction | No solid | No solid | Weak diffraction | Form 1 (freebase) | No solid |

Figure 21A:
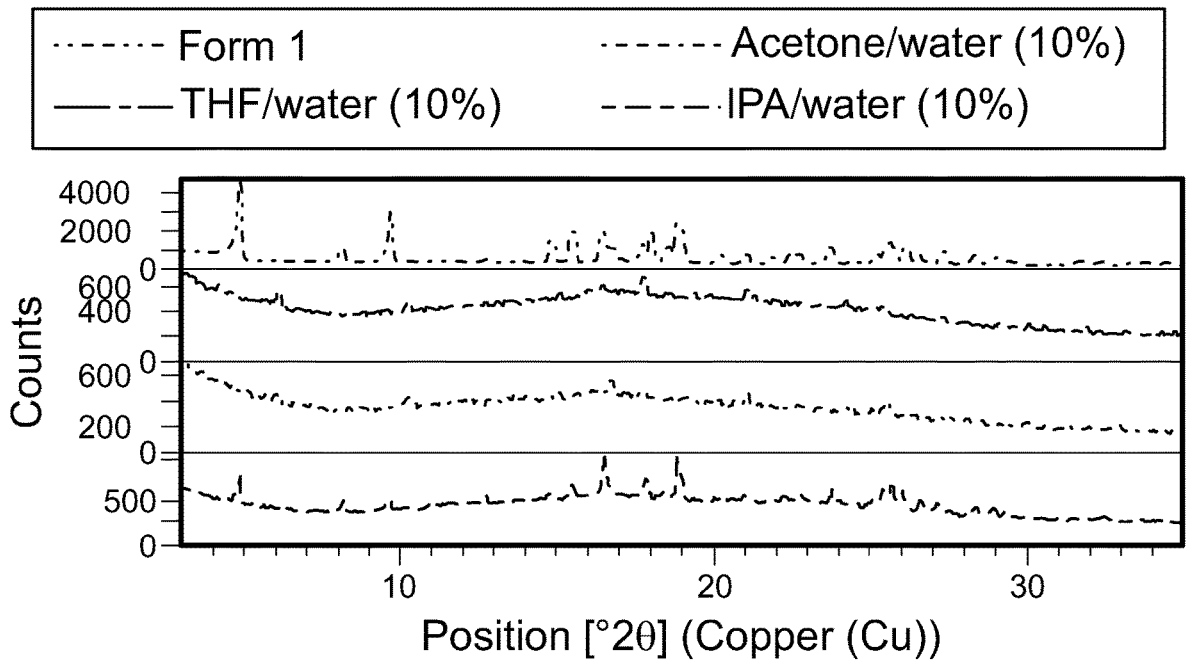
FIGS. 21A-21B are x-ray powder diffraction scans from a salt screen of the compound of Formula (I) with citric acid.
Figure 21B:
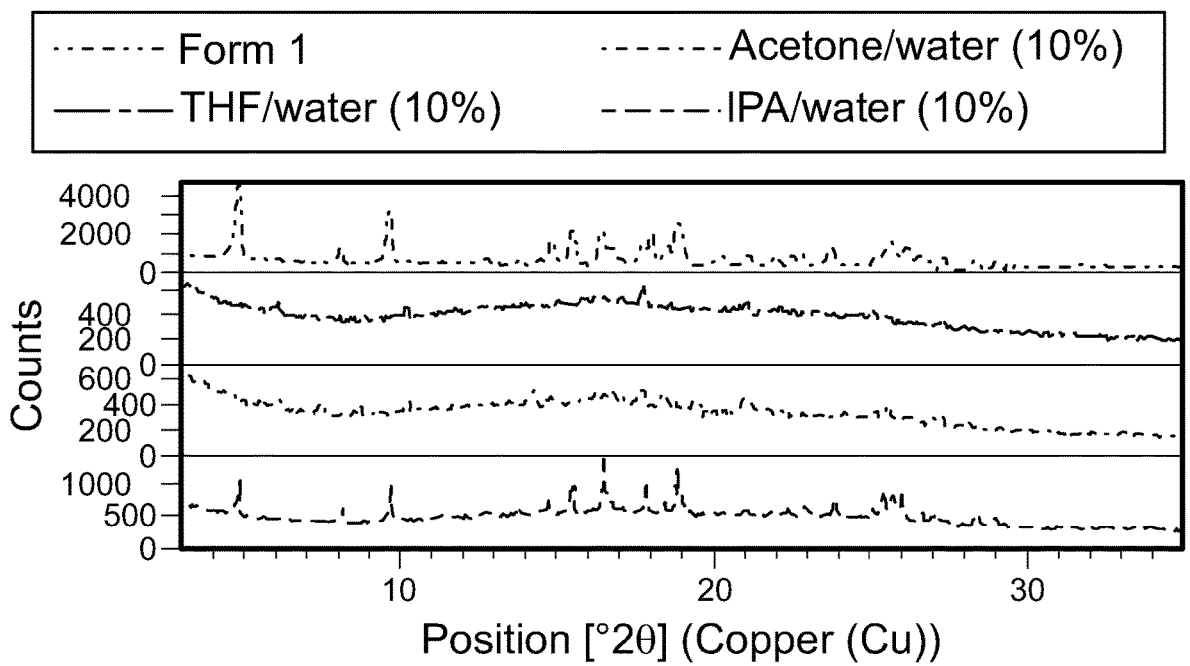

The post-cycling and post-stability XRPD scans for citric acid are shown in FIGS. 21A and 21B, respectively.

TABLE 25

D-Glucuronic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Pale yellow solution | Pale yellow solution | Pale yellow solution | White solid | White solid | Colorless solution |
| XRPD post-cycling | No solid | No solid | Form 1 (freebase) | No solid | Form 8 | Form 8 |
| XRPD post-stability | No solid | No solid | Form 1 (freebase) | No solid | Form 8 | Form 1 (freebase) |

Figure 22A:
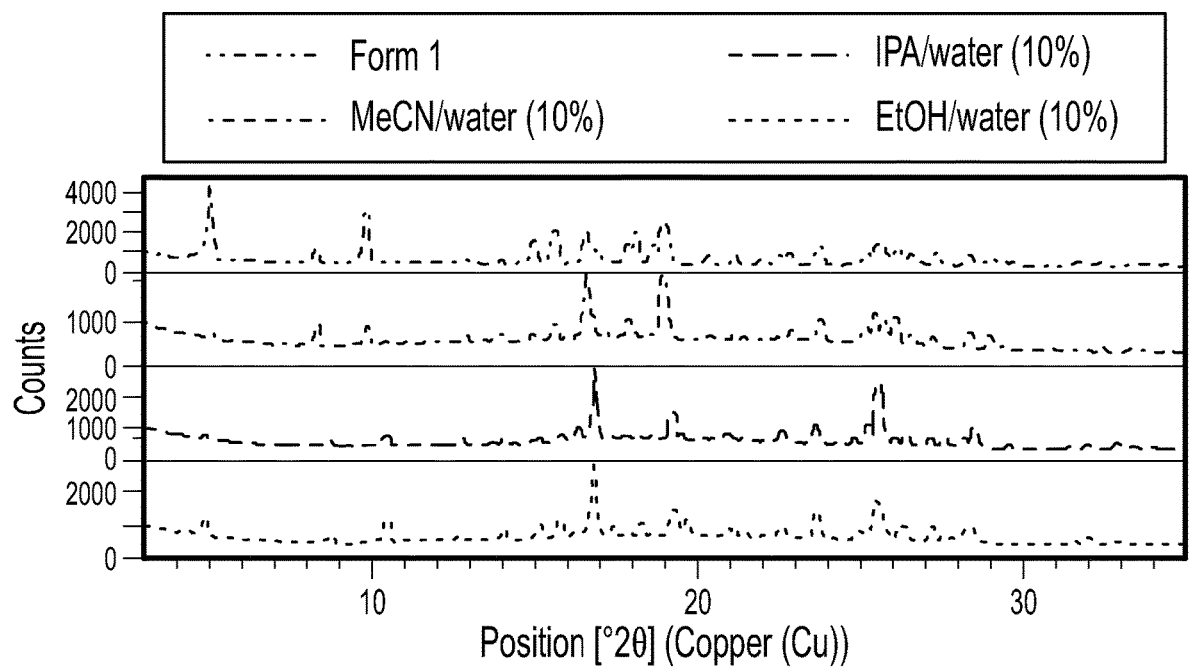
FIGS. 22A-22B are x-ray powder diffraction scans from a salt screen of the compound of Formula (I) with D-glucuronic acid.
Figure 22B:
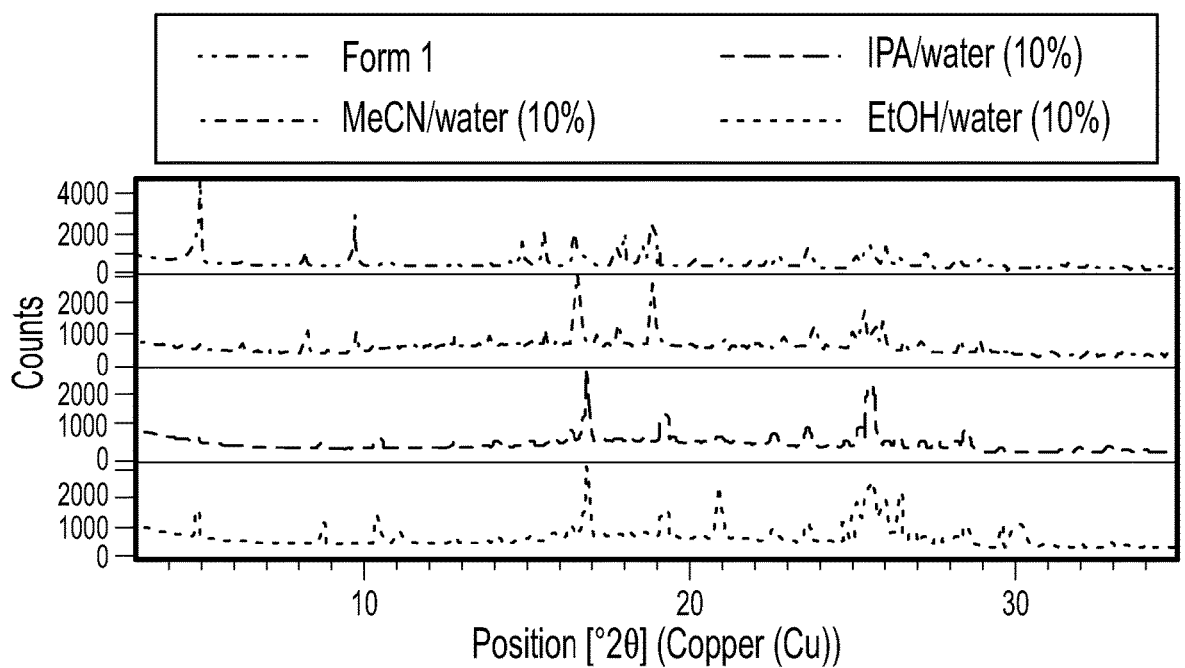

The post-cycling and post-stability XRPD scans for D-glucuronic acid are shown in FIGS. 22A and 22B, respectively.

TABLE 26

L-Malic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow solid | Pale yellow solution | White solid | White solid | White solid | White solid |
| XRPD post-cycling | Amorphous | No solid | No solid | Form 1 (freebase) | Form 8 | Form 8 |
| XRPD post-stability | Amorphous | No solid | No solid | Form 1 (freebase) | Form 8 | Form 1 (freebase) |

Figure 23A:
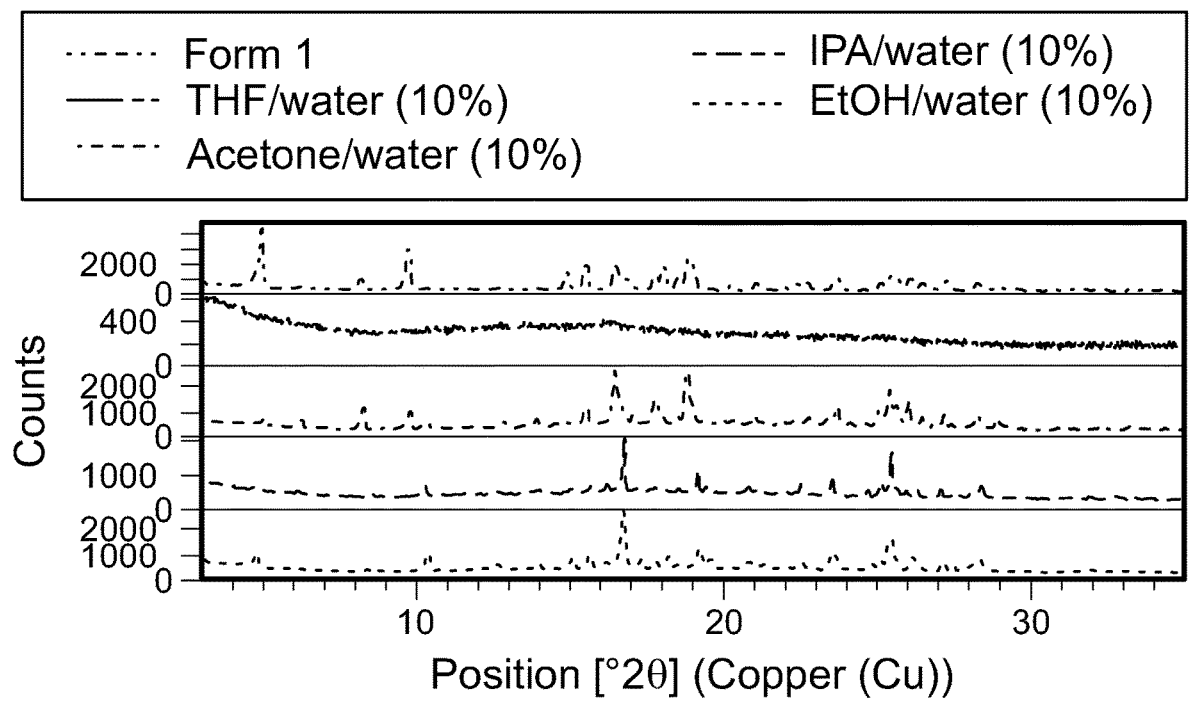
FIGS. 23A-23B are x-ray powder diffraction scans from a salt screen of the compound of Formula (I) with L-malic acid.
Figure 23B:
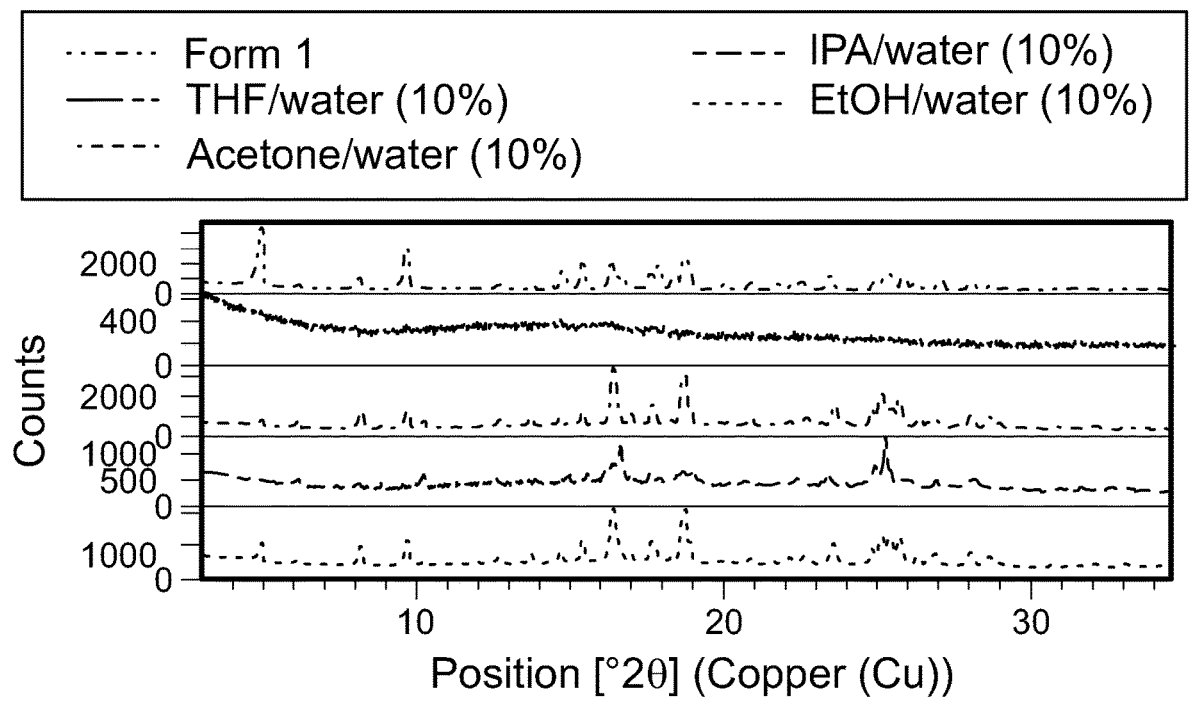

The post-cycling and post-stability XRPD scans for L-malic acid are shown in FIGS. 23A and 23B, respectively.

TABLE 27

Hippuric acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | White solid in yellow solution | White solid | White solid | White solid | White solid | White solid |
| XRPD post-cycling | Form 8 | Form 1 (freebase)/ Form 8 | Form 1 (freebase) | Form 1 (freebase) | Form 8 | Form 8 |
| XRPD post-stability | Form 8 | Form 1 (freebase)/ Form 8 | Form 1 (freebase) | Form 1 (freebase) | Form 1 (freebase)/ Form 8 | Form 1 (freebase)/ Form 8 |

Figure 24A:
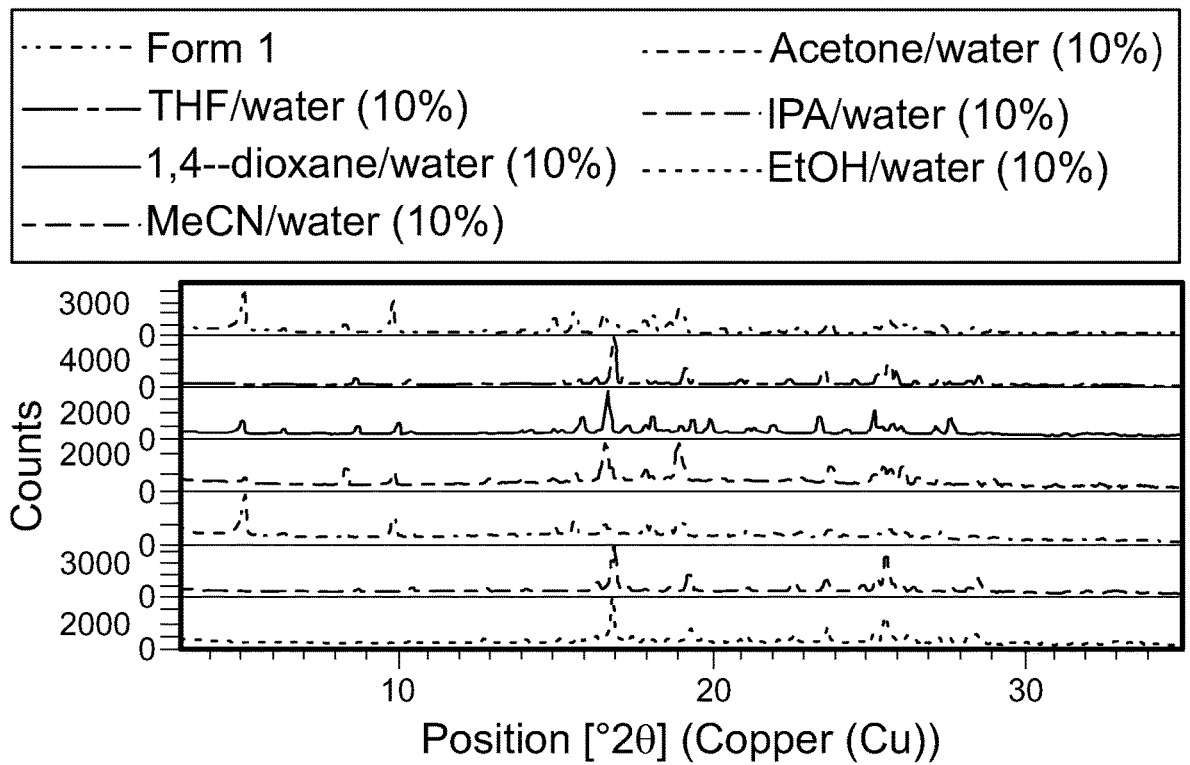
FIGS. 24A-24B are x-ray powder diffraction scans from a salt screen of the compound of Formula (I) with hippuric acid.
Figure 24B:
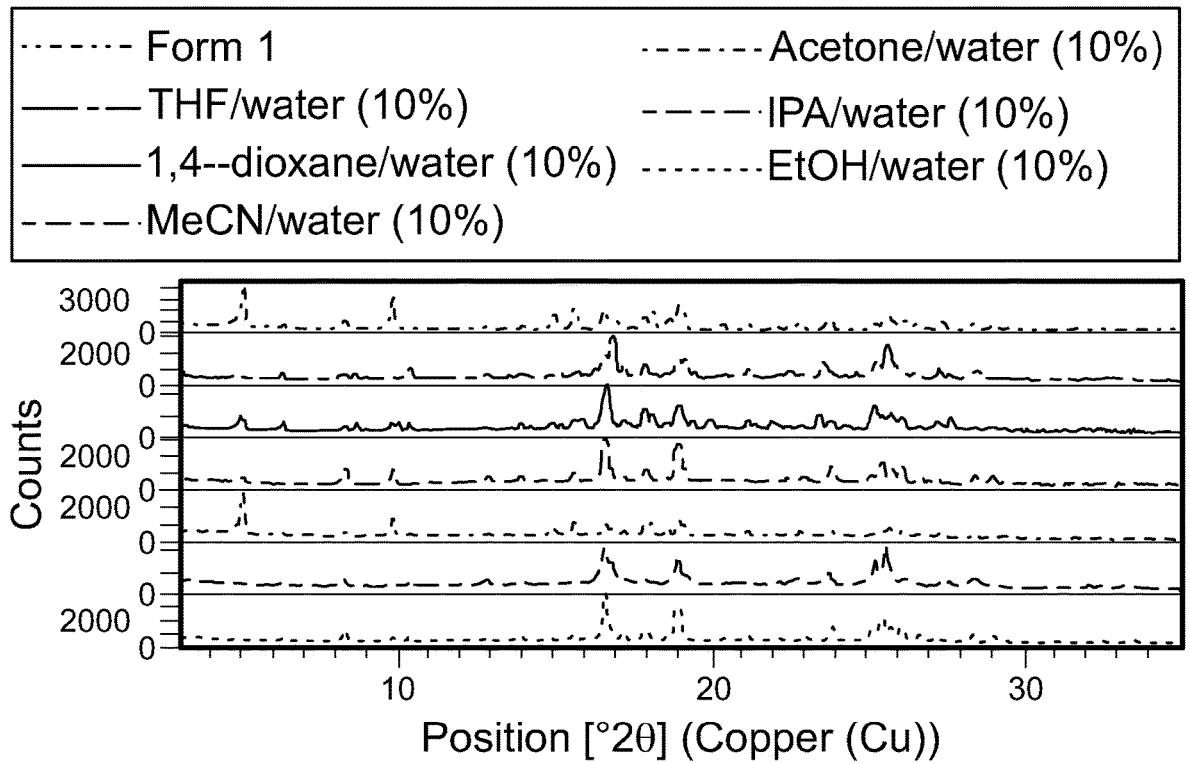

The post-cycling and post-stability XRPD scans for hippuric acid are shown in FIGS. 24A and 24B, respectively.

TABLE 28

D-Gluconic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow solid | White solid | White solid | White solid | White solid | White solid |
| XRPD post-cycling | Form 13 | Form 7 | Form 1 (freebase) | Form 1 (freebase) | Form 8 | Form 1 (freebase)/ Form 8 |
| XRPD post-stability | Form 13 | Form 7 | Form 1 (freebase) | Form 1 (freebase) | Form 1 (freebase)/ Form 8 | Form 1 (freebase)/ Form 8 |

Figure 25A:
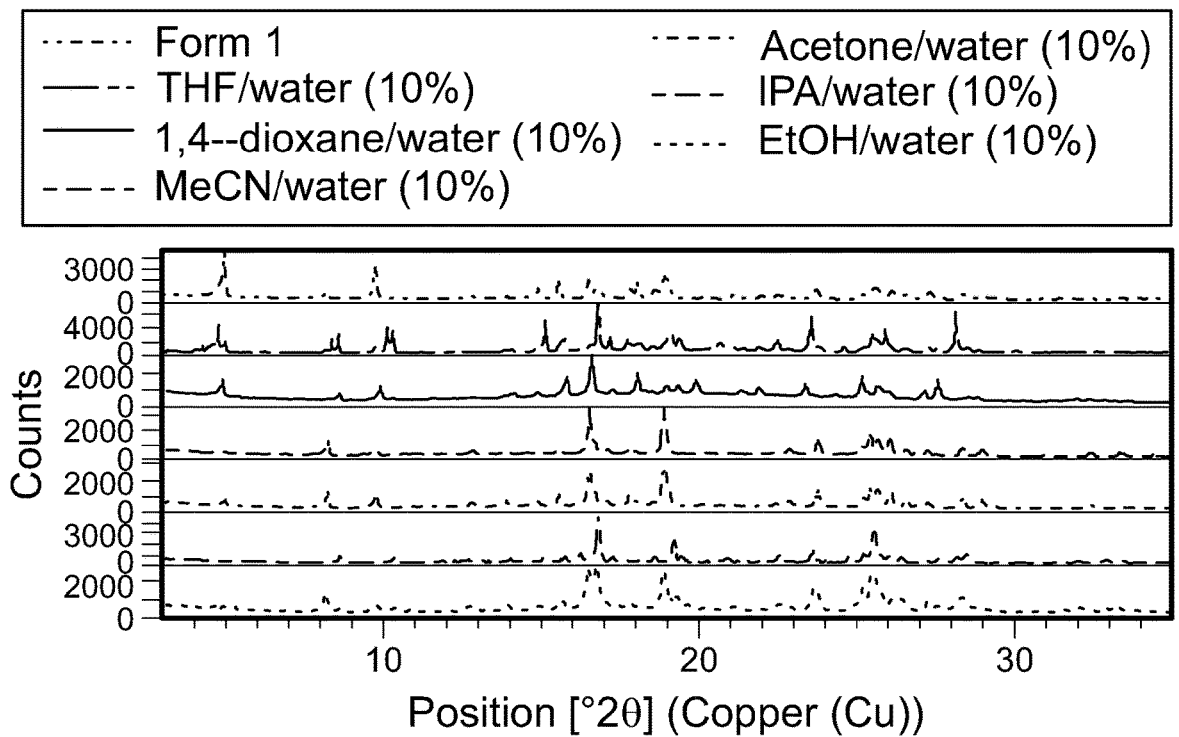
FIGS. 25A-25B are x-ray powder diffraction scans from a salt screen of the compound of Formula (I) with D-gluconic acid.
Figure 25B:
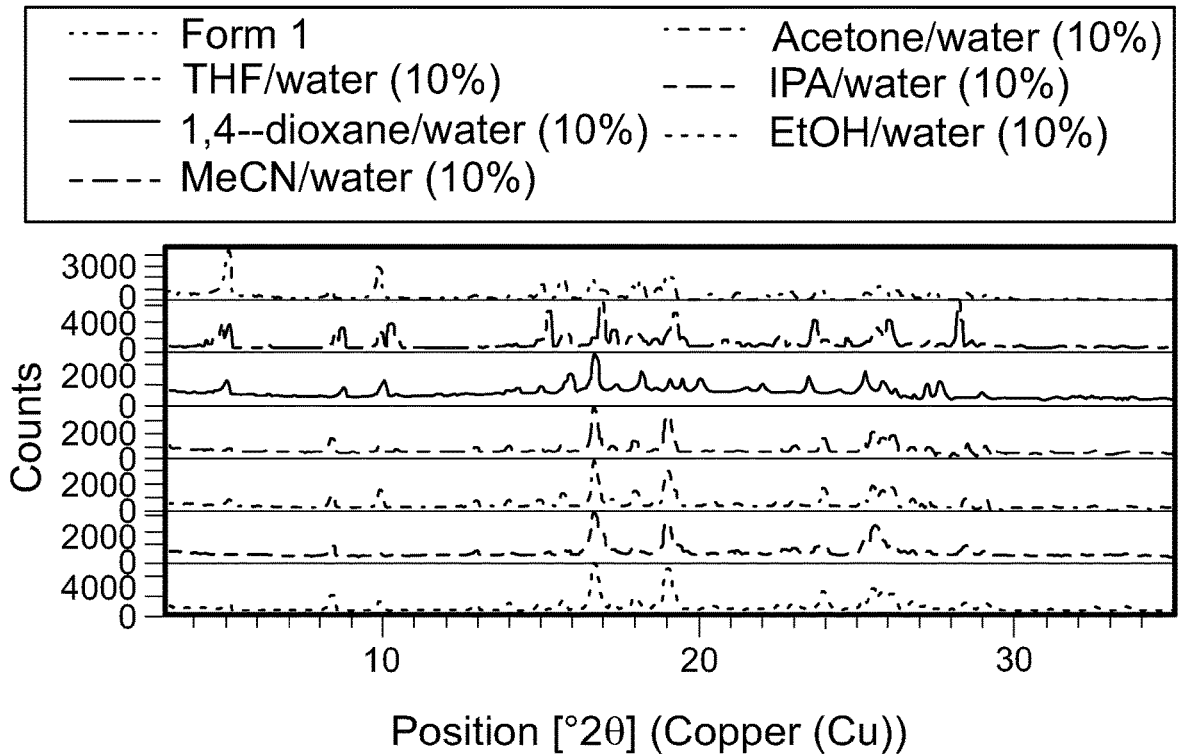

The post-cycling and post-stability XRPD scans for D-gluconic acid are shown in FIGS. 25A and 25B, respectively.

TABLE 29

L-Lactic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Pale yellow solid | White solid | White solid | White solid | White solid | White solid |
| XRPD post-cycling | Form 13 | Form 1 (freebase) | Form 1 (freebase) | Form 1 (freebase) | Form 8 | Form 8 |
| XRPD post-stability | Form 13 | Form 1 (freebase) | Form 1 (freebase) | Form 1 (freebase) | Form 8 | Form 1 (freebase)/ Form 8 |

Figure 26A:
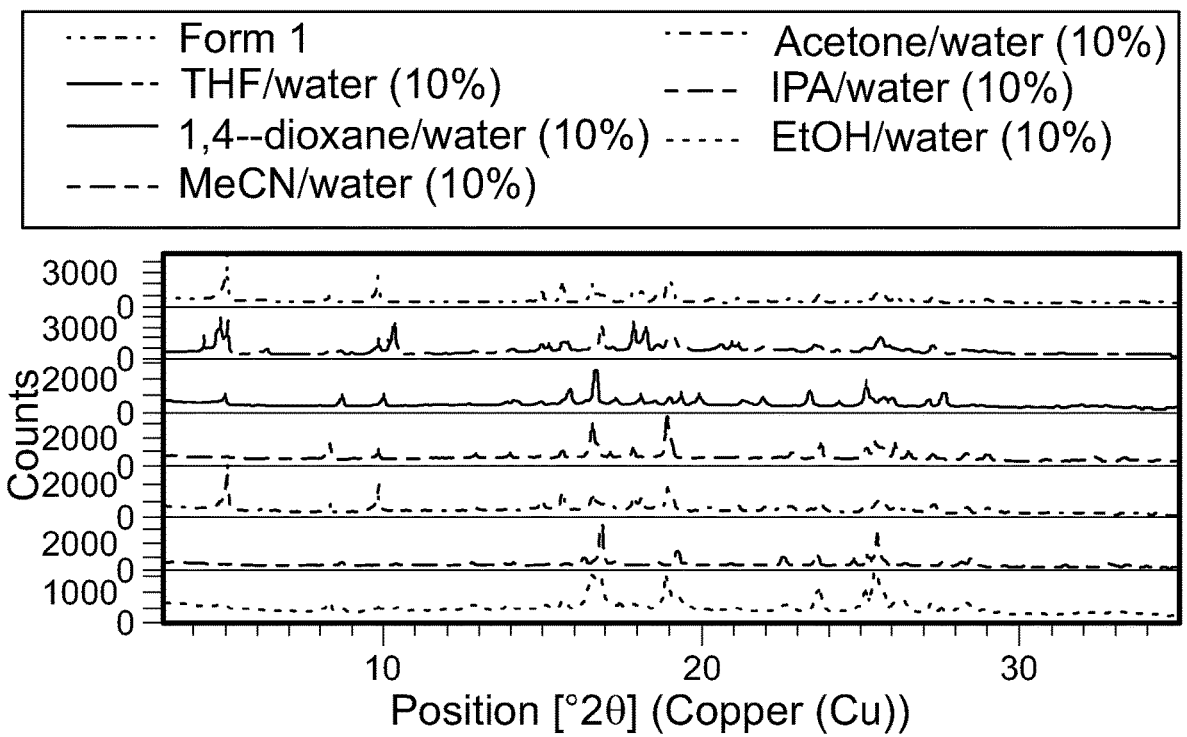
FIGS. 26A-26B are x-ray powder diffraction scans from a salt screen of the compound of Formula (I) with L-lactic acid.
Figure 26B:
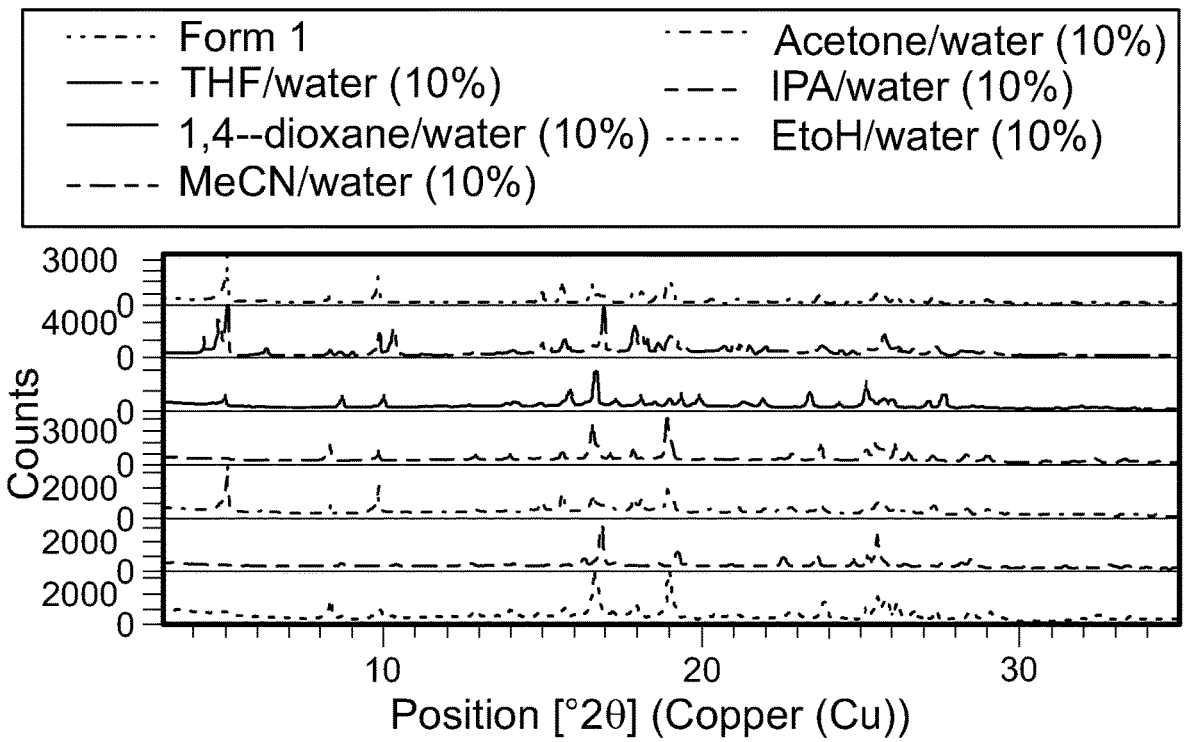

The post-cycling and post-stability XRPD scans for L-lactic acid are shown in FIGS. 26A and 26B, respectively.

TABLE 30

L-Ascorbic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | Yellow solution | White solid in yellow solution | Orange solid | Orange solid | Yellow solid | Yellow solid |
| XRPD post-cycling | No solid | Form 1 (freebase) | Form 1 (freebase) | Form 1 (freebase) | Form 8 | Form 1 (freebase)/ Form 8 |
| XRPD post-stability | No solid | Form 1 (freebase)/ Form 2 | Form 1 (freebase) | Form 1 (freebase)/ Form 2 | Form 1 (freebase)/ Form 8 | Form 1 (freebase)/ Form 8 |

Figure 27A:
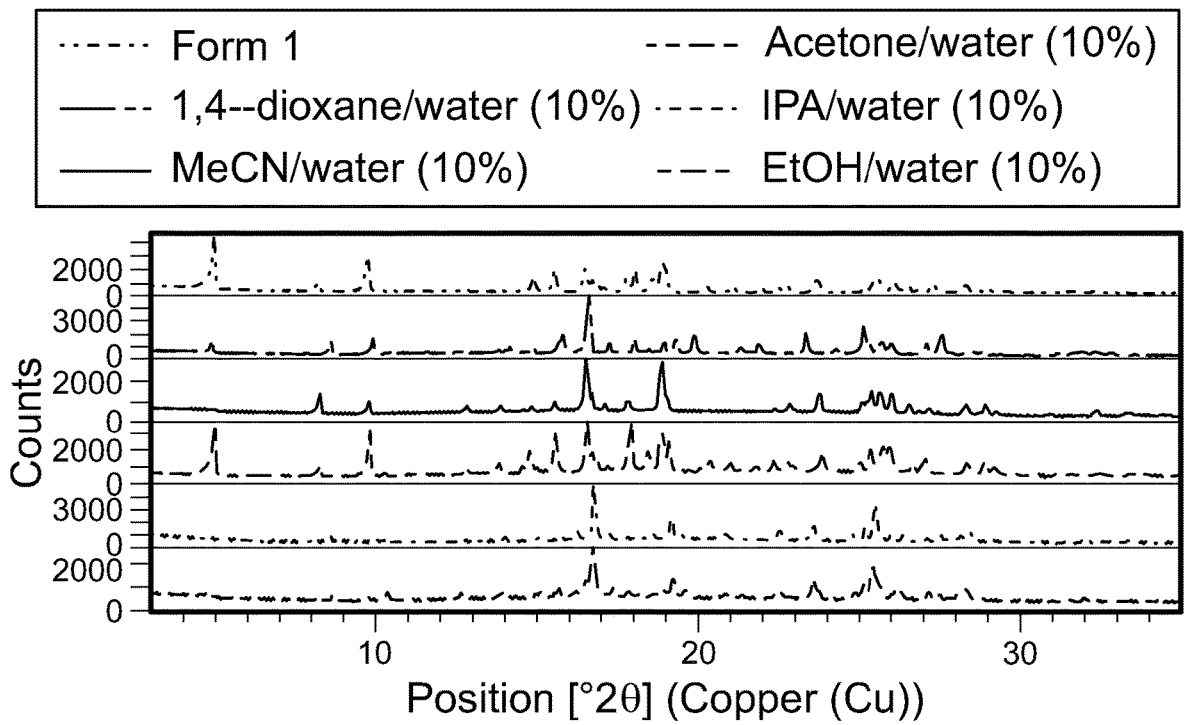
FIGS. 27A-27B are x-ray powder diffraction scans from a salt screen of the compound of Formula (I) with L-ascorbic acid.
Figure 27B:
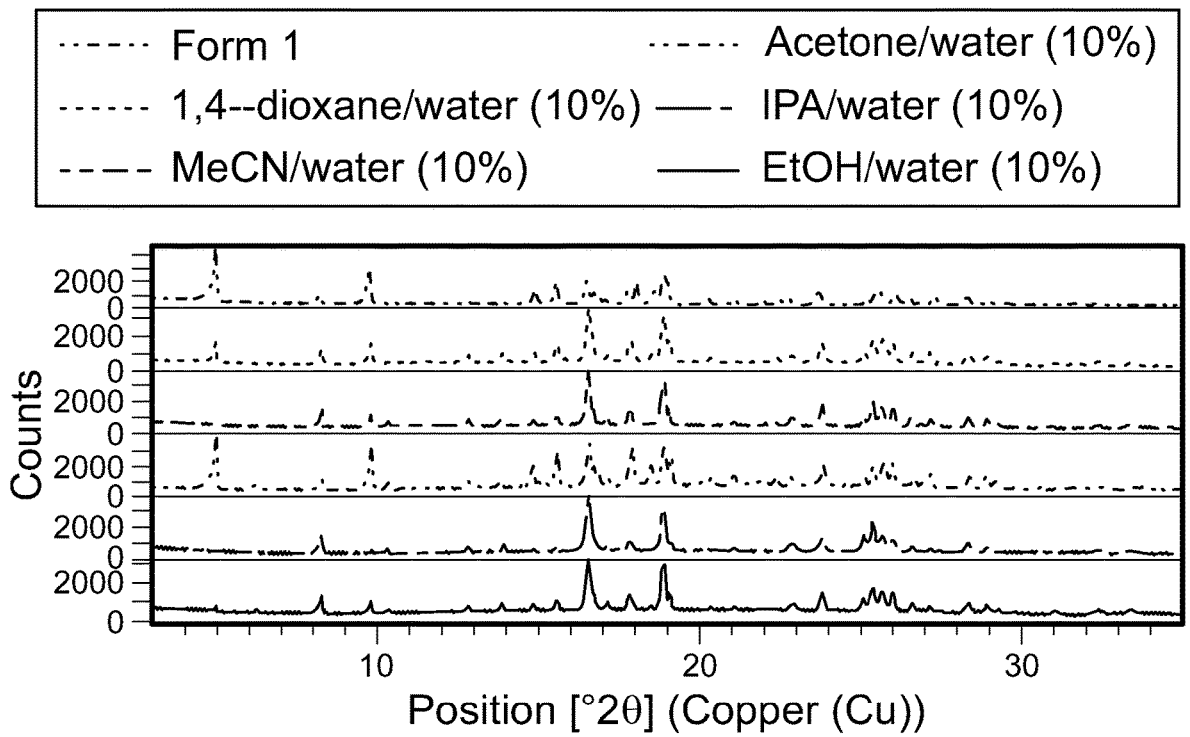

The post-cycling and post-stability XRPD scans for L-ascorbic acid are shown in FIGS. 27A and 27B, respectively.

TABLE 31

Benzoic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | White solid | White solid | White solid | White solid | White solid | White solid |
| XRPD post-cycling | Form 8 | Form 1 (freebase)/ Form 8 | Form 1 (freebase)/ Form 8 | Form 1 (freebase) | Form 8 | Form 8 |
| XRPD post-stability | Form 1 (freebase)/ Form 8 | Form 1 (freebase)/ Form 8 | Form 1 (freebase)/ Form 8 | Form 1 (freebase) | Form 1 (freebase)/ Form 8 | Form 1 (freebase)/ Form 8 |

Figure 28A:
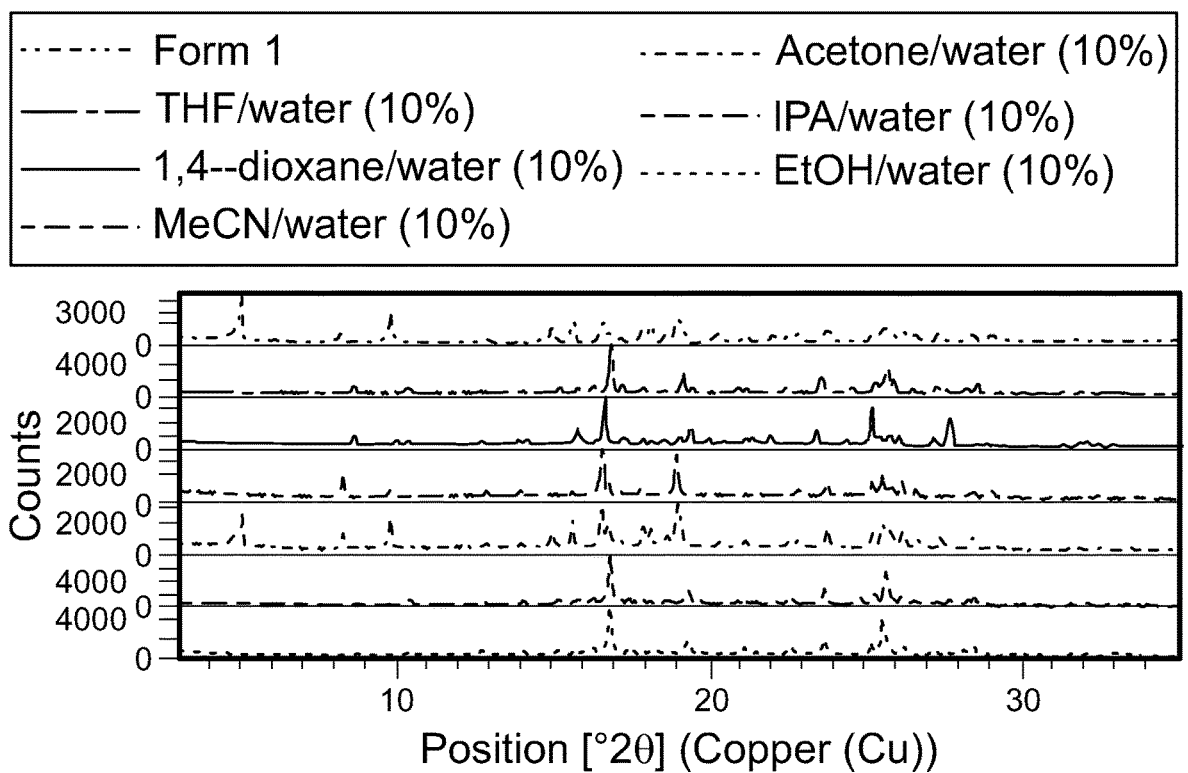
FIGS. 28A-28B are x-ray powder diffraction scans from a salt screen of the compound of Formula (I) with benzoic acid.
Figure 28B:
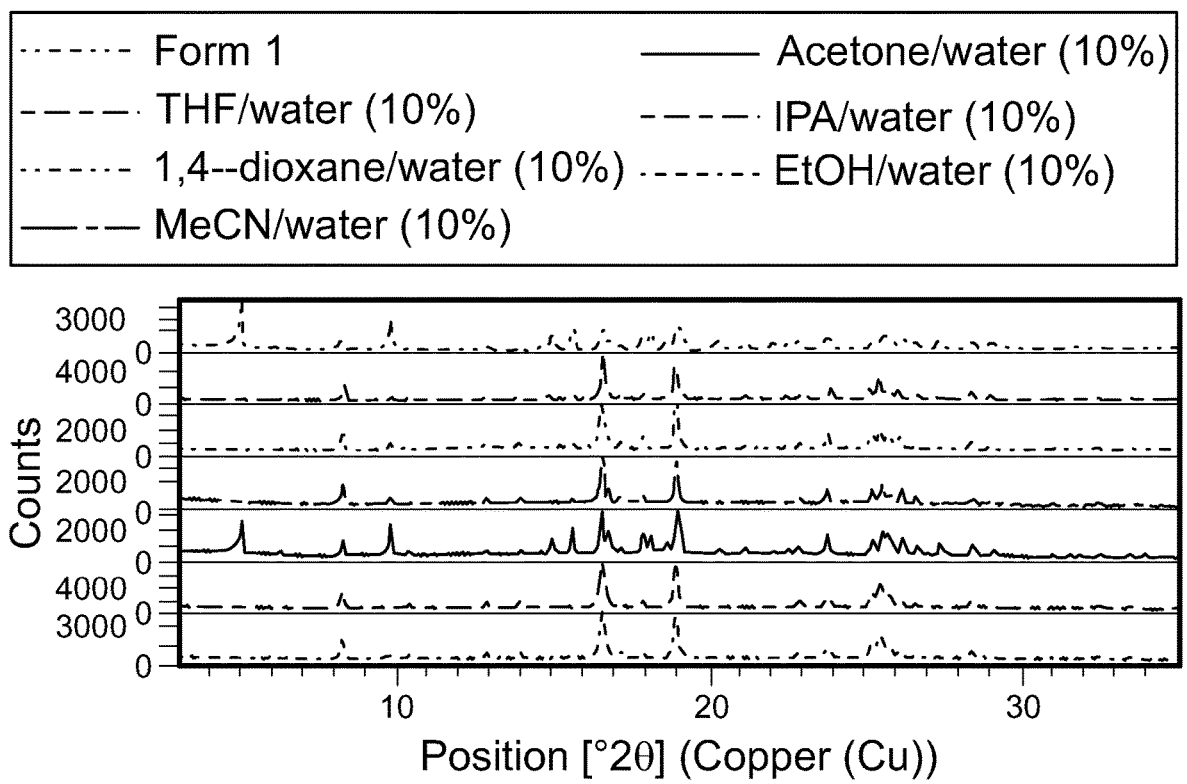

The post-cycling and post-stability XRPD scans for benzoic acid are shown in FIGS. 28A and 28B, respectively.

TABLE 32

Succinic acid observations and XRPD results

| | Solvent | | | | | |
|---|---|---|---|---|---|---|
| | THF/ water (1%) | Dioxane/ water (10%) | MeCN/ water (20%) | Acetone/ water (10%) | IPA/ water (10%) | EtOH/ water (10%) |
| Pre-cycling | Slurry | Slurry | Slurry | Slurry | Slurry | Slurry |
| Post-cycling | White solid in yellow solution | White solid in yellow solution | White solid | White solid | White solid | White solid |
| XRPD post-cycling | Form 1 (freebase)/ Form 8 | Form 1 (freebase)/ Form 8 | Form 8 | Form 1 (freebase) | Form 8 | Weak diffraction |
| XRPD post-stability | Form 1 (freebase)/ Form 8 | Form 1 (freebase) | Form 8 | Form 1 (freebase) | Form 1 (freebase) | Form 1 (freebase) |

Figure 29A:
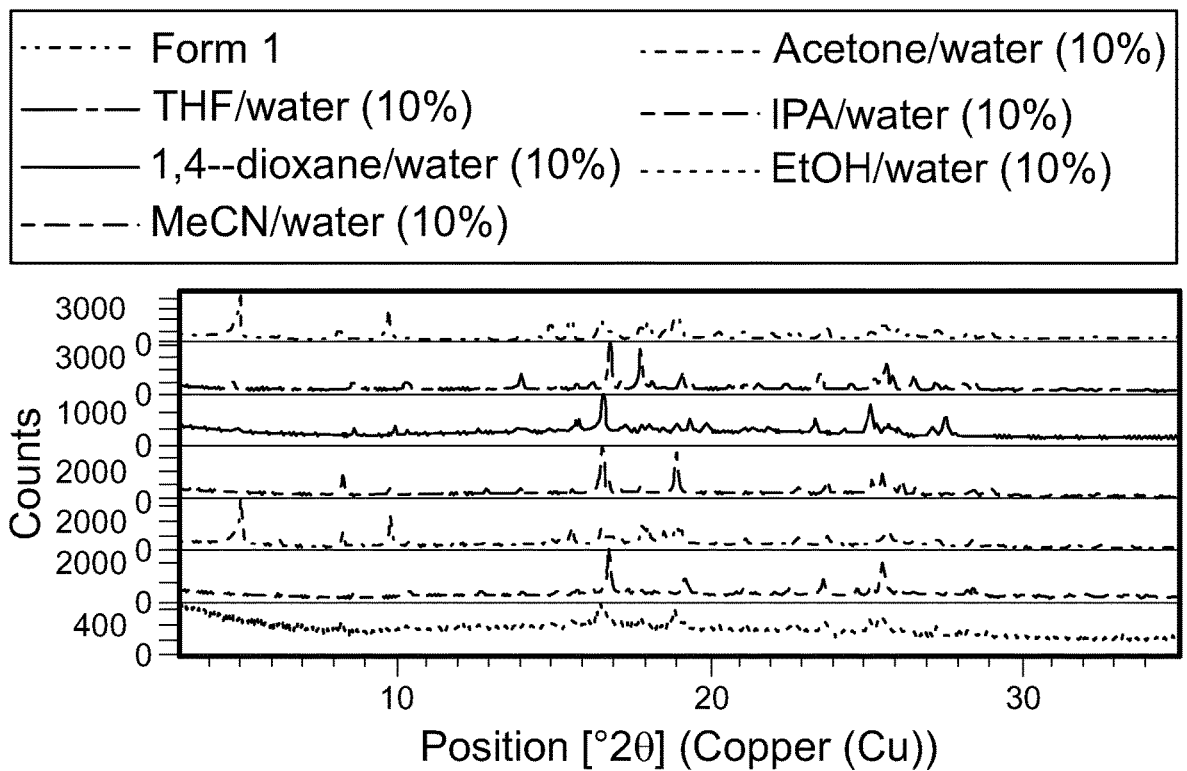
FIGS. 29A-29B are x-ray powder diffraction scans from a salt screen of the compound of Formula (I) with succinic acid.
Figure 29B:
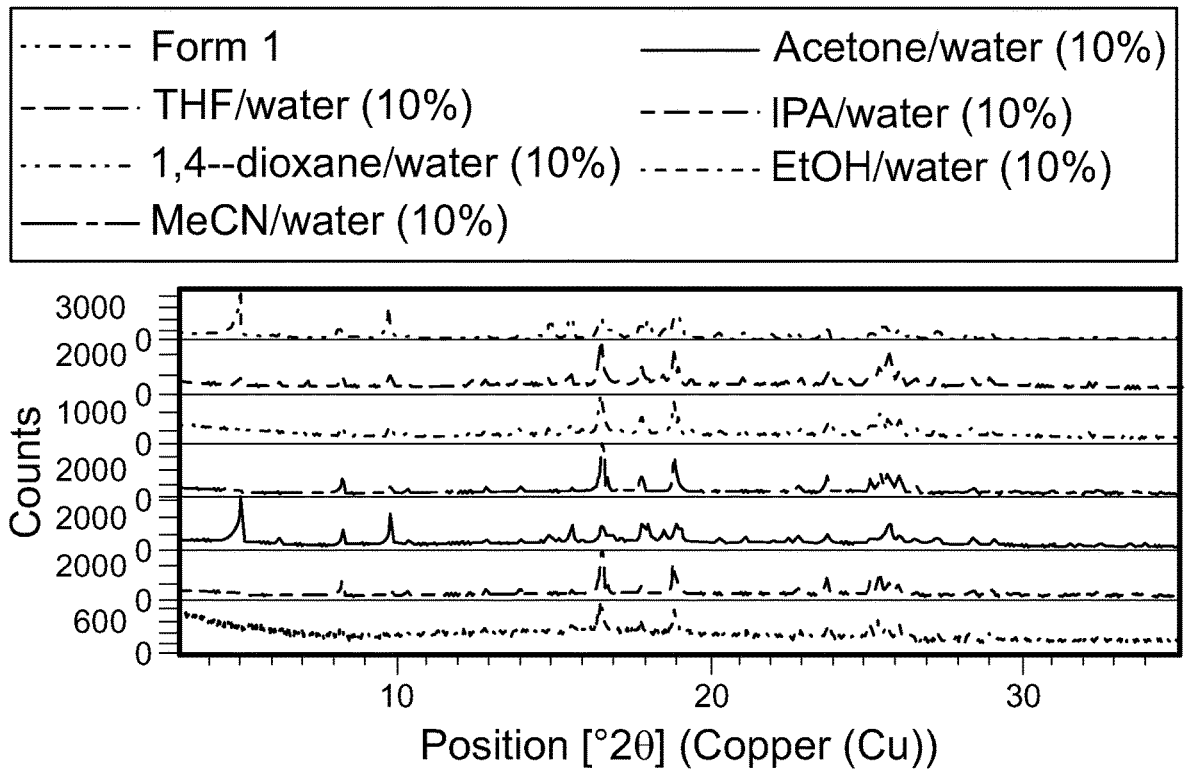

The post-cycling and post-stability XRPD scans for succinic acid are shown in FIGS. 29A and 29B, respectively.

From the XRPD results of the primary salt screen, initial salt hits were identified and are shown below in Table 33.

TABLE 33

Initial salt hits from XRPD

| | |
|---|---|
| 1 | Sulfate prepared in IPA/water (10%) |
| 2 | Tosylate prepared in acetone/water (10%) |
| 3 | Naphthalene-2-sulfonate prepared in THF/water (10%) |
| 4 | Oxalate prepared in 1,4-dioxane/water (10%) |
| 5 | Oxalate prepared from evaporation from THF/water |
| 6 | Phosphate prepared in acetone/water (10%) |
| 7 | Phosphate prepared in IPA/water (10%) |
| 8 | Tartrate prepared in IPA/water (10%) |
| 9 | Fumarate prepared in THF/water |

Each salt was thermally analyzed using TG/DTA to identify possible salt forms. Eight of the nine initial hits were determined to be solvates or hydrates. The following results were obtained.

Figure 30:
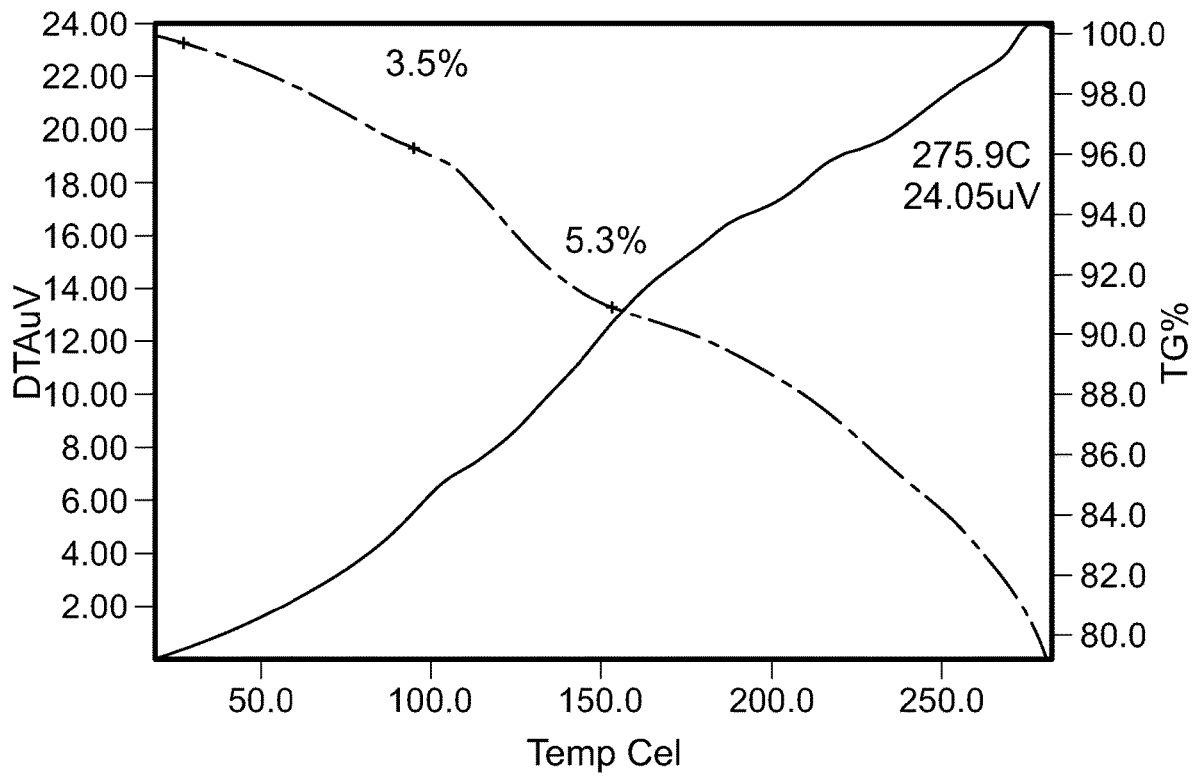
FIG. 30 is a thermogravimetric/differential thermal analysis scan of the sulfate salt of the compound of Formula (I) identified in the primary salt screen.

Sulfate (IPA/water (10%)): weight loss was observed from the onset of heating. No distinct thermal transitions were observed. Thermal degradation was observed around 257° C. The TG/DTA scan of the sulfate salt is shown in FIG. 30.

Figure 31:
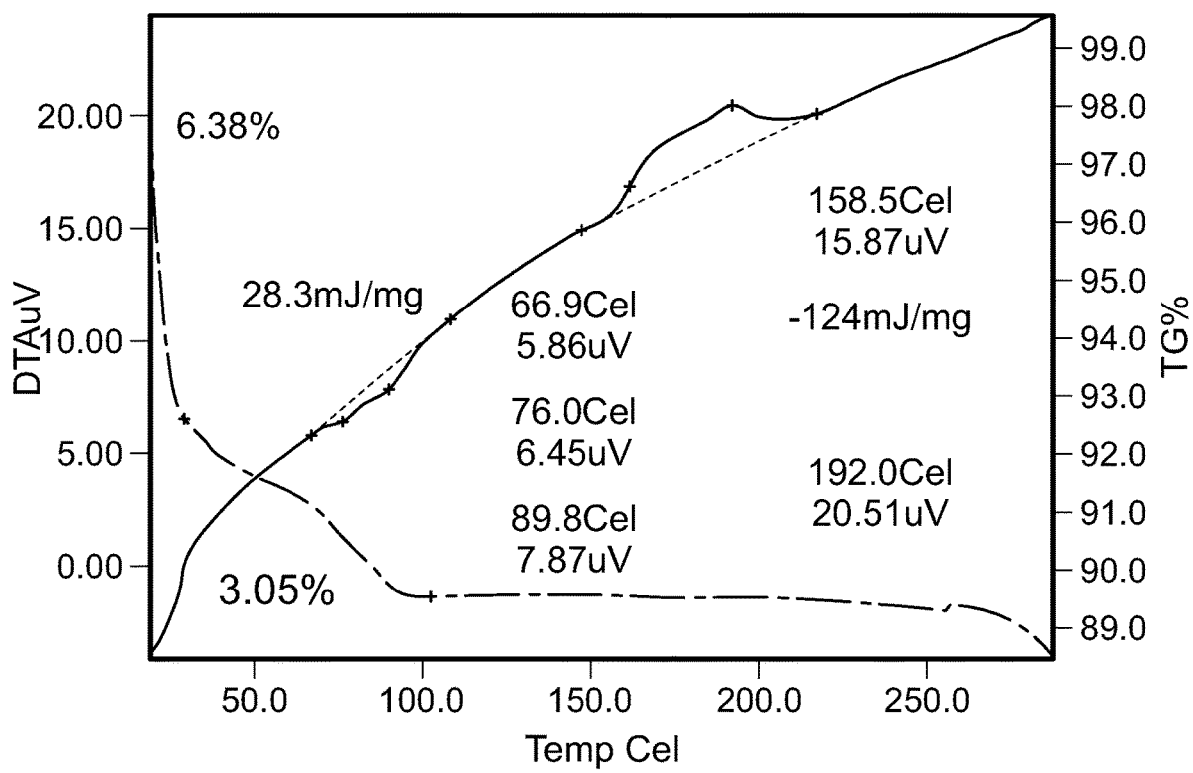
FIG. 31 is a thermogravimetric/differential thermal analysis scan of the tosylate salt of the compound of Formula (I) identified in the primary salt screen.

Tosylate (acetone/water (10%)): a weight loss of approximately 6% was observed from the onset of heating followed by a second weight loss of 3% due to solvent loss. A broad endotherm was observed from an onset of about 28° C. followed by a broad exotherm from an onset of around 158° C. Thermal degradation was observed from around 192° C. The TG/DTA scan of the tosylate salt is shown in FIG. 31.

Figure 32:
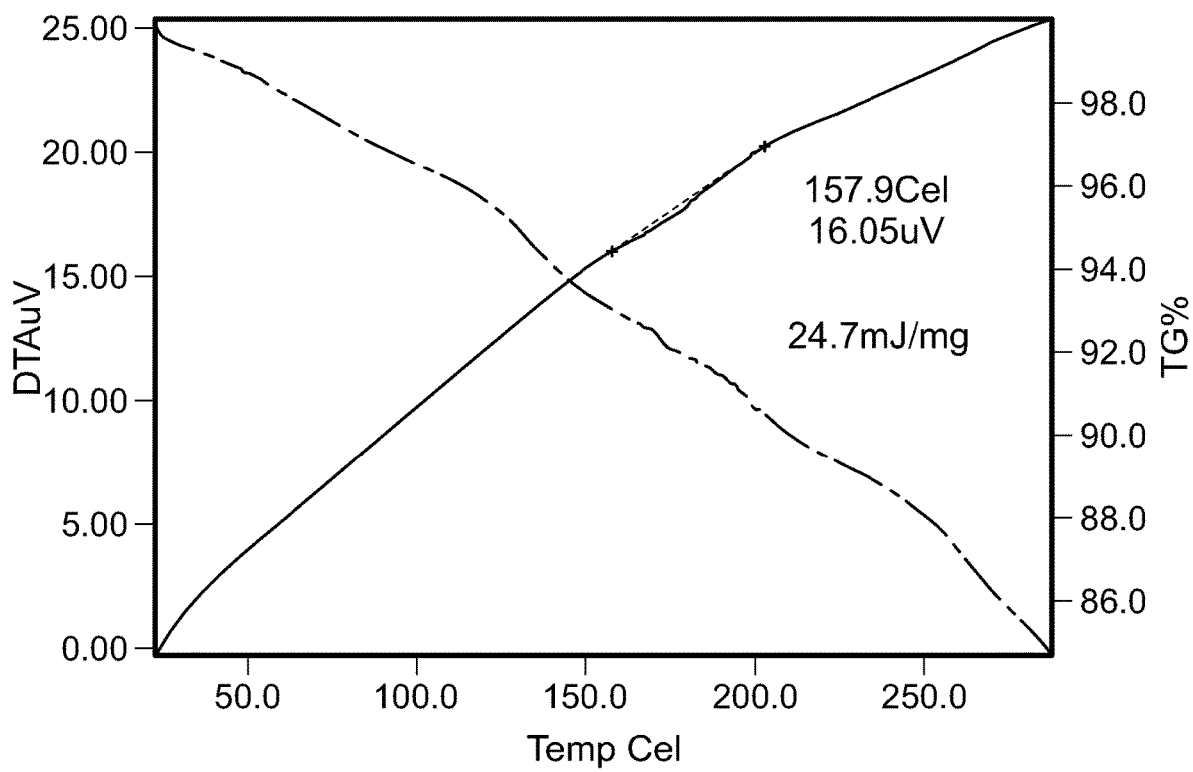
FIG. 32 is a thermogravimetric/differential thermal analysis scan of the naphthalene-2-sulfonate salt of the compound of Formula (I) identified in the primary salt screen.

Naphthalene-2-sulfonate (THF/water (10%)): weight loss was observed from the onset of heating. No distinct thermal transitions were observed. The TG/DTA scan of the naphthalene-2-sulfonate salt is shown in FIG. 32.

Figure 33:
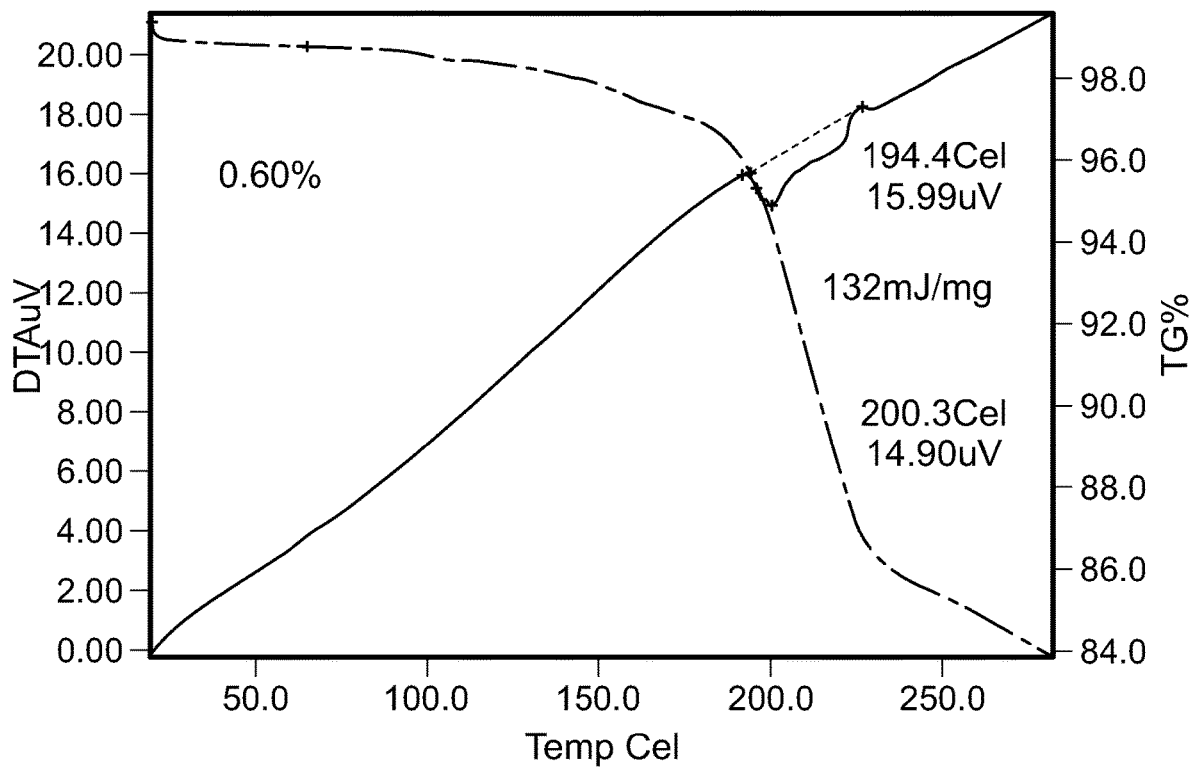
FIG. 33 is a thermogravimetric/differential thermal analysis scan of the oxalate salt (1,4-dioxane/10% water) of the compound of Formula (I) identified in the primary salt screen.

Oxalate (1,4-dioxane/water (10%)): a weight loss of approximately 0.6% was observed from the onset of heating. A broad endotherm was observed from an onset of 194° C. followed by thermal degradation. The TG/DTA scan of the oxalate salt is shown in FIG. 33.

Figure 34:
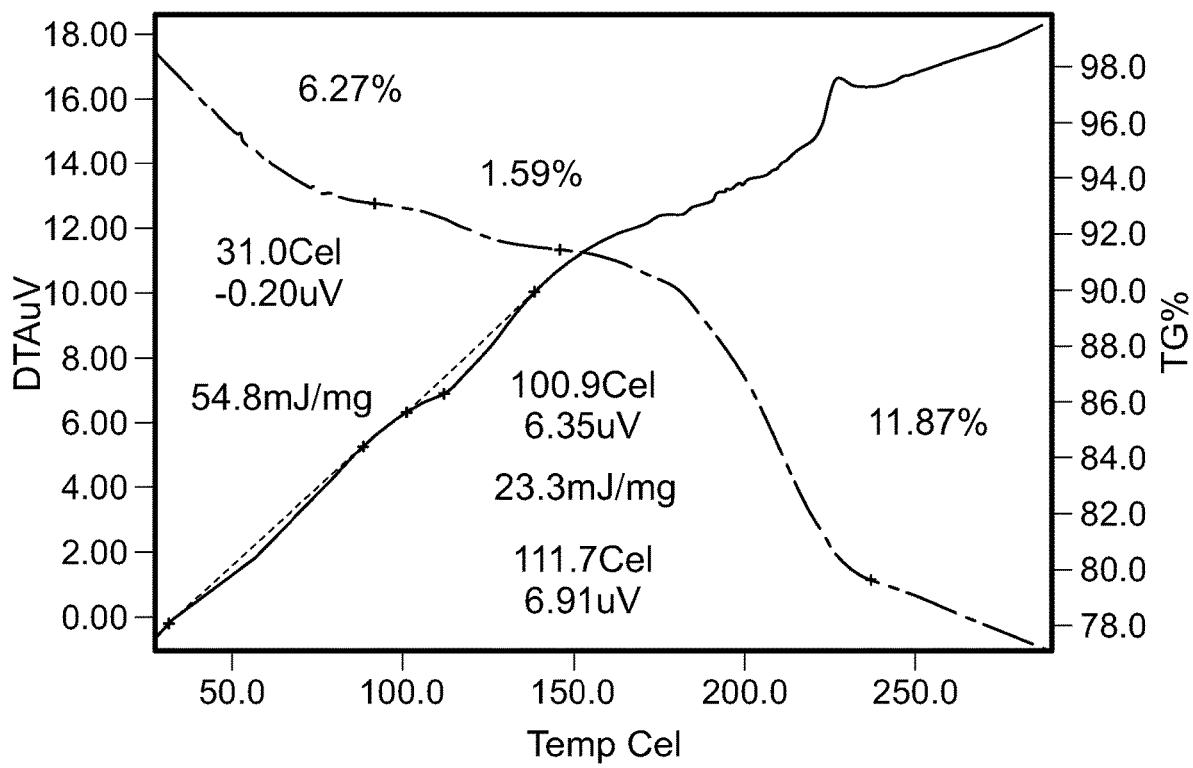
FIG. 34 is a thermogravimetric/differential thermal analysis scan of the oxalate salt (evaporation) of the compound of Formula (I) identified in the primary salt screen.

Oxalate (evaporation from THF/water): a broad endotherm was observed from an onset of around 31° C. with a corresponding weight loss of approximately 6.2%. A broad endotherm was observed from an onset of around 100° C. with a corresponding weight loss of approximately 1.6%. Thermal degradation was observed from around 150° C. DSC analysis showed a broad endotherm from an onset of around 27° C. The TG/DTA scan of the oxalate salt is shown in FIG. 34.

Figure 35:
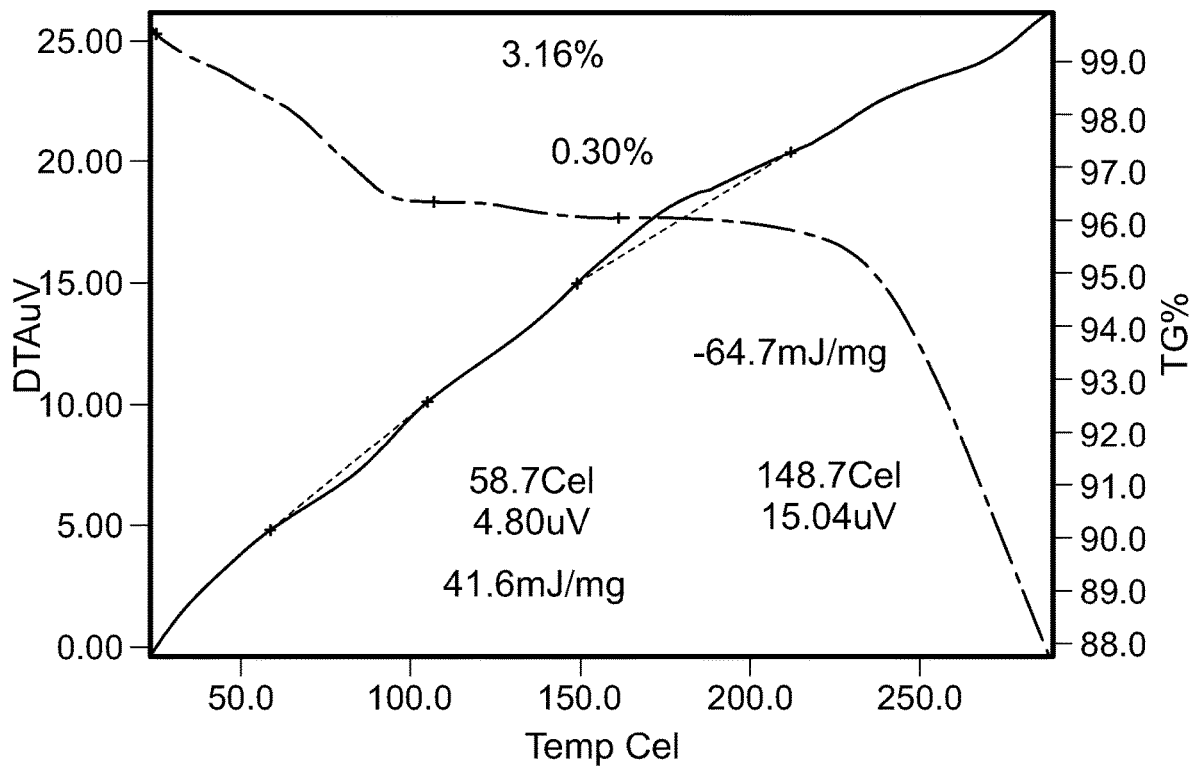
FIG. 35 is a thermogravimetric/differential thermal analysis scan of the phosphate salt (acetone/10% water) of the compound of Formula (I) identified in the primary salt screen.

Phosphate (acetone/water (10%)): A weight loss of approximately 3% was observed from the onset of heating. The TG/DTA scan of the phosphate salt is shown in FIG. 35.

Figure 36:
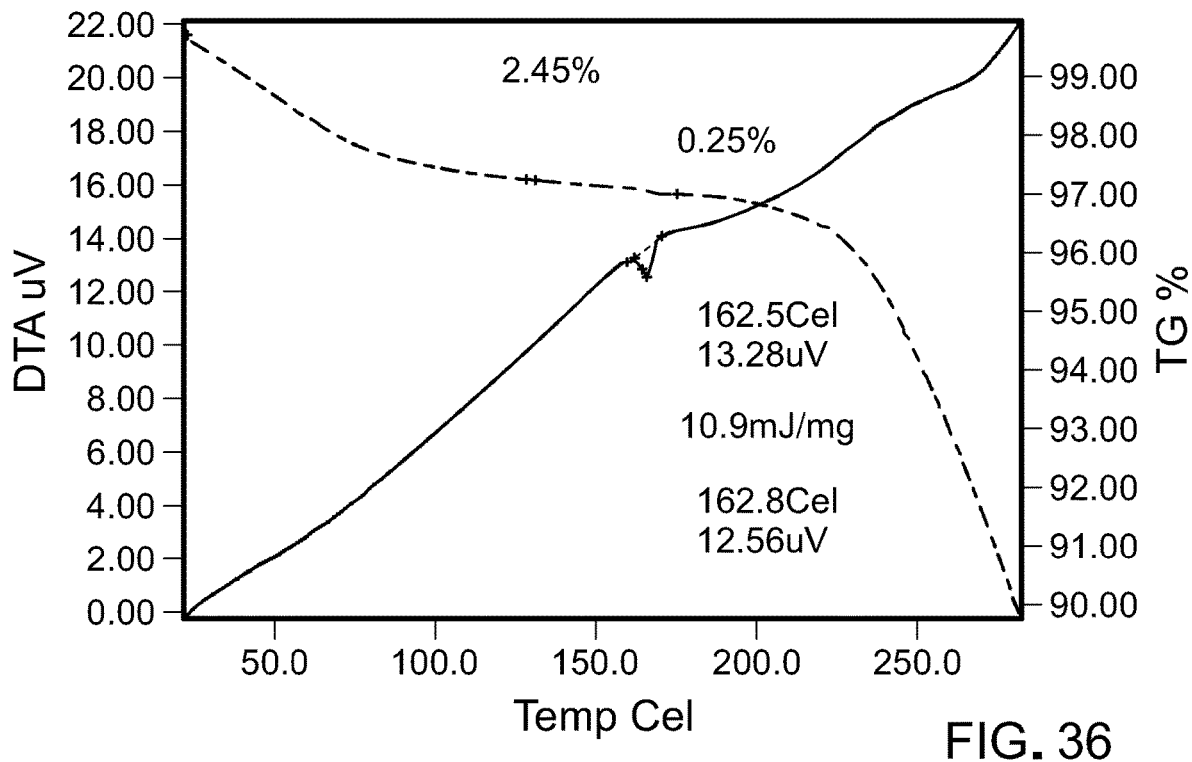
FIG. 36 is a thermogravimetric/differential thermal analysis scan of the phosphate salt (IPA/10% water) of the compound of Formula (I) identified in the primary salt screen.

Phosphate (IPA/water (10%)): A weight loss of approximately 2.5% was observed from the onset of heating. A small endotherm was observed at an onset of around 162° C. Thermal degradation was observed after 200° C. The TG/DTA scan of the phosphate salt is shown in FIG. 36.

Figure 37:
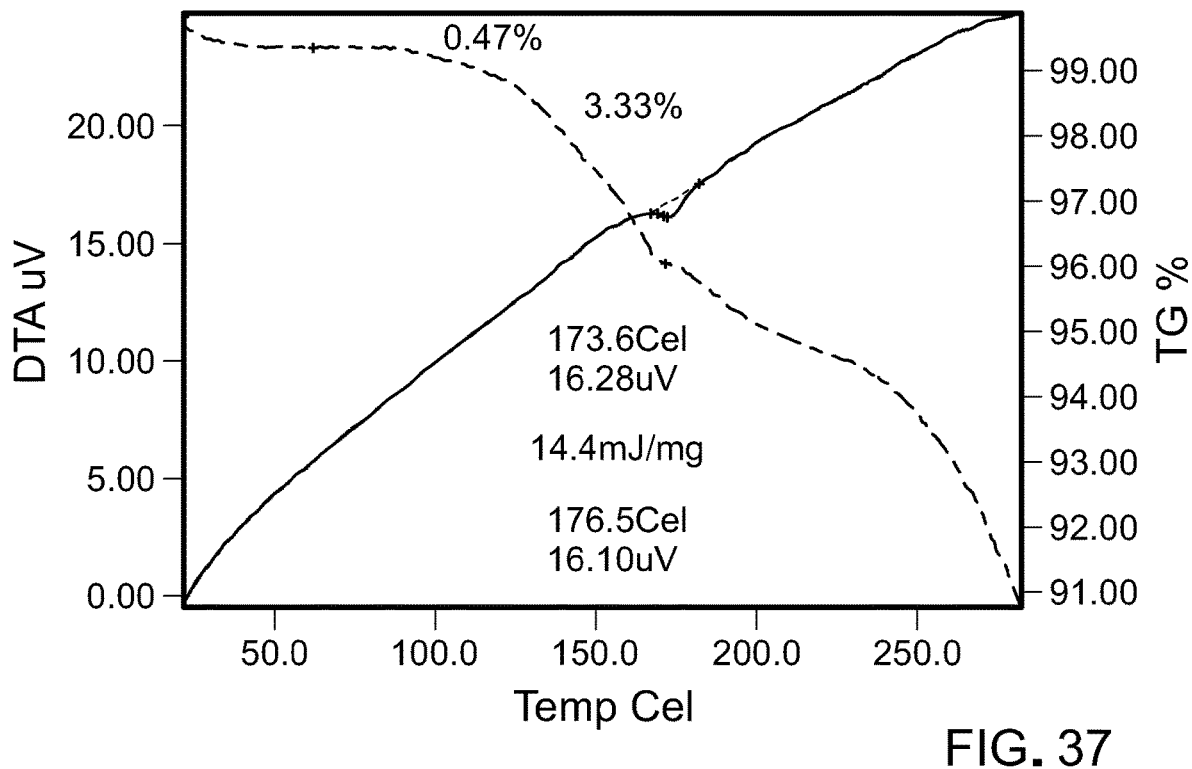
FIG. 37 is a thermogravimetric/differential thermal analysis scan of the tartrate salt of the compound of Formula (I) identified in the primary salt screen.

Tartrate (IPA/water (10%)): A weight loss of approximately 3.7% was observed from the onset of heating. A small endotherm was observed from an onset of around 173° C. followed by thermal degradation. The TG/DTA scan of the tartrate salt is shown in FIG. 37.

Figure 38:
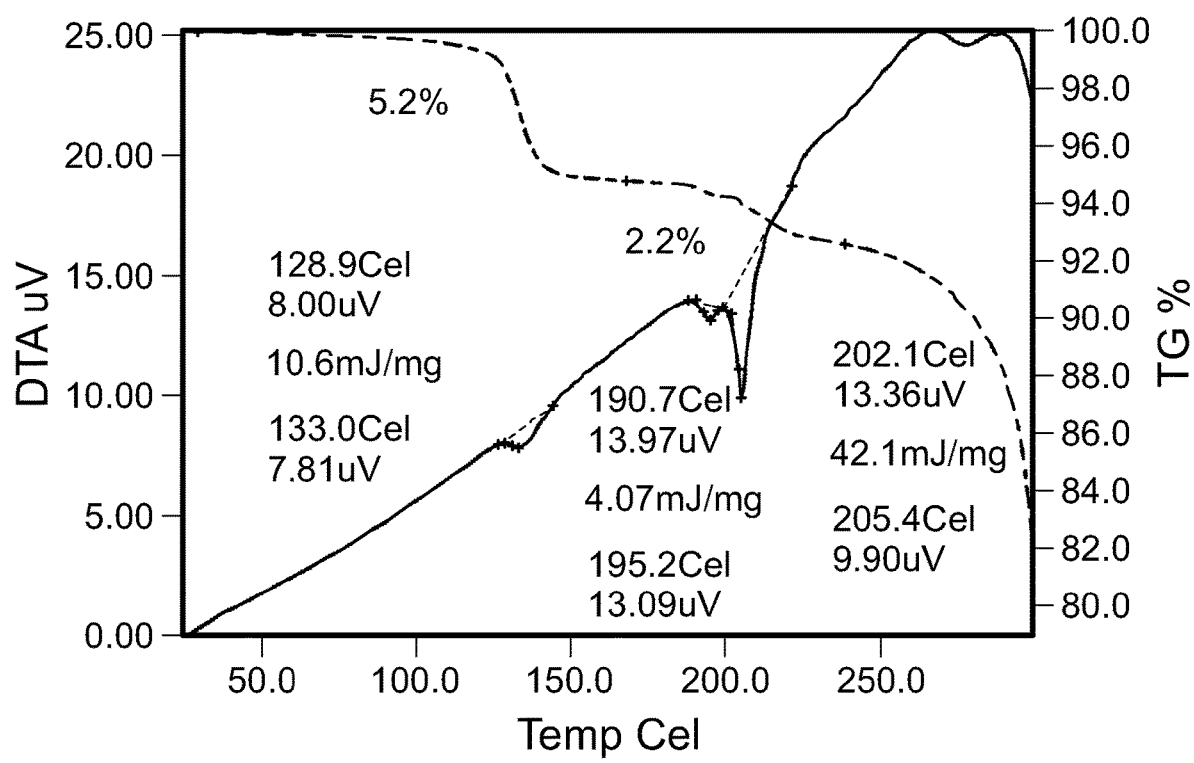
FIG. 38 is a thermogravimetric/differential thermal analysis scan of the fumarate salt of the compound of Formula (I) identified in the primary salt screen.

Fumarate (THF/water): A weight loss of 5.2% was observed from an onset of 128° C. corresponding to a small endotherm at the same temperature. A second small endotherm was observed at an onset of around 190° C. with a corresponding weight loss of 2.2%. A sharp melting endotherm was observed at an onset of 202° C. relating to the melt of Form 2 (free base). The TG/DTA scan of the fumarate salt is shown in FIG. 38.

D. Secondary Salt Screen

The phosphate salt prepared in IPA/water (10%) during the primary salt screen was scaled-up and further characterization. The scale-up procedure was as follows. 300 mg of the compound of Formula (I) was suspended in 3 mL of IPA/water (10%) (10 mL/g), then 1.0 equivalent of a 1M stock solution of phosphoric acid was added. The mixture was shaken and heat cycled for 4 hour increments at 40° C. overnight. The resulting solid was filtered and washed with IPA.

Figure 5A:
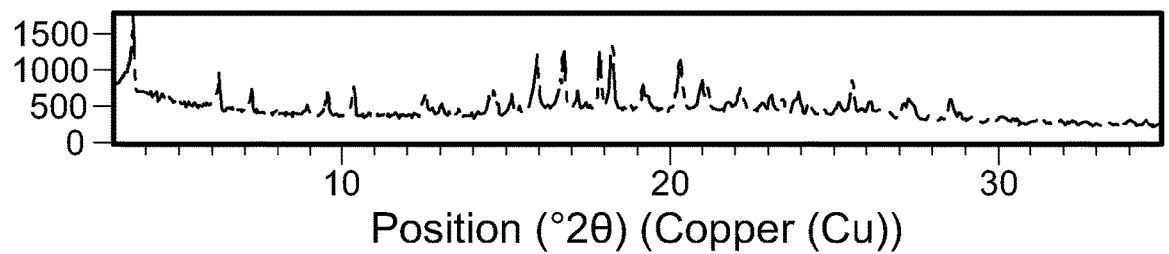
FIGS. 5A-5F are scans of the phosphate salt of the compound of Formula (I).
Figure 5B:
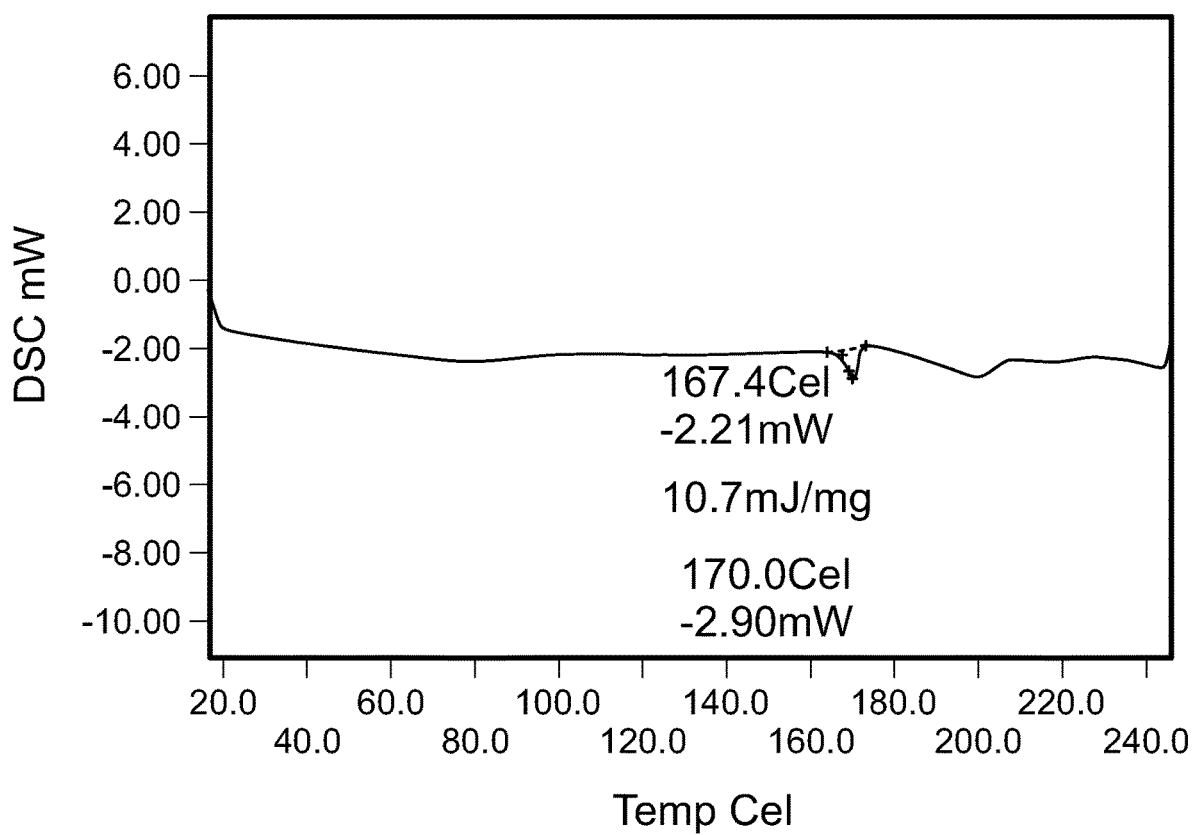
Figure 5C:
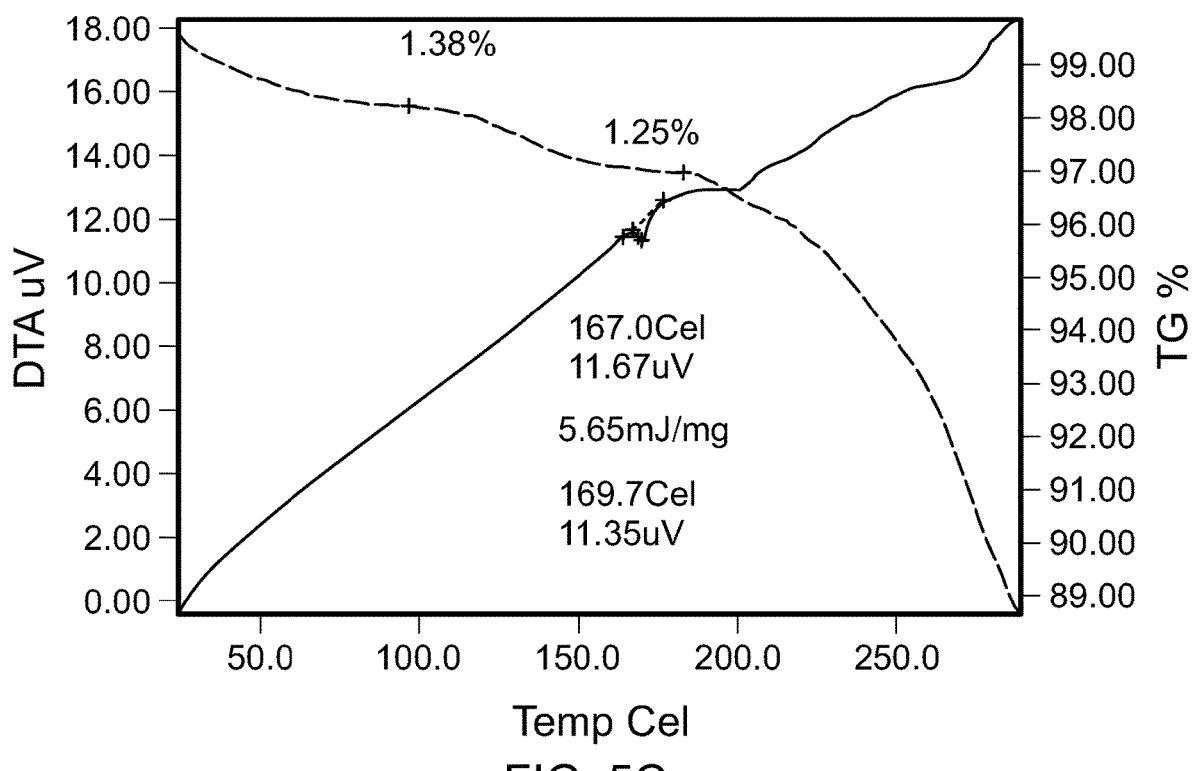
Figure 5D:
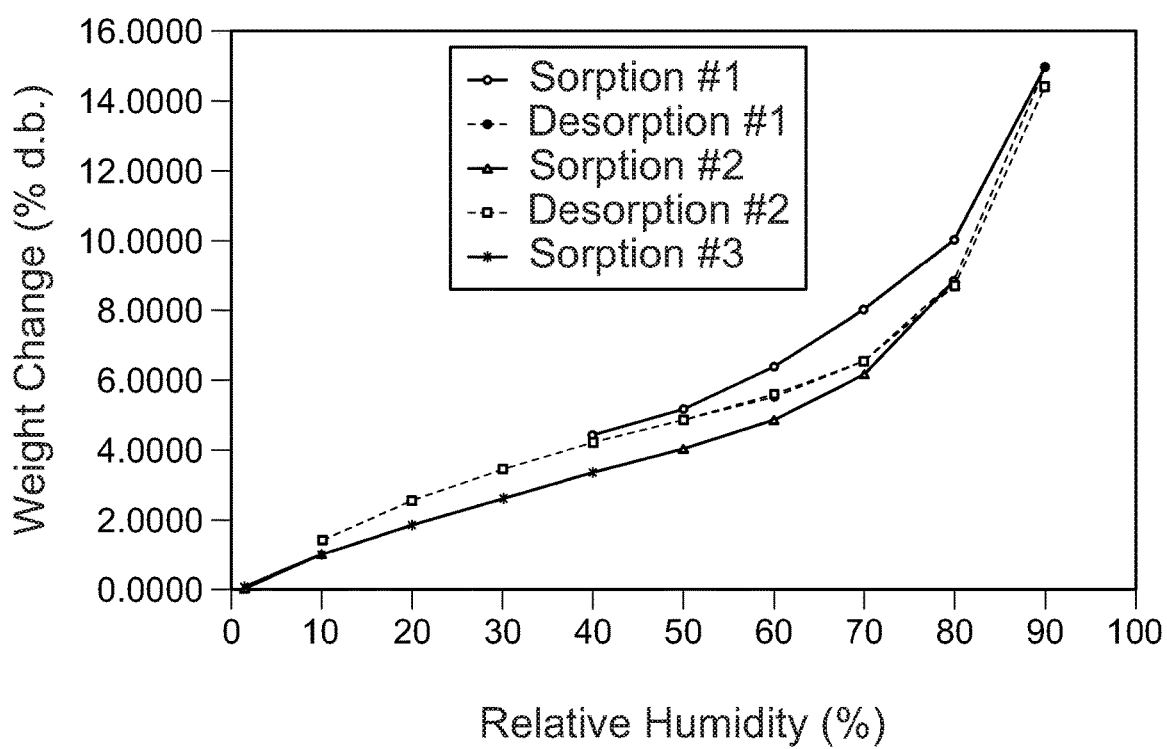
Figure 5E:
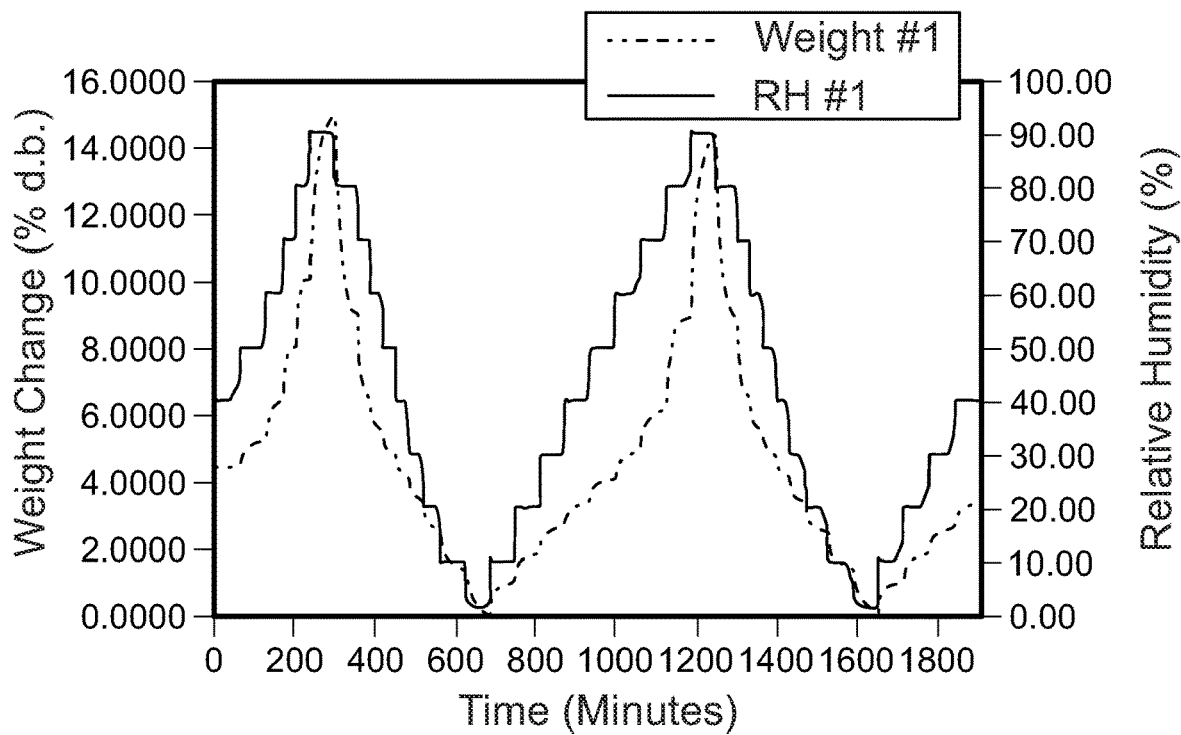
Figure 5F:
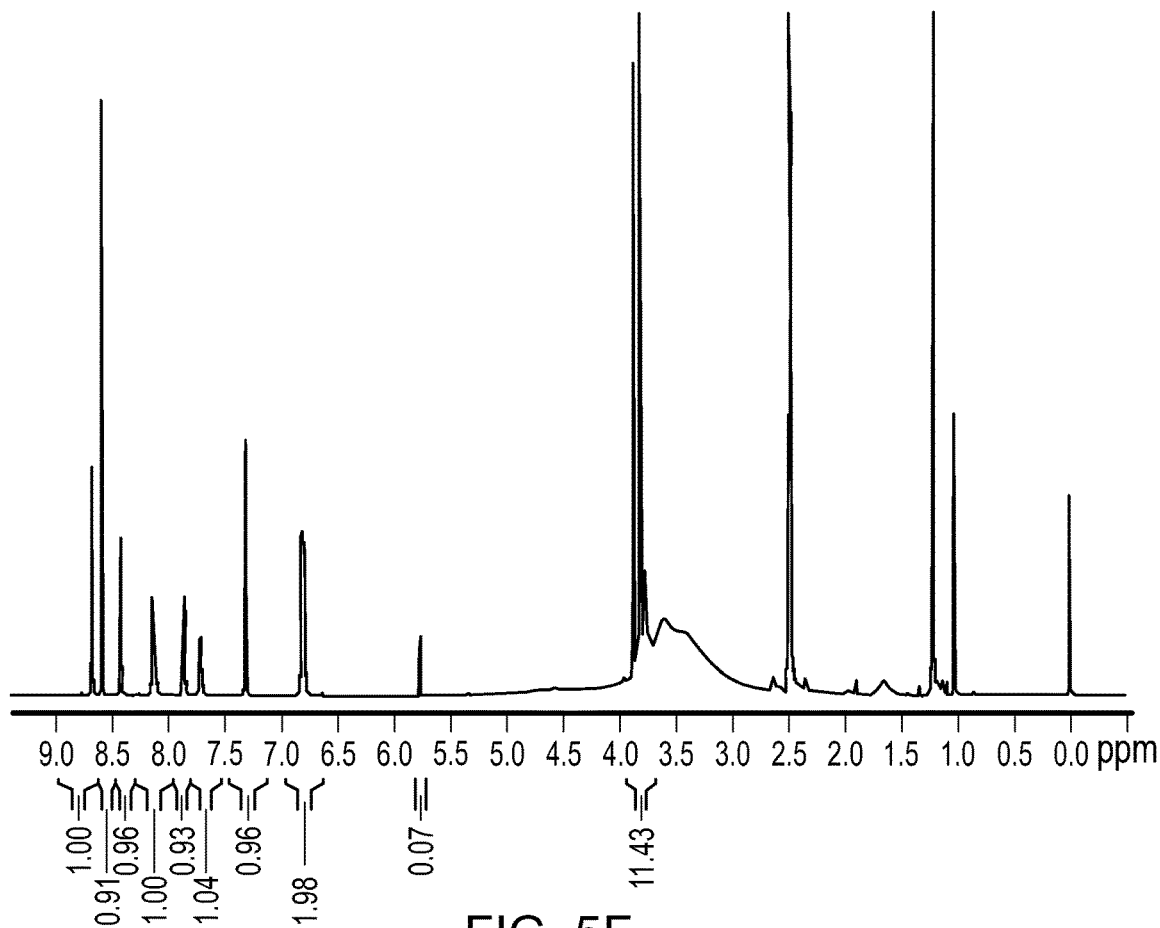

The scaled-up phosphate salt material appeared crystalline by XRPD and PLM. The XRPD peaks of the phosphate salt are shown in Table 34, below, and in FIG. 5A. The diffraction pattern was consistent with data obtained during the primary screen. Thermal analysis identified a melting point of around 167° C. (FIG. 5C). There was a weight loss of approximately 1.3% observed from the onset of heating. A second weight loss of approximately 1.2% was observed from an onset of around 167° C. The material appeared highly hygroscopic by GVS (FIGS. 5D and 5E), with a weight increase of approximately 14%, but no change in form or crystallinity was observed post-GVS analysis. A broad water peak was observed in a $^1$H NMR spectrum, indicative of salt formation (FIG. 5F). The salt was determined to be 97.7% pure by HPLC. CAD analysis determined the salt to have a ratio of 1.4:1, $PO_4$:free base.

TABLE 34

XRPD peaks of the phosphate salt

| Pos. [°2θ] | FWHM Left [°2θ] | Area [cts*°2θ] | d-spacing [Å] | Height [cts] | Rel. Int. [%] |
|---|---|---|---|---|---|
| 3.61 | 0.10 | 151.75 | 24.51 | 1503.25 | 100.00 |
| 6.20 | 0.15 | 87.25 | 14.26 | 576.19 | 38.33 |
| 7.19 | 0.15 | 57.90 | 12.30 | 382.36 | 25.44 |
| 8.91 | 0.15 | 35.23 | 9.93 | 232.63 | 15.48 |
| 9.54 | 0.10 | 40.79 | 9.27 | 404.11 | 26.88 |
| 10.31 | 0.15 | 69.31 | 8.58 | 457.72 | 30.45 |
| 12.50 | 0.10 | 41.74 | 7.08 | 413.47 | 27.51 |
| 13.00 | 0.15 | 39.81 | 6.81 | 262.90 | 17.49 |
| 14.61 | 0.10 | 44.88 | 6.06 | 444.57 | 29.57 |
| 15.12 | 0.10 | 35.26 | 5.86 | 349.27 | 23.23 |
| 15.89 | 0.15 | 133.60 | 5.58 | 882.27 | 58.69 |
| 16.72 | 0.10 | 101.45 | 5.30 | 1004.92 | 66.85 |
| 17.84 | 0.10 | 92.25 | 4.97 | 913.84 | 60.79 |
| 18.22 | 0.10 | 108.09 | 4.87 | 1070.70 | 71.23 |
| 19.13 | 0.10 | 48.49 | 4.64 | 480.33 | 31.95 |
| 20.28 | 0.13 | 108.57 | 4.38 | 860.39 | 57.24 |
| 20.92 | 0.10 | 56.42 | 4.25 | 558.88 | 37.18 |
| 22.15 | 0.18 | 82.62 | 4.01 | 467.65 | 31.11 |
| 23.05 | 0.10 | 39.45 | 3.86 | 390.79 | 26.00 |
| 23.88 | 0.10 | 41.78 | 3.73 | 413.88 | 27.53 |
| 24.21 | 0.13 | 39.71 | 3.68 | 314.69 | 20.93 |
| 24.61 | 0.15 | 30.06 | 3.62 | 198.52 | 13.21 |
| 25.10 | 0.13 | 37.82 | 3.55 | 299.73 | 19.94 |
| 25.52 | 0.13 | 75.71 | 3.49 | 599.97 | 39.91 |
| 27.04 | 0.10 | 26.96 | 3.30 | 267.03 | 17.76 |
| 27.30 | 0.26 | 78.12 | 3.27 | 309.55 | 20.59 |
| 28.52 | 0.18 | 61.69 | 3.13 | 349.18 | 23.23 |
| 29.21 | 0.15 | 16.56 | 3.06 | 109.36 | 7.28 |
| 30.07 | 0.20 | 21.19 | 2.97 | 104.97 | 6.98 |
| 31.22 | 0.15 | 18.15 | 2.87 | 119.87 | 7.97 |
| 34.03 | 0.20 | 8.71 | 2.63 | 43.12 | 2.87 |

Portions of the phosphate salt form were weighed out into 3 glass vials for salt stability studies. Each vial was stored for 7 days at either: 1) ambient temperature and light; 40° C. and 75% RG; or 3) 80° C. After 7 days, each sample was analyzed by XRPD to determine crystallinity and form. The material appeared stable under stressed conditions with no change in form or crystallinity observed after the 7-day stability tests at any of the conditions tested. The material stored at RT was found to be 98.03% pure. The material stored at 40° C./75% RH was found to be 97.44% pure. The material stored at 80° C. was found to be 64.96% pure. One major impurity was identified, most likely a degradant.

The thermodynamic solubility of the phosphate salt was investigated at pH 1, pH 4.5, and pH 6.8. The procedure for investigating thermodynamic solubility was as follows. Approximately 10 mg of the phosphate salt was weighed into a 2 mL glass vial. 2 mL of the desired buffer solution was added to the vial, and the resultant slurry was agitated at RT overnight. Each solution was centrifuged and observed solids were collected. There was an insufficient amount of solids collected to analyze the phosphate salts from the pH 1 and pH 4.5 buffers. The phosphate salt from the pH 6.8 buffer was analyzed by XRPD and was shown to be Form 1. The mother liquor from each experiment was analyzed by HPLC to determine the solubility of each salt at each pH value. The results are shown in Table 35, below.

TABLE 35

Thermodynamic solubility

| Salt | pH of buffer | Concentration (mg/mL) | XRPD results |
|---|---|---|---|
| Phosphate | 1 | 4.1 | Insufficient solid |
| | 4.5 | 0.97 | Insufficient solid |
| | 6.8 | <0.02 | Form 1 |

Example 6: Polymorph Screens

A. Instrumentation and Methods of Analysis

The instruments and methods of analysis used in the polymorph screens described in Examples 3 are described in Example 2, above.

B. Solvent Solubility Screen

A solvent solubility screen was conducted in 32 solvent systems as follows. Approximately 10 mg of the compound of Formula (I) was placed in each of 32 vials and 5 volume aliquots of the appropriate solvent system was added to the appropriate vial. Between each addition, the mixture was checked for dissolution. If no dissolution was apparent, the mixture was heated to around 40° C. and checked again. This procedure was continued until dissolution was observed or until 100 volumes of solvent had been added. Undissolved material from the solubility screen was isolated and analyzed by XRPD. The solvent systems and the approximate solubility of the compound of Formula (I) in each solvent system tested is shown below in Table 36, where (P) indicates partial solubility at 100 volumes.

TABLE 36

Solubility screen solvent list

| | Solvent | Approximate solubility (mg/mL) |
|---|---|---|
| 1 | 1,4-Dioxane | <5 (P) |
| 2 | 1-Butanol | <5 |
| 3 | 1-Propanol | <5 |

TABLE 36-continued

Solubility screen solvent list

| | Solvent | Approximate solubility (mg/mL) |
|---|---|---|
| 4 | Acetone | <5 |
| 5 | Acetone:Water (50%) | <5 |
| 6 | Anisole | <5 (P) |
| 7 | CHCl$_3$ | <5 (P) |
| 8 | Cyclohexane | <5 |
| 9 | Cyclohexanone | <5 (P) |
| 10 | DCM | <5 (P) |
| 11 | t-Butylmethyl ether | N/A |
| 12 | DMSO | 41 |
| 13 | Ethanol | <5 |
| 14 | EtOAc | <5 |
| 15 | Heptane | N/A |
| 16 | IPA | <5 |
| 17 | Isopropyl acetate | N/A |
| 18 | Isopropylether | N/A |
| 19 | MeCN | N/A |
| 20 | MeCN:Water (20%) | 5 |
| 21 | MEK | <5 |
| 22 | MeOAc | <5 |
| 23 | MeOH | N/A |
| 24 | 2-Ethoxyethanol | <5 (P) |
| 25 | 2-Methyl THF | <5 (P) |
| 26 | MIBK | <5 |
| 27 | Nitromethane | <5 (P) |
| 28 | NMP | 17 |
| 29 | THF | <5 (P) |
| 30 | THF:Water (1%) | 48 |
| 31 | Toluene | N/A |
| 32 | Water | <5 |

The material was found to have low solubility in the majority of solvent systems investigated with moderate solubility observed in only 3 solvent systems (DMSO, NMP, and THF/water (1%)).

Figure 39:
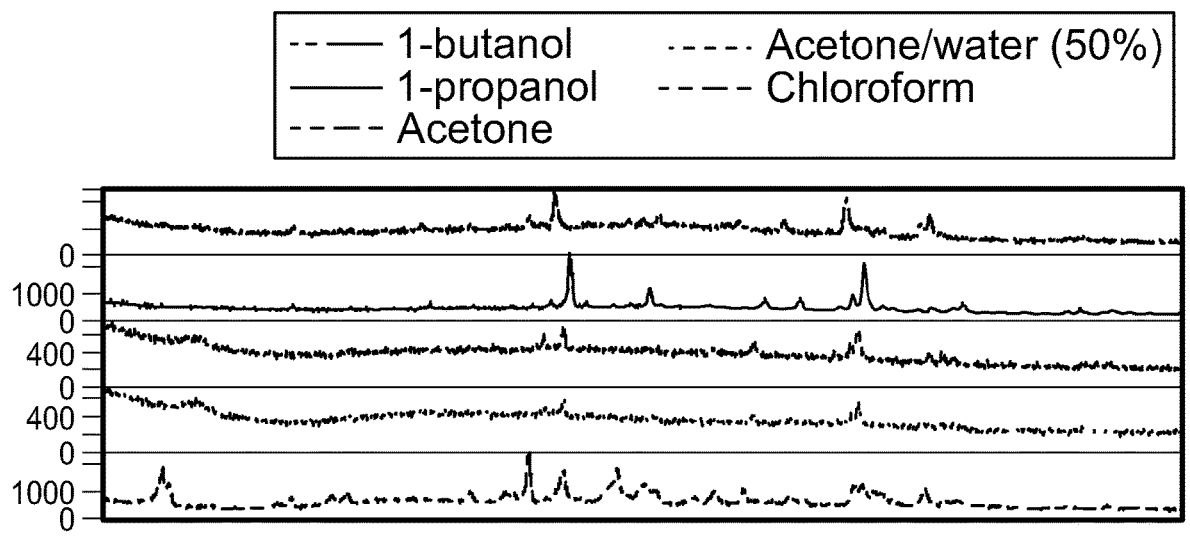
FIG. 39 shows x-ray powder diffraction scans of the observed solids from the solvents tested in the solvent solubility screen of Form I.
Figure 39:
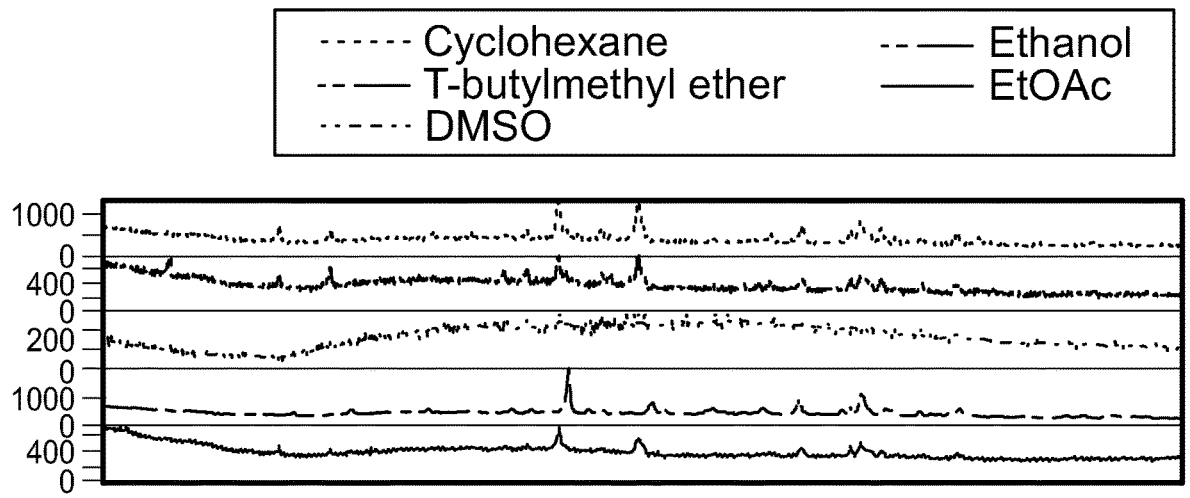
Figure 39:
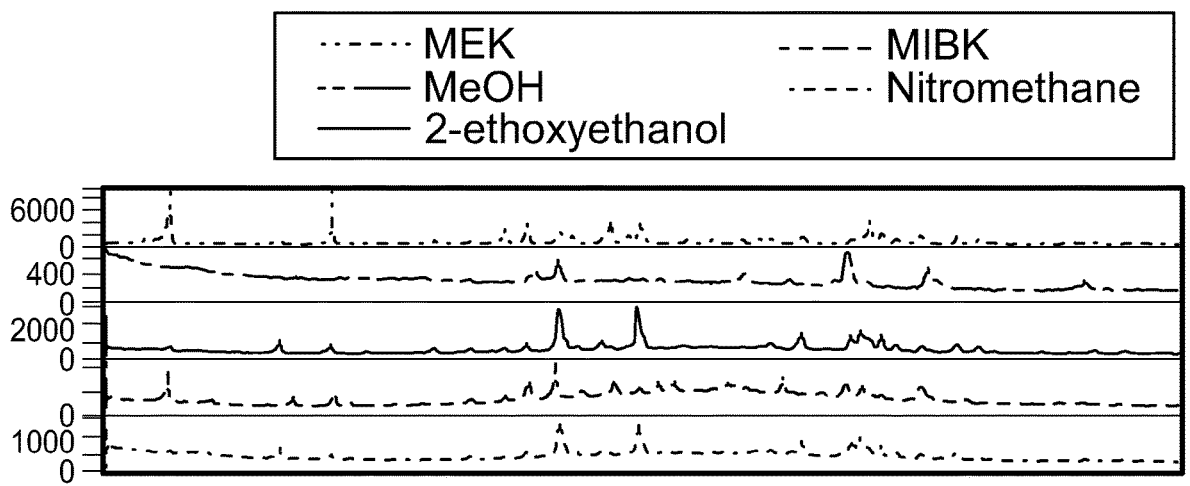
Figure 39:
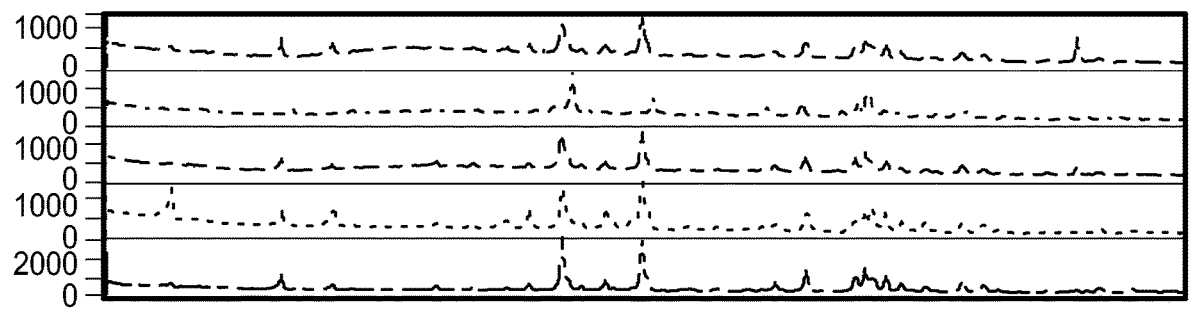
Figure 39:
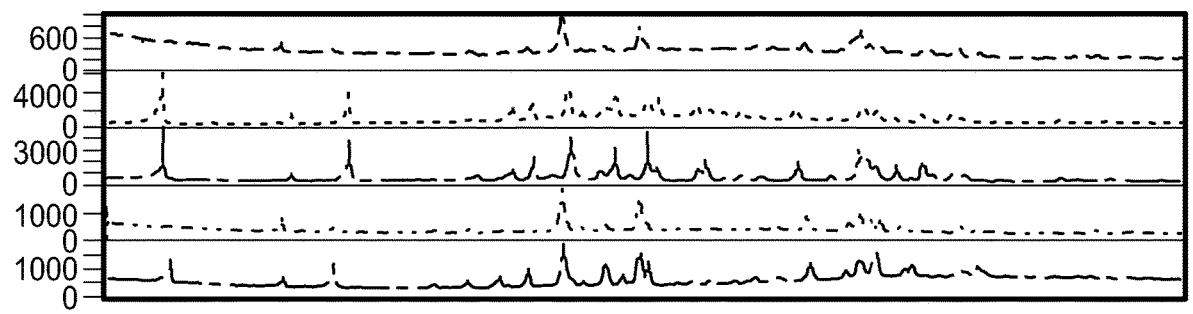
Figure 40A:
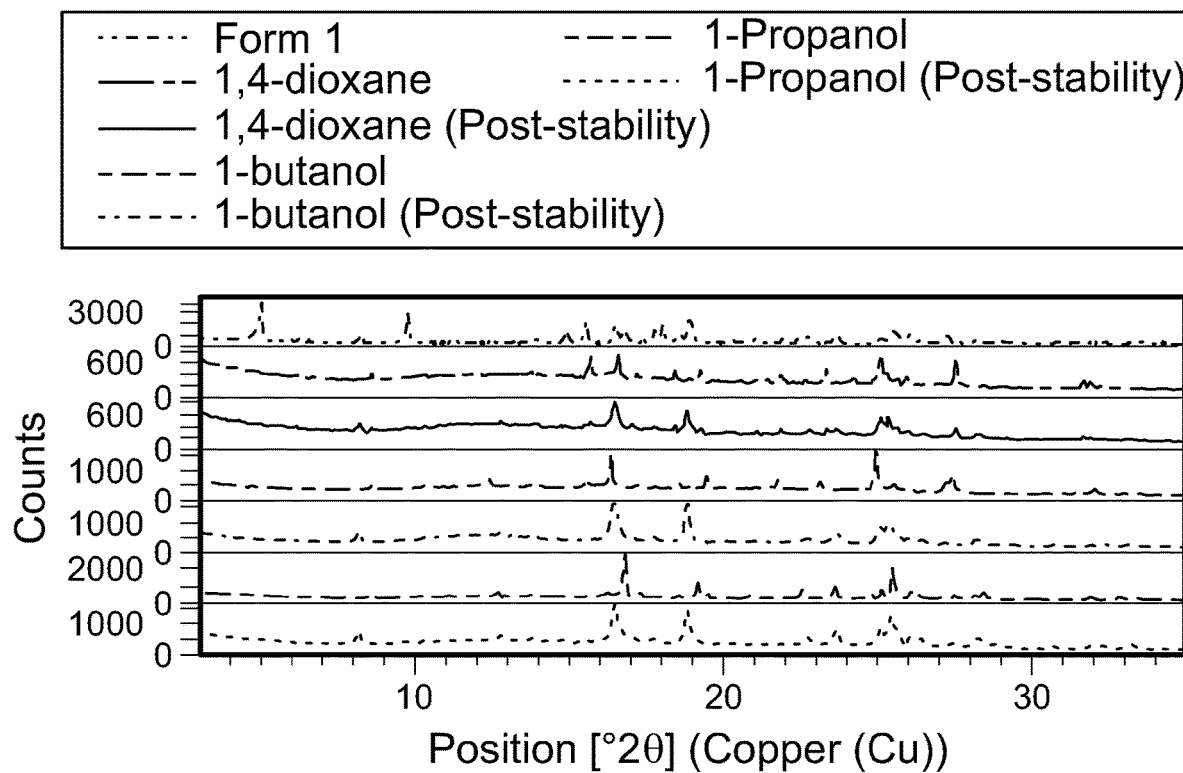
FIGS. 40A-40D show x-ray powder diffraction scans of the compound of Formula (I) after temperature cycling experiments in various solvents and storage at 40° C. and 75% RH overnight.
Figure 40A:
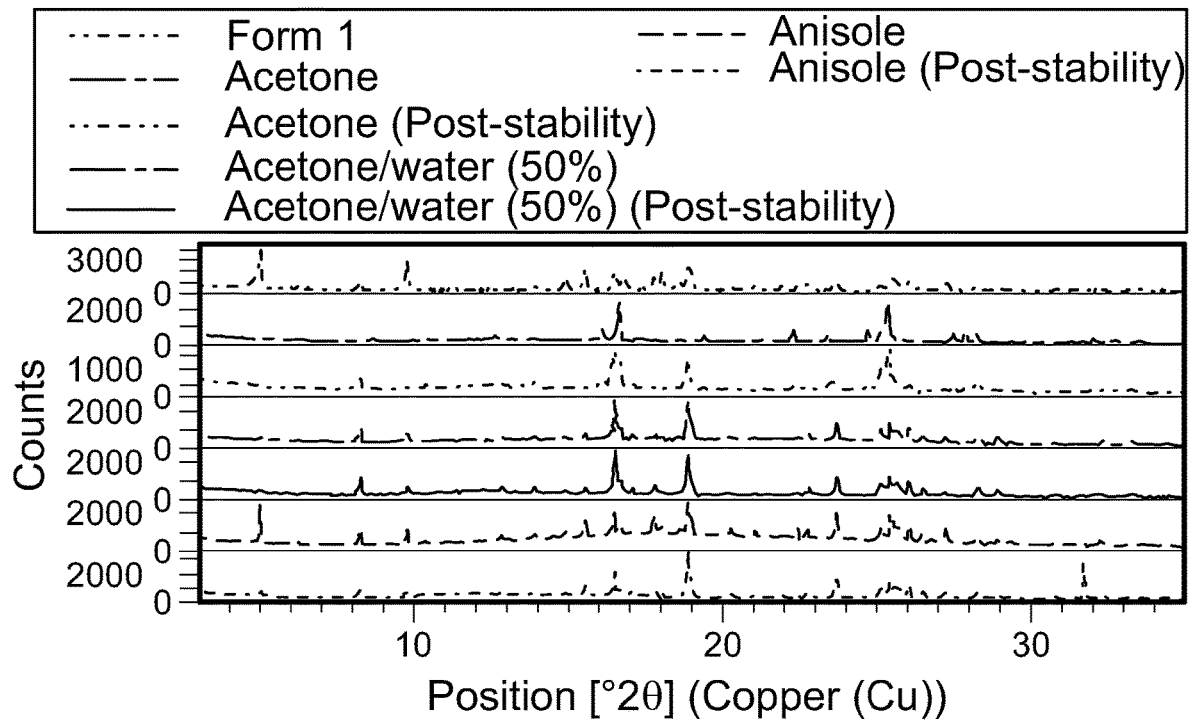
Figure 40B:
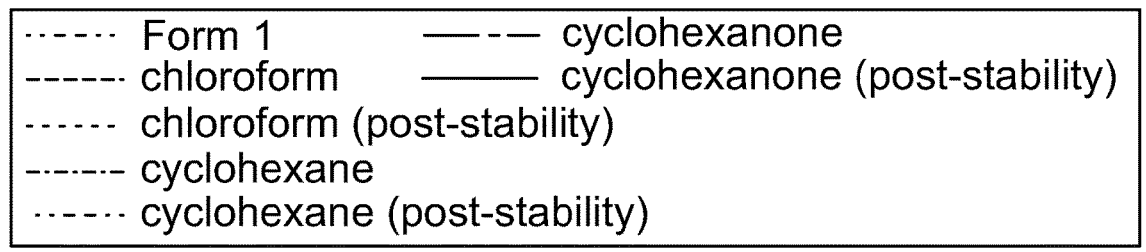
Figure 40B:
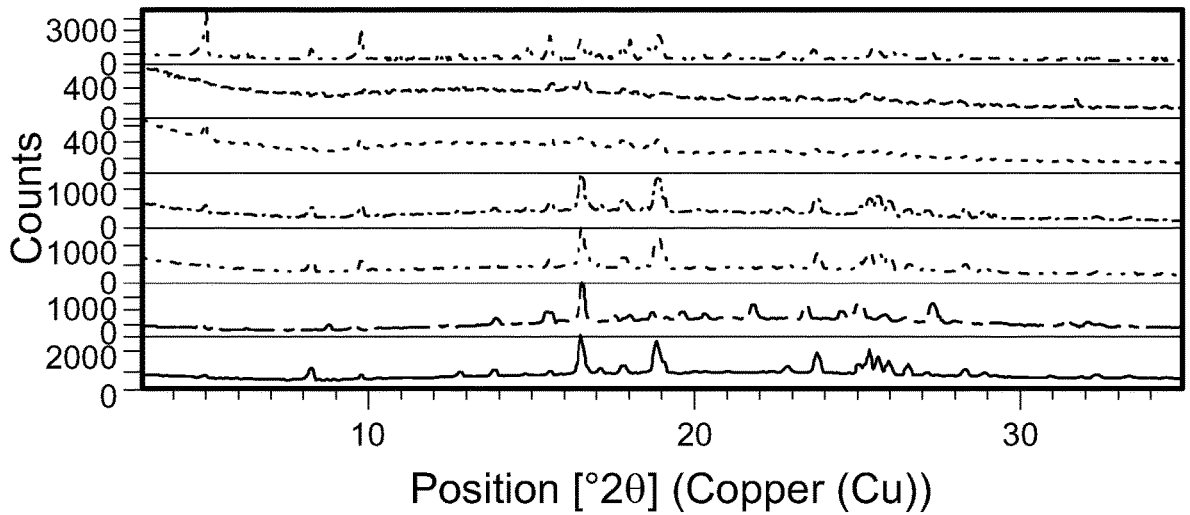
Figure 40B:
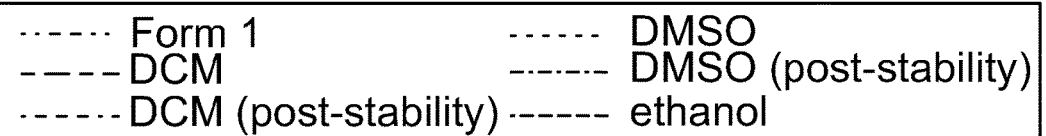
Figure 40B:
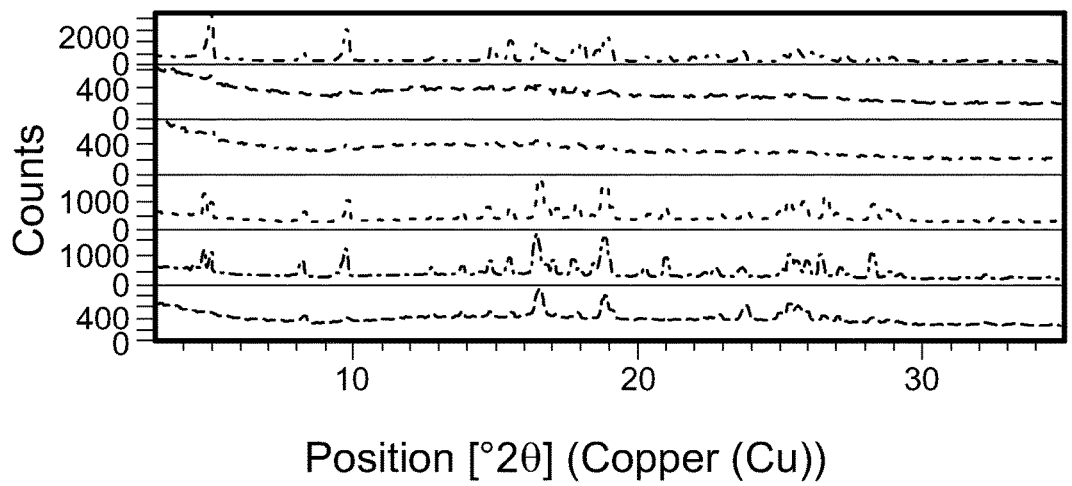
Figure 40C:
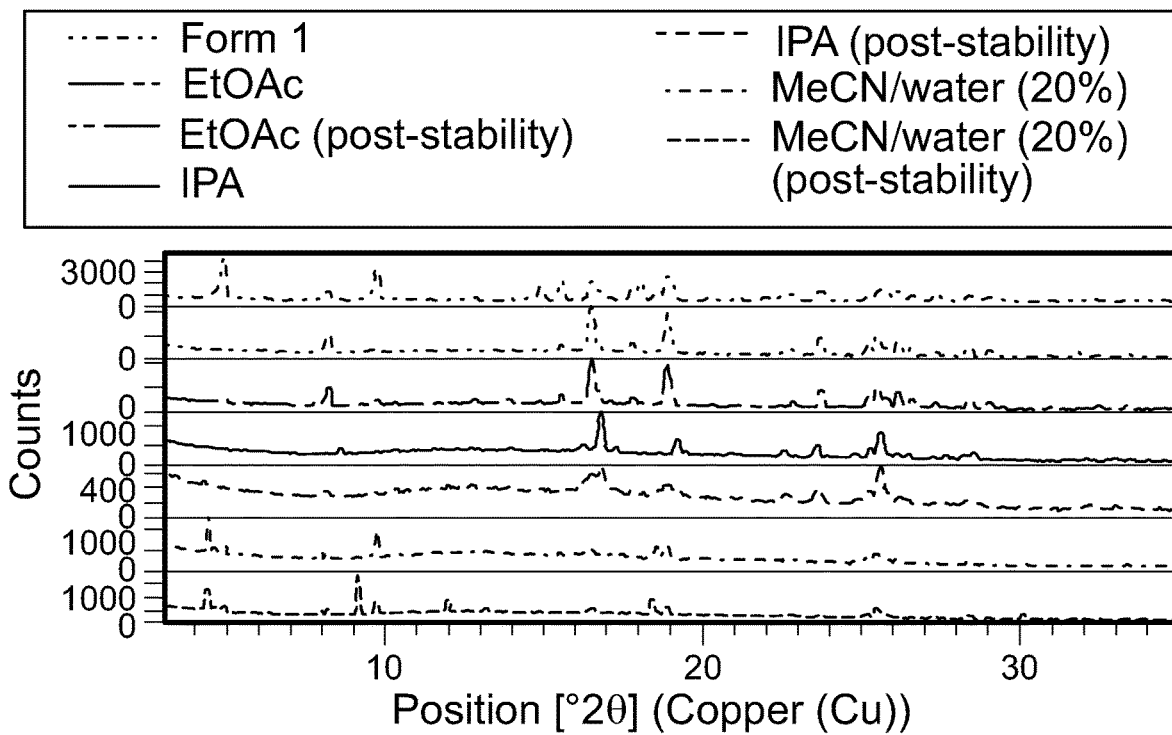
Figure 40C:
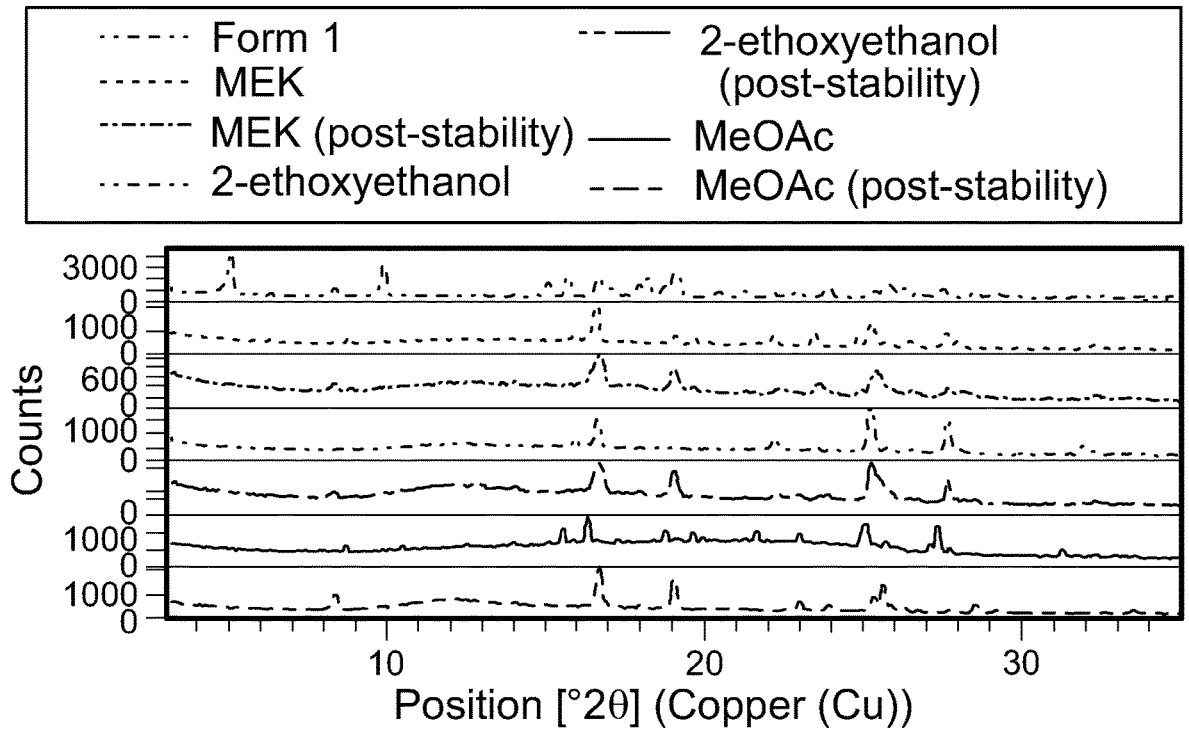
Figure 40D:
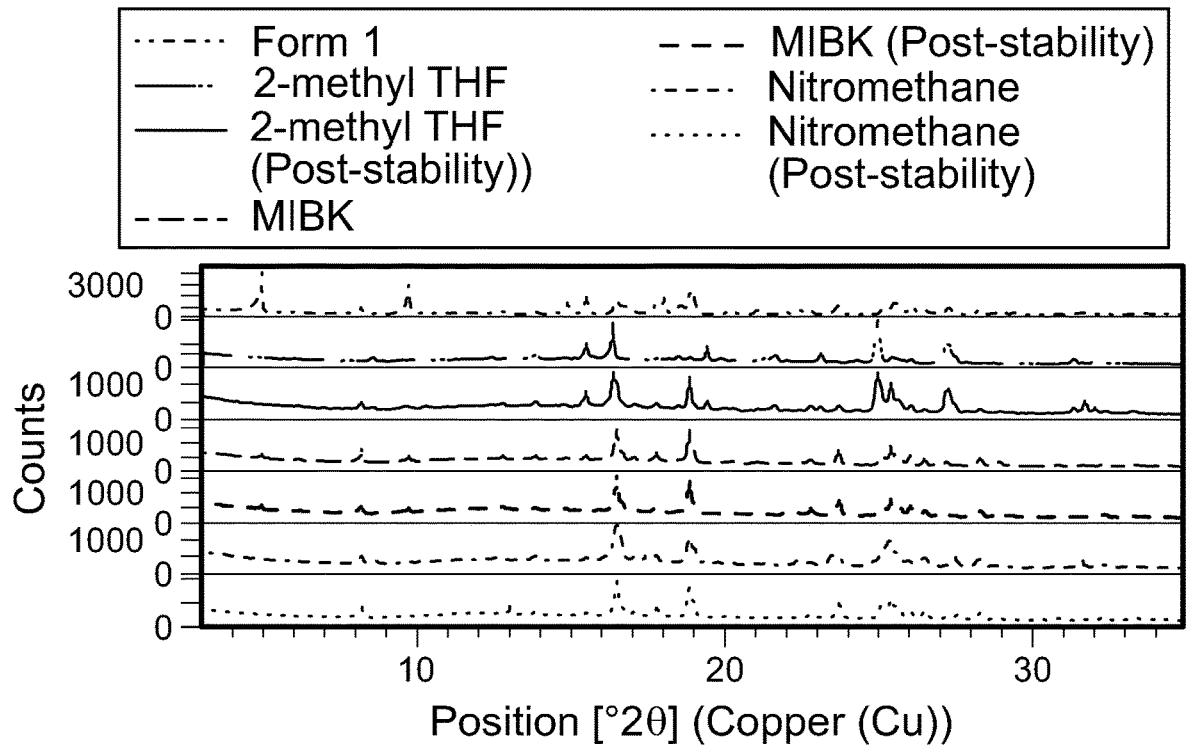
Figure 40D:
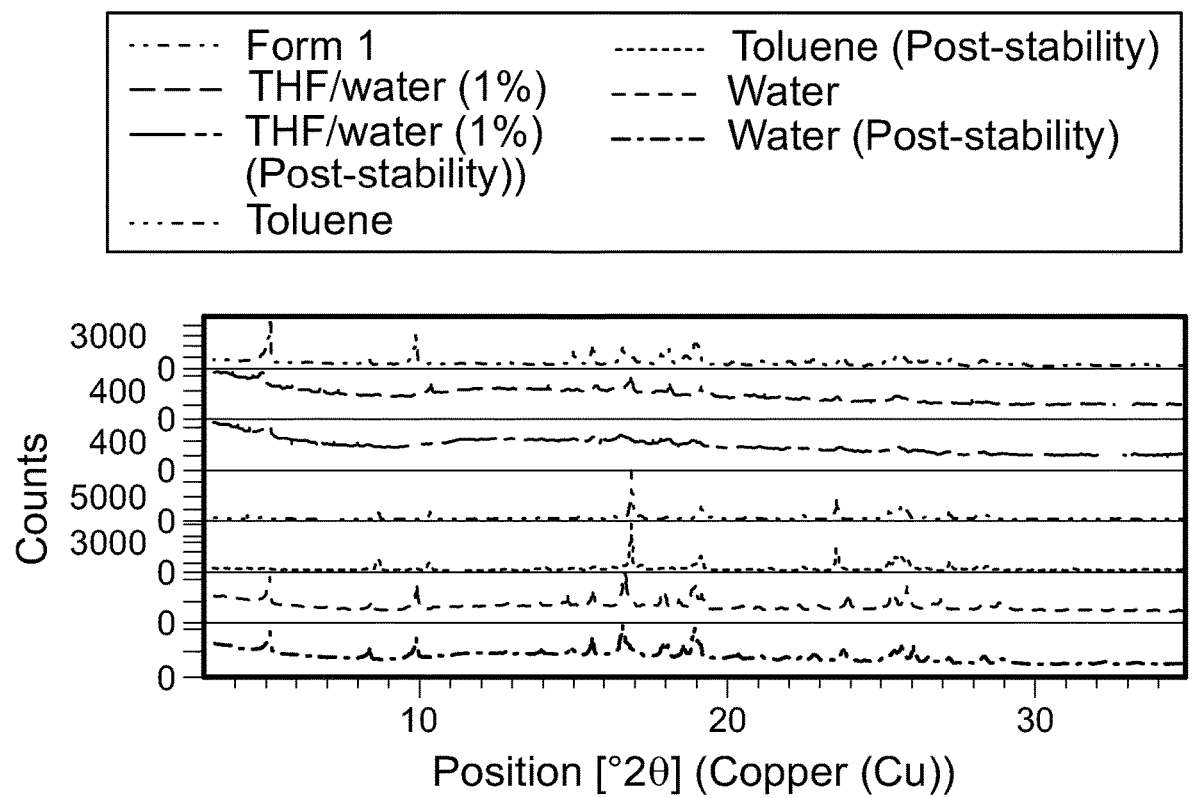

Observed solids were filtered and analyzed by XRPD to determine form and crystallinity. The results are shown in Table 37, below. FIG. 39 shows the XRPD scans of the observed solids.

TABLE 37

XRPD results for observed solids

| | Solvent | Form |
|---|---|---|
| 1 | 1,4-Dioxane | Insufficient solid |
| 2 | 1-Butanol | Form 7 |
| 3 | 1-Propanol | Form 8 |
| 4 | Acetone | Amorphous |
| 5 | Acetone:Water (50%) | Amorphous |
| 6 | Anisole | Insufficient solid |
| 7 | CHCl$_3$ | Form 1/Form 13 |
| 8 | Cyclohexane | Form 1 |
| 9 | Cyclohexanone | Insufficient solid |
| 10 | DCM | Insufficient solid |
| 11 | t-Butylmethyl ether | Form 1 |
| 12 | DMSO | Amorphous |
| 13 | Ethanol | Form 8 |
| 14 | EtOAc | Weak diffraction |
| 15 | Heptane | Form 1 |
| 16 | IPA | Form 2 |
| 17 | Isopropyl acetate | Form 1 |
| 18 | Isopropylether | Form 1 |
| 19 | MeCN | Form 1 |
| 20 | MeCN:Water (20%) | Form 2/Form 13 |
| 21 | MEK | Insufficient solid |
| 22 | MeOAc | Form 7 |
| 23 | MeOH | Form 1 |
| 24 | 2-Ethoxyethanol | Insufficient solid |
| 25 | 2-Methyl THF | Form 7 |
| 26 | MIBK | Form 1 |
| 27 | Nitromethane | Form 1 |

TABLE 37-continued

XRPD results for observed solids

| | Solvent | Form |
|---|---|---|
| 28 | NMP | Insufficient solid |
| 29 | THF | Form 13 |
| 30 | THF:Water (1%) | Form 8 |
| 31 | Toluene | Form 1 |
| 32 | Water | Form 2/Form 13 |

C. Primary Polymorph Screen

A primary polymorph screen was conducted using the solvent systems shown in Table 38, below, selected using the data from the solvent solubility screen described above.

TABLE 38

Primary polymorph screen solvent list

| | Solvent |
|---|---|
| 1 | Acetone |
| 2 | Acetone/water (50%) |
| 3 | Anisole |
| 4 | 1-Butanol |
| 5 | 2-Butanone |
| 6 | Chloroform |
| 7 | Cyclohexane |
| 8 | Cyclohexanone |
| 9 | Dichloromethane |
| 10 | 1,4-Dioxane |
| 11 | Ethanol |
| 12 | Ethyl acetate |
| 13 | Dimethyl sulfoxide |
| 14 | MeCN/water (20%) |
| 15 | Methyl acetate |
| 16 | 2-Ethoxyethanol |
| 17 | Nitromethane |
| 18 | Methylisobutyl ketone |
| 19 | 2-Methyl THF |
| 20 | 2-Propanol |
| 21 | 1-Propanol |
| 22 | Tetrahydrofuran |
| 23 | N-Methyl pyrrolidone |
| 24 | THF/water (1%) |
| 25 | Water |

1. Temperature Cycling (Maturation) Experiments

Slurries for temperature cycling (maturation) experiments were prepared using the solvent systems from Table 38, above, as follows. Approximately 40 mg of crystalline compound of Formula (I) was suspended in the appropriate solvent system. In any cases where dissolution occurred, additional material was added until a slurry was obtained. The resultant slurries were subjected to successive 4-hour heat-cool cycles between 40° C. and RT for 72 hours.

After temperature cycling, each mixture was filtered and isolated solids were analyzed (wet) by XRPD to determine crystallinity and form. The samples were then stored at 40° C. and 75% RH overnight and reanalyzed by XRPD to determine any changes in form or crystallinity. Results are shown in Table 39, below, and FIGS. 40A-40D.

TABLE 39

Temperature cycling (maturation) experiments

| Solvent | Observations | Post-temperature cycling | Post-stability tests |
|---|---|---|---|
| 1,4-Dioxane | Solid | Weak diffraction | Form 1 |
| 1-Butanol | Solid | Weak diffraction | Form 1 |
| 1-Propanol | Solid | Form 8 | Form 1 |
| Acetone | Solid | Weak diffraction | Form 1 |
| Acetone:Water (50%) | Solid | Form 1 | Form 1 |
| Anisole | Solid | Form 1 | Form 1 |
| $CHCl_3$ | Solid | Amorphous | Form 1 |
| Cyclohexane | Solid | Form 1 | Form 1 |
| Cyclohexanone | Solid | Weak diffraction | Form 1 |
| DCM | Solid | Amorphous | Form 1 |
| DMSO | Solid | Form 1 | Form 1 |
| Ethanol | Solid | Weak diffraction | Form 1 |
| EtOAc | Solid | Form 1 | Form 1 |
| IPA | Solid | Form 8 | Form 1 |
| MeCN:Water (20%) | Solid | Weak diffraction | Form 1 |
| MEK | Solid | Weak diffraction | Form 1 |
| MeOAc | Solid | Weak diffraction | Form 1 |
| 2-Ethoxyethanol | Solid | Weak diffraction | Form 1 |
| 2-Methyl THF | Solid | Weak diffraction | Form 1 |
| MIBK | Solid | Form 1 | Form 1 |
| Nitromethane | Solid | Weak diffraction | Form 1 |
| NMP | Insufficient solid | Insufficient solid | Insufficient solid |
| THF | Solid | Weak diffraction | Form 1 |
| THF:Water (1%) | Solid | Weak diffraction | Form 1/ Form 8 |
| Water | Solid | Form 1 | Form 1 |

The supernatant from each experiment was split equally into 3 vials for evaporation, crash cooling, and anti-solvent addition experiments (described below).

2. Evaporation Experiments

Figure 41:
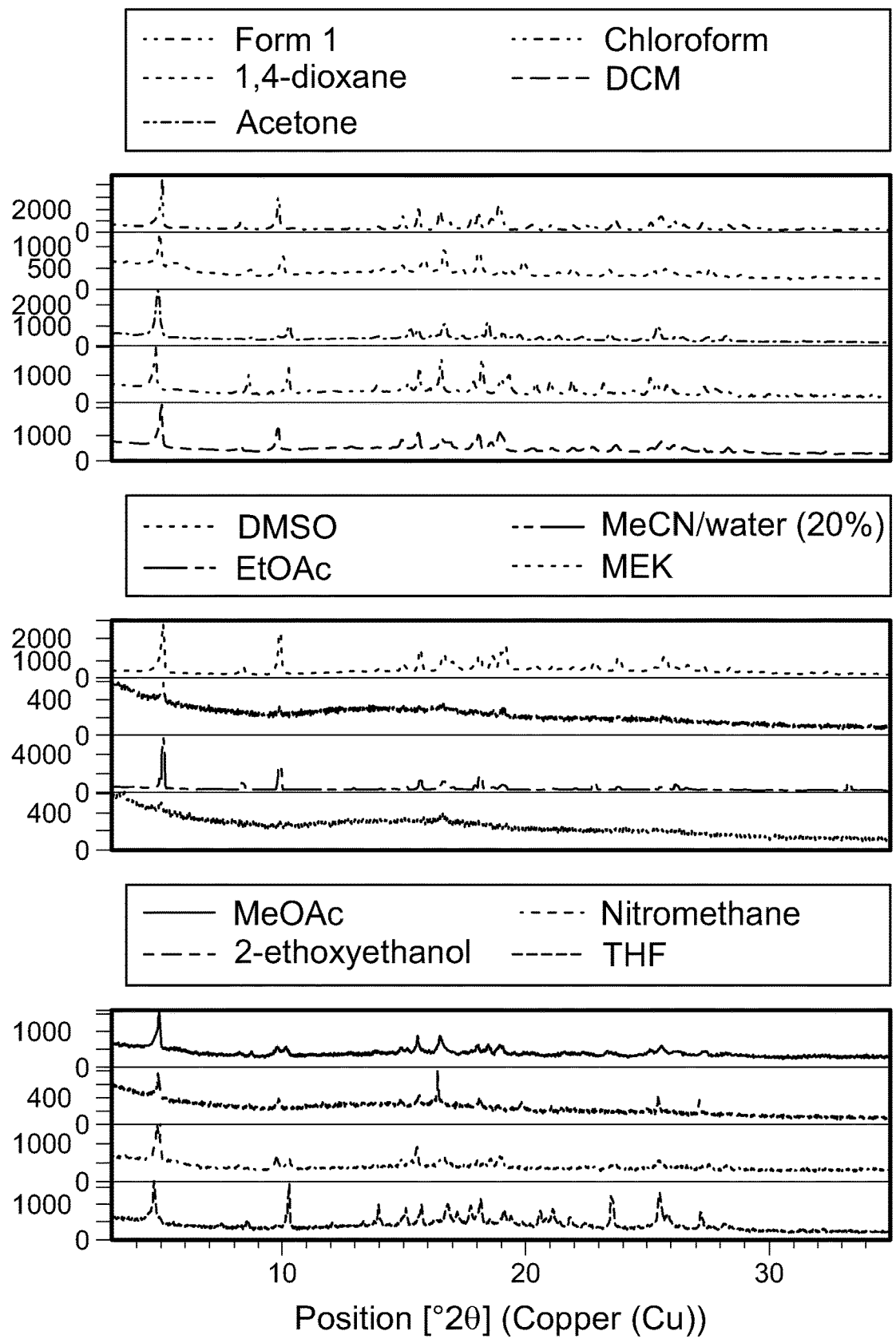
FIG. 41 shows x-ray powder diffraction scans of the compound of Formula (I) after evaporation experiments using various solvents.

For evaporation experiments, sub-samples of supernatant from the slurries containing the compound of Formula (I) were transferred to vials. The vials were then uncapped and allowed to evaporate at ambient temperature. Any material recovered was analyzed by XRPD, with no prior drying. Results are shown in Table 40, below, and FIG. 41.

TABLE 40

Evaporation experiments

| Solvent | Solid | Observations | Form |
|---|---|---|---|
| 1,4-Dioxane | Yes | Pale yellow solid | Form 17 |
| 1-Butanol | No | N/A | N/A |
| 1-Propanol | No | N/A | N/A |
| Acetone | Yes | White solid | Form 1/Form 8 |
| Acetone:Water (50%) | Yes | White needle-like crystals | N/A |
| Anisole | Yes | White solid | N/A |
| $CHCl_3$ | Yes | Yellow solid | Form 1/Form 8 |
| Cyclohexane | No | N/A | N/A |
| Cyclohexanone | No | N/A | N/A |
| DCM | Yes | White solid | Form 1 |
| DMSO | Yes | White solid | Form 1 |
| Ethanol | Yes | White solid | N/A |
| EtOAc | Yes | White solid | Amorphous |
| IPA | No | N/A | N/A |
| MeCN:Water (20%) | Yes | White needle-like crystals | Form 1 |
| MEK | Yes | White solid | Amorphous |
| MeOAc | Yes | White solid | Form 1 |
| 2-Ethoxyethanol | Yes | White solid | Form 1 |
| 2-Methyl THF | Yes | White solid | N/A |
| MIBK | No | N/A | N/A |
| Nitromethane | Yes | Pale yellow solid | Form 1 |
| NMP | No | N/A | N/A |
| THF | Yes | Yellow solid | Form 1/Form 8 |
| THF:Water (1%) | No | N/A | N/A |
| Water | No | N/A | N/A |

3. Crash Cooling Experiments

Figure 42:
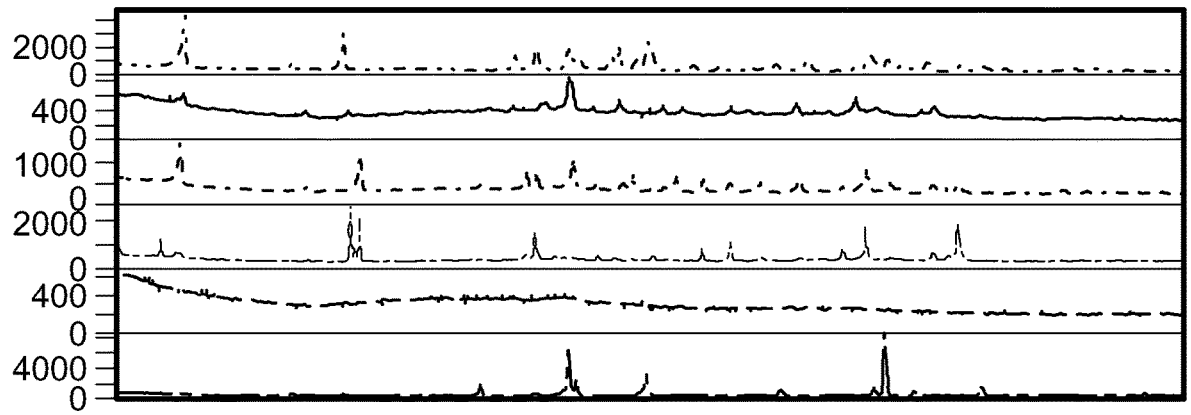
FIG. 42 shows x-ray powder diffraction scans of the compound of Formula (I) after crash-cooling experiments using various solvents.
Figure 42:
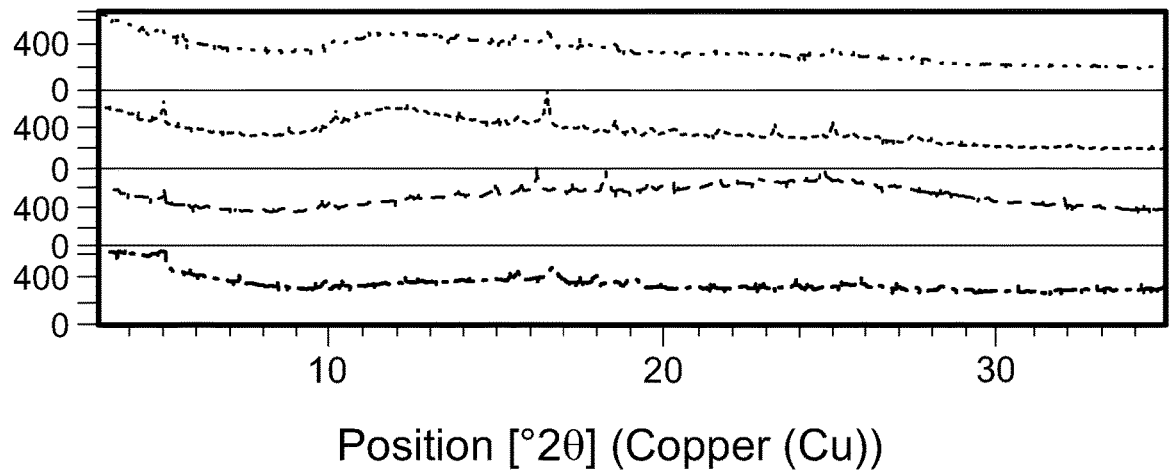

Crash cooling experiments were performed at 5° C. and −20° C. Sub-samples of supernatant from the slurries containing the compound of Formula (I) were transferred into vials and left to cool at 5° C. in the refrigerator. When enough material was obtained (by precipitation), the material was analyzed, with no prior drying, by XRPD. For samples in which precipitation had not occurred, the samples were transferred to a freezer and left to cool at −20° C. When enough material was obtained, the material was analyzed, with no prior drying, by XRPD. The results of the crash cooling experiments conducted at 5° C. are shown in Table 41, below, and FIG. 42. No solids were observed in the samples stored at −20° C. after 10 days.

TABLE 41

Crash cooling experiments (5° C.)

| Solvent | Solid | Temperature | Observations | Form |
|---|---|---|---|---|
| 1,4-Dioxane | Yes | 2° C. | White solid | Amorphous |
| 1-Butanol | No | N/A | N/A | N/A |
| 1-Propanol | No | N/A | N/A | N/A |
| Acetone | Yes | 2° C. | White solid | Form 1/Form 8 |
| Acetone:Water (50%) | No | | | N/A |
| Anisole | Yes | 2° C. | White solid | Form 18 |
| CHCl₃ | No | N/A | N/A | N/A |
| Cyclohexane | No | N/A | N/A | N/A |
| Cyclohexanone | Yes | 2° C. | White solid | Amorphous |
| DCM | Yes | 2° C. | White solid | N/A |
| DMSO | N/A | N/A | N/A | N/A |
| Ethanol | No | N/A | N/A | N/A |
| EtOAc | Yes | 2° C. | White solid | Amorphous |
| IPA | No | N/A | N/A | N/A |
| MeCN:Water (20%) | Yes | 2° C. | White needle-like crystals | Form 1 |
| MEK | Yes | 2° C. | White solid | Amorphous |
| MeOAc | Yes | 2° C. | White solid | Amorphous |
| 2-Ethoxyethanol | Yes | 2° C. | White solid | Amorphous |
| 2-Methyl THF | No | N/A | N/A | N/A |
| MIBK | No | N/A | N/A | N/A |
| Nitromethane | Yes | 2° C. | White needle-like crystals | Amorphous |
| NMP | No | N/A | N/A | N/A |
| THF | No | N/A | N/A | N/A |
| THF:Water (1%) | No | N/A | N/A | N/A |
| Water | No | N/A | N/A | N/A |

4. Anti-Solvent Addition Experiments

Figure 43:
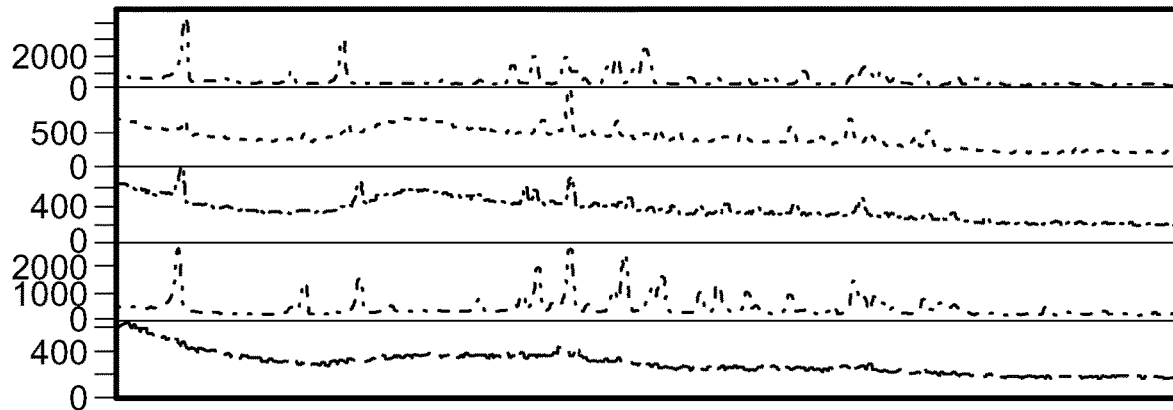
FIG. 43 shows x-ray powder diffraction scans of the compound of Formula (I) after anti-solvent experiments using various solvents.
Figure 43:
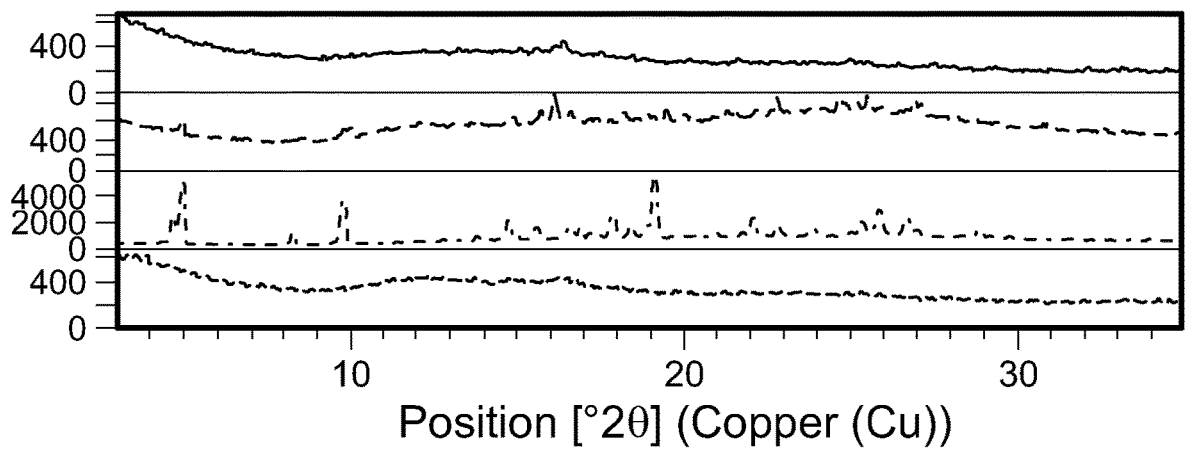

Anti-solvent addition experiments were performed by transferring sub-samples of supernatant from the slurries containing the compound of Formula (I) into vials and adding anti-solvent stepwise to the saturated solutions. When enough material was obtained, the material was analyzed, with no prior drying, by XRPD. The solvents used in the anti-solvent addition experiments are shown in Table 42, below. The results of the anti-solvent addition experiments are shown in Table 43, below, and FIG. 43.

TABLE 42

Anti-solvent addition experiments solvents and anti-solvents

| Sample | Solvent | Anti-solvent |
|---|---|---|
| 1 | Acetone | MTBE |
| 2 | Acetone/water (50%) | MTBE |
| 3 | Anisole | MTBE |
| 4 | 1-Butanol | MTBE |
| 5 | 2-Butanone | MTBE |
| 6 | Chloroform | MTBE |
| 7 | Cyclohexane | MTBE |
| 8 | Cyclohexanone | Heptane |
| 9 | Dichloromethane | MTBE |
| 10 | 1,4-Dioxane | DIPE |
| 11 | Ethanol | DIPE |
| 12 | Ethyl acetate | MTBE |
| 13 | Dimethyl sulfoxide | N/A |
| 14 | MeCN/water (20%) | MTBE |
| 15 | Methyl acetate | MTBE |
| 16 | 2-Ethoxyethanol | Water |
| 17 | Nitromethane | MTBE |
| 18 | Methylisobutyl ketone | DIPE |
| 19 | 2-Methyl THF | Water |
| 20 | 2-Propanol | MTBE |
| 21 | 1-Propanol | MTBE |
| 22 | Tetrahydrofuran | MTBE |
| 23 | N-Methyl pyrrolidone | Water |
| 24 | THF/water (1%) | MTBE |
| 25 | Water | MTBE |

TABLE 43

Anti-solvent addition experiments

| Solvent | Anti-solvent | Vol. of anti-solvent | Solid | Observations | Form |
|---|---|---|---|---|---|
| 1,4-Dioxane | DIPE | 0.5 | Yes | White solid | Form 1 |
| 1-Butanol | MTBE | 1 | Yes | White solid | N/A |
| 1-Propanol | MTBE | 1.5 | No | N/A | N/A |
| Acetone | MTBE | 1 | Yes | White solid | Form 1/Form 8 |
| Acetone:Water (50%) | MTBE | 1 | Yes | White needle-like crystals | N/A |
| Anisole | Water | 1 | Yes | White solid | N/A |
| CHCl₃ | MTBE | 1.5 | Yes | White solid | Form 1/Form 8 |
| Cyclohexane | MTBE | 1 | No | N/A | N/A |
| Cyclohexanone | Heptane | 1 | Yes | White solid | Amorphous |
| DCM | MTBE | 1 | Yes | White solid | N/A |
| DMSO | N/A | N/A | No | N/A | N/A |
| Ethanol | DIPE | 1 | No | N/A | N/A |
| EtOAc | MTBE | 1 | No | N/A | N/A |
| IPA | MTBE | 1 | No | N/A | N/A |
| MeCN:Water (20%) | MTBE | 1 | No | N/A | N/A |
| MEK | MTBE | 1 | Yes | White solid | N/A |
| MeOAc | MTBE | 1 | Yes | White solid | Amorphous |
| 2-Ethoxyethanol | Water | 1 | Yes | White solid | Amorphous |
| 2-Methyl THF | Water | 1 | No | N/A | N/A |
| MIBK | DIPE | 1 | No | N/A | N/A |
| Nitromethane | MTBE | 1 | No | N/A | N/A |
| NMP | Water | 1 | Yes | Yellow needle-like crystals | Form 1 |
| THF | MTBE | 1 | Yes | White solid | Amorphous |
| THF:Water (1%) | MTBE | 1 | No | N/A | N/A |
| Water | MTBE | 1 | No | N/A | N/A |

D. Secondary Polymorph Screen

Four forms were identified during the primary polymorph solvent screen: Form 1, Form 2, Form 7, and Form 8. Each form was prepared on a 300 mg scale and was fully characterized by XRPD, TG/DTA, DSC, GVS with post-GVS XRPD, ¹H NMR spectroscopy, HPLC-UV, and PLM.

Seven-day stability tests were also conducted as follows. A portion of each polymorph form was weighed out into 3 glass vials. Each vial was stored for 7 days at either: 1) ambient temperature and light; 40° C. and 75% RH; or 3) 80° C. After 7 days, each sample was analyzed by XRPD to determine crystallinity and form. These additional studies indicated that Form 1 was the most stable form of the compound of Formula (I) identified during the polymorph screen. Forms 2 and 7 were determined to be hydrated forms of the compound of Formula (I) that, upon heating, dehydrate to Form 1. Form 8 was identified as an IPA solvate which, upon heating, desolvates to Form 1. No change in appearance was observed after 7 days for any of the samples and no change in form was observed by XRPD after 7 days for any of the samples, though the sample of Form 8 that was stored at 40° C./75% RH appeared to have a higher amorphous content.

1. Form 1

Form 1 was the most stable form of the compound of Formula (I) identified during the polymorph screen. Form 1 was prepared on a 300 mg scale as follows. Approximately 500 mg of the compound of Formula (I) free base was weighed into a 20 mL scintillation vial. Ethyl acetate (4 mL) was added to the vial and the resultant slurry was temperature cycled between 40° C. and room temperature for 72 hours. The sample was filtered and the collected material was dried overnight under vacuum at 40° C.

Figure 1F:
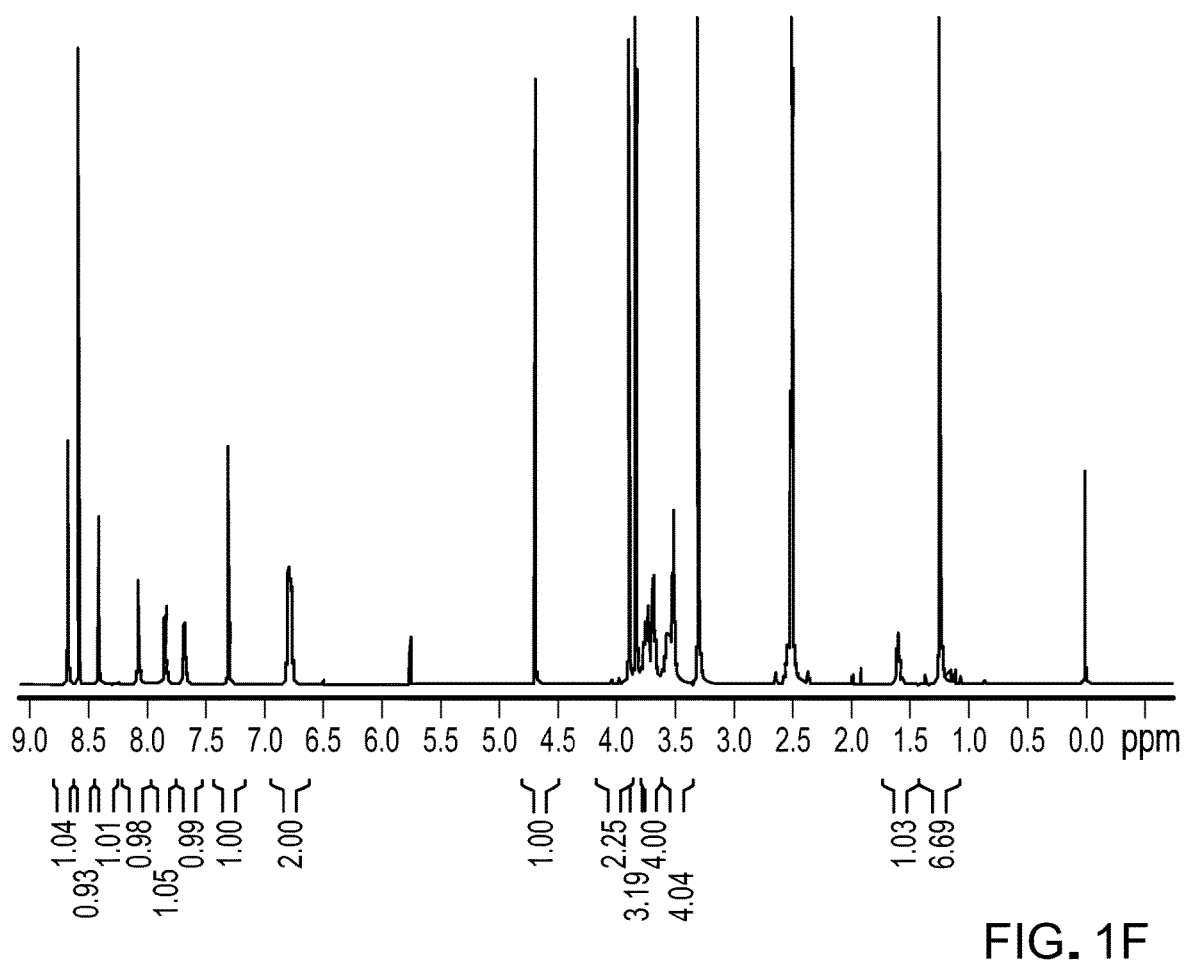

Post-drying XRPD (40° C. under vacuum) of the material appeared to be Form 1. The XRPD peaks of Form 1 are shown in Table 44, below, and FIG. 1A. The material was crystalline. Highly birefringent agglomerates of particles were observed by PLM. A small endothermic event was observed by DSC (FIG. 1B) at an onset of around 190° C. A melting transition was observed from an onset of around 203° C. A small endothermic event was observed by TG/DTA (FIG. 1C) at an onset of around 190° C. with a corresponding weight loss of 0.4%. A melting transition was observed from an onset of around 204° C. with a corresponding weight loss of 0.2%. Degradation was observed after the melting transition. The material appeared moderately hygroscopic by GVS (FIGS. 1D and 1E) with a weight increase of 2.6% at 90% RH. No change in form was observed by XRPD post-GVS analysis. Trace amounts of solvent were observed by $^1$H NMR (FIG. 1F). The spectra obtained was consistent with that of the received material (compound of Formula (I)).

TABLE 44

XRPD peaks of Form 1

| Pos. [°2θ] | FWHM Left [°2θ] | Area [cts*°2θ] | d-spacing [Å] | Height [cts] | Rel. Int. [%] |
|---|---|---|---|---|---|
| 4.95 | 0.19 | 24.33 | 17.84 | 97.48 | 6.05 |
| 8.23 | 0.19 | 61.56 | 10.74 | 246.62 | 15.32 |
| 9.75 | 0.19 | 82.45 | 9.07 | 330.34 | 20.52 |
| 12.77 | 0.19 | 41.33 | 6.93 | 165.59 | 10.28 |
| 13.80 | 0.19 | 35.96 | 6.41 | 144.06 | 8.95 |
| 14.77 | 0.19 | 46.81 | 5.99 | 187.52 | 11.65 |
| 15.51 | 0.19 | 79.80 | 5.71 | 319.71 | 19.86 |
| 16.53 | 0.12 | 267.93 | 5.36 | 1610.16 | 100.00 |
| 17.11 | 0.19 | 44.95 | 5.18 | 180.08 | 11.18 |
| 17.82 | 0.12 | 93.39 | 4.97 | 561.24 | 34.86 |
| 18.86 | 0.16 | 220.48 | 4.70 | 1060.02 | 65.83 |
| 22.34 | 0.19 | 29.93 | 3.98 | 119.89 | 7.45 |
| 22.81 | 0.19 | 29.57 | 3.89 | 118.47 | 7.36 |
| 23.75 | 0.19 | 145.46 | 3.74 | 582.78 | 36.19 |
| 24.99 | 0.12 | 52.20 | 3.56 | 313.71 | 19.48 |
| 25.32 | 0.12 | 99.61 | 3.52 | 598.63 | 37.18 |
| 25.59 | 0.19 | 132.87 | 3.48 | 532.35 | 33.06 |
| 25.96 | 0.19 | 158.21 | 3.43 | 633.84 | 39.36 |
| 26.56 | 0.12 | 46.49 | 3.35 | 279.36 | 17.35 |
| 27.07 | 0.37 | 96.42 | 3.29 | 193.14 | 12.00 |
| 28.28 | 0.12 | 55.67 | 3.15 | 334.57 | 20.78 |
| 28.86 | 0.19 | 64.48 | 3.09 | 258.35 | 16.04 |

TABLE 44-continued

XRPD peaks of Form 1

| Pos. [°2θ] | FWHM Left [°2θ] | Area [cts*°2θ] | d-spacing [Å] | Height [cts] | Rel. Int. [%] |
|---|---|---|---|---|---|
| 32.32 | 0.31 | 26.00 | 2.77 | 62.49 | 3.88 |
| 33.33 | 0.37 | 32.74 | 2.69 | 65.59 | 4.07 |

2. Form 2

Form 2 was isolated from Form 7 and was considered to be a hydrated form of the compound of Formula (I) that dehydrated to Form 1 upon heating. Form 2 was prepared on a 300 mg scale as follows. Approximately 500 mg of the compound of Formula (I) free base was weighed into a 20 mL scintillation vial. Ethanol/water (4 mL, 10%) was added to the vial and the resultant slurry was temperature cycled between 40° C. and room temperature for 72 hours. The sample was filtered and the collected material was dried on the filter bed overnight.

Figure 2A:
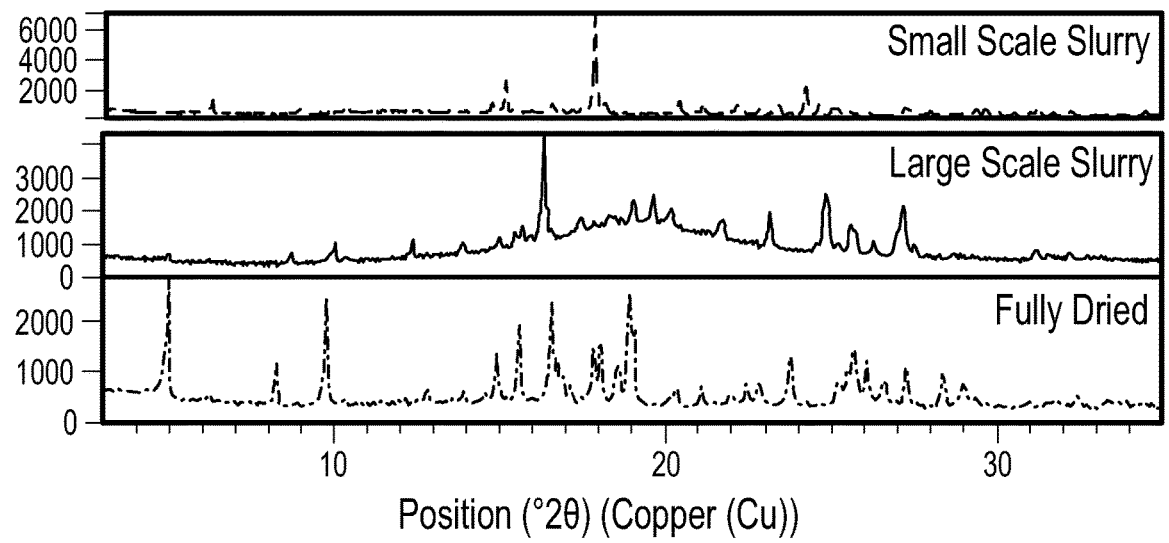
FIGS. 2A-2E are scans of polymorph Form 2 of the compound of Formula (I).
Figure 2B:
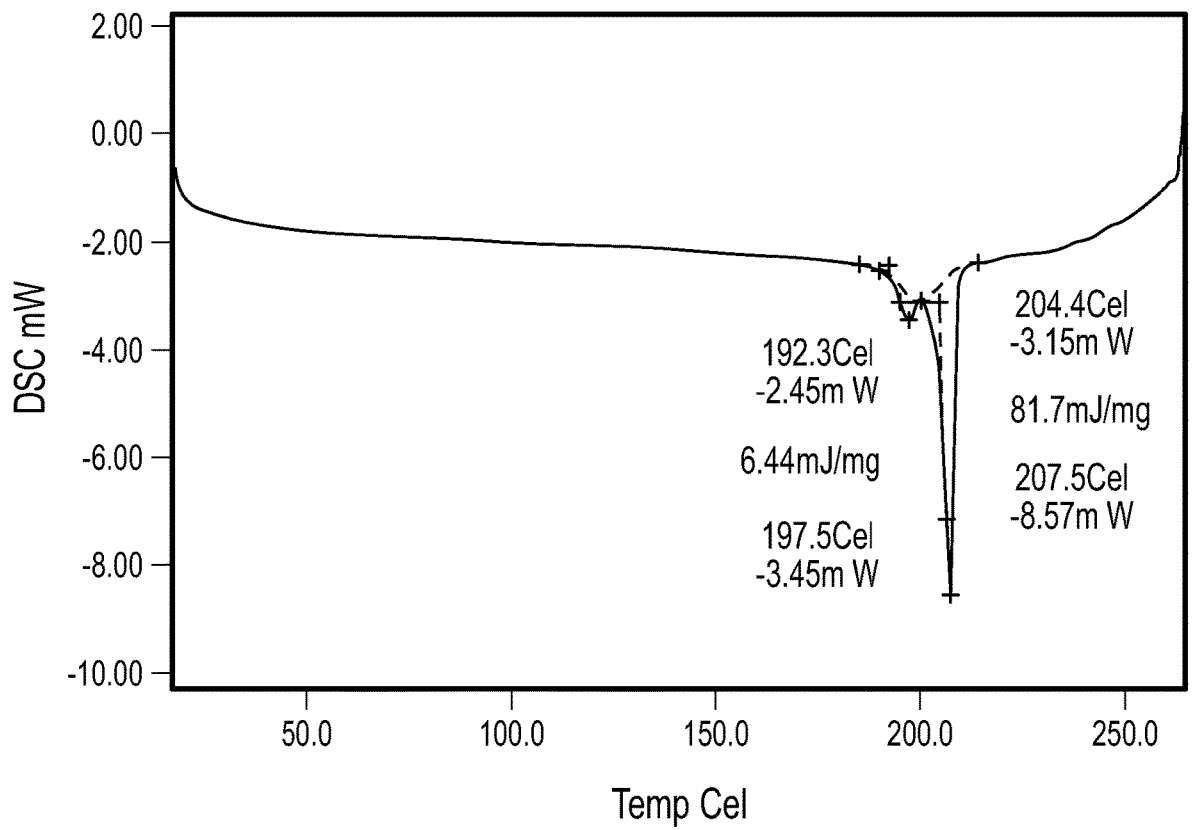
Figure 2C:
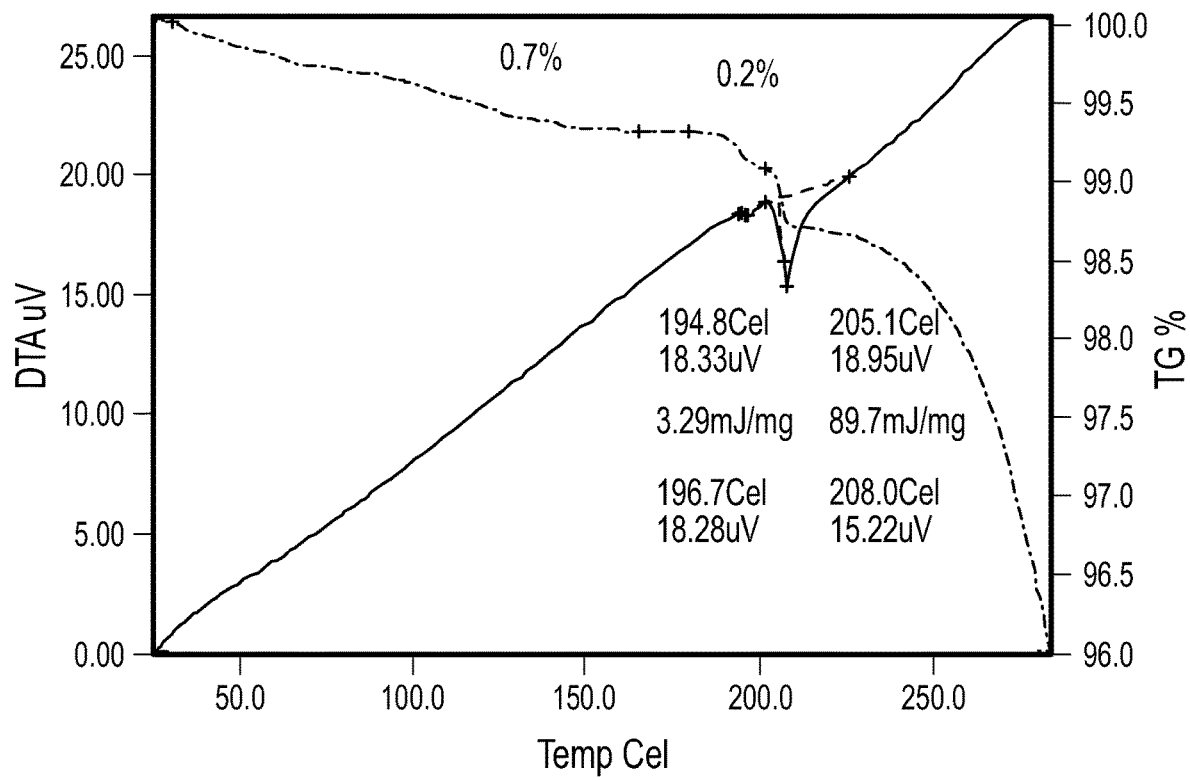
Figure 2D:
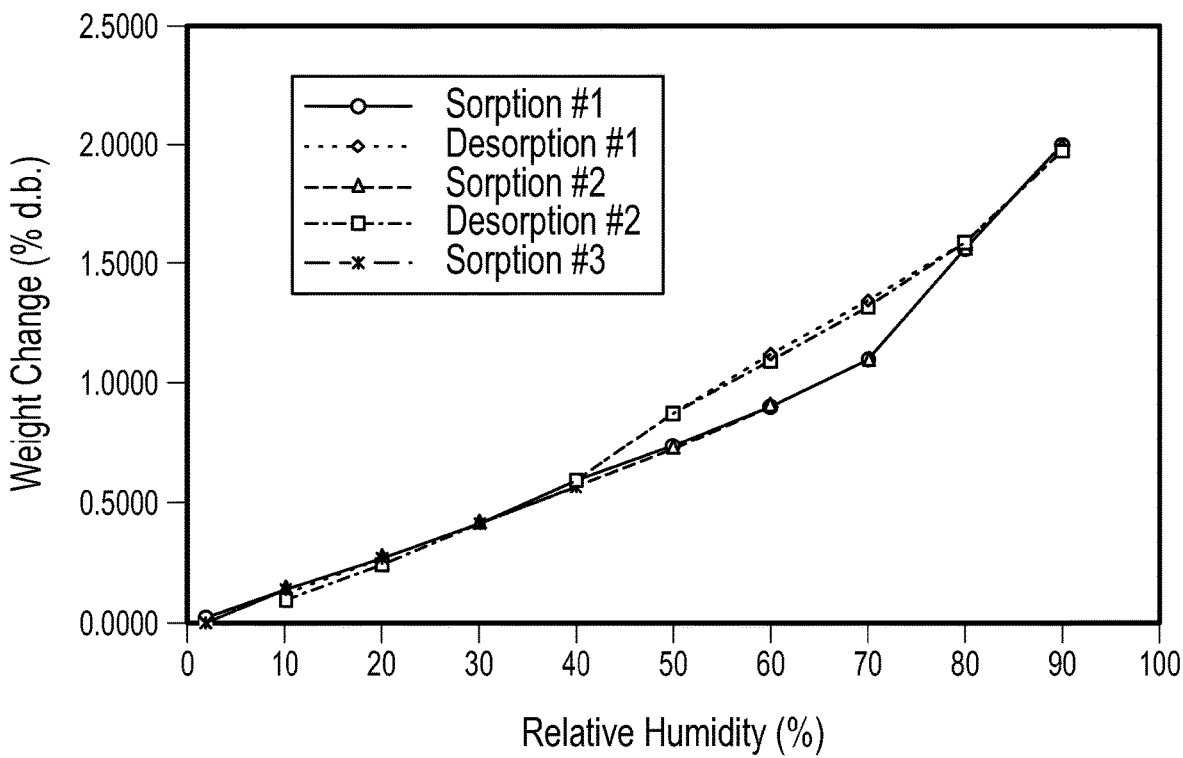
Figure 2E:
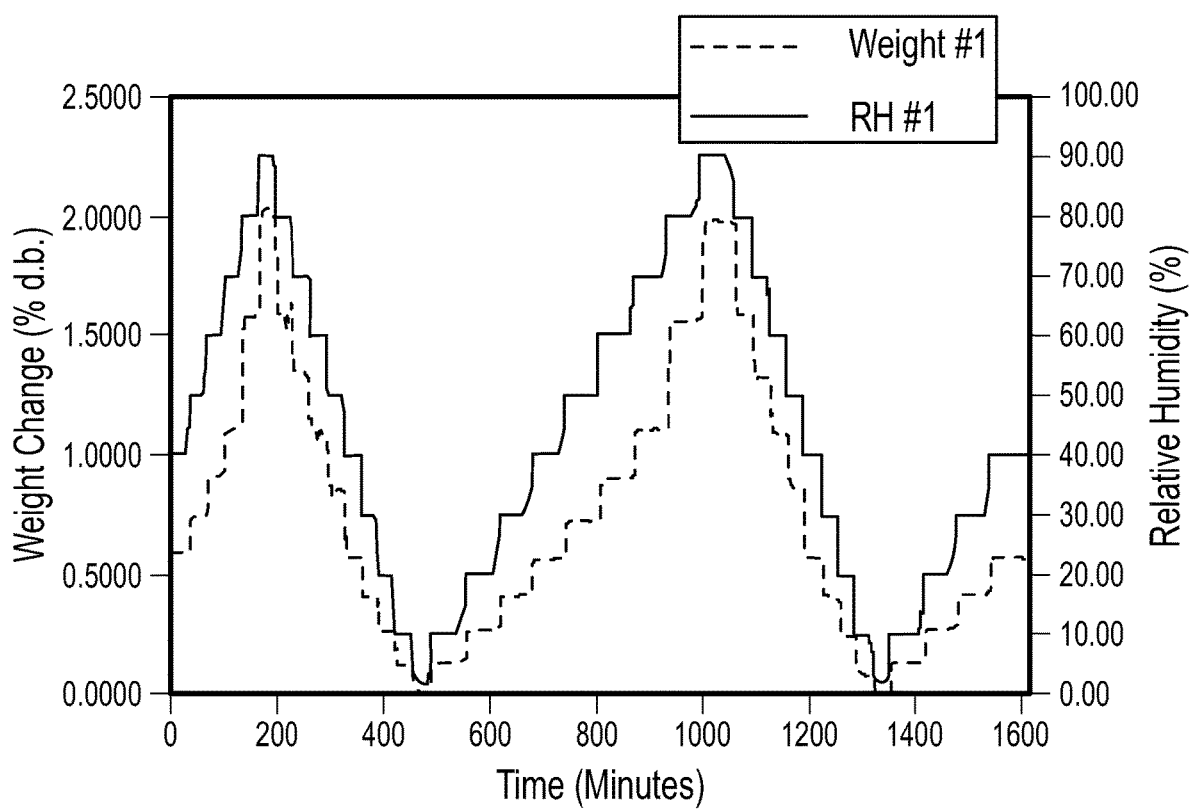

XRPD analysis of the slurry material (scaled-up) was inconsistent with the small scale material observed in the primary salt screen—the diffractogram was consistent with the Form 7 pattern. XRPD analysis conducted post-drying (on filter bed) on the material appeared to be Form 1. The XRPD peaks of Form 2 are shown in Table 45, below, and FIG. 2A. The material was crystalline. Highly birefringent agglomerates of particles were observed by PLM. A small endothermic event was observed by DSC (FIG. 2B) at an onset of around 192° C. A melting transition of Form 1 was observed from an onset of around 204° C. A weight loss of 0.7% was observed by TG/DTA (FIG. 2C) from the onset of heating. A small endothermic event was observed at an onset of around 194° C. with a corresponding weight loss of 0.2%. The solid-solid transition and melting transition of Form 1 was observed from an onset of around 205° C. Degradation was observed after the melting transition. The material appeared moderately hygroscopic by GVS (FIGS. 2D and 2E) with a weight increase of 2% at 90% RH. No change in form was observed by XRPD post-GVS analysis. Trace amounts of solvent were observed by $^1$H NMR (not shown). The spectra obtained was consistent with that of the received material (compound of Formula (I)).

TABLE 45

XRPD peaks of Form 2

| Pos. [°2θ] | FWHM Left [°2θ] | Area [cts*°2θ] | d-spacing [Å] | Height [cts] | Rel. Int. [%] |
|---|---|---|---|---|---|
| 6.19 | 0.15 | 92.45 | 14.28 | 610.55 | 9.20 |
| 8.91 | 0.10 | 34.21 | 9.93 | 338.85 | 5.11 |
| 10.29 | 0.15 | 65.01 | 8.60 | 429.31 | 6.47 |
| 13.43 | 0.41 | 18.88 | 6.59 | 46.76 | 0.70 |
| 13.87 | 0.15 | 11.28 | 6.38 | 74.48 | 1.12 |
| 14.68 | 0.15 | 76.40 | 6.03 | 504.57 | 7.60 |
| 15.12 | 0.10 | 194.68 | 5.86 | 1928.53 | 29.06 |
| 15.87 | 0.15 | 16.00 | 5.58 | 105.68 | 1.59 |
| 16.50 | 0.15 | 76.75 | 5.37 | 506.86 | 7.64 |
| 16.79 | 0.10 | 39.53 | 5.28 | 391.55 | 5.90 |
| 17.14 | 0.10 | 28.80 | 5.17 | 285.27 | 4.30 |
| 17.42 | 0.13 | 43.66 | 5.09 | 346.03 | 5.21 |
| 17.82 | 0.10 | 669.86 | 4.98 | 6635.61 | 100.00 |
| 18.14 | 0.10 | 64.77 | 4.89 | 641.58 | 9.67 |
| 18.72 | 0.15 | 11.62 | 4.74 | 76.73 | 1.16 |
| 19.09 | 0.15 | 11.11 | 4.65 | 73.40 | 1.11 |
| 20.38 | 0.10 | 80.18 | 4.36 | 794.26 | 11.97 |
| 21.08 | 0.15 | 100.83 | 4.21 | 665.90 | 10.04 |
| 22.10 | 0.15 | 85.85 | 4.02 | 566.98 | 8.54 |
| 22.81 | 0.10 | 44.29 | 3.90 | 438.70 | 6.61 |

TABLE 45-continued

XRPD peaks of Form 2

| Pos. [°2θ] | FWHM Left [°2θ] | Area [cts*°2θ] | d-spacing [Å] | Height [cts] | Rel. Int. [%] |
|---|---|---|---|---|---|
| 23.37 | 0.10 | 62.75 | 3.81 | 621.59 | 9.37 |
| 24.20 | 0.10 | 182.81 | 3.68 | 1810.90 | 27.29 |
| 24.61 | 0.10 | 61.83 | 3.62 | 612.45 | 9.23 |
| 25.00 | 0.13 | 45.50 | 3.56 | 360.61 | 5.43 |
| 25.48 | 0.10 | 27.06 | 3.50 | 268.10 | 4.04 |
| 26.14 | 0.10 | 10.42 | 3.41 | 103.22 | 1.56 |
| 27.21 | 0.10 | 49.21 | 3.28 | 487.46 | 7.35 |
| 27.40 | 0.10 | 29.76 | 3.26 | 294.85 | 4.44 |
| 27.97 | 0.13 | 22.74 | 3.19 | 180.20 | 2.72 |
| 29.03 | 0.15 | 32.60 | 3.08 | 215.30 | 3.24 |
| 29.36 | 0.13 | 49.11 | 3.04 | 389.19 | 5.87 |
| 29.63 | 0.13 | 56.71 | 3.01 | 449.38 | 6.77 |
| 29.98 | 0.13 | 44.37 | 2.98 | 351.62 | 5.30 |
| 30.50 | 0.10 | 13.45 | 2.93 | 133.23 | 2.01 |
| 31.20 | 0.10 | 58.94 | 2.87 | 583.89 | 8.80 |
| 31.66 | 0.10 | 19.31 | 2.83 | 191.32 | 2.88 |
| 32.22 | 0.13 | 43.31 | 2.78 | 343.20 | 5.17 |
| 32.61 | 0.20 | 9.60 | 2.75 | 47.53 | 0.72 |
| 34.09 | 0.13 | 20.42 | 2.63 | 161.81 | 2.44 |
| 34.46 | 0.10 | 25.96 | 2.60 | 257.14 | 3.88 |

3. Form 7

Form 7 was considered to be a hydrated form of the compound of Formula (I) that dehydrated to Form 1 upon heating. Form 7 was prepared on a 300 mg scale as follows. Approximately 500 mg of the compound of Formula (I) free base was weighed into a 20 mL scintillation vial. 4 mL of 1,4-dioxane/water (10%) was added to the vial and the resultant slurry was temperature cycled between 40° C. and room temperature for 72 hours. The sample was filtered and the collected material was dried on the filter bed overnight.

Figure 3A:
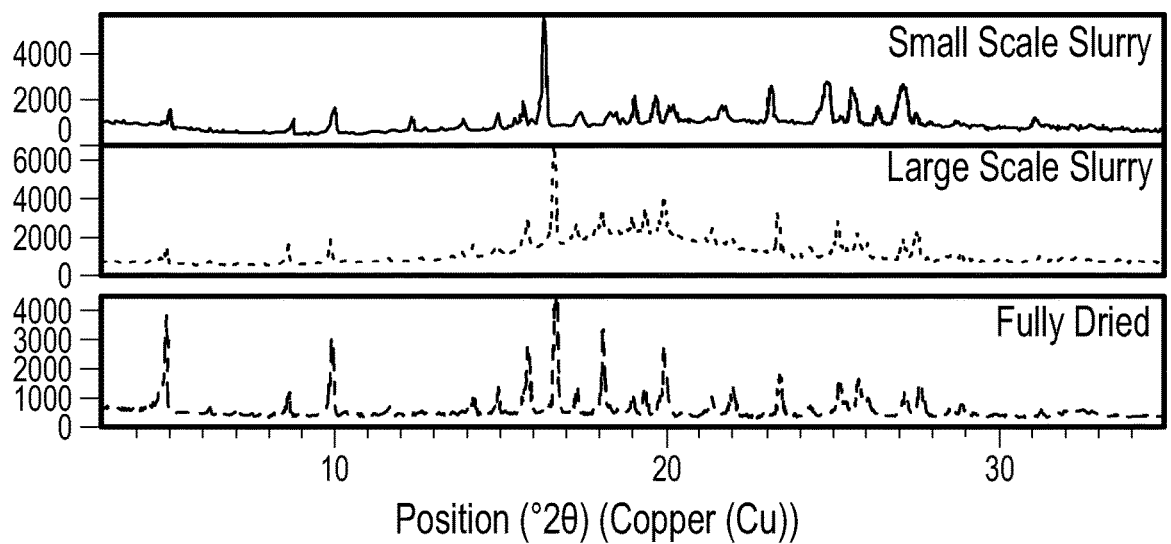
FIGS. 3A-3F are scans of polymorph Form 7 of the compound of Formula (I).
Figure 3B:
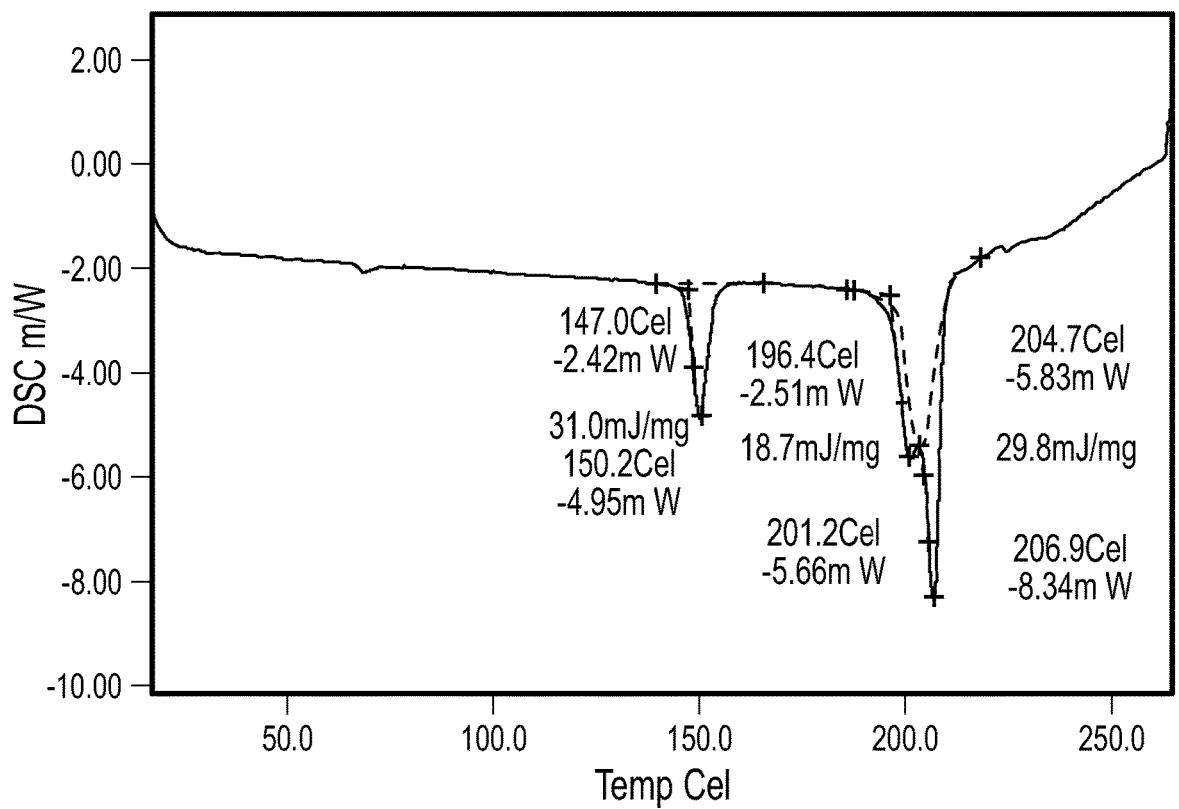
Figure 3C:
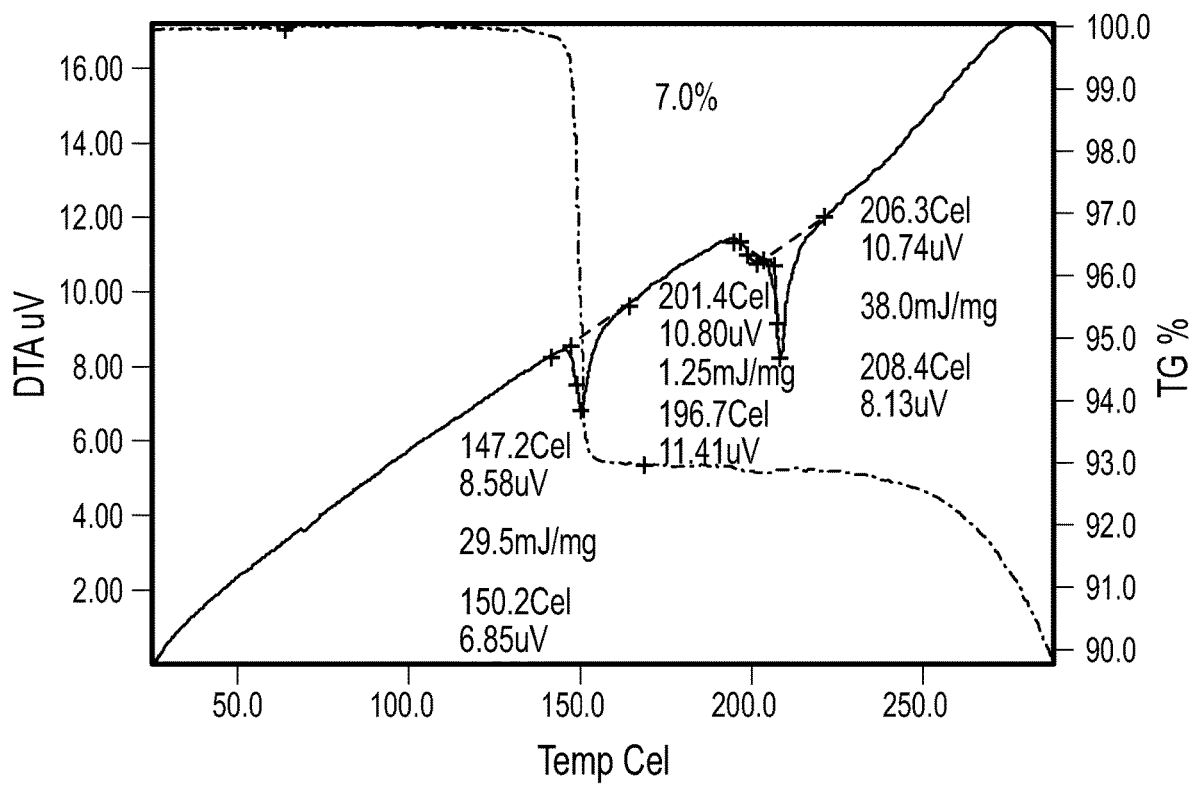
Figure 3D:
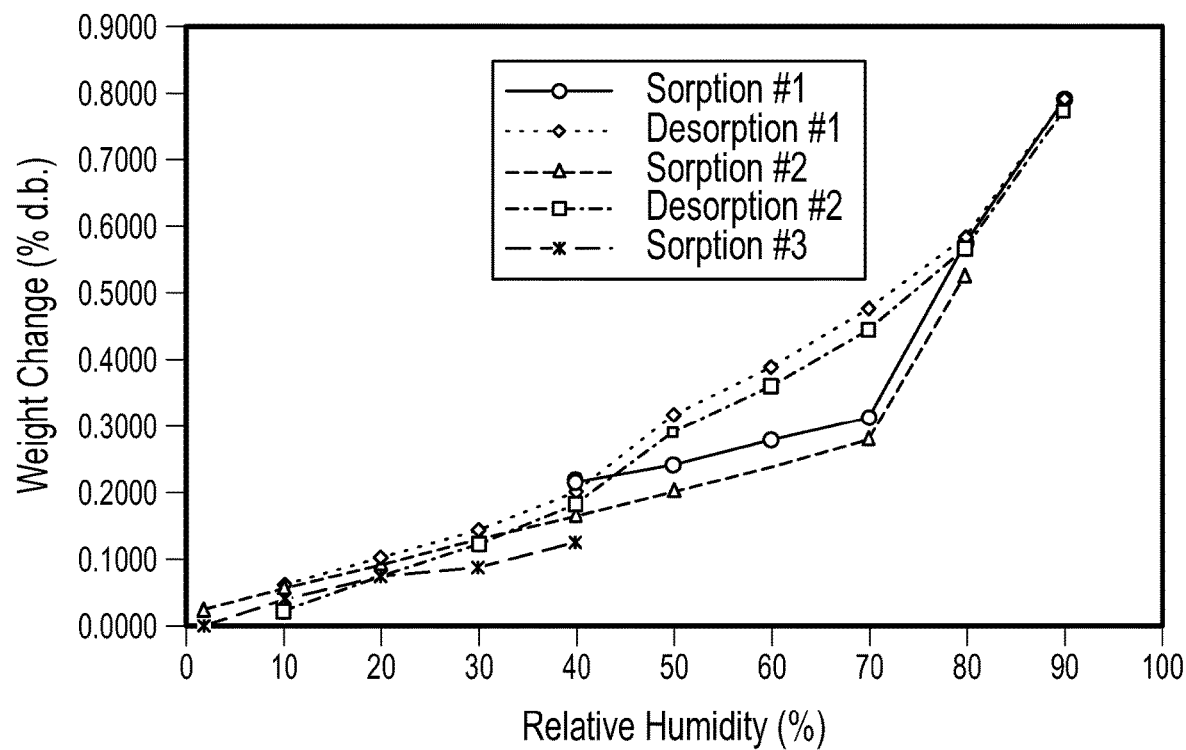
Figure 3E:
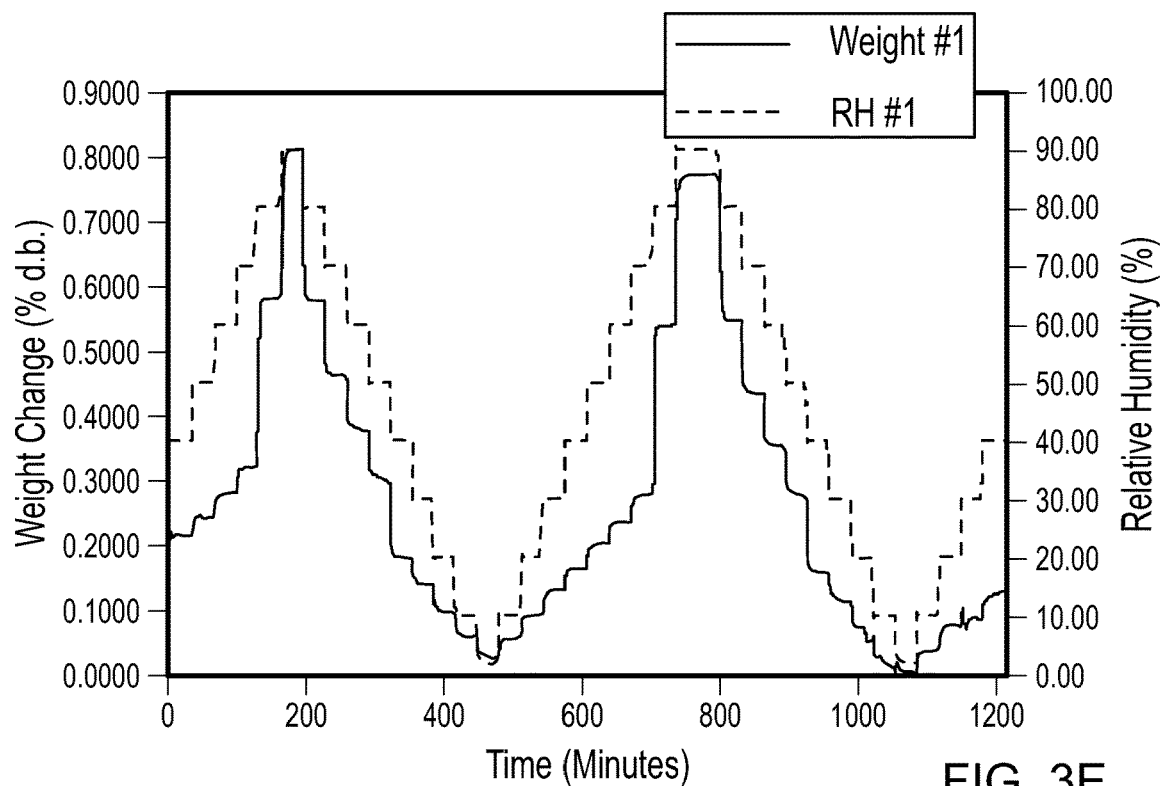
Figure 3F:
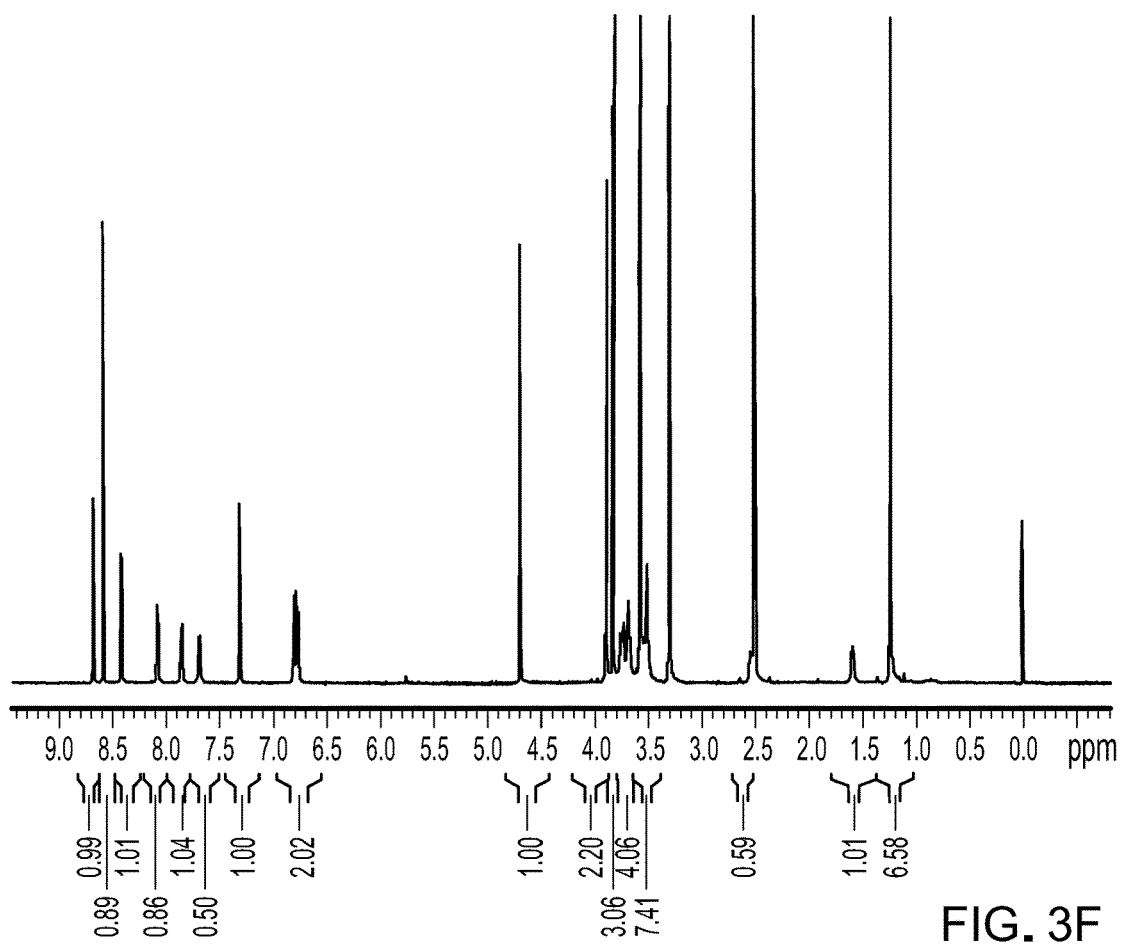

XRPD analysis of the slurry material was consistent with the small scale material identified in the primary salt screen. XRPD post-drying (on filter bed) of the material appeared to be Form 1. The XRPD peaks of Form 7 are shown in Table 46, below, and FIG. 3A. The material was crystalline. Highly birefringent agglomerates of particles were observed by PLM. An endotherm was observed by DSC (FIG. 3B) from an onset of around 147° C. A small endotherm was observed from an onset of around 196° C. relating to the transition observed in Form 1. A melting transition of Form 1 was observed from an onset of around 205° C. An endotherm was observed by TG/DTA (FIG. 3C) from an onset of around 147° C. with a corresponding weight loss of approximately 7% relating to the loss of solvent. The weight loss equated to approximately 2 equivalents of water present. A small endotherm was observed from an onset of around 196° C. relating to the transition observed in Form 1. The melting transition of Form 1 was observed from an onset of around 206° C. The material showed slight hygroscopicity by GVS (FIGS. 3D and 3E) with a weight increase of 0.8% at 90% RH, and no change in form was observed by XRPD post-GVS analysis. Trace amounts of solvent were observed by $^1$H NMR (FIG. 3F).

TABLE 46

XRPD peaks of Form 7

| Pos. [°2θ] | FWHM Left [°2θ] | Area [cts*°2θ] | d-spacing [Å] | Height [cts] | Rel. Int. [%] |
|---|---|---|---|---|---|
| 4.88 | 0.15 | 124.64 | 18.10 | 823.10 | 14.40 |
| 6.19 | 0.15 | 19.85 | 14.28 | 131.10 | 2.29 |
| 8.59 | 0.15 | 142.39 | 10.30 | 940.35 | 16.45 |

TABLE 46-continued

XRPD peaks of Form 7

| Pos. [°2θ] | FWHM Left [°2θ] | Area [cts*°2θ] | d-spacing [Å] | Height [cts] | Rel. Int. [%] |
|---|---|---|---|---|---|
| 9.87 | 0.15 | 176.65 | 8.96 | 1166.58 | 20.41 |
| 10.31 | 0.15 | 28.54 | 8.58 | 188.50 | 3.30 |
| 11.62 | 0.10 | 34.57 | 7.62 | 342.41 | 5.99 |
| 12.58 | 0.10 | 36.56 | 7.03 | 362.18 | 6.34 |
| 14.14 | 0.15 | 140.39 | 6.27 | 927.13 | 16.22 |
| 14.84 | 0.15 | 143.38 | 5.97 | 946.87 | 16.57 |
| 15.77 | 0.26 | 452.10 | 5.62 | 1791.38 | 31.34 |
| 16.58 | 0.15 | 865.48 | 5.35 | 5715.58 | 100.00 |
| 17.26 | 0.10 | 199.94 | 5.14 | 1980.57 | 34.65 |
| 18.04 | 0.10 | 290.40 | 4.92 | 2876.67 | 50.33 |
| 18.97 | 0.10 | 237.60 | 4.68 | 2353.62 | 41.18 |
| 19.34 | 0.15 | 399.14 | 4.59 | 2635.93 | 46.12 |
| 19.91 | 0.10 | 334.71 | 4.46 | 3315.58 | 58.01 |
| 21.35 | 0.10 | 180.69 | 4.16 | 1789.93 | 31.32 |
| 21.84 | 0.10 | 138.81 | 4.07 | 1375.00 | 24.06 |
| 23.34 | 0.10 | 258.86 | 3.81 | 2564.23 | 44.86 |
| 24.28 | 0.13 | 108.82 | 3.67 | 862.39 | 15.09 |
| 25.12 | 0.10 | 217.06 | 3.55 | 2150.16 | 37.62 |
| 25.73 | 0.10 | 158.86 | 3.46 | 1573.65 | 27.53 |
| 26.04 | 0.10 | 95.40 | 3.42 | 945.00 | 16.53 |
| 27.11 | 0.10 | 121.21 | 3.29 | 1200.73 | 21.01 |
| 27.51 | 0.15 | 243.26 | 3.24 | 1606.48 | 28.11 |
| 28.47 | 0.20 | 64.59 | 3.14 | 319.91 | 5.60 |
| 28.84 | 0.13 | 73.98 | 3.10 | 586.26 | 10.26 |
| 30.18 | 0.15 | 26.71 | 2.96 | 176.40 | 3.09 |
| 31.17 | 0.15 | 38.53 | 2.87 | 254.43 | 4.45 |
| 31.61 | 0.10 | 27.96 | 2.83 | 276.98 | 4.85 |
| 32.81 | 0.15 | 32.51 | 2.73 | 214.67 | 3.76 |
| 33.58 | 0.20 | 21.74 | 2.67 | 107.69 | 1.88 |

4. Form 8

Form 8 was identified as an isopropyl alcohol (IPA) solvate which desolvates upon heating to Form 1. Form 8 was prepared on a 300 mg scale as follows. Approximately 500 mg of the compound of Formula (I) free base was weighed into a 20 mL scintillation vial. 4 mL of IPA was added to the vial and the resultant slurry was temperature cycled between 40° C. and room temperature for 72 hours. The sample was filtered and the collected material was dried overnight under vacuum at 40° C.

Figure 4A:
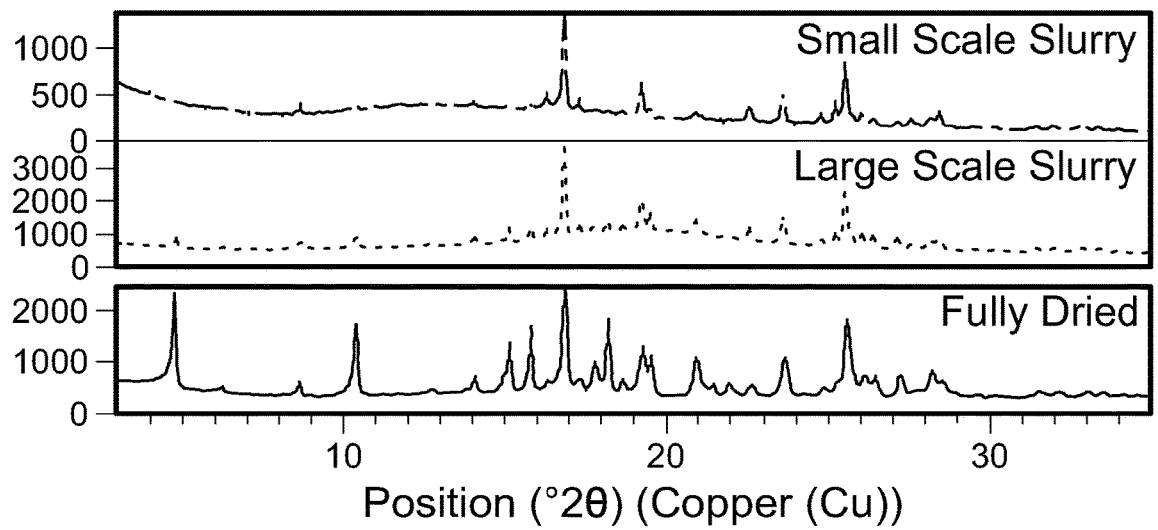
FIGS. 4A-4F are scans of polymorph Form 8 of the compound of Formula (I).
Figure 4B:
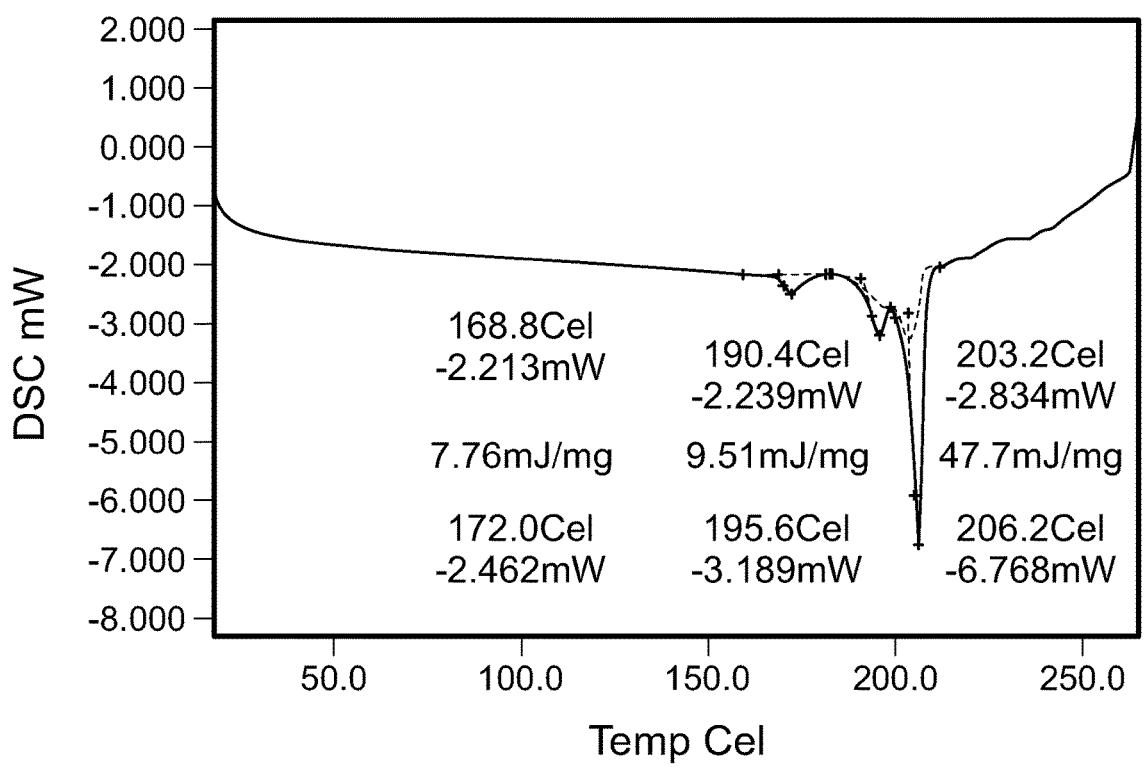
Figure 4C:
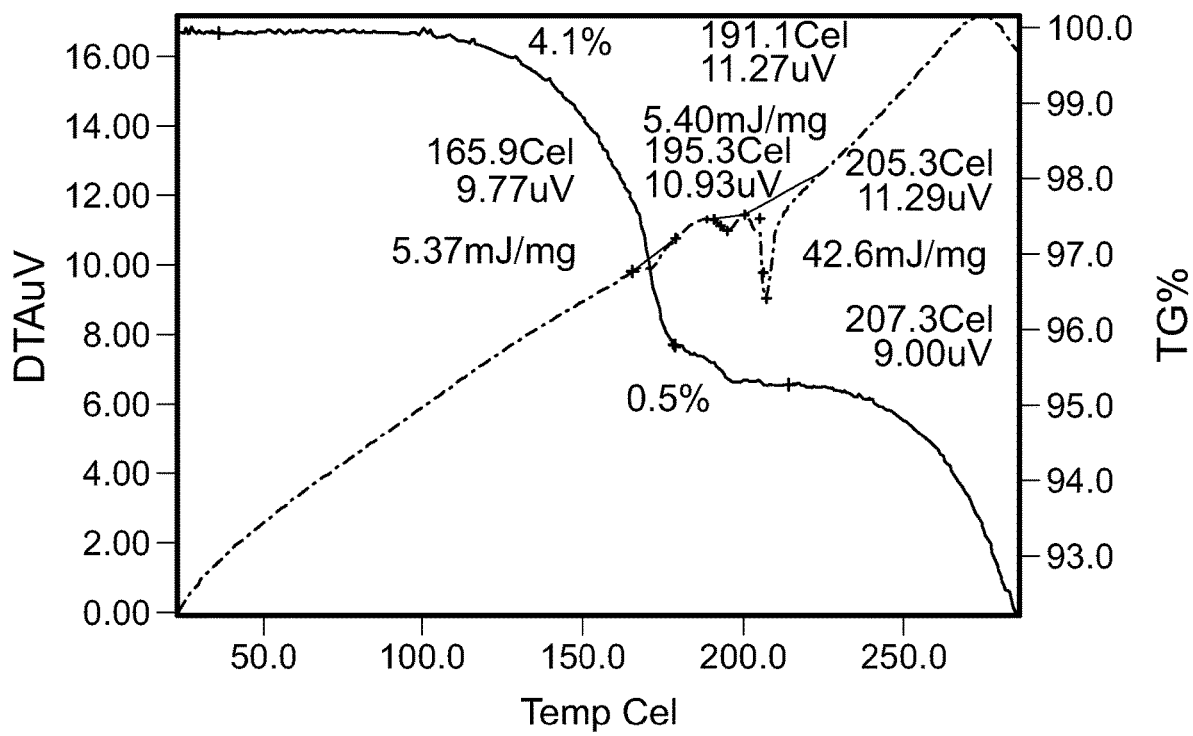
Figure 4D:
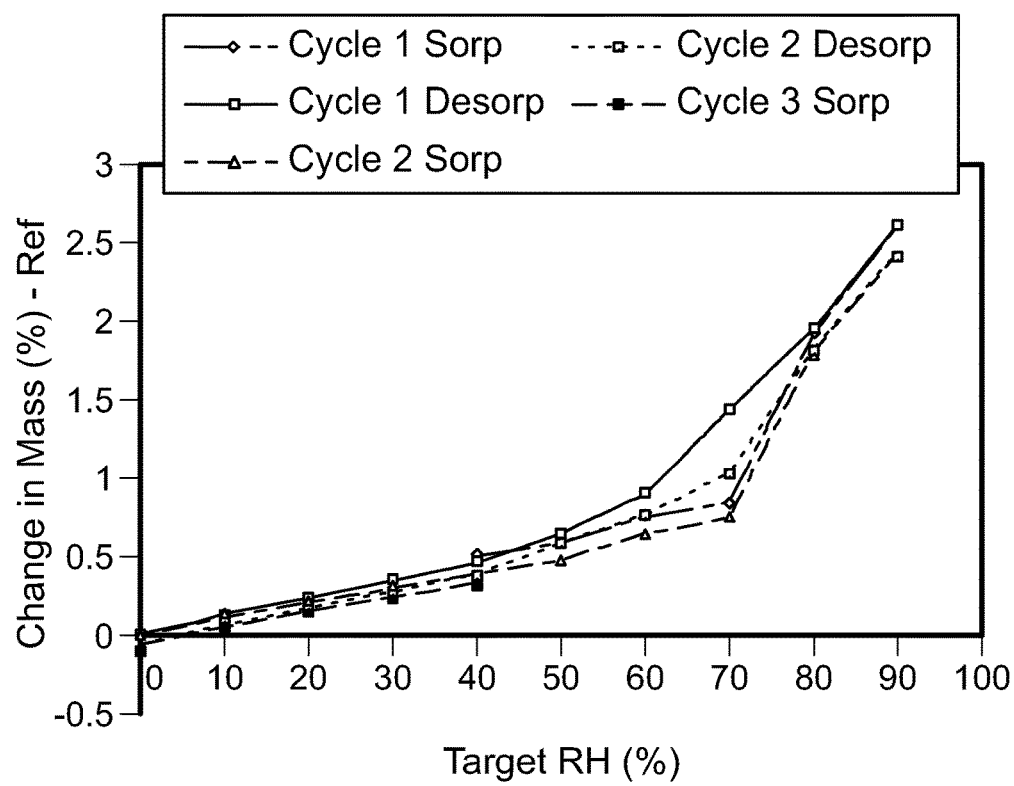
Figure 4E:
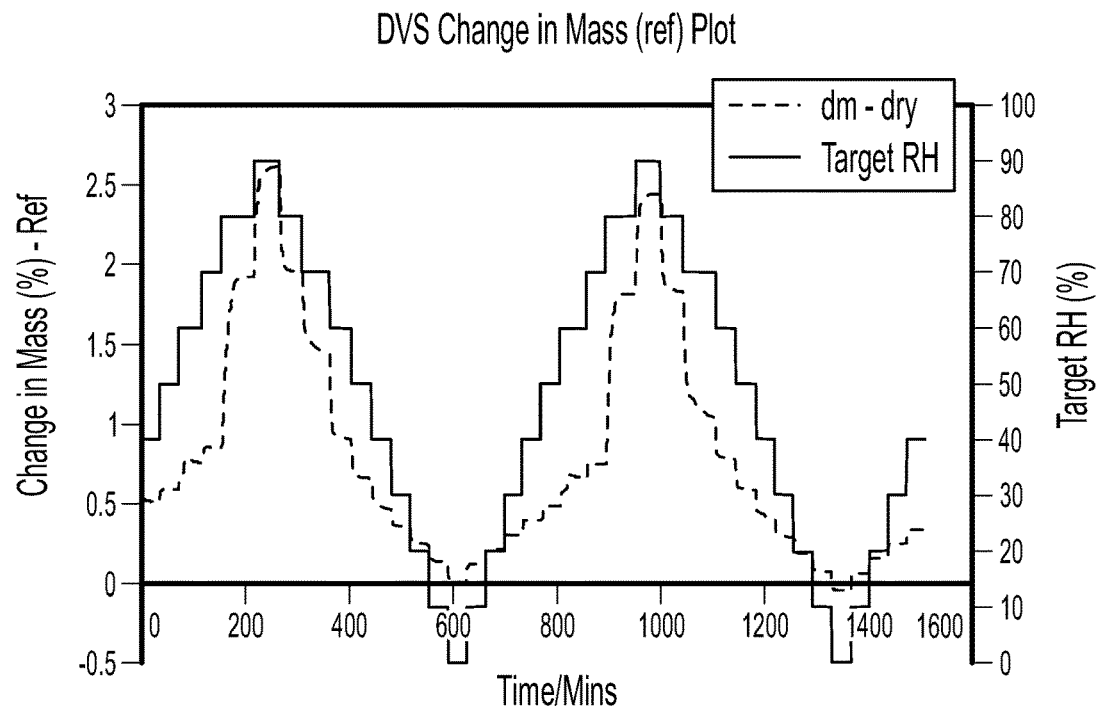
Figure 4F:
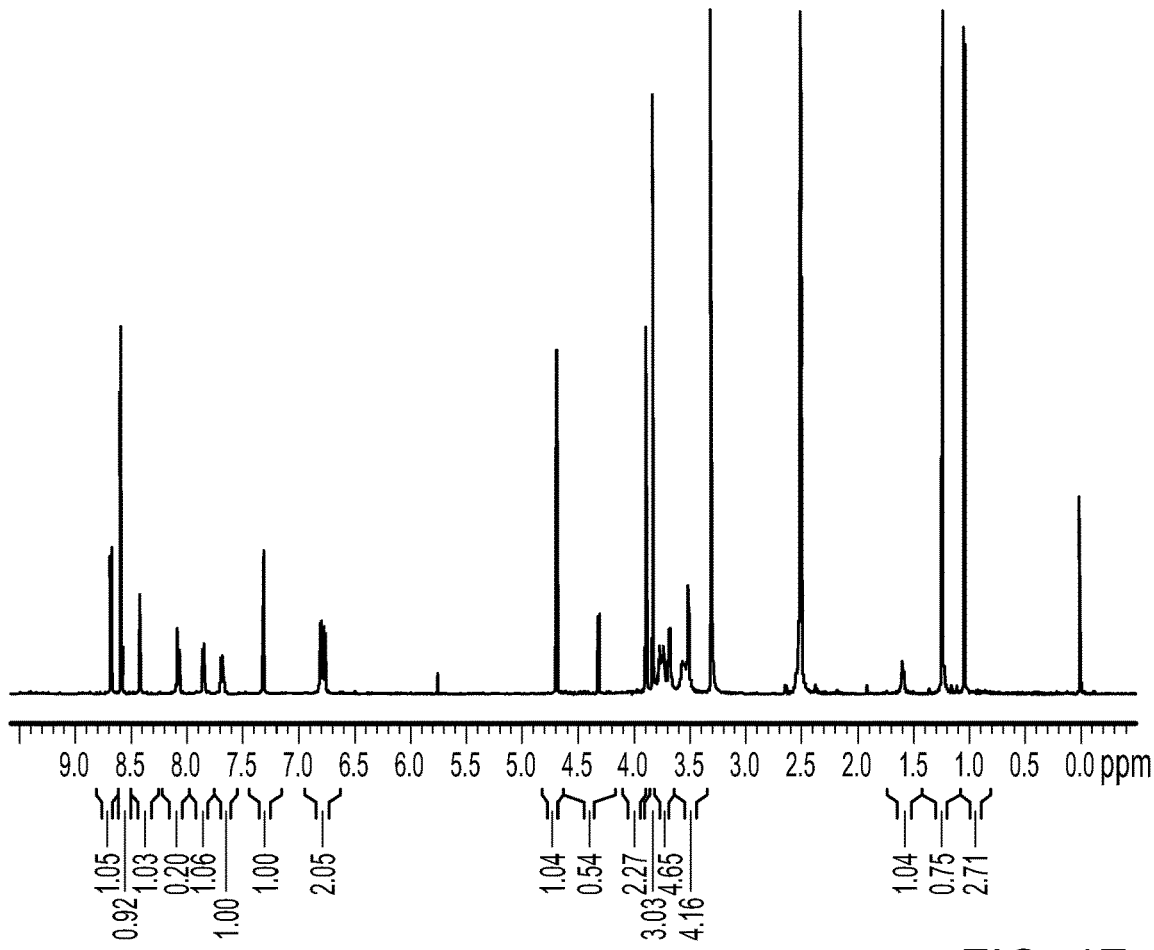

XRPD analysis of the slurry material was consistent with the small scale material observed in the primary polymorph and salt screens. XRPD post-drying (40° C. under vacuum) analysis of the material appeared to be Form 8. The XRPD peaks of Form 8 are shown in Table 47, below, and FIG. 4A. The material was crystalline. Highly birefringent agglomerates of particles were observed by PLM. An endotherm was observed by DSC (FIG. 4B) from an onset of around 168° C. A small endotherm was observed from an onset of around 190° C. relating to the transition observed in Form 1. A melting transition of Form 1 was observed from an onset of around 203° C. An endotherm was observed by TG/DTA (FIG. 4C) from an onset of around 165° C. with a corresponding weight loss of approximately 4% relating to the loss of solvent. The weight loss equated to approximately 0.5 equivalents of IPA present in the sample. A small endotherm was observed from an onset of around 191° C. relating to the transition observed in Form 1. A melting transition of Form 1 was observed from an onset of around 205° C. The material appeared moderately hygroscopic by GVS (FIGS. 4D and 4E) with a weight increase of 2.6% at 90% RH. A higher amorphous content was observed by XRPD post-GVS analysis. 0.5 equivalents of IPA were observed by $^1$H NMR (FIG. 4F).

TABLE 47

XRPD peaks of Form 8

| Pos. [°2θ] | FWHM Left [°2θ] | Area [cts*°2θ] | d-spacing [Å] | Height [cts] | Rel. Int. [%] |
|---|---|---|---|---|---|
| 6.19 | 0.15 | 92.45 | 14.28 | 610.55 | 9.20 |
| 8.91 | 0.10 | 34.21 | 9.93 | 338.85 | 5.11 |
| 10.29 | 0.15 | 65.01 | 8.60 | 429.31 | 6.47 |
| 13.43 | 0.41 | 18.88 | 6.59 | 46.76 | 0.70 |
| 13.87 | 0.15 | 11.28 | 6.38 | 74.48 | 1.12 |
| 14.68 | 0.15 | 76.40 | 6.03 | 504.57 | 7.60 |
| 15.12 | 0.10 | 194.68 | 5.86 | 1928.53 | 29.06 |
| 15.87 | 0.15 | 16.00 | 5.58 | 105.68 | 1.59 |
| 16.50 | 0.15 | 76.75 | 5.37 | 506.86 | 7.64 |
| 16.79 | 0.10 | 39.53 | 5.28 | 391.55 | 5.90 |
| 17.14 | 0.10 | 28.80 | 5.17 | 285.27 | 4.30 |
| 17.42 | 0.13 | 43.66 | 5.09 | 346.03 | 5.21 |
| 17.82 | 0.10 | 669.86 | 4.98 | 6635.61 | 100.00 |
| 18.14 | 0.10 | 64.77 | 4.89 | 641.58 | 9.67 |
| 18.72 | 0.15 | 11.62 | 4.74 | 76.73 | 1.16 |
| 19.09 | 0.15 | 11.11 | 4.65 | 73.40 | 1.11 |
| 20.38 | 0.10 | 80.18 | 4.36 | 794.26 | 11.97 |
| 21.08 | 0.15 | 100.83 | 4.21 | 665.90 | 10.04 |
| 22.10 | 0.15 | 85.85 | 4.02 | 566.98 | 8.54 |
| 22.81 | 0.10 | 44.29 | 3.90 | 438.70 | 6.61 |
| 23.37 | 0.10 | 62.75 | 3.81 | 621.59 | 9.37 |
| 24.20 | 0.10 | 182.81 | 3.68 | 1810.90 | 27.29 |
| 24.61 | 0.10 | 61.83 | 3.62 | 612.45 | 9.23 |
| 25.00 | 0.13 | 45.50 | 3.56 | 360.61 | 5.43 |
| 25.48 | 0.10 | 27.06 | 3.50 | 268.10 | 4.04 |
| 26.14 | 0.10 | 10.42 | 3.41 | 103.22 | 1.56 |
| 27.21 | 0.10 | 49.21 | 3.28 | 487.46 | 7.35 |
| 27.40 | 0.10 | 29.76 | 3.26 | 294.85 | 4.44 |
| 27.97 | 0.13 | 22.74 | 3.19 | 180.20 | 2.72 |
| 29.03 | 0.15 | 32.60 | 3.08 | 215.30 | 3.24 |
| 29.36 | 0.13 | 49.11 | 3.04 | 389.19 | 5.87 |
| 29.63 | 0.13 | 56.71 | 3.01 | 449.38 | 6.77 |
| 29.98 | 0.13 | 44.37 | 2.98 | 351.62 | 5.30 |
| 30.50 | 0.10 | 13.45 | 2.93 | 133.23 | 2.01 |
| 31.20 | 0.10 | 58.94 | 2.87 | 583.89 | 8.80 |
| 31.66 | 0.10 | 19.31 | 2.83 | 191.32 | 2.88 |
| 32.22 | 0.13 | 43.31 | 2.78 | 343.20 | 5.17 |
| 32.61 | 0.20 | 9.60 | 2.75 | 47.53 | 0.72 |
| 34.09 | 0.13 | 20.42 | 2.63 | 161.81 | 2.44 |
| 34.46 | 0.10 | 25.96 | 2.60 | 257.14 | 3.88 |

Example 7: RET Enzyme Assay

The compound of Formula (I) was screened for its ability to inhibit wildtype and V804M mutant RET kinase using CisBio's HTRF® KinEASE™-TK assay technology. Briefly, N-terminal GST tagged recombinant human RET cytoplasmic domain (aa 658-end) from Eurofins (0.25 nM RET; Catalog No. 14-570M) or N-terminal GST tagged recombinant human V804M mutant RET cytoplasmic domain (aa 658-end) from Millipore (0.25 nM enzyme; Catalog No. 14-760) was incubated with 250 nM TK-substrate biotin (CisBio, part of Catalog No. 62TK0PEC) and 1 mM ATP along with test compound in a buffer consisting of 25 mM HEPES pH 7.4, 10 mM $MgCl_2$, 0.01% Triton X-100, and 2% DMSO in a volume of 8 μL. The compound was typically prepared in a threefold serial dilution in DMSO and added to the assay to give the appropriate final concentration. After a 30-minute incubation at 22° C., the reaction was quenched by adding 8 of quench solution containing 31.25 nM Sa-XL665 and 1×TK-ab-Cryptate in HTRF detection buffer (all from CisBio, part of Cat. No. 62TK0PEC). After a 1 hour incubation at 22° C., the extent of reaction was determined using a PerkinElmer EnVision multimode plate reader via HTRF dual wavelength detection, and the percent of control (POC) was calculated using a ratiometric emission factor. 100 POC was determined using no test compounds and 0 POC was determined using pre-quenched control reactions. The POC values were fit to a 4 parameter logistic curve, and the $IC_{50}$ is defined as the concentration of inhibitor at which the POC equals 50 for the fitted curve. The compound of Formula (I) was found to have $IC_{50}$ values of 14.0 nM and 24.1 nM for inhibiting wildtype RET enzyme and V804M mutant RET kinase, respectively.

Example 8: RET Cell Assay

The cellular potency of a compound inhibiting RET kinase was determined in HEK-293 cells expressing a Kif5b-RET fusion protein. Briefly, HEK-293 cells expressing a Kif5b-RET fusion protein were plated at 50K cells/well in 96-well poly-D-lysine-coated plates the day prior to the assay. The cells were incubated for 1 hour with test compound in DMEM (Dulbecco's Modified Eagle Medium) at a final DMSO concentration of 0.5%. The compound of Formula (I) was typically prepared in a threefold serial dilution in DMSO and added to the assay to give the appropriate final concentration. After 1 hour the media was removed, the cells were fixed with 3.8% formaldehyde for 20 min, washed with PBS, and permeabilized for 10 min with 100% methanol. The plates were then washed with PBS-0.05% Tween20, and blocked with LI-COR Blocking solution (LI-COR catalog #927-40000) for 1 hour. Plates were washed with PBS-0.05% Tween20, then incubated with anti-phospho-RET(Tyr1062) (Santa Cruz catalog # sc-20252-R) antibody and anti-GAPDH (Millipore catalog # MAB374) antibody for 2 hours. The plates were washed with PBS-0.05% Tween20, and incubated with anti-rabbit 680 (Molecular Probes catalog No. A21109) and anti-mouse 800 (LI-COR catalog No. 926-32210) secondary antibodies for 1 hour. All antibodies were diluted in LI-COR Block containing 0.05% Tween. The plates were washed with PBS-0.05% Tween20, 100 μL PBS was added to each well, and the plates were read on a LI-COR Aerius fluorescent plate reader. The phospho-RET signal was normalized to the GAPDH signal. 100 POC (percent of control) was determined using no test compounds and 0 POC was determined using 1 μM of a control inhibitor. The POC values were fit to a 4 parameter logistic curve. The $IC_{50}$ value is the point where the curve crosses 50 POC. The compound of Formula (I) was found to have an $IC_{50}$ value of 4.2 nM for inhibiting RET kinase in HEK-293 cells expressing a Kif5b-RET fusion protein.

Example 9: Powder Blend in a Hard Gelatin Capsule

Powder blend formulations were prepared and encapsulated in a hard gelatin capsule in a 10 mg, 20 mg, or 80 mg dosage form (see Tables 48 and 49). The components of the formulation included the compound of Formula (I), microcrystalline cellulose (Avicel® PH-102, FMC Corporation, Philadelphia, Pa.) and silicon dioxide (CAB-O-SIL® M-5P fumed silica; Cabot Corporation, Billerica, Mass.).

For the 10 mg capsule (20% compound of Formula (I)), the components were mixed for a set amount of time and then filled into hard gelatin capsules by weight. For the 20 mg and 80 mg capsules (30% compound of Formula (I)), the compound of Formula (I) was micronized, then blended with silicon dioxide and microcrystalline cellulose for a set amount of time. The blend was then milled and blended a second time. After passing an in-process control (IPC) for blend uniformity, the blend was filled by weight into hard gelatin capsules. The capsules then passed an IPC for uniformity of fill weight prior to placing the finished capsules into high-density polyethylene bottles, induction sealing, and labeling.

TABLE 48

10 mg powder blend formulation

| Component | Wt % |
|---|---|
| Formula (I) | 20% |
| Microcrystalline cellulose | 79% |
| Silicon dioxide | 1% |

TABLE 49

20 mg and 80 mg powder blend formulations

| Component | Wt % |
|---|---|
| Formula (I) | 30% |
| Microcrystalline cellulose | 69% |
| Silicon dioxide | 1% |

Example 10: Spray Dried Dispersion Blend

A blend incorporating a spray dried dispersion was prepared. The components of the formulation are shown in Table 49, below, and included the compound of Formula (I), hydroxypropyl methylcellulose acetate succinate (HPMC-AS; Shin-Etsu AQOAT®, Shin-Etsu Chemical Co., Plaquemine, La.), mannitol (Parteck® M100, EMD Millipore Corp., Billerica, Mass.), microcrystalline cellulose (Avicel® PH-102, FMC Corporation, Philadelphia, Pa.), poloxamer 188 (Kolliphor® P 188, BASF), croscarmellose sodium (Ac-Di-Sol SD-711, FMC Health and Nutrition, Philadelphia, Pa.), and magnesium stearate (Hyqual® NF-GenAR®, Avantor, Center Valley, Pa.).

The manufacture of the blend consisted of weighing dichloromethane, methanol and the compound of Formula (I). The components were mixed until all the solids were dissolved and then HPMC-AS was weighed and added in portions with continued mixing. Once a homogenous solution was obtained it was spray dried using set parameters and the resulting solid was dried under vacuum with heat until the spray dried intermediate (SDI) passed an IPC for residual solvent. After the SDI passed release specifications, it was weighed with mannitol, microcrystalline cellulose, poloxamer 188 and croscarmellose sodium and then blended for a set amount of time. The mixture was milled and then blended for a set amount of time. The blended mixture was tested for content uniformity and then the magnesium stearate was added and the mixture was blended. The blended mixture was roller compacted using set parameters and the resulting granules were blended for a set amount of time and the resulting mixture filled by weight into hard gelatin capsules. Filled capsules must pass an IPC for uniformity of fill weight prior to placing the finished capsules into high-density polyethylene bottles, induction sealing, and labeling.

TABLE 49

Spray dried dispersion blend formulation

| Component | Wt % |
|---|---|
| Formula (I) | 6.67 |
| HPMC-AS | 13.4 |

TABLE 49-continued

Spray dried dispersion blend formulation

| Component | Wt % |
|---|---|
| Mannitol | 36.13 |
| Microcrystalline cellulose | 36.13 |
| Poloxamer 188 | 5.00 |
| Croscarmellose sodium | 2.50 |
| Magnesium stearate | 0.25 |

Example 11: Oral Suspension

Compounding of Powder for Oral Suspension and Dispensing

The drug product, the compound of Formula (I) in crystalline Form 1, powder for oral suspension, included the drug substance (the compound of Formula (I) in crystalline Form 1) filled into a 300 mL Kylix Bottle, Amber Type III Glass, PP28 Neck and capped with a 28 mm White Tamper Evident and Child Resistant Screw Cap TriSeal® Wad. The compound of Formula (I) in crystalline Form 1 powder for oral suspension was stored at a controlled room temperature of between 15° C. and 30° C. The compound of Formula (I) in crystalline Form 1 powder for oral suspension was prepared into a liquid suspension prior to administration.

The compound of Formula (I) in crystalline Form 1 powder for oral suspension was provided to the pharmacy where it was compounded into a 20 mg/mL suspension with the addition of 1:1 Ora-Sweet® SF and Ora-Plus®. The components of the suspension are shown the table below.

TABLE 50

The compound of Formula (I) 20 mg/mL Suspension

| Component | Quantity for Reconstituion |
|---|---|
| The compound of Formula (I) (Form 1) | 5.0 g (5000 mg) |
| Ora-Sweet ® SF (NDC# 0574-0302-16) | 125 mL |
| Ora-Plus ® (NDC# 0574-0303-16) | 125 mL |

Compounding of Suspension

The compound of Formula (I) suspension is compounded as follows:

The cap from the amber glass bottle containing 5.0 g of The compound of Formula (I) in crystalline Form 1 drug substance was removed.

To the amber glass bottle, 125 mL of Ora-Plus® and 125 mL of Ora-Sweet® SF was added to make a total volume of 250 mL.

The bottle was tightly capped, swirled and then shaken by hand until no solids were observed on the bottom of the bottle. A vortex can be used if available.

The provided label for the prepared Oral suspension was placed over the original bottle label. Booklet label pages were removed, and destruction was documented if necessary.

Insertion of an Adaptor
1. The bottle was held cap end up.
2. The cap was unscrewed, keeping the open end up to avoid spilling.
3. The bottle and cap were set down, and an adaptor was picked up.
4. An adaptor was inserted into the bottle via the ribbed end. Some force was used to insert all the way.
5. The cap was replaced.

Administration of Suspension

Prior to measuring out each dose, the bottle was shaken by hand to ensure a smooth uniform suspension of the liquid. Formation of bubbles was avoided, as possible.

Administration of suspension for oral dosing was done with a graduated syringe with an inner diameter opening of ≥2 mm. Acceptable 1 mL and 5 mL syringes and bottle adapters were used. Graduations of 0.1 ml are preferred, but graduations of 0.2 ml or 0.5 ml are acceptable. The dosing syringe was filled with an equal volume of water after each dose administration to be sure all residue of the suspension was ingested. A new syringe was used for each dose.

Syringe Usage

1. The bottle was held, cap end up, and and the cap was unscrewed, keeping the open end up to avoid spilling.
2. The syringe tip was inserted into the bottle.
3. The bottle was inverted, the compound of Formula (I) oral suspension was drawn into the syringe to the desired volume. The syringe plunger was not pulled out of the syringe.
4. The bottle was inverted, the syringe was removed, and the bottle was recapped.

Patients were instructed to store the prepared suspension in the refrigerator.

We claim:

1. A solid formulation comprising:
a compound of the Formula (I):

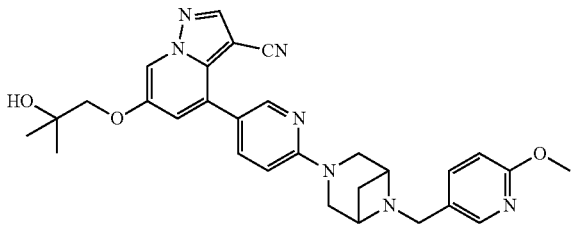

or a pharmaceutically acceptable salt, amorphous form, or polymorph form thereof in an amount from about 15 wt % to about 35 wt %;
a diluent or filler in an amount from about 65 wt % to about 85 wt %; and
a glidant in an amount from about 0.1 wt % to about 5 wt %.

2. The solid formulation of claim 1, wherein the diluent or filler is microcrystalline cellulose.

3. The solid formulation of claim 2, wherein the glidant is fumed silica or silicon dioxide.

4. The solid formulation of claim 3 that is formulated as a tablet, capsule, sachet, powder, granules, coated particle, coated tablet, enterocoated tablet, enterocoated capsule, melting strip, or melting film.

5. The solid formulation of claim 4, wherein the powder is further encapsulated in a hard gelatin capsule.

6. The solid formulation claim 1, wherein the solid formulation is prepared from a polymorph form of the compound of Formula (I) or a pharmaceutically acceptable salt thereof.

7. The solid formulation of claim 1, wherein the compound of Formula (I) or a pharmaceutically acceptable salt, amorphous form, or polymorph form thereof is present in an amount of about 30 wt %; the diluent or filler is present in an amount of about 69 wt %; and the glidant is present in an amount of about 1 wt %.

8. A liquid formulation comprising:
a compound of the Formula (I)

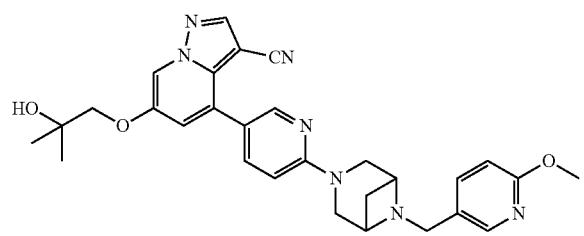

or a pharmaceutically acceptable salt thereof; and
an aqueous sweetener.

9. The liquid formulation of claim 8, wherein the aqueous sweetener comprises sucrose, glycerin, sorbitol, or a combination thereof.

10. The liquid formulation claim 8, wherein the aqueous sweetener comprises glycerin, sorbitol, sodium saccharin, xanthan gum, or a combination thereof.

11. The liquid formulation of claim 10, wherein the aqueous sweetener does not comprise sucrose.

12. The liquid formulation of claim 8, wherein the aqueous sweetener comprises sucrose, saccharin, mannitol, sorbitol, dextrose, acesulfame, aspartame, fructose, maltitol, sucralose, or a combination thereof.

13. The solid formulation of claim 1, formulated to provide the compound of Formula I in about a 40 mg or 80 mg dosage form.

14. A method of treating a cancer in a patient in need thereof, the method comprising administering to the patient a therapeutically effective amount of a solid formulation, wherein the solid formulation comprises a compound of the Formula (I):

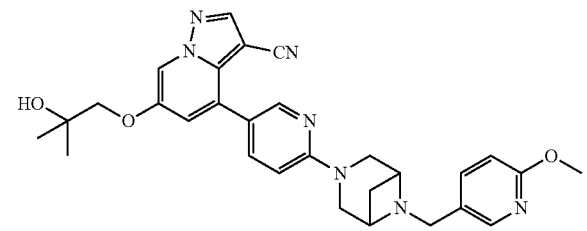

or a pharmaceutically acceptable salt, amorphous form, or polymorph form thereof in an amount from about 15 wt % to about 35 wt %;
a diluent or filler in an amount from about 65 wt % to about 85 wt %; and
a glidant in an amount from about 0.1 wt % to about 5 wt %;
wherein the cancer is selected from lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

15. The method of claim 14, wherein the cancer is lung cancer.

16. The method of claim 14, wherein the cancer is medullary thyroid cancer.

17. A method of treating a cancer in a patient in need thereof, the method comprising administering to the patient a therapeutically effective amount of a liquid formulation, wherein the liquid formulation comprises a compound of the Formula (I)

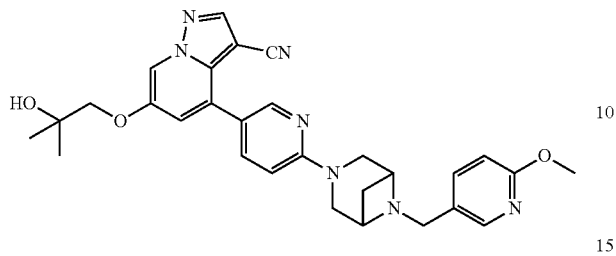

or a pharmaceutically acceptable salt thereof; and
an aqueous sweetener;
wherein the cancer is selected from lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

18. The method of treating a cancer in a patient in need thereof according to claim 17, wherein the patient is a pediatric patient.

* * * * *

SEQUENCE LISTING

```
<160> NUMBER OF SEQ ID NOS: 1

<210> SEQ ID NO 1
<211> LENGTH: 1114
<212> TYPE: PRT
<213> ORGANISM: Homo sapiens

<400> SEQUENCE: 1

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285
```

-continued

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
    690                 695                 700

```
Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Phe Gly
            725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
            755                 760                 765

Leu Arg Asp Leu Leu Ser Glu Phe Asn Val Leu Lys Gln Val Asn His
770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
            805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
            835                 840                 845

Gly Asp Leu Ile Ser Phe Ala Trp Gln Ile Ser Gln Gly Met Gln Tyr
850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
            885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
            915                 920                 925

Thr Thr Gln Ser Asp Val Trp Ser Phe Gly Val Leu Leu Trp Glu Ile
            930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
            965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
            995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Met Ser Asp Pro Asn
    1055                1060                1065

Trp Pro Gly Glu Ser Pro Val Pro Leu Thr Arg Ala Asp Gly Thr
    1070                1075                1080
```

```
Asn Thr Gly Phe Pro Arg Tyr Pro Asn Asp Ser Val Tyr Ala Asn
    1085                1090                1095

Trp Met Leu Ser Pro Ser Ala Ala Lys Leu Met Asp Thr Phe Asp
    1100                1105                1110

Ser
```

UNITED STATES PATENT AND TRADEMARK OFFICE
CERTIFICATE OF CORRECTION

PATENT NO. : 10,786,489 B2
APPLICATION NO. : 16/156903
DATED : September 29, 2020
INVENTOR(S) : Mark Reynolds et al.

Page 1 of 1

It is certified that error appears in the above-identified patent and that said Letters Patent is hereby corrected as shown below:

On the Title Page

Item (54) Title: Delete "METHYLPROPXY" and insert -- METHYLPROPOXY --, therefor.

In the Specification

In Column 1, Line 2: Delete "METHYLPROPXY" and insert -- METHYLPROPOXY --, therefor.

In the Claims

In Claim 6, Column 297, Line 42: after "formulation" insert -- of --.

In Claim 10, Column 298, Line 16: after "formulation" insert -- of --.

Signed and Sealed this
Twenty-second Day of December, 2020

Andrei Iancu
*Director of the United States Patent and Trademark Office*